(12) United States Patent
Edwards et al.

(10) Patent No.: US 6,222,029 B1
(45) Date of Patent: Apr. 24, 2001

(54) 5' ESTS FOR SECRETED PROTEINS EXPRESSED IN BRAIN

(75) Inventors: Jean-Baptiste Dumas Milne Edwards, Paris; Aymeric Duclert, Saint Maur; Bruno Lacroix, Saint-Genis Laval, all of (FR)

(73) Assignee: Genset, Paris (FR)

(*) Notice: Subject to any disclaimer, the term of this patent is extended or adjusted under 35 U.S.C. 154(b) by 0 days.

(21) Appl. No.: 08/905,223

(22) Filed: Aug. 1, 1997

(51) Int. Cl.$^7$ .......................... C07H 21/04; C12N 15/85; C12N 15/09

(52) U.S. Cl. .......................... 536/24.1; 435/6; 435/69.1; 435/320.1; 536/23.1; 536/23.4

(58) Field of Search .......................... 435/6, 69.1, 320.1, 435/23.4; 536/23.1, 24.1, 24.3, 24.31, 24.33

(56) References Cited

FOREIGN PATENT DOCUMENTS

| 0 279 582 | 8/1988 | (EP) . |
|---|---|---|
| 625 572 A1 | 11/1994 | (EP) . |
| WO 97 07198 | 2/1977 | (WO) . |
| WO 96/34981 A2 | 11/1996 | (WO) . |
| WO 96/34981 A3 | 11/1996 | (WO) . |

OTHER PUBLICATIONS

Harris et al., "Polycystic kidney disease 1: Identification and analysis of the primary defect", J. Am. Soc. Nephrol. 6 (4): 1125–1133, 1995.*
Ahn et al., "The structural and functional diversity of dystrophin", Nature Genetics 3 (4): 283–291, Apr. 1993.*
Cawthon et al., "cDNA sequence and genomic structure of EVI2B, a gene lying within an intron of the neurofibromatosis type 1 gene", Genomics 9 (3): 446–460, 1991.*
Robakis et al., "Molecular cloning and characterization of a cDNA encoding the cerebrovascular and the neuritic plaque amyloid peptides", Proc. Natl. Acad. Sci. USA 84: 4190–4194, Jun. 1987.*
Sorge et al., "High level transcription of the glucocerebrosidase pseudogene in normal subjects and patients with Gaucher disease", J. Clin. Invest. 86: 1137–1141, Oct. 1990.*
Sakai et al., GenBank Acc. No. R86508, U.S. National Library of Medicine, accessed by PTO on Oct. 29, 1998, Aug. 1995.*
Marra et al., GenBank Acc. No. W80295, U.S. National Library of Medicine, accessed by PTO on Oct. 29, 1998, Jun. 1996.*
Evans et al., GenBank Acc. No. B00705, U.S. National Library of Medicine, accessed by PTO on Oct. 29, 1998, Jun. 1996.*
Hillier et al., GenBank Acc. No. H77787, U.S. National Library of Medicine, accessed by PTO on Oct. 29, 1998, Nov. 1995.*
Hillier et al., GenBank Acc. No. W81369, U.S. National Library of Medicine, accessed by PTO on Oct. 29, 1998, Jun. 1996.*
Hillier et al., GenBank Acc. No. N48413, U.S. National Library of Medicine, accessed by PTO on Oct. 29, 1998, Jan. 1995.*
Weinstock, GenBank Acc. No. T37106, U.S. National Library of Medicine, accessed by PTO on Oct. 29, 1998, Jan. 1995.*
Hillier et al., GenBank Acc. No. R14311, U.S. National Library of Medicine, accessed by PTO on Oct. 29, 1998, Apr. 1995.*
Hillier et al. (e), GenBank Acc. No. R83284, U.S. National Library of Medicine, accessed by PTO on Oct. 29, 1998, Aug. 1995.*
Auffray et al., GenBank Acc. Z43527, U.S. National Library of Medicine, accessed by PTO on Oct. 29, 1998, Nov. 1994.*
Adams et al., Nature 377 : 1–174 (1995) "Initial assessment of human gene diversity and expression patterns based upon 83 million nucleotides of cDNA sequence".
Hillier et al., Genome Res. 6 : 807–88 (1996) "Generation and Analysis of 280,000 Human Expressed Sequence Tags".
Carninci et al., Genomics 37 : 327–336 (1996) "High–Efficiency Full–Lenghth cDNA Cloning by Biotinylated CAP Trapper".
Kato et al., Gene 150 : 243–50 (1994) "Construction of human full length cDNA bank".
Von Heijne, Nucleic Acid Res. 14 : 4683–90 (1986) "A new method for predicting signal sequence cleavage sites".
Adams et al. (1993) 3,400 new expressed sequence tags identify diversity of transcripts in human brain. Nature Genetics 4:256–267.
Adams et al. (1993) Rapid cDNA sequencing (expressed sequence tags) from a directionally cloned human infant brain cDNA library. Nature Genetics 4:373–380.
Greenwood et al. (1995) Cloning of the gene encoding human somatostatin recptor 2: sequence analysis of the 5'–flanking promoter region. Gene 2:291–292.
Lin et al. (1995) Inhibition of nuclear translocation of transcription factor NF–KB by a synthetic peptide containing a cell membrane–permeable motif and nuclear localization sequence. J. Biol. Chem. 270:14255–14258.

(List continued on next page.)

*Primary Examiner*—Scott D. Priebe
(74) *Attorney, Agent, or Firm*—Knobbe Martens Olson & Bear LLP

(57) ABSTRACT

The sequences of 5' ESTs derived from mRNAs encoding secreted proteins are disclosed. The 5' ESTs may be to obtain cDNAs and genomic DNAs corresponding to the 5' ESTs. The 5' ESTs may also be used in diagnostic, forensic, gene therapy, and chromosome mapping procedures. Upstream regulatory sequences may also be otained using the 5' ESTs. The 5' ESTs may also be used to design expression vectors and secretion vectors.

20 Claims, 7 Drawing Sheets

OTHER PUBLICATIONS

Lockhart et al. (1996) Expression monitoring by hybridization to high–density oligonucleotide arrays. BioTechnology 14: 1675–1680.

Tashiro et al. (1993) Signal sequence trap: a cloning strategy for secreted proteins and type I membrane proteins. Science 261:600–603.

Yokoyama–Kobayashi et al. (1995) A signal sequence detection system using secreted protease activity as an indicator. Gene 163:193–196.

Database EMBL, Entry HS181c9, Acc No. Z98743., Aug. 22, 1997.

* cited by examiner

| Minimum signal peptide score | false positive rate | false negative rate | proba(0.1) | proba(0.2) |
|---|---|---|---|---|
| 3.5 | 0.121 | 0.036 | 0.467 | 0.664 |
| 4 | 0.096 | 0.06 | 0.519 | 0.708 |
| 4.5 | 0.078 | 0.079 | 0.565 | 0.745 |
| 5 | 0.062 | 0.098 | 0.615 | 0.782 |
| 5.5 | 0.05 | 0.127 | 0.659 | 0.813 |
| 6 | 0.04 | 0.163 | 0.694 | 0.836 |
| 6.5 | 0.033 | 0.202 | 0.725 | 0.855 |
| 7 | 0.025 | 0.248 | 0.763 | 0.878 |
| 7.5 | 0.021 | 0.304 | 0.78 | 0.889 |
| 8 | 0.015 | 0.368 | 0.816 | 0.909 |
| 8.5 | 0.012 | 0.418 | 0.836 | 0.92 |
| 9 | 0.009 | 0.512 | 0.856 | 0.93 |
| 9.5 | 0.007 | 0.581 | 0.863 | 0.934 |
| 10 | 0.006 | 0.679 | 0.835 | 0.919 |

*FIG. 2*

| Minimum signal peptide score | All ESTs | New ESTs | ESTs matching public EST closer than 40 bp from beginning | ESTs extending known mRNA more than 40 bp | ESTs extending known mRNA more than 40 bp |
|---|---|---|---|---|---|
| 3.5 | 2674 | 947 | 599 | 23 | 150 |
| 4 | 2278 | 784 | 499 | 23 | 126 |
| 4.5 | 1943 | 647 | 425 | 22 | 112 |
| 5 | 1657 | 523 | 353 | 21 | 96 |
| 5.5 | 1417 | 419 | 307 | 19 | 80 |
| 6 | 1190 | 340 | 238 | 18 | 68 |
| 6.5 | 1035 | 280 | 186 | 18 | 60 |
| 7 | 893 | 219 | 161 | 15 | 48 |
| 7.5 | 753 | 173 | 132 | 12 | 36 |
| 8 | 636 | 133 | 101 | 11 | 29 |
| 8.5 | 543 | 104 | 83 | 8 | 26 |
| 9 | 456 | 81 | 63 | 6 | 24 |
| 9.5 | 364 | 57 | 48 | 6 | 18 |
| 10 | 303 | 47 | 35 | 6 | 15 |

*FIG. 4*

| Tissue | All ESTs | New ESTs | ESTs matching public EST closer than 40 bp from beginning | ESTs extending known mRNA more than 40 bp | ESTs extending public EST more than 40 bp |
|---|---|---|---|---|---|
| Brain | 329 | 131 | 75 | 3 | 24 |
| Cancerous prostate | 134 | 40 | 37 | 1 | 6 |
| Cerebellum | 17 | 9 | 1 | 0 | 6 |
| Colon | 21 | 11 | 4 | 0 | 0 |
| Dystrophic muscle | 41 | 18 | 8 | 0 | 1 |
| Fetal brain | 70 | 37 | 16 | 0 | 1 |
| Fetal kidney | 227 | 116 | 46 | 1 | 19 |
| Fetal liver | 13 | 7 | 2 | 0 | 0 |
| Heart | 30 | 15 | 7 | 0 | 1 |
| Hypertrophic prostate | 86 | 23 | 22 | 2 | 2 |
| Kidney | 10 | 7 | 3 | 0 | 0 |
| Large intestine | 21 | 8 | 4 | 0 | 1 |
| Liver | 23 | 9 | 6 | 0 | 0 |
| Lung | 24 | 12 | 4 | 0 | 1 |
| Lung (cells) | 57 | 38 | 6 | 0 | 4 |
| Lymph ganglia | 163 | 60 | 23 | 2 | 12 |
| Lymphocytes | 23 | 6 | 4 | 0 | 2 |
| Muscle | 33 | 16 | 6 | 0 | 4 |
| Normal prostate | 181 | 61 | 45 | 7 | 11 |
| Ovary | 90 | 57 | 12 | 1 | 2 |
| Pancreas | 48 | 11 | 6 | 0 | 1 |
| Placenta | 24 | 5 | 1 | 0 | 0 |
| Prostate | 34 | 16 | 4 | 0 | 2 |
| Spleen | 56 | 28 | 10 | 0 | 1 |
| Substantia nigra | 108 | 47 | 27 | 1 | 6 |
| Surrenals | 15 | 3 | 3 | 1 | 0 |
| Testis | 131 | 68 | 25 | 1 | 8 |
| Thyroid | 17 | 8 | 2 | 0 | 2 |
| Umbilical cord | 55 | 17 | 12 | 1 | 3 |
| Uterus | 28 | 15 | 3 | 0 | 2 |
| Non tissue-specific | 568 | 48 | 177 | 2 | 28 |
| Total | 2677 | 947 | 601 | 23 | 150 |

FIG. 5

Description of Transcription Factor Binding Sites present on promoters isolated from SignalTag sequences Promoter sequence P13H2 (546 bp):

| Matrix | Position | Orientation | Score | Length | Sequence | Location in: SEQ ID NO: 31 |
|---|---|---|---|---|---|---|
| CMYB_01 | -502 | + | 0.983 | 9 | TGTCAGTTG | 17-25 |
| MYOD_Q6 | -501 | - | 0.961 | 10 | CCCAACTGAC | complement of 18-27 |
| S8_01 | -444 | - | 0.960 | 11 | AATAGAATTAG | complement of 75-85 |
| S8_01 | -425 | + | 0.966 | 11 | AACTAAATTAG | 94-104 |
| DELTAEF1_01 | -390 | - | 0.960 | 11 | GCACACCTCAG | complement of 129-139 |
| GATA_C | -364 | - | 0.964 | 11 | AGATAAATCCA | complement of 155-165 |
| CMYB_01 | -349 | + | 0.958 | 9 | CTTCAGTTG | 170-178 |
| GATA1_02 | -343 | + | 0.959 | 14 | TTGTAGATAGGACA | 176-189 |
| GATA_C | -339 | + | 0.953 | 11 | AGATAGGACAT | 180-190 |
| TAL1ALPHAE47_01 | -235 | + | 0.973 | 16 | CATAACAGATGGTAAG | 284-299 |
| TAL1BETAE47_01 | -235 | + | 0.983 | 16 | CATAACAGATGGTAAG | 284-299 |
| TAL1BETAITF2_01 | -235 | + | 0.978 | 16 | CATAACAGATGGTAAG | 284-299 |
| MYOD_Q6 | -232 | - | 0.954 | 10 | ACCATCTGTT | complement of 287-296 |
| GATA1_04 | -217 | - | 0.953 | 13 | TCAAGATAAAGTA | complement of 302-314 |
| IK1_01 | -126 | + | 0.963 | 13 | AGTTGGGAATTCC | 393-405 |
| IK2_01 | -126 | + | 0.985 | 12 | AGTTGGGAATTC | 393-404 |
| CREL_01 | -123 | + | 0.962 | 10 | TGGGAATTCC | 396-405 |
| GATA1_02 | -96 | + | 0.950 | 14 | TCAGTGATATGGCA | 423-436 |
| SRY_02 | -41 | - | 0.951 | 12 | TAAAACAAAACA | complement of 478-489 |
| E2F_02 | -33 | + | 0.957 | 8 | TTTAGCGC | 486-493 |
| MZF1_01 | -5 | - | 0.975 | 8 | TGAGGGGA | complement of 514-521 |

Promoter sequence P15B4 (861 bp):

| Matrix | Position | Orientation | Score | Length | Sequence | Location in: SEQ ID NO: 34 |
|---|---|---|---|---|---|---|
| NFY_Q6 | -748 | - | 0.956 | 11 | GGACCAATCAT | complement of 60-70 |
| MZF1_01 | -738 | + | 0.962 | 8 | CCTGGGGA | 70-77 |
| CMYB_01 | -684 | + | 0.994 | 9 | TGACCGTTG | 124-132 |
| VMYB_02 | -682 | - | 0.985 | 9 | TCCAACGGT | complement of 126-134 |
| STAT_01 | -673 | + | 0.968 | 9 | TTCCTGGAA | 135-143 |
| STAT_01 | -673 | - | 0.951 | 9 | TTCCAGGAA | complement of 135-143 |
| MZF1_01 | -556 | - | 0.956 | 8 | TTGGGGGA | complement of 252-259 |
| IK2_01 | -451 | + | 0.965 | 12 | GAATGGGATTTC | 357-368 |
| MZF1_01 | -424 | + | 0.986 | 8 | AGAGGGGA | 384-391 |
| SRY_02 | -398 | - | 0.955 | 12 | GAAAACAAAACA | complement of 410-421 |
| MZF1_01 | -216 | + | 0.960 | 8 | GAAGGGGA | 592-599 |
| MYOD_Q6 | -190 | + | 0.981 | 10 | AGCATCTGCC | 618-627 |
| DELTAEF1_01 | -176 | + | 0.958 | 11 | TCCCACCTTCC | 632-642 |
| S8_01 | 5 | - | 0.992 | 11 | GAGGCAATTAT | complement of 813-823 |
| MZF1_01 | 16 | - | 0.986 | 8 | AGAGGGGA | complement of 824-831 |

Promoter sequence P29B6 (555 bp):

| Matrix | Position | Orientation | Score | Length | Sequence | Location in: SEQ ID NO: 37 |
|---|---|---|---|---|---|---|
| ARNT_01 | -311 | + | 0.964 | 16 | GGACTCACGTGCTGCT | 191-206 |
| NMYC_01 | -309 | + | 0.965 | 12 | ACTCACGTGCTG | 193-204 |
| USF_01 | -309 | + | 0.985 | 12 | ACTCACGTGCTG | 193-204 |
| USF_01 | -309 | - | 0.985 | 12 | CAGCACGTGAGT | complement of 193-204 |
| NMYC_01 | -309 | - | 0.956 | 12 | CAGCACGTGAGT | complement of 193-204 |
| MYCMAX_02 | -309 | - | 0.972 | 12 | CAGCACGTGAGT | complement of 193-204 |
| USF_C | -307 | + | 0.997 | 8 | TCACGTGC | 195-202 |
| USF_C | -307 | - | 0.991 | 8 | GCACGTGA | complement of 195-202 |
| MZF1_01 | -292 | - | 0.968 | 8 | CATGGGGA | complement of 210-217 |
| ELK1_02 | -105 | + | 0.963 | 14 | CTCTCCGGATTCCT | 397-410 |
| CETS1P54_01 | -102 | + | 0.974 | 10 | TCCGGAAGCC | 400-409 |
| AP1_Q4 | -42 | - | 0.963 | 11 | AGTGACTGAAC | complement of 460-470 |
| AP1FJ_Q2 | -42 | - | 0.961 | 11 | AGTGACTGAAC | complement of 460-470 |
| PADS_C | 45 | + | 1.000 | 9 | TGTGGTCTC | 547-555 |

FIG. 7

5' ESTS FOR SECRETED PROTEINS EXPRESSED IN BRAIN

BACKGROUND OF THE INVENTION

The 50,000–100,000 genes scattered along the human chromosomes offer tremendous promise for the understanding, diagnosis, and treatment of human diseases. In addition, probes capable of specifically hybridizing to loci distributed throughout the human genome find applications in the construction of high resolution chromosome maps and in the identification of individuals.

In the past, the characterization of even a single human gene was a painstaking process, requiring years of effort. Recent developments in the areas of cloning vectors, DNA sequencing, and computer technology have merged to greatly accelerate the rate at which human genes can be isolated, sequenced, mapped, and characterized. Cloning vectors such as yeast artificial chromosomes (YACs) and bacterial artificial chromosomes (BACs) are able to accept DNA inserts ranging from 300 to 1000 kilobases (kb) or 100–400 kb in length respectively, thereby facilitating the manipulation and ordering of DNA sequences distributed over great distances on the human chromosomes. Automated DNA sequencing machines permit the rapid sequencing of human genes. Bioinformatics software enables the comparison of nucleic acid and protein sequences, thereby assisting in the characterization of human gene products.

Currently, two different approaches are being pursued for identifying and characterizing the genes distributed along the human genome. In one approach, large fragments of genomic DNA are isolated, cloned, and sequenced. Potential open reading frames in these genomic sequences are identified using bio-informatics software. However, this approach entails sequencing large stretches of human DNA which do not encode proteins in order to find the protein encoding sequences scattered throughout the genome. In addition to requiring extensive sequencing, the bio-informatics software may mischaracterize the genomic sequences obtained. Thus, the software may produce false positives in which non-coding DNA is mischaracterized as coding DNA or false negatives in which coding DNA is mislabeled as non-coding DNA.

An alternative approach takes a more direct route to identifying and characterizing human genes. In this approach, complementary DNAs (cDNAs) are synthesized from isolated messenger RNAs (mRNAs) which encode human proteins. Using this approach, sequencing is only performed on DNA which is derived from protein coding portions of the genome. Often, only short stretches of the cDNAs are sequenced to obtain sequences called expressed sequence tags (ESTs).

In the past, these short EST sequences were often obtained from oligo-dT primed cDNA libraries. Accordingly, they mainly corresponded to the 3' untranslated region of the mRNA. In part, the prevalence of EST sequences derived from the 3' end of the mRNA is a result of the fact that typical techniques for obtaining cDNAs, are not well suited for isolating cDNA sequences derived from the 5' ends of mRNAs. (Adams et al., *Nature* 377:174, 1996; Hillier et al., *Genome Res.* 6:807–828, 1996).

In addition, in those reported instances where longer cDNA sequences have been obtained, the reported sequences typically correspond to coding sequences and do not include the full 5' untranslated region of the mRNA from which the cDNA is derived. Such incomplete sequences may not include the first exon of the mRNA, particularly in situations where the first exon is short. Furthermore, they may not include some exons, often short ones, which are located upstream of splicing sites. Thus, there is a need to obtain sequences derived from the 5' ends of mRNAs.

While many sequences derived from human chromosomes have practical applications, approaches based on the identification and characterization of those chromosomal sequences which encode a protein product are particularly relevant to diagnostic and therapeutic uses. Of the 50,000–100,000 protein coding genes, those genes encoding proteins which are secreted from the cell in which they are synthesized, as well as the secreted proteins themselves, are particularly valuable as potential therapeutic agents. Such proteins are often involved in cell to cell communication and may be responsible for producing a clinically relevant response in their target cells.

In fact, several secretory proteins, including tissue plasminogen activator, G-CSF, GM-CSF, erythropoietin, human growth hormone, insulin, interferon-α, interferon-β, interferon-γ, and interleukin-2, are currently in clinical use. These proteins are used to treat a wide range of conditions, including acute myocardial infarction, acute ischemic stroke, anemia, diabetes, growth hormone deficiency, hepatitis, kidney carcinoma, chemotherapy induced neutropenia and multiple sclerosis. Thus, there is a need for the identification and characterization of secreted proteins.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably linking the signal sequences to a gene encoding the protein for which secretion is desired. This may prove beneficial in gene therapy strategies in which it is desired to deliver a particular gene product to cells other than the cell in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' portions of the genes for secretory proteins which encode signal peptides.

Public information on the number of human genes for which the promoters and upstream regulatory regions have been identified and characterized is quite limited. In part, this may be due to the difficulty of isolating such regulatory sequences. Upstream regulatory sequences such as transcription factor binding sites are typically too short to be utilized as probes for isolating promoters from human genomic libraries. Recently, some approaches have been developed to isolate human promoters. One of them consists of making a CpG island library (Cross, S. H. et al., Purification of CpG Islands using a Methylated DNA Binding Column, Nature Genetics 6: 236–244 (1994)). The second consists of isolating human genomic DNA sequences containing SpeI binding sites by the use of SpeI binding protein. (Mortlock et al., *Genome Res.* 6:327–335, 1996). Both of these approaches have their limits due to a lack of specificity or of comprehensiveness.

The present 5' ESTs may be used to efficiently identify and isolate upstream regulatory regions which control the location, developmental stage, rate, and quantity of protein synthesis, as well as the stability of the mRNA. (Theil, *BioFactors* 4:87–93, 1993). Once identified and characterized, these regulatory regions may be utilized in gene therapy or protein purification schemes to obtain the desired amount and locations of protein synthesis or to inhibit, reduce, or prevent the synthesis of undesirable gene products.

In addition, the 5' ends of secretory protein genes may include sequences useful as probes for chromosome mapping and the identification of individuals. Thus, there is a need to identify and characterize the sequences upstream of the 5' coding sequences of genes encoding secretory proteins.

SUMMARY OF THE INVENTION

The present invention relates to purified, isolated, or recombinant ESTs which include sequences derived from the authentic 5' ends of their corresponding mRNAs. The term "corresponding mRNA" refers to the mRNA which was the template for the cDNA synthesis which produced the 5' EST. These sequences will be referred to hereinafter as "5' ESTs." As used herein, the term "purified" does not require absolute purity; rather, it is intended as a relative definition. Individual 5' EST clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$–$10^6$ fold purification of the native message. Purification of starting material or natural material to at least one order of magnitude, preferably two or three orders, and more preferably four or five orders of magnitude is expressly contemplated.

As used herein, the term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "recombinant" means that the 5' EST is adjacent to "backbone" nucleic acid to which it is not adjacent in its natural environment. Additionally, to be "enriched" the 5' ESTs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched 5' ESTs represent 15% or more of the number of nucleic acid inserts in the population of recombinant backbone molecules. More preferably, the enriched 5' ESTs represent 50% or more of the number of nucleic acid inserts in the population of recombinant backbone molecules. In a highly preferred embodiment, the enriched 5' ESTs represent 90% or more of the number of nucleic acid inserts in the population of recombinant backbone molecules.

"Stringent", "moderate," and "low" nybridization conditions are as defined in Example 29.

Unless otherwise indicated, a "complementary" sequence is fully complementary.

Thus, 5' ESTs in cDNA libraries in which -one or more 5' ESTs make up 5% or more of the number of nucleic acid inserts in the backbone molecules are "enriched recombinant 5' ESTs" as defined herein. Likewise, 5' ESTs in a population of plasmids in which one or more 5' EST of the present invention have been inserted such that they represent 5% or more of the number of inserts in the plasmid backbone are "enriched recombinant 5' ESTs" as defined herein. However, 5' ESTs in cDNA libraries in which 5' ESTs constitute less than 5% of the number of nucleic acid inserts in the population of backbone molecules, such as libraries in which backbone molecules having a 5' EST insert are extremely rare, are not "enriched recombinant 5' ESTs."

In particular, the present invention relates to 5' ESTs which are derived from genes encoding secreted proteins. Such 5' ESTs include nucleic acid sequences, called signal sequences, which encode signal peptides which direct the extracellular secretion of the proteins encoded by the genes from which the 5' ESTs are derived. Generally, the signal peptides are located at the amino termini of secreted proteins.

Secreted proteins are translated by ribosomes associated with the "rough" endoplasmic reticulum. Generally, secreted proteins are co-translationally transferred to the membrane of the endoplasmic reticulum. Association of the ribosome with the endoplasmic reticulum during translation of secreted proteins is mediated by the signal peptide. The signal peptide is typically cleaved following its co-translational entry into the endoplasmic reticulum. After delivery to the endoplasmic reticulum, secreted proteins may proceed through the Golgi apparatus. In the Golgi apparatus, the proteins may undergo post-translational modification before entering secretory vesicles which transport them across the cell membrane.

The 5' ESTs of the present invention have several important applications. For example, they may be used to obtain cDNA clones which include the full protein coding sequences of the corresponding gene products, including the authentic translation start sites derived from the 5' ends of the coding sequences of the mRNAs from which the 5' ESTs are derived. These cDNAs will be referred to hereinafter as "full length cDNAs." These cDNAs may also include DNA derived from mRNA sequences upstream of the translation start site. The full length cDNA sequences may be used to express the proteins corresponding to the 5' ESTs. As discussed above, secreted proteins are therapeutically important. Thus, the proteins expressed from the cDNAs may be useful in treating or controlling a variety of human conditions. The 5' ESTs may also be used to obtain the corresponding genomic DNA. The term "corresponding genomic DNA" refers to the genomic DNA which encodes the mRNA from which the 5' EST was derived.

The 5' ESTs (or cDNAs or genomic DNAs obtained therefrom) may be used in forensic procedures to identify individuals or in diagnostic procedures to identify individuals having genetic diseases resulting from abnormal expression of the genes corresponding to the 5' ESTs. In addition, the present invention is useful for constructing a high resolution map of the human chromosomes.

The present invention also relates to secretion vectors capable of directing the secretion of a protein of interest.

Such vectors may be used in gene therapy strategies in which it is desired to produce a gene product in one cell which is to be delivered to another location in the body. Secretion vectors may also facilitate the purification of desired proteins.

The present invention also relates to expression vectors capable of directing the expression of an inserted gene in a desired spatial or temporal manner or at a desired level. Such vectors may include sequences upstream of the 5' ESTs, such as promoters or upstream regulatory sequences.

Finally, the present invention may also be used for gene therapy to control or treat genetic diseases. Signal peptides may also be fused to heterologous proteins to direct their extracellular secretion.

Bacterial clones containing Bluescipt plasmids having inserts containing the 5' ESTs of the present invention (SEQ ID NO:s 38–270 are presently stored at 80° C. in 4% (v/v) glycerol in the inventor's laboratories under the designations listed next to the SEQ ID NOs in Table II). The inserts may be recovered from the deposited materials by growing the appropriate clones on a suitable medium. The Bluescript DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the EST insertion. The PCR product which corresponds to the 5' EST can then be manipulated using standard cloning techniques familiar to those skilled in the art.

One aspect of the present invention is a purified or isolated nucleic acid having the sequence of one of SEQ ID NOs: 38–270 or having a sequence complementary thereto. In one embodiment, the nucleic acid is recombinant.

Another aspect of the present invention is a purified or isolated nucleic acid comprising at least 10 consecutive bases of the sequence of one of SEQ ID NOs: 38–270 or one of the sequences complementary thereto.

Yet another aspect of the present invention is a purified or isolated nucleic acid comprising at least 15 consecutive bases of one of the sequences of SEQ ID NOs: 38–270 or one of the sequences complementary thereto. In one embodiment, the nucleic acid is recombinant.

A further aspect of the present invention is a purified or isolated nucleic acid of at least 15 bases capable of hybridizing under stringent conditions to the sequence of one of SEQ ID NOs: 38–270 or one of the sequences complementary to the sequences of SEQ ID NOs: 38–270. In one emodiment, the nucleic acid is recombinant.

Another aspect of the present invention is a purified or isolated nucleic acid encoding a human gene product, said human gene product having a sequence partially encoded by one of the sequences of SEQ ID NO: 38–270.

Still another aspect of the present invention is a method of making a cDNA encoding a human secretory protein, said human secretory protein being partially encoded by one of SEQ ID NOs 38–270, comprising the steps of contacting a collection of mRNA molecules from human cells with a primer comprising at least 15 consecutive nucleotides of a sequence complementary to one of SEQ ID NOs: 38–270; hybridizing said primer to an mRNA in said collection that encodes said protein; reverse transcribing said hybridized primer to make a first cDNA strand from said mRNA; making a second cDNA strand complementary to said first cDNA strand; and isolating the resulting cDNA encoding said protein comprising said first cDNA strand and said second cDNA strand.

Another aspect of the invention is an isolated or purified cDNA encoding a human secretory protein, said human secretory protein comprising the protein encoded by one of SEQ ID NOs 38–270 or a fragment thereof of at least 10 amino acids, said cDNA being obtainable by the method described in the preceding paragraph. In one embodiment, the cDNA comprises the full protein coding sequence of said protein which sequence is partially included in one of the sequences of SEQ ID NOs: 38–270.

Another aspect of the present invention is a method of making a cDNA encoding a human secretory protein that is partially encoded by one of SEQ ID NOs 38–270, comprising the steps of obtaining a cDNA comprising one of the sequences of SEQ ID NOs: 38–270; contacting said cDNA with a detectable probe comprising at least 15 consecutive nucleotides of said sequence of SEQ ID NO: 38–270 or a sequence complementary thereto under conditions which permit said probe to hybridize to said cDNA; identifying a cDNA which hybridizes to said detectable probe; and isolating said cDNA which hybridizes to said probe.

Another aspect of the present invention is an isolated or purified cDNA encoding a human secretory protein, said human secretory protein comprising the protein encoded by one of SEQ ID NOs 38–270 or a fragment thereof of at least 10 amino acids, said cDNA being obtainable by the method described in the preceding paragraph. In one embodiment, the cDNA comprises the full protein coding sequence partially included in one of the sequences of SEQ ID NOs: 38–270.

Another aspect of the present invention is a method of making a cDNA comprising the sequence of SEQ ID NOs: 38–270, comprising the steps of contacting a collection of mRNA molecules from human cells with a first primer capable of hybridizing to the polyA tail of said mRNA; hybridizing said first primer to said polyA tail; reverse transcribing said mRNA to make a first cDNA strand; making a second cDNA strand complementary to said first cDNA strand using at least one primer comprising at least 15 nucleotides of one of the sequences of SEQ ID NOs 38–270; and isolating the resulting cDNA comprising said first cDNA strand and said second cDNA strand.

Another aspect of the present invention is an isolated or purified cDNA encoding a human secretory protein, said human secretory protein comprising the protein encoded by one of SEQ ID NOs 38–270 or a fragment thereof of at least 10 amino acids, said cDNA being obtainable by the method described in the preceding paragraph. In one embodiment, the cDNA comprises the full protein coding sequence partially included in one of the sequences of SEQ ID NOs: 38–270.

In one embodiment of the method described in the paragraph two paragraphs above, the second cDNA strand is made by contacting said first cDNA strand with a first pair of primers, said first pair of primers comprising a second primer comprising at least 15 consecutive nucleotides of one of the sequences of SEQ ID NOs 38–270 and a third primer having a sequence therein which is included within the sequence of said first primer; performing a first polymerase chain reaction with said first pair of nested primers to generate a first PCR product; contacting said first PCR product with a second pair of primers, said second pair of primers comprising a fourth primer, said fourth primer comprising at least 15 consecutive nucleotides of said sequence of one of SEQ ID NO:s 38–270, and a fifth primer, said fourth and fifth primers being capable of hybridizing to sequences within said first PCR product; and performing a second polymerase chain reaction, thereby generating a second PCR product.

One aspect of the present invention is an isolated or purified cDNA encoding a human secretory protein, said human secretory protein comprising the protein encoded by one of SEQ ID NOs 38–270, or a fragment thereof of at least 10 amino acids, said cDNA being obtainable by the method of the preceding paragraph. In one embodiment, the cDNA comprises the full protein coding sequence partially included in one of the sequences of SEQ ID NOs: 38–270.

Another aspect of the present invention is the method described four paragraphs above in which the second cDNA strand is made by contacting said first cDNA strand with a second primer comprising at least 15 consecutive nucleotides of the sequences of SEQ ID NOs: 38–270; hybridizing said second primer to said first strand cDNA; and extending said hybridized second primer to generate said second cDNA strand.

Another aspect of the present invention is an isolated or purified cDNA encoding a human secretory protein, said human secretory protein comprising the protein partially encoded by one of SEQ ID NOs 38–270 or comprising a fragment thereof of at least 10 amino acids, said cDNA being obtainable by the method described in the preceding paragraph. In one embodiment, the cDNA comprises the full protein coding sequence partially included in of one of the sequences of SEQ ID NOs: 38–270.

Another aspect of the present invention is a method of making a protein comprising one of the sequences of SEQ ID NO: 271–503, comprising the steps of obtaining a cDNA encoding the full protein sequence partially included in one of the sequences of sequence of SEQ ID NO: 38–270; inserting said cDNA in an expression vector such that said cDNA is operably linked to a promoter; introducing said expression vector into a host cell whereby said host cell produces the protein encoded by said cDNA; and isolating said protein.

Another aspect of the present invention is an isolated protein obtainable by the method described in the preceding paragraph.

Another aspect of the present invention is a method of obtaining a promoter DNA comprising the steps of obtaining DNAs located upstream of the nucleic acids of SEQ ID NO: 38–270 or the sequences complementary thereto; screening said upstream DNAs to identify a promoter capable of directing transcription initiation; and isolating said DNA comprising said identified promoter. In one embodiment, the obtaining step comprises chromosome walking from said nucleic acids of SEQ ID NO: 38–270 or sequences complementary thereto. In another embodiment, the screening step comprises inserting said upstream sequences into a promoter reporter vector. In another embodiment, the screening step comprises identifying motifs in said upstream DNAs which are transcription factor binding sites or transcription start sites.

Another aspect of the present invention is an isolated promoter obtainable by the method described above.

Another aspect of the present invention is an isolated or purified protein comprising one of the sequences of SEQ ID NO: 271–503.

Another aspect of the present invention is the inclusion of at least one of the sequences of SEQ ID NOs: 38–270, or one of the sequences complementary to the sequences of SEQ ID NOs: 38–270, or a fragment thereof of at least 15 consecutive nucleotides in an array of discrete ESTs or fragments thereof of at least 15 nucleotides in length. In one embodiment, the array includes at least two of the sequences of SEQ ID NOs: 38–270, the sequences complementary to the sequences of SEQ ID NOs: 38–270, or fragments thereof of at least 15 consecutive nucleotides. In another embodiment, the array includes at least five of the sequences of SEQ ID NOs: 38–270, the sequences complementary to the sequences of SEQ ID NOs: 38–270, or fragments thereof of at least 15 consecutive nucleotides.

Another aspect of the present invention is a promoter having a sequence selected from the group consisting of SEQ ID NOs: 31, 34, and 37.

BRIEF DESCRIPTION OF THE DRAWINGS

FIG. 2 is an analysis of the 43 amino terminal amino acids of all human SwissProt proteins to determine the frequency of false positives and false negatives using the techniques for signal peptide identification described herein.

FIG. 4 shows the distribution of 5' ESTs in each category and the number of 5' ESTs in each category having a given minimum von Heijne's score.

FIG. 5 shows the tissues from which the mRNAs corresponding to the 5' ESTs in each of the categories described herein were obtained.

FIG. 7 describes the transcription factor binding sites present in each of these promoters.

DETAILED DESCRIPTION OF THE PREFERRED EMBODIMENTS

Obtaining 5' ESTs

Figure 1:
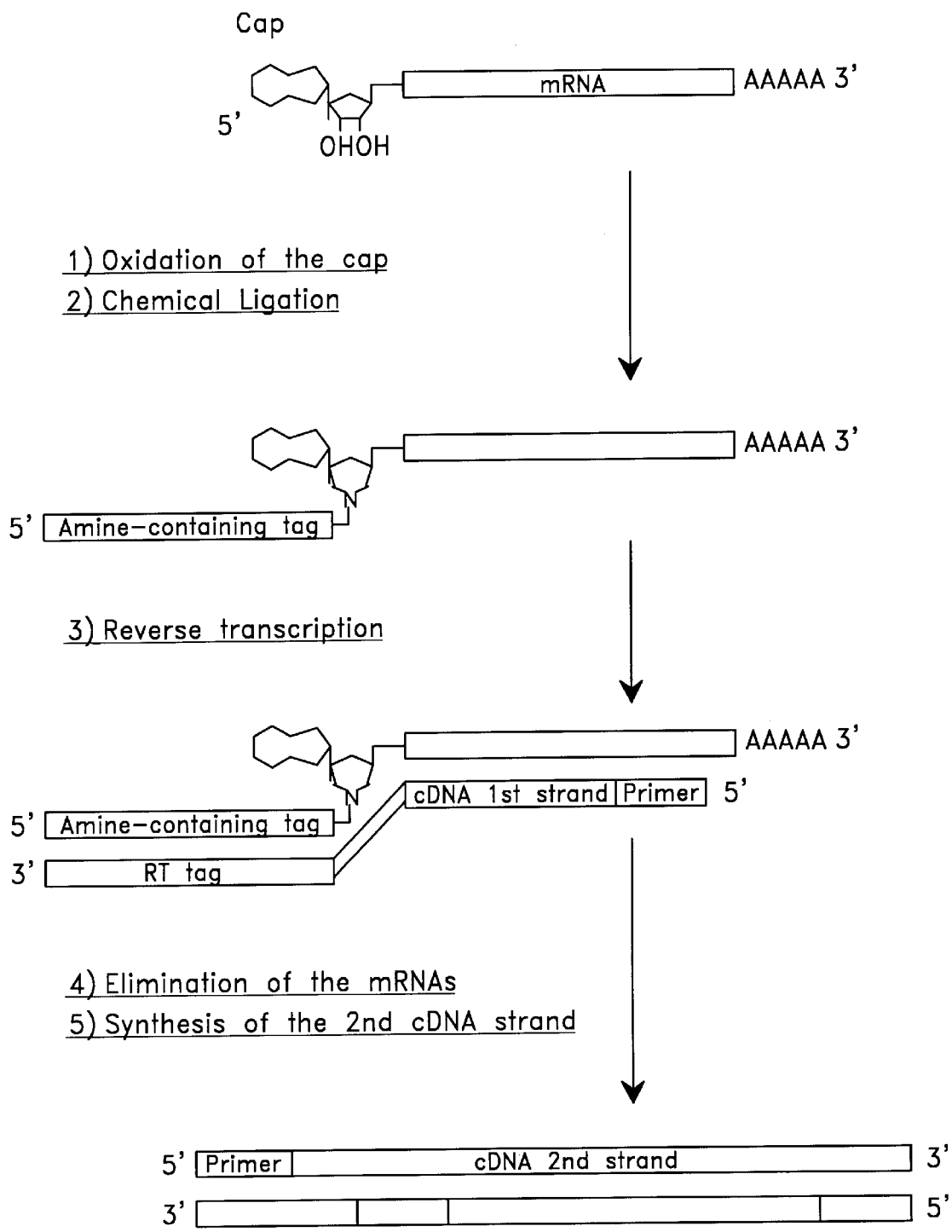
FIG. 1 is a summary of the procedure for obtaining cDNAs which have been selected to include the 5' ends of the mRNAs from which they are derived.

A. Chemical Methods for Obtaining mRNAs having Intact 5' Ends

In order to obtain the 5' ESTs of the present invention, mRNAs having intact 5' ends must be obtained. Currently, there are two approaches for obtaining such mRNAs. One of these approaches is a chemical modification method involving derivatization of the 5' ends of the mRNAs and selection of the derivatized mRNAs.

The 5' ends of eucaryotic mRNAs possess a structure referred to as a "cap" which comprises a guanosine methylated at the 7 position. The cap is joined to the first transcribed base of the mRNA by a 5',5'-triphosphate bond. In some instances, the 5' guanosine is methylated in both the 2 and 7 positions. Rarely, the 5' guanosine is trimethylated at the 2, 7 and 7 positions.

In the chemical method for obtaining mRNAs having intact 5' ends, the 5' cap is specifically derivatized and coupled to a reactive group on an immobilizing substrate. This specific derivatization is based on the fact that only the ribose linked to the methylated guanosine at the 5' end of the mRNA and the ribose linked to the base at the 3' terminus of the mRNA, possess 2',3'-cis diols. Optionally, where the 3' terminal ribose has a 2',3'-cis diol, the 2',3'-cis diol at the 3' end may be chemically modified, substituted, converted, or eliminated, leaving only the ribose linked to the methylated guanosine at the 5' end of the mRNA with a 2',3'-cis diol.

A variety of techniques are available for eliminating the 2',3'-cis diol on the 3' terminal ribose. For example, controlled alkaline hydrolysis may be used to generate mRNA fragments in which the 3' terminal ribose is a 3'-phosphate, 2'-phosphate or (2',3')-cyclophosphate. Thereafter, the fragment which includes the original 3' ribose may be eliminated from the mixture through chromatography on an oligo-dT column. Alternatively, a base which lacks the 2',3'-cis diol may be added to the 3' end of the mRNA using an RNA ligase such as T4 RNA ligase. Example 1 below describes a method for ligation of pCp to the 3' end of messenger RNA.

EXAMPLE 1

Ligation of the Nucleoside Diphosphate pCp to the 3' End of Messenger RNA

1 μg of RNA was incubated in a final reaction medium of 10 μl in the presence of 5 U of $T_4$ phage RNA ligase in the buffer provided by the manufacturer (Gibco-BRL), 40 U of the RNase inhibitor RNasin (Promega) and, 2 μl of $^{32}$pCp (Amersham #PB 10208).

The incubation was performed at 37° C. for 2 hours or overnight at 7–8° C.

Following modification or elimination of the 2',3'-cis diol at the 3' ribose, the 2',3'-cis diol present at the 5' end of the mRNA may be oxidized using reagents such as $NaBH_4$, $NaBH_3CN$, or sodium periodate, thereby converting the 2',3'-cis diol to a dialdehyde. Example 2 describes the oxidation of the 2',3'-cis diol at the 5' end of the mRNA with sodium periodate.

EXAMPLE 2

Oxidation of 2',3'-Cis Diol At the 5' End of the mRNA 0.1 OD unit of either a capped oligoribonucleotide of 47 nucleotides (including the cap) or an uncapped oligoribonucleotide of 46 nucleotides were treated as follows. The oligoribonucleotides were produced by in vitro transcription using the transcription kit "AmpliScribe T7" (Epicentre Technologies). As indicated below, the DNA template for the RNA transcript contained a single cytosine. To synthesize the uncapped RNA, all four NTPs were included in the in vitro transcription reaction. To obtain the capped RNA, GTP was replaced by an analogue of the cap, m7G(5')ppp(5')G. This compound, recognized by polymerase, was incorporated into the 5' end of the nascent transcript during the step of initiation of transcription but was not capable of incorporation during the extension step. Consequently, the resulting RNA contained a cap at its 5' end. The sequences of the oligoribonucleotides produced by the in vitro transcription reaction were:

+Cap:
5'm7GpppGCAUCCUACUCCCAUCCAAUUCCACCCU AACUCCUCCCAUCUC CAC-3' (SEQ ID NO:1)
−Cap:
5'-pppGCAUCCUACUCCCAUCCAAUUCCACCCUAAC UCCUCCCAUCUCCAC-3' (SEQ ID NO:2)

The oligoribonucleotides were dissolved in 9 μl of acetate buffer (0.1 M sodium acetate, pH 5.2) and 3 μl of freshly prepared 0.1 M sodium periodate solution. The mixture was incubated for 1 hour in the dark at 4° C. or room temperature. Thereafter, the reaction was stopped by adding 4 μl of 10% ethylene glycol. The product was ethanol precipitated, resuspended in 10 μl or more of water or appropriate buffer and dialyzed against water.

The resulting aldehyde groups may then be coupled to molecules having a reactive amine group, such as hydrazine, carbazide, thiocarbazide or semicarbazide groups, in order to facilitate enrichment of the 5' ends of the mRNAs. Molecules having reactive amine groups which are suitable for use in selecting mRNAs having intact 5' ends include avidin, proteins, antibodies, vitamins, ligands capable of specifically binding to receptor molecules, or oligonucleotides. Example 3 below describes the coupling of the resulting dialdehyde to biotin.

EXAMPLE 3

Coupling of the Dialdehyde with Biotin

The oxidation product obtained in Example 2 was dissolved in 50 μl of sodium acetate at a pH of between 5 and 5.2 and 50 μl of freshly prepared 0.02 M solution of biotin hydrazide in a methoxyethanol/water mixture (1:1) of formula:

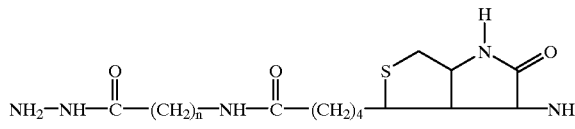

In the compound used in these experiments, n=5. However, it will be appreciated that other commercially available hydrazides may also be used, such as molecules of the formula above in which n varies from 0 to 5.

The mixture was then incubated for 2 hours at 37° C. Following the incubation, the mixture was precipitated with ethanol and dialyzed against distilled water. Example 4 demonstrates the specificity of the biotinylation reaction.

EXAMPLE 4

Specificity of Biotinylation

The specificity of the biotinylation for capped mRNAs was evaluated by gel electrophoresis of the following samples:

Sample 1. The 46 nucleotide uncapped in vitro transcript prepared as in Example 2 and labeled with $^{32}$pCp as described in Example 1.

Sample 2. The 46 nucleotide uncapped in vitro transcript prepared as in Example 2, labeled with $^{32}$pCp as described in Example 1, treated with the oxidation reaction of Example 2, and subjected to the biotinylation conditions of Example 3.

Sample 3. The 47 nucleotide capped in vitro transcript prepared as in Example 2 and labeled with $^{32}$pCp as described in Example 1.

Sample 4. The 47 nucleotide capped in vitro transcript prepared as in Example 2, labeled with $^{32}$pCp as described in Example 1, treated with the oxidation reaction of Example 2, and subjected to the biotinylation conditions of Example 3.

Samples 1 and 2 had indentical migration rates, demonstrating that the uncapped RNAs were not oxidized and biotinylated. Sample 3 migrated more slowly than Samples 1 and 2, while Sample 4 exhibited the slowest migration.

The difference in migration of the RNAs in Samples 3 and 4 demonstrates that the capped RNAs were specifically biotinylated.

In some cases, mRNAs having intact 5' ends may be enriched by binding the molecule containing a reactive amine group to a suitable solid phase substrate such as the inside of the vessel containing the mRNAs, magnetic beads, chromatography matrices, or nylon or nitrocellulose membranes. For example, where the molecule having a reactive amine group is biotin, the solid phase substrate may be coupled to avidin or streptavidin. Alternatively, where the molecule having the reactive amine group is an antibody or receptor ligand, the solid phase substrate may be coupled to the cognate antigen or receptor. Finally, where the molecule having a reactive amine group comprises an oligonucleotide, the solid phase substrate may comprise a complementary oligonucleotide.

The mRNAs having intact 5' ends may be released from the solid phase following the enrichment procedure. For example, where the dialdehyde is coupled to biotin hydrazide and the solid phase comprises streptavidin, the mRNAs may be released from the solid phase by simply heating to 95 degrees Celsius in 2% SDS. In some methods, the molecule having a reactive amine group may also be cleaved from the mRNAs having intact 5' ends following enrichment. Example 5 describes the capture of biotinylated mRNAs with streptavidin coated beads and the release of the biotinylated mRNAs from the beads following enrichment.

EXAMPLE 5

Capture and Release of Biotinylated mRNAs Using Strepatividin Coated Beads

The streptavidin-coated magnetic beads were prepared according to the manufacturer's instructions (CPG Inc., USA). The biotinylated mRNAs were added to a hybridization buffer (1.5 M NaCl, pH 5–6). After incubating for 30 minutes, the unbound and nonbiotinylated material was removed. The beads were washed several times in water with 1% SDS. The beads obtained were incubated for 15 minutes at 95° C. in water containing 2% SDS.

Example 6 demonstrates the efficiency with which biotinylated mRNAs were recovered from the streptavidin coated beads.

EXAMPLE 6

Efficiency of Recovery of Biotinylated mRNAs

The efficiency of the recovery procedure was evaluated as follows. RNAs were labeled with $^{32}$pCp, oxidized, biotinylated and bound to streptavidin coated beads as described above. Subsequently, the bound RNAs were incubated for 5, 15 or 30 minutes at 95° C. in the presence of 2% SDS.

The products of the reaction were analyzed by electrophoresis on 12% polyacrylamide gels under denaturing conditions (7 M urea). The gels were subjected to autoradiography. During this manipulation, the hydrazone bonds were not reduced.

Increasing amounts of nucleic acids were recovered as incubation times in 2% SDS increased, demonstrating that biotinylated mRNAs were efficiently recovered.

In an alternative method for obtaining mRNAs having intact 5' ends, an oligonucleotide which has been derivatized to contain a reactive amine group is specifically coupled to mRNAs having an intact cap. Preferably, the 3' end of the mRNA is blocked prior to the step in which the aldehyde groups are joined to the derivatized oligonucleotide, as described above, so as to prevent the derivatized oligonucleotide from being joined to the 3' end of the mRNA. For example, pCp may be attached to the 3' end of the mRNA using T4 RNA ligase. However, as discussed above, blocking the 3' end of the mRNA is an optional step. Derivatized oligonucleotides may be prepared as described below in Example 7.

EXAMPLE 7

Derivatization of the Oligonucleotide

An oligonucleotide phosphorylated at its 3' end was converted to a 3' hydrazide in 3' by treatment with an aqueous solution of hydrazine or of dihydrazide of the formula $H_2N(R1)NH_2$ at about 1 to 3 M, and at pH 4.5, in the presence of a carbodiimide type agent soluble in water such as 1-ethyl-3-(3-dimethylaminopropyl)carbodiimide at a final concentration of 0.3 M at a temperature of 8° C. overnight.

The derivatized oligonucleotide was then separated from the other agents and products using a standard technique for isolating oligonucleotides.

As discussed above, the mRNAs to be enriched may be treated to eliminate the 3' OH groups which may be present thereon. This may be accomplished by enzymatic ligation of sequences lacking a 3' OH, such as pCp, as described above in Example 1. Alternatively, the 3' OH groups may be eliminated by alkaline hydrolysis as described in Example 8 below.

EXAMPLE 8

Alkaline Hydrolysis of mRNA

The mRNAs may be treated with alkaline hydrolysis as follows. In a total volume of 100 µl of 0.1N sodium hydroxide, 1.5 µg mRNA is incubated for 40 to 60 minutes at 4° C. The solution is neutralized with acetic acid and precipitated with ethanol.

Following the optional elimination of the 3' OH groups, the diol groups at the 5' ends of the mRNAs are oxidized as described below in Example 9.

EXAMPLE 9

Oxidation of Diols

Up to 1 OD unit of RNA was dissolved in 9 µl of buffer (0.1 M sodium acetate, pH 6–7 or water) and 3 µl of freshly prepared 0.1 M sodium periodate solution. The reaction was incubated for 1 h in the dark at 4° C. or room temperature. Following the incubation, the reaction was stopped by adding 4 µl of 10% ethylene glycol. Thereafter the mixture was incubated at room temperature for 15 minutes. After ethanol precipitation, the product was resuspended in 10 µl or more of water or appropriate buffer and dialyzed against water.

Following oxidation of the diol groups at the 5' ends of the mRNAs, the derivatized oligonucleotide was joined to the resulting aldehydes as described in Example 10.

EXAMPLE 10

Reaction of Aldehydes with Derivatized Oligonucleotides

The oxidized mRNA was dissolved in an acidic medium such as 50 µl of sodium acetate pH 4–6. 50 µl of a solution of the derivatized oligonucleotide was added such that an mRNA:derivatized oligonucleotide ratio of 1:20 was obtained and mixture was reduced with a borohydride. The mixture was allowed to incubate for 2 h at 37° C. or overnight (14 h) at 10° C. The mixture was ethanol precipitated, resuspended in 10 µl or more of water or appropriate buffer and dialyzed against distilled water. If desired, the resulting product may be analyzed using acrylamide gel electrophoresis, HPLC analysis, or other conventional techniques.

Following the attachment of the derivatized oligonucleotide to the mRNAs, a reverse transcription reaction may be performed as described in Example 11 below.

EXAMPLE 11

Reverse Transcription of mRNAs

An oligodeoxyribonucleotide was derivatized as follows. 3 OD units of an oligodeoxyribonucleotide of sequence ATCAAGAATTCGCACGAGACCATTA (SEQ ID NO:3) having 5'-OH and 3'-P ends were dissolved in 70 µl of a 1.5 M hydroxybenzotriazole solution, pH 5.3, prepared in dimethylformamide/water (75:25) containing 2 µg of 1-ethyl-3-(3-dimethylaminopropyl)carbodiimide. The mixture was incubated for 2 h 30 min at 22° C. The mixture was then precipitated twice in LiClO$_4$/acetone. The pellet was resuspended in 200 µl of 0.25 M hydrazine and incubated at 8° C. from 3 to 14 h. Following the hydrazine reaction, the mixture was precipitated twice in LiClO$_4$/acetone.

The messenger RNAs to be reverse transcribed were extracted from blocks of placenta having sides of 2 cm which had been stored at −80° C. The mRNA was extracted using conventional acidic phenol techniques. Oligo-dT chromatography was used to purify the mRNAs. The integrity of the mRNAs was checked by Northern-blotting.

The diol groups on 7 µg of the placental mRNAs were oxidized as described above in Example 9. The derivatized oligonucleotide was joined to the mRNAs as described in Example 10 above except that the precipitation step was replaced by an exclusion chromatography step to remove derivatized oligodeoxyribonucleotides which were not joined to mRNAs. Exclusion chromatography was performed as follows:

10 ml of AcA34 (BioSepra#230151) gel were equilibrated in 50 ml of a solution of 10 mM Tris pH 8.0, 300 mM NaCl, 1 mM EDTA, and 0.05% SDS. The mixture was allowed to sediment. The supernatant was eliminated and the gel was resuspended in 50 ml of buffer. This procedure was repeated 2 or 3 times.

A glass bead (diameter 3 mm) was introduced into a 2 ml disposable pipette (length 25 cm). The pipette was filled with the gel suspension until the height of the gel stabilized at 1 cm from the top of the pipette. The column was then equilibrated with 20 ml of equilibration buffer (10 mM Tris HCl pH 7.4, 20 mM NaCl).

10 µl of the mRNA which had been reacted with the derivatized oligonucleotide were mixed in 39 µl of 10 mM urea and 2 µl of blue-glycerol buffer, which had been prepared by dissolving 5 mg of bromophenol blue in 60% glycerol (v/v), and passing the mixture through a filter with a filter of diameter 0.45 µm.

The column was loaded. As soon as the sample had penetrated, equilibration buffer was added. 100 µl fractions were collected. Derivatized oligonucleotide which had not been attached to mRNA appeared in fraction 16 and later fractions. Fractions 3 to 15 were combined and precipitated with ethanol.

The mRNAs which had been reacted with the derivatized oligonucleotide were spotted on a nylon membrane and hybridized to a radioactive probe using conventional techniques. The radioactive probe used in these hybridizations was an oligodeoxyribonucleotide of sequence TAATG-GTCTCGTGCGAATTCTTGAT (SEQ ID NO:4) which was anticomplementary to the derivatized oligonucleotide and was labeled at its 5' end with $^{32}$P. 1/10th of the mRNAs which had been reacted with the derivatized oligonucleotide was spotted in two spots on the membrane and the membrane was visualized by autoradiography after hybridization of the probe. A signal was observed, indicating that the derivatized oligonucleotide had been joined to the mRNA.

The remaining 9/10 of the mRNAs which had been reacted with the derivatized oligonucleotide was reverse transcribed as follows. A reverse transcription reaction was carried out with the reverse transcriptase Superscript II (Gibco-BRL) following the manufacturer's instructions. To prime the reaction, 50 pmol of nonamers with random sequence were used.

A portion of the resulting cDNA was spotted on a positively charged nylon membrane using conventional methods. The cDNAs were spotted on the membrane after the cDNA:RNA heteroduplexes had been subjected to an alkaline hydrolysis in order to eliminate the RNAs. An oligonucleotide having a sequence identical to that of the derivatized oligonucleotide was labeled at its 5' end with $^{32}$P and hybridized to the cDNA blots using conventional techniques. Single-stranded cDNAs resulting from the reverse transcription reaction were spotted on the membrane. As controls, the blot contained 1 pmol, 100 fmol, 50 fmol, 10 fmol and 1 fmol respectively of a control oligodeoxyribonucleotide of sequence identical to that of the derivatized oligonucleotide. The signal observed in the spots containing the cDNA indicated that approximately 15 fmol of the derivatized oligonucleotide had been reverse transcribed.

These results demonstrate that the reverse transcription can be performed through the cap and, in particular, that reverse transcriptase crosses the 5'-P—P—P-5' bond of the cap of eukaryotic messenger RNAs.

The single stranded cDNAs obtained after the above first strand synthesis were used as template for PCR reactions. Two types of reactions were carried out. First, specific amplification of the mRNAs for the alpha globin, dehydrogenase, pp15 and elongation factor E4 were carried out using the following pairs of oligodeoxyribonucleotide primers.

alpha-globin
GLO-S: CCG ACA AGA CCA ACG TCA AGG CCG C (SEQ ID NO:5)
GLO-As: TCA CCA GCA GGC AGT GGC TTA GGA G 3' (SEQ ID NO:6)
dehydrogenase
3 DH-S: AGT GAT TCC TGC TAC TTT GGA TGG C (SEQ ID NO:7)
3 DH-As: GCT TGG TCT TGT TCT GGA GTT TAG A (SEQ ID NO:8)
pp15
PP15-S: TCC AGA ATG GGA GAC AAG CCA ATT T (SEQ ID NO:9)
PP15-As: AGG GAG GAG GAA ACA GCG TGA GTC C (SEQ ID NO:10)
Elongation factor E4
EFA1-S: ATG GGA AAG GAA AAG ACT CAT ATC A (SEQ ID NO:11)
EF1A-As: AGC AGC AAC AAT CAG GAC AGC ACA G (SEQ ID NO:12)

Non specific amplifications were also carried out with the antisense (_As) oligodeoxyribonucleotides of the pairs described above and a primer chosen from the sequence of the derivatized oligodeoxyribonucleotide (ATCAAGAATTCGCACGAGACCATTA) (SEQ ID NO: 13).

A 1.5% agarose gel containing the following samples was stained with ethidium bromide of the PCR products of the reverse transcription (½0th of the products of reverse transcription were used for each PCR reaction).

Sample 1: The products of a PCR reaction using the globin primers of SEQ ID NOs 5 and 6 in the presence of cDNA.

Sample 2: The products of a PCR reaction using the globin primers of SEQ ID NOs 5 and 6 in the the absence of added cDNA.

Sample 3: The products of a PCR reaction using the dehydrogenase primers of SEQ ID NOs 7 and 8 in the presence of cDNA.

Sample 4: The products of a PCR reaction using the dehydrogenase primers of SEQ ID NOs 7 and 8 in the absence of added cDNA.

Sample 5: The products of a PCR reaction using the pp15 primers of SEQ ID NOs 9 and 10 in the presence of cDNA.

Sample 6: The products of a PCR reaction using the pp15 primers of SEQ ID NOs 9 and 10 in the the absence of added cDNA.

Sample 7: The products of a PCR reaction using the EIE4 primers of SEQ ID NOs 11 and 12 in the presence of added cDNA.

Sample 8: The products of a PCR reaction using the EIE4 primers of SEQ ID NOs 11 and 12 in the absence of added cDNA.

In Samples 1, 3, 5 and 7, a band of the size expected for the PCR product was observed, indicating the presence of the corresponding sequence in the cDNA population.

PCR reactions were also carried out with the antisense oligonucleotides of the globin and dehydrogenase primers (SEQ ID NOs 6 and 8) and an oligonucleotide whose sequence corresponds to that of the derivatized oligonucleotide. The presence of PCR products of the expected size in the samples corresponding to samples 1 and 3 above indicated that the derivatized oligonucleotide had been incorporated.

The above examples summarize the chemical procedure for enriching mRNAs for those having intact 5' ends. Further detail regarding the chemical approaches for obtaining mRNAs having intact 5' ends are disclosed in International Application No. WO96/34981, published Nov. 7, 1996, which is incorporated herein by reference.

Strategies based on the above chemical modifications to the 5' cap structure may be utilized to generate cDNAs which have been selected to include the 5' ends of the mRNAs from which they are derived. In one version of such procedures, the 5' ends of the mRNAs are modified as described above. Thereafter, a reverse transcription reaction is conducted to extend a primer complementary to the mRNA to the 5' end of the mRNA. Single stranded RNAs are eliminated to obtain a population of cDNA/mRNA heteroduplexes in which the mRNA includes an intact 5' end. The resulting heteroduplexes may be captured on a solid phase coated with a molecule capable of interacting with the molecule used to derivative the 5' end of the mRNA. Thereafter, the strands of the heteroduplexes are separated to recover single stranded first cDNA strands which include the 5' end of the mRNA. Second strand cDNA synthesis may then proceed using conventional techniques. For example, the procedures disclosed in WO 96/34981 or in Carninci, P. et al. High-Efficiency Full-Length cDNA Cloning by Biotinylated CAP Trapper. Genomics 37:327–336 (1996), the disclosures of which are incorporated herein by reference, may be employed to select cDNAs which include the sequence derived from the 5' end of the coding sequence of the mRNA.

Following ligation of the oligonucleotide tag to the 5' cap of the mRNA, a reverse transcription reaction is conducted to extend a primer complementary to the mRNA to the 5' end of the mRNA. Following elimination of the RNA component of the resulting heteroduplex using standard techniques, second strand cDNA synthesis is conducted with a primer complementary to the oligonucleotide tag.

FIG. 1 summarizes the above procedures for obtaining cDNAs which have been selected to include the 5' ends of the mRNAs from which they are derived.

B. Enzymatic Methods for Obtaining mRNAs having Intact 5' Ends

Other techniques for selecting cDNAs extending to the 5' end of the mRNA from which they are derived are fully enzymatic. Some versions of these techniques are disclosed in Dumas Milne Edwards J. B. (Doctoral Thesis of Paris VI University, Le clonage des ADNc complets: difficultes et perspectives nouvelles. Apports pour l'etude de la regulation de l'expression de la tryptophane hydroxylase de rat, Dec. 20, 1993, EPO 625572 and Kato et al. Construction of a Human Full-Length cDNA Bank. Gene 150:243–250 (1994), the disclosures of which are incorporated herein by reference.

Briefly, in such approaches, isolated mRNA is treated with alkaline phosphatase to remove the phosphate groups present on the 5' ends of uncapped incomplete mRNAs. Following this procedure, the cap present on full length mRNAs is enzymatically removed with a decapping enzyme such as T4 polynucleotide kinase or tobacco acid pyrophosphatase. An oligonucleotide, which may be either a DNA oligonucleotide or a DNA-RNA hybrid oligonucleotide having RNA at its 3' end, is then ligated to the phosphate present at the 5' end of the decapped mRNA using T4 RNA ligase. The oligonucleotide may include a restriction site to facilitate cloning of the cDNAs following their synthesis. Example 12 below describes one enzymatic method based on the doctoral thesis of Dumas.

EXAMPLE 12

Enzymatic Approach for Obtaining 5' ESTs

Twenty micrograms of PolyA+ RNA were dephosphorylated using Calf Intestinal Phosphatase (Biolabs). After a phenol chloroform extraction, the cap structure of mRNA was hydrolysed using the Tobacco Acid Pyrophosphatase (purified as described by Shinshi et al., Biochemistry 15: 2185–2190, 1976 and a hemi 5'DNA/RNA-3' oligonucleotide having an unphosphorylated 5' end, a stretch of adenosine ribophosphate at the 3' end, and an EcoRI site near the 5' end was ligated to the 5'P ends of mRNAs using the T4 RNA ligase (Biolabs). Oligonucleotides suitable for use in this procedure are preferably 30–50 bases in length. Oligonucleotides having an unphosphorylated 5' end may be synthesized by adding a fluorochrome at the 5' end. The inclusion of a stretch of adenosine ribophosphates at the 3' end of the oligonucleotide increases ligation efficiency. It will be appreciated that the oligonucleotide may contain cloning sites other than EcoRI.

Following ligation of the oligonucleotide to the phosphate present at the 5' end of the decapped mRNA, first and second strand cDNA synthesis is carried out using conventional methods or those specified in EPO 625,572 and Kato et al. Construction of a Human Full-Length cDNA Bank. Gene 150:243–250 (1994), and Dumas Milne Edwards, supra, the disclosures of which are incorporated herein by reference. The resulting cDNA may then be ligated into vectors such as those disclosed in Kato et al. Construction of a Human Full-Length cDNA Bank. Gene 150:243–250 (1994) or other nucleic acid vectors known to those skilled in the art using techniques such as those described in Sambrook et al., Molecular Cloning: A Laboratory Manual 2d Ed., Cold Spring Harbor Laboratory Press, 1989, the disclosure of which is incorporated herein by reference.

II. Characterization of 5' ESTs

The above chemical and enzymatic approaches for enriching mRNAs having intact 5' ends were employed to obtain 5' ESTs. First, mRNAs were prepared as described in Example 13 below.

EXAMPLE 13

Preparation of mRNA

Total human RNAs or PolyA+ RNAs derived from 29 different tissues were respectively purchased from LABIMO and CLONTECH and used to generate 44 cDNA libraries as described below. The purchased RNA had been isolated from cells or tissues using acid guanidium thiocyanate-phenol-chloroform extraction (Chomczyniski, P and Sacchi, N., Analytical Biochemistry 162:156–159, 1987). PolyA+ RNA was isolated from total RNA (LABIMO) by two passes of oligodT chromatography, as described by Aviv and Leder (Aviv, H. and Leder, P., Proc. Natl. Acad. Sci. USA 69:1408–1412, 1972) in order to eliminate ribosomal RNA.

The quality and the integrity of the poly A+ were checked. Northern blots hybridized with a globin probe were used to confirm that the mRNAs were not degraded. Contamination of the PolyA+ mRNAs by ribosomal sequences was checked using RNAs blots and a probe derived from the sequence of the 28S RNA. Preparations of mRNAs with less than 5% of ribosomal RNAs were used in library construction. To avoid constructing libraries with RNAs contaminated by exogenous sequences (prokaryotic or fungal), the presence of bacterial 16S ribosomal sequences or of two highly expressed mRNAs was examined using PCR.

Following preparation of the mRNAs, the above described chemical and/or the enzymatic procedures for enriching mRNAs having intact 5' ends discussed above were employed to obtain 5' ESTs from various tissues. In both approaches an oligonucleotide tag was attached to the cap at the 5' ends of the mRNAs. The oligonucleotide tag had an EcoRI site therein to facilitate later cloning procedures.

Following attachment of the oligonucleotide tag to the mRNA by either the chemical or enzymatic methods, the integrity of the mRNA was examined by performing a Northern blot with 200–500 ng of mRNA using a probe complementary to the oligonucleotide tag.

EXAMPLE 14 cDNA Synthesis Using mRNA Templates Having Intact 5' Ends

For the mRNAs joined to oligonucleotide tags using both the chemical and enzymatic methods, first strand cDNA synthesis was performed with Superscript II (Gibco BRL) using random nonamers as primers. In order to protect internal EcoRI sites in the cDNA from digestion at later steps in the procedure, methylated dCTP was used for first strand synthesis. After removal of RNA by an alkaline hydrolysis, the first strand of cDNA was precipitated using isopropanol in order to eliminate residual primers.

For both the chemical and the enzymatic methods, synthesis of the second strand of the cDNA was conducted as follows. After removal of RNA by alkaline hydrolysis, the first strand of cDNA was precipitated using isopropanol in order to eliminate residual primers. The second strand of the cDNA was synthesized with Klenow using a primer corresponding to the 5' end of the ligated oligonucleotide described in Example 12. Preferably, the primer is 20–25 bases in length. Methylated dCTP was also used for second strand synthesis in order to protect internal EcoRI sites in the cDNA from digestion during the cloning process.

Following cDNA synthesis, the cDNAs were cloned into pBlueScript as described in Example 15 below.

EXAMPLE 15

Insertion of cDNAs into BlueScript

Following second strand synthesis, the ends of the cDNA were blunted with T4 DNA polymerase (Biolabs) and the cDNA was digested with EcoRI. Since methylated dCTP was used during cDNA synthesis, the EcoRI site present in the tag was the only site which was hemi-methylated. Consequently, only the EcoRI site in the oligonucleotide tag was susceptible to EcoRI digestion. The cDNA was then size fractionated using exclusion chromatography (AcA, Biosepra). Fractions corresponding to cDNAs of more than 150 bp were pooled and ethanol precipitated. The cDNA was directionally cloned into the SmaI and EcoRI ends of the phagemid pBlueScript vector (Stratagene). The ligation mixture was electroporated into bacteria and propagated under appropriate antibiotic selection.

Clones containing the oligonucleotide tag attached were selected as described in Example 16 below.

EXAMPLE 16

Selection of Clones Having the Oligonucleotide Tag Attached Thereto

The plasmid DNAs containing 5' EST libraries made as described above were purified (Qiagen). A positive selection of the tagged clones was performed using the Gene Trapper kit (Gibco BRL). Briefly, in this selection procedure, the plasmid DNA was converted to single stranded DNA using the geneII product in combination with exonucleaseIII. The resulting single stranded DNA was then hybridized with a biotinylated oligonucleotide having a sequence corresponding to the 3' end of the oligonucleotide described in Example 12. Preferably, the primer has a length of 20–25 bases. Clones including a sequence complementary to the biotinylated oligonucleotide were captured by incubation with streptavidin coated magnetic beads followed by magnetic selection. After capture of the positive clones, the plasmid DNA was released from the magnetic beads and converted into double stranded DNA as recommended by the manufacture. The double stranded DNA was then electroporated into bacteria. The percentage of positive clones having the 5' tag oligonucleotide was estimated using dot blot analysis. Typically the percentage of positive clones was between 90 and 98%.

Following electroporation, the libraries were ordered in 384-microtiter plates (MTP). A copy of the MTP was stored for future needs. Then the libraries were transferred into 96 MTP and sequenced as described below.

EXAMPLE 17

Sequencing of Inserts in Selected Clones

Plasmid inserts were first amplified by PCR on PE 9600 thermocyclers (Perkin-Elmer), using standard SETA-A and SETA-B primers (Genset SA), AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers used were either T7 or 21M13 (available from Genset SA) as appropriate. The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data from the 44 cDNA libraries made as described above were transferred to a proprietary database, where quality control and validation steps were performed. A proprietary base-caller ("Trace"), working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector or ligation oligonucleotides were automatically removed from the EST sequences. However, the resulting EST sequences may contain 1 to 5 bases belonging to the above mentioned sequences at their 5' end. If needed, these can easily be removed on a case by case basis.

Thereafter, the sequences were transferred to the proprietary NETGENE™ Database for further analysis as described below.

Following sequencing as described above, the sequences of the 5' ESTs were entered in a proprietary database called NETGENE™ for storage and manipulation. It will be appreciated by those skilled in the art that the data could be stored and manipulated on any medium which can be read and accessed by a computer. Computer readable media include magnetically readable media, optically readable media, or electronically readable media. For example, the computer readable media may be a hard disc, a floppy disc, a magnetic tape, CD-ROM, RAM, or ROM as well as other types of other media known to those skilled in the art.

In addition, the sequence data may be stored and manipulated in a variety of data processor programs in a variety of formats. For example, the sequence data may be stored as text in a word processing file, such as MicrosoftWORD or WORDPERFECT or as an ASCII file in a variety of database programs familiar to those of skill in the art, such as DB2, SYBASE, or ORACLE.

The computer readable media on which the sequence information is stored may be in a personal computer, a network, a server or other computer systems known to those skilled in the art. The computer or other system preferably includes the storage media described above, and a processor for accessing and manipulating the sequence data. Once the sequence data has been stored it may be manipulated and searched to locate those stored sequences which contain a desired nucleic acid sequence or which encode a protein having a particular functional domain. For example, the stored sequence information may be compared to other known sequences to identify homologies, motifs implicated in biological function, or structural motifs.

Programs which may be used to search or compare the stored sequences include the MacPattern (EMBL), BLAST, and BLAST2 program series (NCBI), basic local alignment search tool programs for nucleotide (BLASTN) and peptide (BLASTX) comparisons (Altschul et al, J. Mol. Biol. 215: 403 (1990)) and FASTA (Pearson and Lipman, Proc. Natl. Acad. Sci. USA, 85: 2444 (1988)). The BLAST programs then extend the alignments on the basis of defined match and mismatch criteria.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Before searching the cDNAs in the NETGENE™ database for sequence motifs of interest, cDNAs derived from mRNAs which were not of interest were identified and eliminated from further consideration as described in Example 18 below.

EXAMPLE 18

Elimination of Undesired Sequences from Further Consideration

5' ESTs in the NETGENE™ database which were derived from undesired sequences such as transfer RNAs, ribosomal RNAs, mitochondrial RNAs, procaryotic RNAs, fungal RNAs, Alu sequences, L1 sequences, or repeat sequences were identified using the FASTA and BLASTN programs with the parameters listed in Table I.

To eliminate 5' ESTs encoding tRNAs from further consideration, the 5' EST sequences were compared to the sequences of 1190 known tRNAs obtained from EMBL release 38, of which 100 were human. The comparison was performed using FASTA on both strands of the 5' ESTs. Sequences having more than 80% homology over more than 60 nucleotides were identified as tRNA. Of the 144,341 sequences screened, 26 were identified as tRNAs and eliminated from further consideration.

To eliminate 5' ESTs encoding rRNAs from further consideration, the 5' EST sequences were compared to the sequences of 2497 known rRNAs obtained from EMBL release 38, of which 73 were human. The comparison was performed using BLASTN on both strands of the 5' ESTs with the parameter S=108. Sequences having more than 80% homology over stretches longer than 40 nucleotides were identified as rRNAs. Of the 144,341 sequences screened, 3,312 were identified as rRNAs and eliminated from further consideration.

To eliminate 5' ESTs encoding mtRNAs from further consideration, the 5' EST sequences were compared to the sequences of the two known mitochondrial genomes for which the entire genomic sequences are available and all sequences transcribed from these mitochondrial genomes including tRNAs, rRNAs, and mRNAs for a total of 38 sequences. The comparison was performed using BLASTN on both strands of the 5' ESTs with the parameter S=108. Sequences having more than 80% homology over stretches longer than 40 nucleotides were identified as mtRNAs. Of the 144,341 sequences screened, 6,110 were identified as mtRNAs and eliminated from further consideration.

Sequences which might have resulted from exogenous contaminants were eliminated from further consideration by comparing the 5' EST sequences to release 46 of the EMBL bacterial and fungal divisions using BLASTN with the parameter S=144. All sequences having more than 90% homology over at least 40 nucleotides were identified as exogenous contaminants. Of the 42 cDNA libraries examined, the average percentages of procaryotic and fungal sequences contained therein were 0.2% and 0.5% respectively. Among these sequences, only one could be identified as a sequence specific to fungi. The others were either fungal or procaryotic sequences having homologies with vertebrate sequences or including repeat sequences which had not been masked during the electronic comparison.

In addition, the 5' ESTs were compared to 6093 Alu sequences and 1115 L1 sequences to mask 5' ESTs containing such repeat sequences from further consideration. 5' ESTs including THE and MER repeats, SSTR sequences or satellite, micro-satellite, or telomeric repeats were also eliminated from further consideration. On average, 11.5% of the sequences in the libraries contained repeat sequences. Of this 11.5%, 7% contained Alu repeats, 3.3% contained L1 repeats and the remaining 1.2% were derived from the other types of repetitive sequences which were screened. These percentages are consistent with those found in cDNA libraries prepared by other groups. For example, the cDNA libraries of Adams et al. contained between 0% and 7.4% Alu repeats depending on the source of the RNA which was used to prepare the cDNA library (Adams et al., *Nature* 377:174, 1996).

The sequences of those 5' ESTs remaining after the elimination of undesirable sequences were compared with the sequences of known human mRNAs to determine the accuracy of the sequencing procedures described above.

EXAMPLE 19

Measurement of Sequencing Accuracy by Comparison to Known Sequences

To further determine the accuracy of the sequencing procedure described above, the sequences of 5' ESTs derived from known sequences were identified and compared to the known sequences. First, a FASTA analysis with overhangs shorter than 5 bp on both ends was conducted on the 5' ESTs to identify those matching an entry in the public human mRNA database. The 6655 5' ESTs which matched a known human mRNA were then realigned with their cognate mRNA and dynamic programming was used to include substitutions, insertions, and deletions in the list of "errors" which would be recognized. Errors occurring in the last 10 bases of the 5' EST sequences were ignored to avoid the inclusion of spurious cloning sites in the analysis of sequencing accuracy.

This analysis revealed that the sequences incorporated in the NETGENE™ database had an accuracy of more than 99.5%.

To determine the efficiency with which the above selection procedures select cDNAs which include the 5' ends of their corresponding mRNAs, the following analysis was performed.

EXAMPLE 20

Determination of Efficiency of 5' EST Selection

To determine the efficiency at which the above selection procedures isolated cDNAs which included sequences close to the 5' end of the mRNAs from which they were derived, the sequences of the ends of the 5' ESTs which were derived from the elongation factor 1 subunit α and ferritin heavy chain genes were compared to the known cDNA sequences for these genes. Since the transcription start sites for the elongation factor 1 subunit α and ferritin heavy chain are well characterized, they may be used to determine the percentage of 5' ESTs derived from these genes which included the authentic transcription start sites.

For both genes, more than 95% of the cDNAs included sequences close to or upstream of the 5' end of the corresponding mRNAs.

To extend the analysis of the reliability of the procedures for isolating 5' ESTs from cDNAs in the NETGENE™ database, a similar analysis was conducted using a database composed of human mRNA sequences extracted from GenBank database release 97 for comparison. For those 5' ESTs derived from mRNAs included in the GeneBank database, more than 85% had their 5' ends close to the 5' ends of the known sequence. As some of the mRNA sequences available in the GenBank database are deduced from genomic sequences, a 5' end matching with these sequences will be counted as an internal match. Thus, the method used here underestimates the yield of cDNAs including the authentic 5' ends of their corresponding mRNAs.

The cDNA libraries made above included multiple 5' ESTs derived from the same mRNA. The sequences of such 5' ESTs were compared to one another and the longest 5' ESTs for each mRNA were identified. Overlapping cDNAs were assembled into continuous sequences (contigs). The resulting continuous sequences were then compared to public databases to gauge their similarity to known sequences, as described in Example 21 below.

EXAMPLE 21

Clustering of the 5' ESTs and Calculation of Novelty Indices for cDNA Libraries

For each sequenced cDNA library, the sequences were clustered by the 5' end. Each sequence in the library was compared to the others with BLASTN2 (direct strand, parameters S=107). ESTs with High Scoring Segment Pairs (HSPs) at least 25 bp long, having 95% identical bases and beginning closer than 10 bp from each EST 5' end were grouped. The longest sequence found in the cluster was used as representative of the cluster. A global clustering between libraries was then performed leading to the definition of super-contigs.

To assess the yield of new sequences within the cDNA libraries, a novelty rate (NR) was defined as: NR=100 X (Number of new unique sequences found in the library/Total number of sequences from the library). Typically, novelty rating range between 10% and 41% depending on the tissue from which the cDNA library was obtained. For most of the libraries, the random sequencing of 5' EST libraries was pursued until the novelty rate reached 20%.

Following characterization as described above, the collection of 5' ESTs in NETGENE™ was screened to identify those 5' ESTs bearing potential signal sequences as described in Example 22 below.

EXAMPLE 22

Identification of Potential Signal Sequences in 5' ESTs

The 5' ESTs in the NETGENE™ database were screened to identify those having an uninterrupted open reading frame (ORF) longer than 45 nucleotides beginning with an ATG codon and extending to the end of the EST. Approximately half of the cDNA sequences in NETGENE™ contained such an ORF. The ORFs of these 5' ESTs were searched to identify potential signal motifs using slight modifications of the procedures disclosed in Von Heijne, G. A New Method for Predicting Signal Sequence Cleavage Sites. Nucleic Acids Res. 14:4683–4690 (1986), the disclosure of which is incorporated herein by reference. Those 5' EST sequences encoding a 15 amino acid long stretch with a score of at least 3.5 in the Von Heijne signal peptide identification matrix were considered to possess a signal sequence. Those 5' ESTs which matched a known human mRNA or EST sequence and had a 5' end more than 20 nucleotides downstream of the known 5' end were excluded from further analysis. The remaining cDNAs having signal sequences therein were included in a database called SIGNALTAG™.

To confirm the accuracy of the above method for identifying signal sequences, the analysis of Example 23 was performed.

EXAMPLE 23

Confirmation of Accuracy of Identification of Potential Signal Sequences in 5' ESTs The accuracy of the above procedure for identifying signal sequences encoding signal peptides was evaluated by applying the method to the 43 amino terminal amino acids of all human SwissProt proteins. The computed Von Heijne score for each protein was compared with the known characterization of the protein as being a secreted protein or a non-secreted protein. In this manner, the number of non-secreted proteins having a score higher than 3.5 (false positives) and the number of secreted proteins having a score lower than 3.5 (false negatives) could be calculated.

Figure 3:
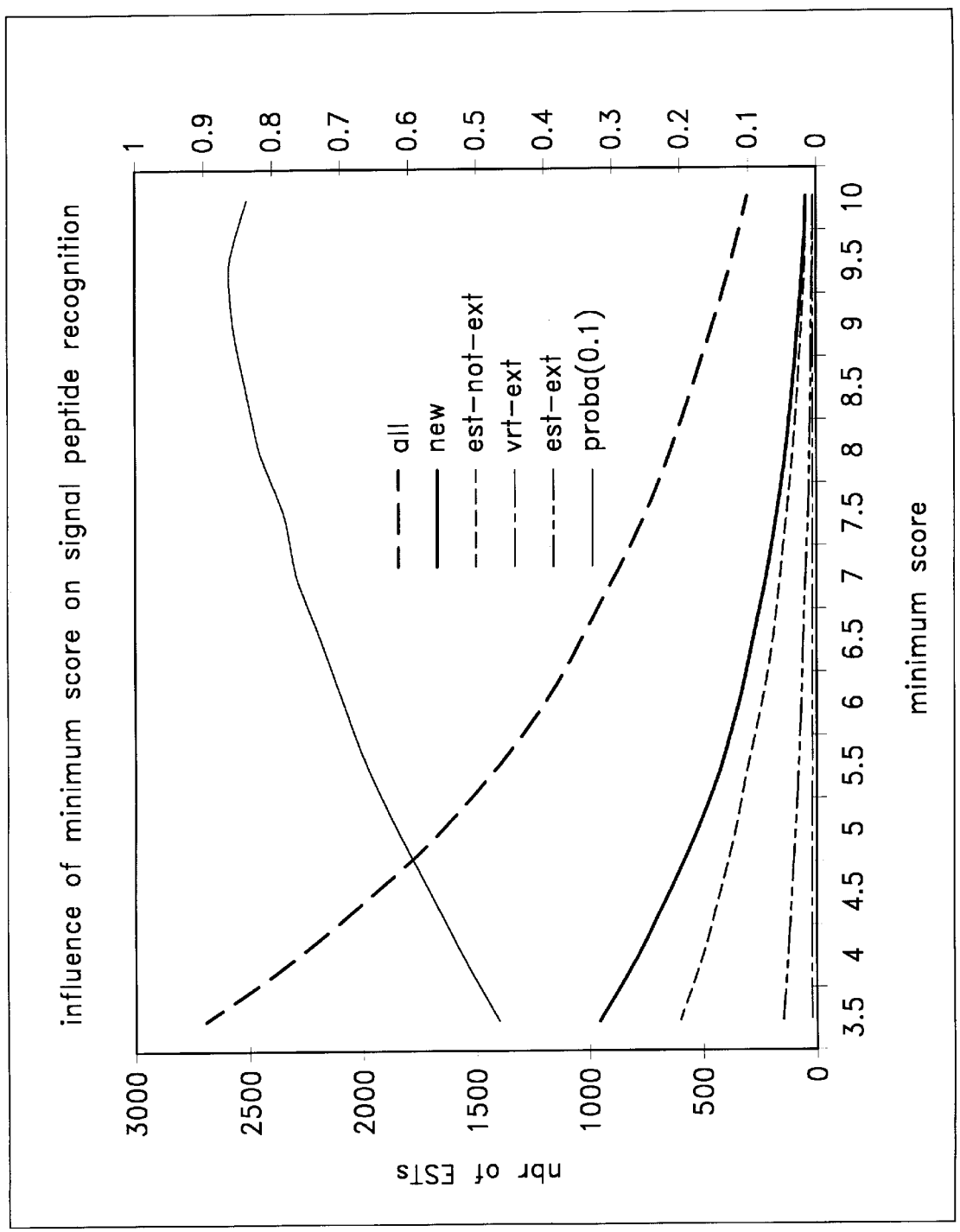
FIG. 3 shows the distribution of von Heijne scores for 5' ESTs in each of the categories described herein and the probability that these 5' ESTs encode a signal peptide.

Using the results of the above analysis, the probability that a peptide encoded by the 5' region of the mRNA is in fact a genuine signal peptide based on its Von Heijne's score was calculated based on either the assumption that 10% of human proteins are secreted or the assumption that 20% of human proteins are secreted. The results of this analysis are shown in FIGS. 2 and 3.

Using the above method of identifying secretory proteins, 5' ESTs for human glucagon, gamma interferon induced monokine precursor, secreted cyclophilin-like protein, human pleiotropin, and human biotinidase precursor all of which are polypeptides which are known to be secreted, were obtained. Thus, the above method successfully identified those 5' ESTs which encode a signal peptide.

To confirm that the signal peptide encoded by the 5' ESTs actually functions as a signal peptide, the signal sequences from the 5' ESTs may be cloned into a vector designed for the identification of signal peptides. Some signal peptide identification vectors are designed to confer the ability to grow in selective medium on host cells which have a signal sequence operably inserted into the vector. For example, to confirm that a 5' EST encodes a genuine signal peptide, the signal sequence of the 5' EST may be inserted upstream and in frame with a non-secreted form of the yeast invertase gene in signal peptide selection vectors such as those described in U.S. Pat. No. 5,536,637, the disclosure of which is incorporated herein by reference. Growth of host cells containing signal sequence selection vectors having the signal sequence from the 5' EST inserted therein confirms that the 5' EST encodes a genuine signal peptide.

Those 5' ESTs which encoded a signal peptide, as determined by the method of Example 22 above, were further grouped into four categories based on their homology to known sequences. The categorization of the 5' ESTs is described in Example 24 below.

EXAMPLE 24

Categorization of 5' ESTs Encoding a Signal Peptide

Those 5' ESTs having a sequence not matching any known vertebrate sequence nor any publicly available EST sequence were designated "new." Of the sequences in the SIGNALTAG™ database, 947 of the 5' ESTs having a Von Heijne's score of at least 3.5 fell into this category.

Those 5' ESTs having a sequence not matching any vertebrate sequence but matching a publicly known EST were designated "EST-ext", provided that the known EST sequence was extended by at least 40 nucleotides in the 5' direction. Of the sequences in the SIGNALTAG™ database, 150 of the 5' ESTs having a Von Heijne's score of at least 3.5 fell into this category.

Those ESTs not matching any vertebrate sequence but matching a publicly known EST without extending the known EST by at least 40 nucleotides in the 5' direction were designated "EST." Of the sequences in the SIGNALTAG™ database, 599 of the 5' ESTs having a Von Heijne's score of at least 3.5 fell into this category.

Those 5' ESTs matching a human mRNA sequence but extending the known sequence by at least 40 nucleotides in the 5' direction were designated "VERT-ext." Of the sequences in the SIGNALTAG™ database, 23 of the 5' ESTs having a Von Heijne's score of at least 3.5 fell into this category. Included in this category was a 5' EST which extended the known sequence of the human translocase mRNA by more than 200 bases in the 5' direction. A 5' EST which extended the sequence of a human tumor suppressor gene in the 5' direction was also identified.

FIG. 4 shows the distribution of 5' ESTs in each category and the number of 5' ESTs in each category having a given minimum von Heijne's score.

Each of the 5' ESTs was categorized based on the tissue from which its corresponding mRNA was obtained, as described below in Example 25.

EXAMPLE 25

Categorization of Expression Patterns

FIG. 5 shows the tissues from which the mRNAs corresponding to the 5' ESTs in each of the above described categories were obtained.

Table II provides the sequence identification numbers of 5' EST sequences derived from brain, the categories in which these sequences fall, and the von Heijne's score of the signal peptides which they encode. The 5' EST sequences and the amino acid sequences they encode are provided in the appended sequence listings. Table III provides the sequence ID numbers of the 5' ESTs and the sequences of the signal peptides which they encode. The sequences of the 5' ESTs and the polypeptides they encode are provided in the sequence listing appended hereto.

The sequences of DNA SEQ ID NOs: 38–270 can readily be screened for any errors therein and any sequence ambiguities can be resolved by resequencing a fragment containing such errors or amibiguities on both strands. Such fragments may be obtained from the plasmids stored in the inventors' laboratory or can be isolated using the techniques described herein. Resolution of any such ambiguities or errors may be facilitated by using primers which hybridize to sequences located close to the ambiguous or erroneous sequences. For example, the primers may hybridize to sequences within 50–75 bases of the amibiguity or error. Upon resolution of an error or ambiguity, the corresponding corrections can be made in the protein sequences encoded by the DNA containing the error or amibiguity.

In addition to categorizing the 5' ESTs by the tissue from which the cDNA library in which they were first identified was obtained, the spatial and temporal expression patterns of the mRNAs corresponding to the 5' ESTs, as well as their expression levels, may be determined as described in Example 26 below. Characterization of the spatial and temporal expression patterns and expression levels of these mRNAs is useful for constructing expression vectors capable of producing a desired level of gene product in a desired spatial or temporal manner, as will be discussed in more detail below.

In addition, 5' ESTs whose corresponding mRNAs are associated with disease states may also be identified. For example, a particular disease may result from lack of expression, over expression, or under expression of an mRNA corresponding to a 5' EST. By comparing mRNA expression patterns and quantities in samples taken from healthy individuals with those from individuals suffering from a particular disease, 5' ESTs responsible for the disease may be identified.

EXAMPLE 26

Evaluation of Expression Levels and Patterns of mRNAs Corresponding to 5' ESTs

Expression levels and patterns of mRNAs corresponding to 5' ESTs may be analyzed by solution hybridization with long probes as described in International Patent Application No. WO 97/05277, the entire contents of which are hereby incorporated by reference. Briefly, a 5' EST corresponding to a portion of a gene is inserted at a cloning site immediately downstream of a bacteriophage (T3, T7 or SP6) RNA polymerase promoter to produce antisense RNA. Preferably, the 5' EST has 100 or more nucleotides. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

The 5' ESTs may also be tagged with nucleotide sequences for the serial analysis of gene expression (SAGE) as disclosed in UK Patent Application No. 2 305 241 A, the entire contents of which are incorporated by reference. In this method, cDNAs are prepared from a cell, tissue, organism or other source of nucleic acid for which it is desired to determine gene expression patterns. The resulting cDNAs are separated into two pools. The cDNAs in each pool are cleaved with a first restriction endonuclease, called an "anchoring enzyme," having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer and an internal restriction site for a "tagging endonuclease" is ligated to the digested cDNAs in the first pool. Digestion with the second endonuclease produces short "tag" fragments from the cDNAs.

A second oligonucleotide having a second sequence for hybridization of an amplification primer and an internal restriction site is ligated to the digested cDNAs in the second pool. The cDNA fragments in the second pool are also digested with the "tagging endonuclease" to generate short "tag" fragments derived from the cDNAs in the second pool. The "tags" resulting from digestion of the first and second pools with the anchoring enzyme and the tagging endonuclease are ligated to one another to produce "ditags." In some embodiments, the ditags are concatamerized to produce ligation products containing from 2 to 200 ditags. The tag sequences are then determined and compared to the sequences of the 5' ESTs to determine which 5' ESTs are expressed in the cell, tissue, organism, or other source of nucleic acids from which the tags were derived. In this way, the expression pattern of the 5' ESTs in the cell, tissue, organism, or other source of nucleic acids is obtained.

Quantitative analysis of gene expression may also be performed using arrays. As used herein, the term array means a one dimensional, two dimensional, or multidimensional arrangement of full length cDNAs, 5' ESTs or fragments thereof of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full length cDNAs, 5' ESTs, or fragments thereof in a complementary DNA microarray as described by Schena et al. (*Science* 270:467–470, 1995; *Proc. Natl. Acad Sci. U.S.A* 93:10614–10619, 1996). cDNAs, 5' ESTs or fragments thereof are amplified by PCR and arrayed from 96-well microtiter plates onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 $cm^2$ microarrays under a 14×14 mm glass coverslip for 6–12 hours at 60° C. Arrays are washed for 5 min at 25° C. in low stringency wash buffer (1× SSC/0.2% SDS), then for 10 min at room temperature in high stringency wash buffer (0.1× SSC/0.2% SDS). Arrays are scanned in 0.1× SSC using a fluorescence laser scanning device fitted with a custom filter set. Accurate differential expression measurements are obtained by taking the average of the ratios of two independent hybridizations.

Quantitative analysis of the expression of genes may also be performed with full length cDNAs, 5' ESTs, or fragments thereof in complementary DNA arrays as described by Pietu et al. (Genome Research 6:492–503, 1996). The cDNAs, 5' ESTs or fragments thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of the 5' ESTs can be done through high density nucleotide arrays as described by Lockhart et al. (Nature Biotechnology 14: 1675–1680, 1996) and Sosnowsky et al. (Proc. Natl. Acad. Sci. 94:1119–1123, 1997). Oligonucleotides of 15–50 nucleotides corresponding to sequences of the 5' ESTs are synthesized directly on the chip (Lockhart et al., supra) or synthesized and then addressed to the chip (Sosnowski et al., supra). Preferably, the oligonucleotides are about 20 nucleotides in length.

cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Natl. Acad. Sci. 94:1119–1123), the dyes or labeling compounds are detected and quantified. Duplicate hybridizations are performed. Comparative analysis of the intensity of the signal originating from cDNA probes on the same target oligonucleotide in different cDNA samples indicates a differential expression of the mRNA corresponding to the 5' EST from which the oligonucleotide sequence has been designed.

III. Use of 5' ESTs to Clone cDNAs Containing the Authentic 5' End of the Corresponding mRNA As Well As the Entire Protein Coding Sequence of the Corresponding mRNA and to Clone the Corresponding Genomic DNAs Once 5' ESTs which include the 5' end of the corresponding mRNAs have been selected using the procedures described above, they can be utilized to isolate cDNAs which include the entire coding sequence of the protein encoded by the corresponding mRNA, including the authentic translation start site, hereinafter referred to as "full length cDNAs". Example 27 below describes a general method for obtaining such cDNAs. Example 28 below describes the cloning and sequencing of a cDNA which includes the entire coding sequence and authentic 5' end of the corresponding mRNA for several secreted proteins.

The methods of Examples 27, 28, and 29 can also be used to obtain cDNAs which encode less than the entire coding sequence of the proteins encoded by the 5' ESTs. The cDNAs isolated using these methods encode at least 10 amino acids of the proteins encoded by the sequences of SEQ ID NOs: 38–270. Preferably, the cDNAs encode at least 20 amino acids of the proteins encoded by the sequences of SEQ ID NOs: 38–270. More preferably, the cDNAs encode at least 30 amino amino acids of the sequences of SEQ ID NOs: 38–270. In a preferred embodiment, the cDNAs encode a full length protein sequence, which includes the protein coding sequences of SEQ ID NOs: 38–270.

EXAMPLE 27

General Method for Using 5' ESTs to Clone and Sequence cDNAs Which Include the Entire Coding Region and the Authentic 5' End of the Corresponding mRNA The following general method has been used to quickly and efficiently isolate cDNAs having the authentic 5' ends of their corresponding mRNAs as well as the full protein coding sequence. This method may be applied to obtain such cDNAs for any 5' EST in the NETGENE™ database, including those 5' ESTs encoding secreted proteins.

The method takes advantage of the known 5' sequence of the mRNA. An RTPCR reaction is conducted on purified mRNA using a poly 14dT primer containing a 49 nucleotide sequence at its 5' end which permits the addition of a known sequence at the end of the cDNA which corresponds to the 3' end of the mRNA. For example, the primer may have the following sequence: 5'-ATC GTT GAG ACT CGT ACC AGC AGA GTC ACG AGA GAG ACT ACA CGG TAC TGG TTT TTT TTT TTT TTVN-3' (SEQ ID NO:14). Those skilled in the art will appreciate that other sequences may also be added to the poly dT sequence and used to prime the first strand synthesis. Using this primer and an enzyme having reverse transcriptase activity, such as SuperScriptII (Gibco BRL), a reverse transcript which is anchored at the 3' polyA site of the RNAs is generated.

After removal of the mRNA hybridized to the first cDNA strand by alkaline hydrolysis, the products of the alkaline hydrolysis and the residual poly dT primer are eliminated with an exclusion column such as an Aca34 (Biosepra) matrix, a mix of agarose and acrylamide.

A pair of nested primers on each end is designed based on the known 5' sequence from the 5' EST and the known 3' end resulting from the primer used in the first strand synthesis. Preferably, the nested primers at the 5' end are separated from one another by four to nine bases. The 5' primer sequences may be selected to have melting temperatures and specificities suitable for use in PCR using formulas or software well known to those skilled in the art. If it is desired to obtain cDNAs containing the full length protein coding sequence, including the authentic translation initiation site, primers comprising sequences upstream of the translation initiation site are used. Alternatively, the PCR product is sequenced, the coding region is determined, and RTPCR is performed on an appropriate mRNA using primers at each end of the coding region.

Preferably, the nested primers at the 3' end are separated from one another by four to nine bases. For example, the nested 3' primers may have the following sequences: (5'-CCA GCA GAG TCA CGA GAG AGA CTA CAC GG-3' (SEQ ID NO:15), and 5'-CAC GAG AGA GAC TAC ACG GTA CTG G-3' (SEQ ID NO:16). These primers were selected because they have melting temperatures and specificities compatible with their use in PCR. However, those skilled in the art will appreciate that other sequences may also be used as primers.

The first PCR run of 25 cycles is performed using the Clontech Tth Polymerase Mix and the outer primer from each of the nested pairs. ½500 of the resulting PCR product is then used in a 20 cycle PCR using the same enzyme and the inner primer from each of the nested pairs. Thereafter, the primers and nucleotides are removed, and the final product is sequenced with a Die Terminator approach using the AmpliTaqFS kit available from Perkin Elmer. In addition, the double stranded cDNA produced by the above reactions is cloned into a vector capable of replicating in an appropriate host cell if it contains the full length protein coding sequence. If not, a cDNA product containing the full length protein coding sequence is obtained as described above and cloned into an appropriate vector.

In order to sequence long fragments primer walking is performed using automated computer software such as ASMG (Sutton, G. G. et al. TIGR Assembler: A New Tool for Assembling Large Shotgun Sequencing Projects. genome Science and Technology 1: 9–19 (1995)) to construct contigs and software such as OSP (Illier, L and Green, P. OSP: A Computer Program for Choosing PCR and DNA sequencing Primers. PCR Methods Appl. 1(2): 124–128 (1991) to choose primers.

cDNAs which include the entire coding sequence of secreted proteins may be obtained as described in Example 28 below.

Once a cDNA has been obtained, it can be sequenced to determine the amino acid sequence it encodes. Once the encoded amino acid sequence has been determined, one can create and identify any of the many conceivable cDNAs that will encode that protein by simply using the known genetic code.

In a preferred embodiment, the coding sequence may be selected using the known codon or codon pair preferences for the host organism in which the cDNA is to be expressed.

EXAMPLE 28

Cloning and Sequencing of a Full Length cDNA Encoding a Secreted Protein

The procedure described in Example 27 above was used to obtain full length cDNAs. Using this approach, the full length cDNA of SEQ ID NO:17 (internal identification number 48-19-3-G1-FL1) was obtained. This cDNA falls into the "EST-ext" category described above and encodes the signal peptide MKKVLLLITAILAVAVG (SEQ ID NO: 18) having a von Heijne score of 8.2.

The full length cDNA of SEQ ID NO:19 (internal identification number 58-34-2-E7-FL2) was also obtained using this procedure. This cDNA falls into the "EST-ext" category described above and encodes the signal peptide MWW-FQQGLSFLPSALVIWTSA (SEQ ID NO:20) having a von Heijne score of 5.5.

Another full length cDNA obtained using the procedure described above has the sequence of SEQ ID NO:21 (internal identification number 51-27-E8-FL1). This cDNA, falls into the "EST-ext" category described above and encodes the signal peptide MVLTTLPSANSANSPVNMPT-TGPNSLSYASSALSPCLT (SEQ ID NO:22) having a von Heijne score of 5.9.

The above procedure was also used to obtain a full length cDNA having the sequence of SEQ ID NO:23 (internal identification number 76-4-1-G5-FL1). This cDNA falls into the "EST-ext" category described above and encodes the signal peptide ILSTVTALTFAXA (SEQ ID NO:24) having a von Heijne score of 5.5.

The full length cDNA of SEQ ID NO:25 (internal identification number 51-3-3-B10-FL3) was also obtained using this procedure. This cDNA falls into the "new" category described above and encodes a signal peptide LVLTLCTL-PLAVA (SEQ ID NO:26) having a von Heijne score of 10.1.

The full length cDNA of SEQ ID NO:27 (internal identification number 58-35-2-F10-FL2) was also obtained using this procedure. This cDNA falls into the "new" category described above and encodes a signal peptide LWLLF-FLVTAIHA (SEQ ID NO:28) having a von Heijne score of 10.7.

Bacterial clones containing plasmids containing the full length cDNAs described above are presently stored in the inventor's laboratories under the internal identification numbers provided above. The inserts may be recovered from the deposited materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the EST insertion. The PCR product which corresponds to the 5' EST can then be manipulated using standard cloning techniques familiar to those skilled in the art.

In addition to PCR based methods for obtaining cDNAs which include the authentic 5' end of the corresponding mRNA as well as the full protein coding sequence of the corresponding mRNA, traditional hybridization based methods may also be employed. These methods may also be used to obtain the genomic DNAs which encode the mRNAs from which the 5' ESTs were derived. Example 29 below provides an example of such methods.

EXAMPLE 29

Methods for Obtaining cDNAs Which Include the Entire Coding Region and the Authentic 5' End of the Corresponding mRNA A cDNA library or genomic DNA is obtained from a commercial source or made using techniques familiar to those skilled in the art. The library includes cDNAs which are derived from the mRNA corresponding to a 5' EST. The cDNA library or genomic DNA library is hybridized to a detectable probe comprising at least 10 consecutive nucleotides from the 5' EST using conventional techniques. Preferably, the probe comprises at least 12, 15, or 17 consecutive nucleotides from the 5' EST. More preferably, the probe comprises at least 20–30 consecutive nucleotides from the 5' EST. In some embodiments, the probe comprises more than 30 nucleotides from the 5' EST. Techniques for identifying cDNA clones in a cDNA library which hybridize to a given probe sequence are disclosed in Sambrook et al., Molecular Cloning: A Laboratory Manual 2d Ed., Cold Spring Harbor Laboratory Press, 1989, the disclosure of which is incorporated herein by reference. The same techniques may be used to isolate genomic DNAs.

Briefly, cDNA or genomic DNA clones which hybridize to the detectable probe are identified and isolated for further manipulation as follows. A probe comprising at least 10 consecutive nucleotides from the 5' EST is labeled with a detectable label such as a radioisotope or a fluorescent molecule. Preferably, the probe comprises at least 12, 15, or 17 consecutive nucleotides from the 5' EST. More preferably, the probe comprises 20–30 consecutive nucleotides from the 5' EST. In some embodiments, the probe comprises more than 30 nucleotides from the 5' EST.

Techniques for labeling the probe are well known and include phosphorylation with polynucleotide kinase, nick translation, and in vitro transcription. The cDNAs or genomic DNAs in the library are transferred to a nitrocellulose or nylon filter and denatured. After incubation of the filter with a blocking solution, the filter is contacted with the labeled probe and incubated for a sufficient amount of time for the probe to hybridize to cDNAs or genomic DNAs containing a sequence capable of hybridizing to the probe.

By varying the stringency of the hybridization conditions used to identify cDNAs or genomic DNAs which hybridize to the detectable probe, cDNAS having different levels of homology to the probe can be identified and isolated. To identify cDNAs or genomic DNAs having a high degree of homology to the probe sequence, the melting temperature of the probe may be calculated using the following formulas:

For probes between 14 and 70 nucleotides in length the melting temperature (Tm) is calculated using the formula: Tm=81.5+16.6(log [Na+])+0.41(fraction G+C)−(600/N) where N is the length of the probe.

If the hybridization is carried out in a solution containing formamide, the melting temperature may be calculated using the equation Tm=81.5+16.6(log [Na+])+0.41(fraction G+C)−(0.63% formamide)−(600/N) where N is the length of the probe.

Prehybridization may be carried out in 6× SSC, 5× Denhardt's reagent, 0.5% SDS, 100 μg denatured fragmented salmon sperm DNA or 6× SSC, 5× Denhardt's reagent, 0.5% SDS, 100 μg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprised double stranded DNA, it is denatured before addition to the hybridization solution. The filter is contacted with the hybridization solution for a sufficient period of time to allow the probe to hybridize to cDNAs or genomic DNAs containing sequences complementary thereto. For probes over 200 nucleotides in length, the hybridization may be carried out at 15–25° C. below the Tm. For shorter probes, such as oligonucleotide probes, the hybridization may be conducted at 15–25° C. below the Tm. Preferably, for hybridizations in 6× SSC, the hybridization is conducted at approximately 68° C. Preferably, for hybridizations in 50% formamide containing solutions, the hybridization is conducted at approximately 42° C.

All of the foregoing hybridizations would be considerted to be under "stringent" conditions.

Following hybridization, the filter is washed in 2× SSC, 0.1% SDS at room temperature for 15 minutes. The filter is then washed with 0.1× SSC, 0.5% SDS at room temperature for 30 minutes to 1 hour. Thereafter, the solution is washed at the hybridization temperature in 0.1× SSC, 0.5% SDS. A final wash is conducted in 0.1×SSC at room temperature.

cDNAs or genomic DNAs which have hybridized to the probe are identified by autoradiography.

The above procedure may be modified to identify cDNAs or genomic DNAs having decreasing levels of homology to the probe sequence. For example, to obtain cDNAs or genomic DNAs of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2× SSC, 0.5% SDS at the temperature of hybridization. These conditions are considered to be "moderate" conditions above 50° C. and "low" conditions below 50° C.

Alternatively, the hybridization may be carried out in buffers, such as 6× SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6× SSC, 0.5% SDS at 50° C. These conditions are considered to be "moderate" conditions above 25% formamide and "low" conditions below 25% formamide.

cDNAs or genomic DNAs which have hybridized to the probe are identified by autoradiography.

Alternatively, cDNAs may be prepared by obtaining mRNA from the tissue, cell, or organism of interest using mRNA preparation procedures utilizing poly A selection procedures or other techniques known to those skilled in the art. A first primer capable of hybridizing to the poly A tail of the mRNA is hybridized to the mRNA and a reverse transcription reaction is performed to generate a first cDNA strand.

The first cDNA strand is hybridized to a second primer containing at least 10 consecutive nucleotides of the sequences of SEQ ID NOs 38–270. Preferably, the primer comprises at least 12, 15, or 17 consecutive nucleotides from the sequences of SEQ ID NOs 38–270. More preferably, the primer comprises 20–30 consecutive nucleotides from the sequences of to SEQ ID NOs 38–270. In some embodiments, the primer comprises more than 30 nucleotides from the sequences of SEQ ID NOs 38–270. If it is desired to obtain cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RTPCR may be performed as described above using primers from both ends of the cDNA to be obtained.

cDNAs containing 5' fragments of the mRNA may be prepared by contacting an mRNA comprising the sequences of SEQ ID NOs: 38–270 with a primer comprising at least 10 consecutive nucleotides of the sequences complementary to SEQ ID NOs: 38–270, hybridizing the primer to the mRNAs, and reverse transcribing the hybridized primer to make a first cDNA strand from the mRNAs. Preferably, the primer comprises at least 12, 15, or 17 consecutive nucleotides from the 5' EST. More preferably, the primer comprises 20–30 consecutive nucleotides from the 5' EST.

Thereafter, a second cDNA strand complementary to the first cDNA strand is synthesized. The second cDNA strand may be made by hybridizing a primer complementary to sequences in the first cDNA strand to the first cDNA strand and extending the primer to generate the second cDNA strand.

The resulting double stranded cDNA strand is isolated and cloned. The cDNA may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in Current Protocols in Molecular Biology, John Wiley 503 Sons, Inc. 1997 and Sambrook et al. Molecular Cloning: A Laboratory Manual, Second Edition, Cold Spring Harbor Laboratory Press, 1989, the entire disclosures of which are incorporated herein by reference.

Alternatively, kits for obtaining full length cDNAs, such as the GeneTrapper (Cat. No. 10356-020, Gibco, BRL), may be used for obtaining full length cDNAs. In this approach, cDNA inserts are cloned into double stranded phagemids. The cDNA library in the double stranded phagemids is then rendered single stranded by treatment with an endonuclease, such as the Gene II product of the phage F1, and Exonulease III as described in the manual accompanying the GeneTrapper kit, which is incorporated herein by reference. A biotinylated oligonucleotide comprising the sequence of a 5' EST, or a fragment containing at least 10 nucleotides thereof, is hybridized to the single stranded phagemids. Preferably, the fragment comprises at least 12, 15, or 17 consecutive nucleotides from the 5' EST. More preferably, the fragment comprises 20–30 consecutive nucleotides from the 5' EST. In some procedures, the fragment may comprise more than 30 consecutive nucleotides from the 5' EST.

Hybrids between the biotinylated oligonucleotide and phagemids having inserts containing the 5' EST sequence are isolated by incubating the hybrids with streptavidin coated paramagnetic beads and retrieving the beads with a magnet. Therafter, the resulting phagemids containing the 5' EST sequence are released from the beads and converted into doublestranded DNA using a primer specific for the 5' EST sequence. The resulting double stranded DNA is transformed into bacteria. cDNAs containing the 5' EST sequence are identified by colony PCR or colony hybridization.

A plurality of cDNAs containing full length protein coding sequences may be provided as cDNA libraries for subsequent evaluation of the encoded proteins or use in diagnostic assays as described below.

IV. Expression of Proteins Encoded by cDNAs Isolated Using 5' ESTs cDNAs containing the full protein coding sequences of their corresponding mRNAs may be used to express the secreted proteins which they encode as described in Example 30 below. If desired, the cDNAs may contain the sequences encoding the signal peptide to facilitate secretion of the expressed protein. It will be appreciated that a plurality of cDNAs containing the full protein coding sequences may be simultaneously cloned into expression vectors to create an expression library for analysis of the encoded proteins as described below.

EXAMPLE 30

Expression of the Proteins Encoded by the Genes Corresponding to the 5' ESTs To express the proteins encoded by the genes corresponding to 5' ESTs, cDNAs containing the entire protein coding region are obtained as described in Examples 27–29. If desired, the cDNAs may contain the sequences encoding the signal peptide to facilitate secretion of the expressed protein. The cDNAs may also contain sequences upstream of the sequences encoding the signal peptide, such as sequences which regulate expression levels or sequences which confer tissue specific expression. The cDNA is operably linked to a promoter in an expression vector using conventional cloning technology. The expression vector may be any of the mammalian, yeast, insect or bacterial expression systems known in the art. Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767, incorporated herein by this reference.

The following is provided as one exemplary method to express the proteins encoded by the cDNAs corresponding to the 5' ESTs. First, the methionine initiation codon for the gene and the poly A sequence of the gene are identified. If the cDNA lacks a poly A sequence, this sequence can be added to the construct by, for example, splicing out the Poly A sequence from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The cDNA is obtained by PCR from the bacterial vector using oligonucleotide primers complementary to the cDNA and containing restriction endonuclease sequences for Pst I incorporated into the 5' primer and BglII at the 5' end of the corresponding cDNA 3' primer, taking care to ensure that the cDNA is positioned in frame with the poly A sequence. The purified fragment obtained from the resulting PCR reaction is digested with PstI, blunt ended with an exonuclease, digested with Bgl II, purified and ligated to pXT1, now containing a poly A sequence and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Proteins in the culture medium are separated by gel electrophoresis. If desired, the proteins may be ammonium sulfate precipitated or separated based on size or charge prior to electrophoresis.

As a control, the expression vector lacking a cDNA insert is introduced into host cells or organisms and the proteins in the medium are harvested. The secreted proteins present in the medium are detected using techniques such as Coomassie or silver staining or using antibodies against the protein encoded by the cDNA. Coomassie and silver staining techniques are familiar to those skilled in the art.

Antibodies capable of specifically recognizing the protein of interest may be generated using synthetic 15-mer peptides having a sequence encoded by the appropriate 5' EST. The synthetic peptides are injected into mice to generate antibody to the polypeptide encoded by the cDNA.

Secreted proteins from the host cells or organisms containing an expression vector which contains the cDNA derived from a 5' EST are compared to those from the control cells or organism. The presence of a band in the medium from the cells containing the expression vector which is absent in the medium from the medium from the control cells indicates that the cDNA encodes a secreted protein. Generally, the band corresponding to the protein encoded by the cDNA will have a mobility near that expected based on the number of amino acids in the open reading frame of the cDNA. However, the band may have a mobility different than that expected as a result of modifications such as glycosylation, ubiquitination, or enzymatic cleavage.

The protein encoded by the cDNA may be purified using standard immunochromatography techniques. In such procedures, a solution containing the secreted protein, such as the culture medium or a cell extract, is applied to a column having antibodies against the secreted protein attached to the chromatography matrix. The secreted protein is allowed to bind the immunochromatography column. Thereafter, the column is washed to remove non-specifically bound proteins. The specifically bound secreted protein is then released from the column and recovered using standard techniques.

If antibody production is not possible, the cDNA sequence may be incorporated into expression vectors designed for use in purification schemes employing chimeric polypeptides. In such strategies the coding sequence of the cDNA is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites may be engineered between the β-globin gene or the nickel binding polypeptide and the cDNA. Thus, the two polypeptides of the chimera may be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

Following expression and purification of the secreted proteins encoded by the 5' ESTs, the purified proteins may be tested for the ability to bind to the surface of various cell types as described in Example 31 below. It will be appreciated that a plurality of proteins expressed from these cDNAs may be included in a panel of proteins to be simultaneously evaluated for the activities specifically described below, as well as other biological roles for which assays for determining activity are available.

EXAMPLE 31

Analysis of Secreted Proteins to Determine Whether They Bind to the Cell Surface The proteins encoded by the 5' ESTs are cloned into expression vectors such as those described in Example 30. The proteins are purified by size, charge, immunochromatography or other techniques familiar to those skilled in the art. Following purification, the proteins are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected by autoradiography. Alternatively, unlabeled proteins may be incubated with the cells and detected with antibodies having a detectable label, such as a fluorescent molecule, attached thereto.

Specificity of cell surface binding may be analyzed by conducting a competition analysis in which various amounts of unlabeled protein are incubated along with the labeled protein. The amount of labeled protein bound to the cell surface decreases as the amount of competitive unlabeled protein increases. As a control, various amounts of an unlabeled protein unrelated to the labeled protein is included in some binding reactions. The amount of labeled protein bound to the cell surface does not decrease in binding reactions containing increasing amounts of unrelated unlabeled protein, indicating that the protein encoded by the cDNA binds specifically to the cell surface.

As discussed above, secreted proteins have been shown to have a number of important physiological effects and, consequently, represent a valuable therapeutic resource. The secreted proteins encoded by the cDNAs made according to Examples 27–29 may be evaluated to determine their physiological activities as described below.

EXAMPLE 32

Assaying the Proteins Expressed from cDNAs for Cytokine, Cell Proliferation or Cell Differentiation Activity As discussed above, secreted proteins may act as cytokines or may affect cellular proliferation or differentiation. The proteins encoded by the above cDNAs may be evaluated for their ability to regulate T cell or thymocyte proliferation in assays such as those described in the following references, which are incorporated herein by reference: Current Protocols in Immunology, Ed. by J. E. Coligan et al., Greene Publishing Associates and Wiley-Interscience; Takai et al. J. Immunol. 137:3494–3500, 1986. Bertagnolli et al. J. Immunol. 145:1706–1712, 1990. Bertagnolli et al., Cellular Immunology 133:327–341, 1991. Bertagnolli, et al. J. Immunol. 149:3778–3783, 1992; Bowman et al., J. Immunol. 152:1756–1761, 1994.

In addition, numerous assays for cytokine production and/or the proliferation of spleen cells, lymph node cells and thymocytes are known. These include the techniques disclosed in Current Protocols in Immunology. J. E. Coligan et al. Eds., Vol 1 pp. 3.12.1–3.12.14 John Wiley and Sons, Toronto. 1994; and Schreiber, R. D. In Current Protocols in Immunology., supra Vol 1 pp. 6.8.1–6.8.8, John Wiley and Sons, Toronto. 1994.

The proteins encoded by the cDNAs may also be assayed for the ability to regulate the proliferation and differentiation of hematopoietic or lymphopoietic cells. Many assays for such activity are familiar to those skilled in the art, including the assays in the following references, which are incorporated herein by reference: Bottomly, K., Davis, L. S. and Lipsky, P. E., Measurement of Human and Murine Interleukin 2 and Interleukin 4, In Current Protocols in Immunology., J. E. Coligan et al. Eds. Vol 1 pp. 6.3.1–6.3.12, John Wiley and Sons, Toronto. 1991; deVries et al., J. Exp. Med. 173:1205–1211, 1991; Moreau et al., Nature 36:690–692, 1988; Greenberger et al., Proc. Natl. Acad. Sci. U.S.A. 80:2931–2938, 1983; Nordan, R., Measurement of Mouse and Human Interleukin 6 In Current Protocols in Immunology. J. E. Coligan et al. Eds. Vol 1 pp. 6.6.1–6.6.5, John Wiley and Sons, Toronto. 1991; Smith et al., Proc. Natl. Acad. Sci. U.S.A. 83:1857–1861, 1986; Bennett, F., Giannotti, J., Clark, S. C. and Turner, K. J., Measurement of Human Interleukin 11 in Current Protocols in Immunology. J. E. Coligan et al. Eds. Vol 1 pp. 6.15.1 John Wiley and Sons, Toronto. 1991; Ciarletta, A., Giannotti, J., Clark, S. C. and Turner, K. J., Measurement of Mouse and Human Interleukin 9 In Current Protocols in Immunology. J. E. Coligan et al., Eds. Vol 1 pp. 6.13.1, John Wiley and Sons, Toronto. 1991.

The proteins encoded by the cDNAs may also be assayed for their ability to regulate T-cell responses to antigens. Many assays for such activity are familiar to those skilled in the art, including the assays described in the following references, which are incorporated herein by reference: Chapter 3 (In Vitro Assays for Mouse Lymphocyte Function), Chapter 6 (Cytokines and Their Cellular Receptors) and Chapter 7, (Immunologic Studies in Humans) in Current Protocols in Immunology, J. E. Coligan et al. Eds. Greene Publishing Associates and Wiley-Interscience; Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Those proteins which exhibit cytokine, cell proliferation, or cell differentiation activity may then be formulated as pharmaceuticals and used to treat clinical conditions in which induction of cell proliferation or differentiation is beneficial. Alternatively, as described in more detail below, genes encoding these proteins or nucleic acids regulating the expression of these proteins may be introduced into appropriate host cells to increase or decrease the expression of the proteins as desired.

EXAMPLE 33

Assaying the Proteins Expressed from cDNAs for Activity as Immune System Regulators The proteins encoded by the cDNAs may also be evaluated for their effects as immune regulators. For example, the proteins may be evaluated for their activity to influence thymocyte or splenocyte cytotoxicity. Numerous assays for such activity are familiar to those skilled in the art including the assays described in the following references, which are incorporated herein by reference: Chapter 3 (In Vitro Assays for Mouse Lymphocyte Function 3.1–3.19) and Chapter 7 (Immunologic studies in Humans) in Current Protocols in Immunology, J. E. Coligan et al. Eds, Greene Publishing Associates and Wiley-Interscience; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

The proteins encoded by the cDNAs may also be evaluated for their effects on T-cell dependent immunoglobulin responses and isotype switching. Numerous assays for such activity are familiar to those skilled in the art, including the assays disclosed in the following references, which are incorporated herein by reference: Maliszewski, J. Immunol. 144:3028–3033, 1990; Mond, J. J. and Brunswick, M Assays for B Cell Function: In vitro Antibody Production, Vol 1 pp. 3.8.1–3.8.16 in Current Protocols in Immunology. J. E. Coligan et al Eds., John Wiley and Sons, Toronto. 1994.

The proteins encoded by the cDNAs may also be evaluated for their effect on immune effector cells, including their effect on Th1 cells and cytotoxic lymphocytes. Numerous assays for such activity are familiar to those skilled in the art, including the assays disclosed in the following references, which are incorporated herein by reference: Chapter 3 (In Vitro Assays for Mouse Lymphocyte Function 3.1–3.19) and Chapter 7 (Immunologic Studies in Humans) in Current Protocols in Immunology, J. E. Coligan et al. Eds., Greene Publishing Associates and Wiley-Interscience; Takai et al., J. Immunol. 137:3494–3500, 1986; Takai et al.; J. Immunol. 140:508–512, 1988; Bertagnolli et al., J. Immunol. 149:3778–3783, 1992.

The proteins encoded by the cDNAs may also be evaluated for their effect on dendritic cell mediated activation of naive T-cells. Numerous assays for such activity are familiar to those skilled in the art, including the assays disclosed in the following references, which are incorporated herein by reference: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

The proteins encoded by the cDNAs may also be evaluated for their influence on the lifetime of lymphocytes. Numerous assays for such activity are familiar to those skilled in the art, including the assays disclosed in the following references, which are incorporated herein by reference: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Those proteins which exhibit activity as immune system regulators activity may then be formulated as pharmaceuticals and used to treat clinical conditions in which regulation of immune activity is beneficial. Alternatively, as described in more detail below, genes encoding these proteins or nucleic acids regulating the expression of these proteins may be introduced into appropriate host cells to increase or decrease the expression of the proteins as desired.

EXAMPLE 34

Assaying the Proteins Expressed from cDNAs for Hematopoiesis Regulating Activity The proteins encoded by the cDNAs may also be evaluated for their hematopoiesis regulating activity. For example, the effect of the proteins on embryonic stem cell differentiation may be evaluated. Numerous assays for such activity are familiar to those skilled in the art, including the assays disclosed in the following references, which are incorporated herein by reference: Johansson et al. Cellular Biology 15:141–151, 1995; Keller et al., Molecular and Cellular Biology 13:473–486, 1993; McClanahan et al., Blood 81:2903–2915, 1993.

The proteins encoded by the cDNAs may also be evaluated for their influence on the lifetime of stem cells and stem cell differentiation. Numerous assays for such activity are familiar to those skilled in the art, including the assays disclosed in the following references, which are incorporated herein by reference: Freshney, M. G. Methylcellulose Colony Forming Assays, in Culture of Hematopoietic Cells. R. I. Freshney, et al. Eds. pp. 265–268, Wiley-Liss, Inc., New York, N.Y. 1994; Hirayama et al., Proc. Natl. Acad. Sci. USA 89:5907–5911, 1992; McNiece, I. K. and Briddell, R. A. Primitive Hematopoietic Colony Forming Cells with High Proliferative Potential, in Culture of Hematopoietic Cells. R.I. Freshney, et al. eds. Vol pp. 23–39, Wiley-Liss, Inc., New York, N.Y. 1994; Neben et al., Experimental Hematology 22:353–359, 1994; Ploemacher, R. E. Cobblestone Area Forming Cell Assay, In Culture of Hematopoietic Cells. R. I. Freshney, et al. Eds. pp. 1–21, Wiley-Liss, Inc., New York, N.Y. 1994; Spooncer, E., Dexter, M. and Allen, T. Long Term Bone Marrow Cultures in the Presence of Stromal Cells, in Culture of Hematopoietic Cells. R. I. Freshney, et al. Eds. pp. 163–179, Wiley-Liss, Inc., New York, N.Y. 1994; Sutherland, H. J. Long Term Culture Initiating Cell Assay, in Culture of Hematopoietic Cells. R. I. Freshney, et al. Eds. pp. 139–162, Wiley-Liss, Inc., New York, N.Y. 1994.

Those proteins which exhibit hematopoiesis regulatory activity may then be formulated as pharmaceuticals and used to treat clinical conditions in which regulation of hematopoeisis is beneficial. Alternatively, as described in more detail below, genes encoding these proteins or nucleic acids regulating the expression of these proteins may be introduced into appropriate host cells to increase or decrease the expression of the proteins as desired.

EXAMPLE 35

Assaying the Proteins Expressed from cDNAs for Regulation of Tissue Growth

The proteins encoded by the cDNAs may also be evaluated for their effect on tissue growth. Numerous assays for such activity are familiar to those skilled in the art, including the assays disclosed in International Patent Publication No. WO95/16035, International Patent Publication No. WO95/05846 and International Patent Publication No. WO91/07491, which are incorporated herein by reference.

Those proteins which are involved in the regulation of tissue growth may then be formulated as pharmaceuticals and used to treat clinical conditions in which regulation of tissue growth is beneficial. Alternatively, as described in more detail below, genes encoding these proteins or nucleic acids regulating the expression of these proteins may be introduced into appropriate host cells to increase or decrease the expression of the proteins as desired.

EXAMPLE 36

Assaying the Proteins Expressed from cDNAs for Regulation of Reproductive Hormones or Cell Movement The proteins encoded by the cDNAs may also be evaluated for their ability to regulate reproductive hormones, such as follicle stimulating hormone. Numerous assays for such activity are familiar to those skilled in the art, including the assays disclosed in the following references, which are incorporated herein by reference: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986. Chapter 6.12 (Measurement of Alpha and Beta Chemokines) Current Protocols in Immunology, J. E. Coligan et al. Eds. Greene Publishing Associates and Wiley-Intersciece; Taub et al. J. Clin. Invest. 95:1370–1376, 1995; Lind et al. APMIS 103:140–146, 1995; Muller et al. Eur. J. Immunol. 25:1744–1748; Gruber et al. J. of Immunol. 152:5860–5867, 1994; Johnston et al. J. of Immunol. 153:1762–1768, 1994.

Those proteins which exhibit activity as reproductive hormones or regulators of cell movement may then be formulated as pharmaceuticals and used to treat clinical conditions in which regulation of reproductive hormones or cell movement are beneficial. Alternatively, as described in more detail below, genes encoding these proteins or nucleic acids regulating the expression of these proteins may be introduced into appropriate host cells to increase or decrease the expression of the proteins as desired.

EXAMPLE 37

Assaying the Proteins Expressed from cDNAs for Regulation of Blood Clotting

The proteins encoded by the cDNAs may also be evaluated for their effects on blood clotting. Numerous assays for such activity are familiar to those skilled in the art, including the assays disclosed in the following references, which are incorporated herein by reference: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Those proteins which are involved in the regulation of blood clotting may then be formulated as pharmaceuticals and used to treat clinical conditions in which regulation of blood clotting is beneficial. Alternatively, as described in more detail below, genes encoding these proteins or nucleic acids regulating the expression of these proteins may be introduced into appropriate host cells to increase or decrease the expression of the proteins as desired.

EXAMPLE 38

Assaying the Proteins Expressed from cDNAs for Involvement in Receptor/Ligand Interactions The proteins encoded by the cDNAs may also be evaluated for their involvement in receptor/ligand interactions. Numerous assays for such involvement are familiar to those skilled in the art, including the assays disclosed in the following references, which are incorporated herein by reference: Chapter 7.28 (Measurement of Cellular Adhesion under Static Conditions 7.28.1–7.28.22) in Current Protocols in Immunology, J. E. Coligan et al. Eds. Greene Publishing Associates and Wiley-Interscience; Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160, 1989; Stoltenborg et al., J. Immunol. Methods 175:59–68, 1994; Stitt et al., Cell 80:661–670, 1995; Gyuris et al., *Cell* 75:791–803, 1993.

EXAMPLE 39

Identification of Proteins Which Interact with Polypeptides Encoded by 5' ESTs

Proteins which interact with the polypeptides encoded by full length cDNAs derived from the 5' ESTs or fragments thereof, such as receptor proteins, may be identified using two hybrid systems such as the Matchmaker Two Hybrid System 2 (Catalog No. K1604-1, Clontech). As described in the manual accompanying the Matchmaker Two Hybrid System 2 (Catalog No. K1604-1, Clontech), which is incorporated herein by reference, the full length cDNAs derived from 5' ESTs, or fragments thereof, are inserted into an expression vector such that they are in frame with DNA encoding the DNA binding domain of the yeast transcriptional activator GAL4. cDNAs in a cDNA library which encode proteins which might interact with the polypeptides encoded by full length cDNAs derived from the 5' ESTs or fragments thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the full length cDNAs derived from the 5' ESTs or fragments thereof.

It will be appreciated by those skilled in the art that the proteins expressed from the cDNAs may be assayed for numerous activities in addition to those specifically enumerated above. For example, the expressed proteins may be evaluated for applications involving control and regulation of inflammation, tumor proliferation or metastasis, infection, or other clinical conditions. In addition, the proteins expressed from the cDNAs may be useful as nutritional agents or cosmetic agents.

The proteins expressed from the cDNAs may be used to generate antibodies capable of specifically binding to the expressed protein.

EXAMPLE 40

Production of an Antibody to a Human Protein

Substantially pure protein or polypeptide is isolated from the transfected or transformed cells as described in Example 30. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

V. Use of 5' ESTs or Sequences Obtainable Therefrom as Reagents

The 5' ESTs of the present invention (or cDNAs or genomic DNAs obtainable therefrom) therefrom may be used as reagents in isolation procedures, diagnostic assays, and forensic procedures. For example, sequences from the 5' ESTs (or cDNAs or genomic DNAs obtainable therefrom), may be detectably labeled and used as probes to isolate other sequences capable of hybridizing to them. In addition, sequences from the 5' ESTs (or cDNAs or genomic DNAs obtainable therefrom), may be used to design PCR primers to be used in isolation, diagnostic, or forensic procedures.

EXAMPLE 41

Preparation of PCR Primers and Amplification of DNA

The 5' EST sequences (or cDNAs or genomic DNAs obtainable therefrom) may be used to prepare PCR primers for a variety of applications, including isolation procedures for cloning nucleic acids capable of hybridizing to such sequences, diagnostic techniques and forensic techniques. The PCR primers are at least 10 bases, and preferably at least 12, 15, or 17 bases in length. More preferably, the PCR primers are at least 20–30 bases in length. In some embodiments, the PCR primers may be more than 30 bases in length. It is preferred that the primer pairs have approximately the same G/C ratio, so that melting temperatures are approximately the same. A variety of PCR techniques are familiar to those skilled in the art. For a review of PCR technology, see Molecular Cloning to Genetic Engineering White, B. A. Ed. in Methods in Molecular Biology 67: Humana Press, Totowa 1997. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

EXAMPLE 42

Use of 5' ESTs or Nucleic Acids Obtainable Therefrom as Probes

Probes derived from 5' ESTs (or cDNAs or genomic DNAs obtainable therefrom), including full length cDNAs or genomic sequences, may be labeled with detectable labels familiar to those skilled in the art, including radioisotopes and non-radioactive labels, to provide a detectable probe. The detectable probe may be single stranded or double stranded and may be made using techniques known in the art, including in vitro transcription, nick translation, or kinase reactions.

A nucleic acid sample containing a sequence capable of hybridizing to the labeled probe is contacted with the labeled probe. If the nucleic acid in the sample is double stranded, it may be denatured prior to contacting the probe. In some applications, the nucleic acid sample may be immobilized on a surface such as a nitrocellulose or nylon membrane. The nucleic acid sample may comprise nucleic acids obtained from a variety of sources, including genomic DNA, cDNA libraries, RNA, or tissue samples.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described in Example 30 above.

PCR primers made as described in Example 41 above may be used in forensic analyses, such as the DNA fingerprinting techniques described in Examples 43–47 below. Such analyses may utilize detectable probes or primers based on the sequences of the 5' ESTs or of cDNAs or genomic DNAs isolated using the 5' ESTs.

EXAMPLE 43

Forensic Matching by DNA Sequencing

In one exemplary method, DNA samples are isolated from forensic specimens of, for example, hair, semen, blood or skin cells by conventional methods. A panel of PCR primers based on a number of the 5' ESTs of Example 25, or cDNAs or genomic DNAs isolated therefrom as described above, is then utilized in accordance with Example 41 to amplify DNA of approximately 100–200 bases in length from the forensic specimen. Corresponding sequences are obtained from a test subject. Each of these identification DNAs is then sequenced using standard techniques, and a simple database comparison determines the differences, if any, between the sequences from the subject and those from the sample. Statistically significant differences between the suspect's DNA sequences and those from the sample conclusively prove a lack of identity. This lack of identity can be proven, for example, with only one sequence. Identity, on the other hand, should be demonstrated with a large number of sequences, all matching. Preferably, a minimum of 50 statistically identical sequences of 100 bases in length are used to prove identity between the suspect and the sample.

EXAMPLE 44

Positive Identification by DNA Sequencing

The technique outlined in the previous example may also be used on a larger scale to provide a unique fingerprint-type identification of any individual. In this technique, primers are prepared from a large number of sequences from Example 25, or cDNA or genomic DNA sequences obtainable therefrom. Preferably, 20 to 50 different primers are used. These primers are used to obtain a corresponding number of PCR-generated DNA segments from the individual in question in accordance with Example 41. Each of these DNA segments is sequenced, using the methods set forth in Example 43. The database of sequences generated through this procedure uniquely identifies the individual from whom the sequences were obtained. The same panel of primers may then be used at any later time to absolutely correlate tissue or other biological specimen with that individual.

EXAMPLE 45

Southern Blot Forensic Identification

The procedure of Example 44 is repeated to obtain a panel of at least 10 amplified sequences from an individual and a specimen. Preferably, the panel contains at least 50 amplified sequences. More preferably, the panel contains 100 amplified sequences. In some embodiments, the panel contains 200 amplified sequences. This PCR-generated DNA is then digested with one or a combination of, preferably, four base specific restriction enzymes. Such enzymes are commercially available and known to those of skill in the art. After digestion, the resultant gene fragments are size separated in multiple duplicate wells on an agarose gel and transferred to nitrocellulose using Southern blotting techniques well known to those with skill in the art. For a review of Southern blotting see Davis et al. (*Basic Methods in Molecular Biology*, 1986, Elsevier Press. pp 62–65).

A panel of probes based on the sequences of the 5' ESTs (or cDNAs or genomic DNAs obtainable therefrom), or fragments thereof of at least 10 bases, are radioactively or colorimetrically labeled using methods known in the art, such as nick translation or end labeling, and hybridized to the Southern blot using techniques known in the art (Davis et al., supra). Preferably, the probe comprises at least 12, 15, or 17 consecutive nucleotides from the 5' EST. More preferably, the probe comprises at least 20–30 consecutive nucleotides from the 5' EST. In some embodiments, the probe comprises more than 30 nucleotides from the 5' EST.

Preferably, at least 5 to 10 of these labeled probes are used, and more preferably at least about 20 or 30 are used to provide a unique pattern. The resultant bands appearing from the hybridization of a large sample of 5' ESTs will be a unique identifier. Since the restriction enzyme cleavage will be different for every individual, the band pattern on the Southern blot will also be unique. Increasing the number of 5' EST probes will provide a statistically higher level of confidence in the identification since there will be an increased number of sets of bands used for identification.

EXAMPLE 46

Dot Blot Identification Procedure

Another technique for identifying individuals using the 5' EST sequences disclosed herein utilizes a dot blot hybridization technique.

Genomic DNA is isolated from nuclei of subject to be identified. Oligonucleotide probes of approximately 30 bp in length are synthesized that correspond to at least 10, preferably 50 sequences from the 5' ESTs or cDNAs or genomic DNAs obtainable therefrom. The probes are used to hybridize to the genomic DNA through conditions known to those in the art. The oligonucleotides are end labeled with $P^{32}$ using polynucleotide kinase (Pharmacia). Dot Blots are created by spotting the genomic DNA onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al. supra). The $^{32}P$ labeled DNA fragments are sequentially hybridized with successively stringent conditions to detect minimal differences between the 30 bp sequence and the DNA. Tetramethylammonium chloride is useful for identifying clones containing small numbers of nucleotide mismatches (Wood et al., Proc. Natl. Acad. Sci. USA 82(6):1585–1588 (1985)) which is hereby incorporated by reference. A unique pattern of dots distinguishes one individual from another individual.

5' EST sequences (or cDNAs or genomic DNAs obtainable therefrom) or oligonucleotides containing at least 10 consecutive bases from the preceding sequences can be used as probes in the following alternative fingerprinting technique. Preferably, the probe comprises at least 12, 15, or 17 consecutive nucleotides from the 5' EST. More preferably, the probe comprises at least 20–30 consecutive nucleotides from the 5' EST. In some embodiments, the probe comprises more than 30 nucleotides from the 5' EST. Preferably, a plurality of probes having sequences from different genes are used in the alternative fingerprinting technique. Example 47 below provides a representative alternative fingerprinting procedure in which the probes are derived from 5' ESTs. However, those skilled in the art will appreciate that the procedure of Example 47 may readily be implemented with probes containing sequences from cDNAs or genomic sequences obtainable from the 5' ESTs.

EXAMPLE 47

Alternative "Fingerprint" Identification Technique 20-mer oligonucleotides are prepared from a large number, e.g. 50, 100, or 200, 5' EST sequences using commercially available oligonucleotide services such as Genset, Paris, France. Cell samples from the test subject are processed for DNA using techniques well known to those with skill in the art. The nucleic acid is digested with restriction enzymes such as EcoRI and XbaI. Following digestion, samples are applied to wells for electrophoresis. The procedure, as known in the art, may be modified to accommodate polyacrylamide electrophoresis, however in this example, samples containing 5 ug of DNA are loaded into wells and separated on 0.8% agarose gels. The gels are transferred onto nitrocellulose using standard Southern blotting techniques.

10 ng of each of the oligonucleotides are pooled and end-labeled with $P^{32}$. The nitrocellulose is prehybridized with blocking solution and hybridized with the labeled probes. Following hybridization and washing, the nitrocellulose filter is exposed to X-Omat AR X-ray film. The resulting hybridization pattern will be unique for each individual.

It is additionally contemplated within this example that the number of probe sequences used can be varied for additional accuracy or clarity.

The antibodies generated in Examples 30 and 40 above may be used to identify the tissue type or cell species from which a sample is derived as described above.

EXAMPLE 48

Identification of Tissue Types or Cell Species by Means of Labeled Tissue Specific Antibodies Identification of specific tissues is accomplished by the visualization of tissue specific antigens by means of antibody preparations according to Examples 30 and 40 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

A. Immunohistochemical Techniques

Purified, high-titer antibodies, prepared as described above, are conjugated to a detectable marker, as described, for example, by Fudenberg, H., Chap. 26 in: Basic 503 Clinical Immunology, 3rd Ed. Lange, Los Altos, Calif. (1980) or Rose, N. et al., Chap. 12 in: Methods in Immunodiagnosis, 2d Ed. John Wiley 503 Sons, New York (1980).

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibody complexes achieved by means of an electron microscope. In yet another approach, the antibodies are radiolabeled, with, for example $^{125}I$, and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 µm, unfixed) of the unknown tissue and known control, are mounted and each slide covered with different dilutions of the antibody preparation. Sections of known and unknown tissues should also be treated with preparations to provide a positive control, a negative control, for example, pre-immune sera, and a control for non-specific staining, for example, buffer.

Treated sections are incubated in a humid chamber for 30 min at room temperature, rinsed, then washed in buffer for 30–45 min. Excess fluid is blotted away, and the marker developed.

If the tissue specific antibody was not labeled in the first incubation, it can be labeled at this time in a second antibody-antibody reaction, for example, by adding fluorescein- or enzyme-conjugated antibody against the immunoglobulin class of the antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. et al., Section 19-2 in: Basic Methods in Molecular Biology (P. Leder, ed), Elsevier, New York (1986), using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 µl, and containing from about 1 to 100 µg protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., (above) Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 30 and 40. In this procedure, as in procedure A above, appropriate positive and negative sample and reagent controls are run.

In either procedure A or B, a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

The visualization of tissue specific antigen binding at levels above those seen in control tissues to one or more tissue specific antibodies, prepared from the gene sequences identified from EST sequences, can identify tissues of unknown origin, for example, forensic samples, or differentiated tumor tissue that has metastasized to foreign bodily sites.

In addition to their applications in forensics and identification, 5' ESTs (or cDNAs or genomic DNAs obtainable therefrom) may be mapped to their chromosomal locations. Example 49 below describes radiation hybrid (RH) mapping of human chromosomal regions using 5' ESTs. Example 50 below describes a representative procedure for mapping a 5' EST to its location on a human chromosome. Example 51 below describes mapping of 5' ESTs on metaphase chromosomes by Fluorescence In Situ Hybridization (FISH). Those skilled in the art will appreciate that the method of Examples 49–51 may also be used to map cDNAs or genomic DNAs obtainable from the 5' ESTs to their chromosomal locations.

EXAMPLE 49

Radiation Hybrid Mapping of 5' ESTs to the Human Genome

Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. (*Genomics* 4:509–517, 1989) and Cox et al., (*Science* 250:245–250, 1990), the entire contents of which are hereby incorporated by reference. The random and independent nature of the subclones permits efficient mapping of any human genome marker. Human DNA isolated from a panel of 80–100 cell lines provides a mapping reagent for ordering 5' ESTs. In this approach, the frequency of breakage between markers is used to measure distance, allowing construction of fine resolution maps as has been done using conventional ESTs (Schuler et al., *Science* 274:540–546, 1996, hereby incorporated by reference).

RH mapping has been used to generate a high-resolution whole genome radiation hybrid map of human chromosome 17q22-q25.3 across the genes for growth hormone (GH) and thymidine kinase (TK) (Foster et al., *Genomics* 33:185–192, 1996), the region surrounding the Gorlin syndrome gene (Obermayr et al., *Eur. J Hum. Genet.* 4:242–245, 1996), 60 loci covering the entire short arm of chromosome 12 (Raeymaekers et al., *Genomics* 29:170–178, 1995), the region of human chromosome 22 containing the neurofibromatosis type 2 locus (Frazer et al., *Genomics* 14:574–584, 1992) and 13 loci on the long arm of chromosome 5 (Warrington et al., *Genomics* 11:701–708, 1991).

EXAMPLE 50

Mapping of 5' ESTs to Human Chromosome Using PCR Techniques

5' ESTs may be assigned to human chromosomes using PCR based methodologies. In such approaches, oligonucleotide primer pairs are designed from 5' EST sequences to minimize the chance of amplifying through an intron. Preferably, the oligonucleotide primers are 18–23 bp in length and are designed for PCR amplification. The creation of PCR primers from known sequences is well known to those with skill in the art. For a review of PCR technology see Erlich, H. A., *PCR Technology: Principles and Applications for DNA Amplification.* 1992. W. H. Freeman and Co., New York.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 $\mu$Cu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the distance between the ends of the primer sequences in the 5' EST from which the primers are derived, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given 5' EST. DNA is isolated from the somatic hybrids and used as starting templates for PCR reactions using the primer pairs from the 5' ESTs. Only those somatic cell hybrids with chromosomes containing the human gene corresponding to the 5' EST will yield an amplified fragment. The 5' ESTs are assigned to a chromosome by analysis of the segregation pattern of PCR products from the somatic hybrid DNA templates. The single human chromosome present in all cell hybrids that give rise to an amplified fragment is the chromosome containing that 5' EST. For a review of techniques and analysis of results from somatic cell gene mapping experiments. (See Ledbetter et al., *Genomics* 6:475–481 (1990).)

Alternatively, the 5' ESTs (or cDNAs or genomic DNAs obtainable therefrom) may be mapped to individual chromosomes using FISH as described in Example 51 below.

EXAMPLE 51

Mapping of 5' ESTs to Chromosomes Using Fluorescence in situ Hybridization

Fluorescence in situ hybridization allows the 5' EST (or cDNAs or genomic DNAs obtainable therefrom) to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of a 5' EST (or cDNA or genomic DNAs obtained therefrom) are obtained by FISH as described by Cherif et al. (*Proc. Natl. Acad Sci. U.S.A.,* 87:6639–6643, 1990). Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 $\mu$M) is added for 17 h, followed by addition of 5-bromodeoxyuridine (5-BudR, 0.1 mM) for 6 h. Colcemid (1 $\mu$g/ml) is added for the last 15 min before harvesting the cells. Cells are collected, washed in RPMI, incubated with a hypotonic solution of KCl (75 mM) at 37° C. for 15 min and fixed in three changes of methanol:acetic acid (3:1). The cell suspension is dropped onto a glass slide and air dried. The 5' EST (or cDNA or genomic DNA obtainable therefrom) is labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2× SSC, 10% dextran sulfate, 1 mg/ml sonicated salmon sperm DNA, pH 7) and the probe is denatured at 70° C. for 5–10 min.

Slides kept at −20° C. are treated for 1 h at 37° C. with RNase A (100 $\mu$g/ml), rinsed three times in 2× SSC and dehydrated in an ethanol series. Chromosome preparations are denatured in 70% formamide, 2× SSC for 2 min at 70° C., then dehydrated at 4° C. The slides are treated with proteinase K (10 $\mu$g/100 ml in 20 mM Tris-HCl, 2 mM $CaCl_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular 5' EST (or cDNA or genomic DNA obtainable therefrom) may be localized to a particular cytogenetic R-band on a given chromosome.

Once the 5' ESTs (or cDNAs or genomic DNAs obtainable therefrom) have been assigned to particular chromosomes using the techniques described in Examples 49–51 above, they may be utilized to construct a high resolution map of the chromosomes on which they are located or to identify the chromosomes in a sample.

EXAMPLE 52

Use of 5' ESTs to Construct or Expand Chromosome Maps

Chromosome mapping involves assigning a given unique sequence to a particular chromosome as described above. Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the 5' ESTs are obtained. This approach is described in Ramaiah Nagaraja et al. Genome Research 7:210–222, March 1997. Briefly, in this approach each chromosome is broken into overlapping pieces which are inserted into the YAC vector. The YAC inserts are screened using PCR or other methods to determine whether they include the 5' EST whose position is to be determined. Once an insert has been found which includes the 5' EST, the insert can be analyzed by PCR or other methods to determine whether the insert also contains other sequences known to be on the chromosome or in the region from which the 5' EST was derived. This process can be repeated for each insert in the YAC library to determine the location of each of the 5' ESTs relative to one another and to other known chromosomal markers. In this way, a high resolution map of the distribution of numerous unique markers along each of the organisms chromosomes may be obtained.

As described in Example 53 below 5' ESTs (or cDNAs or genomic DNAs obtainable therefrom) may also be used to identify genes associated with a particular phenotype, such as hereditary disease or drug response.

EXAMPLE 53

Identification of Genes Associated with Hereditary Diseases or Drug Response

This example illustrates an approach useful for the association of 5' EST sequences (or cDNAs or genomic DNAs obtainable therefrom) with particular phenotypic characteristics. In this example, a particular 5' EST (or cDNAs or genomic DNAs obtainable therefrom) is used as a test probe to associate that 5' EST (or cDNAs or genomic DNAs obtainable therefrom) with a particular phenotypic characteristic.

5' ESTs (or cDNAs or genomic DNAs obtainable therefrom) are mapped to a particular location on a human chromosome using techniques such as those described in Examples 49 and 50 or other techniques known in the art. A search of Mendelian Inheritance in Man (V. McKusick, Mendelian Inheritance in Man (available on line through Johns Hopkins University Welch Medical Library) reveals the region of the human chromosome which contains the 5' EST (or cDNAs or genomic DNAs obtainable therefrom) to be a very gene rich region containing several known genes and several diseases or phenotypes for which genes have not been identified. The gene corresponding to this 5' EST (or cDNAs or genomic DNAs obtainable therefrom) thus becomes an immediate candidate for each of these genetic diseases.

Cells from patients with these diseases or phenotypes are isolated and expanded in culture. PCR primers from the 5' EST sequences (or cDNAs or genomic DNAs obtainable therefrom) are used to screen genomic DNA, mRNA or cDNA obtained from the patients. 5' ESTs (or cDNAs or genomic DNAs obtainable therefrom) that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the 5' EST may be responsible for the genetic disease.

VI. Use of 5' ESTs (or cDNAs or Genomic DNAs Obtainable Therefrom) to Construct Vectors The present 5' ESTs (or cDNAs or genomic DNAs obtainable therefrom) may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described in Example 54 below.

EXAMPLE 54

Construction of Secretion Vectors

The secretion vectors of the present invention include a promoter capable of directing gene expression in the host cell, tissue, or organism of interest. Such promoters include the Rous Sarcoma Virus promoter, the SV40 promoter, the human cytomegalovirus promoter, and other promoters familiar to those skilled in the art.

A signal sequence from a 5' EST (or cDNAs or genomic DNAs obtainable therefrom) is operably linked to the promoter such that the mRNA transcribed from the promoter will direct the translation of the signal peptide. The host cell, tissue, or organism may be any cell, tissue, or organism which recognizes the signal peptide encoded by the signal sequence in the 5' EST (or cDNAs or genomic DNAs obtainable therefrom). Suitable hosts include mammalian cells, tissues or organisms, avian cells, tissues, or organisms, insect cells, tissues or organisms, or yeast.

In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA site such that the polyA site is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediated transfection, viral particles or as naked DNA. The protein encoded by the inserted gene is then purified or enriched from the supernatant using conventional techniques such as ammonium sulfate precipitation, immunoprecipitation, immunochromatography, size exclusion chromatography, ion exchange chromatography, and hplc. Alternatively, the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and fused to the signal sequence. The vector is introduced into an appropriate host cell. The protein expressed from the promoter is secreted extracellularly, thereby producing a therapeutic effect.

The 5' ESTs may also be used to clone sequences located upstream of the 5' ESTs which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion. Example 55 describes a method for cloning sequences upstream of the 5' ESTs.

EXAMPLE 55

Use of 5' ESTs to Clone Upstream Sequences from Genomic DNA

Sequences derived from 5' ESTs may be used to isolate the promoters of the corresponding genes using chromosome walking techniques. In one chromosome walking technique, which utilizes the GenomeWalker™ kit available from Clontech, five complete genomic DNA samples are each digested with a different restriction enzyme which has a 6 base recognition site and leaves a blunt end. Following digestion, oligonucleotide adapters are ligated to each end of the resulting genomic DNA fragments.

For each of the five genomic DNA libraries, a first PCR reaction is performed according to the manufacturer's instructions (which are incorporated herein by reference) using an outer adaptor primer provided in the kit and an outer gene specific primer. The gene specific primer should be selected to be specific for the 5' EST of interest and should have a melting temperature, length, and location in the 5' EST which is consistent with its use in PCR reactions. Each first PCR reaction contains 5 ng of genomic DNA, 5 µl of 10× Tth reaction buffer, 0.2 mM of each dNTP, 0.2 µM each of outer adaptor primer and outer gene specific primer, 1.1 mM of Mg(OAc)$_2$, and 1 µl of the Tth polymerase 50× mix in a total volume of 50 µl. The reaction cycle for the first PCR reaction is as follows: 1 min—94° C./2 sec—94° C., 3 min—72° C. (7 cycles)/2 sec—94° C., 3 min—67° C. (32 cycles)/5 min—67° C.

The product of the first PCR reaction is diluted and used as a template for a second PCR reaction according to the manufacturer's instructions using a pair of nested primers which are located internally on the amplicon resulting from the first PCR reaction For example, 5 µl of the reaction product of the first PCR reaction mixture may be diluted 180 times. Reactions are made in a 50 µl volume having a composition identical to that of the first PCR reaction except the nested primers are used. The first nested primer is specific for the adaptor, and is provided with the GenomeWalker™ kit. The second nested primer is specific for the particular 5' EST for which the promoter is to be cloned and should have a melting temperature, length, and location in the 5' EST which is consistent with its use in PCR reactions. The reaction parameters of the second PCR reaction are as follows: 1 min—94° C./2 sec—94° C., 3 min—72° C. (6 cycles)/2 sec—94° C., 3 min—67° C. (25 cycles)/5 min—67° C.

The product of the second PCR reaction is purified, cloned, and sequenced using standard techniques. Alternatively, tow or more human genomic DNA libraries can be constructed by using two or more restriction enzymes. The digested genomic DNA is cloned into vectors which can be converted into single stranded, circular, or linear DNA. A biotinylated oligonucleotide comprising at least 15 nucleotides from the 5' EST sequence is hybridized to the single stranded DNA. Hybrids between the biotinylated oligonucleotide and the single stranded DNA containing the EST sequence are isolated as described in Example 29 above. Thereafter, the single stranded DNA containing the EST sequence is released from the beas and converted into double stranded DNA using a primer specific for the 5' EST sequence or a primer corresponding to a sequence included in the cloning vector. The resulting double stranded DNA is transformed into bacteria. cDNAS containing the 5' sequence are identified by colony PCR or colony hybridization.

Once the upstream genomic sequences have been cloned and sequenced as described above, prospective promoters and transcription start sites within the upstream sequences may be identified by comparing the sequences upstream of the 5 ESTs with databases containing known transcription start sites, transcription factor binding sites, or promoter sequences.

In addition, promoters in the upstream sequences may be identified using promoter reporter vectors as described in Example 56.

EXAMPLE 56

Identification of Promoters in Cloned Upstream Sequences

The genomic sequences upstream of the 5' ESTs are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the 5' ESTs are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Appropriate host cells for the promoter reporter vectors may be chosen based on the results of the above described determination of expression patterns of the ESTs. For example, if the expression pattern analysis indicates that the mRNA corresponding to a particular 5' EST is expressed in fibroblasts, the promoter reporter vector may be introduced into a human fibroblast cell line.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

EXAMPLE 57

Cloning and Identification of Promoters

Using the method described in Example 55 above, sequences upstream of several genes were obtained. Using the primer pairs GGG AAG ATG GAG ATA GTA TTG CCT G (SEQ ID NO:29) and CTG CCA TGT ACA TGA TAG AGA GAT TC (SEQ ID NO:30), the promoter having the internal designation P13H2 (SEQ ID NO:31) was obtained.

Using the primer pairs GTA CCA GGGG ACT GTG ACC ATT GC (SEQ ID NO:32) and CTG TGA CCA TTG CTC CCA AGA GAG (SEQ ID NO:33), the promoter having the internal designation P15B4 (SEQ ID NO:34) was obtained.

Using the primer pairs CTG GGA TGG AAG GCA CGG TA (SEQ ID NO:35) and GAG ACC ACA CAG CTA GAC AA (SEQ ID NO:36), the promoter having the internal designation P29B6 (SEQ ID NO:37) was obtained.

Figure 6:
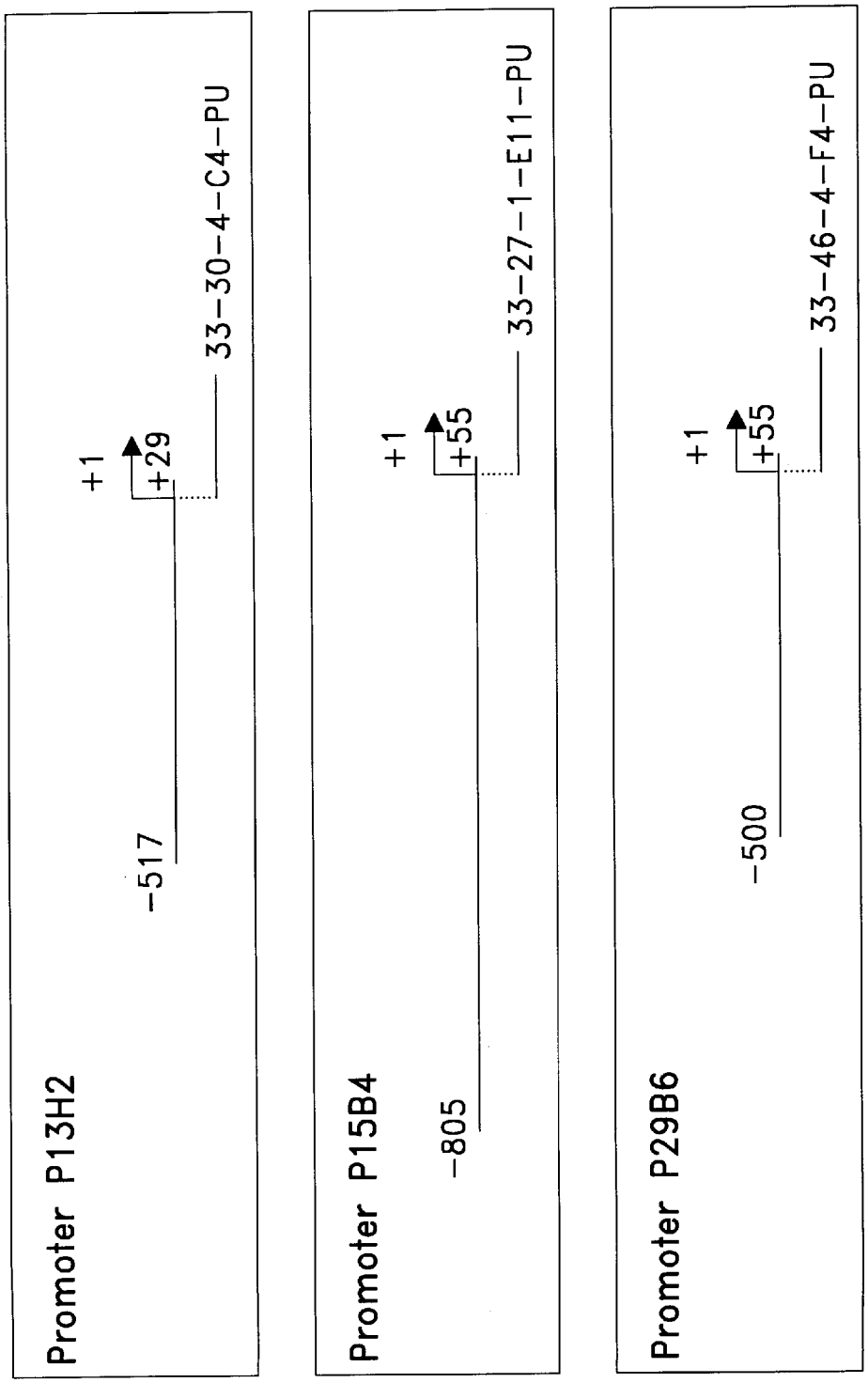
FIG. 6 provides a schematic description of the promoters isolated and the way they are assembled with the corresponding 5' tags.

FIG. 6 provides a schematic description of the promoters isolated and the way they are assembled with the corresponding 5' tags. The upstream sequences were screened for the presence of motifs resembling transcription factor binding sites or known transcription start sites using the computer program MatInspector release 2.0, August 1996.

FIG. 7 describes the transcription factor binding sites present in each of these promoters. The columns labeled matrice provides the name of the MatInspector matrix used. The column labeled position provides the 5' postion of the promoter site. Numeration of the sequence starts from the transcription site as determined by matching the genomic sequence with the 5' EST sequence. The column labeled "orientation" indicates the DNA strand on which the site is found, with the + strand bding the coding strand as determined by matching the genomic sequence with the sequence of the 5' EST. The column labeled "score" provides the MatInspector score found for this site. The column labeled "length" provides the length of the site in nucleotides. The column labeled "sequence" provides the sequence of the site found.

Bacterial clones containing plasmids containing the promoter sequences described above described above are presently stored in the inventor's laboratories under the internal identification numbers provided above. The inserts may be recovered from the deposited materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the EST insertion. The PCR product which corresponds to the 5' EST can then be manipulated using standard cloning techniques familiar to those skilled in the art.

The promoters and other regulatory sequences located upstream of the 5' ESTs may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described in Example 26 above. For example, if a promoter which confers a high level of expression in muscle is desired, the promoter sequence upstream of a 5' EST derived from an mRNA which is expressed at a high level in muscle, as determined by the method of Example 26, may be used in the expression vector.

Preferably, the desired promoter is placed near multiple restriction sites to facilitate the cloning of the desired insert downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA site downstream of the multiple restriction sites for directing the polyadenylation of mRNA transcribed from the gene inserted into the expression vector.

Following the identification of promoter sequences using the procedures of Examples 55–57, proteins which interact with the promoter may be identified as described in Example 58 below.

EXAMPLE 58

Identification of Proteins Which Interact with Promoter Sequences, Upstream Regulatory Sequences, or mRNA Sequences within the promoter region which are likely to bind transcription factors may be identified by homology to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art.

Nucleic acids encoding proteins which interact with sequences in the promoter may be identified using one-hybrid systems such as those described in the manual accompanying the Matchmaker One-Hybrid System kit avalilabe from Clontech (Catalog No. K1603-1), the disclosure of which is incorporated herein by reference. Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

VII. Use of 5' ESTs (or cDNAs or Genomic DNAs Obtainable Therefrom) in Gene Therapy The present invention also comprises the use of 5' ESTs (or cDNAs or genomic DNAs obtainable therefrom) in gene therapy strategies, including antisense and triple helix strategies as described in Examples 57 and 58 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 59

Preparation and Use of Antisense Oligonucleotides

The antisense nucleic acid molecules to be used in gene therapy may be either DNA or RNA sequences. They may comprise a sequence complementary to the sequence of the 5' EST or cDNAs or genomic DNAs obtainable therefrom. The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., Ann. Rev. Biochem. 55:569–597 (1986) and Izant and Weintraub, Cell 36:1007–1015 (1984), which are hereby incorporated by reference.

In some strategies, antisense molecules are obtained from a nucleotide sequence encoding a protein by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies are described by Rossi et al., Pharmacol. Ther. 50(2):245–254, (1991).

Various types of antisense oligonucleotides complementary to the sequence of the 5' EST or cDNAs or genomic DNAs obtainable therefrom may be used. In one preferred embodiment, stable and semi-stable antisense oligonucleotides described in International Application No. PCT WO94/23026, hereby incorporated by reference, are used. In these moleucles, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense molecules are introduced onto cell samples at a number of different concentrations preferably between $1\times10^{-10}M$ to $1\times10^{-4}M$. Once the minimum concentration that can adequately control gene expression is identified, the optimized dose is translated into a dosage suitable for use in vivo. For example, an inhibiting concentration in culture of $1\times10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

The 5' ESTs of the present invention (or cDNAs or genomic DNAs obtainable therefrom) may also be used in gene therapy approaches based on intracellular triple helix formation. Triple helix oligonucleotides are used to inhibit transcription from a genome. They are particularly useful for studying alterations in cell activity as it is associated with a particular gene. The 5' EST sequences (or cDNAs or genomic DNAs obtainable therefrom) of the present invention or, more preferably, a portion of those sequences, can be used to inhibit gene expression in individuals having diseases associated with expression of a particular gene. Similarly, a portion of the 5' EST (or cDNAs or genomic DNAs obtainable therefrom) can be used to study the effect of inhibiting transcription of a particular gene within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from either the 5' EST or from the gene corresponding to the 5' EST are contemplated within the scope of this invention.

EXAMPLE 60

Preparation and Use of Triple Helix Probes

The sequences of the 5' ESTs (or cDNAs or genomic DNAs obtainable therefrom) are scanned to identify 10-mer to 20-mer homopyrimidine or homopurine stretches which could be used in triple-helix based strategies for inhibiting gene expression. Following identification of candidate homopyrimidine or homopurine stretches, their efficiency in inhibiting gene expression is assessed by introducing varying amounts of oligonucleotides containing the candidate sequences into tissue culture cells which normally express the target gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced gene expression using techniques such as Northern blotting, RNase protection assays, or PCR based strategies to monitor the transcription levels of the target gene in cells which have been treated with the oligonucleotide. The cell functions to be monitored are predicted based upon the homologies of the target gene corresponding to the 5' EST from which the oligonucleotide was derived with known gene sequences that have been associated with a particular function. The cell functions can also be predicted based on the presence of abnormal physiologies within cells derived from individuals with a particular inherited disease, particularly when the 5' EST is associated with the disease using techniques described in Example 53.

The oligonucleotides which are effective in inhibiting gene expression in tissue culture cells may then be introduced in vivo using the techniques described above and in Example 59 at a dosage calculated based on the in vitro results, as described in Example 59.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (Science 245:967–971 (1989), which is hereby incorporated by this reference).

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE 1

Parameters used for each step of EST analysis

| Step | Search Characteristics | | | Selection Characteristics | |
|---|---|---|---|---|---|
| | Program | Strand | Parameters | Identity (%) | Length (bp) |
| Miscellaneous | blastn | both | S = 61 X = 16 | 90 | 17 |
| tRNA | fasta | both | — | 80 | 60 |
| rRNA | blastn | both | S = 108 | 80 | 40 |
| mtRNA | blastn | both | S = 108 | 80 | 40 |
| Procaryotic | blastn | both | S = 144 | 90 | 40 |
| Fungal | blastn | both | S = 144 | 90 | 40 |
| Alu | fasta* | both | — | 70 | 40 |
| L1 | blastn | both | S = 72 | 70 | 40 |
| Repeats | blastn | both | S = 72 | 70 | 40 |
| Promoters | blastn | top | S = 54 X = 16 | 90 | 15† |
| Vertebrate | fasta* | both | S = 108 | 90 | 30 |
| ESTs | blastn | both | S = 108 X = 16 | 90 | 30 |
| Proteins | blastx☆ | top | E = 0.001 | — | — |

*use "Quick Fast" Database Scanner
†alignement further constrained to begin closer than 10 bp to EST\5' end
☆using BLOSUM62 substitution matrix

TABLE II

| SEQ. ID NO. | CATEGORY | VON HEIJNE SCORE | TISSUE SOURCE | INTERNAL DESIGNATION |
|---|---|---|---|---|
| ID38 | new | 10.8 | Brain | 33-19-2-H2-PU |
| ID39 | new | 10.8 | Brain | 33-56-1-E8-PU |
| ID40 | new | 10 | Brain | 33-79-3-D12-PU |
| ID41 | new | 9.6 | Brain | 33-72-2-B2-PU |
| ID42 | new | 9.5 | Brain | 33-13-2-B9-PU |
| ID43 | new | 9.1 | Brain | 33-113-1-E9-PU |
| ID44 | new | 9 | Brain | 33-28-4-E8-PU |
| ID45 | new | 8.8 | Brain | 33-12-3-F2-PU |
| ID46 | new | 8.8 | Brain | 33-70-1-C11-PU |
| ID47 | new | 8.5 | Brain | 33-74-1-B2-PU |
| ID48 | new | 8.5 | Brain | 33-29-3-F1-PU |
| ID49 | new | 8.4 | Brain | 33-8-2-A1-PU |
| ID50 | new | 8.3 | Brain | 17-17-3-A9-PU |
| ID51 | new | 8.3 | Brain | 33-106-2-A8-PU |
| ID52 | new | 8.3 | Brain | 33-112-4-E7-PU |
| ID53 | new | 8.2 | Brain | 33-98-1-E6-PU |
| ID54 | new | 8.2 | Brain | 33-76-1-B6-PU |
| ID55 | new | 8 | Brain | 33-35-4-G8-PU |
| ID56 | new | 7.9 | Brain | 33-17-3-E4-PU |
| ID57 | new | 7.9 | Brain | 33-110-4-B5-PU |
| ID58 | new | 7.8 | Brain | 33-40-1-A11-PU |
| ID59 | new | 7.7 | Brain | 33-71-1-A8-PU |
| ID60 | new | 7.7 | Brain | 33-96-3-G7-PU |
| ID61 | new | 7.6 | Brain | 33-112-3-D12-PU |
| ID62 | new | 7.6 | Brain | 33-62-2-B3-PU |
| ID63 | new | 7.6 | Brain | 33-6-4-G6-PU |
| ID64 | new | 7.5 | Brain | 33-82-4-E2-PU |
| ID65 | new | 7.4 | Brain | 33-81-3-H11-PU |
| ID66 | new | 7.3 | Brain | 33-64-1-B4-PU |
| ID67 | new | 7.2 | Brain | 33-31-1-B12-PU |
| ID68 | new | 7 | Brain | 33-24-4-F9-PU |
| ID69 | new | 7 | Brain | 33-110-3-E9-PU |
| ID70 | new | 7 | Brain | 33-4-2-G5-PU |
| ID71 | new | 6.9 | Brain | 33-74-2-A4-PU |
| ID72 | new | 6.9 | Brain | 33-52-4-F9-PU |
| ID73 | new | 6.9 | Brain | 33-74-1-B11-PU |
| ID74 | new | 6.8 | Brain | 33-10-4-D9-PU |
| ID75 | new | 6.8 | Brain | 33-15-2-H3-PU |
| ID76 | new | 6.7 | Brain | 33-38-2-D5-PU |
| ID77 | new | 6.7 | Brain | 33-78-3-D2-PU |
| ID78 | new | 6.7 | Brain | 33-96-3-D3-PU |
| ID79 | new | 6.6 | Brain | 33-76-4-B11-PU |
| ID80 | new | 6.3 | Brain | 33-39-1-C6-PU |
| ID81 | new | 6.1 | Brain | 33-106-3-B12-PU |
| ID82 | new | 6 | Brain | 33-4-2-B7-PU |
| ID83 | new | 5.9 | Brain | 33-99-2-E4-PU |
| ID84 | new | 5.9 | Brain | 33-34-1-B1-PU |
| ID85 | new | 5.8 | Brain | 33-67-4-E9-PU |
| ID86 | new | 5.7 | Brain | 33-11-3-H11-PU |
| ID87 | new | 5.6 | Brain | 33-13-2-A8-PU |
| ID88 | new | 5.6 | Brain | 33-83-4-B6-PU |
| ID89 | new | 5.6 | Brain | 33-70-1-E4-PU |
| ID90 | new | 5.6 | Brain | 33-5-3-H11-PU |
| ID91 | new | 5.6 | Brain | 33-10-3-G5-PU |
| ID92 | new | 5.5 | Brain | 33-97-4-G4-PU |
| ID93 | new | 5.5 | Brain | 33-46-4-F4-PU |
| ID94 | new | 5.4 | Brain | 33-4-1-G11-PU |
| ID95 | new | 5.3 | Brain | 33-105-1-H5-PU |
| ID96 | new | 5.3 | Brain | 33-74-2-B10-PU |
| ID97 | new | 5.3 | Brain | 33-49-3-E5-PU |
| ID98 | new | 5.3 | Brain | 33-114-2-A1-PU |
| ID99 | new | 5.2 | Brain | 33-71-1-G12-PU |
| ID100 | new | 5.2 | Brain | 33-47-3-E6-PU |
| ID101 | new | 5.2 | Brain | 33-1-2-E8-PU |
| ID102 | new | 5.2 | Brain | 33-93-4-E12-PU |
| ID103 | new | 5.1 | Brain | 33-1-2-H1-PU |
| ID104 | new | 5.1 | Brain | 17-10-1-H8-PU |
| ID105 | new | 5 | Brain | 33-110-2-B8-PU |
| ID106 | new | 5 | Brain | 33-104-3-D9-PU |
| ID107 | new | 5 | Brain | 33-72-2-H11-PU |
| ID108 | new | 4.9 | Brain | 33-7-4-D6-PU |
| ID109 | new | 4.9 | Brain | 33-31-4-G2-PU |
| ID110 | new | 4.9 | Brain | 33-109-1-E8-PU |
| ID111 | new | 4.8 | Brain | 17-1-2-B11-PU |
| ID112 | new | 4.8 | Brain | 33-19-4-H3-PU |
| ID113 | new | 4.8 | Brain | 33-14-4-E1-PU |
| ID114 | new | 4.8 | Brain | 33-70-3-H1-PU |
| ID115 | new | 4.7 | Brain | 33-86-4-H10-PU |
| ID116 | new | 4.7 | Brain | 33-107-3-D5-PU |
| ID117 | new | 4.7 | Brain | 33-23-4-B9-PU |
| ID118 | new | 4.7 | Brain | 33-82-4-H5-PU |
| ID119 | new | 4.6 | Brain | 33-16-3-F4-PU |
| ID120 | new | 4.6 | Brain | 33-97-4-C5-PU |
| ID121 | new | 4.6 | Brain | 33-100-3-B10-PU |
| ID122 | new | 4.6 | Brain | 33-59-3-E3-PU |
| ID123 | new | 4.5 | Brain | 33-25-1-G2-PU |
| ID124 | new | 4.5 | Brain | 17-16-3-B2-PU |
| ID125 | new | 4.4 | Brain | 33-52-4-E7-PU |
| ID126 | new | 4.4 | Brain | 33-91-1-D1-PU |
| ID127 | new | 4.4 | Brain | 33-26-1-B9-PU |
| ID128 | new | 4.4 | Brain | 33-97-3-H6-PU |
| ID129 | new | 4.4 | Brain | 33-109-2-E8-PU |
| ID130 | new | 4.3 | Brain | 33-59-2-B7-PU |
| ID131 | new | 4.3 | Brain | 33-28-4-D1-PU |
| ID132 | new | 4.3 | Brain | 33-29-4-E2-PU |
| ID133 | new | 4.1 | Brain | 33-70-1-H6-PU |
| ID134 | new | 4.1 | Brain | 33-7-1-B2-PU |
| ID135 | new | 4.1 | Brain | 33-52-4-F8-PU |
| ID136 | new | 4.1 | Brain | 33-23-2-A6-PU |
| ID137 | new | 4.1 | Brain | 33-39-3-E5-PU |
| ID138 | new | 4.1 | Brain | 33-81-4-H6-PU |
| ID139 | new | 4.1 | Brain | 33-105-3-F5-PU |
| ID140 | new | 4 | Brain | 33-35-2-H11-PU |
| ID141 | new | 4 | Brain | 33-50-3-E12-PU |
| ID142 | new | 4 | Brain | 33-16-3-H7-PU |
| ID143 | new | 4 | Brain | 33-79-2-H4-PU |
| ID144 | new | 3.9 | Brain | 33-32-4-B12-PU |
| ID145 | new | 3.9 | Brain | 33-110-4-A5-PU |
| ID146 | new | 3.9 | Brain | 33-109-2-H1-PU |
| ID147 | new | 3.9 | Brain | 33-100-1-E6-PU |
| ID148 | new | 3.9 | Brain | 33-78-2-E7-PU |
| ID149 | new | 3.9 | Brain | 33-82-4-G3-PU |
| ID150 | new | 3.9 | Brain | 17-1-1-A9-PU |
| ID151 | new | 3.9 | Brain | 33-89-4-E1-PU |
| ID152 | new | 3.9 | Brain | 33-89-1-B4-PU |
| ID153 | new | 3.9 | Brain | 33-96-3-A3-PU |
| ID154 | new | 3.8 | Brain | 33-92-3-D1-PU |
| ID155 | new | 3.8 | Brain | 33-104-4-H4-PU |
| ID156 | new | 3.8 | Brain | 33-106-1-B8-PU |

TABLE II-continued

| SEQ. ID NO. | CATEGORY | VON HEIJNE SCORE | TISSUE SOURCE | INTERNAL DESIGNATION |
|---|---|---|---|---|
| ID157 | new | 3.6 | Brain | 33-1-3-D1-PU |
| ID158 | new | 3.6 | Brain | 33-40-2-F5-PU |
| ID159 | new | 3.6 | Brain | 33-4-1-E8-PU |
| ID160 | new | 3.6 | Brain | 33-36-3-E2-PU |
| ID161 | new | 3.6 | Brain | 17-18-3-A6-PU |
| ID162 | new | 3.6 | Brain | 33-12-1-B1-PU |
| ID163 | new | 3.6 | Brain | 33-29-1-H1-PU |
| ID164 | new | 3.6 | Brain | 33-103-1-E1-PU |
| ID165 | new | 3.5 | Brain | 33-10-4-H2-PU |
| ID166 | new | 3.5 | Brain | 33-25-1-H2-PU |
| ID167 | new | 3.5 | Brain | 33-10-4-G2-PU |
| ID168 | new | 3.5 | Brain | 33-67-1-F4-PU |
| ID169 | ext-est-not-vrt | 12.5 | Brain | 33-77-4-E2-PU |
| ID170 | ext-est-not-vrt | 10.1 | Brain | 33-31-3-C11-PU |
| ID171 | ext-est-not-vrt | 9.8 | Brain | 33-28-2-H7-PU |
| ID172 | ext-est-not-vrt | 9.2 | Brain | 33-112-3-C8-PU |
| ID173 | ext-est-not-vrt | 7.9 | Brain | 33-23-3-A11-PU |
| ID174 | ext-est-not-vrt | 7.9 | Brain | 33-29-2-E11-PU |
| ID175 | ext-est-not-vrt | 7.9 | Brain | 33-66-4-C7-PU |
| ID176 | ext-est-not-vrt | 7.1 | Brain | 33-78-1-D7-PU |
| ID177 | ext-est-not-vrt | 6.6 | Brain | 33-31-3-D7-PU |
| ID178 | ext-est-not-vrt | 6.3 | Brain | 33-19-1-C11-PU |
| ID179 | ext-est-not-vrt | 6 | Brain | 33-67-1-A5-PU |
| ID180 | ext-est-not-vrt | 5.9 | Brain | 33-58-3-C8-PU |
| ID181 | ext-est-not-vrt | 4.9 | Brain | 33-107-4-C3-PU |
| ID182 | ext-est-not-vrt | 4.9 | Brain | 33-7-2-G12-PU |
| ID183 | ext-est-not-vrt | 4.8 | Brain | 33-11-1-G5-PU |
| ID184 | ext-est-not-vrt | 4.7 | Brain | 33-31-4-D9-PU |
| ID185 | ext-est-not-vrt | 4.6 | Brain | 33-26-4-E10-PU |
| ID186 | ext-est-not-vrt | 4.5 | Brain | 33-70-4-F7-PU |
| ID187 | ext-est-not-vrt | 4.5 | Brain | 33-19-2-D1-PU |
| ID188 | ext-est-not-vrt | 4.4 | Brain | 33-48-4-F8-PU |
| ID189 | ext-est-not-vrt | 4.3 | Brain | 33-109-3-B10-PU |
| ID190 | ext-est-not-vrt | 4.1 | Brain | 33-30-2-A6-PU |
| ID191 | ext-est-not-vrt | 3.8 | Brain | 33-75-3-D7-PU |
| ID192 | ext-est-not-vrt | 3.7 | Brain | 33-109-4-C1-PU |
| ID193 | est-not-ext | 10.5 | Brain | 33-97-3-D4-PU |
| ID194 | est-not-ext | 10.1 | Brain | 33-61-2-F6-PU |
| ID195 | est-not-ext | 9.5 | Brain | 33-54-1-B9-PU |
| ID196 | est-not-ext | 9.3 | Brain | 33-39-4-D1-PU |
| ID197 | est-not-ext | 9.1 | Brain | 33-57-4-H5-PU |
| ID198 | est-not-ext | 9 | Brain | 33-60-2-B3-PU |
| ID199 | est-not-ext | 8.6 | Brain | 33-52-1-A1-PU |
| ID200 | est-not-ext | 8.4 | Brain | 33-82-2-H10-PU |
| ID201 | est-not-ext | 7.5 | Brain | 33-79-4-B11-PU |
| ID202 | est-not-ext | 7.5 | Brain | 33-18-3-H3-PU |
| ID203 | est-not-ext | 7.5 | Brain | 33-21-1-D6-PU |
| ID204 | est-not-ext | 7.4 | Brain | 33-17-3-F9-PU |
| ID205 | est-not-ext | 7.4 | Brain | 33-70-2-G3-PU |
| ID206 | est-not-ext | 7.4 | Brain | 33-89-3-H4-PU |
| ID207 | est-not-ext | 7.4 | Brain | 33-46-3-E10-PU |
| ID208 | est-not-ext | 7 | Brain | 33-36-2-F9-PU |
| ID209 | est-not-ext | 6.8 | Brain | 33-39-1-C4-PU |
| ID210 | est-not-ext | 6.8 | Brain | 33-65-4-C6-PU |
| ID211 | est-not-ext | 6.4 | Brain | 33-18-2-G6-PU |
| ID212 | est-not-ext | 6.4 | Brain | 33-36-3-C6-PU |
| ID213 | est-not-ext | 6 | Brain | 33-79-2-B6-PU |
| ID214 | est-not-ext | 5.9 | Brain | 33-71-4-D11-PU |
| ID215 | est-not-ext | 5.9 | Brain | 17-12-2-A3-PU |
| ID216 | est-not-ext | 5.9 | Brain | 33-95-1-A12-PU |
| ID217 | est-not-ext | 5.8 | Brain | 33-5-3-E3-PU |
| ID218 | est-not-ext | 5.8 | Brain | 33-74-2-D3-PU |
| ID219 | est-not-ext | 5.7 | Brain | 33-50-3-H8-PU |
| ID220 | est-not-ext | 5.6 | Brain | 33-19-1-A2-PU |
| ID221 | est-not-ext | 5.5 | Brain | 33-22-1-D3-PU |
| ID222 | est-not-ext | 5.5 | Brain | 33-97-1-G4-PU |
| ID223 | est-not-ext | 5.4 | Brain | 33-65-4-D10-PU |
| ID224 | est-not-ext | 5.4 | Brain | 33-79-4-C4-PU |
| ID225 | est-not-ext | 5.3 | Brain | 33-20-2-C5-PU |
| ID226 | est-not-ext | 5.2 | Brain | 33-34-4-A5-PU |
| ID227 | est-not-ext | 5.2 | Brain | 33-6-2-F11-PU |
| ID228 | est-not-ext | 5.2 | Brain | 33-2-2-G5-PU |
| ID229 | est-not-ext | 5.1 | Brain | 33-98-1-G7-PU |
| ID230 | est-not-ext | 5.1 | Brain | 33-20-3-B10-PU |
| ID231 | est-not-ext | 5 | Brain | 33-106-2-D9-PU |
| ID232 | est-not-ext | 4.9 | Brain | 33-72-2-A9-PU |
| ID233 | est-not-ext | 4.9 | Brain | 33-83-3-G8-PU |
| ID234 | est-not-ext | 4.8 | Brain | 33-31-3-E6-PU |
| ID235 | est-not-ext | 4.7 | Brain | 33-28-4-E2-PU |
| ID236 | est-not-ext | 4.6 | Brain | 33-101-3-F4-PU |
| ID237 | est-not-ext | 4.6 | Brain | 33-98-4-C1-PU |
| ID238 | est-not-ext | 4.5 | Brain | 33-31-2-E11-PU |
| ID239 | est-not-ext | 4.5 | Brain | 33-26-2-B6-PU |
| ID240 | est-not-ext | 4.4 | Brain | 33-75-4-H7-PU |
| ID241 | est-not-ext | 4.3 | Brain | 33-13-1-C6-PU |
| ID242 | est-not-ext | 4.3 | Brain | 33-35-4-G1-PU |
| ID243 | est-not-ext | 4.3 | Brain | 33-76-3-G11-PU |
| ID244 | est-not-ext | 4.2 | Brain | 33-72-1-A3-PU |
| ID245 | est-not-ext | 4.2 | Brain | 33-71-2-A2-PU |
| ID246 | est-not-ext | 4.2 | Brain | 33-23-3-H10-PU |
| ID247 | est-not-ext | 4.2 | Brain | 33-13-1-C1-PU |
| ID248 | est-not-ext | 4.2 | Brain | 33-43-2-G12-PU |
| ID249 | est-not-ext | 4.2 | Brain | 33-91-4-E10-PU |
| ID250 | est-not-ext | 4.1 | Brain | 33-113-2-B8-PU |
| ID251 | est-not-ext | 4 | Brain | 33-104-3-G9-PU |
| ID252 | est-not-ext | 3.9 | Brain | 33-66-2-B10-PU |
| ID253 | est-not-ext | 3.9 | Brain | 33-1-2-E9-PU |
| ID254 | est-not-ext | 3.9 | Brain | 33-51-1-G7-PU |
| ID255 | est-not-ext | 3.9 | Brain | 33-32-3-D11-PU |
| ID256 | est-not-ext | 3.8 | Brain | 33-43-2-H10-PU |
| ID257 | est-not-ext | 3.8 | Brain | 33-48-4-H11-PU |
| ID258 | est-not-ext | 3.8 | Brain | 33-8-4-C5-PU |
| ID259 | est-not-ext | 3.8 | Brain | 33-24-1-F5-PU |
| ID260 | est-not-ext | 3.8 | Brain | 33-70-1-A9-PU |
| ID261 | est-not-ext | 3.8 | Brain | 33-30-4-C4-PU |
| ID262 | est-not-ext | 3.8 | Brain | 33-10-2-G7-PU |
| ID263 | est-not-ext | 3.6 | Brain | 33-18-4-E12-PU |
| ID264 | est-not-ext | 3.6 | Brain | 33-52-1-G7-PU |
| ID265 | est-not-ext | 3.6 | Brain | 33-57-1-H10-PU |
| ID266 | est-not-ext | 3.5 | Brain | 33-80-3-E2-PU |
| ID267 | est-not-ext | 3.5 | Brain | 33-36-1-D3-PU |
| ID268 | ext-vrt-not-genomic | 11.3 | Brain | 33-101-1-A2-PU |
| ID269 | ext-vrt-not-genomic | 6.6 | Brain | 33-55-2-E8-PU |
| ID270 | ext-vrt-not-genomic | 4.8 | Brain | 33-14-2-H3-PU |

BRAIN-2.LIS

080197

TABLE III

| SEQ. ID NO. | SIGNAL PEPTIDE |
|---|---|
| ID38 | MLLLLGLCLGLSLC (amino acids −14 through −1 of SEQ ID NO: 271) |
| ID39 | MENGGAGTLQIRQVLLFFVLLGMSQA (amino acids −26 through −1 of SEQ ID NO: 272) |
| ID40 | MRGPEPGPQPTMEGDVLDTLEALGYKGPLLEEQALTKAAEGGLSSPEFSELCIWLGSQIK SLCNLEESITSAGRDDLESFQLEISGFLKEMACPYSVLISGDIKDRLKKKEDCLKLLLFL STELQA (amino acids −126 through −1 of SEQ ID NO: 273) |
| ID41 | MEKSWMLWNFVERWLIALASWSWALC (amino acids −26 through −1 of SEQ ID NO: 274) |
| ID42 | MQQTRTEAVAGAFSHCLGFCGMRLGLLLLARHWCIA (amino acids −36 through −1 of SEQ ID NO: 275) |
| ID43 | MEKGNAFLKNRLVVFLLLLPLASGP (amino acids −24 through −1 of SEQ ID NO: 276) |
| ID44 | MFPFNQAGLPTLLMLIVFHAASMA (amino acids −24 through −1 of SEQ ID NO: 277) |
| ID45 | MTSRSLRRCSCLRVTHNKEILASTVSLGVEGYMLGGGSRINSSNLNDGEEECSPDSLLVW KKKSLLLWMSSLPSLG (amino acids −76 through −1 of SEQ ID NO: 278) |
| ID46 | MWTASAMDFRTCIASXLPALCYVQACRALMIAASVLGLPAILLLLTVLPCIXM (amino acids −53 through −1 of SEQ ID NO: 279) |
| ID47 | MGPPPTHIKYLHLNIYCNCKSTAPGIRSHSLGFALLSLSHPTCQA (amino acids −45 through −1 of SEQ ID NO: 280) |
| ID48 | MFCLLTFLAFTTLLFA (amino acids −16 through −1 of SEQ ID NO: 281) |
| ID49 | MHCGSTPGLCPCWVPFLKCLLAVLSSLFA (amino acids −29 through −1 of SEQ ID NO: 282) |
| ID50 | MNLVCSALLLLGIVSS (amino acids −16 through −1 of SEQ ID NO: 283) |
| ID51 | MSVLDDRQRDILVVQKRHSSLEAAMLIGLLAWLQT (amino acids −35 through −1 of SEQ ID NO: 284) |
| ID52 | MGVNGRRLLIICHYLPLSLC (amino acids −20 through −1 of SEQ ID NO: 285) |
| ID53 | MKLRECPALRWSQLSQHKLECLLLYLAESSG (amino acids −31 through −1 of SEQ ID NO: 286) |
| ID54 | MDPRGILKAFPKRQKIHADASSKVLAKIPRREEGEEAEEWLSSLRAHVVRTGIGRARAEL FEKQIVQHGGQLCPAQGPGVTHIVVDEGMDYERALRLLRLPQLPPXCSA (amino acids −109 through −1 of SEQ ID NO: 287) |
| ID55 | MFWKLSLSLFLVAVLVKVAEA (amino acids −21 through −1 of SEQ ID NO: 288) |
| ID56 | MAFLGLFSLLVLQSMATG (amino acids −18 through −1 of SEQ ID NO: 289) |
| ID57 | MAFLGLFSLLVLQSMATG (amino acids −18 through −1 of SEQ ID NO: 290) |
| ID58 | MSFSLNFTLPANTTSSPVTGGKETDCGPSLGLAAGIPLLVATALLVALLFTLIHR (amino acids −55 through −1 of SEQ ID NO: 291) |
| ID59 | MSTWYLALNKSYKNKDSVRIYLSLCTVSIKFTYFHDIQTNCLTTWKHSRCRFYWAFGGSI LQHSVDPLVLFLSLALLVTP (amino acids −80 through −1 of SEQ ID NO: 292) |
| ID60 | MAIGISLQLLCCIFTLVLQ (amino acids −19 through −1 of SEQ ID NO: 293) |
| ID61 | MQATSNLLNLLLLSLFAGL (amino acids −19 through −1 of SEQ ID NO: 294) |
| ID62 | MMKWKPEDLGSVPCEAFSVTLLCGWPGSHWC (amino acids −31 through −1 of SEQ ID NO: 295) |
| ID63 | MQATSNLLNLLLLSLFAGL (amino acids −19 through −1 of SEQ ID NO: 296) |
| ID64 | MASSHWNETTTSVYQYLGFQVQKIYPFHDNWNTACFVILLLFIFTVVS (amino acids −48 through −1 of SEQ ID NO: 297) |
| ID65 | MLWFSGVGALAERYCRRSPGITCCVLLLLNCSG (amino acids −33 through −1 of SEQ ID NO: 298) |
| ID66 | MLFLQMGKQSWTLIFFLNVTQLVRG (amino acids −25 through −1 of SEQ ID NO: 299) |
| ID67 | MELRXXPPGGREVQLLLGLCSPPXXSL (amino acids −27 through −1 of SEQ ID NO: 300) |
| ID68 | MLWSLLSSSGSHFG (amino acids −14 through −1 of SEQ ID NO: 301) |
| ID69 | MDISGLIPGLVSTFILLSXSDHYGRKFPMILSSVGALATSVWLCLLCYFAFP (amino acids −52 through −1 of SEQ ID NO: 302) |
| ID70 | MXVFFSKNRFEMYFSLLLFVILLITSLIFC (amino acids −30 through −1 of SEQ ID NO: 303) |
| ID71 | MPVPACWISSSLSLLASHHSVSC (amino acids −23 through −1 of SEQ ID NO: 304) |
| ID72 | MCPVFSKQLLACGSLLPGLWQ (amino acids −21 through −1 of SEQ ID NO: 305) |
| ID73 | MALTIHGERMRPDWESPWITSSQAQSLSLGGSPSSRGPLVPRGEYLASCPEGVRSHSHLL PRSLLPLSAWPPWAWH (amino acids −76 through −1 of SEQ ID NO: 306) |
| ID74 | MAARFRCGHLCVPEVPRGPASHAEGGGGRLSRKAAHQAQLCWRAGGDGRGNFNPMNFLVA GTFASSCHSPPLLWSLPPRILIASSLPTLSHP (amino acids −92 through −1 of SEQ ID NO: 307) |
| ID75 | MASTISAYKEKMKELSVLSLICSCFYTQP (amino acids −29 through −1 of SEQ ID NO: 308) |
| ID76 | MLQVYGKPVYQGHRSTLKKGPYLRFNSPSPKSRPQRPKVIERVKGTKVKSIRTQTDFYAT KPKKMDSKMKHSVPVLPHGDQQYLFSPSREMPTFSGTLEGHLIPMAILLGQTQS (amino acids −114 through −1 of SEQ ID NO: 309) |
| ID77 | MSVLEISGMIMNRVNSHIPGIGYQIFGNAVSLILGLTPFVFRLSQATDLEQLTAHSASEL YVIAFGSNEDVIVLSMVIISFVVRVSLVWIFFFLLCVAERTYKQRLLFAKLFGHLTSA (amino acids −118 through −1 of SEQ ID NO: 310) |
| ID78 | MCKGIKAGDTCEKLVGYSAVYRVCFGMACFFFIFCLLTLKINNSKSCRAHIHNGFWFFKL LLLGAMCSG (amino acids −69 through −1 of SEQ ID NO: 311) |
| ID79 | MSDSAGGRAGLRRYPKLPVWVVEDHQEVLPFIYRAIGSKHLPASNVSFLHFDSHPDLLIP VNMPADTVFDKETLFGELSIENWIMPAVYAGHFSHVVWFHPTWA (amino acids −104 through −1 of SEQ ID NO: 312) |
| ID80 | MSSCRGQKVAGGLRVVSPFPLCQPAGEPSRGKMRSSCVLLTALVALA (amino acids −47 through −1 of SEQ ID NO: 313) |
| ID81 | MIIPFKIKNLGGRVLLSGREMFPASVRAPDLAVALSLLPAWT (amino acids −42 through −1 of SEQ ID NO: 314) |

TABLE III-continued

| SEQ. ID NO. | SIGNAL PEPTIDE |
|---|---|
| ID82 | MVCSAPRKIVVRAFITIIFIYYAIKKRANEPAAYLMLKPEALILLLLAQKGPS (amino acids −53 through −1 of SEQ ID NO: 315) |
| ID83 | MTESSMKKLASTLLDAITDKDPLVQEQVCSALCSLGEVRP (amino acids −40 through −1 of SEQ ID NO: 316) |
| ID84 | MQETDCNKRWGRGLGGLWSETGRRFHCKSFVFLFHCTSGLSSC (amino acids −43 through −1 of SEQ ID NO: 317) |
| ID85 | MLLEVPWLSSTVSCAQG (amino acids −17 through −1 of SEQ ID NO: 318) |
| ID86 | MSGGRMQARCSQQSTWSPAFLAVAGPGWA (amino acids −29 through −1 of SEQ ID NO: 319) |
| ID87 | MLQMLWHFLASFFPRAGC (amino acids −18 through −1 of SEQ ID NO: 320) |
| ID88 | MYSHPVSSLVCLLAMGKGLG (amino acids −20 through −1 of SEQ ID NO: 321) |
| ID89 | MGRKEEDDCSXWKKQTTNIRKTFIFMEVLGSGAFS (amino acids −35 through −1 of SEQ ID NO: 322) |
| ID90 | MMIAVFGNANDRNVLTLLPNQSLFSLARA (amino acids −29 through −1 of SEQ ID NO: 323) |
| ID91 | MFFELPLVVTAWFFGMCRS (amino acids −19 through −1 of SEQ ID NO: 324) |
| ID92 | MNHNIIICVMYIVPFLMTKCLYFCHSCKRGSFLLIVANVHFSQT (amino acids −44 through −1 of SEQ ID NO: 325) |
| ID93 | MSCGSAASLTGLCXCCLQALG (amino acids −21 through −1 of SEQ ID NO: 326) |
| ID94 | MQAVDNLTSAPGNTSLCTRDYKITQVLFPLLYTVLFFVGLITNGLA (amino acids −46 through −1 of SEQ ID NO: 327) |
| ID95 | MAAAMXLLCSSCCSWGPAAG (amino acids −20 through −1 of SEQ ID NO: 328) |
| ID96 | MDFIKDQSLSHRSVVKVLSLRKAQA (amino acids −25 through −1 of SEQ ID NO: 329) |
| ID97 | MTRPFWASCSTWATSRISCAFSLASSTA (amino acids −28 through −1 of SEQ ID NO: 330) |
| ID98 | MKSCAVSLTTAAVAFG (amino acids −16 through −1 of SEQ ID NO: 331) |
| ID99 | MSIHECACLSLSLICLRMSLS (amino acids −21 through −1 of SEQ ID NO: 332) |
| ID100 | MLSGLSFLSVFSLWC (amino acids −15 through −1 of SEQ ID NO: 333) |
| ID101 | MGLKDKSQAPASGLGVLRGQRSGSFISMPAPASGQXPEESRSPAPPVASRSQNRGYRPWH GPLWVHQSVRFGLYSILHFPFWVHG (amino acids −65 through −1 of SEQ ID NO: 334) |
| ID102 | MSDQIKFIMDSLNKEPFRKNYNLITFDSLEPMQLLQVLSDVLA (amino acids −43 through −1 of SEQ ID NO: 335) |
| ID103 | MSPSCLHPDLWSMCLEVPSFTATDSVNCGCCLELATEPARNIRSTTRASLLRCSSFTSTR NSTGISALPPAAPMAWPFSASLSTLPVPLTHSSVASLTATPSLA (amino acids −104 through −1 of SEQ ID NO: 336) |
| ID104 | MDLSFHLLLDPSSTQS (amino acids −16 through −1 of SEQ ID NO: 337) |
| ID105 | MPHFLDWFVXVYLVISVLILVGFGAC (amino acids −26 through −1 of SEQ ID NO: 338) |
| TD106 | MSKLKVIPEKSLTNNSRIVGLLAQLEKINA (amino acids −30 through −1 of SEQ ID NO: 339) |
| ID107 | MMSASRLAGTLIPAMAFLSCVRP (amino acids −23 through −1 of SEQ ID NO: 340) |
| ID108 | MVDGTQLRGLTRMYQVPLXLDRDETLVRLRFTMVALVTVCCXLVAFLFC (amino acids −49 through −1 of SEQ ID NO: 341) |
| ID109 | MKQNFLVLNSVWYLISMLQMLAVIIT (amino acids −26 through −1 of SEQ ID NO: 342) |
| ID110 | MECQNSSLKKCLLVEKSLVKASYLIAFQTAASKKPFSIAEELIKPYLVEMCLEVLGSSA (amino acids −59 through −1 of SEQ ID NO: 343) |
| ID111 | MHSSIKTKGSVMWLVALLEMCVC (amino acids −23 through −1 of SEQ ID NO: 344) |
| ID112 | MTVLPLEAISSLSSFVLG (amino acids −18 through −1 of SEQ ID NO: 345) |
| ID113 | MGTASRSNIARHLQTNLILFCVGAVGACTL (amino acids −30 through −1 of SEQ ID NO: 346) |
| ID114 | MNSSKEEMRELAALFYSVVVSTVSG (amino acids −25 through −1 of SEQ ID NO: 347) |
| ID115 | MSQDGGXGELKHMVMSFRVSELQVLLGFAGRNKSGRKHELLAKALHLLKSSC (amino acids −52 through −1 of SEQ ID NO: 348) |
| ID116 | MPCISLLGLLYNFVQVLCYLSIFCLGVLF (amino acids −29 through −1 of SEQ ID NO: 349) |
| ID117 | MKIAVLFCFFLLIIF (amino acids −15 through −1 of SEQ ID NO: 350) |
| ID118 | MAKQKPHVLGSRVMPASCVSERRRKPSFQVSTWSSASLRGSWQ (amino acids −43 through −1 of SEQ ID NO: 351) |
| ID119 | MGFLYLKSVFDVSLG (amino acids −15 through −1 of SEQ ID NO: 352) |
| ID120 | MRMGPGRKRDFSPVPWSQYFESMEDVEVENETGKDTFRVYKSGSEGPVLLLLHGGGHSAL S (amino acids −61 through −1 of SEQ ID NO: 353) |
| ID121 | MIFLLYLLPSSEE (amino acids −13 through −1 of SEQ ID NO: 354) |
| ID122 | MRMGPGRKRDFSPVPWSQYFESMEDVEVENETGKDTFRVYKSGSEGPVLLLLHGGGHSAL S (amino acids −61 through −1 of SEQ ID NO: 355) |
| ID123 | MLSLLNLISILASIPS (amino acids −16 through −1 of SEQ ID NO: 356) |
| ID124 | MGTTSNMVTTIHLMLLWPVHPLLVG (amino acids −25 through −1 of SEQ ID NO: 357) |
| ID125 | MGDPERPEAAGLDQDERSSSDTNESEIKSNEEPLLRKSSRRFVTFPIQYPDIWKMYKQAQ ASFWTAEEVDLSKDLPHWNKLKADEKYFISHILAFFAASDG (amino acids −101 through −1 of SEQ ID NO: 358) |
| ID126 | MDAGLFSLLPHPPCVG (amino acids −16 through −1 of SEQ ID NO: 359) |
| ID127 | MLITLTYLIQGESA (amino acids −14 through −1 of SEQ ID NO: 360) |
| ID128 | MYTGFRIEATLLTRVQCLCAIPFAFS (amino acids −26 through −1 of SEQ ID NO: 361) |
| ID129 | MYKQAQASFWTAEEVDLSKDLPHWNKLKADEKYFISHILAFFAASDG (amino acids −47 through −1 of SEQ ID NO: 362) |
| ID130 | MLLHLCSVKNLYQNRFLGLAAMASPSRN (amino acids −28 through −1 of SEQ ID NO: 363) |
| ID131 | MPCPTWTCLKSFPSPTSS (amino acids −18 through −1 of SEQ ID NO: 364) |

TABLE III-continued

| SEQ. ID NO. | SIGNAL PEPTIDE |
|---|---|
| ID132 | MEDLFSPSIXPPAPNISVPILLGWGLNLTLGQG (amino acids −33 through −1 of SEQ ID NO: 365) |
| ID133 | MAETKDAAQMLVTFKDVAVTFTREEWRQLDLAQRTLYREVMLETCGLLVSLG (amino acids −52 through −1 of SEQ ID NO: 366) |
| ID134 | MLILSQNIAQLEA (amino acids −13 through −1 of SEQ ID NO: 367) |
| ID135 | MLLGASAQGLWAHSWTCSCSA (amino acids −21 through −1 of SEQ ID NO: 368) |
| ID136 | MAAPLELSCWGGGWG (amino acids −15 through −1 of SEQ ID NO: 369) |
| ID137 | MSXVGIDLGFLNCYIAVARS (amino acids −20 through −1 of SEQ ID NO: 370) |
| ID138 | MEYSTKXFVVFSTMFTASSP (amino acids −19 through −1 of SEQ ID NO: 371) |
| ID139 | MPMASSPPPSPHPQEPAPLLPSLPRLSLPFRLPWASTATA (amino acids −40 through −1 of SEQ ID NO: 372) |
| ID140 | MQHVXGHXPDPIAIMYVCPPCGHTTWALGLKFLSSSSQ (amino acids −38 through −1 of SEQ ID NO: 373) |
| ID141 | MGWEMTCIKSFFWARSHAGFLKCLLLSSLQ (amino acids −30 through −1 of SEQ ID NO: 374) |
| ID142 | MVFGGVCPSVTSIIAESLQGWNLVQLSFAATTPVLA (amino acids −36 through −1 of SEQ ID NO: 375) |
| ID143 | MHFITWSLLFLYQCSL (amino acids −16 through −1 of SEQ ID NO: 376) |
| ID144 | MSGASPIERTPMEEAPSSCPTSSCWFSVASPSSSWS (amino acids −36 through −1 of SEQ ID NO: 377) |
| ID145 | MEWAGKQRDFQVRAAPGWDHLASFPGPSLRLFSGSQA (amino acids −37 through −1 of SEQ ID NO: 378) |
| ID146 | MIAFFDEDNPRKRRSYSFTQSAGILCQETTYSTPHTKLEKAKSPTADAKVVSLSLQTSSA (amino acids −60 through −1 of SEQ ID NO: 379) |
| ID147 | MGKSIXSLCSVXLKARLKGXLEAVHLCLRAQKRRTALFCTLPCPVERG (amino acids −48 through −1 of SEQ ID NO: 380) |
| ID148 | MCLHMTLFRVPFTFS (amino acids −15 through −1 of SEQ ID NO: 381) |
| ID149 | MLNILKTLTSAALP (amino acids −14 through −1 of SEQ ID NO: 382) |
| ID150 | MRARVWPRSHGIPVPSFLSKSSLSHTPSPLLCLYHPPVYT (amino acids −40 through −1 of SEQ ID NO: 383) |
| ID151 | MWNAVAIICNGSWCQTXSTSGLESLCLSLLIPGPKP (amino acids −36 through −1 of SEQ ID NO: 384) |
| ID152 | MLRLGLFKISWARC (amino acids −14 through −1 of SEQ ID NO: 385) |
| ID153 | MPFAEDKTYKYICRNFSNFCNVDVVEILPYLPCLTA (amino acids −36 through −1 of SEQ ID NO: 386) |
| ID154 | MPGSSGLRFICKSRNHPQFGSFSGTDSLSFLPPCPC (amino acids −36 through −1 of SEQ ID NO: 387) |
| ID155 | MDVTGDEEEEIKQEINMLKKYSHHRNIATYYGAFIKKNPPGMDDQLXLVMEFCGAGS (amino acids −57 through −1 of SEQ ID NO: 388) |
| ID156 | MIFGLYFVLAVKLFLVFLLNICKG (amino acids −24 through −1 of SEQ ID NO: 389) |
| ID157 | MRKKRVEELIVFPGEVTSFSSIKCSSWISSLASG (amino acids −34 through −1 of SEQ ID NO: 390) |
| ID158 | MPSSSLAELCLMQQDACLFSXFLAVSRH (amino acids −26 through −1 of SEQ ID NO: 391) |
| ID159 | MDLWSCLFPVMLMEPSKGLEDSEWKMALQMRMQLPCLVLG (amino acids −40 through −1 of SEQ ID NO: 392) |
| ID160 | MSGKGKCRPIALRRAVPLPTTSTLTSA (amino acids −27 through −1 of SEQ ID NO: 393) |
| ID161 | MTPKAIQKSSGLFCPSQA (amino acids −18 through −1 of SEQ ID NO: 394) |
| ID162 | MPDQFDQAVVLNQLRYSGMLETVRIRKAGYAVRRPFQDFYKRYKVLMRNLALPEDVRGKC TSLLQLYDASNS (amino acids −72 through −1 of SEQ ID NO: 395) |
| ID163 | MCLVSFFLELNVLQQ (amino acids −15 through −1 of SEQ ID NO: 396) |
| ID164 | MRSLACLTPCGHA (amino acids −13 through −1 of SEQ ID NO: 397) |
| ID165 | MHLLSNWANPASS (amino acids −13 through −1 of SEQ ID NO: 398) |
| ID166 | MWSGKWALVSPFAMLHSVWRLIPA (amino acids −24 through −1 of SEQ ID NO: 399) |
| ID167 | MKVHMHTKFCLICLLTFIFH (amino acids −20 through −1 of SEQ ID NO: 400) |
| ID168 | MGRRHWVLTHSALSLFYTADTSHG (amino acids −24 through −1 of SEQ ID NO: 401) |
| ID169 | MAVFVVLLALVAGVLG (amino acids −16 through −1 of SEQ ID NO: 402) |
| ID170 | MAPLLLQLAVLGAALA (amino acids −16 through −1 of SEQ ID NO: 403) |
| ID171 | MPVTVTRTTITTTTTSSSGLGSPMIVGSPRALTQPLGLLRLLQLVSTCVA (amino acids −50 through −1 of SEQ ID NO: 404) |
| ID172 | MELVLVFLCSLLAPMVLA (amino acids −18 through −1 of SEQ ID NO: 405) |
| ID173 | MGPIWSSYYGNCRSLLFVMDASDPTQLSASCVQLLGLLSAEQLAEA (amino acids −46 through −1 of SEQ ID NO: 406) |
| ID174 | MSGGRAPAVLLGGVASLLLSFVWMPALLPVASRLLLLPRVLLTMASG (amino acids −47 through −1 of SEQ ID NO: 407) |
| ID175 | MALSCTLNRYLLLMAQEHLEFRLPEIXSLLLLFGGQFASS (amino acids −40 through −1 of SEQ ID NO: 408) |
| ID176 | MAARGVIAPVGESLRYAEYLQPSAKRPDADVDQQRLVRSLIAVGLGVAALAFA (amino acids −53 through −1 of SEQ ID NO: 409) |
| ID177 | MRMCAGSIYKSATQAVLGXLFLGGLCRG (amino acids −28 through −1 of SEQ ID NO: 410) |
| ID178 | MAERRRPLSPIPSXRRPSEPSRPRPAAAGXRSLPRPGDEELQLPCAVHDLIFWRDVKKTG FVFGTTLIMLLSWQLSVS (amino acids −78 through −1 of SEQ ID NO: 411) |

TABLE III-continued

| SEQ. ID NO. | SIGNAL PEPTIDE |
|---|---|
| ID179 | MAAPVLLRVSVPRWERVARYAVCAAGILLSIYAYHVEREKERDPEHRALCDLGPWVKCSA ALASRWGRGFGLLGSIFGKDGVLNQPNSVFGLIFYILQLLLGMTASAVA (amino acids −109 through −1 of SEQ ID NO: 412) |
| ID180 | MSFLQDPSFFTMGMWSIGAGALGAAALALLLANT (amino acids −34 through −1 of SEQ ID NO: 413) |
| ID181 | MASLLCCGPKLAACGIVLSAWGVIMLIMLGIFFNVHS (amino acids −37 through −1 of SEQ ID NO: 414) |
| ID182 | MILPYRMXSLFLHAVSSSFT (amino acids −20 through −1 of SEQ ID NO: 415) |
| ID183 | MATLVELPDSVLLEIFSYLPVRDRIRISRVCHRWKRLVDDRWLWRHVDLTLYTVRALAGR AWA (amino acids −63 through −1 of SEQ ID NO: 416) |
| ID184 | MKNACIVLPPTPPPSLQPSASLLAPNRFLFSCFCFLSHKFG (amino acids −41 through −1 of SEQ ID NO: 417) |
| ID185 | MAFGLQMFIQRKFPYPLQWSLLVAVVAG (amino acids −28 through −1 of SEQ ID NO: 418) |
| ID186 | MYCKILVLMLHTELIRTDYSSVDQLLLNYPAEEGLGRERSLLWTPLLSPGSLR (amino acids −53 through −1 of SEQ ID NO: 419) |
| ID187 | MAVSHSVKERTISENSLIILLQGLQG (amino acids −26 through −1 of SEQ ID NO: 420) |
| ID188 | MESGGRPSLCQFILLGTTSVVTA (amino acids −23 through −1 of SEQ ID NO: 421) |
| ID189 | MAALDLRAXWIRWSCSCLGXLXGAGGETNGVERPGGGGLALARQGSLRDGRQVGRAPAVC FPHGAPGLPPRQRXXGGXPEVQGGESWCPRPRGGGASRTGLRRRKGFTKTPEPESSEAPQ DPLNWFGILVPHSLRQAQA (amino acids −139 through −1 of SEQ ID NO: 422) |
| ID190 | MAFLPSPAWWISLLPSLLSIC (amino acids −21 through −1 of SEQ ID NO: 423) |
| ID191 | MEPKVAELKQKIEDTLCPFGFEVYPFQVAWYNELLPPAFHLPLPGPTLA (amino acids −49 through −1 of SEQ ID NO: 424) |
| ID192 | MLVLRSGLTKALA (amino acids −13 through −1 of SEQ ID NO: 425) |
| ID193 | MSGGHLADLTLLFVLLLFSLLPA (amino acids −23 through −1 of SEQ ID NO: 426) |
| ID194 | MKPSRTPARLWMLPQQQAGAVVVAAPTERHPTHHMAGWLLGALTLLGLVTS (amino acids −51 through −1 of SEQ ID NO: 427) |
| ID195 | MGESIPLAAPVPVEQAVLETFFSHLGIFSYDKAKDNVEKEREANKSAGGSWLSLLAALAH LAAA (amino acids −64 through −1 of SEQ ID NO: 428) |
| ID196 | MQMSYAIRCAFYQLLLAALMLVAMLQLLYLSLLSGLHG (amino acids −38 through −1 of SEQ ID NO: 429) |
| ID197 | MLRAELKIAVVLFAFHLLLSFILG (amino acids −24 through −1 of SEQ ID NO: 430) |
| ID198 | MNHQQTLIGRLLCDLHGLSLSPPVANNVQALFRMLTPEAYSCLLILLLRTFLCSA (amino acids −55 through −1 of SEQ ID NO: 431) |
| ID199 | MIITAVVSISVTIFCFQTKVDFTSCTGLFCVLGIVLLVTG (amino acids −40 through −1 of SEQ ID NO: 432) |
| ID200 | MAAGGRMEDGSLDITQSIEDDPLLDAQLLPHHSLQAHFRPRFHPLPTVIIVNLLWFIHLV FVVLX (amino acids −65 through −1 of SEQ ID NO: 433) |
| ID201 | MSPGCMLLFVFGFVGG (amino acids −16 through −1 of SEQ ID NO: 434) |
| ID202 | MKLLLGIALLAYVAS (amino acids −15 through −1 of SEQ ID NO: 435) |
| ID203 | MDILVPLLQLLVLLLTLPLHLHA (amino acids −23 through −1 of SEQ ID NO: 436) |
| ID204 | MEAASPSNSTGVERXADLMDADSLLLSLELASGSG (amino acids −35 through −1 of SEQ ID NO: 437) |
| ID205 | MIRQERSTSYQEAVRPALPSSKPCLLTSPAVLVKLLSSSASTS (amino acids −43 through −1 of SEQ ID NO: 438) |
| ID206 | MKLIDYGLSGYQEESAEVKAMDFITSTAILPLLFGCLGVFG (amino acids −41 through '1 of SEQ ID NO: 439) |
| ID207 | MRCLTTPMLLRALAQAARA (amino acids −19 through −1 of SEQ ID NO: 440) |
| ID208 | MSRFLNVLRSWLVMVSIIAMGNTLQSFRDHTFLYEKLYTGKPNLVNGLQARTFGIWTLLS SVIRCLC (amino acids −67 through −1 of SEQ ID NO: 441) |
| ID209 | MIFLTLSLDSRVSA (amino acids −14 through −1 of SEQ ID NO: 442) |
| ID210 | MQCFSFIKTMMILFNLLIFLCGAALLXVG (amino acids −29 through −1 of SEQ ID NO: 443) |
| ID211 | MAEAALEAVRXSYENSRPLQGSSACLLLCPTWTNP (amino acids −35 through −1 of SEQ ID NO: 444) |
| ID212 | MATASPSVFLLMVNGQVES (amino acids −19 through −1 of SEQ ID NO: 445) |
| ID213 | MAGIKALISLSFGGAIGLMFLMLGCALP (amino acids −28 through −1 of SEQ ID NO: 446) |
| ID214 | MIGDILLFGTLLMNAGA (amino acids −17 through −1 of SEQ ID NO: 447) |
| ID215 | MKTMILTLSLFGSCIS (amino acids −16 through −1 of SEQ ID NO: 448) |
| ID216 | MDWRVPPSXXDPGHQDIPLPVTXXFISVSVLSSLGIVLA (amino acids −39 through −1 of SEQ ID NO: 449) |
| ID217 | MAAAALPAWLSLQSRA (amino acids −16 through −1 of SEQ ID NO: 450) |
| ID218 | MAMVSAMSWVLYLWISACAMLLCHG (amino acids −25 through −1 of SEQ ID NO: 451) |
| ID219 | MGKEWGWQEMENGGAAPAWGAGPFVHPAPPPVEKTLSWGCGFGLHSGFGGSGGGVGLCRL LCLVRLFCC (amino acids −69 through −1 of SEQ ID NO: 452) |
| ID220 | MLQTSNYSLVLSLQFLLLSYD (amino acids −21 through −1 of SEQ ID NO: 453) |
| ID221 | MWFEILPGLSVMGVCLLIPGLATA (amino acids −24 through −1 of SEQ ID NO: 454) |
| ID222 | MRPSPLSGILADPLXLFPFSEG (amino acids −22 through −1 of SEQ ID NO: 455) |
| ID223 | MRESLSXRSWHLPASLMMAQXFIPAVA (amino acids −27 through −1 of SEQ ID NO: 456) |
| ID224 | MSGVVPTAPEQPAXEMENQTKPPDPRPDAPPEYSSHXFTRTPWKQLSLHLLATPACYG (amino acids −58 through −1 of SEQ ID NO: 457) |
| ID225 | MWRYQFGWGVITRGPREIPFPPSLLASESLLPPLPDLVLTCTSLGFVTRVWMSLNLNELS LYSRTWVFTCLVFFCFG (amino acids −77 through −1 of SEQ ID NO: 458) |

TABLE III-continued

| SEQ. ID NO. | SIGNAL PEPTIDE |
|---|---|
| ID226 | MVKLLVAKILCMVGVFFFMLLGSLLPVKI (amino acids −29 through −1 of SEQ ID NO: 459) |
| ID227 | MPVSIMCLIGLKANASS (amino acids −17 through −1 of SEQ ID NO: 460) |
| ID228 | MKVILLYLVLEKLVSRA (amino acids −17 through −1 of SEQ ID NO: 461) |
| ID229 | MAVTLSLLLGGRVCXPSLA (amino acids −19 through −1 of SEQ ID NO: 462) |
| ID230 | MLNQTSGRTSLLPELGVVTPAQG (amino acids −23 through −1 of SEQ ID NO: 463) |
| ID231 | MTSENLVQTAPKKKKNKGKKGLEPSQSTAAKVPKKAKTWIPEVHDQKADVSAWKDLFVPR PVLRALSFLGFSAPTPIQA (amino acids −79 through −1 of SEQ ID NO: 464) |
| ID232 | MAAFGRQXXXWHXLIPLTWACMA (amino acids −23 through −1 of SEQ ID NO: 465) |
| ID233 | MSLTSSPKKRRSICFDRFLMFQSQSGPSSLGESYRTGVGFLIPEGWFLSGCPHGSSA (amino acids −57 through −1 of SEQ ID NO: 466) |
| ID234 | MGELGNRSRCILFLSENPCLSESIFQSLXFCLSPPPSPS (amino acids −39 through −1 of SEQ ID NO: 467) |
| ID235 | MAELGLNEHHQNEVINYMRFARSKRGLRLKTVDSCFQDLKESRLVEDTFTIDEVSEVLNG LQAVVHSEVESELINTAYTNVLLLRQXFAQAEK (amino acids −93 through −1 of SEQ ID NO: 468) |
| ID236 | MVTLPSGTWAFSCPYLALVDGGMLGSAREDAHASVVSWAVGLLYAVAQG (amino acids −49 through −1 of SEQ ID NO: 469) |
| ID237 | MASASARGNQDKDAHFPPPSKQSLLFCPKXXLHIHRAEISKIMRECQEESFWKRALPFSL VSMLVTQG (amino acids −68 through −1 of SEQ ID NO: 470) |
| ID238 | MLLMKSILLKVVCVLCIYLKFKLMALIYVPDKNNTNNNILRYNHNEISIGISVQCHFILS LCVLCIVLT (amino acids −69 through −1 of SEQ ID NO: 471) |
| ID239 | MAQRLLLRRFLASVIS (amino acids −16 through −1 of SEQ ID NO: 472) |
| ID240 | MAASKVKQDMPPXGGYGPIDYKRNLPRRGLSGYSMLAIGIGTLIYGHWSIMKWNRERRRL QIEDFEARIALLPLLQA (amino acids −77 through −1 of SEQ ID NO: 473) |
| ID241 | MRHLVTEELFPCSNLEDVVEDNSHSYFTLRITMACKGVPSTLLSLAILSHISTP (amino acids −54 through −1 of SEQ ID NO: 474) |
| ID242 | MSAEVKVTGQNQEQFLLLAKSAKGAALATLIHQVLEAPGVYVFGELLDMPNVRELAESXF ASTFRLLXVFAYGTYA (amino acids −76 through −1 of SEQ ID NO: 475) |
| ID243 | MLLSIGMLMLSATQVXTILXVQLFAFLNLLPVEA (amino acids −34 through −1 of SEQ ID NO: 476) |
| ID244 | MGWEVVSLSYCGVSWG (amino acids −16 through −1 of SEQ ID NO: 477) |
| ID245 | MRECISVHVGQAGVQIGNACWELFCLEHGIQA (amino acids −32 through −1 of SEQ ID NO: 478) |
| ID246 | MAGPLQGGGARALDLLRGLPRVSLA (amino acids −25 through −1 of SEQ ID NO: 479) |
| ID247 | MPAGVPMSTYLKMFAASXLAMCAGA (amino acids −25 through −1 of SEQ ID NO: 480) |
| ID248 | MAVQCVRLARRSLPALALSLRASP (amino acids −24 through −1 of SEQ ID NO: 481) |
| ID249 | MFSIISRSRACSMYFKENAKPSQLRLMHHYLSTPTSA (amino acids −37 through −1 of SEQ ID NO: 482) |
| ID250 | MKRLLPATSLAGPVLS (amino acids −16 through −1 of SEQ ID NO: 483) |
| ID251 | MLIITNPWPKYFDAAGRLTPEFSQRLTNKIRELLQQMERGLKSADXXDGTGYTGWAGIAV LYLHLYDVFG (amino acids −70 through −1 of SEQ ID NO: 494) |
| ID252 | MCATETVRAWLAQGSSSAGWG (amino acids −21 through −1 of SEQ ID NO: 485) |
| ID253 | MLLLATHPETVGQVTLRVXPVSLEVSIQMCAAAAAAFCLKXXGANT (amino acids −46 through −1 of SEQ ID NO: 486) |
| ID254 | MAASSATPAPXXSQRCGADAGSAARIVFRWGRGRRGARSPEGSGHHGRANSGLGGAQLQG GAXG (amino acids −64 through −1 of SEQ ID NO: 487) |
| ID255 | MLRRPLAGLAAAALGRA (amino acids −17 through −1 of SEQ ID NO: 488) |
| ID256 | MDRPGFVAALVAGGVAG (amino acids −17 through −1 of SEQ ID NO: 489) |
| ID257 | MIVWFEGISMDLLTLLFQRRS (amino acids −21 through −1 of SEQ ID NO: 490) |
| ID258 | MRTFVHFALDALMFPARRRA (amino acids −20 through −1 of SEQ ID NO: 491) |
| ID259 | MAAPPQLRALLVVVNALLRKRRYHAALAVLKGFRNGAVYGAKIRAPHALVMTFLFRNGSL Q (amino acids −61 through −1 of SEQ ID NO: 492) |
| ID260 | MPVDLGXALGLLPSLAKA (amino acids −18 through −1 of SEQ ID NO: 493) |
| ID261 | MNLFIMYMAGNTISIFPTMMVCMMAWRPIQALMAISATFKMLESSSQKFLQGLVYLIGNL MGLALAVYKCQS (amino acids −72 through −1 of SEQ ID NO: 494) |
| ID262 | MISLTDTQKIGMGLTGFGVFFLFFGMILFFDKALLAIGNVLFVAGLAFVIG (amino acids −51 through −1 of SEQ ID NO: 495) |
| ID263 | MAASGAPRILVDLLKLXVAPLAVFQMLKSMCAG (amino acids −33 through −1 of SEQ ID NO: 496) |
| ID264 | MASVSSATFSGHGARSLLQFLRLVGQ (amino acids −26 through −1 of SEQ ID NO: 497) |
| ID265 | MWYLAVLLVLFTLNIL (amino acids −16 through −1 of SEQ ID NO: 498) |
| ID266 | MFTFGRLFQIITVVTCLQFIQDCCIHSRQINSLLEXSSLSRC (amino acids −42 through −1 of SEQ ID NO: 499) |
| ID267 | MIQDRDRCAQAAAVAAVGNLEPRGTPGPEDEAFCLPGCVGTLCQLDWWIWG (amino acids −51 through −1 of SEQ ID NO: 500) |
| ID268 | MKIIFPILSNPVFRRTVKLLLCLLWIGYSQG (amino acids −31 through −1 of SEQ ID NO: 501) |
| ID269 | MVSRMVSTMLSGLLFWLASGWTPAFA (amino acids −26 through −1 of SEQ ID NO: 502) |
| ID270 | MTATLAAAADIATMVSGSSGLAXA (amino acids −24 through −1 of SEQ ID NO: 503) |

What is claimed is:

1. A purified polynucleotide encoding a polypeptide comprising:
   (a) a first nucleic acid sequence encoding the amino acid sequence of SEQ ID NO: 271 or a fragment of SEQ ID NO: 271 which comprises amino acids −14 to −1; and
   (b) a second nucleic acid encoding a polypeptide that is heterologous to the polypeptide encoded by the gene corresponding to SEQ ID NO: 38, said second nucleic acid being fused in frame to the nucleic acid sequence of (a).

2. The purified polynucleotide of claim 1 wherein the nucleic acid sequence of (a) is a nucleic acid sequence encoding amino acids −14 to −1 of SEQ ID NO: 271.

3. A purified polynucleotide encoding a polypeptide comprising:

(a) a first nucleic acid sequence encoding the amino acid sequence of SEQ ID NO: 273 or a fragment of SEQ ID NO: 273 which comprises amino acids −126 to −1; and (b) a second nucleic acid encoding a polypeptide that is heterologous to the polypeptide encoded by the gene corresponding to SEQ ID NO: 40, said second nucleic acid being fused in frame to the nucleic acid sequence of (a).

4. The purified polynucleotide of claim 3 wherein the nucleic acid sequence of (a) is a nucleic acid sequence encoding amino acids −126 to −1 of SEQ ID NO: 273.

5. A purified polynucleotide encoding a polypeptide comprising:

(a) a first nucleic acid sequence encoding the amino acid sequence of SEQ ID NO: 276 or a fragment of SEQ ID NO: 276 which comprises amino acids −24 to −1; and (b) a second nucleic acid encoding a polypeptide that is heterologous to the polypeptide encoded by the gene corresponding to SEQ ID NO: 43, said second nucleic acid being fused in frame to the nucleic acid sequence of (a).

6. The purified polynucleotide of claim 5 wherein the nucleic acid sequence of (a) is a nucleic acid sequence encoding amino acids −24 to −1 of SEQ ID NO: 276.

7. A purified polynucleotide encoding a polypeptide comprising:

(a) a first nucleic acid sequence encoding the amino acid sequence of SEQ ID NO: 283 or a fragment of SEQ ID NO: 283 which comprises amino acids −16 to −1; and (b) a second nucleic acid encoding a polypeptide that is heterologous to the polypeptide encoded by the gene corresponding to SEQ ID NO: 50, said second nucleic acid being fused in frame to the nucleic acid sequence of (a).

8. The purified polynucleotide of claim 7, wherein the nucleic acid sequence of (a) is a nucleic acid sequence encoding amino acids −16 to −1 of SEQ ID NO: 283.

9. A purified polynucleotide encoding a polypeptide comprising:

(a) a first nucleic acid sequence encoding the amino acid sequence of SEQ ID NO: 292 or a fragment of SEQ ID NO: 292 which comprises amino acids −80 to −1; and (b) a second nucleic acid encoding a polypeptide that is heterologous to the polypeptide encoded by the gene corresponding to SEQ ID NO: 59, said second nucleic acid being fused in frame to the nucleic acid sequence of (a).

10. The purified polynucleotide of claim 9 wherein the nucleic acid sequence of (a) is a nucleic acid sequence encoding amino acids −80 to −1 of SEQ ID NO: 292.

11. A purified polynucleotide encoding a polypeptide comprising:

(a) a first nucleic acid sequence encoding the amino acid sequence of SEQ ID NO: 305 or a fragment of SEQ ID NO: 305 which comprises amino acids −21 to −1; and (b) a second nucleic acid encoding a polypeptide that is heterologous to the polypeptide encoded by the gene corresponding to SEQ ID NO: 72, said second nucleic acid being fused in frame to the nucleic acid sequence of (a).

12. The purified polynucleotide of claim 11 wherein the nucleic acid sequence of (a) is a nucleic acid sequence encoding amino acids −21 to −1 of SEQ ID NO: 305.

13. A purified polynucleotide encoding a polypeptide comprising:

(a) a first nucleic acid sequence encoding the amino acid sequence of SEQ ID NO: 318 or a fragment of SEQ ID NO: 318 which comprises amino acids −17 to −1; and (b) a second nucleic acid encoding a polypeptide that is heterologous to the polypeptide encoded by the gene corresponding to SEQ ID NO: 85, said second nucleic acid being fused in frame to the nucleic acid sequence of (a).

14. The purified polynucleotide of claim 13 wherein the nucleic acid sequence of (a) is a nucleic acid sequence encoding amino acids −17 to −1 of SEQ ID NO: 318.

15. A purified polynucleotide encoding a polypeptide comprising:

(a) a first nucleic acid sequence encoding the amino acid sequence of SEQ ID NO: 337 or a fragment of SEQ ID NO: 337 which comprises amino acids −16 to −1; and (b) a second nucleic acid encoding a polypeptide that is heterologous to the polypeptide encoded by the gene corresponding to SEQ ID NO: 104, said second nucleic acid being fused in frame to the nucleic acid sequence of (a).

16. The purified polynucleotide of claim 15 wherein the nucleic acid sequence of (a) is a nucleic acid sequence encoding amino acids −16 to −1 of SEQ ID NO: 337.

17. A purified polynucleotide encoding a polypeptide comprising:

(a) a first nucleic acid sequence encoding the amino acid sequence of SEQ ID NO: 364 or a fragment of SEQ ID NO: 364 which comprises amino acids −18 to −1; and (b) a second nucleic acid encoding a polypeptide that is heterologous to the polypeptide encoded by the gene corresponding to SEQ ID NO: 131, said second nucleic acid being fused in frame to the nucleic acid sequence of (a).

18. The purified polynucleotide of claim 17 wherein the nucleic acid sequence of (a) is a nucleic acid sequence encoding amino acids −18 to −1 of SEQ ID NO: 364.

19. A purified polynucleotide encoding a polypeptide comprising:

(a) a first nucleic acid sequence encoding the amino acid sequence of SEQ ID NO: 399 or a fragment of SEQ ID NO: 399 which comprises amino acids −24 to −1; and (b) a second nucleic acid encoding a polypeptide that is heterologous to the polypeptide encoded by the gene corresponding to SEQ ID NO: 166, said second nucleic acid being fused in frame to the nucleic acid sequence of (a).

20. The purified polynucleotide of claim 19 wherein the nucleic acid sequence of (a) is a nucleic acid sequence encoding amino acids −24 to −1 of SEQ ID NO: 399.

* * * * *

SEQUENCE LISTING (1) GENERAL INFORMATION:

(iii) NUMBER OF SEQUENCES: 503

(2) INFORMATION FOR SEQ ID NO: 1:

(i) SEQUENCE CHARACTERISTICS:
       (A) LENGTH: 47 base pairs
       (B) TYPE: NUCLEIC ACID
       (C) STRANDEDNESS: SINGLE
       (D) TOPOLOGY: LINEAR (ii) MOLECULE TYPE: Other nucleic acid (ix) FEATURE:
       (A) NAME/KEY: Cap
       (B) LOCATION: 1
       (D) OTHER INFORMATION: m7Gppp added to 1

(xi) SEQUENCE DESCRIPTION: SEQ ID NO: 1:

GGCAUCCUAC UCCCAUCCAA UUCCACCCUA ACUCCUCCCA UCUCCAC                47

(2) INFORMATION FOR SEQ ID NO: 2:

(i) SEQUENCE CHARACTERISTICS:
       (A) LENGTH: 46 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 2:

GCAUCCUACU CCCAUCCAAU UCCACCCUAA CUCCUCCCAU CUCCAC                 46

(2) INFORMATION FOR SEQ ID NO: 3:

(i) SEQUENCE CHARACTERISTICS:
       (A) LENGTH: 25 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 3:

ATCAAGAATT CGCACGAGAC CATTA                                        25

(2) INFORMATION FOR SEQ ID NO: 4:

(i) SEQUENCE CHARACTERISTICS:
       (A) LENGTH: 25 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 4:

TAATGGTCTC GTGCGAATTC TTGAT                                        25

(2) INFORMATION FOR SEQ ID NO: 5:

(i) SEQUENCE CHARACTERISTICS:
       (A) LENGTH: 25 base pairs
       (B) TYPE: NUCLEIC ACID
       (C) STRANDEDNESS: SINGLE (D) TOPOLOGY: LINEAR (ii) MOLECULE TYPE: Other nucleic acid (xi) SEQUENCE DESCRIPTION: SEQ ID NO: 5:

CCGACAAGAC CAACGTCAAG GCCGC                                25

(2) INFORMATION FOR SEQ ID NO: 6:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 6:

TCACCAGCAG GCAGTGGCTT AGGAG                                25

(2) INFORMATION FOR SEQ ID NO: 7:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 7:

AGTGATTCCT GCTACTTTGG ATGGC                                25

(2) INFORMATION FOR SEQ ID NO: 8:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 8:

GCTTGGTCTT GTTCTGGAGT TTAGA                                25

(2) INFORMATION FOR SEQ ID NO: 9:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 9:

TCCAGAATGG GAGACAAGCC AATTT                                25

(2) INFORMATION FOR SEQ ID NO: 10:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 10:

AGGGAGGAGG AAACAGCGTG AGTCC                                           25

(2) INFORMATION FOR SEQ ID NO: 11:

(i) SEQUENCE CHARACTERISTICS:
       (A) LENGTH: 25 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 11:

ATGGGAAAGG AAAAGACTCA TATCA                                           25

(2) INFORMATION FOR SEQ ID NO: 12:

(i) SEQUENCE CHARACTERISTICS:
       (A) LENGTH: 25 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 12:

AGCAGCAACA ATCAGGACAG CACAG                                           25

(2) INFORMATION FOR SEQ ID NO: 13:

(i) SEQUENCE CHARACTERISTICS:
       (A) LENGTH: 25 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 13:

ATCAAGAATT CGCACGAGAC CATTA                                           25

(2) INFORMATION FOR SEQ ID NO: 14:

(i) SEQUENCE CHARACTERISTICS:
       (A) LENGTH: 67 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 14:

ATCGTTGAGA CTCGTACCAG CAGAGTCACG AGAGAGACTA CACGGTACTG GTTTTTTTTT     60

TTTTTVN                                                               67

(2) INFORMATION FOR SEQ ID NO: 15:

(i) SEQUENCE CHARACTERISTICS:
       (A) LENGTH: 29 base pairs
       (B) TYPE: NUCLEIC ACID
       (C) STRANDEDNESS: SINGLE
       (D) TOPOLOGY: LINEAR (ii) MOLECULE TYPE: Other nucleic acid (xi) SEQUENCE DESCRIPTION: SEQ ID NO: 15:

```
CCAGCAGAGT CACGAGAGAG ACTACACGG                                              29

(2) INFORMATION FOR SEQ ID NO: 16:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 16:

CACGAGAGAG ACTACACGGT ACTGG                                                  25

(2) INFORMATION FOR SEQ ID NO: 17:

(i) SEQUENCE CHARACTERISTICS:
        (A) LENGTH: 526 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Lymph ganglia (ix) FEATURE:
        (A) NAME/KEY: other
        (B) LOCATION: complement(261..376)
        (C) IDENTIFICATION METHOD: blastn
        (D) OTHER INFORMATION:  identity 96 region 166..281 id N70479
            est (ix) FEATURE:
        (A) NAME/KEY: other
        (B) LOCATION: complement(380..486)
        (C) IDENTIFICATION METHOD: blastn
        (D) OTHER INFORMATION:  identity 97 region 54..160 id N70479
            est (ix) FEATURE:
        (A) NAME/KEY: other
        (B) LOCATION: complement(110..145)
        (C) IDENTIFICATION METHOD: blastn
        (D) OTHER INFORMATION:  identity 94 region 403..438 id N70479
            est (ix) FEATURE:
        (A) NAME/KEY: other
        (B) LOCATION: complement(196..229)
        (C) IDENTIFICATION METHOD: blastn
        (D) OTHER INFORMATION:  identity 94 region 315..348 id N70479
            est (ix) FEATURE:
        (A) NAME/KEY: sig_peptide
        (B) LOCATION: 90..140
        (C) IDENTIFICATION METHOD: Von Heijne matrix
        (D) OTHER INFORMATION:  score 8.2 seq LLLITAILAVAVG/FP (xi) SEQUENCE DESCRIPTION: SEQ ID NO: 17:

AATATRARAC AGCTACAATA TTCCAGGGCC ARTCACTTGC CATTTCTCAT AACAGCGTCA             60

GAGAGAAAGA ACTGACTGAR ACGTTTGAG ATG AAG AAA GTT CTC CTC CTG ATC             113
                                 Met Lys Lys Val Leu Leu Leu Ile
                                     -15                     -10

ACA GCC ATC TTG GCA GTG GCT GTW GGT TTC CCA GTC TCT CAA GAC CAG             161
Thr Ala Ile Leu Ala Val Ala Val Gly Phe Pro Val Ser Gln Asp Gln
            -5                  1                   5

GAA CGA GAA AAA AGA AGT ATC AGT GAC AGC GAT GAA TTA GCT TCA GGR             209
```

```
Glu Arg Glu Lys Arg Ser Ile Ser Asp Ser Asp Glu Leu Ala Ser Gly
         10                  15                  20

WTT TTT GTG TTC CCT TAC CCA TAT CCA TTT CGC CCA CTT CCA CCA ATT    257
Xaa Phe Val Phe Pro Tyr Pro Tyr Pro Phe Arg Pro Leu Pro Pro Ile
    25                  30                  35

CCA TTT CCA AGA TTT CCA TGG TTT AGA CGT AAN TTT CCT ATT CCA ATA    305
Pro Phe Pro Arg Phe Pro Trp Phe Arg Arg Xaa Phe Pro Ile Pro Ile
40                  45                  50                  55

CCT GAA TCT GCC CCT ACA ACT CCC CTT CCT AGC GAA AAG TAAACAARAA     354
Pro Glu Ser Ala Pro Thr Thr Pro Leu Pro Ser Glu Lys
                60                  65

GGAAAAGTCA CRATAAACCT GGTCACCTGA AATTGAAATT GAGCCACTTC CTTGAARAAT  414

CAAAATTCCT GTTAATAAAA RAAAAACAAA TGTAATTGAA ATAGCACACA GCATTCTCTA  474

GTCAATATCT TTAGTGATCT TCTTTAATAA ACATGAAAGC AAAAAAAAAA AA          526

(2) INFORMATION FOR SEQ ID NO: 18:

(i) SEQUENCE CHARACTERISTICS:
        (A) LENGTH: 17 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (ix) FEATURE:
        (A) NAME/KEY: sig_peptide
        (B) LOCATION: 1..17
        (C) IDENTIFICATION METHOD: Von Heijne matrix
        (D) OTHER INFORMATION:  score 8.2 seq LLLITAILAVAVG/FP (xi) SEQUENCE DESCRIPTION: SEQ ID NO: 18:

Met Lys Lys Val Leu Leu Leu Ile Thr Ala Ile Leu Ala Val Ala Val
 1               5                  10                  15
Gly (2) INFORMATION FOR SEQ ID NO: 19:

(i) SEQUENCE CHARACTERISTICS:
        (A) LENGTH: 822 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (D) DEVELOPMENTAL STAGE: Fetal
        (F) TISSUE TYPE: kidney (ix) FEATURE:
        (A) NAME/KEY: other
        (B) LOCATION: 260..464
        (C) IDENTIFICATION METHOD: blastn
        (D) OTHER INFORMATION:  identity 96 region 153..357 id H57434
            est (ix) FEATURE:
        (A) NAME/KEY: other
        (B) LOCATION: 118..184
        (C) IDENTIFICATION METHOD: blastn
        (D) OTHER INFORMATION:  identity 98 region 98..164 id H57434
            est (ix) FEATURE:
        (A) NAME/KEY: other
```

(B) LOCATION: 56..113
            (C) IDENTIFICATION METHOD: blastn
            (D) OTHER INFORMATION: identity 98 region 35..92 id H57434
                est (ix) FEATURE:
            (A) NAME/KEY: other
            (B) LOCATION: 454..485
            (C) IDENTIFICATION METHOD: blastn
            (D) OTHER INFORMATION: identity 100 region 348..379 id H57434
                est (ix) FEATURE:
            (A) NAME/KEY: other
            (B) LOCATION: 118..545
            (C) IDENTIFICATION METHOD: blastn
            (D) OTHER INFORMATION: identity 98 region 1..428 id N27248
                est (ix) FEATURE:
            (A) NAME/KEY: other
            (B) LOCATION: 65..369
            (C) IDENTIFICATION METHOD: blastn
            (D) OTHER INFORMATION: identity 98 region 41..345 id H94779
                est (ix) FEATURE:
            (A) NAME/KEY: other
            (B) LOCATION: 61..399
            (C) IDENTIFICATION METHOD: blastn
            (D) OTHER INFORMATION: identity 99 region 6..344 id H09880
                est (ix) FEATURE:
            (A) NAME/KEY: other
            (B) LOCATION: 408..458
            (C) IDENTIFICATION METHOD: blastn
            (D) OTHER INFORMATION: identity 92 region 355..405 id H09880
                est (ix) FEATURE:
            (A) NAME/KEY: other
            (B) LOCATION: 60..399
            (C) IDENTIFICATION METHOD: blastn
            (D) OTHER INFORMATION: identity 97 region 56..395 id H29351
                est (ix) FEATURE:
            (A) NAME/KEY: other
            (B) LOCATION: 393..432
            (C) IDENTIFICATION METHOD: blastn
            (D) OTHER INFORMATION: identity 90 region 391..430 id H29351
                est (ix) FEATURE:
            (A) NAME/KEY: sig_peptide
            (B) LOCATION: 346..408
            (C) IDENTIFICATION METHOD: Von Heijne matrix
            (D) OTHER INFORMATION: score 5.5 seq SFLPSALVIWTSA/AF (xi) SEQUENCE DESCRIPTION: SEQ ID NO: 19:

```
ACTCCTTTTA GCATAGGGGC TTCGGCGCCA GCGGCCAGCG CTAGTCGGTC TGGTAAGTGC      60

CTGATGCCGA GTTCCGTCTC TCGCGTCTTT TCCTGGTCCC AGGCAAAGCG GASGNAGATC     120

CTCAAACGGC CTAGTGCTTC GCGCTTCCGG AGAAAATCAG CGGTCTAATT AATTCCTCTG     180

GTTTGTTGAA GCAGTTACCA AGAATCTTCA ACCCTTTCCC ACAAAAGCTA ATTGAGTACA     240

CGTTCCTGTT GAGTACACGT TCCTGTTGAT TTACAAAAGG TGCAGGTATG AGCAGGTCTG     300

AAGACTAACA TTTTGTGAAG TTGTAAAACA GAAAACCTGT TAGAA ATG TGG TGG TTT     357
                                              Met Trp Trp Phe
                                              -20

CAG CAA GGC CTC AGT TTC CTT CCT TCA GCC CTT GTA ATT TGG ACA TCT       405
Gln Gln Gly Leu Ser Phe Leu Pro Ser Ala Leu Val Ile Trp Thr Ser
    -15                 -10                  -5
```

```
GCT GCT TTC ATA TTT TCA TAC ATT ACT GCA GTA ACA CTC CAC CAT ATA    453
Ala Ala Phe Ile Phe Ser Tyr Ile Thr Ala Val Thr Leu His His Ile
 1               5                  10                  15

GAC CCG GCT TTA CCT TAT ATC AGT GAC ACT GGT ACA GTA GCT CCA RAA    501
Asp Pro Ala Leu Pro Tyr Ile Ser Asp Thr Gly Thr Val Ala Pro Xaa
                20                  25                  30

AAA TGC TTA TTT GGG GCA ATG CTA AAT ATT GCG GCA GTT TTA TGT CAA    549
Lys Cys Leu Phe Gly Ala Met Leu Asn Ile Ala Ala Val Leu Cys Gln
                35                  40                  45

AAA TAGAAATCAG GAARATAATT CAACTTAAAG AAKTTCATTT CATGACCAAA         602
Lys

CTCTTCARAA ACATGTCTTT ACAAGCATAT CTCTTGTATT GCTTTCTACA CTGTTGAATT   662

GTCTGGCAAT ATTTCTGCAG TGGAAAATTT GATTTARMTA GTTCTTGACT GATAAATATG   722

GTAAGGTGGG CTTTTCCCCC TGTGTAATTG GCTACTATGT CTTACTGAGC CAAGTTGTAW   782

TTTGAAATAA AATGATATGA GAGTGACACA AAAAAAAAA                         822

(2) INFORMATION FOR SEQ ID NO: 20:

(i) SEQUENCE CHARACTERISTICS:
        (A) LENGTH: 21 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens (ix) FEATURE:
         (A) NAME/KEY: sig_peptide
         (B) LOCATION: 1..21
         (C) IDENTIFICATION METHOD: Von Heijne matrix
         (D) OTHER INFORMATION:  score 5.5 seq SFLPSALVIWTSA/AF (xi) SEQUENCE DESCRIPTION: SEQ ID NO: 20:

Met Trp Trp Phe Gln Gln Gly Leu Ser Phe Leu Pro Ser Ala Leu Val
 1               5                  10                  15

Ile Trp Thr Ser Ala
            20

(2) INFORMATION FOR SEQ ID NO: 21:

(i) SEQUENCE CHARACTERISTICS:
        (A) LENGTH: 405 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
         (A) ORGANISM: Homo Sapiens
         (F) TISSUE TYPE: Testis (ix) FEATURE:
         (A) NAME/KEY: other
         (B) LOCATION: complement(103..398)
         (C) IDENTIFICATION METHOD: blastn
         (D) OTHER INFORMATION:  identity 96 region 1..296 id AA442893
             est (ix) FEATURE:
         (A) NAME/KEY: sig_peptide
         (B) LOCATION: 185..295
         (C) IDENTIFICATION METHOD: Von Heijne matrix
         (D) OTHER INFORMATION:  score 5.9 seq LSYASSALSPCLT/AP
```

-continued (xi) SEQUENCE DESCRIPTION: SEQ ID NO: 21:

```
ATCACCTTCT TCTCCATCCT TSTCTGGGCC AGTCCCCARC CCAGTCCCTC TCCTGACCTG      60

CCCAGCCCAA GTCAGCCTTC AGCACGCGCT TTTCTGCACA CAGATATTCC AGGCCTACCT     120

GGCATTCCAG GACCTCCGMA ATGATGCTCC AGTCCCTTAC AAGCGCTTCC TGGATGAGGG     180

TGGC ATG GTG CTG ACC ACC CTC CCC TTG CCC TCT GCC AAC AGC CCT GTG     229
     Met Val Leu Thr Thr Leu Pro Leu Pro Ser Ala Asn Ser Pro Val
         -35                 -30                 -25

AAC ATG CCC ACC ACT GGC CCC AAC AGC CTG AGT TAT GCT AGC TCT GCC      277
Asn Met Pro Thr Thr Gly Pro Asn Ser Leu Ser Tyr Ala Ser Ser Ala
        -20                 -15                 -10

CTG TCC CCC TGT CTG ACC GCT CCA AAK TCC CCC CGG CTT GCT ATG ATG      325
Leu Ser Pro Cys Leu Thr Ala Pro Xaa Ser Pro Arg Leu Ala Met Met
     -5                   1                   5                  10

CCT GAC AAC TAAATATCCT TATCCAAATC AATAAARWRA RAATCCTCCC TCCARAAGGG    384
Pro Asp Asn

TTTCTAAAAA CAAAAAAAAA A                                              405
```

(2) INFORMATION FOR SEQ ID NO: 22:

(i) SEQUENCE CHARACTERISTICS:
        (A) LENGTH: 37 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (ix) FEATURE:
        (A) NAME/KEY: sig_peptide
        (B) LOCATION: 1..37
        (C) IDENTIFICATION METHOD: Von Heijne matrix
        (D) OTHER INFORMATION: score 5.9 seq LSYASSALSPCLT/AP (xi) SEQUENCE DESCRIPTION: SEQ ID NO: 22:

```
Met Val Leu Thr Thr Leu Pro Leu Pro Ser Ala Asn Ser Pro Val Asn
 1               5                  10                  15

Met Pro Thr Thr Gly Pro Asn Ser Leu Ser Tyr Ala Ser Ser Ala Leu
            20                  25                  30

Ser Pro Cys Leu Thr
        35
```

(2) INFORMATION FOR SEQ ID NO: 23:

(i) SEQUENCE CHARACTERISTICS:
        (A) LENGTH: 496 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Cancerous prostate (ix) FEATURE:
        (A) NAME/KEY: other
        (B) LOCATION: 149..331
        (C) IDENTIFICATION METHOD: blastn
        (D) OTHER INFORMATION: identity 98 region 1..183 id AA397994
            est (ix) FEATURE:
        (A) NAME/KEY: other (B) LOCATION: 328..485
              (C) IDENTIFICATION METHOD: blastn
              (D) OTHER INFORMATION: identity 96 region 179..336 id
                  AA397994 est (ix) FEATURE:
              (A) NAME/KEY: other
              (B) LOCATION: complement(182..496)
              (C) IDENTIFICATION METHOD: blastn
              (D) OTHER INFORMATION: identity 97 region 14..328 id AA399680
                  est (ix) FEATURE:
              (A) NAME/KEY: sig_peptide
              (B) LOCATION: 196..240
              (C) IDENTIFICATION METHOD: Von Heijne matrix
              (D) OTHER INFORMATION: score 5.5 seq ILSTVTALTFAXA/LD (xi) SEQUENCE DESCRIPTION: SEQ ID NO: 23:

AAAAAATTGG TCCCAGTTTT CACCCTGCCG CAGGGCTGGC TGGGGAGGGC AGCGGTTTAG      60

ATTAGCCGTG GCCTAGGCCG TTTAACGGGG TGACACGAGC NTGCAGGGCC GAGTCCAAGG    120

CCCGGAGATA GGACCAACCG TCAGGAATGC GAGGAATGTT TTTCTTCGGA CTCTATCGAG    180

GCACACAGAC AGACC ATG GGG ATT CTG TCT ACA GTG ACA GCC TTA ACA TTT    231
                Met Gly Ile Leu Ser Thr Val Thr Ala Leu Thr Phe
                    -15              -10               -5

GCC ARA GCC CTG GAC GGC TGC AGA AAT GGC ATT GCC CAC CCT GCA AGT    279
Ala Xaa Ala Leu Asp Gly Cys Arg Asn Gly Ile Ala His Pro Ala Ser
 1           5                        10

GAG AAG CAC AGA CTC GAG AAA TGT AGG GAA CTC GAG ASC ASC CAC TCG    327
Glu Lys His Arg Leu Glu Lys Cys Arg Glu Leu Glu Xaa Xaa His Ser
 15               20                    25

GCC CCA GGA TCA ACC CAS CAC CGA AGA AAA ACA ACC AGA AGA AAT TAT    375
Ala Pro Gly Ser Thr Xaa His Arg Arg Lys Thr Thr Arg Arg Asn Tyr
 30              35                   40                   45

TCT TCA GCC TGAAATGAAK CCGGGATCAA ATGGTTGCTG ATCARAGCCC ATATTTAAAT    434
Ser Ser Ala

TGGAAAAGTC AAATTGASCA TTATTAAATA AAGCTTGTTT AATATGTCTC AAACAAAAAA    494

AA                                                                   496

(2) INFORMATION FOR SEQ ID NO: 24:

(i) SEQUENCE CHARACTERISTICS:
              (A) LENGTH: 15 amino acids
              (B) TYPE: AMINO ACID
              (D) TOPOLOGY: LINEAR (ii) MOLECULE TYPE: PROTEIN (vi) ORIGINAL SOURCE:
              (A) ORGANISM: Homo Sapiens (ix) FEATURE:
              (A) NAME/KEY: sig_peptide
              (B) LOCATION: 1..15
              (C) IDENTIFICATION METHOD: Von Heijne matrix
              (D) OTHER INFORMATION: score 5.5 seq ILSTVTALTFAXA/LD (xi) SEQUENCE DESCRIPTION: SEQ ID NO: 24:

Met Gly Ile Leu Ser Thr Val Thr Ala Leu Thr Phe Ala Xaa Ala
 1               5                   10                  15

(2) INFORMATION FOR SEQ ID NO: 25:

(i) SEQUENCE CHARACTERISTICS:
              (A) LENGTH: 623 base pairs
              (B) TYPE: NUCLEIC ACID (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Testis (ix) FEATURE:
        (A) NAME/KEY: sig_peptide
        (B) LOCATION: 49..96
        (C) IDENTIFICATION METHOD: Von Heijne matrix
        (D) OTHER INFORMATION:   score 10.1 seq LVLTLCTLPLAVA/SA (xi) SEQUENCE DESCRIPTION: SEQ ID NO: 25:

```
AAAGATCCCT GCAGCCCGGC AGGAGAGAAG GCTGAGCCTT CTGGCGTC ATG GAG AGG          57
                                                     Met Glu Arg
                                                         -15

CTC GTC CTA ACC CTG TGC ACC CTC CCG CTG GCT GTG GCG TCT GCT GGC          105
Leu Val Leu Thr Leu Cys Thr Leu Pro Leu Ala Val Ala Ser Ala Gly
            -10                 -5                   1

TGC GCC ACG ACG CCA GCT CGC AAC CTG AGC TGC TAC CAG TGC TTC AAG          153
Cys Ala Thr Thr Pro Ala Arg Asn Leu Ser Cys Tyr Gln Cys Phe Lys
  5                  10                  15

GTC AGC AGC TGG ACG GAG TGC CCG CCC ACC TGG TGC AGC CCG CTG GAC          201
Val Ser Ser Trp Thr Glu Cys Pro Pro Thr Trp Cys Ser Pro Leu Asp
 20              25                  30                      35

CAA GTC TGC ATC TCC AAC GAG GTG GTC GTC TCT TTT AAA TGG AGT GTA          249
Gln Val Cys Ile Ser Asn Glu Val Val Val Ser Phe Lys Trp Ser Val
             40                  45                      50

CGC GTC CTG CTC AGC AAA CGC TGT GCT CCC AGA TGT CCC AAC GAC AAC          297
Arg Val Leu Leu Ser Lys Arg Cys Ala Pro Arg Cys Pro Asn Asp Asn
         55                  60                  65

ATG AAK TTC GAA TGG TCG CCG GCC CCC ATG GTG CAA GGC GTG ATC ACC          345
Met Xaa Phe Glu Trp Ser Pro Ala Pro Met Val Gln Gly Val Ile Thr
     70                  75                  80

AGG CGC TGC TGT TCC TGG GCT CTC TGC AAC AGG GCA CTG ACC CCA CAG          393
Arg Arg Cys Cys Ser Trp Ala Leu Cys Asn Arg Ala Leu Thr Pro Gln
 85                  90                  95

GAG GGG CGC TGG GCC CTG CRA GGG GGG CTC CTG CTC CAG GAC CCT TCG          441
Glu Gly Arg Trp Ala Leu Xaa Gly Gly Leu Leu Leu Gln Asp Pro Ser
100              105                 110                     115

AGG GGC ARA AAA ACC TGG GTG CGG CCA CAG CTG GGG CTC CCA CTC TGC          489
Arg Gly Xaa Lys Thr Trp Val Arg Pro Gln Leu Gly Leu Pro Leu Cys
             120                 125                     130

CTT CCC AWT TCC AAC CCC CTC TGC CCA RGG GAA ACC CAG GAA GGA              534
Leu Pro Xaa Ser Asn Pro Leu Cys Pro Xaa Glu Thr Gln Glu Gly
         135                 140                 145

TAACACTGTG GGTGCCCCCA CCTGTGCATT GGGACCACRA CTTCACCCTC TTGGARACAA        594

TAAACTCTCA TGCCCCCAAA AAAAAAAA                                           623
```

(2) INFORMATION FOR SEQ ID NO: 26:

(i) SEQUENCE CHARACTERISTICS:
        (A) LENGTH: 16 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (ix) FEATURE:

(A) NAME/KEY: sig_peptide
                (B) LOCATION: 1..16
                (C) IDENTIFICATION METHOD: Von Heijne matrix
                (D) OTHER INFORMATION: score 10.1 seq LVLTLCTLPLAVA/SA (xi) SEQUENCE DESCRIPTION: SEQ ID NO: 26:

Met Glu Arg Leu Val Leu Thr Leu Cys Thr Leu Pro Leu Ala Val Ala
 1               5                  10                  15

(2) INFORMATION FOR SEQ ID NO: 27:

(i) SEQUENCE CHARACTERISTICS:
                (A) LENGTH: 848 base pairs
                (B) TYPE: NUCLEIC ACID
                (C) STRANDEDNESS: DOUBLE
                (D) TOPOLOGY: LINEAR (ii) MOLECULE TYPE: cDNA (vi) ORIGINAL SOURCE:
                (A) ORGANISM: Homo Sapiens
                (D) DEVELOPMENTAL STAGE: Fetal
                (F) TISSUE TYPE: kidney (ix) FEATURE:
                (A) NAME/KEY: sig_peptide
                (B) LOCATION: 32..73
                (C) IDENTIFICATION METHOD: Von Heijne matrix
                (D) OTHER INFORMATION: score 10.7 seq LWLLFFLVTAIHA/EL (xi) SEQUENCE DESCRIPTION: SEQ ID NO: 27:

```
AACTTTGCCT TGTGTTTTCC ACCCTGAAAG A ATG TTG TGG CTG CTC TTT TTT CTG        55
                                   Met Leu Trp Leu Leu Phe Phe Leu
                                                        -10

GTG ACT GCC ATT CAT GCT GAA CTC TGT CAA CCA GGT GCA GAA AAT GCT          103
Val Thr Ala Ile His Ala Glu Leu Cys Gln Pro Gly Ala Glu Asn Ala
 -5                  1               5                      10

TTT AAA GTG AGA CTT AGT ATC AGA ACA GCT CTG GGA GAT AAA GCA TAT         151
Phe Lys Val Arg Leu Ser Ile Arg Thr Ala Leu Gly Asp Lys Ala Tyr
             15                  20                  25

GCC TGG GAT ACC AAT GAA GAA TAC CTC TTC AAA GCG ATG GTA GCT TTC         199
Ala Trp Asp Thr Asn Glu Glu Tyr Leu Phe Lys Ala Met Val Ala Phe
         30                  35                  40

TCC ATG AGA AAA GTT CCC AAC AGA GAA GCA ACA GAA ATT TCC CAT GTC         247
Ser Met Arg Lys Val Pro Asn Arg Glu Ala Thr Glu Ile Ser His Val
             45                  50                  55

CTA CTT TGC AAT GTA ACC CAG AGG GTA TCA TTC TGG TTT GTG GTT ACA         295
Leu Leu Cys Asn Val Thr Gln Arg Val Ser Phe Trp Phe Val Val Thr
         60                  65                  70

GAC CCT TCA AAA AAT CAC ACC CTT CCT GCT GTT GAG GTG CAA TCA GCC         343
Asp Pro Ser Lys Asn His Thr Leu Pro Ala Val Glu Val Gln Ser Ala
 75                  80                  85                  90

ATA AGA ATG AAC AAG AAC CGG ATC AAC AAT GCC TTC TTT CTA AAT GAC         391
Ile Arg Met Asn Lys Asn Arg Ile Asn Asn Ala Phe Phe Leu Asn Asp
                 95                  100                 105

CAA ACT CTG GAA TTT TTA AAA ATC CCT TCC ACA CTT GCA CCA CCC ATG         439
Gln Thr Leu Glu Phe Leu Lys Ile Pro Ser Thr Leu Ala Pro Pro Met
             110                 115                 120

GAC CCA TCT GTG CCC ATC TGG ATT ATT ATA TTT GGT GTG ATA TTT TGC         487
Asp Pro Ser Val Pro Ile Trp Ile Ile Ile Phe Gly Val Ile Phe Cys
         125                 130                 135

ATC ATC ATA GTT GCA ATT GCA CTA CTG ATT TTA TCA GGG ATC TGG CAA         535
Ile Ile Ile Val Ala Ile Ala Leu Leu Ile Leu Ser Gly Ile Trp Gln
         140                 145                 150

CGT ADA ARA AAG AAC AAA GAA CCA TCT GAA GTG GAT GAC GCT GAA RAT         583
```

```
Arg Xaa Xaa Lys Asn Lys Glu Pro Ser Glu Val Asp Asp Ala Glu Xaa
155                 160                 165                 170

AAK TGT GAA AAC ATG ATC ACA ATT GAA AAT GGC ATC CCC TCT GAT CCC        631
Xaa Cys Glu Asn Met Ile Thr Ile Glu Asn Gly Ile Pro Ser Asp Pro
                175                 180                 185

CTG GAC ATG AAG GGA GGG CAT ATT AAT GAT GCC TTC ATG ACA GAG GAT        679
Leu Asp Met Lys Gly Gly His Ile Asn Asp Ala Phe Met Thr Glu Asp
                190                 195                 200

GAG AGG CTC ACC CCT CTC TGAAGGGCTG TTGTTCTGCT TCCTCAARAA               727
Glu Arg Leu Thr Pro Leu
            205

ATTAAACATT TGTTTCTGTG TGACTGCTGA GCATCCTGAA ATACCAAGAG CAGATCATAT      787

WTTTTGTTTC ACCATTCTTC TTTTGTAATA AATTTTGAAT GTGCTTGAAA AAAAAAAAA       847

C                                                                      848

(2) INFORMATION FOR SEQ ID NO: 28:

(i) SEQUENCE CHARACTERISTICS:
        (A) LENGTH: 14 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (ix) FEATURE:
        (A) NAME/KEY: sig_peptide
        (B) LOCATION: 1..14
        (C) IDENTIFICATION METHOD: Von Heijne matrix
        (D) OTHER INFORMATION:   score 10.7 seq LWLLFFLVTAIHA/EL (xi) SEQUENCE DESCRIPTION: SEQ ID NO: 28:

Met Leu Trp Leu Leu Phe Phe Leu Val Thr Ala Ile His Ala
 1               5                  10

(2) INFORMATION FOR SEQ ID NO: 29:

(i) SEQUENCE CHARACTERISTICS:
        (A) LENGTH: 25 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 29:

GGGAAGATGG AGATAGTATT GCCTG                                            25

(2) INFORMATION FOR SEQ ID NO: 30:

(i) SEQUENCE CHARACTERISTICS:
        (A) LENGTH: 26 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 30:

CTGCCATGTA CATGATAGAG AGATTC                                           26

(2) INFORMATION FOR SEQ ID NO: 31:

(i) SEQUENCE CHARACTERISTICS:
```

```
            (A) LENGTH: 546 base pairs
            (B) TYPE: NUCLEIC ACID
            (C) STRANDEDNESS: DOUBLE
            (D) TOPOLOGY: LINEAR (ii) MOLECULE TYPE: Genomic DNA (ix) FEATURE:
            (A) NAME/KEY: promoter
            (B) LOCATION: 1..517

(ix) FEATURE:
            (A) NAME/KEY: transcription start site
            (B) LOCATION: 518

(ix) FEATURE:
            (A) NAME/KEY: TF binding-site
            (B) LOCATION: 17..25
            (C) IDENTIFICATION METHOD: matinspector prediction
            (D) OTHER INFORMATION:  name CMYB_01 score 0.983 sequence
                TGTCAGTTG (ix) FEATURE:
            (A) NAME/KEY: TF binding-site
            (B) LOCATION: complement(18..27)
            (C) IDENTIFICATION METHOD: matinspector prediction
            (D) OTHER INFORMATION:  name MYOD_Q6 score 0.961 sequence
                CCCAACTGAC (ix) FEATURE:
            (A) NAME/KEY: TF binding-site
            (B) LOCATION: complement(75..85)
            (C) IDENTIFICATION METHOD: matinspector prediction
            (D) OTHER INFORMATION:  name S8_01 score 0.960 sequence
                AATAGAATTAG (ix) FEATURE:
            (A) NAME/KEY: TF binding-site
            (B) LOCATION: 94..104
            (C) IDENTIFICATION METHOD: matinspector prediction
            (D) OTHER INFORMATION:  name S8_01 score 0.966 sequence
                AACTAAATTAG (ix) FEATURE:
            (A) NAME/KEY: TF binding-site
            (B) LOCATION: complement(129..139)
            (C) IDENTIFICATION METHOD: matinspector prediction
            (D) OTHER INFORMATION:  name DELTAEF1_01 score 0.960 sequence
                GCACACCTCAG (ix) FEATURE:
            (A) NAME/KEY: TF binding-site
            (B) LOCATION: complement(155..165)
            (C) IDENTIFICATION METHOD: matinspector prediction
            (D) OTHER INFORMATION:  name GATA_C score 0.964 sequence
                AGATAAATCCA (ix) FEATURE:
            (A) NAME/KEY: TF binding-site
            (B) LOCATION: 170..178
            (C) IDENTIFICATION METHOD: matinspector prediction
            (D) OTHER INFORMATION:  name CMYB_01 score 0.958 sequence
                CTTCAGTTG (ix) FEATURE:
            (A) NAME/KEY: TF binding-site
            (B) LOCATION: 176..189
            (C) IDENTIFICATION METHOD: matinspector prediction
            (D) OTHER INFORMATION:  name GATA1_02 score 0.959 sequence
                TTGTAGATAGGACA (ix) FEATURE:
            (A) NAME/KEY: TF binding-site
            (B) LOCATION: 180..190
            (C) IDENTIFICATION METHOD: matinspector prediction
            (D) OTHER INFORMATION:  name GATA_C score 0.953 sequence
                AGATAGGACAT (ix) FEATURE:
```

-continued

```
        (A) NAME/KEY: TF binding-site
        (B) LOCATION: 284..299
        (C) IDENTIFICATION METHOD: matinspector prediction
        (D) OTHER INFORMATION:  name TAL1ALPHAE47_01 score 0.973
            sequence CATAACAGATGGTAAG (ix) FEATURE:
        (A) NAME/KEY: TF binding-site
        (B) LOCATION: 284..299
        (C) IDENTIFICATION METHOD: matinspector prediction
        (D) OTHER INFORMATION:  name TAL1BETAE47_01 score 0.983
            sequence CATAACAGATGGTAAG (ix) FEATURE:
        (A) NAME/KEY: TF binding-site
        (B) LOCATION: 284..299
        (C) IDENTIFICATION METHOD: matinspector prediction
        (D) OTHER INFORMATION:  name TAL1BETAITF2_01 score 0.978
            sequence CATAACAGATGGTAAG (ix) FEATURE:
        (A) NAME/KEY: TF binding-site
        (B) LOCATION: complement(287..296)
        (C) IDENTIFICATION METHOD: matinspector prediction
        (D) OTHER INFORMATION:  name MYOD_Q6 score 0.954 sequence
            ACCATCTGTT (ix) FEATURE:
        (A) NAME/KEY: TF binding-site
        (B) LOCATION: complement(302..314)
        (C) IDENTIFICATION METHOD: matinspector prediction
        (D) OTHER INFORMATION:  name GATA1_04 score 0.953 sequence
            TCAAGATAAAGTA (ix) FEATURE:
        (A) NAME/KEY: TF binding-site
        (B) LOCATION: 393..405
        (C) IDENTIFICATION METHOD: matinspector prediction
        (D) OTHER INFORMATION:  name IK1_01 score 0.963 sequence
            AGTTGGGAATTCC (ix) FEATURE:
        (A) NAME/KEY: TF binding-site
        (B) LOCATION: 393..404
        (C) IDENTIFICATION METHOD: matinspector prediction
        (D) OTHER INFORMATION:  name IK2_01 score 0.985 sequence
            AGTTGGGAATTC (ix) FEATURE:
        (A) NAME/KEY: TF binding-site
        (B) LOCATION: 396..405
        (C) IDENTIFICATION METHOD: matinspector prediction
        (D) OTHER INFORMATION:  name CREL_01 score 0.962 sequence
            TGGGAATTCC (ix) FEATURE:
        (A) NAME/KEY: TF binding-site
        (B) LOCATION: 423..436
        (C) IDENTIFICATION METHOD: matinspector prediction
        (D) OTHER INFORMATION:  name GATA1_02 score 0.950 sequence
            TCAGTGATATGGCA (ix) FEATURE:
        (A) NAME/KEY: TF binding-site
        (B) LOCATION: complement(478..489)
        (C) IDENTIFICATION METHOD: matinspector prediction
        (D) OTHER INFORMATION:  name SRY_02 score 0.951 sequence
            TAAAACAAAACA (ix) FEATURE:
        (A) NAME/KEY: TF binding-site
        (B) LOCATION: 486..493
        (C) IDENTIFICATION METHOD: matinspector prediction
        (D) OTHER INFORMATION:  name E2F_02 score 0.957 sequence
            TTTAGCGC (ix) FEATURE:
        (A) NAME/KEY: TF binding-site
        (B) LOCATION: complement(514..521)
```

(C) IDENTIFICATION METHOD: matinspector prediction
        (D) OTHER INFORMATION: name MZF1_01 score 0.975 sequence
            TGAGGGGA (xi) SEQUENCE DESCRIPTION: SEQ ID NO: 31:

TGAGTGCAGT GTTACATGTC AGTTGGGTTA AGTTTGTTAA TGTCATTCAA ATCTTCTATG    60

TCTTGATTTG CCTGCTAATT CTATTATTTC TGGAACTAAA TTAGTTTGAT GGTTCTATTA   120

GTTATTGACT GAGGTGTGCT AATCTCCCAT TATGTGGATT TATCTATTTC TTCAGTTGTA   180

GATAGGACAT TGATAGATAC ATAAGTACCA GGACAAAAGC AGGGAGATCT TTTTTCCAAA   240

ATCAGGAGAA AAAAATGACA TCTGGAAAAC CTATAGGGAA AGGCATAACA GATGGTAAGG   300

ATACTTTATC TTGAGTAGGA GAGCCTTCCT GTGGCAACGT GGAGAAGGGA AGAGGTCGTA   360

GAATTGAGGA GTCAGCTCAG TTAGAAGCAG GGAGTTGGGA ATTCCGTTCA TGTGATTTAG   420

CATCAGTGAT ATGGCAAATG TGGGACTAAG GGTAGTGATC AGAGGGTTAA AATTGTGTGT   480

TTTGTTTTAG CGCTGCTGGG GCATCGCCTT GGGTCCCCTC AAACAGATTC CCATGAATCT   540

CTTCAT                                                              546

(2) INFORMATION FOR SEQ ID NO: 32:

(i) SEQUENCE CHARACTERISTICS:
        (A) LENGTH: 23 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 32:

GTACCAGGGA CTGTGACCAT TGC                                            23

(2) INFORMATION FOR SEQ ID NO: 33:

(i) SEQUENCE CHARACTERISTICS:
        (A) LENGTH: 24 base pairs
        (B) TYPE: NUCLEIC ACID
        (C) STRANDEDNESS: SINGLE
        (D) TOPOLOGY: LINEAR (ii) MOLECULE TYPE: Other nucleic acid (xi) SEQUENCE DESCRIPTION: SEQ ID NO: 33:

CTGTGACCAT TGCTCCCAAG AGAG                                           24

(2) INFORMATION FOR SEQ ID NO: 34:

(i) SEQUENCE CHARACTERISTICS:
        (A) LENGTH: 861 base pairs
        (B) TYPE: NUCLEIC ACID
        (C) STRANDEDNESS: DOUBLE
        (D) TOPOLOGY: LINEAR (ii) MOLECULE TYPE: Genomic DNA (ix) FEATURE:
        (A) NAME/KEY: promoter
        (B) LOCATION: 1..806

(ix) FEATURE:
        (A) NAME/KEY: transcription start site
        (B) LOCATION: 807

(ix) FEATURE:
        (A) NAME/KEY: TF binding-site
        (B) LOCATION: complement(60..70)
        (C) IDENTIFICATION METHOD: matinspector prediction

```
          (D) OTHER INFORMATION:  name NFY_Q6 score 0.956 sequence
              GGACCAATCAT (ix) FEATURE:
     (A) NAME/KEY: TF binding-site
     (B) LOCATION: 70..77
     (C) IDENTIFICATION METHOD: matinspector prediction
     (D) OTHER INFORMATION:  name MZF1_01 score 0.962 sequence
         CCTGGGGA (ix) FEATURE:
     (A) NAME/KEY: TF binding-site
     (B) LOCATION: 124..132
     (C) IDENTIFICATION METHOD: matinspector prediction
     (D) OTHER INFORMATION:  name CMYB_01 score 0.994 sequence
         TGACCGTTG (ix) FEATURE:
     (A) NAME/KEY: TF binding-site
     (B) LOCATION: complement(126..134)
     (C) IDENTIFICATION METHOD: matinspector prediction
     (D) OTHER INFORMATION:  name VMYB_02 score 0.985 sequence
         TCCAACGGT (ix) FEATURE:
     (A) NAME/KEY: TF binding-site
     (B) LOCATION: 135..143
     (C) IDENTIFICATION METHOD: matinspector prediction
     (D) OTHER INFORMATION:  name STAT_01 score 0.968 sequence
         TTCCTGGAA (ix) FEATURE:
     (A) NAME/KEY: TF binding-site
     (B) LOCATION: complement(135..143)
     (C) IDENTIFICATION METHOD: matinspector prediction
     (D) OTHER INFORMATION:  name STAT_01 score 0.951 sequence
         TTCCAGGAA (ix) FEATURE:
     (A) NAME/KEY: TF binding-site
     (B) LOCATION: complement(252..259)
     (C) IDENTIFICATION METHOD: matinspector prediction
     (D) OTHER INFORMATION:  name MZF1_01 score 0.956 sequence
         TTGGGGGA (ix) FEATURE:
     (A) NAME/KEY: TF binding-site
     (B) LOCATION: 357..368
     (C) IDENTIFICATION METHOD: matinspector prediction
     (D) OTHER INFORMATION:  name IK2_01 score 0.965 sequence
         GAATGGGATTTC (ix) FEATURE:
     (A) NAME/KEY: TF binding-site
     (B) LOCATION: 384..391
     (C) IDENTIFICATION METHOD: matinspector prediction
     (D) OTHER INFORMATION:  name MZF1_01 score 0.986 sequence
         AGAGGGGA (ix) FEATURE:
     (A) NAME/KEY: TF binding-site
     (B) LOCATION: complement(410..421)
     (C) IDENTIFICATION METHOD: matinspector prediction
     (D) OTHER INFORMATION:  name SRY_02 score 0.955 sequence
         GAAAACAAAACA (ix) FEATURE:
     (A) NAME/KEY: TF binding-site
     (B) LOCATION: 592..599
     (C) IDENTIFICATION METHOD: matinspector prediction
     (D) OTHER INFORMATION:  name MZF1_01 score 0.960 sequence
         GAAGGGGA (ix) FEATURE:
     (A) NAME/KEY: TF binding-site
     (B) LOCATION: 618..627
     (C) IDENTIFICATION METHOD: matinspector prediction
     (D) OTHER INFORMATION:  name MYOD_Q6 score 0.981 sequence
         AGCATCTGCC
```

(ix) FEATURE:
            (A) NAME/KEY: TF binding-site
            (B) LOCATION: 632..642
            (C) IDENTIFICATION METHOD: matinspector prediction
            (D) OTHER INFORMATION: name DELTAEF1_01 score 0.958 sequence
                TCCCACCTTCC (ix) FEATURE:
            (A) NAME/KEY: TF binding-site
            (B) LOCATION: complement(813..823)
            (C) IDENTIFICATION METHOD: matinspector prediction
            (D) OTHER INFORMATION: name S8_01 score 0.992 sequence
                GAGGCAATTAT (ix) FEATURE:
            (A) NAME/KEY: TF binding-site
            (B) LOCATION: complement(824..831)
            (C) IDENTIFICATION METHOD: matinspector prediction
            (D) OTHER INFORMATION: name MZF1_01 score 0.986 sequence
                AGAGGGGA (xi) SEQUENCE DESCRIPTION: SEQ ID NO: 34:

TACTATAGGG CACGCGTGGT CGACGGCCGG GCTGTTCTGG AGCAGAGGGC ATGTCAGTAA     60

TGATTGGTCC CTGGGGAAGG TCTGGCTGGC TCCAGCACAG TGAGGCATTT AGGTATCTCT    120

CGGTGACCGT TGGATTCCTG GAAGCAGTAG CTGTTCTGTT TGGATCTGGT AGGGACAGGG    180

CTCAGAGGGC TAGGCACGAG GGAAGGTCAG AGGAGAAGGS AGGSARGGCC CAGTGAGARG    240

GGAGCATGCC TTCCCCCAAC CCTGGCTTSC YCTTGGYMAM AGGGCGKTTY TGGGMACTTR    300

AAYTCAGGGC CCAASCAGAA SCACAGGCCC AKTCNTGGCT SMAAGCACAA TAGCCTGAAT    360

GGGATTTCAG GTTAGNCAGG GTGAGAGGGG AGGCTCTCTG GCTTAGTTTT GTTTTGTTTT    420

CCAAATCAAG GTAACTTGCT CCCTTCTGCT ACGGGCCTTG GTCTTGGCTT GTCCTCACCC    480

AGTCGGAACT CCCTACCACT TTCAGGAGAG TGGTTTTAGG CCCGTGGGGC TGTTCTGTTC    540

CAAGCAGTGT GAGAACATGG CTGGTAGAGG CTCTAGCTGT GTGCGGGCC TGAAGGGGAG     600

TGGGTTCTCG CCCAAAGAGC ATCTGCCCAT TTCCCACCTT CCCTTCTCCC ACCAGAAGCT    660

TGCCTGAGCT GTTTGGACAA AAATCCAAAC CCCACTTGGC TACTCTGGCC TGGCTTCAGC    720

TTGGAACCCA ATACCTAGGC TTACAGGCCA TCCTGAGCCA GGGGCCTCTG GAAATTCTCT    780

TCCTGATGGT CCTTTAGGTT TGGGCACAAA ATATAATTGC CTCTCCCCTC TCCCATTTTC    840

TCTCTTGGGA GCAATGGTCA C                                             861

(2) INFORMATION FOR SEQ ID NO: 35:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: Other nucleic acid (xi) SEQUENCE DESCRIPTION: SEQ ID NO: 35:

CTGGGATGGA AGGCACGGTA                                                20

(2) INFORMATION FOR SEQ ID NO: 36:

(i) SEQUENCE CHARACTERISTICS:
            (A) LENGTH: 20 base pairs
            (B) TYPE: NUCLEIC ACID
            (C) STRANDEDNESS: SINGLE
            (D) TOPOLOGY: LINEAR (ii) MOLECULE TYPE: Other nucleic acid (xi) SEQUENCE DESCRIPTION: SEQ ID NO: 36:

GAGACCACAC AGCTAGACAA                                                           20

(2) INFORMATION FOR SEQ ID NO: 37:

(i) SEQUENCE CHARACTERISTICS:
          (A) LENGTH: 555 base pairs
          (B) TYPE: NUCLEIC ACID
          (C) STRANDEDNESS: DOUBLE
          (D) TOPOLOGY: LINEAR (ii) MOLECULE TYPE: Genomic DNA (ix) FEATURE:
          (A) NAME/KEY: promoter
          (B) LOCATION: 1..500

(ix) FEATURE:
          (A) NAME/KEY: transcription start site
          (B) LOCATION: 501

(ix) FEATURE:
          (A) NAME/KEY: TF binding-site
          (B) LOCATION: 191..206
          (C) IDENTIFICATION METHOD: matinspector prediction
          (D) OTHER INFORMATION:  name ARNT_01 score 0.964 sequence
              GGACTCACGTGCTGCT (ix) FEATURE:
          (A) NAME/KEY: TF binding-site
          (B) LOCATION: 193..204
          (C) IDENTIFICATION METHOD: matinspector prediction
          (D) OTHER INFORMATION:  name NMYC_01 score 0.965 sequence
              ACTCACGTGCTG (ix) FEATURE:
          (A) NAME/KEY: TF binding-site
          (B) LOCATION: 193..204
          (C) IDENTIFICATION METHOD: matinspector prediction
          (D) OTHER INFORMATION:  name USF_01 score 0.985 sequence
              ACTCACGTGCTG (ix) FEATURE:
          (A) NAME/KEY: TF binding-site
          (B) LOCATION: complement(193..204)
          (C) IDENTIFICATION METHOD: matinspector prediction
          (D) OTHER INFORMATION:  name USF_01 score 0.985 sequence
              CAGCACGTGAGT (ix) FEATURE:
          (A) NAME/KEY: TF binding-site
          (B) LOCATION: complement(193..204)
          (C) IDENTIFICATION METHOD: matinspector prediction
          (D) OTHER INFORMATION:  name NMYC_01 score 0.956 sequence
              CAGCACGTGAGT (ix) FEATURE:
          (A) NAME/KEY: TF binding-site
          (B) LOCATION: complement(193..204)
          (C) IDENTIFICATION METHOD: matinspector prediction
          (D) OTHER INFORMATION:  name MYCMAX_02 score 0.972 sequence
              CAGCACGTGAGT (ix) FEATURE:
          (A) NAME/KEY: TF binding-site
          (B) LOCATION: 195..202
          (C) IDENTIFICATION METHOD: matinspector prediction
          (D) OTHER INFORMATION:  name USF_C score 0.997 sequence
              TCACGTGC (ix) FEATURE:
          (A) NAME/KEY: TF binding-site
          (B) LOCATION: complement(195..202)
          (C) IDENTIFICATION METHOD: matinspector prediction
          (D) OTHER INFORMATION:  name USF_C score 0.991 sequence
              GCACGTGA (ix) FEATURE:
              (A) NAME/KEY: TF binding-site
              (B) LOCATION: complement(210..217)
              (C) IDENTIFICATION METHOD: matinspector prediction
              (D) OTHER INFORMATION:   name MZF1_01 score 0.968 sequence
                  CATGGGGA (ix) FEATURE:
              (A) NAME/KEY: TF binding-site
              (B) LOCATION: 397..410
              (C) IDENTIFICATION METHOD: matinspector prediction
              (D) OTHER INFORMATION:   name ELK1_02 score 0.963 sequence
                  CTCTCCGGAAGCCT (ix) FEATURE:
              (A) NAME/KEY: TF binding-site
              (B) LOCATION: 400..409
              (C) IDENTIFICATION METHOD: matinspector prediction
              (D) OTHER INFORMATION:   name CETS1P54_01 score 0.974 sequence
                  TCCGGAAGCC (ix) FEATURE:
              (A) NAME/KEY: TF binding-site
              (B) LOCATION: complement(460..470)
              (C) IDENTIFICATION METHOD: matinspector prediction
              (D) OTHER INFORMATION:   name AP1_Q4 score 0.963 sequence
                  AGTGACTGAAC (ix) FEATURE:
              (A) NAME/KEY: TF binding-site
              (B) LOCATION: complement(460..470)
              (C) IDENTIFICATION METHOD: matinspector prediction
              (D) OTHER INFORMATION:   name AP1FJ_Q2 score 0.961 sequence
                  AGTGACTGAAC (ix) FEATURE:
              (A) NAME/KEY: TF binding-site
              (B) LOCATION: 547..555
              (C) IDENTIFICATION METHOD: matinspector prediction
              (D) OTHER INFORMATION:   name PADS_C score 1.000 sequence
                  TGTGGTCTC (xi) SEQUENCE DESCRIPTION: SEQ ID NO: 37:

CTATAGGGCA CGCKTGGTCG ACGGCCCGGG CTGGTCTGGT CTGTKGTGGA GTCGGGTTGA      60

AGGACAGCAT TTGTKACATC TGGTCTACTG CACCTTCCCT CTGCCGTGCA CTTGGCCTTT     120

KAWAAGCTCA GCACCGGTGC CCATCACAGG GCCGGCAGCA CACACATCCC ATTACTCAGA     180

AGGAACTGAC GGACTCACGT GCTGCTCCGT CCCCATGAGC TCAGTGGACC TGTCTATGTA     240

GAGCAGTCAG ACAGTGCCTG GGATAGAGTG AGAGTTCAGC CAGTAAATCC AAGTGATTGT     300

CATTCCTGTC TGCATTAGTA ACTCCCAACC TAGATGTGAA AACTTAGTTC TTTCTCATAG     360

GTTGCTCTGC CCATGGTCCC ACTGCAGACC CAGGCACTCT CCGGAAGCCT GGAAATCACC     420

CGTGTCTTCT GCCTGCTCCC GCTCACATCC CACACTTGTG TTCAGTCACT GAGTTACAGA     480

TTTTGCCTCC TCAATTTCTC TTGTCTTAGT CCCATCCTCT GTTCCCCTGG CCAGTTTGTC     540

TAGCTGTGTG GTCTC                                                     555

(2) INFORMATION FOR SEQ ID NO: 38:

(i) SEQUENCE CHARACTERISTICS:
              (A) LENGTH: 155 base pairs
              (B) TYPE: NUCLEIC ACID
              (C) STRANDEDNESS: DOUBLE
              (D) TOPOLOGY: LINEAR (ii) MOLECULE TYPE: CDNA (vi) ORIGINAL SOURCE:
              (A) ORGANISM: Homo Sapiens
              (F) TISSUE TYPE: Brain (ix) FEATURE:
            (A) NAME/KEY: sig_peptide
            (B) LOCATION: 45..86
            (C) IDENTIFICATION METHOD: Von Heijne matrix
            (D) OTHER INFORMATION: score 10.8 seq LLLLGLCLGLSLC/VG (xi) SEQUENCE DESCRIPTION: SEQ ID NO: 38:

AGTGTCCCGC CGGGTCCCCG AGCGTCCCGC GCCCTCGCCC CGCC ATG CTC CTG CTG    56
                                                  Met Leu Leu Leu

CTG GGG CTG TGC CTG GGG CTG TCC CTG TGT GTG GGG TCG CAG GAA GAG   104
Leu Gly Leu Cys Leu Gly Leu Ser Leu Cys Val Gly Ser Gln Glu Glu
-10              -5                   1               5

GCG CAG AGC TGG GGC CAC TCT TCG GAG CAG GAT GGA CTC AGG GTC CCG   152
Ala Gln Ser Trp Gly His Ser Ser Glu Gln Asp Gly Leu Arg Val Pro
             10                  15                  20

AGG                                                                155
Arg (2) INFORMATION FOR SEQ ID NO: 39:

(i) SEQUENCE CHARACTERISTICS:
            (A) LENGTH: 427 base pairs
            (B) TYPE: NUCLEIC ACID
            (C) STRANDEDNESS: DOUBLE
            (D) TOPOLOGY: LINEAR (ii) MOLECULE TYPE: cDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 191..268
            (C) IDENTIFICATION METHOD: Von Heijne matrix
            (D) OTHER INFORMATION: score 10.8 seq VLLFFVLLGMSQA/GS (xi) SEQUENCE DESCRIPTION: SEQ ID NO: 39:

AAGTACACGC GGMGAACTGG GAAGACAGAA AGWWCAATCC TTTAAGGGAG AACCTAGAAG    60

CCATTCAACA AGGTTAAAAT CTTTAGGCTT CCGAGGATTT GGTAGACAGA TCAGAGGCAC   120

GTTTCCCACA ACTGCGAAGA GGCGCTGAGG CAATTCTGCA AGAAGATTTT GGGGTTTTGG   180

AAAAGAAGCT ATG GAA AAC GGA GGG GCA GGC ACT CTG CAG ATA AGG CAA     229
           Met Glu Asn Gly Gly Ala Gly Thr Leu Gln Ile Arg Gln
           -25                 -20                 -15

GTC CTG CTT TTC TTT GTT TTG CTG GGA ATG TCT CAG GCG GGC TCT GAA   277
Val Leu Leu Phe Phe Val Leu Leu Gly Met Ser Gln Ala Gly Ser Glu
             -10                 -5                   1

ACT GGG AAC TTT TTG GTG ATG GAG GAA TTG CAG AGC GGG AGC TTT GTA   325
Thr Gly Asn Phe Leu Val Met Glu Glu Leu Gln Ser Gly Ser Phe Val
      5                   10                  15

GGA AAT TTG GCA AAG ACC CTG GGA CTC GAG GTG AGT GAG CTG TCT TCG   373
Gly Asn Leu Ala Lys Thr Leu Gly Leu Glu Val Ser Glu Leu Ser Ser
 20                  25                  30                  35

CGG GGG GCT CGG GTG GTT TCT AAT GAT AAC AAA GAG TGT TTG CAG CTG   421
Arg Gly Ala Arg Val Val Ser Asn Asp Asn Lys Glu Cys Leu Gln Leu
             40                  45                  50

GAC ACG                                                            427
Asp Thr (2) INFORMATION FOR SEQ ID NO: 40:

(i) SEQUENCE CHARACTERISTICS:

(A) LENGTH: 398 base pairs
            (B) TYPE: NUCLEIC ACID
            (C) STRANDEDNESS: DOUBLE
            (D) TOPOLOGY: LINEAR (ii) MOLECULE TYPE: cDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 12..389
            (C) IDENTIFICATION METHOD: Von Heijne matrix
            (D) OTHER INFORMATION: score 10 seq LKLLLFLSTELQA/SQ (xi) SEQUENCE DESCRIPTION: SEQ ID NO: 40:

```
AAAAAAGGAC C ATG AGA GGG CCG GAG CCG GGT CCC CAA CCG ACG ATG GAG          50
            Met Arg Gly Pro Glu Pro Gly Pro Gln Pro Thr Met Glu
               -125                -120                -115

GGA GAC GTG CTG GAC ACA CTG GAG GCG CTG GGG TAT AAA GGA CCA TTG           98
Gly Asp Val Leu Asp Thr Leu Glu Ala Leu Gly Tyr Lys Gly Pro Leu
           -110                -105                -100

TTA GAA GAG CAA GCC CTT ACA AAG GCG GCA GAG GGT GGA TTA TCT TCA          146
Leu Glu Glu Gln Ala Leu Thr Lys Ala Ala Glu Gly Gly Leu Ser Ser
        -95                 -90                 -85

CCT GAA TTT TCA GAG CTC TGT ATT TGG TTA GGC TCT CAA ATA AAA TCA          194
Pro Glu Phe Ser Glu Leu Cys Ile Trp Leu Gly Ser Gln Ile Lys Ser
    -80                 -75                 -70

TTA TGC AAC TTG GAA GAA AGT ATC ACG TCT GCT GGA AGA GAT GAT CTA          242
Leu Cys Asn Leu Glu Glu Ser Ile Thr Ser Ala Gly Arg Asp Asp Leu
-65                 -60                 -55                 -50

GAG AGC TTC CAG CTT GAG ATA AGT GGC TTT TTA AAA GAA ATG GCA TGT          290
Glu Ser Phe Gln Leu Glu Ile Ser Gly Phe Leu Lys Glu Met Ala Cys
                -45                 -40                 -35

CCA TAT TCT GTA CTC ATA TCA GGA GAT ATT AAA GAT CGT TTA AAA AAG          338
Pro Tyr Ser Val Leu Ile Ser Gly Asp Ile Lys Asp Arg Leu Lys Lys
            -30                 -25                 -20

AAG GAG GAC TGT TTG AAA CTT CTA TTA TTT TTA AGT ACA GAA CTT CAA          386
Lys Glu Asp Cys Leu Lys Leu Leu Leu Phe Leu Ser Thr Glu Leu Gln
        -15                 -10                  -5

GCT TCA CAG ATA                                                          398
Ala Ser Gln Ile
   1
```

(2) INFORMATION FOR SEQ ID NO: 41:

(i) SEQUENCE CHARACTERISTICS:
            (A) LENGTH: 201 base pairs
            (B) TYPE: NUCLEIC ACID
            (C) STRANDEDNESS: DOUBLE
            (D) TOPOLOGY: LINEAR (ii) MOLECULE TYPE: cDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 70..147
            (C) IDENTIFICATION METHOD: Von Heijne matrix
            (D) OTHER INFORMATION: score 9.6 seq WLIALASWSWALC/RI (xi) SEQUENCE DESCRIPTION: SEQ ID NO: 41:

```
AGCCCGGTTT CGTGCCCGCG GCCGACTGCG CASCTGTCCG CGAGTCTGAG ATACTTACAG    60
```

```
AGAGCTACA ATG GAA AAG TCC TGG ATG CTG TGG AAC TTT GTT GAA AGA TGG       111
          Met Glu Lys Ser Trp Met Leu Trp Asn Phe Val Glu Arg Trp
              -25                 -20                 -15

CTA ATA GCC TTG GCT TCA TGG TCT TGG GCT CTC TGC CGT ATT TCT CTT         159
Leu Ile Ala Leu Ala Ser Trp Ser Trp Ala Leu Cys Arg Ile Ser Leu
    -10                 -5                       1

TTA CCT TTA ATA GTG ACT TTT CAT CTG TAT GGA GGT TCG GGG                 201
Leu Pro Leu Ile Val Thr Phe His Leu Tyr Gly Gly Ser Gly
 5              10                  15

(2) INFORMATION FOR SEQ ID NO: 42:

(i) SEQUENCE CHARACTERISTICS:
        (A) LENGTH: 272 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 6..113
        (C) IDENTIFICATION METHOD: Von Heijne matrix
        (D) OTHER INFORMATION:  score 9.5 seq LGLLLLARHWCIA/GV (xi) SEQUENCE DESCRIPTION: SEQ ID NO: 42:

AGATT ATG CAG CAG ACT CGC ACA GAG GCT GTC GCG GGC GCG TTC TCT CAC       50
      Met Gln Gln Thr Arg Thr Glu Ala Val Ala Gly Ala Phe Ser His
          -35                 -30                 -25

TGC CTG GGC TTC TGT GGA ATG AGA CTC GGG CTC CTT CTA CTT GCA AGA         98
Cys Leu Gly Phe Cys Gly Met Arg Leu Gly Leu Leu Leu Leu Ala Arg
    -20                 -15                 -10

CAC TGG TGC ATT GCA GGT GTG TTT CCG CAG AAG TTT GAT GGT GAC AGT         146
His Trp Cys Ile Ala Gly Val Phe Pro Gln Lys Phe Asp Gly Asp Ser
 -5              1               5                   10

GCC TAC GTG GGG ATG AGT GAC GGA AAC CCA GAG CTC CTG TCA ACC AGC         194
Ala Tyr Val Gly Met Ser Asp Gly Asn Pro Glu Leu Leu Ser Thr Ser
                15                  20                  25

CAG ACC TAC AAC GGC CAG AGC GAG AAC AAC GAA GAC TAT GAG ATC CCC         242
Gln Thr Tyr Asn Gly Gln Ser Glu Asn Asn Glu Asp Tyr Glu Ile Pro
        30                  35                  40

CCG ATA ACA CCT CCC AAC CTC CCG GAA GCG                                 272
Pro Ile Thr Pro Pro Asn Leu Pro Glu Ala
    45                  50

(2) INFORMATION FOR SEQ ID NO: 43:

(i) SEQUENCE CHARACTERISTICS:
        (A) LENGTH: 186 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 28..99
        (C) IDENTIFICATION METHOD: Von Heijne matrix
```

(D) OTHER INFORMATION: score 9.1 seq LVVFLLLPLASGP/QV (xi) SEQUENCE DESCRIPTION: SEQ ID NO: 43:

ATTTACGTCT TTTCAGTTTT TTTAGAG ATG GAA AAG GGA AAC GCG TTT TTA AAG      54
                              Met Glu Lys Gly Asn Ala Phe Leu Lys
                                                               -20

AAT AGG TTA GTT GTT TTT CTT CTC CTG CCC CTA GCA TCA GGA CCA CAG       102
Asn Arg Leu Val Val Phe Leu Leu Leu Pro Leu Ala Ser Gly Pro Gln
-15                 -10                 -5                    1

GTA AAA AGG AAA AGC GAA ATT ACG AAA CTT ATA AAG GCC ACG CGA ATC       150
Val Lys Arg Lys Ser Glu Ile Thr Lys Leu Ile Lys Ala Thr Arg Ile
            5                   10                  15

ATT TGT TTA TTC AAT AAA TTT AGT AGA GGA AAC GGG                       186
Ile Cys Leu Phe Asn Lys Phe Ser Arg Gly Asn Gly
        20                  25

(2) INFORMATION FOR SEQ ID NO: 44:

(i) SEQUENCE CHARACTERISTICS:
        (A) LENGTH: 400 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 164..235
        (C) IDENTIFICATION METHOD: Von Heijne matrix
        (D) OTHER INFORMATION: score 9 seq LLMLIVFHAASMA/LQ (xi) SEQUENCE DESCRIPTION: SEQ ID NO: 44:

AGTTAATTTG AACAAAATAT AGTAAGTATA CTATTATTTT CCATGTCTTT CTAGGCTTTT      60

TAAACTCTGC AGTGTATTTA CTGTACTCTC GTAGAAGGAG TGCCATCAAC TGCAATTGGT     120

ACAAATTGTG CTTATTTTTC TGCTCTTTTC ACGTTCCCAA AAT ATG TTC CCA TTC      175
                                                Met Phe Pro Phe

AAC CAG GCA GGT CTT CCT ACT CTT CTC ATG CTC ATT GTT TTT CAT GCT      223
Asn Gln Ala Gly Leu Pro Thr Leu Leu Met Leu Ile Val Phe His Ala
-20                 -15                 -10                 -5

GCT TCC ATG GCT TTA CAG AGA CTC TTC CTC TTC GCT TTG GTC TGG CAT      271
Ala Ser Met Ala Leu Gln Arg Leu Phe Leu Phe Ala Leu Val Trp His
                1                   5                  10

TCA AAA CCC TCA GGA CTG ATG ACA GGC AAA CTA GAA TCT CAA ATT CCC      319
Ser Lys Pro Ser Gly Leu Met Thr Gly Lys Leu Glu Ser Gln Ile Pro
            15                  20                  25

CAT GAA AAG TTG ACT CAT ATC TCT GTC ATG CAT GGT CCC CTC AGT TCC      367
His Glu Lys Leu Thr His Ile Ser Val Met His Gly Pro Leu Ser Ser
        30                  35                  40

CAT CAC TCA TAC ACT CAC ATA CAT TTA TTT TTA                          400
His His Ser Tyr Thr His Ile His Leu Phe Leu
45                  50                  55

(2) INFORMATION FOR SEQ ID NO: 45:

(i) SEQUENCE CHARACTERISTICS:
        (A) LENGTH: 297 base pairs
        (B) TYPE: NUCLEIC ACID
        (C) STRANDEDNESS: DOUBLE
        (D) TOPOLOGY: LINEAR

```
     (ii) MOLECULE TYPE: CDNA (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: 1..228
          (C) IDENTIFICATION METHOD: Von Heijne matrix
          (D) OTHER INFORMATION:  score 8.8 seq SLLLWMSSLPSLG/EK (xi) SEQUENCE DESCRIPTION: SEQ ID NO: 45:

ATG ACT TCA CGT AGC TTG CGT CGC TGC TCC TGT CTC CGT GTA ACT CAC        48
Met Thr Ser Arg Ser Leu Arg Arg Cys Ser Cys Leu Arg Val Thr His
    -75             -70                 -65

AAT AAA GAG ATT TTG GCA TCA ACC GTG AGC TTA GGG GTA GAA GGG TAT        96
Asn Lys Glu Ile Leu Ala Ser Thr Val Ser Leu Gly Val Glu Gly Tyr
-60             -55                 -50                 -45

ATG TTA GGA GGT GGG AGC AGA ATC AAT TCT TCA AAT CTT AAT GAT GGT       144
Met Leu Gly Gly Gly Ser Arg Ile Asn Ser Ser Asn Leu Asn Asp Gly
                -40                 -35                 -30

GAA GAA GAG TGC TCA CCA GAT TCC CTT CTG GTC TGG AAA AAG AAA TCC       192
Glu Glu Glu Cys Ser Pro Asp Ser Leu Leu Val Trp Lys Lys Lys Ser
            -25                 -20                 -15

CTT CTT TTG TGG ATG TCA TCT CTA CCA TCT CTC GGT GAA AAA TAT TTC       240
Leu Leu Leu Trp Met Ser Ser Leu Pro Ser Leu Gly Glu Lys Tyr Phe
        -10                  -5                   1

AAG AGA ATC CTA AGA TGG AGA GAG CAT TGG AAG TCA TCC GGC CCA ATT       288
Lys Arg Ile Leu Arg Trp Arg Glu His Trp Lys Ser Ser Gly Pro Ile
  5                 10                  15                  20

CCC TTG TGG                                                           297
Pro Leu Trp (2) INFORMATION FOR SEQ ID NO: 46:

(i) SEQUENCE CHARACTERISTICS:
          (A) LENGTH: 213 base pairs
          (B) TYPE: NUCLEIC ACID
          (C) STRANDEDNESS: DOUBLE
          (D) TOPOLOGY: LINEAR (ii) MOLECULE TYPE: CDNA (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: 10..168
          (C) IDENTIFICATION METHOD: Von Heijne matrix
          (D) OTHER INFORMATION:  score 8.8 seq ILLLLTVLPCIXM/GQ (xi) SEQUENCE DESCRIPTION: SEQ ID NO: 46:

AACTGTAGC ATG TGG ACA GCC AGT GCC ATG GAT TTC AGA ACC TGC ATT GCC      51
          Met Trp Thr Ala Ser Ala Met Asp Phe Arg Thr Cys Ile Ala
                      -50                 -45                 -40

AGT KGA CTG CCT GCT TTG TGC TAC GTG CAG GCC TGC CGC GCC CTG ATG        99
Ser Xaa Leu Pro Ala Leu Cys Tyr Val Gln Ala Cys Arg Ala Leu Met
            -35                 -30                 -25

ATT GCT GCC TCG GTC CTG GGT CTG CCG GCC ATT TTA CTG CTG CTG ACT       147
Ile Ala Ala Ser Val Leu Gly Leu Pro Ala Ile Leu Leu Leu Leu Thr
        -20                 -15                 -10

GTT CTT CCC TGC ATC SGG ATG GGC CAG GAG CCC GGT GTG GCT AAG TAC       195
Val Leu Pro Cys Ile Xaa Met Gly Gln Glu Pro Gly Val Ala Lys Tyr
     -5                   1                   5
```

```
AGG SGG GCC CAG CTG GCT                                              213
Arg Xaa Ala Gln Leu Ala
 10              15
```

(2) INFORMATION FOR SEQ ID NO: 47:

(i) SEQUENCE CHARACTERISTICS:
        (A) LENGTH: 319 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 62..196
        (C) IDENTIFICATION METHOD: Von Heijne matrix
        (D) OTHER INFORMATION: score 8.5 seq FALLSLSHPTCQA/GA (xi) SEQUENCE DESCRIPTION: SEQ ID NO: 47:

```
ATTGGTGCAG AGGCCCTTCT TGTCTCCACA CCAGAAGGAG CTGAGCAGAG GGGCCACAGC        60

G ATG GGA CCC CCT CCA ACC CAC ATT AAA TAC CTC CAC CTG AAT ATT TAT      109
  Met Gly Pro Pro Pro Thr His Ile Lys Tyr Leu His Leu Asn Ile Tyr
      -45                 -40                 -35                 -30

TGC AAC GGC AAG AGC ACT GCA CCT GGA ATC CGG TCT CAC AGC CTT GGA        157
Cys Asn Gly Lys Ser Thr Ala Pro Gly Ile Arg Ser His Ser Leu Gly
                -25                 -20                 -15

TTT GCC TTG CTA AGC CTC AGT CAT CCA ACC TGC CAG GCA GGT GCA CCT        205
Phe Ala Leu Leu Ser Leu Ser His Pro Thr Cys Gln Ala Gly Ala Pro
            -10                  -5                   1

GCC GCA GCC CTG CCT TCT CTG TGG AGC TGG TGC TCT CGG GGT GCA CGA        253
Ala Ala Ala Leu Pro Ser Leu Trp Ser Trp Cys Ser Arg Gly Ala Arg
  5                  10                  15

GTC AGG GTT GGG AGG ATG CTT TCT CAC CTG TAC ACC TGT GGA TGG TAC        301
Val Arg Val Gly Arg Met Leu Ser His Leu Tyr Thr Cys Gly Trp Tyr
 20                  25                  30                  35

GAT CAC AAC CCC CAT GGG                                                319
Asp His Asn Pro His Gly
                40
```

(2) INFORMATION FOR SEQ ID NO: 48:

(i) SEQUENCE CHARACTERISTICS:
        (A) LENGTH: 260 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 204..251
        (C) IDENTIFICATION METHOD: Von Heijne matrix
        (D) OTHER INFORMATION: score 8.5 seq LLTFLAFTTLLFA/PP (xi) SEQUENCE DESCRIPTION: SEQ ID NO: 48:

```
ACTGTTATTC TTCACATATT ATCTCTATTA GTADVWGGCT TCTAGTCACC CAAGTTAGAA        60
```

```
ATCTGTGAGT CATCTTTTGT TTCTTCCCTT TCCCTTACTG TTTAGTTTTA ATTGCTAAGT        120

CTTGTTAATA CTACATCAGG TATGATTTTA AAAACATTTT TGATGTTCTA CTGCCACCAC        180

CTTAGTTCTG GTACTCATTT TGC ATG TTT TGT CTT TTG ACT TTC CTT GCT TTT       233
                          Met Phe Cys Leu Leu Thr Phe Leu Ala Phe
                          -15                 -10

ACA ACT CTT CTT TTC GCA CCC CCA TGG                                     260
Thr Thr Leu Leu Phe Ala Pro Pro Trp
   -5                           1
```

(2) INFORMATION FOR SEQ ID NO: 49:

(i) SEQUENCE CHARACTERISTICS:
        (A) LENGTH: 365 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 126..212
        (C) IDENTIFICATION METHOD: Von Heijne matrix
        (D) OTHER INFORMATION:  score 8.4 seq LKCLLAVLSSLFA/AI (xi) SEQUENCE DESCRIPTION: SEQ ID NO: 49:

```
ACAAATGTGT TATGATTTTC CAGGCCCTTC TTCATCTGCT CTCCCTTCCT TTTGAGCATT         60

ATCCCATTTC ATGCCCCCAC ACAGATTCTA GCCATACCCC ATGACTTACA ATTTCCCCAC        120

AAAGA ATG CAC TGT GGC TCC ACT CCA GGA CTT TGC CCA TGC TGG GTC CCC       170
      Met His Cys Gly Ser Thr Pro Gly Leu Cys Pro Cys Trp Val Pro
          -25                 -20                 -15

TTC CTG AAA TGC CTT CTA GCT GTT CTC TCT TCC CTG TTT GCT GCC ATT         218
Phe Leu Lys Cys Leu Leu Ala Val Leu Ser Ser Leu Phe Ala Ala Ile
            -10                 -5                          1

TCC GTG GAC AGA CTA TAC TTG TCT TTC TGT TCT AAT TGC TCT GAA ATA         266
Ser Val Asp Arg Leu Tyr Leu Ser Phe Cys Ser Asn Cys Ser Glu Ile
        5                   10                  15

TAC CTC TGG CCC CCC AGC TTT CCT GCT CCC CCA TCC CCT GTA GTC CTT         314
Tyr Leu Trp Pro Pro Ser Phe Pro Ala Pro Pro Ser Pro Val Val Leu
        20                  25                  30

CTA GTT TTC CTG TGT CCC CAT GGG ACT TCT TTA TCC TTT TTG AAG CTA         362
Leu Val Phe Leu Cys Pro His Gly Thr Ser Leu Ser Phe Leu Lys Leu
  35                  40                  45                  50

CCG                                                                     365
Pro
```

(2) INFORMATION FOR SEQ ID NO: 50:

(i) SEQUENCE CHARACTERISTICS:
        (A) LENGTH: 69 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide (B) LOCATION: 1..48
            (C) IDENTIFICATION METHOD: Von Heijne matrix
            (D) OTHER INFORMATION:   score 8.3 seq VCSALLLLGIVSS/KP (xi) SEQUENCE DESCRIPTION: SEQ ID NO: 50:

```
ATG AAT TTA GTT TGT TCA GCT CTT TTA CTT CTT GGA ATA GTA TCT TCC        48
Met Asn Leu Val Cys Ser Ala Leu Leu Leu Leu Gly Ile Val Ser Ser
    -15             -10                  -5

AAA CCC TAT ATG AGA AAG CGG                                            69
Lys Pro Tyr Met Arg Lys Arg
  1           5
```

(2) INFORMATION FOR SEQ ID NO: 51:

(i) SEQUENCE CHARACTERISTICS:
        (A) LENGTH: 184 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 44..148
        (C) IDENTIFICATION METHOD: Von Heijne matrix
        (D) OTHER INFORMATION:   score 8.3 seq AAMLIGLLAWLQT/VP (xi) SEQUENCE DESCRIPTION: SEQ ID NO: 51:

```
AAATTACAAG AAAGCTGGAC TTGCCGCTGT GGTCTCAGGA GAA ATG AGT GTT CTT        55
                                             Met Ser Val Leu
                                                 -35

GAT GAC AGG CAA AGG GAC ATC TTA GTT GTC CAG AAG CGG CAC TCT TCC        103
Asp Asp Arg Gln Arg Asp Ile Leu Val Val Gln Lys Arg His Ser Ser
    -30                 -25                 -20

CTG GAA GCC GCC ATG TTA ATA GGA TTA CTA GCC TGG CTC CAG ACA GTG        151
Leu Glu Ala Ala Met Leu Ile Gly Leu Leu Ala Trp Leu Gln Thr Val
-15                 -10                  -5                   1

CCT GCT CAT GGC TGC CAG TTC TTA CCG ATC CGG                            184
Pro Ala His Gly Cys Gln Phe Leu Pro Ile Arg
        5                   10
```

(2) INFORMATION FOR SEQ ID NO: 52:

(i) SEQUENCE CHARACTERISTICS:
        (A) LENGTH: 251 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 138..197
        (C) IDENTIFICATION METHOD: Von Heijne matrix
        (D) OTHER INFORMATION:   score 8.3 seq LLIICHYLPLSLC/IP (xi) SEQUENCE DESCRIPTION: SEQ ID NO: 52:

```
AATTTTTTTT CACTTTCCTA AAAGCCTTCC CTTTGCCCAT GATGCCAATG ACTAGCTCTG      60

TCCTGAAGCA ATAGCTAGTA CTTTCCCTCC TTCCTGCCAC CTAGCATCCA GCCGAACCTT     120
```

```
GAATCAATAC CAGTAAA ATG GGT GTG AAC GGA AGG AGG CTG CTC ATT ATT        170
                   Met Gly Val Asn Gly Arg Arg Leu Leu Ile Ile
                   -20             -15                     -10

TGC CAT TAT TTA CCT CTG AGT CTG TGC ATT CCC ATT CCT TCC CAT ATT        218
Cys His Tyr Leu Pro Leu Ser Leu Cys Ile Pro Ile Pro Ser His Ile
            -5                   1               5

AAT TCT CTC CCG CGC AAC ACC CCC CCT GTC AGG                            251
Asn Ser Leu Pro Arg Asn Thr Pro Pro Val Arg
        10                  15
```

(2) INFORMATION FOR SEQ ID NO: 53:

(i) SEQUENCE CHARACTERISTICS:
        (A) LENGTH: 154 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 26..118
        (C) IDENTIFICATION METHOD: Von Heijne matrix
        (D) OTHER INFORMATION: score 8.2 seq LECLLLYLAESSG/LR (xi) SEQUENCE DESCRIPTION: SEQ ID NO: 53:

```
ACAGAACTAA CCTAGAAAGA ATGAT ATG AAA CTT CGT GAG TGC CCG GCC CTC        52
                            Met Lys Leu Arg Glu Cys Pro Ala Leu
                                -30             -25

CGA TGG TCC CAG CTG TCC CAG CAC AAG CTG GAG TGT CTA TTG CTT TAC       100
Arg Trp Ser Gln Leu Ser Gln His Lys Leu Glu Cys Leu Leu Leu Tyr
        -20             -15             -10

CTG GCA GAG AGC TCC GGG CTC AGA ACA GGA AAT GTG GGA GTT CTC CAC       148
Leu Ala Glu Ser Ser Gly Leu Arg Thr Gly Asn Val Gly Val Leu His
    -5                  1               5                       10

CCA AGG                                                                154
Pro Arg
```

(2) INFORMATION FOR SEQ ID NO: 54:

(i) SEQUENCE CHARACTERISTICS:
        (A) LENGTH: 485 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 78..404
        (C) IDENTIFICATION METHOD: Von Heijne matrix
        (D) OTHER INFORMATION: score 8.2 seq LLRLPQLPPXCSA/GE (xi) SEQUENCE DESCRIPTION: SEQ ID NO: 54:

```
ACCCTTTCGT CCGCTCTCAT TGGCTCTGCT GCAGCCCTGA CCAACGCTCC AATAGGCCGG       60

GATCCAGCCA TACTTCA ATG GAT CCC AGG GGT ATC TTG AAG GCA TTT CCC         110
                   Met Asp Pro Arg Gly Ile Leu Lys Ala Phe Pro
                        -105                            -100
```

```
AAG CGG CAG AAA ATT CAT GCT GAT GCA TCA TCA AAA GTA CTT GCA AAG        158
Lys Arg Gln Lys Ile His Ala Asp Ala Ser Ser Lys Val Leu Ala Lys
        -95             -90                 -85

ATT CCT AGG AGG GAA GAG GGA GAA GAA GCA GAA GAG TGG CTG AGC TCC        206
Ile Pro Arg Arg Glu Glu Gly Glu Glu Ala Glu Glu Trp Leu Ser Ser
        -80             -75                 -70

CTT CGG GCC CAT GTT GTG CGC ACT GGC ATT GGA CGA GCC CGG GCA GAA        254
Leu Arg Ala His Val Val Arg Thr Gly Ile Gly Arg Ala Arg Ala Glu
    -65             -60                 -55

CTC TTT GAG AAG CAG ATT GTT CAG CAT GGC GGC CAG CTA TGC CCT GCC        302
Leu Phe Glu Lys Gln Ile Val Gln His Gly Gly Gln Leu Cys Pro Ala
-50             -45                 -40                 -35

CAG GGC CCA GGT GTC ACT CAC ATT GTG GTG GAT GAA GGC ATG GAC TAT        350
Gln Gly Pro Gly Val Thr His Ile Val Val Asp Glu Gly Met Asp Tyr
                -30              -25                 -20

GAG CGA GCC CTC CGC CTT CTC AGA CTA CCC CAG CTG CCC CCG GKT TGC        398
Glu Arg Ala Leu Arg Leu Leu Arg Leu Pro Gln Leu Pro Pro Xaa Cys
            -15             -10                  -5

TCA GCT GGT GAA GTC AGC CTG GCT GAG CTT GTG CCT TCA GGA GAG GAG        446
Ser Ala Gly Glu Val Ser Leu Ala Glu Leu Val Pro Ser Gly Glu Glu
         1               5                  10

GCT GGT GGA TGT AGC TGG ATT CAG CAT CTT CAT CCC AGT                    485
Ala Gly Gly Cys Ser Trp Ile Gln His Leu His Pro Ser
 15              20                  25
```

(2) INFORMATION FOR SEQ ID NO: 55:

(i) SEQUENCE CHARACTERISTICS:
        (A) LENGTH: 276 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 199..261
        (C) IDENTIFICATION METHOD: Von Heijne matrix
        (D) OTHER INFORMATION: score 8 seq LFLVAVLVKVAEA/RK (xi) SEQUENCE DESCRIPTION: SEQ ID NO: 55:

```
AGCCTCTCCT GCACCCTCAG CCGGCGCGCT TCTCTTATGG GCGTCTGCTG CAGTCTGGCT     60

GCGGTCGAAC TGAAAGCGGC GGCGGGAGAC CAAACTTAGA CCCCGCTGTG GACTAGAGAA    120

CTCAGAGAAG GCAGAGGGAG AGGGAGAGAG AGASABWBAA GGGACCCGAG GAGGAGGCTT    180

CCATCACGTC ATTGCAGG ATG TTC TGG AAG CTT TCC CTG TCC TTG TTC CTG      231
                    Met Phe Trp Lys Leu Ser Leu Ser Leu Phe Leu
                            -20                 -15

GTG GCG GTG CTG GTG AAG GTG GCG GAA GCC CGG AAG AAC CGG TCG          276
Val Ala Val Leu Val Lys Val Ala Glu Ala Arg Lys Asn Arg Ser
-10              -5              1                   5
```

(2) INFORMATION FOR SEQ ID NO: 56:

(i) SEQUENCE CHARACTERISTICS:
        (A) LENGTH: 197 base pairs
        (B) TYPE: NUCLEIC ACID
        (C) STRANDEDNESS: DOUBLE
        (D) TOPOLOGY: LINEAR

```
    (ii) MOLECULE TYPE: cDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 120..173
         (C) IDENTIFICATION METHOD: Von Heijne matrix
         (D) OTHER INFORMATION:   score 7.9 seq LFSLLVLQSMATG/AT (xi) SEQUENCE DESCRIPTION: SEQ ID NO: 56:

AAGTTTCCCG GGAGAGACGA AAGCAGGAAC GAGAGCGGAG GNAGCACAGT CCGCCGAGCA        60

CAAGCTCCAG CATCCCGTCA GGGGTTGCAG GTGTGTGGGA GGCTTGAAAC TGTTACAAT        119

ATG GCT TTC CTT GGA CTC TTC TCT TTG CTG GTT CTG CAA AGT ATG GCT        167
Met Ala Phe Leu Gly Leu Phe Ser Leu Leu Val Leu Gln Ser Met Ala
        -15                 -10                  -5

ACA GGG GCC ACT TTC CCT GAG GAA GCC CCG                                 197
Thr Gly Ala Thr Phe Pro Glu Glu Ala Pro
         1               5

(2) INFORMATION FOR SEQ ID NO: 57:

(i) SEQUENCE CHARACTERISTICS:
        (A) LENGTH: 299 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 90..143
         (C) IDENTIFICATION METHOD: Von Heijne matrix
         (D) OTHER INFORMATION:   score 7.9 seq LFSLLVLQSMATG/AT (xi) SEQUENCE DESCRIPTION: SEQ ID NO: 57:

AGAGAGCGGA SSTAGCACAG TCCGCCGAGC ACAAGCTCCA GCATCCCGTC AGGGTTGCAG        60

GTGTGTGGGA GGCTTGAAAC TGTTACAAT ATG GCT TTC CTT GGA CTC TTC TCT        113
                                Met Ala Phe Leu Gly Leu Phe Ser
                                                -15

TTG CTG GTT CTG CAA AGT ATG GCT ACA GGG GCC ACT TTC CCT GAG GAA        161
Leu Leu Val Leu Gln Ser Met Ala Thr Gly Ala Thr Phe Pro Glu Glu
-10                  -5                  1                5

GCC ATT GCT GAC TTG TCA GTG AAT ATG TAT AAT CGT CTT AGA GCA GTT        209
Ala Ile Ala Asp Leu Ser Val Asn Met Tyr Asn Arg Leu Arg Ala Val
            10                  15                  20

GGA AGC TGG AGA AGG GAA GGA GCC AGC AGA CAA ATT GCT TCG TGT CTG        257
Gly Ser Trp Arg Arg Glu Gly Ala Ser Arg Gln Ile Ala Ser Cys Leu
        25                  30                  35

CCT GCC TTT CTC CTC CAT TTA CCC CTT ACA CAC ACA CAC GGG                 299
Pro Ala Phe Leu Leu His Leu Pro Leu Thr His Thr His Gly
        40                  45                  50

(2) INFORMATION FOR SEQ ID NO: 58:

(i) SEQUENCE CHARACTERISTICS:
        (A) LENGTH: 370 base pairs
        (B) TYPE: NUCLEIC ACID
        (C) STRANDEDNESS: DOUBLE
        (D) TOPOLOGY: LINEAR
```

(ii) MOLECULE TYPE: CDNA (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: 62..226
             (C) IDENTIFICATION METHOD: Von Heijne matrix
             (D) OTHER INFORMATION: score 7.8 seq ALLVALLFTLIHR/RR (xi) SEQUENCE DESCRIPTION: SEQ ID NO: 58:

```
AAGTGAGAAA GGAGCTTACC AAAGGCAGTG TACGAAGAAG GTTCCTGGGA GACTGTCAGA      60

A ATG AGT TTT TCA CTG AAC TTC ACC CTG CCG GCG AAC ACA ACG TCC TCT    109
  Met Ser Phe Ser Leu Asn Phe Thr Leu Pro Ala Asn Thr Thr Ser Ser
  -55             -50                 -45                 -40

CCT GTC ACA GGT GGG AAA GAA ACG GAC TGT GGG CCC TCT CTT GGA TTA      157
Pro Val Thr Gly Gly Lys Glu Thr Asp Cys Gly Pro Ser Leu Gly Leu
            -35                 -30                 -25

GCG GCG GGC ATA CCA TTG CTG GTG GCC ACA GCC CTG CTG GTG GCT TTA      205
Ala Ala Gly Ile Pro Leu Leu Val Ala Thr Ala Leu Leu Val Ala Leu
        -20                 -15                 -10

CTA TTT ACT TTG ATT CAC CGA AGA AGA AGC AGC ATT GAG GCC ATG GAG      253
Leu Phe Thr Leu Ile His Arg Arg Arg Ser Ser Ile Glu Ala Met Glu
    -5                   1                   5

GAA AGT GAC AGA CCA TGT GAA ATT TCA GAA ATT GAT GAC AAT CCC AAG      301
Glu Ser Asp Arg Pro Cys Glu Ile Ser Glu Ile Asp Asp Asn Pro Lys
 10                  15                  20                  25

ATA TCT GAG AAT CCT AGG AGA TCA CCC ACA CAT GAG AAG AAT ACG ATG      349
Ile Ser Glu Asn Pro Arg Arg Ser Pro Thr His Glu Lys Asn Thr Met
                 30                  35                  40

GGA GCA CAA GAG GCC CGC TGG                                          370
Gly Ala Gln Glu Ala Arg Trp
                45
```

(2) INFORMATION FOR SEQ ID NO: 59:

(i) SEQUENCE CHARACTERISTICS:
             (A) LENGTH: 336 base pairs
             (B) TYPE: NUCLEIC ACID
             (C) STRANDEDNESS: DOUBLE
             (D) TOPOLOGY: LINEAR (ii) MOLECULE TYPE: CDNA (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: 91..330
             (C) IDENTIFICATION METHOD: Von Heijne matrix
             (D) OTHER INFORMATION: score 7.7 seq LVLFLSLALLVTP/TS (xi) SEQUENCE DESCRIPTION: SEQ ID NO: 59:

```
TATTCCTTGG AGTTCCACGA CTGAATTAAG ACTGTTGTGG GRDCCATAAT TTTCAAATAC     60

TTGCCCTATA TTCGTGTTGA GGGTTCACAC ATG AGC ACA TGG TAT TTG GCA CTT    114
                                 Met Ser Thr Trp Tyr Leu Ala Leu
                                 -80                 -75

AAT AAG TCC TAT AAG AAT AAA GAC AGC GTT AGG ATT TAT CTC AGC TTG      162
Asn Lys Ser Tyr Lys Asn Lys Asp Ser Val Arg Ile Tyr Leu Ser Leu
        -70                 -65                 -60

TGC ACA GTG AGC ATT AAA TTT ACA TAC TTT CAT GAT ATA CAG ACT AAT      210
```

```
Cys Thr Val Ser Ile Lys Phe Thr Tyr Phe His Asp Ile Gln Thr Asn
    -55             -50                 -45

TGT CTT ACA ACA TGG AAA CAT TCG AGA TGC AGA TTT TAT TGG GCA TTT         258
Cys Leu Thr Thr Trp Lys His Ser Arg Cys Arg Phe Tyr Trp Ala Phe
-40             -35              -30                  -25

GGT GGT TCC ATT TTA CAG CAC TCA GTG GAT CCC CTT GTT TTG TTC CTA         306
Gly Gly Ser Ile Leu Gln His Ser Val Asp Pro Leu Val Leu Phe Leu
            -20              -15                  -10

AGC CTG GCC CTG TTA GTG ACA CCC ACT TCG                                 336
Ser Leu Ala Leu Leu Val Thr Pro Thr Ser
        -5                   1
```

(2) INFORMATION FOR SEQ ID NO: 60:

(i) SEQUENCE CHARACTERISTICS:
        (A) LENGTH: 394 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 266..322
        (C) IDENTIFICATION METHOD: Von Heijne matrix
        (D) OTHER INFORMATION:   score 7.7 seq LQLLCCIFTLVLQ/HY (xi) SEQUENCE DESCRIPTION: SEQ ID NO: 60:

```
ATACTATAAG GCTAGAATTG ACTTGGAGTC AAGGCGAGTT CCATAGGTTT AATGCGTGGC        60

ACCTATCTCA ACAACTGCAA AATCACTGTA ACTTGTAAAA AATCCCAGGG CCACTCATGG       120

ACAGCCACAT CTTTAAACCC ACACAAAAAT ACAGACACTT TGATTACATG AAAGTTAGAA       180

GCTCTAAACT AGAGCAAGGT CAGTTGTGGT AAGAAGGTAT TAGATTCAAG CATCCACAAA       240

AGTTTATAGT CTGTCAGTCA TAAGG ATG GCT ATT GGG ATT TCT TTA CAG TTA         292
                           Met Ala Ile Gly Ile Ser Leu Gln Leu
                                                        -15

CTC TGT TGT ATT TTC ACT TTG GTT TTA CAG CAC TAT CTC TTA GGA AGT         340
Leu Cys Cys Ile Phe Thr Leu Val Leu Gln His Tyr Leu Leu Gly Ser
-10              -5                   1                   5

CAT CCA TAT ATT ACC TGC ATA CAC AGT CAG CTT CTT CTC GAT ATA CAG         388
His Pro Tyr Ile Thr Cys Ile His Ser Gln Leu Leu Leu Asp Ile Gln
             10              15                  20

CAG CAG                                                                 394
Gln Gln
```

(2) INFORMATION FOR SEQ ID NO: 61:

(i) SEQUENCE CHARACTERISTICS:
        (A) LENGTH: 429 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 208..264

(C) IDENTIFICATION METHOD: Von Heijne matrix
        (D) OTHER INFORMATION:  score 7.6 seq LLNLLLLSLFAGL/DP (xi) SEQUENCE DESCRIPTION: SEQ ID NO: 61:

GAGAATGCCT GCNGAATGAT CGCCCCCCAG GGCGGCTGCC GCCGCTGCCG CTGCTGCTGT      60

TATTGCTACT GCTGCTGCCG CCGCCTCTGC TTCCACTCGG CTCTGACTGG CAGGCARAAA     120

RTGCAACTTG AMSGARGGRH ARGTCTCTGG CAGTGAGTGG AGAGCCTACA TAAAAGAGAG     180

TAAAGAGGGG CAAAAACCCA GATCAGA ATG CAG GCG ACG TCC AAC CTT CTC AAC     234
                              Met Gln Ala Thr Ser Asn Leu Leu Asn
                                                              -15

CTC CTG CTG CTG TCT TTG TTT GCC GGA TTA GAT CCT TCC AAG AAC AAA       282
Leu Leu Leu Leu Ser Leu Phe Ala Gly Leu Asp Pro Ser Lys Asn Lys
-10                 -5                   1               5

AAG AGA GGA AGT TCT TTT TCA TTT AAG TTT CCT TTA CTA GAT GAT ACC       330
Lys Arg Gly Ser Ser Phe Ser Phe Lys Phe Pro Leu Leu Asp Asp Thr
            10                  15                  20

CCA TTC CTA NGA TCC AGA ATT GAA AAT AGT GCT ACA CAT CAT CTA CAC       378
Pro Phe Leu Xaa Ser Arg Ile Glu Asn Ser Ala Thr His His Leu His
            25                  30                  35

TAT GGA CTA AAC ATG ATT CTG TGG GTT AAT TGG AAA CCT AAG CTC ACT       426
Tyr Gly Leu Asn Met Ile Leu Trp Val Asn Trp Lys Pro Lys Leu Thr
     40                  45                  50

TTG                                                                   429
Leu
55

(2) INFORMATION FOR SEQ ID NO: 62:

(i) SEQUENCE CHARACTERISTICS:
        (A) LENGTH: 189 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 88..180
        (C) IDENTIFICATION METHOD: Von Heijne matrix
        (D) OTHER INFORMATION:  score 7.6 seq VTLLCGWPGSHWC/AP (xi) SEQUENCE DESCRIPTION: SEQ ID NO: 62:

AACAGGCGTA ASKACATGGC CCAGCTCGAT CCCTCCCTTT TGTTCAACAA ACTAAATTCG      60

AGCAGGAGGC TCTAGGATTC CACAGGC ATG ATG AAA TGG AAG CCG GAG GAT CTG    114
                              Met Met Lys Trp Lys Pro Glu Asp Leu
                                  -30                     -25

GGA TCG GTT CCT TGT GAG GCT TTC TCT GTT ACT CTG CTG TGC GGC TGG      162
Gly Ser Val Pro Cys Glu Ala Phe Ser Val Thr Leu Leu Cys Gly Trp
        -20                 -15                 -10

CCA GGG TCG CAT TGG TGT GCC CCA CCA                                  189
Pro Gly Ser His Trp Cys Ala Pro Pro
         -5                  1

(2) INFORMATION FOR SEQ ID NO: 63:

(i) SEQUENCE CHARACTERISTICS:
        (A) LENGTH: 243 base pairs
        (B) TYPE: NUCLEIC ACID
        (C) STRANDEDNESS: DOUBLE (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 10..66
            (C) IDENTIFICATION METHOD: Von Heijne matrix
            (D) OTHER INFORMATION:   score 7.6 seq LLNLLLLSLFAGL/DP (xi) SEQUENCE DESCRIPTION: SEQ ID NO: 63:

```
AAGATCAGA ATG CAG GCG ACG TCC AAC CTT CTC AAC CTC CTG CTG CTG TCT        51
          Met Gln Ala Thr Ser Asn Leu Leu Asn Leu Leu Leu Leu Ser
                   -15                     -10

TTG TTT GCC GGA TTA GAT CCT TCC AAG ACT CAG ATT AGT CCT AAA GAA          99
Leu Phe Ala Gly Leu Asp Pro Ser Lys Thr Gln Ile Ser Pro Lys Glu
 -5               1               5                   10

GGG TGG CAG GTG TAC AGC TCA GCT CAG GAT CCT GAT GGG CGG TGC ATT         147
Gly Trp Gln Val Tyr Ser Ser Ala Gln Asp Pro Asp Gly Arg Cys Ile
             15                  20                  25

TGC ACA GTT GTW GCT CCA GAA CAA AAC CTG TGT TCC CGG GAT GCC AAA         195
Cys Thr Val Val Ala Pro Glu Gln Asn Leu Cys Ser Arg Asp Ala Lys
         30                  35                  40

AGC AGG CAA CTT CGC CAA CTA CTG GAA AAG GTT CAG AAC ATG TCC CGG         243
Ser Arg Gln Leu Arg Gln Leu Leu Glu Lys Val Gln Asn Met Ser Arg
     45                  50                  55
```

(2) INFORMATION FOR SEQ ID NO: 64:

(i) SEQUENCE CHARACTERISTICS:
            (A) LENGTH: 397 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 158..301
            (C) IDENTIFICATION METHOD: Von Heijne matrix
            (D) OTHER INFORMATION:   score 7.5 seq FVILLLFIFTVVS/LV (xi) SEQUENCE DESCRIPTION: SEQ ID NO: 64:

```
ACAAACAGAC GMTACCATCG CTTCAGCAGC ATCCTCTCAG ACAAGAGCCA CTATTTCTGA         60

TTCAGATCAC CTGTCATCGA AGTTTAAAGA AGGGGAAACA GGAGACAGAA ATACACTGAA        120

CCAAAAAGAT TCAAAAGAGC AAGTGGAATC TCTAAGA ATG GCT TCC AGC CAC TGG        175
                                           Met Ala Ser Ser His Trp
                                                               -45

AAT GAA ACC ACT ACC TCT GTT TAT CAG TAC CTT GGT TTT CAA GTT CAA         223
Asn Glu Thr Thr Thr Ser Val Tyr Gln Tyr Leu Gly Phe Gln Val Gln
         -40                 -35                 -30

AAA ATT TAC CCT TTC CAT GAC AAC TGG AAC ACT GCC TGC TTT GTC ATC         271
Lys Ile Tyr Pro Phe His Asp Asn Trp Asn Thr Ala Cys Phe Val Ile
     -25                 -20                 -15

CTG CTT TTA TTT ATA TTT ACA GTG GTA TCT TTA GTG GTG CTG GCT TTC         319
Leu Leu Leu Phe Ile Phe Thr Val Val Ser Leu Val Val Leu Ala Phe
-10                  -5                   1                   5
```

```
CTT TAT GAA GTG CTT GAC TGC TGC TGC TGT GTA AAA AAC AAA ACC GTG          367
Leu Tyr Glu Val Leu Asp Cys Cys Cys Cys Val Lys Asn Lys Thr Val
        10                  15                  20

AAA GAC TTG AAA AGT GAA CCC AAC CCT CGG                                  397
Lys Asp Leu Lys Ser Glu Pro Asn Pro Arg
        25                  30

(2) INFORMATION FOR SEQ ID NO: 65:

(i) SEQUENCE CHARACTERISTICS:
        (A) LENGTH: 182 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 78..176
        (C) IDENTIFICATION METHOD: Von Heijne matrix
        (D) OTHER INFORMATION:  score 7.4 seq ITCCVLLLLNCSG/VW (xi) SEQUENCE DESCRIPTION: SEQ ID NO: 65:

ATCGACTGTG AGCTGCGGCA GAGAGCAGAG GCGGCGGCGC GGGACCTGCA GTCGCCAGGG          60

ATTCCCTCCA GGTGACG ATG CTC TGG TTC TCC GGC GTC GGG GCT CTG GCT           110
                   Met Leu Trp Phe Ser Gly Val Gly Ala Leu Ala
                       -30                 -25

GAG CGT TAC TGC CGC CGC TCG CCT GGG ATT ACG TGC TGC GTC TTG CTG          158
Glu Arg Tyr Cys Arg Arg Ser Pro Gly Ile Thr Cys Cys Val Leu Leu
        -20                 -15                 -10

CTA CTC AAT TGC TCA GGG GTC TGG                                          182
Leu Leu Asn Cys Ser Gly Val Trp
        -5                  1

(2) INFORMATION FOR SEQ ID NO: 66:

(i) SEQUENCE CHARACTERISTICS:
        (A) LENGTH: 256 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 164..238
        (C) IDENTIFICATION METHOD: Von Heijne matrix
        (D) OTHER INFORMATION:  score 7.3 seq LIFFLNVTQLVRG/RG (xi) SEQUENCE DESCRIPTION: SEQ ID NO: 66:

AGTAAATAAA AAGTTTGCTT TATTAAATTA TGTTTAGATA GTGSTTATAG TGCTTTACCC          60

CTTCAAAATA GTAACTTCTA TCAATCATTT AGGATGTGTG TCAGACTATT CTGTGTCCTT         120

TAAGTGTGTK AACTAGTTTT AACCCTCTGC AAATATCTGA GGT ATG CTC TTT TTA          175
                                                Met Leu Phe Leu
                                                -25

CAG ATG GGA AAA CAA TCT TGG ACT TTA ATA TTT TTT CTT AAT GTT ACA          223
Gln Met Gly Lys Gln Ser Trp Thr Leu Ile Phe Phe Leu Asn Val Thr
        -20                 -15                 -10
```

```
CAA TTA GTA AGA GGC AGG GGG CCA GGC GGA CGG                            256
Gln Leu Val Arg Gly Arg Gly Pro Gly Gly Arg
 -5               1               5
```

(2) INFORMATION FOR SEQ ID NO: 67:

(i) SEQUENCE CHARACTERISTICS:
        (A) LENGTH: 126 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 19..99
        (C) IDENTIFICATION METHOD: Von Heijne matrix
        (D) OTHER INFORMATION:   score 7.2 seq LLLGLCSPPXXSL/AS (xi) SEQUENCE DESCRIPTION: SEQ ID NO: 67:

```
AATTGATTAG GAGATTAT ATG GAG CTG CGG GAS NTG CCG CCT GGG GGA AGA        51
                    Met Glu Leu Arg Xaa Xaa Pro Pro Gly Gly Arg
                    -25                         -20

GAG GTG CAG CTT CTG CTA GGT TTG TGC TCT CCT CCC AGS RTC TCC TTG        99
Glu Val Gln Leu Leu Leu Gly Leu Cys Ser Pro Pro Xaa Xaa Ser Leu
    -15             -10                         -5

GCT TCC TTC CCC AAA GCA GCT CAG ATG                                    126
Ala Ser Phe Pro Lys Ala Ala Gln Met
 1           5
```

(2) INFORMATION FOR SEQ ID NO: 68:

(i) SEQUENCE CHARACTERISTICS:
        (A) LENGTH: 117 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 46..87
        (C) IDENTIFICATION METHOD: Von Heijne matrix
        (D) OTHER INFORMATION:   score 7 seq LWSLLSSSGSHFG/IP (xi) SEQUENCE DESCRIPTION: SEQ ID NO: 68:

```
AGCAGGCCTT TGGGAGAGAA ACCTAATGCC TAAGCCTCAT CCTTTT ATG CTC TGG TCT     57
                                                  Met Leu Trp Ser

CTT CTT TCC TCT TCA GGC TCA CAT TTT GGT ATC CCT CAC CAC ACA TTT        105
Leu Leu Ser Ser Ser Gly Ser His Phe Gly Ile Pro His His Thr Phe
-10                 -5                   1               5

CCC CAA GAA GGG                                                        117
Pro Gln Glu Gly
             10
```

(2) INFORMATION FOR SEQ ID NO: 69:

(i) SEQUENCE CHARACTERISTICS:
        (A) LENGTH: 445 base pairs (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 110..265
        (C) IDENTIFICATION METHOD: Von Heijne matrix
        (D) OTHER INFORMATION:   score 7 seq SVWLCLLCYFAFP/FQ (xi) SEQUENCE DESCRIPTION: SEQ ID NO: 69:

```
ATGCACCATG ATATTTTTAT ACACGTTGTG TTAACTACTG TAAACACATT GTCTTCTTTA      60

TATTTCTTTG CAGGAAGTTC AGAAAAAAGT GTCACGTTTT AATCTGCAG ATG GAC ATA     118
                                                     Met Asp Ile
                                                             -50

AGT GGA TTA ATT CCT GGT CTA GTG TCT ACA TTC ATA CTT TTG TCT AKH       166
Ser Gly Leu Ile Pro Gly Leu Val Ser Thr Phe Ile Leu Leu Ser Xaa
            -45                 -40                 -35

AGT GAT CAC TAC GGA CGA AAA TTC CCT ATG ATT TTG TCT TCC GTT GGT       214
Ser Asp His Tyr Gly Arg Lys Phe Pro Met Ile Leu Ser Ser Val Gly
        -30                 -25                 -20

GCT CTT GCA ACC AGC GTT TGG CTC TGT TTG CTT TGC TAT TTT GCC TTT       262
Ala Leu Ala Thr Ser Val Trp Leu Cys Leu Leu Cys Tyr Phe Ala Phe
    -15                 -10                  -5

CCA TTC CAG CTT TTG ATT GCA TCT ACC TTC ATT GGT GCA TTT NGT GGC       310
Pro Phe Gln Leu Leu Ile Ala Ser Thr Phe Ile Gly Ala Phe Xaa Gly
  1                   5                  10                  15

AAT TAT ACC ACA TTT TGG GGA GCT TGC TTT GCC TAT ATA GTT GAT CAG       358
Asn Tyr Thr Thr Phe Trp Gly Ala Cys Phe Ala Tyr Ile Val Asp Gln
                20                  25                  30

TGT AAA GAA CRS DKA CAA AAA ACA ATT CGA ATA GCT ATC ATT GAC TTT       406
Cys Lys Glu Xaa Xaa Gln Lys Thr Ile Arg Ile Ala Ile Ile Asp Phe
                35                  40                  45

CTA CTT GGA CTT GTT ACT GGA CTA ACA GTA CTG TCA TCT                   445
Leu Leu Gly Leu Val Thr Gly Leu Thr Val Leu Ser Ser
        50                  55                  60
```

(2) INFORMATION FOR SEQ ID NO: 70:

(i) SEQUENCE CHARACTERISTICS:
        (A) LENGTH: 244 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 137..226
        (C) IDENTIFICATION METHOD: Von Heijne matrix
        (D) OTHER INFORMATION:   score 7 seq LFVILLITSLIFC/SL (xi) SEQUENCE DESCRIPTION: SEQ ID NO: 70:

```
ACTTTTTGAA TTTGTTGCTG GTACAGTTGC ATGTATTCTC TTAAAATTAT TTTGAGGCCT      60

CATATCTGGT TATTTCTCCT TTCTCATTCC TTATCTTGCG TGTTTTTACC TTTTTTTCAT     120
```

```
AACTAAGTTT TTGAGG ATG TWA GTG TTC TTT TCA AAG AAC CGG TTC GAA ATG     172
               Met Xaa Val Phe Phe Ser Lys Asn Arg Phe Glu Met
               -30             -25                 -20

TAC TTT TCT TTG CTA CTT TTT GTT ATT TTA TTG ATC ACA TCT TTA ATC       220
Tyr Phe Ser Leu Leu Leu Phe Val Ile Leu Leu Ile Thr Ser Leu Ile
        -15             -10                 -5

TTT TGT TCT CTA TAC GTG GCG CGT                                       244
Phe Cys Ser Leu Tyr Val Ala Arg
        1               5
```

(2) INFORMATION FOR SEQ ID NO: 71:

(i) SEQUENCE CHARACTERISTICS:
        (A) LENGTH: 390 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 289..357
        (C) IDENTIFICATION METHOD: Von Heijne matrix
        (D) OTHER INFORMATION:   score 6.9 seq SLSLLASHHSVSC/SN (xi) SEQUENCE DESCRIPTION: SEQ ID NO: 71:

```
AAGTACAAAG CCTACTCCAA AGACTGCAGC TTGAAGATAA AAGAGAGCAC TGCGTCCTTT      60

TGAAAATAAA GGCAGACACA AAGAAGAAAG GAGCTACCTT ACCCCAGCAT ATACCTGCGG     120

GATGTTCTCT CCAGTTCATT TTTACCTGGT GTCTTGAAAT CCGAGCAATT CCTAAAAAGG     180

CATTTTTGCG AGCCCTTGTG GACTATACCA GTGACAGTGC TGAAAAGCGC AGGCTACAGG     240

AGCTGTGCAG TAAACAAGGG GCAGCCGATT ATAGCCGCTT TGTACGAG ATG CCT GTG      297
                                                   Met Pro Val

CCT GCT TGT TGG ATC TCC TCC TCG CTT TCC CTT CTT GCC AGC CAC CAC       345
Pro Ala Cys Trp Ile Ser Ser Ser Leu Ser Leu Leu Ala Ser His His
-20             -15             -10                 -5

TCA GTC TCC TGC TCG AAC ATC TTC CTA AAC TTC AAC CCA GAC CGG           390
Ser Val Ser Cys Ser Asn Ile Phe Leu Asn Phe Asn Pro Asp Arg
                1               5                   10
```

(2) INFORMATION FOR SEQ ID NO: 72:

(i) SEQUENCE CHARACTERISTICS:
        (A) LENGTH: 374 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 198..260
        (C) IDENTIFICATION METHOD: Von Heijne matrix
        (D) OTHER INFORMATION:   score 6.9 seq LLACGSLLPGLWQ/HL (xi) SEQUENCE DESCRIPTION: SEQ ID NO: 72:

```
ATATATTTCT GAGGCAGTAC CCATCTCACT TGTAAACTTA AAAGACACCG CAGAGATTTG      60
```

-continued

```
AGGGACTCAG AAGTCAAATA GAGTAGGTTA AAAACCTCTT ATTTTTCAAA TTAATTGTTT        120

TAAGAAACAA GCATACCTGT GTAAGTGAAA TATCTTAATT TGTGTTGAAT CAAGTTAGGA        180

GACAGAGATT CTCATGA ATG TGT CCT GTG TTC TCA AAG CAG CTG CTA GCC          230
                    Met Cys Pro Val Phe Ser Lys Gln Leu Leu Ala
                        -20                 -15

TGT GGG TCT CTC CTA CCT GGG TTA TGG CAG CAC CTC ACA GCC AAT CAC         278
Cys Gly Ser Leu Leu Pro Gly Leu Trp Gln His Leu Thr Ala Asn His
-10                 -5                   1                   5

TGG CCT CCA TTC TCC SCT TTC CTC TGT ACA GTT TGC TCT GGT TCC TCA         326
Trp Pro Pro Phe Ser Xaa Phe Leu Cys Thr Val Cys Ser Gly Ser Ser
                10                  15                  20

GAG CAG ATT TCC GAG TAT ACT GCT TCA GCC ACG CCC CCA CTG TGC CTG         374
Glu Gln Ile Ser Glu Tyr Thr Ala Ser Ala Thr Pro Pro Leu Cys Leu
            25                  30                  35
```

(2) INFORMATION FOR SEQ ID NO: 73:

(i) SEQUENCE CHARACTERISTICS:
        (A) LENGTH: 416 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 33..260
        (C) IDENTIFICATION METHOD: Von Heijne matrix
        (D) OTHER INFORMATION: score 6.9 seq LLPLSAWPPWAWH/HH (xi) SEQUENCE DESCRIPTION: SEQ ID NO: 73:

```
ACGCTCAGCA GGTCCACTCC CGTGTTCCGG TC ATG GCT TTA ACA ATT CAT GGG          53
                                   Met Ala Leu Thr Ile His Gly
                                       -75                 -70

GAA AGA ATG CGC CCC GAT TGG GAG AGC CCC TGG ATC ACG TCT TCC CAA         101
Glu Arg Met Arg Pro Asp Trp Glu Ser Pro Trp Ile Thr Ser Ser Gln
                -65                 -60                 -55

GCT CAG TCC CTG TCT CTT GGA GGG AGT CCG TCC TCG AGG GGC CCT CTG         149
Ala Gln Ser Leu Ser Leu Gly Gly Ser Pro Ser Ser Arg Gly Pro Leu
            -50                 -45                 -40

GTG CCC AGG GGA GAG TAT CTT GCG TCC TGT CCT GAG GGC GTC CGC TCA         197
Val Pro Arg Gly Glu Tyr Leu Ala Ser Cys Pro Glu Gly Val Arg Ser
        -35                 -30                 -25

CAC AGC CAC CTG CTC CCC CGC TCC CTC CTT CCC TTG TCA GCA TGG CCA         245
His Ser His Leu Leu Pro Arg Ser Leu Leu Pro Leu Ser Ala Trp Pro
    -20                 -15                 -10

CCG TGG GCC TGG CAT CAC CAT GGG CCT GGC ACA CAG TCC CTC GTG GGC         293
Pro Trp Ala Trp His His His Gly Pro Gly Thr Gln Ser Leu Val Gly
 -5                  1                   5                  10

TGC CTT TGT GCC ATG AGC CCA CTG CTG CCG ACT CAC CTG TCC CTC CCA         341
Cys Leu Cys Ala Met Ser Pro Leu Leu Pro Thr His Leu Ser Leu Pro
                 15                  20                  25

GTA CTG GAA CCT TCT GGA ACA CCA GCA CTA AAA GAT AGG AGG CCC TGT         389
Val Leu Glu Pro Ser Gly Thr Pro Ala Leu Lys Asp Arg Arg Pro Cys
             30                  35                  40

GAG GTT GGC ATC CCC ATC CCC CCC AGG                                     416
Glu Val Gly Ile Pro Ile Pro Pro Arg
             45                  50
```

(2) INFORMATION FOR SEQ ID NO: 74:

(i) SEQUENCE CHARACTERISTICS:
        (A) LENGTH: 295 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 11..286
        (C) IDENTIFICATION METHOD: Von Heijne matrix
        (D) OTHER INFORMATION:  score 6.8 seq ILIASSLPTLSHP/AP (xi) SEQUENCE DESCRIPTION: SEQ ID NO: 74:

```
AAGAGTCACA ATG GCA GCC AGA TTC AGG TGC GGC CAT TTG TGT GTC CCC        49
           Met Ala Ala Arg Phe Arg Cys Gly His Leu Cys Val Pro
               -90                 -85                 -80

GAG GTT CCT CGC GGG CCG GCA TCC CAC GCC GAG GGT GGT GGT GGC AGG        97
Glu Val Pro Arg Gly Pro Ala Ser His Ala Glu Gly Gly Gly Gly Arg
            -75                 -70                 -65

CTT TCC AGA AAG GCA GCA CAC CAG GCT CAG CTC TGC TGG CGA GCA GGA       145
Leu Ser Arg Lys Ala Ala His Gln Ala Gln Leu Cys Trp Arg Ala Gly
            -60                 -55                 -50

GGC GAC GGC AGA GGA AAC TTC AAC CCG ATG AAC TTC CTG GTT GCG GGG       193
Gly Asp Gly Arg Gly Asn Phe Asn Pro Met Asn Phe Leu Val Ala Gly
            -45                 -40                 -35

ACA TTT GCC TCC TCC TGC CAC TCA CCA CCT CTG CTC TGG TCC CTC CCT       241
Thr Phe Ala Ser Ser Cys His Ser Pro Pro Leu Leu Trp Ser Leu Pro
    -30                 -25                 -20

CCA AGA ATC CTC ATA GCG TCC TCT CTC CCC ACT CTC TCC CAT CCC GCG       289
Pro Arg Ile Leu Ile Ala Ser Ser Leu Pro Thr Leu Ser His Pro Ala
-15             -10                 -5                   1

CCT GGG                                                               295
Pro Gly
```

(2) INFORMATION FOR SEQ ID NO: 75:

(i) SEQUENCE CHARACTERISTICS:
        (A) LENGTH: 361 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 101..187
        (C) IDENTIFICATION METHOD: Von Heijne matrix
        (D) OTHER INFORMATION:  score 6.8 seq VLSLICSCFYTQP/HP (xi) SEQUENCE DESCRIPTION: SEQ ID NO: 75:

```
ACTCTCCCCT CCCCTCCCCG GCACTGCAGC ACCAGCCGTC TGCAGCTCCG GCCGCCACTT        60

GCGCCTCTCC AGCCTCCGCA GCCCAACCGC CGCCAGCACC ATG GCC AGC ACC ATT       115
                                            Met Ala Ser Thr Ile
                                                -25
```

```
TCC GCC TAC AAG GAG AAG ATG AAG GAG CTG TCG GTG CTG TCG CTC ATC      163
Ser Ala Tyr Lys Glu Lys Met Lys Glu Leu Ser Val Leu Ser Leu Ile
            -20             -15                 -10

TGC TCC TGC TTC TAC ACA CAG CCG CAC CCC AAT ACC GTC TAC CAG TAC      211
Cys Ser Cys Phe Tyr Thr Gln Pro His Pro Asn Thr Val Tyr Gln Tyr
        -5                   1                   5

GGG GAC ATG GAG GTG AAG CAG CTG GAC AAG CGG GCC TCA GGC CAG AGC      259
Gly Asp Met Glu Val Lys Gln Leu Asp Lys Arg Ala Ser Gly Gln Ser
         10                  15                 20

TTC GAG GTC ATC CTC AAG TCC CCT TCT GAC CTG TCC CCA GAG AGC CCT      307
Phe Glu Val Ile Leu Lys Ser Pro Ser Asp Leu Ser Pro Glu Ser Pro
 25              30                  35                  40

ATG CTC TCC TCC CCA CCC AAG AAG AAG GAC ACC TCC CTG GAG GAG CTG      355
Met Leu Ser Ser Pro Pro Lys Lys Lys Asp Thr Ser Leu Glu Glu Leu
                 45                  50                  55

CAA AAG                                                              361
Gln Lys
```

(2) INFORMATION FOR SEQ ID NO: 76:

(i) SEQUENCE CHARACTERISTICS:
        (A) LENGTH: 361 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 2..343
        (C) IDENTIFICATION METHOD: Von Heijne matrix
        (D) OTHER INFORMATION:   score 6.7 seq LIPMAILLGQTQS/NS (xi) SEQUENCE DESCRIPTION: SEQ ID NO: 76:

```
A ATG TTA CAA GTC TAT GGA AAG CCA GTT TAT CAG GGC CAT CGA AGC ACT     49
  Met Leu Gln Val Tyr Gly Lys Pro Val Tyr Gln Gly His Arg Ser Thr
              -110                -105                -100

CTT AAA AAA GGA CCA TAT CTC AGA TTT AAT TCT CCA TCT CCT AAG TCC      97
Leu Lys Lys Gly Pro Tyr Leu Arg Phe Asn Ser Pro Ser Pro Lys Ser
         -95                 -90                 -85

AGA CCA CAG AGA CCA AAA GTA ATA GAA CGA GTT AAA GGC ACT AAG GTA     145
Arg Pro Gln Arg Pro Lys Val Ile Glu Arg Val Lys Gly Thr Lys Val
         -80                 -75                 -70

AAG TCA ATA AGA ACA CAG ACT GAC TTC TAT GCA ACA AAA CCT AAG AAG     193
Lys Ser Ile Arg Thr Gln Thr Asp Phe Tyr Ala Thr Lys Pro Lys Lys
         -65                 -60                 -55

ATG GAT TCT AAA ATG AAA CAT TCT GTT CCT GTG TTA CCT CAT GGC GAT     241
Met Asp Ser Lys Met Lys His Ser Val Pro Val Leu Pro His Gly Asp
-50                  -45                 -40                 -35

CAG CAA TAT TTG TTC AGC CCA AGT AGA GAA ATG CCT ACT TTT TCA GGT     289
Gln Gln Tyr Leu Phe Ser Pro Ser Arg Glu Met Pro Thr Phe Ser Gly
             -30                 -25                 -20

ACA TTG GAA GGT CAT CTG ATT CCT ATG GCA ATT CTT TTA GGA CAA ACC     337
Thr Leu Glu Gly His Leu Ile Pro Met Ala Ile Leu Leu Gly Gln Thr
             -15                 -10                  -5

CAA AGT AAT AGT GAT ACC ATG CCG                                     361
Gln Ser Asn Ser Asp Thr Met Pro
         1                   5
```

(2) INFORMATION FOR SEQ ID NO: 77:

(i) SEQUENCE CHARACTERISTICS:
        (A) LENGTH: 388 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 8..361
        (C) IDENTIFICATION METHOD: Von Heijne matrix
        (D) OTHER INFORMATION: score 6.7 seq LLFAKLFGHLTSA/RR (xi) SEQUENCE DESCRIPTION: SEQ ID NO: 77:

```
AGCAGAC ATG TCT GTA CTT GAA ATC AGT GGA ATG ATA ATG AAC AGA GTG        49
        Met Ser Val Leu Glu Ile Ser Gly Met Ile Met Asn Arg Val
               -115            -110            -105

AAC AGC CAT ATA CCA GGA ATA GGA TAC CAG ATT TTT GGA AAT GCA GTC        97
Asn Ser His Ile Pro Gly Ile Gly Tyr Gln Ile Phe Gly Asn Ala Val
            -100             -95              -90

TCT CTC ATA CTG GGT TTA ACT CCA TTT GTT TTC CGA CTT TCT CAA GCT       145
Ser Leu Ile Leu Gly Leu Thr Pro Phe Val Phe Arg Leu Ser Gln Ala
         -85             -80              -75

ACA GAC TTG GAA CAA CTC ACA GCA CAT TCT GCT TCA GAA CTT TAT GTG       193
Thr Asp Leu Glu Gln Leu Thr Ala His Ser Ala Ser Glu Leu Tyr Val
     -70              -65              -60

ATT GCA TTT GGT TCT AAT GAA GAT GTC ATA GTT CTT TCT ATG GTT ATA       241
Ile Ala Phe Gly Ser Asn Glu Asp Val Ile Val Leu Ser Met Val Ile
 -55              -50              -45

ATA AGT TTT GTG GTT CGC GTG TCT CTT GTG TGG ATT TTC TTT TTT TTG       289
Ile Ser Phe Val Val Arg Val Ser Leu Val Trp Ile Phe Phe Phe Leu
-40              -35              -30              -25

CTC TGT GTA GCA GAA AGA ACT TAT AAA CAG CGA TTA CTT TTT GCA AAA       337
Leu Cys Val Ala Glu Arg Thr Tyr Lys Gln Arg Leu Leu Phe Ala Lys
             -20              -15              -10

CTC TTT GGA CAT TTA ACA TCT GCA AGG AGG GCT CGA AAA TCT GAG GTT       385
Leu Phe Gly His Leu Thr Ser Ala Arg Arg Ala Arg Lys Ser Glu Val
              -5               1               5

CCT                                                                    388
Pro
```

(2) INFORMATION FOR SEQ ID NO: 78:

(i) SEQUENCE CHARACTERISTICS:
        (A) LENGTH: 291 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 79..285
        (C) IDENTIFICATION METHOD: Von Heijne matrix
        (D) OTHER INFORMATION: score 6.7 seq FFKLLLLGAMCSG/AR (xi) SEQUENCE DESCRIPTION: SEQ ID NO: 78:

```
AAGACTGTGA CTGGAAGAGG AGAAAGAACT GCATGCTTGT AACGGCCCGG ATGGGAGTGT          60

ATTCCTTTTT TTGAAGAT ATG TGT AAA GGC ATT AAA GCT GGT GAC ACC TGT         111
                    Met Cys Lys Gly Ile Lys Ala Gly Asp Thr Cys
                        -65             -60

GAG AAG CTG GTG GGA TAT TCT GCC GTG TAT AGA GTC TGT TTT GGA ATG         159
Glu Lys Leu Val Gly Tyr Ser Ala Val Tyr Arg Val Cys Phe Gly Met
        -55             -50                 -45

GCT TGT TTC TTC TTT ATC TTC TGT CTA CTG ACC TTG AAA ATC AAC AAC         207
Ala Cys Phe Phe Phe Ile Phe Cys Leu Leu Thr Leu Lys Ile Asn Asn
        -40             -35             -30

AGC AAA AGT TGT AGA GCT CAT ATT CAC AAT GGC TTT TGG TTC TTT AAA         255
Ser Lys Ser Cys Arg Ala His Ile His Asn Gly Phe Trp Phe Phe Lys
        -25             -20             -15

CTT CTG CTG TTG GGG GCC ATG TGC TCA GGA GCA AGG                         291
Leu Leu Leu Leu Gly Ala Met Cys Ser Gly Ala Arg
-10             -5                      1

(2) INFORMATION FOR SEQ ID NO: 79:

(i) SEQUENCE CHARACTERISTICS:
          (A) LENGTH: 402 base pairs
          (B) TYPE: NUCLEIC ACID
          (C) STRANDEDNESS: DOUBLE
          (D) TOPOLOGY: LINEAR (ii) MOLECULE TYPE: CDNA (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: 61..372
          (C) IDENTIFICATION METHOD: Von Heijne matrix
          (D) OTHER INFORMATION:   score 6.6 seq HFSHVVWFHPTWA/QQ (xi) SEQUENCE DESCRIPTION: SEQ ID NO: 79:

ATTTTCCCGG GTCTTCTCCA GCTGCCACCG CTTTACTGCA AAACTGACGG GCGCAAAAAC          60

ATG AGT GAC TCC GCG GGA GGG CGC GCT GGT CTC CGG CGT TAC CCC AAG         108
Met Ser Asp Ser Ala Gly Gly Arg Ala Gly Leu Arg Arg Tyr Pro Lys
            -100            -95                 -90

CTC CCA GTG TGG GTG GTG GAG GAT CAT CAG GAG GTT CTA CCC TTT ATA         156
Leu Pro Val Trp Val Val Glu Asp His Gln Glu Val Leu Pro Phe Ile
        -85             -80                 -75

TAC CGG GCC ATA GGC TCA AAG CAT CTT CCT GCC AGT AAT GTA AGT TTT         204
Tyr Arg Ala Ile Gly Ser Lys His Leu Pro Ala Ser Asn Val Ser Phe
        -70             -65             -60

TTA CAT TTC GAC TCA CAT CCA GAC CTC CTT ATT CCT GTG AAT ATG CCA         252
Leu His Phe Asp Ser His Pro Asp Leu Leu Ile Pro Val Asn Met Pro
        -55             -50             -45

GCA GAC ACC GTG TTT GAT AAG GAA ACA CTC TTT GGA GAA TTA AGT ATT         300
Ala Asp Thr Val Phe Asp Lys Glu Thr Leu Phe Gly Glu Leu Ser Ile
-40             -35             -30              -25

GAA AAT TGG ATT ATG CCT GCA GTT TAT GCT GGC CAT TTT TCA CAT GTA         348
Glu Asn Trp Ile Met Pro Ala Val Tyr Ala Gly His Phe Ser His Val
            -20             -15             -10

GTA TGG TTT CAT CCC ACA TGG GCT CAG CAG ATC AGA GAG GGC AGA CAC         396
Val Trp Phe His Pro Thr Trp Ala Gln Gln Ile Arg Glu Gly Arg His
            -5              1               5

CAC TTT                                                                  402
His Phe
    10
```

(2) INFORMATION FOR SEQ ID NO: 80:

(i) SEQUENCE CHARACTERISTICS:
        (A) LENGTH: 338 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 12..152
        (C) IDENTIFICATION METHOD: Von Heijne matrix
        (D) OTHER INFORMATION: score 6.3 seq SSCVLLTALVALA/AY (xi) SEQUENCE DESCRIPTION: SEQ ID NO: 80:

```
AAAACGCGTG A ATG AGT AGC TGC CGC GGG CAG AAA GTT GCC GGA GGT CTC        50
             Met Ser Ser Cys Arg Gly Gln Lys Val Ala Gly Gly Leu
                 -45                 -40                 -35

CGG GTG GTA TCG CCC TTT CCT CTT TGC CAG CCC GCT GGC GAG CCG AGC        98
Arg Val Val Ser Pro Phe Pro Leu Cys Gln Pro Ala Gly Glu Pro Ser
            -30                 -25                 -20

CGG GGC AAG ATG AGG TCG TCC TGT GTC CTG CTC ACC GCC CTG GTG GCG       146
Arg Gly Lys Met Arg Ser Ser Cys Val Leu Leu Thr Ala Leu Val Ala
            -15                 -10                  -5

CTG GCC GCC TAT TAC GTC TAC ATC CCG CTG CCT GGC TCC GTG TCC GAC       194
Leu Ala Ala Tyr Tyr Val Tyr Ile Pro Leu Pro Gly Ser Val Ser Asp
              1                   5                  10

CCC TGG AAG CTG ATG CTG CTG GAC GCC ACT TTC CGG GGT GCA CAS MMD       242
Pro Trp Lys Leu Met Leu Leu Asp Ala Thr Phe Arg Gly Ala Xaa Xaa
 15                  20                  25                  30

NTA AGT RAC CTG GTC CAS TAC CTG GGA CTG AGC SRT CAC CTG CTG GCA       290
Xaa Ser Xaa Leu Val Xaa Tyr Leu Gly Leu Ser Xaa His Leu Leu Ala
                 35                  40                  45

CTG ANN WTA WNA TTG TTT CTT TTG GCA AAA AAA GCG CGT GGT CTT CTG       338
Leu Xaa Xaa Xaa Leu Phe Leu Leu Ala Lys Lys Ala Arg Gly Leu Leu
                 50                  55                  60
```

(2) INFORMATION FOR SEQ ID NO: 81:

(i) SEQUENCE CHARACTERISTICS:
        (A) LENGTH: 229 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 14..139
        (C) IDENTIFICATION METHOD: Von Heijne matrix
        (D) OTHER INFORMATION: score 6.1 seq DLAVALSLLPAWT/ES (xi) SEQUENCE DESCRIPTION: SEQ ID NO: 81:

```
ATTAAAGTCA AAG ATG ATT ATT CCT TTC AAA ATA AAG AAT CTA GGA GGG         49
               Met Ile Ile Pro Phe Lys Ile Lys Asn Leu Gly Gly
                   -40                 -35
```

```
CGA GTC CTG CTG TCG GGA AGG GAG ATG TTT CCT GCT TCC GTC CGT GCT        97
Arg Val Leu Leu Ser Gly Arg Glu Met Phe Pro Ala Ser Val Arg Ala
-30                     -25                 -20                 -15

CCT GAC CTG GCG GTG GCC CTG TCC CTG CTA CCT GCG TGG ACA GAG TCT       145
Pro Asp Leu Ala Val Ala Leu Ser Leu Leu Pro Ala Trp Thr Glu Ser
                -10                  -5                       1

CCA ACA CGC GGC AGC CAC CAG AGC CAG GCC CGA GCG CAC AGC CGT GCA       193
Pro Thr Arg Gly Ser His Gln Ser Gln Ala Arg Ala His Ser Arg Ala
          5                  10                 15

TTG CGA AAG CAA AGC CGA AAC ACG AGG TCG CCC CGG                       229
Leu Arg Lys Gln Ser Arg Asn Thr Arg Ser Pro Arg
     20                 25                 30
```

(2) INFORMATION FOR SEQ ID NO: 82:

(i) SEQUENCE CHARACTERISTICS:
        (A) LENGTH: 249 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 70..228
        (C) IDENTIFICATION METHOD: Von Heijne matrix
        (D) OTHER INFORMATION: score 6 seq ALILLLLAQKGPS/XF (xi) SEQUENCE DESCRIPTION: SEQ ID NO: 82:

```
ACGTAAAAAC AGGTAGTTAC AAGGAGTGTC TTGATAATGA AATTTGTGGT ATAGAGTACT       60

GGTGAATGT ATG GTG TGT AGT GCT CCT AGA AAA ATA GTA GTT AGG GCA TTT      111
           Met Val Cys Ser Ala Pro Arg Lys Ile Val Val Arg Ala Phe
           -50                 -45                 -40

ATT ACG ATA ATA TTC ATA TAT TAT GCT ATA AAG AAG AGG GCA AAT GAA        159
Ile Thr Ile Ile Phe Ile Tyr Tyr Ala Ile Lys Lys Arg Ala Asn Glu
         -35                 -30                 -25

CCT GCA GCA TAT TTG ATG TTG AAG CCT GAG GCT CTG ATT CTC CTT CTG        207
Pro Ala Ala Tyr Leu Met Leu Lys Pro Glu Ala Leu Ile Leu Leu Leu
         -20                 -15                 -10

TTA GCT CAA AAG GGC CCC AGT HAG TTT CTG TTA GTG TGG AGA                249
Leu Ala Gln Lys Gly Pro Ser Xaa Phe Leu Leu Val Trp Arg
         -5                   1                   5
```

(2) INFORMATION FOR SEQ ID NO: 83:

(i) SEQUENCE CHARACTERISTICS:
        (A) LENGTH: 289 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 110..229
        (C) IDENTIFICATION METHOD: Von Heijne matrix
        (D) OTHER INFORMATION: score 5.9 seq VCSALCSLGEVRP/XE (xi) SEQUENCE DESCRIPTION: SEQ ID NO: 83:

```
ACCCTGCTGG GCGGGAAGGC GGCGCCCCGG CCGAGGTGGC GGCGGCTCCT CAGATGGGAG         60

AAGAAGTTGT CCATGTTCAC ACTGGGTGAA GGAAGCTGAA ACCACAGAC ATG ACT GAG        118
                                                      Met Thr Glu
                                                      -40

TCC TCC ATG AAG AAG CTG GCC TCC ACC CTG CTG GAC GCC ATC ACC GAT         166
Ser Ser Met Lys Lys Leu Ala Ser Thr Leu Leu Asp Ala Ile Thr Asp
        -35             -30             -25

AAG GAC CCC CTG GTG CAG GAG CAG GTC TGC AGT GCC CTG TGC TCC CTC         214
Lys Asp Pro Leu Val Gln Glu Gln Val Cys Ser Ala Leu Cys Ser Leu
    -20             -15             -10

GGG GAG GTG CGG CCV TGG GAG ACG CTC CGT GCC TGC GAG GAG TAT CTG         262
Gly Glu Val Arg Pro Xaa Glu Thr Leu Arg Ala Cys Glu Glu Tyr Leu
 -5              1               5               10

CGG CAS ATG ACA AGC TGG CAC ACC CGG                                     289
Arg Xaa Met Thr Ser Trp His Thr Arg
         15              20
```

(2) INFORMATION FOR SEQ ID NO: 84:

(i) SEQUENCE CHARACTERISTICS:
        (A) LENGTH: 252 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 76..204
        (C) IDENTIFICATION METHOD: Von Heijne matrix
        (D) OTHER INFORMATION: score 5.9 seq VFLFHCTSGLSSC/KC (xi) SEQUENCE DESCRIPTION: SEQ ID NO: 84:

```
AGTARAACAA AAGGATATGC ACACACACAT ATTTAAATAC ATGTAGTTTT TTGCATAAAT         60

TATCACTGAG AGGAA ATG CAA GAA ACT GAT TGT AAT AAA CGC TGG GGA AGG        111
                 Met Gln Glu Thr Asp Cys Asn Lys Arg Trp Gly Arg
                 -40                 -35

GGC CTG GGT GGC CTG TGG TCA GAA ACA GGA AGG AGA TTT CAT TGC AAA         159
Gly Leu Gly Gly Leu Trp Ser Glu Thr Gly Arg Arg Phe His Cys Lys
        -30             -25             -20

TCT TTT GTA TTT CTT TTT CAC TGT ACT TCT GGA TTA TCT TCA TGC AAA         207
Ser Phe Val Phe Leu Phe His Cys Thr Ser Gly Leu Ser Ser Cys Lys
-15             -10             -5                             1

TGT TCT AAA AAG CAT TYM AAA TAT TGC TTC TGT TTT GTG GCA AGT             252
Cys Ser Lys Lys His Xaa Lys Tyr Cys Phe Cys Phe Val Ala Ser
             5              10              15
```

(2) INFORMATION FOR SEQ ID NO: 85:

(i) SEQUENCE CHARACTERISTICS:
        (A) LENGTH: 366 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
            (A) NAME/KEY: sig_peptide
            (B) LOCATION: 232..282
            (C) IDENTIFICATION METHOD: Von Heijne matrix
            (D) OTHER INFORMATION: score 5.8 seq VPWLSSTVSCAQG/LR (xi) SEQUENCE DESCRIPTION: SEQ ID NO: 85:

```
ATGAGTGGTC MGGAGATAAC ACTTAATGCT TTATTCTTAA GTGTTGGAAG GAGCAAGTAA     60

GTGGTCTAGT GAGCTGTTTT TAGAGGAACT GTATAATATG TAACACATTG TCATTATATT    120

CACTAACTCC CAAAGTATTC TTGAGATATT GANACAAAAC AAAGAGCTTG AATAGAAACC    180

CTGAGCAACA ATGTATTTAC TTTCCACTTG CAGCAGAACT TGGCCTTTCA G ATG CTC     237
                                                        Met Leu
```

| | | | | | | | | | | | | | | | | |
|---|---|---|---|---|---|---|---|---|---|---|---|---|---|---|---|---|
| CTT | GAA | GTG | CCT | TGG | CTT | AGC | AGT | ACT | GTC | TCT | TGT | GCC | CAG | GGT | CTG | 285 |
| Leu | Glu | Val | Pro | Trp | Leu | Ser | Ser | Thr | Val | Ser | Cys | Ala | Gln | Gly | Leu | |
| -15 | | | | -10 | | | | -5 | | | | | | | 1 | |

| | | | | | | | | | | | | | | | | |
|---|---|---|---|---|---|---|---|---|---|---|---|---|---|---|---|---|
| AGA | TTG | GCA | CAA | CAC | AGA | GTG | CCT | TTC | TTT | TAT | TCA | AAT | GTC | TCA | TTA | 333 |
| Arg | Leu | Ala | Gln | His | Arg | Val | Pro | Phe | Phe | Tyr | Ser | Asn | Val | Ser | Leu | |
| | | | | 5 | | | | | 10 | | | | | 15 | | |

| | | | | | | | | | | |
|---|---|---|---|---|---|---|---|---|---|---|
| TGC | AAA | TTA | TTG | CTG | CCA | GCC | AMM | CTG | CAC | GGG | 366 |
| Cys | Lys | Leu | Leu | Leu | Pro | Ala | Xaa | Leu | His | Gly | |
| | | | 20 | | | | 25 | | | | |

(2) INFORMATION FOR SEQ ID NO: 86:

(i) SEQUENCE CHARACTERISTICS:
            (A) LENGTH: 437 base pairs
            (B) TYPE: NUCLEIC ACID
            (C) STRANDEDNESS: DOUBLE
            (D) TOPOLOGY: LINEAR (ii) MOLECULE TYPE: cDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 123..209
            (C) IDENTIFICATION METHOD: Von Heijne matrix
            (D) OTHER INFORMATION: score 5.7 seq SPAFLAVAGPGWA/RP (xi) SEQUENCE DESCRIPTION: SEQ ID NO: 86:

```
AGCTCTCCCA TGCTGGTCTG TGGGGACTCC ATGTCCAAAC ACGCAGATCC TGCCTCCCAG     60

GCTTTAATTG ATCCTGCTGC CCTCTGGGAG CACCCACACA AGCCAGGCTC TCACTGGACC    120
```

| | | | | | | | | | | | | | | | |
|---|---|---|---|---|---|---|---|---|---|---|---|---|---|---|---|
| TC | ATG | TCT | GGA | GGG | CGG | ATG | CAG | GCA | CGG | TGC | TCC | CAG | CAA | AGC | ACC | 167 |
| | Met | Ser | Gly | Gly | Arg | Met | Gln | Ala | Arg | Cys | Ser | Gln | Gln | Ser | Thr | |
| | | | | -25 | | | | | -20 | | | | | -15 | | |

| | | | | | | | | | | | | | | | |
|---|---|---|---|---|---|---|---|---|---|---|---|---|---|---|---|
| TGG | AGT | CCT | GCC | TTC | CTT | GCA | GTG | GCC | GGG | CCG | GGC | TGG | GCA | CGT | CCT | 215 |
| Trp | Ser | Pro | Ala | Phe | Leu | Ala | Val | Ala | Gly | Pro | Gly | Trp | Ala | Arg | Pro | |
| | | | | -10 | | | | | -5 | | | | | | 1 | |

| | | | | | | | | | | | | | | | |
|---|---|---|---|---|---|---|---|---|---|---|---|---|---|---|---|
| GGC | TGT | DCC | CTG | AGG | ACC | AAG | TAT | GAC | TCT | CAG | CTG | GCC | CGG | CAC | CTC | 263 |
| Gly | Cys | Xaa | Leu | Arg | Thr | Lys | Tyr | Asp | Ser | Gln | Leu | Ala | Arg | His | Leu | |
| | | | | 5 | | | | | 10 | | | | | 15 | | |

| | | | | | | | | | | | | | | | |
|---|---|---|---|---|---|---|---|---|---|---|---|---|---|---|---|
| TTG | CAG | CCT | CAG | TTC | CCT | GGT | CTG | ACC | CTT | GGG | ACC | CTG | GTG | CAA | CCT | 311 |
| Leu | Gln | Pro | Gln | Phe | Pro | Gly | Leu | Thr | Leu | Gly | Thr | Leu | Val | Gln | Pro | |
| | | | 20 | | | | | 25 | | | | | 30 | | | |

| | | | | | | | | | | | | | | | |
|---|---|---|---|---|---|---|---|---|---|---|---|---|---|---|---|
| GCC | CAC | TGG | GGC | ATG | GGA | GGG | GGC | ACA | GGA | GGG | GTC | TTG | GGC | GAG | GGA | 359 |
| Ala | His | Trp | Gly | Met | Gly | Gly | Gly | Thr | Gly | Gly | Val | Leu | Gly | Glu | Gly | |
| 35 | | | | 40 | | | | 45 | | | | | 50 | | | |

| | | | | | | | | | | | | | | | |
|---|---|---|---|---|---|---|---|---|---|---|---|---|---|---|---|
| GGG | GGG | CAC | AGC | TAT | GCA | GAG | CAT | GGC | ACC | TGC | CTC | CAG | TCG | TGC | TCC | 407 |
| Gly | Gly | His | Ser | Tyr | Ala | Glu | His | Gly | Thr | Cys | Leu | Gln | Ser | Cys | Ser | |
| | | 55 | | | | 60 | | | | | 65 | | | | | |

```
ACA GAC GTG CTD ANG CAT GTC CTC CTG GCG                                      437
Thr Asp Val Leu Xaa His Val Leu Leu Ala
             70                  75
```

(2) INFORMATION FOR SEQ ID NO: 87:

(i) SEQUENCE CHARACTERISTICS:
        (A) LENGTH: 437 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 63..116
        (C) IDENTIFICATION METHOD: Von Heijne matrix
        (D) OTHER INFORMATION: score 5.6 seq WHFLASFFPRAGC/HG (xi) SEQUENCE DESCRIPTION: SEQ ID NO: 87:

```
AACTGTGGTC ACATCCCTCA AAAGTGAACA GTCGCCATCG GAGGCGTTTG GAGGAGACCG             60

TG ATG TTG CAG ATG CTG TGG CAT TTC CTA GCT AGC TTT TTC CCC AGG              107
   Met Leu Gln Met Leu Trp His Phe Leu Ala Ser Phe Phe Pro Arg
           -15                 -10                 -5

GCT GGG TGC CAC GGC TCC AGA GAG GGG GAC GAT CGT GAA GTC AGA GGC             155
Ala Gly Cys His Gly Ser Arg Glu Gly Asp Asp Arg Glu Val Arg Gly
             1               5                  10

ACC CCA GCC CCT GCC TGG AGA GAC CAG ATG GCA AGC TTT TTG GGG AAA             203
Thr Pro Ala Pro Ala Trp Arg Asp Gln Met Ala Ser Phe Leu Gly Lys
         15                  20                  25

CAG GAC GGA AGG GCT GAG GCC ACG GAA AAA AGA CCC ACC ATT TTG CTG             251
Gln Asp Gly Arg Ala Glu Ala Thr Glu Lys Arg Pro Thr Ile Leu Leu
     30                  35                  40                  45

GTG GTT GGA CCT GCA GAG CAG TTT CCT AAG AAA ATT GTA CAA GCT GGA             299
Val Val Gly Pro Ala Glu Gln Phe Pro Lys Lys Ile Val Gln Ala Gly
                 50                  55                  60

GAT AAG GAC CTT GAT GGG CAG CTA GAC TTT GAA GAA TTT GTC CAT TAT             347
Asp Lys Asp Leu Asp Gly Gln Leu Asp Phe Glu Glu Phe Val His Tyr
             65                  70                  75

CTC CAA GAT CAT GAG AAG AAG CTG AGG CTG GTG TTT AAG AGT TTG GAC             395
Leu Gln Asp His Glu Lys Lys Leu Arg Leu Val Phe Lys Ser Leu Asp
         80                  85                  90

AAA AAG AAT GAT GGA CGC ATT GAC GCG CAG GAG ATC ATG CAG                     437
Lys Lys Asn Asp Gly Arg Ile Asp Ala Gln Glu Ile Met Gln
     95                  100                 105
```

(2) INFORMATION FOR SEQ ID NO: 88:

(i) SEQUENCE CHARACTERISTICS:
        (A) LENGTH: 113 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide (B) LOCATION: 3..62
        (C) IDENTIFICATION METHOD: Von Heijne matrix
        (D) OTHER INFORMATION: score 5.6 seq SLVCLLAMGKGLG/SS (xi) SEQUENCE DESCRIPTION: SEQ ID NO: 88:

```
AC ATG TAT TCC CAT CCC GTG TCC TCA CTG GTG TGT CTC CTG GCC ATG       47
   Met Tyr Ser His Pro Val Ser Ser Leu Val Cys Leu Leu Ala Met
   -20              -15              -10

GGC AAG GGA CTC GGG TCA TCC CAG GCC CTG GTC CAG CCA GAC ACC TGG      95
Gly Lys Gly Leu Gly Ser Ser Gln Ala Leu Val Gln Pro Asp Thr Trp
 -5               1               5                  10

CCC CAC ACC TCC CCG CGG                                              113
Pro His Thr Ser Pro Arg
             15
```

(2) INFORMATION FOR SEQ ID NO: 89:

(i) SEQUENCE CHARACTERISTICS:
        (A) LENGTH: 362 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 87..191
        (C) IDENTIFICATION METHOD: Von Heijne matrix
        (D) OTHER INFORMATION: score 5.6 seq FIFMEVLGSGAFS/EV (xi) SEQUENCE DESCRIPTION: SEQ ID NO: 89:

```
AACAGACCTG TACGAGCTGG AGTGGGAGCT CAAGCAGGAT TCTTCCCGAG TCCCTGGCAT      60

CCTCAGAAGC TTCAACTCTG GAGGCA ATG GGT CGA AAG GAA GAA GAT GAC TGC     113
                             Met Gly Arg Lys Glu Glu Asp Asp Cys
                             -35                 -30

AGT DCC TGG AAG AAA CAG ACC ACC AAC ATC CGG AAA ACC TTC ATT TTT      161
Ser Xaa Trp Lys Lys Gln Thr Thr Asn Ile Arg Lys Thr Phe Ile Phe
    -25             -20                 -15

ATG GAA GTG CTG GGA TCA GGA GCT TTC TCA GAA GTT TTC CTG GTG AAG      209
Met Glu Val Leu Gly Ser Gly Ala Phe Ser Glu Val Phe Leu Val Lys
-10              -5              1                5

CAA AGA CTG ACT GGG AAG CTC TTT GCT CTG AAG TGC ATC AAG AAG TCA      257
Gln Arg Leu Thr Gly Lys Leu Phe Ala Leu Lys Cys Ile Lys Lys Ser
             10              15              20

CCT GCC TTC CGG GAC AGC AGC CTG GAG AAT GAG ATT GCT GTG TTG AAA      305
Pro Ala Phe Arg Asp Ser Ser Leu Glu Asn Glu Ile Ala Val Leu Lys
         25              30              35

AAG ATC AAG CAT GAA AAC ATT GTG ACC CTG GAG GAC ATC TAT GAG AGC      353
Lys Ile Lys His Glu Asn Ile Val Thr Leu Glu Asp Ile Tyr Glu Ser
         40              45              50

ACA CAA GGG                                                          362
Thr Gln Gly
 55
```

(2) INFORMATION FOR SEQ ID NO: 90:

(i) SEQUENCE CHARACTERISTICS:
        (A) LENGTH: 384 base pairs
        (B) TYPE: NUCLEIC ACID
        (C) STRANDEDNESS: DOUBLE
        (D) TOPOLOGY: LINEAR

```
    (ii) MOLECULE TYPE: cDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 241..327
         (C) IDENTIFICATION METHOD: Von Heijne matrix
         (D) OTHER INFORMATION:   score 5.6 seq LLPNQSLFSLARA/VR (xi) SEQUENCE DESCRIPTION: SEQ ID NO: 90:

AAGCGGCGCA CCGGGHGAAG ATGGCGTTGG AGGTCGGCGA TATGGAAGAT GGGCAGCTTT      60

CCGACTCGGA TTCCGACATG ACGGTCGCAC CCAGCGACAG GCCGCTGCAA TTGCCAAAAG     120

TGCTAGGTGG CGACAGTGCT ATGAGGGCCT TCCAGAACAC GGCAACTGCA TGTGCACCAG     180

TATCACATTA TCGAGCTGTT GAAAGTGTGG ATTCAAGTGA AGAAAGTTTT TCTGATTCAG     240

ATG ATG ATA GCT GTC TTT GGA AAC GCA AAC GAC AGA AAT GTT TTA ACC      288
Met Met Ile Ala Val Phe Gly Asn Ala Asn Asp Arg Asn Val Leu Thr
            -25                 -20                 -15

CTC CTC CCA AAC CAG AGC CTT TTC AGT TTG GCC AGA GCA GTC AGA AAC      336
Leu Leu Pro Asn Gln Ser Leu Phe Ser Leu Ala Arg Ala Val Arg Asn
            -10                 -5                   1

CAC CTG TTG CTG GAG GAA AGA AGA TTA ACA ACA TAT GGG GTG CTG TGC      384
His Leu Leu Leu Glu Glu Arg Arg Leu Thr Thr Tyr Gly Val Leu Cys
  5                  10                  15

(2) INFORMATION FOR SEQ ID NO: 91:

(i) SEQUENCE CHARACTERISTICS:
         (A) LENGTH: 314 base pairs
         (B) TYPE: NUCLEIC ACID
         (C) STRANDEDNESS: DOUBLE
         (D) TOPOLOGY: LINEAR (ii) MOLECULE TYPE: cDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 141..197
         (C) IDENTIFICATION METHOD: Von Heijne matrix
         (D) OTHER INFORMATION:   score 5.6 seq LVVTAWFFGMCRS/KA (xi) SEQUENCE DESCRIPTION: SEQ ID NO: 91:

ATCCCAGAAC ACCATTGGGA GAACGCCAGG ACACCGTGAA GGCTGAGCCG CCACTCGGTT      60

CTGATGCCGC ATCCATTGGT CAGTGCACGT TCTTTGAGCT TCCACTTGAG TGCACGTTCT     120

TTGAGCTTCC ACTTGAGTGC ATG TTC TTT GAG CTT CCA CTT GTA GTG ACT GCC    173
                      Met Phe Phe Glu Leu Pro Leu Val Val Thr Ala
                                      -15                  -10

TGG TTC TTC GGG ATG TGC AGG AGC AAA GCG CTC TTA GGC AAT GCT CGT      221
Trp Phe Phe Gly Met Cys Arg Ser Lys Ala Leu Leu Gly Asn Ala Arg
        -5                   1                   5

TCT GCC CTG TGT TTA CAA ACC AAG GCC TGT GCC AGC TCT ACT CAG CCT      269
Ser Ala Leu Cys Leu Gln Thr Lys Ala Cys Ala Ser Ser Thr Gln Pro
        10                  15                  20

GAC ACC CAT AAT GAG CAC CAT CCC AGG AAT CCC TGT CCC TAC TTG          314
Asp Thr His Asn Glu His His Pro Arg Asn Pro Cys Pro Tyr Leu
 25                 30                  35
```

(2) INFORMATION FOR SEQ ID NO: 92:

(i) SEQUENCE CHARACTERISTICS:
        (A) LENGTH: 316 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 155..286
        (C) IDENTIFICATION METHOD: Von Heijne matrix
        (D) OTHER INFORMATION:   score 5.5 seq FLLIVANVHFSQT/WV (xi) SEQUENCE DESCRIPTION: SEQ ID NO: 92:

```
ATAAATAGCA TTGTTTACAT CGACCAAATA TTGCCTGTTT CCTTTAATTC AAATGCATTA      60

GGTTCCCGCC TCCCTCTCCT TCCCCGCCAT GTTGCTGTTT TAAGGCTTCA TATGTATTAA     120

CATTTCTCTG ATCAAAATTG TGGCTGTTTT CCTT ATG AAC CAT AAT ATA ATC ATT     175
                                    Met Asn His Asn Ile Ile Ile
                                                            -40

TGT GTG ATG TAC ATT GTG CCA TTT TTG ATG ACT AAA TGT CTA TAT TTC       223
Cys Val Met Tyr Ile Val Pro Phe Leu Met Thr Lys Cys Leu Tyr Phe
        -35             -30             -25

TGC CAT TCC TGT AAG AGA GGG AGT TTT TTA CTG ATA GTA GCA AAT GTT       271
Cys His Ser Cys Lys Arg Gly Ser Phe Leu Leu Ile Val Ala Asn Val
    -20             -15             -10

CAC TTC AGT CAA ACT TGG GTG TTC AGT GGT AAA CCA TAT AAA GGG           316
His Phe Ser Gln Thr Trp Val Phe Ser Gly Lys Pro Tyr Lys Gly
 -5              1               5                  10
```

(2) INFORMATION FOR SEQ ID NO: 93:

(i) SEQUENCE CHARACTERISTICS:
        (A) LENGTH: 405 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 247..309
        (C) IDENTIFICATION METHOD: Von Heijne matrix
        (D) OTHER INFORMATION:   score 5.5 seq LTGLCXCCLQALG/LA (xi) SEQUENCE DESCRIPTION: SEQ ID NO: 93:

```
ATTGTCTTAG TCCCATCCTC TGTTCCCCTG GCCAGTTTGT CTAGCTGTGT GGTCTCTGTT      60

CTCTCCCTAC CGTGCCTTCC ATCCCAGCCA TCCCTGACTA CGTGTTTCCC CCACAGACAT     120

CACACTGGTT CACCTCGTTG ACCACCGTTT CCTTCTCCCC AAGTCTCCCG GGCAAGGGCT     180

GATTCTCCAG TCTCCTCTGG GAAGCTGGCC CTGAACCACT TAGAACCTAT CGCTCCTTCG     240

TCACCT ATG TCA TGT GGC AGC GCT GCC TCA CTT ACG GGT CTG TGT KSG        288
       Met Ser Cys Gly Ser Ala Ala Ser Leu Thr Gly Leu Cys Xaa
           -20             -15             -10

TGC TGC CTC CAA GCC CTG GGG CTT GCG TGG CGC CGT CGC GGT TTG ACG       336
Cys Cys Leu Gln Ala Leu Gly Leu Ala Trp Arg Arg Arg Gly Leu Thr
```

```
                   -5                     1                         5
GGA  CCG  GGC  CTC  CCC  CCT  GTG  TTG  CAG  ATA  TGC  TGT  CCA  AGG  AGC  CTC       384
Gly  Pro  Gly  Leu  Pro  Pro  Val  Leu  Gln  Ile  Cys  Cys  Pro  Arg  Ser  Leu
 10             Pro       15                  20                       25

CGT  GGT  GTG  ACG  GCT  CCT  ACT                                                    405
Arg  Gly  Val  Thr  Ala  Pro  Thr
                    30
```

(2) INFORMATION FOR SEQ ID NO: 94:

(i) SEQUENCE CHARACTERISTICS:
        (A) LENGTH: 302 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 99..236
        (C) IDENTIFICATION METHOD: Von Heijne matrix
        (D) OTHER INFORMATION:   score 5.4 seq VLFFVGLITNGLA/MR (xi) SEQUENCE DESCRIPTION: SEQ ID NO: 94:

```
AAAAATACCA GATGCCACTC TGCAGGCTGC AATAACTACT ACTTACTGGA TACATTCAAA        60

CCCTCCAGAA TCAACAGTTA TCAGGTAACC AACAAGAA ATG CAA GCC GTC GAC AAC       116
                                         Met Gln Ala Val Asp Asn
                                                          -45

CTC ACC TCT GCG CCT GGG AAC ACC AGT CTG TGC ACC AGA GAC TAC AAA         164
Leu Thr Ser Ala Pro Gly Asn Thr Ser Leu Cys Thr Arg Asp Tyr Lys
-40             -35             -30                 -25

ATC ACC CAG GTC CTC TTC CCA CTG CTC TAC ACT GTC CTG TTT TTT GTT         212
Ile Thr Gln Val Leu Phe Pro Leu Leu Tyr Thr Val Leu Phe Phe Val
            -20             -15             -10

GGA CTT ATC ACA AAT GGC CTG GCG ATG AGG ATT TTC TTT CAA ATC CGG         260
Gly Leu Ile Thr Asn Gly Leu Ala Met Arg Ile Phe Phe Gln Ile Arg
         -5                    1                5

AGT AAA TCA AAC TTT ATT ATT TTT CTT AAG AAC ACA GTS AAG                 302
Ser Lys Ser Asn Phe Ile Ile Phe Leu Lys Asn Thr Val Lys
 10             15                  20
```

(2) INFORMATION FOR SEQ ID NO: 95:

(i) SEQUENCE CHARACTERISTICS:
        (A) LENGTH: 99 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 16..75
        (C) IDENTIFICATION METHOD: Von Heijne matrix
        (D) OTHER INFORMATION:   score 5.3 seq LCSSCCSWGPAAG/AL (xi) SEQUENCE DESCRIPTION: SEQ ID NO: 95:

```
AGAAGTAGCC GCAGG ATG GCG GCG GCT ATG CSS TTG CTC TGC TCG TCC TGT        51
```

```
                Met Ala Ala Ala Met Xaa Leu Leu Cys Ser Ser Cys
                    -20                 -15                 -10

TGC TCC TGG GGC CCG GCG GCT GGT GCC TTG CAG AAC CCC CAA CGC GGG        99
Cys Ser Trp Gly Pro Ala Ala Gly Ala Leu Gln Asn Pro Gln Arg Gly
        -5                   1                   5
```

(2) INFORMATION FOR SEQ ID NO: 96:

(i) SEQUENCE CHARACTERISTICS:
        (A) LENGTH: 485 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 396..470
        (C) IDENTIFICATION METHOD: Von Heijne matrix
        (D) OTHER INFORMATION: score 5.3 seq SVVKVLSLRKAQA/QS (xi) SEQUENCE DESCRIPTION: SEQ ID NO: 96:

```
ATTTCTGCCC ACGGGCATAA GTTCAAAAGA AAGCTGCGAA AAGTTGGAGA CTGCTGATGA         60

AACCAGTCAT CTCCAGCCAC TCAACAAGCG TCAGAGGACA AGCTCTGTGG TGGAAGAGCA        120

TTTCCAAGCC TCAGTATCTC CCACTGAAGC CGCACCCCCT GCCACAGGAG ACCAGAGTCC        180

TGGCCTGGGC ACCCAGCCAA AGCTGCCATC CAGCAGTGGC CTTCCTGCTG CAGACGTGTC        240

CCCTGCCACA GCTGAAGAGC CCTTGTCACC TTCCACACCC ACCCGCCGGC CTCCCTTCAC        300

CCGAGGGCGA CTCCGGCTGC TCTCCTTTCG ATCCATGGAG GAGGCCAGAC TGGTGCCCAC        360

AGTGAAAGAS CAAATACCCT GTGCTGAAGG ACGTC ATG GAC TTC ATT AAG GAT          413
                                       Met Asp Phe Ile Lys Asp
                                           -25                 -20

CAG TCG CTC TCG CAC AGG AGT GTT GTG AAG GTT CTT TCC CTG AGG AAA         461
Gln Ser Leu Ser His Arg Ser Val Val Lys Val Leu Ser Leu Arg Lys
            -15                 -10                  -5

GCC CAG GCC CAG AGC ATC CTG GAA                                          485
Ala Gln Ala Gln Ser Ile Leu Glu
             1               5
```

(2) INFORMATION FOR SEQ ID NO: 97:

(i) SEQUENCE CHARACTERISTICS:
        (A) LENGTH: 283 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 59..142
        (C) IDENTIFICATION METHOD: Von Heijne matrix
        (D) OTHER INFORMATION: score 5.3 seq RISCAFSLASSTA/RQ (xi) SEQUENCE DESCRIPTION: SEQ ID NO: 97:

```
AGTGTGTGAA GCGTACCTAR GGCGGGAGGC GACATGGWGA CAGGGGCGGY CGWGCTGT          58
```

```
ATG ACC AGG CCC TTT TGG GCA TCC TGC AGC ACG TGG GCA ACG TCC AGG         106
Met Thr Arg Pro Phe Trp Ala Ser Cys Ser Thr Trp Ala Thr Ser Arg
        -25                 -20                 -15

ATT TCC TGC GCG TTC TCT TTG GCT TCC TCT ACC GCA AGA CAG ACT TCT         154
Ile Ser Cys Ala Phe Ser Leu Ala Ser Ser Thr Ala Arg Gln Thr Ser
        -10                 -5                   1

ATC GCT TGC TGC GCC ACC CAT CGG ACC GCA TGG GCT TCC CGC CCG GGG         202
Ile Ala Cys Cys Ala Thr His Arg Thr Ala Trp Ala Ser Arg Pro Gly
 5                  10                  15                  20

CCG CGC AGG CCT TGG TGC TGC AGG TAT TCA AAA CCT TTG ACC ACA TGG         250
Pro Arg Arg Pro Trp Cys Cys Arg Tyr Ser Lys Pro Leu Thr Thr Trp
                25                  30                  35

CCC GTC AGG ATG ATG AGA AGA GAA GGC AGY KGA                             283
Pro Val Arg Met Met Arg Arg Glu Gly Ser Xaa
                40                  45
```

(2) INFORMATION FOR SEQ ID NO: 98:

(i) SEQUENCE CHARACTERISTICS:
        (A) LENGTH: 390 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 286..333
        (C) IDENTIFICATION METHOD: Von Heijne matrix
        (D) OTHER INFORMATION:   score 5.3 seq CAVSLTTAAVAFG/DE (xi) SEQUENCE DESCRIPTION: SEQ ID NO: 98:

```
ACTNTGTGCT GGTGCTGGCA AAGTTTGTGA TTTTAAGAAA TTCTGCTGTG CTCTCCAGCA         60

CTGCGAGCTT CTGCCTTCCC TGTAGTTTCC CAGATGTGAT CCAGGTAGCC GAGATTCCGC        120

TGCCCGTGCT TCGGTAGCTT AAGTCTTTGC CTCAGCTTTT TTCCTTGCAG CCGCTGAGGA        180

GGCGATAAAA TTGGCGTCAC AGTCTCAAGC AGCGATTGAA GGCGTCTTTT CAACTACTCG        240

ATTAAGGTTG GGTATCGTCG TGGGACTTGG AAATTTGTTG TTTCC ATG AAA TCC TGC        297
                                                 Met Lys Ser Cys
                                                         -15

GCA GTG TCG CTC ACT ACC GCC GCT GTT GCC TTC GGT GAT GAG GCA AAG         345
Ala Val Ser Leu Thr Thr Ala Ala Val Ala Phe Gly Asp Glu Ala Lys
        -10                 -5                   1

AAA ATG GCG GAA GGA AAA GCG AGC CGC GAG AGT GAA GAG GAG ACG             390
Lys Met Ala Glu Gly Lys Ala Ser Arg Glu Ser Glu Glu Glu Thr
 5                  10                  15
```

(2) INFORMATION FOR SEQ ID NO: 99:

(i) SEQUENCE CHARACTERISTICS:
        (A) LENGTH: 254 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:

(A) NAME/KEY: sig_peptide
            (B) LOCATION: 138..200
            (C) IDENTIFICATION METHOD: Von Heijne matrix
            (D) OTHER INFORMATION: score 5.2 seq LSLSLICLRMSLS/LY (xi) SEQUENCE DESCRIPTION: SEQ ID NO: 99:

ATGTGATTWT KTTCCTATTT ATTTTAAATA CACACACCCA CAGGGCTCTG CCCCTGTAAA         60

AGAAAAAAAA TCAAAACAAA CAAATAAATA ACCCCAAAGA GATGGACCCA GGGGAGAACG        120

CGTAAGTRTG AAGGGGC ATG AGT ATA CAC GAG TGT GCG TGT CTT TCC CTC          170
                   Met Ser Ile His Glu Cys Ala Cys Leu Ser Leu
                        -20                  -15

TCC CTT ATT TGT CTC CGT ATG AGT CTC TCC TTG TAC CCT CCC CCT GCC         218
Ser Leu Ile Cys Leu Arg Met Ser Leu Ser Leu Tyr Pro Pro Pro Ala
-10               -5                   1                 5

TCG ATG ATA TTA CTC CCC CAG ACT TGG AAG CCG CGC                         254
Ser Met Ile Leu Leu Pro Gln Thr Trp Lys Pro Arg
         10                  15

(2) INFORMATION FOR SEQ ID NO: 100:

(i) SEQUENCE CHARACTERISTICS:
        (A) LENGTH: 303 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 178..222
        (C) IDENTIFICATION METHOD: Von Heijne matrix
        (D) OTHER INFORMATION: score 5.2 seq SGLSFLSVFSLWC/EP (xi) SEQUENCE DESCRIPTION: SEQ ID NO: 100:

AAGATCTRGA ARCAGTRACC CTCTCTCTTT GCATRAGTTT CTCTTTTTTC TCTGAGTTAC         60

AGTTTTGARR RCAGCWRCTA ATTTTTTTAA TCCCTCGAAT AACTCAGTTT TAGGAACATT        120

CGCTCTCCCT AAGCCTTACC TTGAAACCAG TGTAGGATTT TGCTGCCACC CCGGAAG          177

ATG CTG AGT GGA CTC AGC TTC CTA TCC GTT TTC TCC CTC TGG TGT GAG         225
Met Leu Ser Gly Leu Ser Phe Leu Ser Val Phe Ser Leu Trp Cys Glu
-15              -10                  -5                       1

CCC ACA CTC CCG GCG CTG GGA AAT GGC TCT GTT CTA GGA GTG CGG CWR         273
Pro Thr Leu Pro Ala Leu Gly Asn Gly Ser Val Leu Gly Val Arg Xaa
             5                  10                  15

TCA TCC TCT TCC TCT GCC CAG TGC TCT CTG                                 303
Ser Ser Ser Ser Ser Ala Gln Cys Ser Leu
         20                  25

(2) INFORMATION FOR SEQ ID NO: 101:

(i) SEQUENCE CHARACTERISTICS:
        (A) LENGTH: 380 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
            (A) NAME/KEY: sig_peptide
            (B) LOCATION: 120..374
            (C) IDENTIFICATION METHOD: Von Heijne matrix
            (D) OTHER INFORMATION:  score 5.2 seq LYSILHFPFWVHG/RX (xi) SEQUENCE DESCRIPTION: SEQ ID NO: 101:

```
AACTTTGATG GAATCAAAGG TCATGGGCGC CAGGGCAGCT GTTCCACAT GCAGGTGGGG       60

GCCCGCCCTT TGTTCACACC TACATTCAAG GAATTCTGTT GGGCTCATAA TTCGTTGTG      119

ATG GGG TTA AAG GAC AAA TCT CAG GCC CCC GCC TCA GGA CTG GGA GTT       167
Met Gly Leu Lys Asp Lys Ser Gln Ala Pro Ala Ser Gly Leu Gly Val
-85             -80                 -75                 -70

CTC CGA GGG CAA AGG TCG GGC TCA TTC ATT TCT ATG CCT GCC CCA GCC       215
Leu Arg Gly Gln Arg Ser Gly Ser Phe Ile Ser Met Pro Ala Pro Ala
            -65                 -60                 -55

TCA GGC CAG TKC CCG GAA GAA AGC AGG TCC CCA GCT CCA CCA GTG GCT       263
Ser Gly Gln Xaa Pro Glu Glu Ser Arg Ser Pro Ala Pro Pro Val Ala
        -50                 -45                 -40

TCT AGG TCT CAG AAC AGA GGC TAC AGA CCG TGG CAT GGG CCC CTT TGG       311
Ser Arg Ser Gln Asn Arg Gly Tyr Arg Pro Trp His Gly Pro Leu Trp
    -35                 -30                 -25

GTC CAC CAA AGT GTT CGG TTT GGA CTT TAC AGC ATT TTG CAT TTT CCT       359
Val His Gln Ser Val Arg Phe Gly Leu Tyr Ser Ile Leu His Phe Pro
-20                 -15                 -10

TTT TGG GTT CAC GGC CGA YAG                                           380
Phe Trp Val His Gly Arg Xaa
-5              1
```

(2) INFORMATION FOR SEQ ID NO: 102:

(i) SEQUENCE CHARACTERISTICS:
            (A) LENGTH: 265 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 65..193
            (C) IDENTIFICATION METHOD: Von Heijne matrix
            (D) OTHER INFORMATION:  score 5.2 seq PMQLLQVLSDVLA/EI (xi) SEQUENCE DESCRIPTION: SEQ ID NO: 102:

```
AATGCCAGTA TTAAGGATTT TTTTTTCTAT TTTTACTCTT TAGTTAAAAT TATAAGACCT      60

AATT ATG AGT GAT CAA ATT AAA TTC ATT ATG GAC AGT CTC AAT AAG GAG      109
     Met Ser Asp Gln Ile Lys Phe Ile Met Asp Ser Leu Asn Lys Glu
             -40                 -35                 -30

CCC TTT AGG AAG AAC TAT AAT TTA ATC ACG TTT GAT TCC TTG GAG CCA       157
Pro Phe Arg Lys Asn Tyr Asn Leu Ile Thr Phe Asp Ser Leu Glu Pro
        -25                 -20                 -15

ATG CAA CTA TTA CAA GTT CTC AGT GAT GTT CTG GCT GAG ATT GAC CCA       205
Met Gln Leu Leu Gln Val Leu Ser Asp Val Leu Ala Glu Ile Asp Pro
    -10                  -5                  1

AAG GTA AGA GTT TTC TCT TTC TTT TTG ATG GGT AGC AGA AAG CCA ATT       253
Lys Val Arg Val Phe Ser Phe Leu Met Gly Ser Arg Lys Pro Ile
 5                  10                  15                  20

TCT CCC TCT TGG                                                       265
Ser Pro Ser Trp
```

(2) INFORMATION FOR SEQ ID NO: 103:

(i) SEQUENCE CHARACTERISTICS:
        (A) LENGTH: 354 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 25..336
        (C) IDENTIFICATION METHOD: Von Heijne matrix
        (D) OTHER INFORMATION:   score 5.1 seq SSVASLTATPSLA/SP (xi) SEQUENCE DESCRIPTION: SEQ ID NO: 103:

```
AAACCTTGTA CAACACCGGC CGAC ATG TCT CCT TCC TGC CTG CAC CCC GAC            51
                          Met Ser Pro Ser Cys Leu His Pro Asp
                                               -100

CTG TGG TCA ATG TGT CTG GAG GTC CCC TCC TTT ACA GCC ACC GAC TCA           99
Leu Trp Ser Met Cys Leu Glu Val Pro Ser Phe Thr Ala Thr Asp Ser
-95             -90              -85                 -80

GTG AAC TGC GGC TGC TGT TTG GAG CTC GCG ACG GAG CCG GCT CGG AAC          147
Val Asn Cys Gly Cys Cys Leu Glu Leu Ala Thr Glu Pro Ala Arg Asn
            -75             -70                 -65

ATC AGA TCA ACC ACC AGG GCT TCT CTG CTG AGG TGC AGC TCA TTC ACT          195
Ile Arg Ser Thr Thr Arg Ala Ser Leu Leu Arg Cys Ser Ser Phe Thr
        -60             -55                 -50

TCA ACC AGG AAC TCT ACG GGA ATT TCA GCG CTG CCT CCC GCG GCC CCA          243
Ser Thr Arg Asn Ser Thr Gly Ile Ser Ala Leu Pro Pro Ala Ala Pro
        -45             -40                 -35

ATG GCC TGG CCA TTC TCA GCC TCT TTG TCA ACG TTG CCA GTA CCT CTA          291
Met Ala Trp Pro Phe Ser Ala Ser Leu Ser Thr Leu Pro Val Pro Leu
    -30             -25                 -20

ACC CAT TCC TCA GTC GCC TCC TTA ACC GCG ACA CCA TCA CTC GCA TCT          339
Thr His Ser Ser Val Ala Ser Leu Thr Ala Thr Pro Ser Leu Ala Ser
-15             -10                 -5                   1

CCT ACA AGA ATG ATG                                                      354
Pro Thr Arg Met Met
              5
```

(2) INFORMATION FOR SEQ ID NO: 104:

(i) SEQUENCE CHARACTERISTICS:
        (A) LENGTH: 226 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 155..202
        (C) IDENTIFICATION METHOD: Von Heijne matrix
        (D) OTHER INFORMATION:   score 5.1 seq SFHLLLDPSSTQS/SI (xi) SEQUENCE DESCRIPTION: SEQ ID NO: 104:

```
AACTCTGGAA TGAAGGGGGG AATTACGGGT TGGTGGTCGG CTTCATGTTA GGAGGACACC        60

CCTCCATCTG TTCACAGCTC AGCCTGTTTC CAATTTAAAG CCCAGAAGAA GCCTTCCCAG       120

CCTACTCAGA ATCCCACATC CTCTCCTCTC TCTT ATG GAT CTC AGT TTT CAT TTA      175
                                    Met Asp Leu Ser Phe His Leu
                                     -15                     -10

TTA CTA GAT CCT TCC TCT ACT CAA TCA AGC ATA CTG AAG CAC CTC CCA        223
Leu Leu Asp Pro Ser Ser Thr Gln Ser Ser Ile Leu Lys His Leu Pro
            -5              1                   5

TGT                                                                    226
Cys (2) INFORMATION FOR SEQ ID NO: 105:

(i) SEQUENCE CHARACTERISTICS:
        (A) LENGTH: 447 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 289..366
        (C) IDENTIFICATION METHOD: Von Heijne matrix
        (D) OTHER INFORMATION:   score 5 seq VISVLILVGFGAC/IY (xi) SEQUENCE DESCRIPTION: SEQ ID NO: 105:

ATCTCTGATG GGCAGGGAGA GATACCAGGG TGCTGAGCCA GTCCAGGACT GCCCCCTCCT        60

GGCCCACTCA GAGCCCCTGG GTGTGAGAAG CTCGTCTCCC GTGGGTTGCA TTGGCTCTGC       120

CCTATCTCTG CCTCCAGCAC CCAGGGCGGC CGCAGATGGC AGTGTCTCTG GGACAGCAG       180

CTGCGAATGA GTCCACGGGC CAACGCTGAG CTGCTCAGGC TGAGGCGGTG TGCTCAGCAC       240

AGAGCCCCCG GAACTGGCAT CTGCAGGGCG TGAGCCAARG CCGCCGCG ATG CCG CAC       297
                                                     Met Pro His
                                                          -25

TTC CTG GAC TGG TTC GTG MCG GTC TAC TTG GTC ATC TCG GTC CTC ATT       345
Phe Leu Asp Trp Phe Val Xaa Val Tyr Leu Val Ile Ser Val Leu Ile
        -20                 -15                     -10

CTG GTG GGC TTC GGC GCC TGC ATC TAC TAC TTC GAG CCG GGC CTG CAG       393
Leu Val Gly Phe Gly Ala Cys Ile Tyr Tyr Phe Glu Pro Gly Leu Gln
         -5                  1                   5

GAG GCG CAC AAG TGG CGC ATG YAG CGC CCC TGG TGG ACC GCG ACC TCC       441
Glu Ala His Lys Trp Arg Met Xaa Arg Pro Trp Trp Thr Ala Thr Ser
 10              15                  20                      25

ACT GGG                                                               447
Thr Gly (2) INFORMATION FOR SEQ ID NO: 106:

(i) SEQUENCE CHARACTERISTICS:
        (A) LENGTH: 195 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain
```

(ix) FEATURE:
    (A) NAME/KEY: sig_peptide
    (B) LOCATION: 79..168
    (C) IDENTIFICATION METHOD: Von Heijne matrix
    (D) OTHER INFORMATION: score 5 seq IVGLLAQLEKINA/EP (xi) SEQUENCE DESCRIPTION: SEQ ID NO: 106:

```
AACAGAAAGA TGACTTAAAG AACGTGGGGA GTCGCTCGCA GTTCGATTAT CTGCAATTAT      60

GAAATGAAGT AACTCAAG ATG AGC AAG TTA AAA GTG ATA CCA GAA AAA AGC      111
                    Met Ser Lys Leu Lys Val Ile Pro Glu Lys Ser
                    -30             -25                 -20

CTT ACC AAT AAT TCT AGG ATC GTA GGA CTC CTG GCT CAA CTG GAG AAG      159
Leu Thr Asn Asn Ser Arg Ile Val Gly Leu Leu Ala Gln Leu Glu Lys
            -15             -10                 -5

ATC AAT GCT GAG CCT TCA GAA TCW GAC ACT AGC CGG                      195
Ile Asn Ala Glu Pro Ser Glu Ser Asp Thr Ser Arg
            1               5
```

(2) INFORMATION FOR SEQ ID NO: 107:

(i) SEQUENCE CHARACTERISTICS:
    (A) LENGTH: 166 base pairs
    (B) TYPE: NUCLEIC ACID
    (C) STRANDEDNESS: DOUBLE
    (D) TOPOLOGY: LINEAR (ii) MOLECULE TYPE: CDNA (vi) ORIGINAL SOURCE:
    (A) ORGANISM: Homo Sapiens
    (F) TISSUE TYPE: Brain (ix) FEATURE:
    (A) NAME/KEY: sig_peptide
    (B) LOCATION: 38..106
    (C) IDENTIFICATION METHOD: Von Heijne matrix
    (D) OTHER INFORMATION: score 5 seq LIPAMAFLSCVRP/ES (xi) SEQUENCE DESCRIPTION: SEQ ID NO: 107:

```
AACTGCTGCT CACAGAAGCA GTGAGGATGA TGCCAGG ATG ATG TCT GCC TCG CGC     55
                                        Met Met Ser Ala Ser Arg
                                                        -20

CTG GCT GGG ACT CTG ATC CCA GCC ATG GCC TTC CTC TCC TGC GTG AGA     103
Leu Ala Gly Thr Leu Ile Pro Ala Met Ala Phe Leu Ser Cys Val Arg
    -15             -10                 -5

CCA GAA AGC WGG GAG CCC TGC GTG GAG GTG GTT CCT AAT ATT ACT TAT     151
Pro Glu Ser Xaa Glu Pro Cys Val Glu Val Val Pro Asn Ile Thr Tyr
    1               5                   10                  15

CAA TGC ATG GAG CTG                                                  166
Gln Cys Met Glu Leu
            20
```

(2) INFORMATION FOR SEQ ID NO: 108:

(i) SEQUENCE CHARACTERISTICS:
    (A) LENGTH: 278 base pairs
    (B) TYPE: NUCLEIC ACID
    (C) STRANDEDNESS: DOUBLE
    (D) TOPOLOGY: LINEAR (ii) MOLECULE TYPE: CDNA (vi) ORIGINAL SOURCE:
    (A) ORGANISM: Homo Sapiens
    (F) TISSUE TYPE: Brain (ix) FEATURE:
    (A) NAME/KEY: sig_peptide (B) LOCATION: 84..230
        (C) IDENTIFICATION METHOD: Von Heijne matrix
        (D) OTHER INFORMATION:  score 4.9 seq VTVCCXLVAFLFC/IL (xi) SEQUENCE DESCRIPTION: SEQ ID NO: 108:

```
AARAGACTCC GCCCCCTTCC TTGGAGCGCC GCGNCTCGGG CTGAGGGAGC TCGGGCCAAT      60

CAGAGGGACG GCCCCAGART GGC ATG GTA GAT GGA ACG CAG CTG AGA GGT CTG     113
                         Met Val Asp Gly Thr Gln Leu Arg Gly Leu
                                     -45                     -40

ACA AGA ATG TAC CAG GTC CCA CTA MCA CTG GAT CGG GAT GAG ACC CTG       161
Thr Arg Met Tyr Gln Val Pro Leu Xaa Leu Asp Arg Asp Glu Thr Leu
            -35                 -30                 -25

GTA CGG CTC CGC TTC ACC ATG GTG GCC CTG GTC ACG GTC TGC TGT MCA       209
Val Arg Leu Arg Phe Thr Met Val Ala Leu Val Thr Val Cys Cys Xaa
        -20                 -15                 -10

CTT GTC GCC TTC CTC TTC TGC ATC CTC TGG TCC CTG CTC TTC CAC TTC       257
Leu Val Ala Phe Leu Phe Cys Ile Leu Trp Ser Leu Leu Phe His Phe
    -5                  1                   5

AAG GAG ACA ACG GCC ACA GGG                                           278
Lys Glu Thr Thr Ala Thr Gly
 10                  15
```

(2) INFORMATION FOR SEQ ID NO: 109:

(i) SEQUENCE CHARACTERISTICS:
        (A) LENGTH: 217 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 116..193
        (C) IDENTIFICATION METHOD: Von Heijne matrix
        (D) OTHER INFORMATION:  score 4.9 seq LISMLQMLAVIIT/NT (xi) SEQUENCE DESCRIPTION: SEQ ID NO: 109:

```
ACTTGAAGTT CYYCTGGGGG CAATGAGATG GCAGCTATAC AGCGAGTCTG AAAAGAACAT      60

CCACATTCCT AATCCCTAGG AATATGATTA TTGGAAAATA GATATAATTA TACAA ATG      118
                                                              Met

AAA CAG AAC TTC CTT GTT CTC AAC AGT GTC TGG TAC CTA ATA AGC ATG       166
Lys Gln Asn Phe Leu Val Leu Asn Ser Val Trp Tyr Leu Ile Ser Met
-25                 -20                 -15                 -10

TTA CAA ATG TTA GCT GTG ATC ATT ACC AAC ACC ACC ATC ACC ACC ATT       214
Leu Gln Met Leu Ala Val Ile Ile Thr Asn Thr Thr Ile Thr Thr Ile
                -5                  1                   5

GGG                                                                   217
Gly
```

(2) INFORMATION FOR SEQ ID NO: 110:

(i) SEQUENCE CHARACTERISTICS:
        (A) LENGTH: 426 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:

```
            (A) ORGANISM: Homo Sapiens
            (F) TISSUE TYPE: Brain (ix) FEATURE:
            (A) NAME/KEY: sig_peptide
            (B) LOCATION: 55..231
            (C) IDENTIFICATION METHOD: Von Heijne matrix
            (D) OTHER INFORMATION:  score 4.9 seq LVEMCLEVLGSSA/GD (xi) SEQUENCE DESCRIPTION: SEQ ID NO: 110:

AATTCAGAAT TAGAAAACAA ACCAGTAGAT TTTTTTGAAC AAAAATCTTT AGAA ATG         57
                                                              Met

GAA TGT CAA AAT AGT TCT TTA AAA AAG TGT TTA CTA GTT GAA AAG TCA        105
Glu Cys Gln Asn Ser Ser Leu Lys Lys Cys Leu Leu Val Glu Lys Ser
            -55                 -50                 -45

CTT GTG AAA GCT TCT TAT TTA ATT GCT TTC CAA ACT GCT GCA AGC AAG        153
Leu Val Lys Ala Ser Tyr Leu Ile Ala Phe Gln Thr Ala Ala Ser Lys
        -40                 -35                 -30

AAG CCA TTC TCB ATT GCT GAA GAA TTA ATT AAA CCA TAT TTA GTA GAA        201
Lys Pro Phe Ser Ile Ala Glu Glu Leu Ile Lys Pro Tyr Leu Val Glu
    -25                 -20                 -15

ATG TGT TTA GAA GTT TTG GGT TCA AGT GCT GGA GAC AAA ATG AAA ACT        249
Met Cys Leu Glu Val Leu Gly Ser Ser Ala Gly Asp Lys Met Lys Thr
-10                  -5                   1                   5

ATT CCA CTT TCT AAT GTT ACA ATT CAA CAC AGG ATT GAT GAA CTA TCT        297
Ile Pro Leu Ser Asn Val Thr Ile Gln His Arg Ile Asp Glu Leu Ser
                10                  15                  20

GCA GAC ATT GAA GAC CAG CTG ATT CAA AAG GTC AGA GAG TCA AAG TGG        345
Ala Asp Ile Glu Asp Gln Leu Ile Gln Lys Val Arg Glu Ser Lys Trp
        25                  30                  35

TTT GCC CTT CAG ATA GAT GAG TCA TCA GAA ATC TCA AAT ATC ACA CTT        393
Phe Ala Leu Gln Ile Asp Glu Ser Ser Glu Ile Ser Asn Ile Thr Leu
    40                  45                  50

CTT TTG TGC TAT ATT CGT TTC ATT GAT TAT GAT                            426
Leu Leu Cys Tyr Ile Arg Phe Ile Asp Tyr Asp
55                  60                  65

(2) INFORMATION FOR SEQ ID NO: 111:

(i) SEQUENCE CHARACTERISTICS:
            (A) LENGTH: 95 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 15..83
            (C) IDENTIFICATION METHOD: Von Heijne matrix
            (D) OTHER INFORMATION:  score 4.8 seq VMWLVALLEMCVC/KK (xi) SEQUENCE DESCRIPTION: SEQ ID NO: 111:

ATTGAAAAAT AAAA ATG CAC TCT AGT ATA AAA ACG AAG GGA AGC GTC ATG         50
                Met His Ser Ser Ile Lys Thr Lys Gly Ser Val Met
                                -20                 -15

TGG CTT GTT GCT CTT TTG GAG ATG TGT GTG TGT AAG AAG TCC AGG             95
Trp Leu Val Ala Leu Leu Glu Met Cys Val Cys Lys Lys Ser Arg
-10                  -5                   1

(2) INFORMATION FOR SEQ ID NO: 112:
```

```
    (i) SEQUENCE CHARACTERISTICS:
        (A) LENGTH: 473 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 342..395
        (C) IDENTIFICATION METHOD: Von Heijne matrix
        (D) OTHER INFORMATION:   score 4.8 seq LEAISSLSSFVLG/RM (xi) SEQUENCE DESCRIPTION: SEQ ID NO: 112:

ACTGTTTATA GATATTTTGT TTCCCTGAGC AACAGAAAAT GCAGTGCTTA TTTAACTTAG      60

CAGCAATGCC TTGTAAAAAT ATAAGCCTGC AGATGGCAAT GGCCTCTATT TTTCTTCCAC     120

AAGTTTCTTC CAATTCAGAG CCCGTGCCTT CCTTCAGCCA CAGAGCGCAC AACAGCATGG     180

ATGAGATTGA GTCAGCCCTC TTACATTGTT GGCCTACAGC TATGGAGCTA CCTTTGCAGA     240

GTTGTCCACT TGGGGTTTG AGCATGGGAA GTAAATTCAG AGATGCAAGT ATCTGGGAGA      300

GGGCATGAAC TCGTGAGAAA GTCCTCATAT TCTGAGCTCC T ATG ACA GTT TTG CCT     356
                                             Met Thr Val Leu Pro
                                                             -15

TTA GAA GCT ATC TCG TCT CTT AGC AGC TTT GTT TTG GGC AGA ATG AAT      404
Leu Glu Ala Ile Ser Ser Leu Ser Ser Phe Val Leu Gly Arg Met Asn
            -10                 -5                      1

AGC AGA GGG GCA GGA AAG ACC CAG AAT CTT GAT GCC AGC TCC YTG CTT      452
Ser Arg Gly Ala Gly Lys Thr Gln Asn Leu Asp Ala Ser Ser Leu Leu
        5                   10                  15

TTA CTC TGC TGC TTG ATA CTG                                          473
Leu Leu Cys Cys Leu Ile Leu
20                  25

(2) INFORMATION FOR SEQ ID NO: 113:

(i) SEQUENCE CHARACTERISTICS:
        (A) LENGTH: 386 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 12..101
        (C) IDENTIFICATION METHOD: Von Heijne matrix
        (D) OTHER INFORMATION:   score 4.8 seq ILFCVGAVGACTL/SV (xi) SEQUENCE DESCRIPTION: SEQ ID NO: 113:

AATACACAGA A ATG GGG ACT GCG AGC AGA AGC AAC ATC GCT CGC CAT CTG      50
             Met Gly Thr Ala Ser Arg Ser Asn Ile Ala Arg His Leu
             -30                 -25                 -20

CAA ACC AAT CTC ATT CTA TTT TGT GTC GGT GCT GTG GGC GCC TGT ACT      98
Gln Thr Asn Leu Ile Leu Phe Cys Val Gly Ala Val Gly Ala Cys Thr
    -15                 -10                 -5

CTC TCT GTC ACA CAA CCG TGG TAC CTA GAA GTG GAC TAC ACT CAT GAG     146
```

```
Leu Ser Val Thr Gln Pro Trp Tyr Leu Glu Val Asp Tyr Thr His Glu
 1               5                  10                  15

GCC GTC ACC ATA AAG TGT ACC TTC TCC GCA ACC GGA TGC CCT TCT GAG        194
Ala Val Thr Ile Lys Cys Thr Phe Ser Ala Thr Gly Cys Pro Ser Glu
             20                  25                  30

CAA CCA ACA TGC CTG TGG TTT CGC TAC GGT GCT CAC CAG CCT GAG AAC        242
Gln Pro Thr Cys Leu Trp Phe Arg Tyr Gly Ala His Gln Pro Glu Asn
             35                  40                  45

CTG TGC TTG GAC GGG TGC AAA AGT GAG GCA GAS AAG TTC ACA GTG AGG        290
Leu Cys Leu Asp Gly Cys Lys Ser Glu Ala Xaa Lys Phe Thr Val Arg
         50                  55                  60

GAG GCC CTC AAA GAA AAC CAA GTT TCC CTC ACT GTA AAC AGA GTG ACT        338
Glu Ala Leu Lys Glu Asn Gln Val Ser Leu Thr Val Asn Arg Val Thr
         65                  70                  75

TCA AAT GAC AGT GCA ATT TAC ATC TGT GGA ATA GCA TTC CCC AGT GTA        386
Ser Asn Asp Ser Ala Ile Tyr Ile Cys Gly Ile Ala Phe Pro Ser Val
 80                  85                  90                  95
```

(2) INFORMATION FOR SEQ ID NO: 114:

(i) SEQUENCE CHARACTERISTICS:
        (A) LENGTH: 147 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 10..84
        (C) IDENTIFICATION METHOD: Von Heijne matrix
        (D) OTHER INFORMATION:   score 4.8 seq ALFYSVVVSTVSG/NE (xi) SEQUENCE DESCRIPTION: SEQ ID NO: 114:

```
AAGAGTCTG ATG AAT AGC AGT AAA GAA GAA ATG CGC GAA CTG GCA GCG TTG       51
          Met Asn Ser Ser Lys Glu Glu Met Arg Glu Leu Ala Ala Leu
          -25                 -20                 -15

TTT TAT TCT GTA GTG GTA TCA ACA GTG TCG GGG AAT GAG TTG AAA TCA         99
Phe Tyr Ser Val Val Val Ser Thr Val Ser Gly Asn Glu Leu Lys Ser
-10                  -5                   1                   5

ATG ATA GAA CAG CTT ATA AAG ACT ACA AAA GAC AAT CAC AGC CTA CGG        147
Met Ile Glu Gln Leu Ile Lys Thr Thr Lys Asp Asn His Ser Leu Arg
                 10                  15                  20
```

(2) INFORMATION FOR SEQ ID NO: 115:

(i) SEQUENCE CHARACTERISTICS:
        (A) LENGTH: 297 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 55..210
        (C) IDENTIFICATION METHOD: Von Heijne matrix
        (D) OTHER INFORMATION:   score 4.7 seq LLAKALHLLKSSC/AP (xi) SEQUENCE DESCRIPTION: SEQ ID NO: 115:

```
AAGTTGTGCG CCGGTCCCTG GGCCTGAGCT CCGGCTCCGG CTGGGGCGCC TGCG ATG      57
                                                             Met
```

```
TCT CAA GAT GGC GGA STG GGC GAA TTA AAG CAC ATG GTG ATG AGT TTC     105
Ser Gln Asp Gly Gly Xaa Gly Glu Leu Lys His Met Val Met Ser Phe
    -50              -45              -40
```

```
CGG GTG TCT GAG CTC CAG GTG CTT CTT GGC TTT GCT GGC CGG AAC AAG     153
Arg Val Ser Glu Leu Gln Val Leu Leu Gly Phe Ala Gly Arg Asn Lys
-35              -30              -25              -20
```

```
AGT GGA CGG AAG CAC GAG CTC CTG GCC AAG GCT CTG CAC CTC CTG AAG     201
Ser Gly Arg Lys His Glu Leu Leu Ala Lys Ala Leu His Leu Leu Lys
                 -15              -10               -5
```

```
TCC AGC TGT GCC CCT AGT GTC CAG ATG AAG ATC AAA GAG CTT TAC CGA     249
Ser Ser Cys Ala Pro Ser Val Gln Met Lys Ile Lys Glu Leu Tyr Arg
                 1                5                10
```

```
CGA CGC TTT CCC CGG AAG ACC CTG GGG CCC TCT GAT CTC TCC TCC GGG     297
Arg Arg Phe Pro Arg Lys Thr Leu Gly Pro Ser Asp Leu Ser Ser Gly
         15               20               25
```

(2) INFORMATION FOR SEQ ID NO: 116:

(i) SEQUENCE CHARACTERISTICS:
        (A) LENGTH: 141 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 1..87
        (C) IDENTIFICATION METHOD: Von Heijne matrix
        (D) OTHER INFORMATION: score 4.7 seq LCYLSIFCLGVLF/II (xi) SEQUENCE DESCRIPTION: SEQ ID NO: 116:

```
ATG CCT TGT ATA TCT CTC TTA GGT CTA CTT TAT AAT TTT GTT CAA GTC      48
Met Pro Cys Ile Ser Leu Leu Gly Leu Leu Tyr Asn Phe Val Gln Val
            -25              -20              -15
```

```
CTC TGT TAC TTA TCG ATC TTC TGT CTA GGT GTT CTG TTC ATT ATT GAA      96
Leu Cys Tyr Leu Ser Ile Phe Cys Leu Gly Val Leu Phe Ile Ile Glu
            -10               -5                1
```

```
CGT GGT TCA TTA AAA GTC TCC AAA TTA ATC TGT AGG CCA CCA GGG          141
Arg Gly Ser Leu Lys Val Ser Lys Leu Ile Cys Arg Pro Pro Gly
    5                10               15
```

(2) INFORMATION FOR SEQ ID NO: 117:

(i) SEQUENCE CHARACTERISTICS:
        (A) LENGTH: 307 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 167..211
        (C) IDENTIFICATION METHOD: Von Heijne matrix (D) OTHER INFORMATION: score 4.7 seq IAVLFCFFLLIIF/QT (xi) SEQUENCE DESCRIPTION: SEQ ID NO: 117:

AACTAAGVWN KTTCAGCAAA TACTTTTCAA CATTCCCTTC TGTCCTTTCT TTGTTTTTAA      60

AGAAAGCTCT GATTTTGTTT CATTTTCAGC TGGAGACTTA AATGACACCA AGCAAAGCCT     120

ACTTAGTTTA GATCTCCAGA AATTGGCTGG TGGAAAAAAA TCAAAC ATG AAG ATT       175
                                                   Met Lys Ile
                                                       -15

GCA GTT TTG TTT TGT TTT TTT CTG CTT ATC ATT TTT CAA ACT GAC TTT      223
Ala Val Leu Phe Cys Phe Phe Leu Leu Ile Ile Phe Gln Thr Asp Phe
        -10              -5                   1

GGA AAA AAT GAA GAA ATT CCT AGG AAG CAA AGG AGG AAG ATC TAC CAC      271
Gly Lys Asn Glu Glu Ile Pro Arg Lys Gln Arg Arg Lys Ile Tyr His
 5               10                  15                      20

AGA AGG TTG AGG AAA AGT TCA ACC TCA CAC AAG CAG                      307
Arg Arg Leu Arg Lys Ser Ser Thr Ser His Lys Gln
            25                  30

(2) INFORMATION FOR SEQ ID NO: 118:

(i) SEQUENCE CHARACTERISTICS:
        (A) LENGTH: 396 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 253..381
        (C) IDENTIFICATION METHOD: Von Heijne matrix
        (D) OTHER INFORMATION: score 4.7 seq STWSSASLRGSWQ/QG (xi) SEQUENCE DESCRIPTION: SEQ ID NO: 118:

AATACTGATG TCTYCCGAAA AACACAGCCC CAAGGGAGTC GAGACGWTGT ACCAGGTAGA      60

ATAAGGCACA GGGGAGCCGC TTGACAAATC AGACGACGGC AGCCGGCCTG CCTGCCCGGT     120

ATGTGGCCAA ATATGGGCGA GGCCAAGGTT GGGGTGTGAA AGTGCGTGAC GTTTACACCC     180

ACGTGGGCGT CTGTGCACGT GCGTGTGTGC GTGTGAGCTG CCTGTGGGCA TCTGCAGAAG     240

CAGACATTCT TC ATG GCT AAA CAA AAA CCT CAC GTT TTG GGT TCC AGG GTG   291
              Met Ala Lys Gln Lys Pro His Val Leu Gly Ser Arg Val
                      -40                 -35

ATG CCA GCG AGT TGT GTT TCT GAG AGA CGA AGG AAG CCT TCC TTC CAG      339
Met Pro Ala Ser Cys Val Ser Glu Arg Arg Arg Lys Pro Ser Phe Gln
-30              -25                 -20                     -15

GTT TCC ACG TGG AGC AGT GCC TCT CTG CGT GGT TCC TGG CAG CAG GGG      387
Val Ser Thr Trp Ser Ser Ala Ser Leu Arg Gly Ser Trp Gln Gln Gly
            -10                  -5                          1

ATG CCA GGC                                                          396
Met Pro Gly
    5

(2) INFORMATION FOR SEQ ID NO: 119:

(i) SEQUENCE CHARACTERISTICS:
        (A) LENGTH: 193 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 143..187
         (C) IDENTIFICATION METHOD: Von Heijne matrix
         (D) OTHER INFORMATION:  score 4.6 seq FLYLKSVFDVSLG/AR (xi) SEQUENCE DESCRIPTION: SEQ ID NO: 119:

```
ATGGAGATCC ATAACATGAT CCTACATGAA TGTTTCAATA TTGTATTCCT GTAAGTTACT      60

TTTACATTGA CAGTTCTGAA ATTCATGTTG AGTGTTAATT AGGCAGGAAA TCAGAAGGGA     120

GGTTTTGTAG AAGGTCGTAT CC ATG GGT TTT TTA TAT TTG AAA AGT GTT TTC     172
                         Met Gly Phe Leu Tyr Leu Lys Ser Val Phe
                          -15                  -10

GAT GTA TCA TTG GGG GCA AGG                                           193
Asp Val Ser Leu Gly Ala Arg
 -5                   1
```

(2) INFORMATION FOR SEQ ID NO: 120:

(i) SEQUENCE CHARACTERISTICS:
        (A) LENGTH: 460 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 254..436
         (C) IDENTIFICATION METHOD: Von Heijne matrix
         (D) OTHER INFORMATION:  score 4.6 seq LLLLHGGGHSALS/WA (xi) SEQUENCE DESCRIPTION: SEQ ID NO: 120:

```
AAGTTTACGG AGCCGGTGGG CGGTAGGCGG TGCTACGGGT AGCTGGGTGC TGTCCAAAGG      60

CGACAGGGCG TCGTTAGGGG AGCGAGTCGT GACCGGTTGG GCCACACTCA ACGTGGGACG     120

AAGCTTCGCC TACTGTTTGA CTACGTGCGT GCAGCCTCCC CTCGATGTCG GCCCTCGAAA     180

AGAGCATGCA CCTCGGCCGC CTTCCCTCTC GCCCACCTCT ACCCGGCAGC GGGGGCAGTC     240

AGAGCGGASC AAG ATG CGA ATG GGC CCT GGA AGA AAG CGG GAC TTT TCC       289
           Met Arg Met Gly Pro Gly Arg Lys Arg Asp Phe Ser
            -60                  -55                  -50

CCT GTT CCT TGG AGT CAG TAT TTT GAG TCC ATG GAA GAT GTA GAA GTA      337
Pro Val Pro Trp Ser Gln Tyr Phe Glu Ser Met Glu Asp Val Glu Val
             -45                  -40                  -35

GAG AAT GAA ACT GGC AAG GAT ACT TTT CGA GTC TAC AAG AGT GGT TCA      385
Glu Asn Glu Thr Gly Lys Asp Thr Phe Arg Val Tyr Lys Ser Gly Ser
             -30                  -25                  -20

GAG GGT CCA GTC CTG CTC CTT CTG CAT GGA GGA GGT CAT TCT GCC CTT      433
Glu Gly Pro Val Leu Leu Leu Leu His Gly Gly Gly His Ser Ala Leu
             -15                  -10                   -5

TCT TGG GCT GTG TTC ACG GCA GCT ARG                                   460
Ser Trp Ala Val Phe Thr Ala Ala Xaa
  1               5
```

(2) INFORMATION FOR SEQ ID NO: 121:

(i) SEQUENCE CHARACTERISTICS:
        (A) LENGTH: 275 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 207..245
        (C) IDENTIFICATION METHOD: Von Heijne matrix
        (D) OTHER INFORMATION: score 4.6 seq MIFLLYLLPSSEE/RR (xi) SEQUENCE DESCRIPTION: SEQ ID NO: 121:

```
AAACAGACAG GTATGGAGTC TGGGTGGGGC CACGTGTACC CTCCCATCCT TAGAAAGAGT      60

GTGACACCAA GGGACAGATG CTGGCGTASG CGGGTTTTGT TTTGGAGGGT TTTTTGTTTG     120

TTTTTACAAA AATTAAGATA TTTCTGAGTT TATTATGAGG CTTTTAGTTT TACAATCATA     180

CTAAAAGATA ATTGTTCCTC TATAAA ATG ATT TTC CTT CTG TAC CTC TTG CCT     233
                            Met Ile Phe Leu Leu Tyr Leu Leu Pro
                                    -10                     -5

TCT TCT GAA GAA AGG AGA AAA TTG CTT TTT AGT CCC CAC AGG              275
Ser Ser Glu Glu Arg Arg Lys Leu Leu Phe Ser Pro His Arg
         1               5                  10
```

(2) INFORMATION FOR SEQ ID NO: 122:

(i) SEQUENCE CHARACTERISTICS:
        (A) LENGTH: 445 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 236..418
        (C) IDENTIFICATION METHOD: Von Heijne matrix
        (D) OTHER INFORMATION: score 4.6 seq LLLLHGGGHSALS/WA (xi) SEQUENCE DESCRIPTION: SEQ ID NO: 122:

```
GCGGTAGGCG GGTGCTACGG GTAGCTGGGT GCTGTCCAAA GGCGACAGGG CGTCGTTAGG      60

GGAGCGAGTC GTGACCGGTT GGGCCACACT CAACGTGGGA CGAAGCTTCG CCTACTGTTT     120

GACTACGTGC GTGCAGCCTC CCCTCGATGT CGGCCCTCGA AAAGAGCATG CACCTCGGCC     180

GCCTTCCCTC TCGCCCACCT CTACCCGGCA GCGGGGGCAG TCAGAGCGGA SCAAG ATG     238
                                                            Met

CGA ATG GGC CCT GGA AGA AAG CGG GAC TTT TCC CCT GTT CCT TGG AGT     286
Arg Met Gly Pro Gly Arg Lys Arg Asp Phe Ser Pro Val Pro Trp Ser
-60             -55             -50             -45

CAG TAT TTT GAG TCC ATG GAA GAT GTA GAA GTA GAG AAT GAA ACT GGC     334
Gln Tyr Phe Glu Ser Met Glu Asp Val Glu Val Glu Asn Glu Thr Gly
            -40             -35             -30

AAG GAT ACT TTT CGA GTC TAC AAG AGT GGT TCA GAG GGT CCA GTC CTG     382
Lys Asp Thr Phe Arg Val Tyr Lys Ser Gly Ser Glu Gly Pro Val Leu
        -25             -20             -15
```

```
CTC CTT CTG CAT GGA GGA GGT CAT TCT GCC CTT TCT TGG GCT GTG TTC        430
Leu Leu Leu His Gly Gly Gly His Ser Ala Leu Ser Trp Ala Val Phe
        -10              -5                   1

ACG GCA GCG ACA TGG                                                     445
Thr Ala Ala Thr Trp
  5
```

(2) INFORMATION FOR SEQ ID NO: 123:

(i) SEQUENCE CHARACTERISTICS:
        (A) LENGTH: 138 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 49..96
        (C) IDENTIFICATION METHOD: Von Heijne matrix
        (D) OTHER INFORMATION: score 4.5 seq LLNLISILASIPS/QF (xi) SEQUENCE DESCRIPTION: SEQ ID NO: 123:

```
ATATACTGAA TTAAGTGTCT CTTGGTAATA CAGGCTCTTA TCAAACCC ATG CTG AGC         57
                                                    Met Leu Ser
                                                           -15

CTA TTA AAT CTC ATT TCA ATC TTA GCA AGT ATT CCC AGT CAA TTT AAA        105
Leu Leu Asn Leu Ile Ser Ile Leu Ala Ser Ile Pro Ser Gln Phe Lys
        -10              -5                   1

CCA CAG TTT AGC AAG CTG CCA CTC TCA GGC CGG                             138
Pro Gln Phe Ser Lys Leu Pro Leu Ser Gly Arg
  5                  10
```

(2) INFORMATION FOR SEQ ID NO: 124:

(i) SEQUENCE CHARACTERISTICS:
        (A) LENGTH: 94 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 11..85
        (C) IDENTIFICATION METHOD: Von Heijne matrix
        (D) OTHER INFORMATION: score 4.5 seq LMLLWPVHPLLVG/HR (xi) SEQUENCE DESCRIPTION: SEQ ID NO: 124:

```
AAGATTCATC ATG GGC ACC ACC TCC AAC ATG GTC ACC ACC ATC CAT CTC          49
           Met Gly Thr Thr Ser Asn Met Val Thr Thr Ile His Leu
            -25              -20                  -15

ATG TTG CTG TGG CCA GTG CAT CCA TTA CTG GTG GGC CAC CGC GGG             94
Met Leu Leu Trp Pro Val His Pro Leu Leu Val Gly His Arg Gly
        -10              -5                   1
```

(2) INFORMATION FOR SEQ ID NO: 125:

(i) SEQUENCE CHARACTERISTICS:

(A) LENGTH: 481 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 41..343
        (C) IDENTIFICATION METHOD: Von Heijne matrix
        (D) OTHER INFORMATION:  score 4.4 seq ISHILAFFAASDG/IV (xi) SEQUENCE DESCRIPTION: SEQ ID NO: 125:

```
AAGTTCCCTC AGCGCCCGTA GCTTCGGCGG AGTCTGCGCG ATG GGC GAC CCG GAA       55
                                            Met Gly Asp Pro Glu
                                               -100

AGG CCG GAA GCG GCC GGG CTG GAT CAG GAT GAG AGA TCA TCT TCA GAC      103
Arg Pro Glu Ala Ala Gly Leu Asp Gln Asp Glu Arg Ser Ser Ser Asp
    -95             -90             -85

ACC AAC GAA AGT GAA ATA AAG TCA AAT GAA GAG CCA CTC CTA AGA AAG      151
Thr Asn Glu Ser Glu Ile Lys Ser Asn Glu Glu Pro Leu Leu Arg Lys
-80             -75             -70             -65

AGT TCT CGC CGG TTT GTC ATC TTT CCA ATC CAG TAC CCT GAT ATT TGG      199
Ser Ser Arg Arg Phe Val Ile Phe Pro Ile Gln Tyr Pro Asp Ile Trp
            -60             -55             -50

AAA ATG TAT AAA CAG GCA CAG GCT TCC TTC TGG ACA GCA GAA GAG GTC      247
Lys Met Tyr Lys Gln Ala Gln Ala Ser Phe Trp Thr Ala Glu Glu Val
        -45             -40             -35

GAC TTA TCA AAG GAT CTC CCT CAC TGG AAC AAG CTT AAA GCA GAT GAG      295
Asp Leu Ser Lys Asp Leu Pro His Trp Asn Lys Leu Lys Ala Asp Glu
    -30             -25             -20

AAG TAC TTC ATC TCT CAC ATC TTA GCC TTT TTT GCA GCC AGT GAT GGA      343
Lys Tyr Phe Ile Ser His Ile Leu Ala Phe Phe Ala Ala Ser Asp Gly
-15             -10             -5

ATT GTA AAT GAA AAT TTG GTG GAG CGC TTT AGT CAG GAG GTG CAG GTT      391
Ile Val Asn Glu Asn Leu Val Glu Arg Phe Ser Gln Glu Val Gln Val
 1               5              10              15

CCA GAG GCT CGC TGT TTC TAT GGC TTT CAA ATT CTC ATC GAG AAT GTT      439
Pro Glu Ala Arg Cys Phe Tyr Gly Phe Gln Ile Leu Ile Glu Asn Val
        20              25              30

CAC TCA GAG ATG TAC AGT TTG CTG ATA GAC ACT TAC ATC AGA              481
His Ser Glu Met Tyr Ser Leu Leu Ile Asp Thr Tyr Ile Arg
        35              40              45
```

(2) INFORMATION FOR SEQ ID NO: 126:

(i) SEQUENCE CHARACTERISTICS:
        (A) LENGTH: 197 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 3..50
        (C) IDENTIFICATION METHOD: Von Heijne matrix
        (D) OTHER INFORMATION:  score 4.4 seq GLFSLLPHPPCVG/RV (xi) SEQUENCE DESCRIPTION: SEQ ID NO: 126:

```
AG ATG GAT GCA GGC TTA TTT TCT CTG CTT CCC CAT CCT CCA TGT GTT         47
   Met Asp Ala Gly Leu Phe Ser Leu Leu Pro His Pro Pro Cys Val
       -15                 -10                  -5

GGC AGG GTG CTG CCA CAG TCT AGG TAT CAT CTG CAT CCA AGA TCA CCT        95
Gly Arg Val Leu Pro Gln Ser Arg Tyr His Leu His Pro Arg Ser Pro
  1           5                  10                  15

TTG GTA GAA GAT ACC TGT TTC TTC CAG AGG CTT AAA AAA ATT TTA AAT       143
Leu Val Glu Asp Thr Cys Phe Phe Gln Arg Leu Lys Lys Ile Leu Asn
             20                  25                  30

AAA ATA GGA AAC CTT TTC CAT TCA ACA AAG TCC CTT TGT GTC TCA CTT       191
Lys Ile Gly Asn Leu Phe His Ser Thr Lys Ser Leu Cys Val Ser Leu
             35                  40                  45

GCC CCG                                                               197
Ala Pro
```

(2) INFORMATION FOR SEQ ID NO: 127:

(i) SEQUENCE CHARACTERISTICS:
        (A) LENGTH: 121 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 65..106
        (C) IDENTIFICATION METHOD: Von Heijne matrix
        (D) OTHER INFORMATION: score 4.4 seq LITLTYLIQGESA/RT (xi) SEQUENCE DESCRIPTION: SEQ ID NO: 127:

```
ATTTAATAAC TTAAAAATTG GCCAATTTTA TTTTTAGAAA AGCTCTGCAT CATCCTGTGT       60

TTAG ATG TTA ATT ACG CTG ACT TAC CTA ATC CAG GGT GAG TCA GCA CGA      109
     Met Leu Ile Thr Leu Thr Tyr Leu Ile Gln Gly Glu Ser Ala Arg
         -10                  -5                               1

ACC ACG TTC GAG                                                       121
Thr Thr Phe Glu
             5
```

(2) INFORMATION FOR SEQ ID NO: 128:

(i) SEQUENCE CHARACTERISTICS:
        (A) LENGTH: 238 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 146..223
        (C) IDENTIFICATION METHOD: Von Heijne matrix
        (D) OTHER INFORMATION: score 4.4 seq RVQCLCAIPFAFS/LT (xi) SEQUENCE DESCRIPTION: SEQ ID NO: 128:

```
AAAATATGTC TTCAGCTCTA ATCCATTATC ACTCAGATCA TTCTAACCTT TTCCCCTTGC       60
```

```
TTATCTATAA CTTTCCACTT CAACAGTGAG AAACCTGGCT TCCATATCTG TCATCCATAA        120

ATGTACGTAT TTAATTCCAG TACAC ATG TAT ACT GGT TTC AGA ATA GAA GCA         172
                           Met Tyr Thr Gly Phe Arg Ile Glu Ala
                               -25                 -20

ACT TTA TTA ACT AGA GTG CAG TGC TTA TGT GCA ATT CCT TTT GCC TTT         220
Thr Leu Leu Thr Arg Val Gln Cys Leu Cys Ala Ile Pro Phe Ala Phe
        -15                 -10                 -5

AGT CTT ACA GGC ATC CGG                                                 238
Ser Leu Thr Gly Ile Arg
  1               5

(2) INFORMATION FOR SEQ ID NO: 129:

(i) SEQUENCE CHARACTERISTICS:
        (A) LENGTH: 419 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 252..392
        (C) IDENTIFICATION METHOD: Von Heijne matrix
        (D) OTHER INFORMATION:  score 4.4 seq ISHILAFFAASDG/IV (xi) SEQUENCE DESCRIPTION: SEQ ID NO: 129:

AAGCGGACCA CCTGGGTGCT GTCGTAGTTG GAGGTGGCCT GAGGAGCTCA GTTCCCTCAG         60

CGCCCGTAGT TTCGGCGGAG TCTGCGCGAT GGGCGACCCG GAAAGGCCGG GAAGCGGCCG        120

GGCTGGATCA GGATGAGAGA TCATCTTCAG ACACCAACGA AAGTGAAATA AAGTCAAATG        180

AAGAGCCRST CCTAAGAAAG AGTTCTCGCC GGTTTGTCAT CTTTCCAATC CAGTACCCTG        240

ATATTTGGAA A ATG TAT AAA CAG GCA CAG GCT TCC TTC TGG ACA GCA GAA        290
             Met Tyr Lys Gln Ala Gln Ala Ser Phe Trp Thr Ala Glu
                 -45                 -40                     -35

GAG GTC GAC TTA TCA AAG GAT CTC CCT CAC TGG AAC AAG CTT AAA GCA         338
Glu Val Asp Leu Ser Lys Asp Leu Pro His Trp Asn Lys Leu Lys Ala
            -30                 -25                 -20

GAT GAG AAG TAC TTC ATC TCT CAC ATC TTA GCC TTT TTT GCA GCC AGT         386
Asp Glu Lys Tyr Phe Ile Ser His Ile Leu Ala Phe Phe Ala Ala Ser
        -15                 -10                 -5

GAT GGA ATT GTA AAT GAA AAT TTG GTG GAG CGC                             419
Asp Gly Ile Val Asn Glu Asn Leu Val Glu Arg
  1               5

(2) INFORMATION FOR SEQ ID NO: 130:

(i) SEQUENCE CHARACTERISTICS:
        (A) LENGTH: 255 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
```

(B) LOCATION: 112..195
        (C) IDENTIFICATION METHOD: Von Heijne matrix
        (D) OTHER INFORMATION:  score 4.3 seq FLGLAAMASPSRN/SQ (xi) SEQUENCE DESCRIPTION: SEQ ID NO: 130:

AATTACGATG TKKTGTGTGC TTGTGCAAAT ACAGGACGGT TCCTGAAATG TGTCTCTGAG      60

CGTTCTTAAC TGTGTGTRAG GAATTSMTGC GCGTACACGT GGTGGGTCAT T ATG CTG     117
                                                         Met Leu

CTG CAC CTG TGT AGT GTG AAG AAT CTG TAC CAG AAC AGG TTT TTA GGC     165
Leu His Leu Cys Ser Val Lys Asn Leu Tyr Gln Asn Arg Phe Leu Gly
    -25                 -20                 -15

CTG GCC GCC ATG GCG TCT CCT TCT AGA AAC TCC CAG AGC CGA CGC CGG     213
Leu Ala Ala Met Ala Ser Pro Ser Arg Asn Ser Gln Ser Arg Arg Arg
-10             -5                   1                   5

TGC AAG GAG CCG CTC CGA TAC AGC TAC AAC CCC GAC CAG GGG             255
Cys Lys Glu Pro Leu Arg Tyr Ser Tyr Asn Pro Asp Gln Gly
            10                  15                  20

(2) INFORMATION FOR SEQ ID NO: 131:

(i) SEQUENCE CHARACTERISTICS:
        (A) LENGTH: 287 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 123..176
        (C) IDENTIFICATION METHOD: Von Heijne matrix
        (D) OTHER INFORMATION:  score 4.3 seq WTCLKSFPSPTSS/HA (xi) SEQUENCE DESCRIPTION: SEQ ID NO: 131:

AAGAGCATCC TGCGCCCCGG CGCGGGGCCC TGCGGTAGCC TCAGGCCCCT CCCCTGGACC      60

CGCCGCAGAG CCAGTGCAGA ATACAGAAAC TGCAGCCATG ACCACGCACG TCACCCTGGA     120

AG ATG CCC TGT CCA ACG TGG ACC TGC TTG AAG AGC TTC CCC TCC CCG       167
   Met Pro Cys Pro Thr Trp Thr Cys Leu Lys Ser Phe Pro Ser Pro
       -15                 -10                 -5

ACC AGC AGC CAT GCA TCG AGC CTC CAC CTT CCT CCA TCA TGT ACC AGG     215
Thr Ser Ser His Ala Ser Ser Leu His Leu Pro Pro Ser Cys Thr Arg
             1               5                   10

CTA ACT TTG ACA CAA ACT TTG AGG ACA GGA ATG CAT TTG TCA CGG GCA     263
Leu Thr Leu Thr Gln Thr Leu Arg Thr Gly Met His Leu Ser Arg Ala
    15                  20                  25

TTG CAA GGT ACA TTG ACC AGG CAG                                     287
Leu Gln Gly Thr Leu Thr Arg Gln
30                  35

(2) INFORMATION FOR SEQ ID NO: 132:

(i) SEQUENCE CHARACTERISTICS:
        (A) LENGTH: 224 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens (F) TISSUE TYPE: Brain (ix) FEATURE:
         (A) NAME/KEY: sig_peptide
         (B) LOCATION: 6..104
         (C) IDENTIFICATION METHOD: Von Heijne matrix
         (D) OTHER INFORMATION:   score 4.3 seq LLGWGLNLTLGQG/AP (xi) SEQUENCE DESCRIPTION: SEQ ID NO: 132:

```
AAAGG ATG GAG GAT CTC TTT AGC CCC TCA ATT AWG CCG CCG GCG CCC AAC        50
      Met Glu Asp Leu Phe Ser Pro Ser Ile Xaa Pro Pro Ala Pro Asn
          -30                 -25                 -20

ATT TCC GTG CCC ATC TTG CTG GGC TGG GGT CTC AAC CTG ACC TTG GGG          98
Ile Ser Val Pro Ile Leu Leu Gly Trp Gly Leu Asn Leu Thr Leu Gly
        -15                 -10                  -5

CAA GGA GCC CCT GCC TCT GGG CCG CCC AGC CGC CGC GTC CGC CTG GTG         146
Gln Gly Ala Pro Ala Ser Gly Pro Pro Ser Arg Arg Val Arg Leu Val
          1               5                  10

TTC CTG GGG GTC ATC CTG GTG GTG GCG GTG GCA KGC AAC ACC ACA GTG         194
Phe Leu Gly Val Ile Leu Val Val Ala Val Ala Xaa Asn Thr Thr Val
 15              20                  25                  30

CTG TGC CGC CTG TGC GGC GGC GGC GGG CCG                                 224
Leu Cys Arg Leu Cys Gly Gly Gly Gly Pro
              35                  40
```

(2) INFORMATION FOR SEQ ID NO: 133:

(i) SEQUENCE CHARACTERISTICS:
         (A) LENGTH: 347 base pairs
         (B) TYPE: NUCLEIC ACID
         (C) STRANDEDNESS: DOUBLE
         (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 183..338
         (C) IDENTIFICATION METHOD: Von Heijne matrix
         (D) OTHER INFORMATION:   score 4.1 seq VMLETCGLLVSLG/HP (xi) SEQUENCE DESCRIPTION: SEQ ID NO: 133:

```
AGGGACTTCC GGCCTCGCTG GCGTGGACGT TGTGGTGGG GCGTGTTGGT CCGCGCTCTC         60

AGAACTGTGC TGGGAAGGAT GGTAGGGCGA CTGGGGCTCA CCTCCGCACC GTTGTAGGAC       120

CCGGGGTAGG GTTTTGAGCC CGTGGGAGCK GCCCCACGCG GCCTCGTCCT GCCAACGGTC       180

GG ATG GCG GAG ACG AAG GAC GCA GCG CAG ATG TTG GTG ACC TTC AAG         227
   Met Ala Glu Thr Lys Asp Ala Ala Gln Met Leu Val Thr Phe Lys
       -50                 -45                 -40

GAT GTG GCT GTG ACC TTT ACC CGG GAG GAG TGG AGA CAG CTG GAC CTG         275
Asp Val Ala Val Thr Phe Thr Arg Glu Glu Trp Arg Gln Leu Asp Leu
        -35                 -30                 -25

GCC CAG AGG ACC CTG TAC CGA GAG GTG ATG CTG GAG ACC TGT GGG CTT         323
Ala Gln Arg Thr Leu Tyr Arg Glu Val Met Leu Glu Thr Cys Gly Leu
        -20                 -15                 -10

CTG GTT TCA CTA GGG CAT CCT CGG                                         347
Leu Val Ser Leu Gly His Pro Arg
 -5              1
```

(2) INFORMATION FOR SEQ ID NO: 134:

(i) SEQUENCE CHARACTERISTICS:

(A) LENGTH: 432 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 298..336
            (C) IDENTIFICATION METHOD: Von Heijne matrix
            (D) OTHER INFORMATION:  score 4.1 seq MLILSQNIAQLEA/QV (xi) SEQUENCE DESCRIPTION: SEQ ID NO: 134:

```
AATTGARRTG TTTGATAACT GTCACTTTAG GGTTTCAACC AAAACCTTGA CTTTATCATC     60

TTGTTATACA TTTTTCAAAA TGAGGTTAGA GATCAGGGGA ATGAATAGGA GAGAAGTACA    120

TATTTCAGTT CACTGGGCAT AGGTGAATAG AGGAAGGAGA AAATGAACAT ACCCAATCCA    180

CAGAGAAATG GCTCACAGAG CCCAGTGACT ATGCTGAGAC GCTATTAATT CAAGAAAGTT    240

TTAGTATTTG ATTTGTCAAA TGACATTATT GTTTAGGACT TTTATTTTCC CTTACAG      297

ATG TTG ATC TTG TCT CAG AAT ATT GCC CAA CTG GAG GCC CAG GTG GAA     345
Met Leu Ile Leu Ser Gln Asn Ile Ala Gln Leu Glu Ala Gln Val Glu
           -10                  -5                   1

AAG GTT ACA AAG GAA AAG ATT TCA GCT ATT AAT CAA CTG GAG GAA AAT     393
Lys Val Thr Lys Glu Lys Ile Ser Ala Ile Asn Gln Leu Glu Glu Asn
      5                  10                  15

TCA AAG CCA GCT GGC TTC TCG GGA AAA TGG ATG TCA CAA                 432
Ser Lys Pro Ala Gly Phe Ser Gly Lys Trp Met Ser Gln
 20                  25                  30
```

(2) INFORMATION FOR SEQ ID NO: 135:

(i) SEQUENCE CHARACTERISTICS:
            (A) LENGTH: 380 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 90..152
            (C) IDENTIFICATION METHOD: Von Heijne matrix
            (D) OTHER INFORMATION:  score 4.1 seq GLWAHSWTCSCSA/AX (xi) SEQUENCE DESCRIPTION: SEQ ID NO: 135:

```
AATTCACTTC ACCTGGAGTT GAGCCAAGAT TCTCTTTACT CCAAAGCCAG CACTCCTTCT     60

GAGAACAGGA CTTTGATTTG GATGGACGG ATG TTG CTG GGG GCC TCA GCA CAG    113
                                Met Leu Leu Gly Ala Ser Ala Gln
                                    -20                 -15

GGT CTT TGG GCT CAC AGC TGG ACA TGC AGC TGT TCA GCG GCA STG CGG    161
Gly Leu Trp Ala His Ser Trp Thr Cys Ser Cys Ser Ala Ala Xaa Arg
           -10                 -5                   1

TCT GTC CAC CCA GGC GGA GAC TGG ATG CAA CAG TTT CAG GCG GGG TTC    209
Ser Val His Pro Gly Gly Asp Trp Met Gln Gln Phe Gln Ala Gly Phe
      5                  10                  15

CTC CCT CCC CAG GTG CCT GCC CAC CTC TCC CTT ACA TGG GAT GTC TCT    257
```

```
Leu Pro Pro Gln Val Pro Ala His Leu Ser Leu Thr Trp Asp Val Ser
 20              25                  30                  35

CTT CTT CCT CCT TGC CTG GTC CCT AAA GCA CTT GAG TTT GTG GTT CAT    305
Leu Leu Pro Pro Cys Leu Val Pro Lys Ala Leu Glu Phe Val Val His
             40                  45                  50

TTT TTA AAA AAT GAT ATA TTT TAT TTA ACC CAG TAT ATT AAA AAT GTC    353
Phe Leu Lys Asn Asp Ile Phe Tyr Leu Thr Gln Tyr Ile Lys Asn Val
             55                  60                  65

ATT TCA GAA TGT ACG TTT TCC TTT TTT                                380
Ile Ser Glu Cys Thr Phe Ser Phe Phe
             70                  75

(2) INFORMATION FOR SEQ ID NO: 136:

(i) SEQUENCE CHARACTERISTICS:
        (A) LENGTH: 212 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 9..53
        (C) IDENTIFICATION METHOD: Von Heijne matrix
        (D) OTHER INFORMATION:   score 4.1 seq APLELSCWGGGWG/LP (xi) SEQUENCE DESCRIPTION: SEQ ID NO: 136:

AGCGCAAG ATG GCG GCC CCC TTG GAA CTC AGT TGC TGG GGA GGC GGC TGG    50
         Met Ala Ala Pro Leu Glu Leu Ser Cys Trp Gly Gly Gly Trp
         -15              -10                  -5

GGA CTC CCA TCG GTT CAC AGC GAG TCC CTG GTG GTG ATG GCT TAT GCC    98
Gly Leu Pro Ser Val His Ser Glu Ser Leu Val Val Met Ala Tyr Ala
 1               5                  10                  15

AAA TTT TCT GGT GCA CCC TTG AAA GTC AAT GTG ATA GAT AAC ACC TGG   146
Lys Phe Ser Gly Ala Pro Leu Lys Val Asn Val Ile Asp Asn Thr Trp
             20                  25                  30

AGA GGT TCA AGA GGC GAT GTA CCA ATT TTG ACA ACT GAA GAC GAC ATG   194
Arg Gly Ser Arg Gly Asp Val Pro Ile Leu Thr Thr Glu Asp Asp Met
             35                  40                  45

GTT TCT CAG CCA GCA AGG                                            212
Val Ser Gln Pro Ala Arg
             50

(2) INFORMATION FOR SEQ ID NO: 137:

(i) SEQUENCE CHARACTERISTICS:
        (A) LENGTH: 432 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 226..285
        (C) IDENTIFICATION METHOD: Von Heijne matrix
        (D) OTHER INFORMATION:   score 4.1 seq LGFLNCYIAVARS/GG
```

(xi) SEQUENCE DESCRIPTION: SEQ ID NO: 137:

```
AAGGGAMNSA CCCAGGCTGC GGGACSGGTG CAGGCTGCGG CGCTGACGGC CTCTGCTCCT        60

TCCGCGGGTT TCCGACTCCC TGCCCTAGAT TTTCTGCTTA GCGACTTGGG GTCCCCTCTC       120

GTTTGCTTCT GGTAGGAGTC GCAATCCCAK BAGCAATAGC CCAGAAGAGG ACACGGTTCC       180

CGTACCGAAG GTTCAGTACC AGCAGCCCGA CCATCACGCG GCGGG ATG TCT GDR GTT      237
                                                  Met Ser Xaa Val
                                                           -20

GGC ATT GAC CTC GGC TTT CTC AAC TGC TAC ATT GCT GTC GCG AGA AGT        285
Gly Ile Asp Leu Gly Phe Leu Asn Cys Tyr Ile Ala Val Ala Arg Ser
        -15             -10                 -5

GGC GGC ATC GAG ACC ATC GCC AAT GAG TAC AGC GAC AGG TGT ACC CCG        333
Gly Gly Ile Glu Thr Ile Ala Asn Glu Tyr Ser Asp Arg Cys Thr Pro
 1           5                  10                 15

GCC TGT ATA TCA TTG GGA TCA AGA ACT CGA GCC ATT GGA AAT GCA GCA        381
Ala Cys Ile Ser Leu Gly Ser Arg Thr Arg Ala Ile Gly Asn Ala Ala
             20                  25                 30

AAG AGC CAG ATA GTC ACG AAC GTA AGA AAT ACA ATT CAT GGC TTC AAA        429
Lys Ser Gln Ile Val Thr Asn Val Arg Asn Thr Ile His Gly Phe Lys
         35                 40                 45

AAG                                                                    432
Lys
```

(2) INFORMATION FOR SEQ ID NO: 138:

(i) SEQUENCE CHARACTERISTICS:
        (A) LENGTH: 229 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 101..157
        (C) IDENTIFICATION METHOD: Von Heijne matrix
        (D) OTHER INFORMATION:  score 4.1 seq FVVFSTMFTASSP/GE (xi) SEQUENCE DESCRIPTION: SEQ ID NO: 138:

```
AGATGAATAT TTGATACCCA CAGTAGAACT TCTTTMMGAA CTTCTTTCAC AATWGGAGTT        60

AATCTTCTAA AGCCCCGCCA CTGCTTCATC AACTAAGTTT ATG GAA TAT TCT AAA        115
                                             Met Glu Tyr Ser Lys
                                                           -15

TMM TTT GTT GTC TTT TCA ACA ATG TTC ACA GCA TCT TCA CCA GGA GAA        163
Xaa Phe Val Val Phe Ser Thr Met Phe Thr Ala Ser Ser Pro Gly Glu
                -10                 -5                      1

GAC TTT CCC CCC TTC TTT TCA CAG ATG TNS AGA TTG TCA AGA AAC TAC        211
Asp Phe Pro Pro Phe Phe Ser Gln Met Xaa Arg Leu Ser Arg Asn Tyr
         5                  10                 15

TTT CCT TGC CCA CCR WGG                                                229
Phe Pro Cys Pro Pro Xaa
     20
```

(2) INFORMATION FOR SEQ ID NO: 139:

(i) SEQUENCE CHARACTERISTICS:
        (A) LENGTH: 328 base pairs
        (B) TYPE: NUCLEIC ACID
        (C) STRANDEDNESS: DOUBLE (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 113..232
        (C) IDENTIFICATION METHOD: Von Heijne matrix
        (D) OTHER INFORMATION:  score 4.1 seq LPFRLPWASTATA/RC (xi) SEQUENCE DESCRIPTION: SEQ ID NO: 139:

```
AACACCCAGG CCCTGATGCA GCAGCAGGCG GCCCTGGTAG CGGCTCACAG TGCCTACCTC       60

AGCCCCATGG CCACCATGGC TGCCGTGCAG ATGCAGCACA TGGCTGCCAT CA ATG CCA      118
                                                         Met Pro
                                                         -40

ATG GCC TCA TCG CCA CCC CCA TCA CCC CAT CCT CAG GAA CCA GCA CCC        166
Met Ala Ser Ser Pro Pro Pro Ser Pro His Pro Gln Glu Pro Ala Pro
        -35             -30             -25

CTC CTG CCA TCG CTG CCA CGC CTG TCT CTG CCA TTC CGG CTG CCC TGG        214
Leu Leu Pro Ser Leu Pro Arg Leu Ser Leu Pro Phe Arg Leu Pro Trp
    -20             -15             -10

GCG TCA ACG GCT ACA GCC CGG TGC CCA CCC AGC CCA CTG GGC AGC CTG        262
Ala Ser Thr Ala Thr Ala Arg Cys Pro Pro Ser Pro Leu Gly Ser Leu
        -5              1               5                      10

CNC CTG ATG CTC TGT ATC CCA ACG GGG TTC ACC CCT ACC CAG CCC AGA        310
Xaa Leu Met Leu Cys Ile Pro Thr Gly Phe Thr Pro Thr Gln Pro Arg
            15              20              25

GCC CCG CGG CCC CCT GGG                                                328
Ala Pro Arg Pro Pro Gly
            30
```

(2) INFORMATION FOR SEQ ID NO: 140:

(i) SEQUENCE CHARACTERISTICS:
        (A) LENGTH: 217 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 53..166
        (C) IDENTIFICATION METHOD: Von Heijne matrix
        (D) OTHER INFORMATION:  score 4 seq WALGLKFLSSSSQ/NF (xi) SEQUENCE DESCRIPTION: SEQ ID NO: 140:

```
AACAGGAGAC TTGGGAAGGA CCAATGGTAA TTTAAGTGGC TCTTAAAAAG TC ATG CAA       58
                                                         Met Gln

CAT GTW WCT GGA CAC GWW CCT GAT CCT ATT GCG ATA ATG TAT GTG TGC        106
His Val Xaa Gly His Xaa Pro Asp Pro Ile Ala Ile Met Tyr Val Cys
        -35             -30             -25

CCT CCC TGT GGG CAC ACC ACC TGG GCA TTA GGA CTG AAA TTC CTG AGT        154
Pro Pro Cys Gly His Thr Thr Trp Ala Leu Gly Leu Lys Phe Leu Ser
-20             -15             -10                              -5

TCT TCC TCT CAA AAT TTC TGT GCA CCA GTA TTA TTC CTC ATT TTA CAT        202
Ser Ser Ser Gln Asn Phe Cys Ala Pro Val Leu Phe Leu Ile Leu His
            1               5               10
```

-continued

```
ACA GGA GGC CAA CGG                                                217
Thr Gly Gly Gln Arg
         15
```

(2) INFORMATION FOR SEQ ID NO: 141:

(i) SEQUENCE CHARACTERISTICS:
        (A) LENGTH: 202 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 44..133
        (C) IDENTIFICATION METHOD: Von Heijne matrix
        (D) OTHER INFORMATION:   score 4 seq AGFLKCLLLSSLQ/SY (xi) SEQUENCE DESCRIPTION: SEQ ID NO: 141:

```
ATAATAGTGT TATTTCAGTG CATGATTTTT GCCTTTGAGA GAC ATG GGT TGG GAA      55
                                                 Met Gly Trp Glu
                                                     -30

ATG ACA TGT ATT AAG TCT TTT TTC TGG GCC AGG TCT CAT GCT GGG TTC     103
Met Thr Cys Ile Lys Ser Phe Phe Trp Ala Arg Ser His Ala Gly Phe
    -25                 -20                 -15

TTG AAA TGC CTC CTG TTG TCT TCA TTA CAG TCC TAC AAG GAG GCT GCT     151
Leu Lys Cys Leu Leu Leu Ser Ser Leu Gln Ser Tyr Lys Glu Ala Ala
-10                  -5                   1                   5

GTT ATC TTC CCT CTT ACT GAT TTG CTC AAA CTG AAA GAT TAT GGT GAA     199
Val Ile Phe Pro Leu Thr Asp Leu Leu Lys Leu Lys Asp Tyr Gly Glu
                 10                  15                  20

TGG                                                                 202
Trp
```

(2) INFORMATION FOR SEQ ID NO: 142:

(i) SEQUENCE CHARACTERISTICS:
        (A) LENGTH: 361 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 248..355
        (C) IDENTIFICATION METHOD: Von Heijne matrix
        (D) OTHER INFORMATION:   score 4 seq VQLSFAATTPVLA/DK (xi) SEQUENCE DESCRIPTION: SEQ ID NO: 142:

```
AAGTTGGGAG AGGAGCTGCT GGTTGAAGTG AAGGTGAGGA GCTCAGTGCT TCTTTCACTG     60

CCCTATCTGC TGGGCTTTAC GCCCCTGAGG GGCTGACTGT AAAAAACTCT AAGCTGATCC    120

AGCCCCCAAA ATTCACCTTT GGTGAGCTGG AAAGTCCATC TATTTGGGAC GCGAATCATG    180

TCAGTGCGAC AACGCAAAAG GGTTGAAAGC CTTCTACGAT GCAATAAAAT ACGGGCCTAA    240

CCACTTG ATG GTG TTT GGA GGC GTC TGT CCA TCC GTC ACA TCC ATC ATT     289
```

```
            Met Val Phe Gly Gly Val Cys Pro Ser Val Thr Ser Ile Ile
                -35             -30                 -25

GCA GAG TCC CTC CAA GGC TGG AAT CTG GTG CAG CTT TCT TTT GCT GCA        337
Ala Glu Ser Leu Gln Gly Trp Asn Leu Val Gln Leu Ser Phe Ala Ala
        -20             -15                 -10

ACC ACG CCT GTT CTA GCC GAT AAG                                        361
Thr Thr Pro Val Leu Ala Asp Lys
    -5                   1
```

(2) INFORMATION FOR SEQ ID NO: 143:

(i) SEQUENCE CHARACTERISTICS:
        (A) LENGTH: 216 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 145..192
        (C) IDENTIFICATION METHOD: Von Heijne matrix
        (D) OTHER INFORMATION:   score 4 seq ITWSLLFLYQCSL/HF (xi) SEQUENCE DESCRIPTION: SEQ ID NO: 143:

```
ACACATTACC TCTTTTCATT TTAGACAGGT TAATTAGTGT GTATTTCCAT AGTTGTCTTT        60

TACCTCAAGA AATAATCATT TCTTTAGGTA ATTATTTTAA TGGCTTGCCA TTTTGTATGA       120

TTGTTCTTGC AAACATTTCT ATTT ATG CAT TTT ATA ACA TGG AGC TTA CTA          171
                          Met His Phe Ile Thr Trp Ser Leu Leu
                              -15                 -10

TTT TTA TAC CAG TGC TCG CTT CAT TTT ATC ATT ATC AAG GCC GGG             216
Phe Leu Tyr Gln Cys Ser Leu His Phe Ile Ile Ile Lys Ala Gly
        -5                   1               5
```

(2) INFORMATION FOR SEQ ID NO: 144:

(i) SEQUENCE CHARACTERISTICS:
        (A) LENGTH: 378 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 256..363
        (C) IDENTIFICATION METHOD: Von Heijne matrix
        (D) OTHER INFORMATION:   score 3.9 seq CWPSVASPSSSWS/SP (xi) SEQUENCE DESCRIPTION: SEQ ID NO: 144:

```
AAAGTGGCCA GCGGACCATC TCTCGTGCCC TCGCTCTCTG CGCTCCGGGG CAGCTGAGCC        60

CCGGCCACCC GCTCTCCAAG ATGAAGAAGC TCCAGGGAGC TCACCTCCGC AAGCCTGTCA       120

CCCCAGACCT GCTGATGACC CCCAGTGACC AGGGCGATGT CGACCTGGAT GTGGACTTTG       180

CTGCACACCG GGGGAACTGG ACAGGCAAGC TGGACTTCCT GCTGTCCTGC ATTGGCTACT       240

GTGTAGGCCT GGGGA ATG TCT GGC GCT TCC CCT ATC GAG CGT ACA CCA ATG        291
                Met Ser Gly Ala Ser Pro Ile Glu Arg Thr Pro Met
```

```
                    -35                   -30                    -25
GAG GAG GCG CCT TCC TCG TGC CCT ACT TCC TCA TGC TGG CCA TCT GTG         339
Glu Glu Ala Pro Ser Ser Cys Pro Thr Ser Ser Cys Trp Pro Ser Val
                -20                   -15                   -10

GCA TCC CCC TCT TCT TCC TGG AGC TCT CCC TGG GCC AGT                     378
Ala Ser Pro Ser Ser Ser Trp Ser Ser Pro Trp Ala Ser
             -5                    1                    5
```

(2) INFORMATION FOR SEQ ID NO: 145:

(i) SEQUENCE CHARACTERISTICS:
        (A) LENGTH: 321 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 172..282
        (C) IDENTIFICATION METHOD: Von Heijne matrix
        (D) OTHER INFORMATION:   score 3.9 seq PGPSLRLFSGSQA/SV (xi) SEQUENCE DESCRIPTION: SEQ ID NO: 145:

```
AAGGGTCTCC ATGACAACCG GCCTGGCCGG CTAGCAGTGC TCTGCTCACT TGGCTGCGAG         60

GAGCGCCACG AAAGGTCAGA GGAAGGAGCT GTGGGAAGCT CGCAGCAGGT ATCGGAGCTT         120

AAGCCAGTGG ATTTGGGGGC CCTGGGCTCC CTAGCCGGCT GCGGTGTGAG A ATG GAG         177
                                                         Met Glu

TGG GCA GGA AAG CAG CGG GAC TTT CAG GTA AGG GCA GCT CCG GGC TGG         225
Trp Ala Gly Lys Gln Arg Asp Phe Gln Val Arg Ala Ala Pro Gly Trp
-35                 -30                 -25                 -20

GAT CAT TTG GCC TCC TTT CCT GGC CCT TCT CTC CGG CTG TTT TCT GGG         273
Asp His Leu Ala Ser Phe Pro Gly Pro Ser Leu Arg Leu Phe Ser Gly
                -15                 -10                  -5

AGT CAG GCG AGT GTC TGT AGT CTC TGC TCG GGG TTT GGG GCT CAG GAA         321
Ser Gln Ala Ser Val Cys Ser Leu Cys Ser Gly Phe Gly Ala Gln Glu
             1                   5                  10
```

(2) INFORMATION FOR SEQ ID NO: 146:

(i) SEQUENCE CHARACTERISTICS:
        (A) LENGTH: 278 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 78..257
        (C) IDENTIFICATION METHOD: Von Heijne matrix
        (D) OTHER INFORMATION:   score 3.9 seq AKVVSLSLQTSSA/HH (xi) SEQUENCE DESCRIPTION: SEQ ID NO: 146:

```
AAGAACACAA AAAGCTACAG AAGGTCCAGG CTACTGAAAA GCATCAAGAC CAAGCTGTTG          60

TAAGTCAAAC TGCTTTTT ATG ATT GCA TTC TTT GAT GAA GAC AAT CCC AGA          110
                    Met Ile Ala Phe Phe Asp Glu Asp Asn Pro Arg
```

```
                 -60              -55             -50
AAA AGA AGG TCG TAT TCT TTT ACT CAA AGT GCG GGA ATC TTG TGT CAG        158
Lys Arg Arg Ser Tyr Ser Phe Thr Gln Ser Ala Gly Ile Leu Cys Gln
            -45             -40                 -35

GAA ACT ACA TAT TCA ACA CCA CAT ACA AAA CTT GAG AAA GCA AAG TCT        206
Glu Thr Thr Tyr Ser Thr Pro His Thr Lys Leu Glu Lys Ala Lys Ser
            -30             -25                 -20

CCA ACA GCA GAT GCC AAA GTG GTT TCT TTG TCT TTA CAG ACT AGC TCT        254
Pro Thr Ala Asp Ala Lys Val Val Ser Leu Ser Leu Gln Thr Ser Ser
            -15             -10                  -5

GCG CAT CAC AGA GGG GGG MDT GGT                                        278
Ala His His Arg Gly Gly Xaa Gly
         1              5
```

(2) INFORMATION FOR SEQ ID NO: 147:

(i) SEQUENCE CHARACTERISTICS:
        (A) LENGTH: 349 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 89..232
        (C) IDENTIFICATION METHOD: Von Heijne matrix
        (D) OTHER INFORMATION:   score 3.9 seq ALFCTLPCPVERG/QQ (xi) SEQUENCE DESCRIPTION: SEQ ID NO: 147:

```
AAATTTCTT AAATTAGCAG TCTAATGTGT TCTAAAGAGC AGCTCCACTC AGATCTCTTC         60

TTAAGGGTTG CATTTCATCA CAGTATAA ATG GGC AAA TCC ATC AYT TCC CTC         112
                                Met Gly Lys Ser Ile Xaa Ser Leu
                                                    -45

TGC TCA GTG CKC TTG AAR GCG AGA TTG AAG GGM MAA TTA GAA GCT GTT        160
Cys Ser Val Xaa Leu Lys Ala Arg Leu Lys Gly Xaa Leu Glu Ala Val
-40             -35             -30                 -25

CAT TTG TGC TTG CGG GCT CAG AAG CGT CGC ACT GCT TTG TTT TGT ACT        208
His Leu Cys Leu Arg Ala Gln Lys Arg Arg Thr Ala Leu Phe Cys Thr
            -20             -15                 -10

CTA CCG TGT CCT GTT GAA AGG GGT CAA CAA GTG CCG GGG ANV NNN AHG        256
Leu Pro Cys Pro Val Glu Arg Gly Gln Gln Val Pro Gly Xaa Xaa Xaa
         -5              1                5

AGG CTG AGG CTG GCG TCA CCT TCC GTT GCT AAG GTG TTC CAG TGT TTT        304
Arg Leu Arg Leu Ala Ser Pro Ser Val Ala Lys Val Phe Gln Cys Phe
 10              15                  20

CTC TCA AAA CTC TGT GTT TGG AAC ATC AAG GAT GGA TTA TCC CGG            349
Leu Ser Lys Leu Cys Val Trp Asn Ile Lys Asp Gly Leu Ser Arg
 25              30                  35
```

(2) INFORMATION FOR SEQ ID NO: 148:

(i) SEQUENCE CHARACTERISTICS:
        (A) LENGTH: 210 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:

```
            (A) ORGANISM: Homo Sapiens
            (F) TISSUE TYPE: Brain (ix) FEATURE:
            (A) NAME/KEY: sig_peptide
            (B) LOCATION: 52..96
            (C) IDENTIFICATION METHOD: Von Heijne matrix
            (D) OTHER INFORMATION:  score 3.9 seq LHMTLFRVPFTFS/XF (xi) SEQUENCE DESCRIPTION: SEQ ID NO: 148:

ACACAAAGGA AAATGGCAGG GATATGAATT TCTTTCCCAG CTTTTATATA G ATG TGC          57
                                                         Met Cys
                                                         -15

CTG CAT ATG ACA CTC TTT AGA GTT CCT TTC ACT TTT TCT KTT TTT TGG         105
Leu His Met Thr Leu Phe Arg Val Pro Phe Thr Phe Ser Xaa Phe Trp
        -10                 -5                   1

AAG GGG GCG GGG AGG CAG GAG GAG TGC AGT TTT AAG CCT AGC CTA TAC         153
Lys Gly Ala Gly Arg Gln Glu Glu Cys Ser Phe Lys Pro Ser Leu Tyr
    5               10                  15

TAC TAC AAA CTT ATT ATG GTA CTT AAA ATT GCA CTC CTC CTG TCC CCG         201
Tyr Tyr Lys Leu Ile Met Val Leu Lys Ile Ala Leu Leu Leu Ser Pro
 20              25                  30                  35

CCC CCC AAG                                                             210
Pro Pro Lys (2) INFORMATION FOR SEQ ID NO: 149:

(i) SEQUENCE CHARACTERISTICS:
            (A) LENGTH: 143 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: 75..116
            (C) IDENTIFICATION METHOD: Von Heijne matrix
            (D) OTHER INFORMATION:  score 3.9 seq LNILKTLTSAALP/SP (xi) SEQUENCE DESCRIPTION: SEQ ID NO: 149:

AATACACCTT AAACTTTACT ACTTTTTATA AACGGTAGGA AAGGATATAC TGATGTTGTG         60

GGTATTACAA GGTA ATG CTG AAC ATT CTG AAG ACC TTA ACT TCT GCT GCT         110
             Met Leu Asn Ile Leu Lys Thr Leu Thr Ser Ala Ala
                              -10                 -5

CTT CCC TCC CCC TCC CCC CGC CCC AAC AAG AGG                             143
Leu Pro Ser Pro Ser Pro Arg Pro Asn Lys Arg
 1               5

(2) INFORMATION FOR SEQ ID NO: 150:

(i) SEQUENCE CHARACTERISTICS:
            (A) LENGTH: 176 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
```

(A) NAME/KEY: sig_peptide
        (B) LOCATION: 24..143
        (C) IDENTIFICATION METHOD: Von Heijne matrix
        (D) OTHER INFORMATION: score 3.9 seq SPLLCLYHPPVYT/ST (xi) SEQUENCE DESCRIPTION: SEQ ID NO: 150:

```
AGTAATCCCA GGCGTTCGCC CTC ATG CGG GCC AGG GTT TGG CCT CGC TCC CAC      53
                      Met Arg Ala Arg Val Trp Pro Arg Ser His
                      -40                 -35

GGG ATC CCT GTG CCT TCC TTT CTC TCT AAG AGC AGC CTC AGT CAT ACA       101
Gly Ile Pro Val Pro Ser Phe Leu Ser Lys Ser Ser Leu Ser His Thr
-30                 -25                 -20                 -15

CCA TCA CCT CTC CTC TGT CTA TAC CAT CCT CCT GTC TAC ACC AGC ACC       149
Pro Ser Pro Leu Leu Cys Leu Tyr His Pro Pro Val Tyr Thr Ser Thr
                -10                  -5                   1

ACT ACC CCA TCT ATA CCA CCA CGT CTG                                    176
Thr Thr Pro Ser Ile Pro Pro Arg Leu
          5                   10
```

(2) INFORMATION FOR SEQ ID NO: 151:

(i) SEQUENCE CHARACTERISTICS:
        (A) LENGTH: 414 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 262..369
        (C) IDENTIFICATION METHOD: Von Heijne matrix
        (D) OTHER INFORMATION: score 3.9 seq SLCLSLLIPGPKP/LV (xi) SEQUENCE DESCRIPTION: SEQ ID NO: 151:

```
AAAGTAGGAA ATGGCTGCTT CACCCAGGAG GCACCAAGAT GCCCGTGTGT GGCTCTACTG       60

GTGATGCCCT GGTCTTCATT GAAAAGGCCA GCACCCGTTA CGTGGTCAGC ACAGACGTTG      120

CCGTGAATGA GGATTCCTTC CTACAGATAG ACTTCGCTGC CTCCTGCTCA GTCACAGACT      180

CTTGTTATGC GATTGAATTG GAATACTCAG TAGATCTTGG ATTGTCATGG CACCCATTGG      240

TAAGGGACTG TCTGCCTACC A ATG TGG AAT GCA GTC GCT ATC ATC TGC AAC       291
                       Met Trp Asn Ala Val Ala Ile Ile Cys Asn
                           -35                 -30

GGA TCC TGG TGT CAG ACA CDW TCA ACA AGT GGA CTA GAA TCA CTC TGC       339
Gly Ser Trp Cys Gln Thr Xaa Ser Thr Ser Gly Leu Glu Ser Leu Cys
    -25                 -20                 -15

CTC TCC CTC CTT ATA CCA GGT CCC AAG CCA CTC GTT TCC GTT GGC ATC       387
Leu Ser Leu Leu Ile Pro Gly Pro Lys Pro Leu Val Ser Val Gly Ile
-10                  -5                   1                   5

AAC CAG CTC CTT TTG ACA AGC AGC AGA                                    414
Asn Gln Leu Leu Leu Thr Ser Ser Arg
             10                  15
```

(2) INFORMATION FOR SEQ ID NO: 152:

(i) SEQUENCE CHARACTERISTICS:
        (A) LENGTH: 171 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
    (A) ORGANISM: Homo Sapiens
    (F) TISSUE TYPE: Brain (ix) FEATURE:
    (A) NAME/KEY: sig_peptide
    (B) LOCATION: 103..144
    (C) IDENTIFICATION METHOD: Von Heijne matrix
    (D) OTHER INFORMATION: score 3.9 seq LRLGLFKISWARC/LS (xi) SEQUENCE DESCRIPTION: SEQ ID NO: 152:

```
AAAAATTATT TCTGCTTAAA CAACAGTTTC AAATATTTCT CTTTTGAAGA CAAAATTGGT      60

TTAGTTTCAG CAATGTATTG ATATAATTTT ACATTTTTTT AA ATG TTG AGG CTG        114
                                               Met Leu Arg Leu

GGT TTA TTT AAG ATT AGC TGG GCT CGC TGC CTA TCA TAT AGT AAA ACC       162
Gly Leu Phe Lys Ile Ser Trp Ala Arg Cys Leu Ser Tyr Ser Lys Thr
-10              -5                  1               5

CAG CBC GAA                                                           171
Gln Xaa Glu
```

(2) INFORMATION FOR SEQ ID NO: 153:

(i) SEQUENCE CHARACTERISTICS:
        (A) LENGTH: 262 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 80..187
        (C) IDENTIFICATION METHOD: Von Heijne matrix
        (D) OTHER INFORMATION: score 3.9 seq VVEILPYLPCLTA/RD (xi) SEQUENCE DESCRIPTION: SEQ ID NO: 153:

```
AGGGGTACCG AGTCTCGTTT CCTCTCAGTC CATCCACCCT TCATGGGGCC AGAGCCCTCT      60

CTCCAGAATC TGAGCAGCA ATG CCG TTT GCT GAA GAC AAG ACC TAT AAG TAT     112
                    Met Pro Phe Ala Glu Asp Lys Thr Tyr Lys Tyr
                        -35                 -30

ATC TGC CGC AAT TTC AGC AAT TTT TGC AAT GTG GAT GTT GTA GAG ATT      160
Ile Cys Arg Asn Phe Ser Asn Phe Cys Asn Val Asp Val Val Glu Ile
-25              -20                 -15                 -10

CTG CCT TAC CTG CCC TGC CTC ACA GCA AGA GAC CAG GAT CGA CTG CGG      208
Leu Pro Tyr Leu Pro Cys Leu Thr Ala Arg Asp Gln Asp Arg Leu Arg
             -5                  1               5

GCC ACC TGC ACA CTC TCA GGG AAC CGG GAC ACC CTC TGG CAT CTC TTC      256
Ala Thr Cys Thr Leu Ser Gly Asn Arg Asp Thr Leu Trp His Leu Phe
         10                  15                  20

AAT ACC                                                               262
Asn Thr
    25
```

(2) INFORMATION FOR SEQ ID NO: 154:

(i) SEQUENCE CHARACTERISTICS:
        (A) LENGTH: 165 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: 46..153
              (C) IDENTIFICATION METHOD: Von Heijne matrix
              (D) OTHER INFORMATION:  score 3.8 seq GTDSLSFLPPCPC/CP (xi) SEQUENCE DESCRIPTION: SEQ ID NO: 154:

```
AATCATGAAA TCCTTGCAAC TCATTAAGTT TCCTGTTTGC TGTAG ATG CCA GGA AGC        57
                                                  Met Pro Gly Ser
                                                              -35

TCA GGG CTC AGA TTT ATA TGT AAG TCC AGG AAC CAT CCT CAG TTT GGG        105
Ser Gly Leu Arg Phe Ile Cys Lys Ser Arg Asn His Pro Gln Phe Gly
        -30                 -25                 -20

AGT TTC AGT GGA ACT GAC TCC CTT TCC TTC CTA CCA CCC TGC CCC TGT        153
Ser Phe Ser Gly Thr Asp Ser Leu Ser Phe Leu Pro Pro Cys Pro Cys
        -15                 -10                  -5

TGC CCG GCT GCG                                                        165
Cys Pro Ala Ala
  1
```

(2) INFORMATION FOR SEQ ID NO: 155:

(i) SEQUENCE CHARACTERISTICS:
              (A) LENGTH: 261 base pairs
              (B) TYPE: NUCLEIC ACID
              (C) STRANDEDNESS: DOUBLE
              (D) TOPOLOGY: LINEAR (ii) MOLECULE TYPE: cDNA (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: 64..234
              (C) IDENTIFICATION METHOD: Von Heijne matrix
              (D) OTHER INFORMATION:  score 3.8 seq QLXLVMEFCGAGS/VT (xi) SEQUENCE DESCRIPTION: SEQ ID NO: 155:

```
ACATACGGGC AAGTTTATAA GGGTCGTCAT GTCAAAACGG GCCAGCTTGC AGCCATCAAG        60

GTT ATG GAT GTC ACA GGG GAT GAA GAG GAA GAA ATC AAA CAA GAA ATT       108
    Met Asp Val Thr Gly Asp Glu Glu Glu Glu Ile Lys Gln Glu Ile
                -55                 -50                 -45

AAC ATG TTG AAG AAA TAT TCT CAT CAC CGG AAT ATT GCT ACA TAC TAT       156
Asn Met Leu Lys Lys Tyr Ser His His Arg Asn Ile Ala Thr Tyr Tyr
        -40                 -35                 -30

GGT GCT TTT ATC AAA AAG AAC CCA CCA GGC ATG GAT GAC CAA CTT TGR       204
Gly Ala Phe Ile Lys Lys Asn Pro Pro Gly Met Asp Asp Gln Leu Xaa
        -25                 -20                 -15

TTG GTG ATG GAG TTT TGT GGT GCT GGC TCT GTC ACC GAC CTG ATC AAG       252
Leu Val Met Glu Phe Cys Gly Ala Gly Ser Val Thr Asp Leu Ile Lys
-10                  -5                   1                   5

AAC ACA GGG                                                            261
Asn Thr Gly
```

(2) INFORMATION FOR SEQ ID NO: 156:

(i) SEQUENCE CHARACTERISTICS:

(A) LENGTH: 126 base pairs
          (B) TYPE: NUCLEIC ACID
          (C) STRANDEDNESS: DOUBLE
          (D) TOPOLOGY: LINEAR (ii) MOLECULE TYPE: cDNA (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: 49..120
          (C) IDENTIFICATION METHOD: Von Heijne matrix
          (D) OTHER INFORMATION: score 3.8 seq KLFLVFLLNICKG/IV (xi) SEQUENCE DESCRIPTION: SEQ ID NO: 156:

```
ATCTCTAGAA AGAAGAAGGC ATGCTACAAA TAGGAAGGAA TTGTAATA ATG ATA TTT      57
                                                    Met Ile Phe

GGC CTC TAC TTT GTC TTA GCT GTT AAA CTG TTT TTA GTA TTT TTG TTA     105
Gly Leu Tyr Phe Val Leu Ala Val Lys Leu Phe Leu Val Phe Leu Leu
    -20             -15             -10

AAT ATT TGC AAA GGG ATC GTG                                          126
Asn Ile Cys Lys Gly Ile Val
-5              1
```

(2) INFORMATION FOR SEQ ID NO: 157:

(i) SEQUENCE CHARACTERISTICS:
          (A) LENGTH: 383 base pairs
          (B) TYPE: NUCLEIC ACID
          (C) STRANDEDNESS: DOUBLE
          (D) TOPOLOGY: LINEAR (ii) MOLECULE TYPE: cDNA (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: 246..347
          (C) IDENTIFICATION METHOD: Von Heijne matrix
          (D) OTHER INFORMATION: score 3.6 seq IKCSSWISSLASG/IP (xi) SEQUENCE DESCRIPTION: SEQ ID NO: 157:

```
AGTATTGAGT TGGAAGTGCC CATTGGACAT CACGTGGAGA TGAAATAGGC AATTAAAATA     60

TTCAGATCTT GGGTTCAGGA GCGAGACCCA TGTCTGAAAT ATAAACTTGC TCACTGTCAG    120

CCTGTGATGG TCTTTGTGAG ACATAGAATG AATATTAATA AAGAGGTGTA AGGACTGATC    180

CTGGGATCAT CCACAGTAAG GCTGGGGGAA GAGGAGACCT GGCAAAGGAA TCAAAGACAT    240

GATCC ATG AGG AAG AAG CGA GTR GAA GAA CTA ATA GTG TTT CCA GGA GAA    290
      Met Arg Lys Lys Arg Val Glu Glu Leu Ile Val Phe Pro Gly Glu
          -30                 -25                 -20

GTA ACT TCT TTC TCC TCC ATC AAG TGC TCC TCT TGG ATT TCT TCC CTG     338
Val Thr Ser Phe Ser Ser Ile Lys Cys Ser Ser Trp Ile Ser Ser Leu
            -15             -10             -5

GCT TCT GGA ATA CCA CAC TCT CTT GGA TTC TCC CTT CCC CCA GGG          383
Ala Ser Gly Ile Pro His Ser Leu Gly Phe Ser Leu Pro Pro Gly
            1               5               10
```

(2) INFORMATION FOR SEQ ID NO: 158:

(i) SEQUENCE CHARACTERISTICS:
          (A) LENGTH: 427 base pairs
          (B) TYPE: NUCLEIC ACID (C) STRANDEDNESS: DOUBLE
            (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 257..340
         (C) IDENTIFICATION METHOD: Von Heijne matrix
         (D) OTHER INFORMATION:   score 3.6 seq ACLFSXFLAVSRH/PN (xi) SEQUENCE DESCRIPTION: SEQ ID NO: 158:

```
AAGAACCCTT TTTATAGATA GGTCTTGTCT GGATTTGTGC ACGTGGATTT ATAATGAGAG      60

ATTTTCTAGT TGTTTTTGGT TCTCCTCCTC CTCCTCCTCC TTTDHCCTCC TTCTVTTCCT     120

CCTTTTCTTC CTCCTTWTCT TCTAAAACCT CTAATCTCTT ATTCCCTCTA ATGTCTGACC     180

AAAGTACTGC TGTCTGAGAC ATTGGAGGCA TACTGTGCTC CTCTTCTTCC CTCCCTGTGG     240

AGAAGCCTTA AGTTAT ATG CCT TCA TCC AGT CTT GCA GAG TTG TGT CTA ATG     292
               Met Pro Ser Ser Ser Leu Ala Glu Leu Cys Leu Met
                       -25                 -20
```

```
CAG CAA GAT GCC TGC CTG TTT TCT KTG TTC CTA GCW GTC TCC AGG CAT       340
Gln Gln Asp Ala Cys Leu Phe Ser Xaa Phe Leu Ala Val Ser Arg His
    -15                 -10                  -5
```

```
CCA AAC TAT NVK TGT TCC ATC AGT ACT AAG GGT GAG GTG AGA GAG AAA       388
Pro Asn Tyr Xaa Cys Ser Ile Ser Thr Lys Gly Glu Val Arg Glu Lys
  1           5                  10                  15
```

```
CTA GTT CCT TGG ATA ACA CAC CAA ATG GCC AGA ATG TTG                   427
Leu Val Pro Trp Ile Thr His Gln Met Ala Arg Met Leu
            20                  25
```

(2) INFORMATION FOR SEQ ID NO: 159:

(i) SEQUENCE CHARACTERISTICS:
        (A) LENGTH: 158 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: 21..140
         (C) IDENTIFICATION METHOD: Von Heijne matrix
         (D) OTHER INFORMATION:   score 3.6 seq LQMRMQLPCLVLG/EE (xi) SEQUENCE DESCRIPTION: SEQ ID NO: 159:

```
AATTTTCAGT AGGAAACATT ATG GAT CTG TGG AGC TGC TTA TTT CCA GTG ATG      53
                     Met Asp Leu Trp Ser Cys Leu Phe Pro Val Met
                         -40                 -35                 -30
```

```
CTG ATG GAG CCA TCC AAA GGG CTG GAA GAT TCA GAG TGG AAA ATG GCT      101
Leu Met Glu Pro Ser Lys Gly Leu Glu Asp Ser Glu Trp Lys Met Ala
            -25                 -20                 -15
```

```
CTT CAG ATG AGA ATG CAA CTG CCC TGC CTG GTA CTT GGC GAA GAA CAG      149
Leu Gln Met Arg Met Gln Leu Pro Cys Leu Val Leu Gly Glu Glu Gln
        -10                  -5                   1
```

```
ACG CTT GGG                                                          158
Thr Leu Gly
    5
```

(2) INFORMATION FOR SEQ ID NO: 160:

(i) SEQUENCE CHARACTERISTICS:
        (A) LENGTH: 319 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 209..289
        (C) IDENTIFICATION METHOD: Von Heijne matrix
        (D) OTHER INFORMATION:  score 3.6 seq AVPLPTTSTLTSA/ST (xi) SEQUENCE DESCRIPTION: SEQ ID NO: 160:

```
AAGTTCTGTG GGCTCTATTC GGCCATATTA ATAAAGAGAA AGGGAAGGCT GACHGTCCTT      60

CGCCTCCGCC CCCACATACA CACCCCTTCT TCCCACTCCG CTCTCACGAC TAAGCTCTCA     120

CGATTAAGGC ACGCCTGCCT CGATTGTCCA GCCTCTGCCA GAAGAAAGCT TAGCAGCCAG     180

CGCCTCAGTA GAGACCTAAG GGCGCTGA ATG AGT GGG AAA GGG AAA TGC CGA         232
                              Met Ser Gly Lys Gly Lys Cys Arg
                                      -25                 -20

CCA ATT GCG CTG CGG CGG GCT GTG CCA TTA CCT ACA ACA AGC ACA TTA       280
Pro Ile Ala Leu Arg Arg Ala Val Pro Leu Pro Thr Thr Ser Thr Leu
            -15             -10                 -5

ACA TCA GCT TCC ACA GGT TTC CTT TGG ATC CTA AAA GAA                   319
Thr Ser Ala Ser Thr Gly Phe Leu Trp Ile Leu Lys Glu
        1             5                  10
```

(2) INFORMATION FOR SEQ ID NO: 161:

(i) SEQUENCE CHARACTERISTICS:
        (A) LENGTH: 91 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 14..67
        (C) IDENTIFICATION METHOD: Von Heijne matrix
        (D) OTHER INFORMATION:  score 3.6 seq IQKSSGLFCPSQA/QS (xi) SEQUENCE DESCRIPTION: SEQ ID NO: 161:

```
AGAAAATGGA AAA ATG ACC CCA AAG GCA ATT CAG AAA TCA TCA GGG CTC         49
            Met Thr Pro Lys Ala Ile Gln Lys Ser Ser Gly Leu
                    -15                 -10

TTC TGC CCA TCA CAG GCC CAG AGC GCA AGA CCC GCA GAA AAG                91
Phe Cys Pro Ser Gln Ala Gln Ser Ala Arg Pro Ala Glu Lys
 -5              1               5
```

(2) INFORMATION FOR SEQ ID NO: 162:

(i) SEQUENCE CHARACTERISTICS:
        (A) LENGTH: 364 base pairs
        (B) TYPE: NUCLEIC ACID

```
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 56..271
        (C) IDENTIFICATION METHOD: Von Heijne matrix
        (D) OTHER INFORMATION:   score 3.6 seq CTSLLQLYDASNS/EW (xi) SEQUENCE DESCRIPTION: SEQ ID NO: 162:

AAACTCGCTG GGCTCCAAAA GAAACACTGG CTTCTCTCCT TCAGCTCCAG GCTAG ATG          58
                                                             Met

CCA GAC CAG TTT GAC CAG GCG GTT GTG CTG AAC CAG CTG CGG TAC TCA         106
Pro Asp Gln Phe Asp Gln Ala Val Val Leu Asn Gln Leu Arg Tyr Ser
    -70                 -65                 -60

GGG ATG CTG GAG ACT GTG AGA ATC CGC AAA GCT GGG TAT GCG GTC CGA         154
Gly Met Leu Glu Thr Val Arg Ile Arg Lys Ala Gly Tyr Ala Val Arg
-55                 -50                 -45                 -40

AGA CCC TTT CAG GAC TTT TAC AAA AGG TAT AAA GTG CTG ATG AGG AAT         202
Arg Pro Phe Gln Asp Phe Tyr Lys Arg Tyr Lys Val Leu Met Arg Asn
                -35                 -30                 -25

CTG GCT CTG CCT GAG GAC GTC CGA GGG AAG TGC ACG AGC CTG CTG CAG         250
Leu Ala Leu Pro Glu Asp Val Arg Gly Lys Cys Thr Ser Leu Leu Gln
            -20                 -15                 -10

CTC TAT GAT GCC TCC AAC AGC GAG TGG CAG CTG GGG AAG ACC AAG GTC         298
Leu Tyr Asp Ala Ser Asn Ser Glu Trp Gln Leu Gly Lys Thr Lys Val
        -5                   1                   5

TTT CTT CGA GAA TCC TTG GAA CAG AAA CTG GAG AAG CGG AGG GAA GAG         346
Phe Leu Arg Glu Ser Leu Glu Gln Lys Leu Glu Lys Arg Arg Glu Glu
 10                  15                  20                  25

GAA GTG AGC CAC GCT GGG                                                 364
Glu Val Ser His Ala Gly
                30

(2) INFORMATION FOR SEQ ID NO: 163:

(i) SEQUENCE CHARACTERISTICS:
        (A) LENGTH: 185 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 129..173
        (C) IDENTIFICATION METHOD: Von Heijne matrix
        (D) OTHER INFORMATION:   score 3.6 seq LVSFFLELNVLQQ/WP (xi) SEQUENCE DESCRIPTION: SEQ ID NO: 163:

AGTAGACCGC GCACTGGAAG GCGTGCGCGC AGGTGTGCGT GACCATGTGC TTGAAACGGC         60

AGTAGCGCAS RNGNAAGGAT CGCCATCACA CGGCGCACTG GTGCGGCTTC TCCCCCGAGT        120

GGACGAAC ATG TGC TTG GTG TCG TTT TTC CTT GAG CTG AAC GTC TTG CAA        170
         Met Cys Leu Val Ser Phe Phe Leu Glu Leu Asn Val Leu Gln
         -15                 -10                  -5
```

```
CAG TGG CCG GCA GGG                                                185
Gln Trp Pro Ala Gly
    1
```

(2) INFORMATION FOR SEQ ID NO: 164:

(i) SEQUENCE CHARACTERISTICS:
        (A) LENGTH: 234 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 103..141
        (C) IDENTIFICATION METHOD: Von Heijne matrix
        (D) OTHER INFORMATION: score 3.6 seq MRSLACLTPCGHA/GS (xi) SEQUENCE DESCRIPTION: SEQ ID NO: 164:

```
ATACCTCTTC CAGTTGGGAA AAAATGGACT TAAAATGTCC CATGTCCAGG CTGACCTGGA    60

TGATGACAGT TGGTTGATGA GTTAATTTGA ACATGAGCAG AA ATG AGG TCA CTT      114
                                              Met Arg Ser Leu
                                                          -10

GCC TGC CTG ACT CCA TGT GGC CAT GCT GGC TCC AGG TTG CAA AGT TCT    162
Ala Cys Leu Thr Pro Cys Gly His Ala Gly Ser Arg Leu Gln Ser Ser
            -5                  1                   5

TTG AGC AAG TAC CTT GTC TTG CCT AAT CTC GAA TGT CTG TTC TTT TTA    210
Leu Ser Lys Tyr Leu Val Leu Pro Asn Leu Glu Cys Leu Phe Phe Leu
        10                  15                  20

TTT CTT ATC TCA AAT AGG CGC TGG                                    234
Phe Leu Ile Ser Asn Arg Arg Trp
    25                  30
```

(2) INFORMATION FOR SEQ ID NO: 165:

(i) SEQUENCE CHARACTERISTICS:
        (A) LENGTH: 315 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 70..108
        (C) IDENTIFICATION METHOD: Von Heijne matrix
        (D) OTHER INFORMATION: score 3.5 seq MHLLSNWANPASS/RR (xi) SEQUENCE DESCRIPTION: SEQ ID NO: 165:

```
AAGTGGCCAT GGCGGATACA GCGACTACAG CATCGGCGGC GGCGGCTAGT GCCGCTAGCG     60

CCTCGAGCG ATG CAC CTC CTT TCC AAC TGG GCA AAC CCC GCT TCC AGC AGA   111
           Met His Leu Leu Ser Asn Trp Ala Asn Pro Ala Ser Ser Arg
               -10                  -5                          1

CGT CCT TCT ATG GCC GCT TCA GGC ACT TCT TGG ATA TCA TCG ACC CTC     159
Arg Pro Ser Met Ala Ala Ser Gly Thr Ser Trp Ile Ser Ser Thr Leu
            5                   10                  15

GCA CAC TCT TTG TCA CTG AGA GAC GTC TCA GAG AGG CTG TGC AGC TGC     207
```

```
Ala His Ser Leu Ser Leu Arg Asp Val Ser Glu Arg Leu Cys Ser Cys
        20                  25                  30

TGG AGG ACT ATA AGC ATG GGA CCC TGC GCC CGG GGG TCA CCA ATG AAC        255
Trp Arg Thr Ile Ser Met Gly Pro Cys Ala Arg Gly Ser Pro Met Asn
        35                  40                  45

AGC TCT GGA GTG CAC AGA AAA TCA AGC AGG CTA TTC TAC ATC CGG ACA        303
Ser Ser Gly Val His Arg Lys Ser Ser Arg Leu Phe Tyr Ile Arg Thr
50              55                  60                  65

CCA ATG AGA AGA                                                        315
Pro Met Arg Arg (2) INFORMATION FOR SEQ ID NO: 166:

(i) SEQUENCE CHARACTERISTICS:
        (A) LENGTH: 415 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: 62..133
        (C) IDENTIFICATION METHOD: Von Heijne matrix
        (D) OTHER INFORMATION:  score 3.5 seq FAMLHSVWRLIPA/FR (xi) SEQUENCE DESCRIPTION: SEQ ID NO: 166:

AAAGGAGCCA ACYKCACAGT ACATTTCTCT TTGTCATGAA TTGCATACTT TGTTCCAAGT         60

C ATG TGG TCT GGA AAG TGG GCG TTG GTC TCA CCA TTT GCT ATG CTA CAC      109
  Met Trp Ser Gly Lys Trp Ala Leu Val Ser Pro Phe Ala Met Leu His
                -20                 -15                 -10

TCA GTG TGG AGA CTC ATT CCT GCC TTT CGT GGT TAC GCC CAA CAA GAC        157
Ser Val Trp Arg Leu Ile Pro Ala Phe Arg Gly Tyr Ala Gln Gln Asp
            -5                   1                   5

GCT CAG GAA TTT CTT TGT GAA CTT TTA GAT AAA ATA CAA CGT GAA TTA        205
Ala Gln Glu Phe Leu Cys Glu Leu Leu Asp Lys Ile Gln Arg Glu Leu
        10                  15                  20

GAG ACA ACT GGT ACC AGT TTA CCA GCT CTT ATC CCC ACT TCT CAA AGG        253
Glu Thr Thr Gly Thr Ser Leu Pro Ala Leu Ile Pro Thr Ser Gln Arg
25              30                  35                  40

AAA CTC ATC AAA CAA GTT CTG AAT GTT GTA AAT AAC ATT TTT CAT GGA        301
Lys Leu Ile Lys Gln Val Leu Asn Val Val Asn Asn Ile Phe His Gly
                45                  50                  55

CAA CTT CTT AGT CAG GTT ACA TGT CTT GCA TGT GAC AAC AAA TCA AAT        349
Gln Leu Leu Ser Gln Val Thr Cys Leu Ala Cys Asp Asn Lys Ser Asn
            60                  65                  70

ACC ATA GAA CCT TTC TGG GAC TTG TCA TTG GAG TYT CCA GAA AGG TAT        397
Thr Ile Glu Pro Phe Trp Asp Leu Ser Leu Glu Xaa Pro Glu Arg Tyr
        75                  80                  85

CAA TGC AGT NGA AAA GGG                                                415
Gln Cys Ser Xaa Lys Gly
        90

(2) INFORMATION FOR SEQ ID NO: 167:

(i) SEQUENCE CHARACTERISTICS:
        (A) LENGTH: 252 base pairs
        (B) TYPE: NUCLEIC ACID
        (C) STRANDEDNESS: DOUBLE
        (D) TOPOLOGY: LINEAR
```

(ii) MOLECULE TYPE: cDNA (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: 130..189
             (C) IDENTIFICATION METHOD: Von Heijne matrix
             (D) OTHER INFORMATION:  score 3.5 seq KFCLICLLTFIFH/HC (xi) SEQUENCE DESCRIPTION: SEQ ID NO: 167:

```
AAGACGCGCC GGTTTCTGCG ACGCAGTTAG CGCAGTCTGC TTTGGTGAAT ACACGATTTG      60

GTGCAGCCGG GGTTTGGTAC CGAGCGGAGA GGAGATGCAC ACGGCACTCG AGTGTGAGGA     120

AAAATAGAA ATG AAG GTA CAT ATG CAC ACA AAA TTT TGC CTC ATT TGT TTG     171
          Met Lys Val His Met His Thr Lys Phe Cys Leu Ile Cys Leu
              -20             -15                 -10

CTG ACA TTT ATT TTT CAT CAT TGC AAC CAT TGC CAT GAA GAA CAT GAC       219
Leu Thr Phe Ile Phe His His Cys Asn His Cys His Glu Glu His Asp
    -5              1               5               10

CAT GGC CCT GAA GCG CTT CAC AGA CAG CAA GGG                           252
His Gly Pro Glu Ala Leu His Arg Gln Gln Gly
            15                  20
```

(2) INFORMATION FOR SEQ ID NO: 168:

(i) SEQUENCE CHARACTERISTICS:
             (A) LENGTH: 436 base pairs
             (B) TYPE: NUCLEIC ACID
             (C) STRANDEDNESS: DOUBLE
             (D) TOPOLOGY: LINEAR (ii) MOLECULE TYPE: cDNA (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: 290..361
             (C) IDENTIFICATION METHOD: Von Heijne matrix
             (D) OTHER INFORMATION:  score 3.5 seq ALSLFYTADTSHG/SE (xi) SEQUENCE DESCRIPTION: SEQ ID NO: 168:

```
ATATTTCTTG TCAACAGTAT TGAAATGTAA TATGTATGTG TTCATGTATG AGMAATTTTT      60

ACTCCACACA GGTGTTTCAG TAGAGTGGGG CAGGAAAAGA GATCTCTTCG ATTTCTTTCA     120

GGCCTGAGGC TTTTGTGAAA TGCGTCASCC CCTGTGACAG TAGGTTTTGA TGCTAGTGAT     180

CTTCAGATCT TTCTCTCTGG AAATGTGCAG AGAGTGTCAG TTTCCAAGT TCTGAGGTAA      240

CTCTCAGCCC AGATGTGAAA TGGGAGCCTA CCAGCTGGTA TAGAAGGGA ATG GGT AGG     298
                                                    Met Gly Arg

AGG CAC TGG GTG CTG ACT CAT TCA GCA CTG TCC CTT TTC TAT ACT GCT       346
Arg His Trp Val Leu Thr His Ser Ala Leu Ser Leu Phe Tyr Thr Ala
    -20             -15                 -10

GAT ACA TCC CAT GGT TCT GAG AAG CCT TAT CTC AGT CTA TTT GGA AGA       394
Asp Thr Ser His Gly Ser Glu Lys Pro Tyr Leu Ser Leu Phe Gly Arg
    -5              1               5               10

GAG GGA GGW AGA GAA GGR AGT AAC CCA AAG TAC TAC TCA TTT                436
Glu Gly Gly Arg Glu Gly Ser Asn Pro Lys Tyr Tyr Ser Phe
            15                  20                  25
```

(2) INFORMATION FOR SEQ ID NO: 169:

(i) SEQUENCE CHARACTERISTICS:
        (A) LENGTH: 343 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 104..336
        (C) IDENTIFICATION METHOD: blastn
        (D) OTHER INFORMATION:   identity 96 region 1..233 id H07998
            est (ix) FEATURE:
        (A) NAME/KEY: other
        (B) LOCATION: 110..336
        (C) IDENTIFICATION METHOD: blastn
        (D) OTHER INFORMATION:   identity 96 region 1..227 id W37530
            est (ix) FEATURE:
        (A) NAME/KEY: other
        (B) LOCATION: 110..336
        (C) IDENTIFICATION METHOD: blastn
        (D) OTHER INFORMATION:   identity 96 region 1..227 id R79812
            est (ix) FEATURE:
        (A) NAME/KEY: other
        (B) LOCATION: 110..336
        (C) IDENTIFICATION METHOD: blastn
        (D) OTHER INFORMATION:   identity 96 region 1..227 id N24900
            est (ix) FEATURE:
        (A) NAME/KEY: other
        (B) LOCATION: 110..336
        (C) IDENTIFICATION METHOD: blastn
        (D) OTHER INFORMATION:   identity 96 region 1..227 id R34849
            est (ix) FEATURE:
        (A) NAME/KEY: sig_peptide
        (B) LOCATION: 65..112
        (C) IDENTIFICATION METHOD: Von Heijne matrix
        (D) OTHER INFORMATION:   score 12.5 seq FVVLLALVAGVLG/NE (xi) SEQUENCE DESCRIPTION: SEQ ID NO: 169:

```
ATGTCGCCCG TGTCCCGCCG GCCCGTTCCG TGTCGCCCCG CAGTGYTGCG GCCGCCGCKK        60

CACC ATG GCT GTG TTT GTC GTG CTC CTG GCG TTG GTG GCG GGT GTT TTG       109
     Met Ala Val Phe Val Val Leu Leu Ala Leu Val Ala Gly Val Leu
         -15                 -10                  -5

GGG AAC GAG TTT AGT ATA TTA AAA TCA CCA GGG TCT GTT GTT TTC CGA        157
Gly Asn Glu Phe Ser Ile Leu Lys Ser Pro Gly Ser Val Val Phe Arg
  1               5                  10                  15

AAT GGA AAT TGG CCT ATA CCA GGA GAG CGG ATC CCA GAC GTG GCT GCA        205
Asn Gly Asn Trp Pro Ile Pro Gly Glu Arg Ile Pro Asp Val Ala Ala
                 20                  25                  30

TTG TCC ATG GGC TTC TCT GTG AAA GAA GAC CTT TCT TGG CCA GGA CTC        253
Leu Ser Met Gly Phe Ser Val Lys Glu Asp Leu Ser Trp Pro Gly Leu
                 35                  40                  45

GCA GTG GGT AAC CTG TTT CAT CGT CCT CGG GCT AGC GTC ATG GTG ATG        301
Ala Val Gly Asn Leu Phe His Arg Pro Arg Ala Ser Val Met Val Met
         50                  55                  60

GTG AAG GGA GTT AAC AAC TMC CCT CTA CCC CCA NGN TGG NGG                343
```

```
Val Lys Gly Val Asn Asn Xaa Pro Leu Pro Pro Xaa Trp Xaa
 65                  70                  75
```

(2) INFORMATION FOR SEQ ID NO: 170:

(i) SEQUENCE CHARACTERISTICS:
        (A) LENGTH: 234 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 111..209
        (C) IDENTIFICATION METHOD: blastn
        (D) OTHER INFORMATION: identity 90 region 1..99 id N50844
           est (ix) FEATURE:
        (A) NAME/KEY: other
        (B) LOCATION: 186..232
        (C) IDENTIFICATION METHOD: blastn
        (D) OTHER INFORMATION: identity 93 region 75..121 id N50844
           est (ix) FEATURE:
        (A) NAME/KEY: other
        (B) LOCATION: 111..209
        (C) IDENTIFICATION METHOD: blastn
        (D) OTHER INFORMATION: identity 90 region 1..99 id N29905
           est (ix) FEATURE:
        (A) NAME/KEY: other
        (B) LOCATION: 186..232
        (C) IDENTIFICATION METHOD: blastn
        (D) OTHER INFORMATION: identity 93 region 75..121 id N29905
           est (ix) FEATURE:
        (A) NAME/KEY: other
        (B) LOCATION: 186..232
        (C) IDENTIFICATION METHOD: blastn
        (D) OTHER INFORMATION: identity 93 region 75..121 id N62597
           est (ix) FEATURE:
        (A) NAME/KEY: other
        (B) LOCATION: 186..232
        (C) IDENTIFICATION METHOD: blastn
        (D) OTHER INFORMATION: identity 93 region 76..122 id R80247
           est (ix) FEATURE:
        (A) NAME/KEY: other
        (B) LOCATION: 186..232
        (C) IDENTIFICATION METHOD: blastn
        (D) OTHER INFORMATION: identity 93 region 76..122 id H03409
           est (ix) FEATURE:
        (A) NAME/KEY: sig_peptide
        (B) LOCATION: 40..87
        (C) IDENTIFICATION METHOD: Von Heijne matrix
        (D) OTHER INFORMATION: score 10.1 seq LLLQLAVLGAALA/AA (xi) SEQUENCE DESCRIPTION: SEQ ID NO: 170:

```
AAGAGGTGCG GGATTGGGCG GGCTGCCACG GCATGGAGA ATG GCT CCG CTT CTG    54
                                         Met Ala Pro Leu Leu
                                          -15
```

```
TTG CAG CTG GCG GTG CTC GGC GCG GCG CTG GCG GCC GCA GCC CTC GTA      102
Leu Gln Leu Ala Val Leu Gly Ala Ala Leu Ala Ala Ala Ala Leu Val
    -10                  -5                   1                 5

CTG ATT TCC ATC GTT GCA TTT ACA ACT GCT ACA AAA ATG CCA GCA CTC      150
Leu Ile Ser Ile Val Ala Phe Thr Thr Ala Thr Lys Met Pro Ala Leu
                 10                  15                  20

CAT CGA CAT GAA GAA GAG AAA TTC TTC TTA AAT GCC AAA GGC CAG AAA      198
His Arg His Glu Glu Glu Lys Phe Phe Leu Asn Ala Lys Gly Gln Lys
            25                  30                  35

GAA ACT TTA CCC AGC ATA TGG GAC TCA CCT ACC AGG                      234
Glu Thr Leu Pro Ser Ile Trp Asp Ser Pro Thr Arg
        40                  45
```

(2) INFORMATION FOR SEQ ID NO: 171:

(i) SEQUENCE CHARACTERISTICS:
        (A) LENGTH: 386 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 52..228
        (C) IDENTIFICATION METHOD: blastn
        (D) OTHER INFORMATION: identity 94 region 1..177 id AA074050
            est (ix) FEATURE:
        (A) NAME/KEY: other
        (B) LOCATION: 266..387
        (C) IDENTIFICATION METHOD: blastn
        (D) OTHER INFORMATION: identity 99 region 218..339 id
            AA074050 est (ix) FEATURE:
        (A) NAME/KEY: sig_peptide
        (B) LOCATION: 135..284
        (C) IDENTIFICATION METHOD: Von Heijne matrix
        (D) OTHER INFORMATION: score 9.8 seq LLRLLQLVSTCVA/FS (xi) SEQUENCE DESCRIPTION: SEQ ID NO: 171:

```
AGCGGCCGCA GCCAGCCAGG CCGCGCMMGG GACGACTGCA GAGCGCGGTG CTCTTACAGC      60

CTGTTCCAAG TGTGGCTTAA TCCGTCTCCA CCACCAGATC TTTCTCCGTG GATTCCTCTG     120

CTAAGACCGC TGCC ATG CCA GTG ACG GTA ACC CGC ACC ACC ATC ACA ACC      170
             Met Pro Val Thr Val Thr Arg Thr Thr Ile Thr Thr
             -50                 -45                 -40

ACC ACG ACG TCA TCT TCG GGC CTG GGG TCC CCC ATG ATC GTG GGG TCC      218
Thr Thr Thr Ser Ser Ser Gly Leu Gly Ser Pro Met Ile Val Gly Ser
            -35                 -30                 -25

CCT CGG GCC CTG ACA CAG CCC CTG GGT CTC CTT CGC CTG CTG CAG CTG      266
Pro Arg Ala Leu Thr Gln Pro Leu Gly Leu Leu Arg Leu Leu Gln Leu
        -20                 -15                 -10

GTG TCT ACC TGC GTG GCC TTC TCG CTG GTG GCT AGC GTG GGC GCC TGG      314
Val Ser Thr Cys Val Ala Phe Ser Leu Val Ala Ser Val Gly Ala Trp
    -5                   1                   5                  10

ACG GGG TCC ATG GGC AAC TGG TCC ATG TTC ACC TGG TGC TTC TGC TTC      362
Thr Gly Ser Met Gly Asn Trp Ser Met Phe Thr Trp Cys Phe Cys Phe
                15                  20                  25

TCN GTG ACC CTG ATC ATC CTC ATC                                      386
Ser Val Thr Leu Ile Ile Leu Ile
```

30

(2) INFORMATION FOR SEQ ID NO: 172:

(i) SEQUENCE CHARACTERISTICS:
        (A) LENGTH: 326 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 147..290
        (C) IDENTIFICATION METHOD: blastn
        (D) OTHER INFORMATION:   identity 99 region 57..200 id W40499
            est (ix) FEATURE:
        (A) NAME/KEY: other
        (B) LOCATION: 90..151
        (C) IDENTIFICATION METHOD: blastn
        (D) OTHER INFORMATION:   identity 98 region 1..62 id W40499
            est (ix) FEATURE:
        (A) NAME/KEY: other
        (B) LOCATION: 100..319
        (C) IDENTIFICATION METHOD: blastn
        (D) OTHER INFORMATION:   identity 99 region 46..265 id R88049
            est (ix) FEATURE:
        (A) NAME/KEY: other
        (B) LOCATION: 100..319
        (C) IDENTIFICATION METHOD: blastn
        (D) OTHER INFORMATION:   identity 99 region 56..275 id T08712
            est (ix) FEATURE:
        (A) NAME/KEY: other
        (B) LOCATION: 100..319
        (C) IDENTIFICATION METHOD: blastn
        (D) OTHER INFORMATION:   identity 99 region 32..251 id H38484
            est (ix) FEATURE:
        (A) NAME/KEY: other
        (B) LOCATION: 147..319
        (C) IDENTIFICATION METHOD: blastn
        (D) OTHER INFORMATION:   identity 98 region 65..237 id T65344
            est (ix) FEATURE:
        (A) NAME/KEY: other
        (B) LOCATION: 102..151
        (C) IDENTIFICATION METHOD: blastn
        (D) OTHER INFORMATION:   identity 100 region 21..70 id T65344
            est (ix) FEATURE:
        (A) NAME/KEY: sig_peptide
        (B) LOCATION: 111..164
        (C) IDENTIFICATION METHOD: Von Heijne matrix
        (D) OTHER INFORMATION:   score 9.2 seq VFLCSLLAPMVLA/SA (xi) SEQUENCE DESCRIPTION: SEQ ID NO: 172:

AGACTCTTGG GGACTGGGCT GAGGACGGGG TGGTACTGCT CCTGGCAGGG CCAGAGGTGG      60

ATGGGGCTTG AAAAGGGGGT TCAAGGCAGC AGMTCTATGG TTCAGACGCC ATG GAG        116
                                                      Met Glu

```
TTG GTG CTG GTC TTC CTC TGC AGC CTG CTG GCC CCC ATG GTC CTG GCC      164
Leu Val Leu Val Phe Leu Cys Ser Leu Leu Ala Pro Met Val Leu Ala
    -15                 -10                 -5

AGT GCA GCT GAA AAG GAG AAG GAA ATG GAC CCT TTT CAT TAT GAT TAC      212
Ser Ala Ala Glu Lys Glu Lys Glu Met Asp Pro Phe His Tyr Asp Tyr
  1           5                  10                 15

CAG ACC CTG AGG ATT GGG GGA CTG GTG TTC GCT GTG GTC CTC TTC TCG      260
Gln Thr Leu Arg Ile Gly Gly Leu Val Phe Ala Val Val Leu Phe Ser
                20                  25                  30

GTT GGG ATC CTC CTT ATC CTA AGT CGC AGG TGC AAG TGC AGT TTC AAT      308
Val Gly Ile Leu Leu Ile Leu Ser Arg Arg Cys Lys Cys Ser Phe Asn
             35                  40                  45

CAG AAG CCC CGC AAC AGA                                              326
Gln Lys Pro Arg Asn Arg
 50
```

(2) INFORMATION FOR SEQ ID NO: 173:

(i) SEQUENCE CHARACTERISTICS:
        (A) LENGTH: 376 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 74..344
        (C) IDENTIFICATION METHOD: blastn
        (D) OTHER INFORMATION:   identity 96 region 73..343 id H95186
           est (ix) FEATURE:
        (A) NAME/KEY: other
        (B) LOCATION: 25..86
        (C) IDENTIFICATION METHOD: blastn
        (D) OTHER INFORMATION:   identity 93 region 25..86 id H95186
           est (ix) FEATURE:
        (A) NAME/KEY: other
        (B) LOCATION: 138..377
        (C) IDENTIFICATION METHOD: blastn
        (D) OTHER INFORMATION:   identity 100 region 1..240 id N40665
           est (ix) FEATURE:
        (A) NAME/KEY: other
        (B) LOCATION: 203..308
        (C) IDENTIFICATION METHOD: blastn
        (D) OTHER INFORMATION:   identity 95 region 230..335 id W25197
           est (ix) FEATURE:
        (A) NAME/KEY: sig_peptide
        (B) LOCATION: 167..304
        (C) IDENTIFICATION METHOD: Von Heijne matrix
        (D) OTHER INFORMATION:   score 7.9 seq LLGLLSAEQLAEA/SV (xi) SEQUENCE DESCRIPTION: SEQ ID NO: 173:

```
AACGGGCGTC GGGAAGACGC TGCTGGTGAA ACGGCTGCAG GAGGTGAGCT CCCGGGATGG      60

GAAAGGCGAC CTGGGGGAGC CGCCCCCGAC ACGGCCCACG GTGGGCACCA ATCTTACTGA     120

CATCGTGGCA CAGAGAAAGA TCACCATCCG GGAGCTTGGG GGGTGC ATG GGC CCC        175
                                                 Met Gly Pro
                                                  -45
```

```
ATC TGG TCC AGT TAC TAT GGA AAC TGC CGT TCT CTC CTG TTT GTG ATG      223
Ile Trp Ser Ser Tyr Tyr Gly Asn Cys Arg Ser Leu Leu Phe Val Met
            -40                 -35                 -30

GAC GCC TCT GAC CCC ACC CAG CTC TCT GCA TCC TGT GTG CAG CTC TTA      271
Asp Ala Ser Asp Pro Thr Gln Leu Ser Ala Ser Cys Val Gln Leu Leu
        -25                 -20                 -15

GGT CTC CTT TCT GCA GAA CAA CTT GCA GAA GCA TCG GTG CTG ATA CTC      319
Gly Leu Leu Ser Ala Glu Gln Leu Ala Glu Ala Ser Val Leu Ile Leu
    -10                  -5                   1                   5

TTC AAT AAA ATC GAC CTA CCC TGT TAC ATG TCC ACG GAG GAG ATG AAG      367
Phe Asn Lys Ile Asp Leu Pro Cys Tyr Met Ser Thr Glu Glu Met Lys
                10                  15                  20

TCA TTA ATC                                                          376
Ser Leu Ile
```

(2) INFORMATION FOR SEQ ID NO: 174:

(i) SEQUENCE CHARACTERISTICS:
        (A) LENGTH: 277 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 59..278
        (C) IDENTIFICATION METHOD: blastn
        (D) OTHER INFORMATION: identity 97 region 28..247 id R78970
           est (ix) FEATURE:
        (A) NAME/KEY: other
        (B) LOCATION: 59..210
        (C) IDENTIFICATION METHOD: blastn
        (D) OTHER INFORMATION: identity 92 region 29..180 id R64509
           est (ix) FEATURE:
        (A) NAME/KEY: other
        (B) LOCATION: 196..278
        (C) IDENTIFICATION METHOD: blastn
        (D) OTHER INFORMATION: identity 96 region 167..249 id R64509
           est (ix) FEATURE:
        (A) NAME/KEY: other
        (B) LOCATION: 59..210
        (C) IDENTIFICATION METHOD: blastn
        (D) OTHER INFORMATION: identity 92 region 44..195 id H85714
           est (ix) FEATURE:
        (A) NAME/KEY: other
        (B) LOCATION: 196..278
        (C) IDENTIFICATION METHOD: blastn
        (D) OTHER INFORMATION: identity 96 region 182..264 id H85714
           est (ix) FEATURE:
        (A) NAME/KEY: other
        (B) LOCATION: 59..278
        (C) IDENTIFICATION METHOD: blastn
        (D) OTHER INFORMATION: identity 96 region 36..255 id H52756
           est (ix) FEATURE:
        (A) NAME/KEY: other
        (B) LOCATION: 59..278

```
            (C) IDENTIFICATION METHOD: blastn
            (D) OTHER INFORMATION:  identity 96 region 5..224 id H49758
                est (ix) FEATURE:
            (A) NAME/KEY: sig_peptide
            (B) LOCATION: 107..247
            (C) IDENTIFICATION METHOD: Von Heijne matrix
            (D) OTHER INFORMATION:  score 7.9 seq LLLPRVLLTMASG/SP (xi) SEQUENCE DESCRIPTION: SEQ ID NO: 174:

ATCACGTGGC RGCCACCCAG GKAMGAAGAR NANVTCTTCC TGGGGTTVHT TCTCCGANRT          60

GACGTSYSGC CTTTGAGATC AACTCTCCTG TACCAGCGTA GGCCGC ATG AGT GGG           115
                                                Met Ser Gly
                                                        -45

GGG CGG GCT CCC GCG GTC CTG CTC GGC GGA GTG GCC TCT CTG CTC CTG          163
Gly Arg Ala Pro Ala Val Leu Leu Gly Gly Val Ala Ser Leu Leu Leu
            -40                 -35                 -30

TCT TTT GTT TGG ATG CCG GCG CTG CTG CCT GTG GCC TCC CGC CTT TTG          211
Ser Phe Val Trp Met Pro Ala Leu Leu Pro Val Ala Ser Arg Leu Leu
        -25                 -20                 -15

TTG CTA CCC CGA GTC TTG CTG ACC ATG GCC TCT GGA AGC CCT CCG ACC          259
Leu Leu Pro Arg Val Leu Leu Thr Met Ala Ser Gly Ser Pro Pro Thr
    -10                  -5                  1

CAG CCC TCG CCG GCC TGG                                                   277
Gln Pro Ser Pro Ala Trp
 5                  10

(2) INFORMATION FOR SEQ ID NO: 175:

(i) SEQUENCE CHARACTERISTICS:
            (A) LENGTH: 388 base pairs
            (B) TYPE: NUCLEIC ACID
            (C) STRANDEDNESS: DOUBLE
            (D) TOPOLOGY: LINEAR (ii) MOLECULE TYPE: cDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: 180..390
            (C) IDENTIFICATION METHOD: blastn
            (D) OTHER INFORMATION:  identity 98 region 134..344 id H08480
                est (ix) FEATURE:
            (A) NAME/KEY: other
            (B) LOCATION: 115..185
            (C) IDENTIFICATION METHOD: blastn
            (D) OTHER INFORMATION:  identity 100 region 1..71 id H08480
                est (ix) FEATURE:
            (A) NAME/KEY: sig_peptide
            (B) LOCATION: 113..232
            (C) IDENTIFICATION METHOD: Von Heijne matrix
            (D) OTHER INFORMATION:  score 7.9 seq SLLLLFGGQFASS/QE (xi) SEQUENCE DESCRIPTION: SEQ ID NO: 175:

AGCAGAGCTT CCGCTTCCGG CCCTTCAGGC TCTGTCTCTG TGGAGACTGG GCTTTGGGAG          60

GKAGAAAGAG GGACCTAGCG CGGGCCGCGC AGGCGCACGG TGGGCAGCTG CA ATG GCG        118
                                                         Met Ala
                                                             -40

CTG TCG TGT ACC CTT AAC AGG TAT CTG CTC CTC ATG GCG CAG GAG CAT          166
Leu Ser Cys Thr Leu Asn Arg Tyr Leu Leu Leu Met Ala Gln Glu His
```

```
                 -35                    -30                    -25
CTG GAG TTC CGC CTG CCG GAA ATA RRG TCT TTG CTT TTG CTT TTT GGA       214
Leu Glu Phe Arg Leu Pro Glu Ile Xaa Ser Leu Leu Leu Leu Phe Gly
            -20                    -15                    -10

GGT CAG TTT GCC AGC AGT CAA GAA ACT TAT GGA AAG TCA CCA TTT TGG       262
Gly Gln Phe Ala Ser Ser Gln Glu Thr Tyr Gly Lys Ser Pro Phe Trp
         -5                      1                     5                      10

ATT CTT AGC ATT CCC TCT GAA GAT ATT GCA AGA AAT TTG ATG AAA CGG       310
Ile Leu Ser Ile Pro Ser Glu Asp Ile Ala Arg Asn Leu Met Lys Arg
                    15                    20                     25

ACA GTG TGT GCC AAG TCT ATA TTT GAA CTA TGG GGT CAT GGA CAA TCT       358
Thr Val Cys Ala Lys Ser Ile Phe Glu Leu Trp Gly His Gly Gln Ser
                 30                    35                    40

CCT GAG GAG CTG TAC AGT TCT CTT AAA AAC                               388
Pro Glu Glu Leu Tyr Ser Ser Leu Lys Asn
         45                    50
```

(2) INFORMATION FOR SEQ ID NO: 176:

(i) SEQUENCE CHARACTERISTICS:
        (A) LENGTH: 311 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 112..309
        (C) IDENTIFICATION METHOD: blastn
        (D) OTHER INFORMATION:   identity 97 region 69..266 id AA149265
           est (ix) FEATURE:
        (A) NAME/KEY: other
        (B) LOCATION: 41..86
        (C) IDENTIFICATION METHOD: blastn
        (D) OTHER INFORMATION:   identity 97 region 1..46 id AA149265
           est (ix) FEATURE:
        (A) NAME/KEY: other
        (B) LOCATION: 110..309
        (C) IDENTIFICATION METHOD: blastn
        (D) OTHER INFORMATION:   identity 97 region 53..252 id W39570
           est (ix) FEATURE:
        (A) NAME/KEY: other
        (B) LOCATION: 56..86
        (C) IDENTIFICATION METHOD: blastn
        (D) OTHER INFORMATION:   identity 96 region 2..32 id W39570
           est (ix) FEATURE:
        (A) NAME/KEY: other
        (B) LOCATION: 110..309
        (C) IDENTIFICATION METHOD: blastn
        (D) OTHER INFORMATION:   identity 97 region 55..254 id N41332
           est (ix) FEATURE:
        (A) NAME/KEY: other
        (B) LOCATION: 53..86
        (C) IDENTIFICATION METHOD: blastn
        (D) OTHER INFORMATION:   identity 97 region 1..34 id N41332
           est (ix) FEATURE:
        (A) NAME/KEY: sig_peptide
        (B) LOCATION: 39..197
        (C) IDENTIFICATION METHOD: Von Heijne matrix
        (D) OTHER INFORMATION: score 7.1 seq IAVGLGVAALAFA/GR (xi) SEQUENCE DESCRIPTION: SEQ ID NO: 176:

```
AACTGCCGCG GCGCCTTGAG TCTCCGGGCC GCCTTGCC ATG GCT GCC CGT GGT GTC      56
                                         Met Ala Ala Arg Gly Val
                                                         -50

ATC GCT CCA GTT GGC GAG AGT TTG CGC TAC GCT GAG TAC TTG CAG CCC        104
Ile Ala Pro Val Gly Glu Ser Leu Arg Tyr Ala Glu Tyr Leu Gln Pro
        -45             -40             -35

TCG GCC AAA CGG CCA GAC GCC GAC GTC GAC CAG CAG AGA CTG GTA AGA        152
Ser Ala Lys Arg Pro Asp Ala Asp Val Asp Gln Gln Arg Leu Val Arg
    -30             -25             -20

AGT TTG ATA GCT GTA GGA CTG GGT GTT GCA GCT CTT GCA TTT GCA GGT        200
Ser Leu Ile Ala Val Gly Leu Gly Val Ala Ala Leu Ala Phe Ala Gly
-15             -10             -5                              1

CGC TAC GCA TTT CGG ATC TGG AAA CCT CTA GAA CAA GTT ATC ACA GAA        248
Arg Tyr Ala Phe Arg Ile Trp Lys Pro Leu Glu Gln Val Ile Thr Glu
             5              10              15

ACT GCA AAG AAG ATT TCA ACT CCT AGC TTT TCA TCC TAC TAT AAA GGA        296
Thr Ala Lys Lys Ile Ser Thr Pro Ser Phe Ser Ser Tyr Tyr Lys Gly
         20              25              30

GGA TTT GAA CGG AGG                                                    311
Gly Phe Glu Arg Arg
     35
```

(2) INFORMATION FOR SEQ ID NO: 177:

(i) SEQUENCE CHARACTERISTICS:
        (A) LENGTH: 384 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 43..87
        (C) IDENTIFICATION METHOD: blastn
        (D) OTHER INFORMATION: identity 100 region 8..52 id W32101
            est (ix) FEATURE:
        (A) NAME/KEY: other
        (B) LOCATION: 89..129
        (C) IDENTIFICATION METHOD: blastn
        (D) OTHER INFORMATION: identity 100 region 53..93 id W32101
            est (ix) FEATURE:
        (A) NAME/KEY: sig_peptide
        (B) LOCATION: 292..375
        (C) IDENTIFICATION METHOD: Von Heijne matrix
        (D) OTHER INFORMATION: score 6.6 seq VLGXLFLGGLCRG/WD (xi) SEQUENCE DESCRIPTION: SEQ ID NO: 177:

```
AAGAGCCGCG TTYAGTCTAT CGCTGCGGTT GCGAGCGCTG TAGGGAGCCT GTGCTGTGCC       60

GCGCAGTTAG GCAGCAGCAG CCGCGGAGCA GTAGCCGCCG TGGGAGGGAG CCATGAAGCA      120

TTACGAGGTA AGAAGCGAGA AACAGGGGCC GTGTGGCCAC TGCTGACCCA TTCTTTTTCC      180
```

```
TTCTTTGCGG GACCACGGGA CCCCACTTTC TGGTCCTGTG CCCCGAAGGA AGAKCCAGAC        240

GGCGCAGGCG CAGTGGGCAA GCGTTGCGCC CCGGGCCACT CGTAAATTCC A ATG CGC        297
                                                        Met Arg

ATG TGC GCA GGA AGT ATT TAT AAA TCT GCA ACC CAG GCT GTT TTG GGG         345
Met Cys Ala Gly Ser Ile Tyr Lys Ser Ala Thr Gln Ala Val Leu Gly
    -25             -20                 -15

GWA CTT TTT CTT GGG GGT CTC TGC AGG GGC TGG GAC GCT                     384
Xaa Leu Phe Leu Gly Gly Leu Cys Arg Gly Trp Asp Ala
-10             -5                  1
```

(2) INFORMATION FOR SEQ ID NO: 178:

(i) SEQUENCE CHARACTERISTICS:
        (A) LENGTH: 425 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 73..317
        (C) IDENTIFICATION METHOD: blastn
        (D) OTHER INFORMATION:  identity 97 region 1..245 id
            HUM506F10B est (ix) FEATURE:
        (A) NAME/KEY: other
        (B) LOCATION: 314..376
        (C) IDENTIFICATION METHOD: blastn
        (D) OTHER INFORMATION:  identity 98 region 243..305 id
            HUM506F10B est (ix) FEATURE:
        (A) NAME/KEY: other
        (B) LOCATION: 63..193
        (C) IDENTIFICATION METHOD: blastn
        (D) OTHER INFORMATION:  identity 99 region 1..131 id AA056148
            est (ix) FEATURE:
        (A) NAME/KEY: other
        (B) LOCATION: 314..401
        (C) IDENTIFICATION METHOD: blastn
        (D) OTHER INFORMATION:  identity 95 region 254..341 id
            AA056148 est (ix) FEATURE:
        (A) NAME/KEY: other
        (B) LOCATION: 277..317
        (C) IDENTIFICATION METHOD: blastn
        (D) OTHER INFORMATION:  identity 97 region 216..256 id
            AA056148 est (ix) FEATURE:
        (A) NAME/KEY: other
        (B) LOCATION: 397..426
        (C) IDENTIFICATION METHOD: blastn
        (D) OTHER INFORMATION:  identity 96 region 338..367 id
            AA056148 est (ix) FEATURE:
        (A) NAME/KEY: other
        (B) LOCATION: 88..189
        (C) IDENTIFICATION METHOD: blastn
        (D) OTHER INFORMATION:  identity 98 region 1..102 id HSC1FF051
            est (ix) FEATURE:
        (A) NAME/KEY: other

```
        (B) LOCATION: 314..401
        (C) IDENTIFICATION METHOD: blastn
        (D) OTHER INFORMATION:   identity 96 region 230..317 id
            HSC1FF051 est (ix) FEATURE:
        (A) NAME/KEY: other
        (B) LOCATION: 187..271
        (C) IDENTIFICATION METHOD: blastn
        (D) OTHER INFORMATION:   identity 95 region 101..185 id
            HSC1FF051 est (ix) FEATURE:
        (A) NAME/KEY: other
        (B) LOCATION: 269..317
        (C) IDENTIFICATION METHOD: blastn
        (D) OTHER INFORMATION:   identity 93 region 184..232 id
            HSC1FF051 est (ix) FEATURE:
        (A) NAME/KEY: other
        (B) LOCATION: 397..426
        (C) IDENTIFICATION METHOD: blastn
        (D) OTHER INFORMATION:   identity 96 region 314..343 id
            HSC1FF051 est (ix) FEATURE:
        (A) NAME/KEY: other
        (B) LOCATION: 87..200
        (C) IDENTIFICATION METHOD: blastn
        (D) OTHER INFORMATION:   identity 92 region 1..114 id HSC16E081
            est (ix) FEATURE:
        (A) NAME/KEY: other
        (B) LOCATION: 314..401
        (C) IDENTIFICATION METHOD: blastn
        (D) OTHER INFORMATION:   identity 96 region 231..318 id
            HSC16E081 est (ix) FEATURE:
        (A) NAME/KEY: other
        (B) LOCATION: 199..275
        (C) IDENTIFICATION METHOD: blastn
        (D) OTHER INFORMATION:   identity 94 region 114..190 id
            HSC16E081 est (ix) FEATURE:
        (A) NAME/KEY: other
        (B) LOCATION: 269..317
        (C) IDENTIFICATION METHOD: blastn
        (D) OTHER INFORMATION:   identity 91 region 185..233 id
            HSC16E081 est (ix) FEATURE:
        (A) NAME/KEY: other
        (B) LOCATION: 397..426
        (C) IDENTIFICATION METHOD: blastn
        (D) OTHER INFORMATION:   identity 96 region 315..344 id
            HSC16E081 est (ix) FEATURE:
        (A) NAME/KEY: other
        (B) LOCATION: 85..186
        (C) IDENTIFICATION METHOD: blastn
        (D) OTHER INFORMATION:   identity 99 region 24..125 id AA157365
            est (ix) FEATURE:
        (A) NAME/KEY: other
        (B) LOCATION: 183..263
        (C) IDENTIFICATION METHOD: blastn
        (D) OTHER INFORMATION:   identity 90 region 123..203 id
            AA157365 est (ix) FEATURE:
        (A) NAME/KEY: other
        (B) LOCATION: 337..401
        (C) IDENTIFICATION METHOD: blastn
```

(D) OTHER INFORMATION: identity 95 region 278..342 id
                AA157365 est (ix) FEATURE:
            (A) NAME/KEY: other
            (B) LOCATION: 273..326
            (C) IDENTIFICATION METHOD: blastn
            (D) OTHER INFORMATION: identity 90 region 213..266 id
                AA157365 est (ix) FEATURE:
            (A) NAME/KEY: sig_peptide
            (B) LOCATION: 186..419
            (C) IDENTIFICATION METHOD: Von Heijne matrix
            (D) OTHER INFORMATION: score 6.3 seq TLIMLLSWQLSVS/SV (xi) SEQUENCE DESCRIPTION: SEQ ID NO: 178:

```
AATGCGCGCT CGCGNTCCCG CCCTCTAGCT GCGCTCGGCT GAGTCAGTCA GTCTGTCGGA       60

GTCTGTCCTC GGAGCAGGCG GAGTAAAGGG ACTTGAGCGA GCCAGTTGCC GGATTATTCT      120

ATTTCCCCTC CCTCTCTCCC GCCCCGTATC TCTTTTCACC CTTCTCCCAC CCTCGCTCGC      180

GTASC ATG GCG GAG CGT CGG CGG CCA CTC AGT CCC ATT CCA TCT NNT CGT      230
      Met Ala Glu Arg Arg Arg Pro Leu Ser Pro Ile Pro Ser Xaa Arg
          -75                 -70                 -65

CGT CCT TCG GAG CCG AGC CGT CCG CGC CCG GCG GCG GCG GGA SCC AGG        278
Arg Pro Ser Glu Pro Ser Arg Pro Arg Pro Ala Ala Ala Gly Xaa Arg
            -60                 -55                 -50

AGC CTG CCC CGC CCT GGG GAC GAA GAG CTG CAG CTC CCC TGT GCG GTG        326
Ser Leu Pro Arg Pro Gly Asp Glu Glu Leu Gln Leu Pro Cys Ala Val
        -45                 -40                 -35

CAC GAT CTG ATT TTC TGG AGA GAT GTG AAG AAG ACT GGG TTT GTC TTT        374
His Asp Leu Ile Phe Trp Arg Asp Val Lys Lys Thr Gly Phe Val Phe
    -30                 -25                 -20

GGC ACC ACG CTG ATC ATG CTG CTT TCC TGG CAG CTT TCA GTG TCA TCA        422
Gly Thr Thr Leu Ile Met Leu Leu Ser Trp Gln Leu Ser Val Ser Ser
-15                 -10                  -5                  1

GTG                                                                    425
Val
```

(2) INFORMATION FOR SEQ ID NO: 179:

(i) SEQUENCE CHARACTERISTICS:
        (A) LENGTH: 403 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 105..351
        (C) IDENTIFICATION METHOD: blastn
        (D) OTHER INFORMATION: identity 98 region 49..295 id R47336
            est (ix) FEATURE:
        (A) NAME/KEY: other
        (B) LOCATION: 58..107
        (C) IDENTIFICATION METHOD: blastn
        (D) OTHER INFORMATION: identity 98 region 1..50 id R47336 est (ix) FEATURE:
        (A) NAME/KEY: other
        (B) LOCATION: 352..381
        (C) IDENTIFICATION METHOD: blastn (D) OTHER INFORMATION: identity 100 region 295..324 id R47336
                est (ix) FEATURE:
         (A) NAME/KEY: sig_peptide
         (B) LOCATION: 5..331
         (C) IDENTIFICATION METHOD: Von Heijne matrix
         (D) OTHER INFORMATION: score 6 seq LQLLLGMTASAVA/AL (xi) SEQUENCE DESCRIPTION: SEQ ID NO: 179:

```
AAAG ATG GCG GCT CCC GTC CTG CTA AGA GTG TCG GTG CCG CGG TGG GAG        49
     Met Ala Ala Pro Val Leu Leu Arg Val Ser Val Pro Arg Trp Glu
                 -105                -100                -95

CGG GTG GCC CGG TAT GCA GTG TGC GCT GCC GGA ATC CTG CTC TCC ATC        97
Arg Val Ala Arg Tyr Ala Val Cys Ala Ala Gly Ile Leu Leu Ser Ile
             -90                -85                 -80

TAC GCC TAC CAC GTG GAG CGG GAG AAG GAG CGG GAC CCC GAG CAC CGG       145
Tyr Ala Tyr His Val Glu Arg Glu Lys Glu Arg Asp Pro Glu His Arg
         -75                -70                 -65

GCC CTC TGC GAC CTG GGG CCC TGG GTG AAG TGC TCC GCC GCC CTT GCC       193
Ala Leu Cys Asp Leu Gly Pro Trp Val Lys Cys Ser Ala Ala Leu Ala
         -60                -55                 -50

TCC AGA TGG GGT CGA GGA TTT GGT CTT TTG GGT TCC ATT TTT GGA AAG       241
Ser Arg Trp Gly Arg Gly Phe Gly Leu Leu Gly Ser Ile Phe Gly Lys
     -45                -40                 -35

GAT GGT GTA TTA AAC CAG CCA AAC AGT GTC TTT GGA CTT ATA TTT TAT       289
Asp Gly Val Leu Asn Gln Pro Asn Ser Val Phe Gly Leu Ile Phe Tyr
-30                -25                 -20                -15

ATA CTA CAG TTA TTA CTT GGC ATG ACA GCA AGC GCT GTG GCG GCT TTG       337
Ile Leu Gln Leu Leu Leu Gly Met Thr Ala Ser Ala Val Ala Ala Leu
             -10                -5                    1

ATC CTC ATG ACG TCC TCC ATC ATG TCG GTC GTG GGG TCC TGT ACC TGG       385
Ile Leu Met Thr Ser Ser Ile Met Ser Val Val Gly Ser Cys Thr Trp
         5                 10                 15

CCT ACA TTC TGT ACT ACG                                               403
Pro Thr Phe Cys Thr Thr
     20
```

(2) INFORMATION FOR SEQ ID NO: 180:

(i) SEQUENCE CHARACTERISTICS:
        (A) LENGTH: 367 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
         (A) ORGANISM: Homo Sapiens
         (F) TISSUE TYPE: Brain (ix) FEATURE:
         (A) NAME/KEY: other
         (B) LOCATION: 112..260
         (C) IDENTIFICATION METHOD: blastn
         (D) OTHER INFORMATION: identity 92 region 121..269 id W31320
             est (ix) FEATURE:
         (A) NAME/KEY: other
         (B) LOCATION: 47..118
         (C) IDENTIFICATION METHOD: blastn
         (D) OTHER INFORMATION: identity 100 region 57..128 id W31320
             est (ix) FEATURE:
         (A) NAME/KEY: other
         (B) LOCATION: 273..333

(C) IDENTIFICATION METHOD: blastn
            (D) OTHER INFORMATION:  identity 98 region 282..342 id W31320
                  est (ix) FEATURE:
            (A) NAME/KEY: other
            (B) LOCATION: 107..260
            (C) IDENTIFICATION METHOD: blastn
            (D) OTHER INFORMATION:  identity 98 region 2..155 id T27259
                  est (ix) FEATURE:
            (A) NAME/KEY: other
            (B) LOCATION: 273..369
            (C) IDENTIFICATION METHOD: blastn
            (D) OTHER INFORMATION:  identity 100 region 168..264 id T27259
                  est (ix) FEATURE:
            (A) NAME/KEY: other
            (B) LOCATION: 145..260
            (C) IDENTIFICATION METHOD: blastn
            (D) OTHER INFORMATION:  identity 90 region 108..223 id
                  AA157646 est (ix) FEATURE:
            (A) NAME/KEY: other
            (B) LOCATION: 59..118
            (C) IDENTIFICATION METHOD: blastn
            (D) OTHER INFORMATION:  identity 90 region 25..84 id AA157646
                  est (ix) FEATURE:
            (A) NAME/KEY: other
            (B) LOCATION: 273..307
            (C) IDENTIFICATION METHOD: blastn
            (D) OTHER INFORMATION:  identity 94 region 245..279 id SSC8A04
                  est (ix) FEATURE:
            (A) NAME/KEY: sig_peptide
            (B) LOCATION: 50..151
            (C) IDENTIFICATION METHOD: Von Heijne matrix
            (D) OTHER INFORMATION:  score 5.9 seq LGAAALALLLANT/DV (xi) SEQUENCE DESCRIPTION: SEQ ID NO: 180:

AATATACTTC TTTGTCAAGA AAGCAGAGG TGTGGACGCT GTGTATGAA ATG TCT TTC        58
                                                     Met Ser Phe

CTC CAG GAC CCA AGT TTC TTC ACC ATG GGG ATG TGG TCC ATT GGT GCA        106
Leu Gln Asp Pro Ser Phe Phe Thr Met Gly Met Trp Ser Ile Gly Ala
    -30                 -25                 -20

GGA GCC CTG GGG GCT GCT GCC TTG GCA TTG CTG CTT GCC AAC ACA GAC        154
Gly Ala Leu Gly Ala Ala Ala Leu Ala Leu Leu Leu Ala Asn Thr Asp
-15                 -10                  -5                   1

GTG TTT CTG TCC AAG CCC CWK AAA GCG GCC CTG GAG TAC CTG GAG GAT        202
Val Phe Leu Ser Lys Pro Xaa Lys Ala Ala Leu Glu Tyr Leu Glu Asp
                5                  10                  15

ATA GAC CTG AAA ACA CTG GAG AAG GAA CCA AGG ACT TTC AAA GCA AAG        250
Ile Asp Leu Lys Thr Leu Glu Lys Glu Pro Arg Thr Phe Lys Ala Lys
            20                  25                  30

GAG CTA TGG GAA AAA AAT GGA GCT GTG ATT ATG GCC GTG CGG AGG CCA        298
Glu Leu Trp Glu Lys Asn Gly Ala Val Ile Met Ala Val Arg Arg Pro
        35                  40                  45

GGC TGT TTC CTC TGT CGA GAG GAA GCT GCG GAT CTG TCC TCC CTG AAA        346
Gly Cys Phe Leu Cys Arg Glu Glu Ala Ala Asp Leu Ser Ser Leu Lys
50                  55                  60                  65

AGC ATG TTG GAC CAG CTG GGC                                            367
Ser Met Leu Asp Gln Leu Gly
                70

```
(2) INFORMATION FOR SEQ ID NO: 181:

(i) SEQUENCE CHARACTERISTICS:
        (A) LENGTH: 257 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 138..257
        (C) IDENTIFICATION METHOD: blastn
        (D) OTHER INFORMATION:   identity 98 region 83..202 id W31692
            est (ix) FEATURE:
        (A) NAME/KEY: other
        (B) LOCATION: 55..131
        (C) IDENTIFICATION METHOD: blastn
        (D) OTHER INFORMATION:   identity 100 region 1..77 id W31692
            est (ix) FEATURE:
        (A) NAME/KEY: other
        (B) LOCATION: 136..257
        (C) IDENTIFICATION METHOD: blastn
        (D) OTHER INFORMATION:   identity 98 region 78..199 id H50194
            est (ix) FEATURE:
        (A) NAME/KEY: other
        (B) LOCATION: 57..131
        (C) IDENTIFICATION METHOD: blastn
        (D) OTHER INFORMATION:   identity 100 region 1..75 id H50194
            est (ix) FEATURE:
        (A) NAME/KEY: other
        (B) LOCATION: 57..257
        (C) IDENTIFICATION METHOD: blastn
        (D) OTHER INFORMATION:   identity 97 region 1..201 id H46855
            est (ix) FEATURE:
        (A) NAME/KEY: other
        (B) LOCATION: 138..257
        (C) IDENTIFICATION METHOD: blastn
        (D) OTHER INFORMATION:   identity 98 region 81..200 id H49687
            est (ix) FEATURE:
        (A) NAME/KEY: other
        (B) LOCATION: 57..132
        (C) IDENTIFICATION METHOD: blastn
        (D) OTHER INFORMATION:   identity 100 region 1..76 id H49687
            est (ix) FEATURE:
        (A) NAME/KEY: other
        (B) LOCATION: 138..257
        (C) IDENTIFICATION METHOD: blastn
        (D) OTHER INFORMATION:   identity 98 region 80..199 id T54405
            est (ix) FEATURE:
        (A) NAME/KEY: other
        (B) LOCATION: 58..124
        (C) IDENTIFICATION METHOD: blastn
        (D) OTHER INFORMATION:   identity 100 region 2..68 id T54405
            est (ix) FEATURE:
        (A) NAME/KEY: sig_peptide
```

(B) LOCATION: 90..200
        (C) IDENTIFICATION METHOD: Von Heijne matrix
        (D) OTHER INFORMATION: score 4.9 seq MLIMLGIFFNVHS/AV (xi) SEQUENCE DESCRIPTION: SEQ ID NO: 181:

ATCTCTGCCC CCCTGCGAGG GCATCCTGGG CTTTCTCCCA CCGCTTTCCG AGCCCGCTTG      60

CACCTCGGCG ATCCCCGACT CCCTTCTTT ATG GCG TCG CTC CTG TGC TGT GGG      113
                                 Met Ala Ser Leu Leu Cys Cys Gly
                                                 -35             -30

CCG AAG CTG GCC GCC TGC GGC ATC GTC CTC AGC GCC TGG GGA GTG ATC      161
Pro Lys Leu Ala Ala Cys Gly Ile Val Leu Ser Ala Trp Gly Val Ile
            -25             -20                 -15

ATG TTG ATA ATG CTC GGA ATA TTT TTC AAT GTC CAT TCC GCT GTG TTG      209
Met Leu Ile Met Leu Gly Ile Phe Phe Asn Val His Ser Ala Val Leu
            -10              -5                   1

ATT GAG GAC GTT CCC TTC ACG GAG AAA GAT TTT GAG AAC GGC CCC CGG      257
Ile Glu Asp Val Pro Phe Thr Glu Lys Asp Phe Glu Asn Gly Pro Arg
      5                10                  15

(2) INFORMATION FOR SEQ ID NO: 182:

(i) SEQUENCE CHARACTERISTICS:
        (A) LENGTH: 400 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 365..401
        (C) IDENTIFICATION METHOD: blastn
        (D) OTHER INFORMATION: identity 100 region 1..37 id R50224
            est (ix) FEATURE:
        (A) NAME/KEY: sig_peptide
        (B) LOCATION: 305..364
        (C) IDENTIFICATION METHOD: Von Heijne matrix
        (D) OTHER INFORMATION: score 4.9 seq XSLFLHAVSSSFT/QL (xi) SEQUENCE DESCRIPTION: SEQ ID NO: 182:

ATGACCACGG GTTTAACCTT CTTATCCCAG AGACACCCAA TTCTAGAGCT TTATGGAGCC      60

GTACTTCCCC CTGAATCCTA GCTCTAGGAC ATAGATCATG ACTCTCAGCC CTTTTACCCA     120

GGATGGAGCT GGGGCCTGTA TAGCCATATT ATTGTTCTAA GTAAGTTCTA GCCCCACCCT     180

CCCGCCTTCT TGAGTGATAC CTATTACGGA TGAGTTCTGG AAAAGACCCA GCTATGATTC     240

ATAAAAACAC TTCTGGATGA ATCAAGAACC ATTTCTTGTT TKTCCTAGAT AATTCTCTAA     300

AAAT ATG ATT CTT CCA TAT AGA ATG CKA AGC TTA TTT TTA CAT GCA GTT     349
     Met Ile Leu Pro Tyr Arg Met Xaa Ser Leu Phe Leu His Ala Val
     -20              -15                 -10

TCT AGC TCC TTC ACC CAG CTG AGG TCG TGC CAG GGA GAC AGA GTC TGG      397
Ser Ser Ser Phe Thr Gln Leu Arg Ser Cys Gln Gly Asp Arg Val Trp
 -5              1               5                 10

AGA                                                                  400
Arg (2) INFORMATION FOR SEQ ID NO: 183:

(i) SEQUENCE CHARACTERISTICS:

(A) LENGTH: 256 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 86..186
        (C) IDENTIFICATION METHOD: blastn
        (D) OTHER INFORMATION: identity 93 region 5..105 id AA096741
            est (ix) FEATURE:
        (A) NAME/KEY: sig_peptide
        (B) LOCATION: 23..211
        (C) IDENTIFICATION METHOD: Von Heijne matrix
        (D) OTHER INFORMATION: score 4.8 seq LYTVRALAGRAWA/AV (xi) SEQUENCE DESCRIPTION: SEQ ID NO: 183:

```
AGAAGTGCGT SYCGGCGGGA TC ATG GCG ACT TTG GTC GAA CTG CCG GAC TCG        52
                        Met Ala Thr Leu Val Glu Leu Pro Asp Ser
                                     -60                 -55

GTC CTG CTC GAG ATC TTC TCT TAC CTC CCG GTA CGG GAC CGG ATC CGC        100
Val Leu Leu Glu Ile Phe Ser Tyr Leu Pro Val Arg Asp Arg Ile Arg
            -50                 -45                 -40

ATC TCC AGG GTC TGT CAC CGC TGG AAG AGG CTG GTG GAC GAC CGG TGG        148
Ile Ser Arg Val Cys His Arg Trp Lys Arg Leu Val Asp Asp Arg Trp
        -35                 -30                 -25

CTG TGG CGA CAT GTC GAC CTG ACG CTC TAC ACG GTA CGC GCA CTG GCC        196
Leu Trp Arg His Val Asp Leu Thr Leu Tyr Thr Val Arg Ala Leu Ala
    -20                 -15                 -10

GGG CGG GCC TGG GCC GCG GTC GCG GTG CCC GGA SCC CGA AGA CCA CCT        244
Gly Arg Ala Trp Ala Ala Val Ala Val Pro Gly Xaa Arg Arg Pro Pro
 -5                  1                   5                  10

CTC CCA CCC TGG                                                        256
Leu Pro Pro Trp
            15
```

(2) INFORMATION FOR SEQ ID NO: 184:

(i) SEQUENCE CHARACTERISTICS:
        (A) LENGTH: 352 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 183..348
        (C) IDENTIFICATION METHOD: blastn
        (D) OTHER INFORMATION: identity 98 region 78..243 id W52941
            est (ix) FEATURE:
        (A) NAME/KEY: other
        (B) LOCATION: 286..348
        (C) IDENTIFICATION METHOD: blastn
        (D) OTHER INFORMATION: identity 96 region 1..63 id H55390 est (ix) FEATURE:

(A) NAME/KEY: sig_peptide
            (B) LOCATION: 77..199
            (C) IDENTIFICATION METHOD: Von Heijne matrix
            (D) OTHER INFORMATION: score 4.7 seq LFSCFCFLSHKFG/KK (xi) SEQUENCE DESCRIPTION: SEQ ID NO: 184:

```
AAAAAATATC TCCCGGCGTG CGCTGCTTGT GTTATGTTCG GGTTTTAAGT CGTGTCAGCG        60

TTTACATTTT CTTAAT ATG AAA AAT GCC TGC ATT GTT CTG CCG CCA ACT CCC       112
               Met Lys Asn Ala Cys Ile Val Leu Pro Pro Thr Pro
                   -40             -35                 -30

CCT CCC TCC CTG CAA CCC TCG GCC TCT CTG CTG GCG CCT AAT CGT TTT         160
Pro Pro Ser Leu Gln Pro Ser Ala Ser Leu Leu Ala Pro Asn Arg Phe
            -25                 -20                 -15

TTA TTC TCT TGC TTC TGC TTT CTT AGT CAC AAG TTT GGG AAG AAA GTC         208
Leu Phe Ser Cys Phe Cys Phe Leu Ser His Lys Phe Gly Lys Lys Val
            -10                 -5                   1

ATC TAT TTC AAC TAC CTG AGT GAG CTC CAC GAA CAC CTT AAA TAC GAC         256
Ile Tyr Phe Asn Tyr Leu Ser Glu Leu His Glu His Leu Lys Tyr Asp
     5                  10                  15

CAG CTG GTC ATC CCT CCC GAA GTT TTG CGG TAC GAT GAG AAG CTC CAG         304
Gln Leu Val Ile Pro Pro Glu Val Leu Arg Tyr Asp Glu Lys Leu Gln
 20                  25                  30                  35

AGC CTG CAC GAG GGC CGG ACG CCG MCT CCC ACC AAG ACA CCA CCA GGG         352
Ser Leu His Glu Gly Arg Thr Pro Xaa Pro Thr Lys Thr Pro Pro Gly
                 40                  45                  50
```

(2) INFORMATION FOR SEQ ID NO: 185:

(i) SEQUENCE CHARACTERISTICS:
        (A) LENGTH: 274 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 99..260
        (C) IDENTIFICATION METHOD: blastn
        (D) OTHER INFORMATION: identity 96 region 126..287 id T53519
            est (ix) FEATURE:
        (A) NAME/KEY: other
        (B) LOCATION: 40..108
        (C) IDENTIFICATION METHOD: blastn
        (D) OTHER INFORMATION: identity 91 region 1..69 id T53519 est (ix) FEATURE:
        (A) NAME/KEY: other
        (B) LOCATION: 113..269
        (C) IDENTIFICATION METHOD: blastn
        (D) OTHER INFORMATION: identity 96 region 131..287 id W87344
            est (ix) FEATURE:
        (A) NAME/KEY: other
        (B) LOCATION: 147..269
        (C) IDENTIFICATION METHOD: blastn
        (D) OTHER INFORMATION: identity 96 region 138..260 id N56542
            est (ix) FEATURE:
        (A) NAME/KEY: other
        (B) LOCATION: 113..149
        (C) IDENTIFICATION METHOD: blastn (D) OTHER INFORMATION: identity 91 region 105..141 id N56542
                est (ix) FEATURE:
            (A) NAME/KEY: other
            (B) LOCATION: 75..105
            (C) IDENTIFICATION METHOD: blastn
            (D) OTHER INFORMATION: identity 96 region 1..31 id N56542 est (ix) FEATURE:
            (A) NAME/KEY: other
            (B) LOCATION: 113..218
            (C) IDENTIFICATION METHOD: blastn
            (D) OTHER INFORMATION: identity 96 region 117..222 id
                AA053475 est (ix) FEATURE:
            (A) NAME/KEY: other
            (B) LOCATION: 218..269
            (C) IDENTIFICATION METHOD: blastn
            (D) OTHER INFORMATION: identity 94 region 223..274 id
                AA053475 est (ix) FEATURE:
            (A) NAME/KEY: other
            (B) LOCATION: 113..269
            (C) IDENTIFICATION METHOD: blastn
            (D) OTHER INFORMATION: identity 95 region 90..246 id W05444
                est (ix) FEATURE:
            (A) NAME/KEY: sig_peptide
            (B) LOCATION: 110..193
            (C) IDENTIFICATION METHOD: Von Heijne matrix
            (D) OTHER INFORMATION: score 4.6 seq PLQWSLLVAVVAG/SV (xi) SEQUENCE DESCRIPTION: SEQ ID NO: 185:

ACTTCCGCCT GCGCCTGCGC AGCVCAGCTC CSHGAGCCCT GCCAACCATG GTGAACTTGG      60

GTCTGTCCCG GGTGGACGAC GCCGTGGCTG CCAAGCACCC GGCACCGGC ATG GCC TTT    118
                                                      Met Ala Phe

GGC TTG CAG ATG TTC ATT CAG AGG AAG TTT CCA TAC CCT TTG CAG TGG      166
Gly Leu Gln Met Phe Ile Gln Arg Lys Phe Pro Tyr Pro Leu Gln Trp
-25                 -20                 -15                 -10

AGC CTC CTA GTG GCC GTG GTT GCA GGC TCT GTG GTC AGC TAC GGG GTG      214
Ser Leu Leu Val Ala Val Val Ala Gly Ser Val Val Ser Tyr Gly Val
                -5                   1                   5

ACG AGA GTR RAG TCG GAG AAA TGC AAC AAC CTC TGG CTC TTC CTG GAG      262
Thr Arg Val Xaa Ser Glu Lys Cys Asn Asn Leu Trp Leu Phe Leu Glu
            10                  15                  20

ACC GGA CTT GGG                                                      274
Thr Gly Leu Gly
    25

(2) INFORMATION FOR SEQ ID NO: 186:

(i) SEQUENCE CHARACTERISTICS:
        (A) LENGTH: 316 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 45..315
        (C) IDENTIFICATION METHOD: blastn
        (D) OTHER INFORMATION: identity 98 region 1..271 id HSC1ZD051

```
           est (ix) FEATURE:
         (A) NAME/KEY: sig_peptide
         (B) LOCATION: 110..268
         (C) IDENTIFICATION METHOD: Von Heijne matrix
         (D) OTHER INFORMATION:  score 4.5 seq LLWTPLLSPGSLR/VI (xi) SEQUENCE DESCRIPTION: SEQ ID NO: 186:

ATATGAGACT CTGGCCTCCC TGCAGATCTT CTAAGAACCA CACTAATGCA AGCGTGACAG        60

AGAAACCTCT TTCGAATGAC CTACTACAAC TCTGGCATTG GTTAGTTCC ATG TAT TGT       118
                                                      Met Tyr Cys

AAG ATT CTG GTG CTA ATG CTC CAT ACA GAA TTG ATC AGG ACT GAT TAC         166
Lys Ile Leu Val Leu Met Leu His Thr Glu Leu Ile Arg Thr Asp Tyr
-50             -45                 -40                 -35

TCT TCT GTG GAC CAA TTG CTA TTG AAC TAC CCA GCT GAA GAG GGT TTG         214
Ser Ser Val Asp Gln Leu Leu Leu Asn Tyr Pro Ala Glu Glu Gly Leu
            -30                 -25                 -20

GGG AGA GAA CGT TCA TTA TTA TGG ACT CCA CTT TTG TCS CCT GGT AGT         262
Gly Arg Glu Arg Ser Leu Leu Trp Thr Pro Leu Leu Ser Pro Gly Ser
        -15                 -10                  -5

TTA AGG GTG ATA CTA GAA TCC AGA GAA GTT CCT GTC TCC TTG TGG CCC         310
Leu Arg Val Ile Leu Glu Ser Arg Glu Val Pro Val Ser Leu Trp Pro
         1               5                  10

CAA ACG                                                                 316
Gln Thr
15

(2) INFORMATION FOR SEQ ID NO: 187:

(i) SEQUENCE CHARACTERISTICS:
        (A) LENGTH: 423 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 50..246
        (C) IDENTIFICATION METHOD: blastn
        (D) OTHER INFORMATION:  identity 96 region 1..197 id AA043070
            est (ix) FEATURE:
        (A) NAME/KEY: other
        (B) LOCATION: 241..373
        (C) IDENTIFICATION METHOD: blastn
        (D) OTHER INFORMATION:  identity 97 region 191..323 id
            AA043070 est (ix) FEATURE:
        (A) NAME/KEY: other
        (B) LOCATION: 371..408
        (C) IDENTIFICATION METHOD: blastn
        (D) OTHER INFORMATION:  identity 100 region 322..359 id
            AA043070 est (ix) FEATURE:
        (A) NAME/KEY: other
        (B) LOCATION: 186..357
        (C) IDENTIFICATION METHOD: blastn
        (D) OTHER INFORMATION:  identity 95 region 29..200 id W81202
            est (ix) FEATURE:
```

(A) NAME/KEY: other
            (B) LOCATION: 345..423
            (C) IDENTIFICATION METHOD: blastn
            (D) OTHER INFORMATION:  identity 100 region 189..267 id W81202
                est (ix) FEATURE:
            (A) NAME/KEY: other
            (B) LOCATION: 64..177
            (C) IDENTIFICATION METHOD: blastn
            (D) OTHER INFORMATION:  identity 100 region 85..198 id W24858
                est (ix) FEATURE:
            (A) NAME/KEY: other
            (B) LOCATION: 178..227
            (C) IDENTIFICATION METHOD: blastn
            (D) OTHER INFORMATION:  identity 90 region 198..247 id W24858
                est (ix) FEATURE:
            (A) NAME/KEY: sig_peptide
            (B) LOCATION: 166..243
            (C) IDENTIFICATION METHOD: Von Heijne matrix
            (D) OTHER INFORMATION:  score 4.5 seq ENSLIILLQGLQG/RV (xi) SEQUENCE DESCRIPTION: SEQ ID NO: 187:

AACTCTGCGC CCGGAGGACA GAGCGGCCCG GTCGCCGGCA TGGTTTCTCC GTCCTGCTGC        60

AGCCGGCGGG AGGCAGCCAG TCCAGGCGCC CGCTAGCTTC GGCGGCGACC CAGACGGGGA       120

AAGCGGAAGG AATGTCGCGT GCAAGCAGGC AGCTGGTGTG GAAGA ATG GCG GTG AGC      177
                                                 Met Ala Val Ser
                                                     -25

CAT TCA GTG AAG GAG CGG ACC ATC TCT GAG AAC AGC CTG ATC ATC CTA        225
His Ser Val Lys Glu Arg Thr Ile Ser Glu Asn Ser Leu Ile Ile Leu
        -20                 -15                 -10

CTG CAG GGC CTC CAG GGC CGG GTA ACC ACT GTG GAC CTG CGG GAT GAG        273
Leu Gln Gly Leu Gln Gly Arg Val Thr Thr Val Asp Leu Arg Asp Glu
    -5                   1                   5                  10

AGC GTG GCC CAC GGA CGC ATA GAC AAB GTC GAT GCT TTC ATG AAC ATC        321
Ser Val Ala His Gly Arg Ile Asp Xaa Val Asp Ala Phe Met Asn Ile
                15                  20                  25

CGC CTG GCC AAA GTC ACC TAC ACG GAC CGT TGG GGG CAT CAG GTC AAG        369
Arg Leu Ala Lys Val Thr Tyr Thr Asp Arg Trp Gly His Gln Val Lys
            30                  35                  40

CTG GAT GAC CTC TTT GTG ACA GGC CGC AAT GTC CGC TAC GTC CAC ATC        417
Leu Asp Asp Leu Phe Val Thr Gly Arg Asn Val Arg Tyr Val His Ile
        45                  50                  55

CCA GAT                                                                423
Pro Asp
    60

(2) INFORMATION FOR SEQ ID NO: 188:

(i) SEQUENCE CHARACTERISTICS:
            (A) LENGTH: 343 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: 165..302
            (C) IDENTIFICATION METHOD: blastn (D) OTHER INFORMATION: identity 93 region 33..170 id T50032
                        est (ix) FEATURE:
                    (A) NAME/KEY: other
                    (B) LOCATION: 291..339
                    (C) IDENTIFICATION METHOD: blastn
                    (D) OTHER INFORMATION: identity 97 region 160..208 id T50032
                        est (ix) FEATURE:
                    (A) NAME/KEY: other
                    (B) LOCATION: 132..172
                    (C) IDENTIFICATION METHOD: blastn
                    (D) OTHER INFORMATION: identity 97 region 1..41 id T50032 est (ix) FEATURE:
                    (A) NAME/KEY: sig_peptide
                    (B) LOCATION: 71..139
                    (C) IDENTIFICATION METHOD: Von Heijne matrix
                    (D) OTHER INFORMATION: score 4.4 seq QFILLGTTSVVTA/AL (xi) SEQUENCE DESCRIPTION: SEQ ID NO: 188:

```
AAGGTGGAGA GTCGGGGGTC ACCAGGCCTA TCCTTGGCGC CACAGTCGGC CACCGGGGCT      60

CGCCGCCGTC ATG GAG AGC GGA GGG CGG CCC TCG CTG TGC CAG TTC ATC       109
           Met Glu Ser Gly Gly Arg Pro Ser Leu Cys Gln Phe Ile
               -20                  -15

CTC CTG GGC ACC ACC TCT GTG GTC ACC GCC GCC CTG TAC TCC GTG TAC      157
Leu Leu Gly Thr Thr Ser Val Val Thr Ala Ala Leu Tyr Ser Val Tyr
-10              -5                   1                5

CGG CAG AAG GCC CGG GTC TCC CAA GAG CTC AAG GGA GCT AAA AAA GTT      205
Arg Gln Lys Ala Arg Val Ser Gln Glu Leu Lys Gly Ala Lys Lys Val
                 10                  15                  20

CAT TTG GGT GAA GAT TTA AAG AGT ATT CTT TCA GAA GCT CCA GGA AAA      253
His Leu Gly Glu Asp Leu Lys Ser Ile Leu Ser Glu Ala Pro Gly Lys
         25                  30                  35

TGC GTG CCT TAT GCT GTT ATA GAA GGA GCT GTG CGG TCT GTT AAA GAA      301
Cys Val Pro Tyr Ala Val Ile Glu Gly Ala Val Arg Ser Val Lys Glu
     40                  45                  50

ACG CTT AAC AGC CAG TTT GTG GAA AAC TGC AAN GGG GTC CGG              343
Thr Leu Asn Ser Gln Phe Val Glu Asn Cys Xaa Gly Val Arg
55                  60                  65
```

(2) INFORMATION FOR SEQ ID NO: 189:

(i) SEQUENCE CHARACTERISTICS:
                    (A) LENGTH: 481 base pairs
                    (B) TYPE: NUCLEIC ACID
                    (C) STRANDEDNESS: DOUBLE
                    (D) TOPOLOGY: LINEAR (ii) MOLECULE TYPE: cDNA (vi) ORIGINAL SOURCE:
                    (A) ORGANISM: Homo Sapiens
                    (F) TISSUE TYPE: Brain (ix) FEATURE:
                    (A) NAME/KEY: other
                    (B) LOCATION: 133..355
                    (C) IDENTIFICATION METHOD: blastn
                    (D) OTHER INFORMATION: identity 96 region 3..225 id H10707
                        est (ix) FEATURE:
                    (A) NAME/KEY: other
                    (B) LOCATION: 353..482
                    (C) IDENTIFICATION METHOD: blastn
                    (D) OTHER INFORMATION: identity 97 region 224..353 id H10707
                        est

```
   (ix) FEATURE:
        (A) NAME/KEY: other
        (B) LOCATION: 154..354
        (C) IDENTIFICATION METHOD: blastn
        (D) OTHER INFORMATION:  identity 93 region 98..298 id H30624
            est (ix) FEATURE:
        (A) NAME/KEY: other
        (B) LOCATION: 368..403
        (C) IDENTIFICATION METHOD: blastn
        (D) OTHER INFORMATION:  identity 94 region 314..349 id H30624
            est (ix) FEATURE:
        (A) NAME/KEY: other
        (B) LOCATION: 200..354
        (C) IDENTIFICATION METHOD: blastn
        (D) OTHER INFORMATION:  identity 94 region 150..304 id
            HSC1VG011 est (ix) FEATURE:
        (A) NAME/KEY: other
        (B) LOCATION: 111..198
        (C) IDENTIFICATION METHOD: blastn
        (D) OTHER INFORMATION:  identity 92 region 62..149 id
            HSC1VG011 est (ix) FEATURE:
        (A) NAME/KEY: other
        (B) LOCATION: 49..85
        (C) IDENTIFICATION METHOD: blastn
        (D) OTHER INFORMATION:  identity 97 region 1..37 id
            HSC1VG011 est (ix) FEATURE:
        (A) NAME/KEY: other
        (B) LOCATION: 202..344
        (C) IDENTIFICATION METHOD: blastn
        (D) OTHER INFORMATION:  identity 97 region 113..255 id R34406
            est (ix) FEATURE:
        (A) NAME/KEY: other
        (B) LOCATION: 111..198
        (C) IDENTIFICATION METHOD: blastn
        (D) OTHER INFORMATION:  identity 94 region 23..110 id R34406
            est (ix) FEATURE:
        (A) NAME/KEY: other
        (B) LOCATION: 353..482
        (C) IDENTIFICATION METHOD: blastn
        (D) OTHER INFORMATION:  identity 99 region 115..244 id
            HSC23C111 est (ix) FEATURE:
        (A) NAME/KEY: other
        (B) LOCATION: 240..355
        (C) IDENTIFICATION METHOD: blastn
        (D) OTHER INFORMATION:  identity 94 region 1..116 id
            HSC23C111 est (ix) FEATURE:
        (A) NAME/KEY: sig_peptide
        (B) LOCATION: 56..472
        (C) IDENTIFICATION METHOD: Von Heijne matrix
        (D) OTHER INFORMATION:  score 4.3 seq GILVPHSLRQAQA/SF (xi) SEQUENCE DESCRIPTION: SEQ ID NO: 189:

AAAAACTGCG GAGGGTGACA AGGAAGAAGG TGGCTCCAGA TCTGGAGGTG TGTCC ATG         58
                                                              Met

GCG GCG CTT GAC CTG CGA GCG GAS TGG ATT CGC TGG TCC TGC AGC TGC        106
Ala Ala Leu Asp Leu Arg Ala Xaa Trp Ile Arg Trp Ser Cys Ser Cys
         -135              -130              -125

TTG GGG GAM CTG GRA GGA GCT GGA GGG GAA ACG AAC GGT GTT GAA CGC        154
```

```
Leu Gly Xaa Leu Xaa Gly Ala Gly Gly Glu Thr Asn Gly Val Glu Arg
        -120            -115                -110

CCG GGT GGA GGA GGG CTG GCT CTC GCT CGC CAA GGC TCG CTA CGC GAT      202
Pro Gly Gly Gly Gly Leu Ala Leu Ala Arg Gln Gly Ser Leu Arg Asp
    -105            -100                -95

GGG CGC CAA GTC GGT AGG GCC CCT GCA GTA TGC TTC CCA CAT GGA GCC      250
Gly Arg Gln Val Gly Arg Ala Pro Ala Val Cys Phe Pro His Gly Ala
-90             -85              -80              -75

CCA GGT CTG CCT CCA CGC CAG CGA GDC YCA GGA GGG DST CCA GAA GTT      298
Pro Gly Leu Pro Pro Arg Gln Arg Xaa Xaa Gly Gly Xaa Pro Glu Val
            -70              -65              -60

CAA GGT GGT GAG AGC TGG TGT CCA CGC CCC AGA GGA GGT GGG GCC TCG      346
Gln Gly Gly Glu Ser Trp Cys Pro Arg Pro Arg Gly Gly Gly Ala Ser
        -55              -50              -45

CGA ACA GGT CTG CGG AGG CGC AAG GGC CCC ACT AAG ACC CCA GAA CCG      394
Arg Thr Gly Leu Arg Arg Arg Lys Gly Pro Thr Lys Thr Pro Glu Pro
        -40              -35              -30

GAG TCC TCT GAG GCC CCT CAG GAC CCC CTG AAC TGG TTT GGA ATC CTA      442
Glu Ser Ser Glu Ala Pro Gln Asp Pro Leu Asn Trp Phe Gly Ile Leu
        -25              -20              -15

GTT CCT CAC AGT CTA CGT CAG GCT CAA GCA AGC TTC CGG                  481
Val Pro His Ser Leu Arg Gln Ala Gln Ala Ser Phe Arg
-10              -5               1
```

(2) INFORMATION FOR SEQ ID NO: 190:

(i) SEQUENCE CHARACTERISTICS:
        (A) LENGTH: 302 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 176..275
        (C) IDENTIFICATION METHOD: blastn
        (D) OTHER INFORMATION: identity 100 region 2..101 id R68368 est (ix) FEATURE:
        (A) NAME/KEY: sig_peptide
        (B) LOCATION: 216..278
        (C) IDENTIFICATION METHOD: Von Heijne matrix
        (D) OTHER INFORMATION: score 4.1 seq WWISLLPSLLSIC/KV (xi) SEQUENCE DESCRIPTION: SEQ ID NO: 190:

```
AAGCTTTCCC CGTGGTCTGA GTTTGTGGCT GCATTTTTAT CTCTGGTGGC TCTGCTACGG      60

CGGCGCAGAA ATGAGGCAGA AGCGGAAAGG AGATCTCAGC CCTGCTGAGC TGATGATGCT     120

GACTATAGGA GATGTTATTA AACAACTGAT TGAAGCCCAC GAGCAGGGGA AAGACATCGA     180

TCTAAATAAG GTGAAAACCA AGACAGCTGC CAAAT ATG GCC TTT CTG CCC AGC       233
                                       Met Ala Phe Leu Pro Ser
                                                           -20

CCC GCC TGG TGG ATA TCA TTG CTG CCG TCC CTC CTC AGT ATC TGC AAG      281
Pro Ala Trp Trp Ile Ser Leu Leu Pro Ser Leu Leu Ser Ile Cys Lys
-15              -10              -5                1

GTC TTG ATG CCC AAG TTA AAG                                          302
Val Leu Met Pro Lys Leu Lys
            5
```

(2) INFORMATION FOR SEQ ID NO: 191:

(i) SEQUENCE CHARACTERISTICS:
        (A) LENGTH: 414 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 40..271
        (C) IDENTIFICATION METHOD: blastn
        (D) OTHER INFORMATION: identity 97 region 1..232 id R00384
            est (ix) FEATURE:
        (A) NAME/KEY: other
        (B) LOCATION: 294..328
        (C) IDENTIFICATION METHOD: blastn
        (D) OTHER INFORMATION: identity 94 region 257..291 id R00384
            est (ix) FEATURE:
        (A) NAME/KEY: other
        (B) LOCATION: 86..130
        (C) IDENTIFICATION METHOD: blastn
        (D) OTHER INFORMATION: identity 93 region 140..184 id
            MMTEST284 est (ix) FEATURE:
        (A) NAME/KEY: sig_peptide
        (B) LOCATION: 34..180
        (C) IDENTIFICATION METHOD: Von Heijne matrix
        (D) OTHER INFORMATION: score 3.8 seq PAFHLPLPGPTLA/FL (xi) SEQUENCE DESCRIPTION: SEQ ID NO: 191:

```
AATTCCCCAG CAAGCTCAGC GTGTAMSTGC GCT ATG GAG CCG AAA GTC GCA GAG         54
                                    Met Glu Pro Lys Val Ala Glu
                                                        -45

CTG AAG CAG AAG ATC GAG GAC ACG CTA TGT CCT TTT GGC TTC GAG GTT         102
Leu Lys Gln Lys Ile Glu Asp Thr Leu Cys Pro Phe Gly Phe Glu Val
        -40                 -35                 -30

TAC CCC TTC CAG GTG GCA TGG TAC AAT GAA CTC TTG CCT CCA GCC TTC         150
Tyr Pro Phe Gln Val Ala Trp Tyr Asn Glu Leu Leu Pro Pro Ala Phe
    -25                 -20                 -15

CAC CTA CCG CTG CCA GGA CCT ACC CTG GCC TTC CTG GTA CTC AGC ACG         198
His Leu Pro Leu Pro Gly Pro Thr Leu Ala Phe Leu Val Leu Ser Thr
-10                 -5                   1                   5

CCT GCC ATG TTT GAC CGG GCC CTC AAG CCC TTC TTG CAG AGC TGC CAC         246
Pro Ala Met Phe Asp Arg Ala Leu Lys Pro Phe Leu Gln Ser Cys His
            10                  15                  20

CTC CGA ATG CTG ACT GAC CCA GTG GAC CAG TGT GTG GCC TAC CAT CTG         294
Leu Arg Met Leu Thr Asp Pro Val Asp Gln Cys Val Ala Tyr His Leu
        25                  30                  35

GGC CGT GTT AGA GAG AGC CTC CCA GAG CTG CAG ATA GAA ATC ATT GCT         342
Gly Arg Val Arg Glu Ser Leu Pro Glu Leu Gln Ile Glu Ile Ile Ala
    40                  45                  50

GRA HMA CGA GGT GCA CCC CAA CCG ACG CCC CAA GAT CCT GGC CCA GAC         390
Xaa Xaa Arg Gly Ala Pro Gln Pro Thr Pro Gln Asp Pro Gly Pro Asp
55                  60                  65                  70

AGC AGC CAT GTA GCT GGG GCT GCT                                         414
Ser Ser His Val Ala Gly Ala Ala
            75
```

(2) INFORMATION FOR SEQ ID NO: 192:

(i) SEQUENCE CHARACTERISTICS:
        (A) LENGTH: 400 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 324..389
        (C) IDENTIFICATION METHOD: blastn
        (D) OTHER INFORMATION: identity 95 region 301..366 id T08430
            est (ix) FEATURE:
        (A) NAME/KEY: other
        (B) LOCATION: 64..400
        (C) IDENTIFICATION METHOD: blastn
        (D) OTHER INFORMATION: identity 90 region 1..337 id C17891
            est (ix) FEATURE:
        (A) NAME/KEY: other
        (B) LOCATION: 301..400
        (C) IDENTIFICATION METHOD: blastn
        (D) OTHER INFORMATION: identity 95 region 1..100 id C04989
            est (ix) FEATURE:
        (A) NAME/KEY: sig_peptide
        (B) LOCATION: 107..145
        (C) IDENTIFICATION METHOD: Von Heijne matrix
        (D) OTHER INFORMATION: score 3.7 seq MLVLRSGLTKALA/SR (xi) SEQUENCE DESCRIPTION: SEQ ID NO: 192:

```
AGAGTTCGCC AGTGGTCCAG GAGCCGCTTT TTTCCACTCG GGAAGACTTC AGAGAAGTCT      60

CACAAAGGAC TCGGCTGGCT GCTTTTCTCA GTGCCGAAGC CGCGCC ATG CTC GTT        115
                                                 Met Leu Val

CTC AGA AGC GGC CTG ACC AAG GCG CTT GCC TCA CGG ACG CTC GCG CCT      163
Leu Arg Ser Gly Leu Thr Lys Ala Leu Ala Ser Arg Thr Leu Ala Pro
-10             -5                  1               5

CAG GTG TGT TCA TCT TTT GCT ACG GGC CCT AGA CAA TAC GAT GGA ACG      211
Gln Val Cys Ser Ser Phe Ala Thr Gly Pro Arg Gln Tyr Asp Gly Thr
            10                  15                  20

TTC TAT GAA TTT CGT ACT TAT TAC CTT AAA CCT TCA AAT ATG AAT GCG      259
Phe Tyr Glu Phe Arg Thr Tyr Tyr Leu Lys Pro Ser Asn Met Asn Ala
        25                  30                  35

TTC ATG GAA AAT CTT AAG AAA AAC ATT CAT CTT CGG ACC TCT TAC TCT      307
Phe Met Glu Asn Leu Lys Lys Asn Ile His Leu Arg Thr Ser Tyr Ser
    40                  45                  50

GAA TTG GTT GGA TTC TGG AGT GTA GAA TTT GGA GGC AGA ACG AAT AAA      355
Glu Leu Val Gly Phe Trp Ser Val Glu Phe Gly Gly Arg Thr Asn Lys
55                  60                  65                  70

GTG TTT CAT ATT TGG AAG TAT GAT AAT TTT GCT CAT CGA GCT GAA          400
Val Phe His Ile Trp Lys Tyr Asp Asn Phe Ala His Arg Ala Glu
                75                  80                  85
```

(2) INFORMATION FOR SEQ ID NO: 193:

(i) SEQUENCE CHARACTERISTICS:
        (A) LENGTH: 186 base pairs

```
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 112..184
        (C) IDENTIFICATION METHOD: blastn
        (D) OTHER INFORMATION:  identity 98 region 1..73 id
            HSC09D101 est (ix) FEATURE:
        (A) NAME/KEY: other
        (B) LOCATION: 112..184
        (C) IDENTIFICATION METHOD: blastn
        (D) OTHER INFORMATION:  identity 98 region 1..73 id
            HSC2UE011 est (ix) FEATURE:
        (A) NAME/KEY: other
        (B) LOCATION: 112..186
        (C) IDENTIFICATION METHOD: blastn
        (D) OTHER INFORMATION:  identity 90 region 1..75 id
            HSC09C101 est (ix) FEATURE:
        (A) NAME/KEY: other
        (B) LOCATION: 140..184
        (C) IDENTIFICATION METHOD: blastn
        (D) OTHER INFORMATION:  identity 95 region 17..61 id T35421
            est (ix) FEATURE:
        (A) NAME/KEY: sig_peptide
        (B) LOCATION: 106..174
        (C) IDENTIFICATION METHOD: Von Heijne matrix
        (D) OTHER INFORMATION:  score 10.5 seq LLFVLLLFSLLPA/CL (xi) SEQUENCE DESCRIPTION: SEQ ID NO: 193:

ATATTTAAAC GACCCTTCAA AGGCCCTTAG GTTTCCTTGC CTCTGCTCAC AGAACTAGTC      60

CAGCCAGGTG TCGCTGCTGC CTCAGAGCTG TGTGGGGTCG CRTGT ATG TCG GGG GGC    117
                                                Met Ser Gly Gly
                                                             -20

CAT CTT GCC GAT TTA ACG CTG CTT TTT GTG TTG TTG TTG TTT TCC CTC      165
His Leu Ala Asp Leu Thr Leu Leu Phe Val Leu Leu Leu Phe Ser Leu
            -15                 -10                  -5

CTC CCT GCC TGC CTA CCC CGG                                           186
Leu Pro Ala Cys Leu Pro Arg
              1

(2) INFORMATION FOR SEQ ID NO: 194:

(i) SEQUENCE CHARACTERISTICS:
        (A) LENGTH: 335 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(86..336)
        (C) IDENTIFICATION METHOD: blastn
```

(D) OTHER INFORMATION: identity 99 region 79..329 id
                    AA148596 est (ix) FEATURE:
                (A) NAME/KEY: other
                (B) LOCATION: complement(30..91)
                (C) IDENTIFICATION METHOD: blastn
                (D) OTHER INFORMATION: identity 100 region 325..386 id
                    AA148596 est (ix) FEATURE:
                (A) NAME/KEY: other
                (B) LOCATION: complement(2..39)
                (C) IDENTIFICATION METHOD: blastn
                (D) OTHER INFORMATION: identity 92 region 378..415 id
                    AA148596 est (ix) FEATURE:
                (A) NAME/KEY: other
                (B) LOCATION: complement(2..336)
                (C) IDENTIFICATION METHOD: blastn
                (D) OTHER INFORMATION: identity 99 region 67..401 id
                    AA074631 est (ix) FEATURE:
                (A) NAME/KEY: other
                (B) LOCATION: complement(83..336)
                (C) IDENTIFICATION METHOD: blastn
                (D) OTHER INFORMATION: identity 99 region 64..317 id
                    AA078818 est (ix) FEATURE:
                (A) NAME/KEY: other
                (B) LOCATION: complement(8..48)
                (C) IDENTIFICATION METHOD: blastn
                (D) OTHER INFORMATION: identity 97 region 355..395 id
                    AA078818 est (ix) FEATURE:
                (A) NAME/KEY: other
                (B) LOCATION: complement(30..336)
                (C) IDENTIFICATION METHOD: blastn
                (D) OTHER INFORMATION: identity 99 region 64..370 id N21054
                    est (ix) FEATURE:
                (A) NAME/KEY: other
                (B) LOCATION: complement(68..236)
                (C) IDENTIFICATION METHOD: blastn
                (D) OTHER INFORMATION: identity 98 region 172..340 id
                    AA157994 est (ix) FEATURE:
                (A) NAME/KEY: other
                (B) LOCATION: complement(225..336)
                (C) IDENTIFICATION METHOD: blastn
                (D) OTHER INFORMATION: identity 94 region 73..184 id
                    AA157994 est (ix) FEATURE:
                (A) NAME/KEY: other
                (B) LOCATION: complement(28..68)
                (C) IDENTIFICATION METHOD: blastn
                (D) OTHER INFORMATION: identity 100 region 341..381 id
                    AA157994 est (ix) FEATURE:
                (A) NAME/KEY: sig_peptide
                (B) LOCATION: 174..326
                (C) IDENTIFICATION METHOD: Von Heijne matrix
                (D) OTHER INFORMATION: score 10.1 seq LLGALTLLGLVTS/FY (xi) SEQUENCE DESCRIPTION: SEQ ID NO: 194:

AATTCTCAAC GAGCTGCGGG CTCGGCATGC CCAGGGGGGT ACATGGTATG GAGTAGACAT        60

CAACAACGAG GACATTGCTG ACAACTTTGA AGCTTTCGTG TGGGAGCCAG CTATGGTGCG       120

GATCAATGCG CTGACAGCAG CCTCTGAGGC TGCGTGCCTG ATCGTGTCTG TAG ATG         176

```
                                                                 Met
AAA CCA TCA AGA ACC CCC GCT CGA CTG TGG ATG CTC CCA CAG CAG CAG    224
Lys Pro Ser Arg Thr Pro Ala Arg Leu Trp Met Leu Pro Gln Gln Gln
-50                 -45                 -40                 -35

GCC GGG GCC GTG GTC GTG GCC GCC CCC ACT GAG AGG CAC CCC ACC CAT    272
Ala Gly Ala Val Val Val Ala Ala Pro Thr Glu Arg His Pro Thr His
                -30                 -25                 -20

CAC ATG GCT GGC TGG CTG CTG GGT GCA CTT ACC CTC CTT GGC TTG GTT    320
His Met Ala Gly Trp Leu Leu Gly Ala Leu Thr Leu Leu Gly Leu Val
            -15                 -10                 -5

ACT TCA TTT TAC AAG                                                335
Thr Ser Phe Tyr Lys
         1

(2) INFORMATION FOR SEQ ID NO: 195:

(i) SEQUENCE CHARACTERISTICS:
        (A) LENGTH: 419 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 23..200
        (C) IDENTIFICATION METHOD: blastn
        (D) OTHER INFORMATION:   identity 100 region 9..186 id W44639
            est (ix) FEATURE:
        (A) NAME/KEY: other
        (B) LOCATION: 216..356
        (C) IDENTIFICATION METHOD: blastn
        (D) OTHER INFORMATION:   identity 99 region 200..340 id W44639
            est (ix) FEATURE:
        (A) NAME/KEY: other
        (B) LOCATION: 363..412
        (C) IDENTIFICATION METHOD: blastn
        (D) OTHER INFORMATION:   identity 100 region 347..396 id W44639
            est (ix) FEATURE:
        (A) NAME/KEY: sig_peptide
        (B) LOCATION: 27..218
        (C) IDENTIFICATION METHOD: Von Heijne matrix
        (D) OTHER INFORMATION:   score 9.5 seq LSLLAALAHLAAA/EK (xi) SEQUENCE DESCRIPTION: SEQ ID NO: 195:

AGTGGGTCGA KCTGGGGCGC AGTCGC ATG GGG GAG TCT ATC CCG CTG GCC GCC    53
                             Met Gly Glu Ser Ile Pro Leu Ala Ala
                                                -60

CCG GTC CCG GTG GAA CAG GCG GTG CTG GAG ACG TTC TTC TCT CAC CTG    101
Pro Val Pro Val Glu Gln Ala Val Leu Glu Thr Phe Phe Ser His Leu
-55                 -50                 -45                 -40

GGT ATC TTC TCT TAC GAC AAG GCT AAG GAC AAT GTG GAG AAG GAA CGA    149
Gly Ile Phe Ser Tyr Asp Lys Ala Lys Asp Asn Val Glu Lys Glu Arg
            -35                 -30                 -25

GAG GCC AAC AAG AGC GCG GGG GGC AGC TGG CTG TCG CTG CTG GCG GCC    197
Glu Ala Asn Lys Ser Ala Gly Gly Ser Trp Leu Ser Leu Leu Ala Ala
        -20                 -15                 -10

TTG GCG CAC CTG GCC GCG GCC GAG AAG GTC TAT CAC AGC CTC ACC TAC    245
```

```
Leu Ala His Leu Ala Ala Ala Glu Lys Val Tyr His Ser Leu Thr Tyr
         -5                   1                   5

CTG GGG CAG AAA CTA GGG GGC CAG TCT TTC TTC AGC AGG AAG GAT TCC      293
Leu Gly Gln Lys Leu Gly Gly Gln Ser Phe Phe Ser Arg Lys Asp Ser
 10              15                  20                  25

ATC CGC ACC ATC TAT ACT TCA TTG CAT AAT GAG CTG AAG AAG GTG GTG      341
Ile Arg Thr Ile Tyr Thr Ser Leu His Asn Glu Leu Lys Lys Val Val
                 30                  35                  40

ACT GGC CGT GGT GCC DDK TNN TGG GAC TGC TCC TCA CGT GGA AGA ACT      389
Thr Gly Arg Gly Ala Xaa Xaa Trp Asp Cys Ser Ser Arg Gly Arg Thr
             45                  50                  55

CCT TTC CCA CCT GTC AGA GCA GCA TAC GGG                              419
Pro Phe Pro Pro Val Arg Ala Ala Tyr Gly
 60              65
```

(2) INFORMATION FOR SEQ ID NO: 196:

(i) SEQUENCE CHARACTERISTICS:
        (A) LENGTH: 342 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 33..269
        (C) IDENTIFICATION METHOD: blastn
        (D) OTHER INFORMATION: identity 99 region 10..246 id
           AA058587 est (ix) FEATURE:
        (A) NAME/KEY: other
        (B) LOCATION: 272..307
        (C) IDENTIFICATION METHOD: blastn
        (D) OTHER INFORMATION: identity 100 region 248..283 id
           AA058587 est (ix) FEATURE:
        (A) NAME/KEY: other
        (B) LOCATION: 133..259
        (C) IDENTIFICATION METHOD: blastn
        (D) OTHER INFORMATION: identity 100 region 87..213 id R12128
           est (ix) FEATURE:
        (A) NAME/KEY: other
        (B) LOCATION: 47..134
        (C) IDENTIFICATION METHOD: blastn
        (D) OTHER INFORMATION: identity 98 region 2..89 id R12128 est (ix) FEATURE:
        (A) NAME/KEY: other
        (B) LOCATION: 303..337
        (C) IDENTIFICATION METHOD: blastn
        (D) OTHER INFORMATION: identity 97 region 257..291 id R12128
           est (ix) FEATURE:
        (A) NAME/KEY: other
        (B) LOCATION: 49..259
        (C) IDENTIFICATION METHOD: blastn
        (D) OTHER INFORMATION: identity 98 region 2..212 id H19999
           est (ix) FEATURE:
        (A) NAME/KEY: other
        (B) LOCATION: 272..304
        (C) IDENTIFICATION METHOD: blastn

```
            (D) OTHER INFORMATION:   identity 96 region 225..257 id H19999
                est (ix) FEATURE:
            (A) NAME/KEY: other
            (B) LOCATION: 303..337
            (C) IDENTIFICATION METHOD: blastn
            (D) OTHER INFORMATION:   identity 91 region 257..291 id H19999
                est (ix) FEATURE:
            (A) NAME/KEY: other
            (B) LOCATION: 42..252
            (C) IDENTIFICATION METHOD: blastn
            (D) OTHER INFORMATION:   identity 99 region 1..211 id R20025
                est (ix) FEATURE:
            (A) NAME/KEY: other
            (B) LOCATION: 87..259
            (C) IDENTIFICATION METHOD: blastn
            (D) OTHER INFORMATION:   identity 99 region 1..173 id H83838
                est (ix) FEATURE:
            (A) NAME/KEY: other
            (B) LOCATION: 272..337
            (C) IDENTIFICATION METHOD: blastn
            (D) OTHER INFORMATION:   identity 98 region 186..251 id H83838
                est (ix) FEATURE:
            (A) NAME/KEY: sig_peptide
            (B) LOCATION: 85..198
            (C) IDENTIFICATION METHOD: Von Heijne matrix
            (D) OTHER INFORMATION:   score 9.3 seq QLLYLSLLSGLHG/QE (xi) SEQUENCE DESCRIPTION: SEQ ID NO: 196:

AGGCTGCGGT AAATCCGGGC TTGCGGCCGC TGGCGTAGTC TGTGGCCGGG TGGTCGTTGC        60

TGCGCGCCCC GAGCCCCGAG AGCC ATG CAG ATG TCC TAC GCC ATC CGG TGC          111
                          Met Gln Met Ser Tyr Ala Ile Arg Cys
                                        -35                 -30

GCC TTC TAC CAG CTG CTG CTG GCC GCG CTC ATG CTG GTG GCG ATG CTG         159
Ala Phe Tyr Gln Leu Leu Leu Ala Ala Leu Met Leu Val Ala Met Leu
                -25                 -20                 -15

CAG CTG CTC TAC CTG TCG CTG CTG TCC GGA CTG CAC GGG CAG GAG GAG         207
Gln Leu Leu Tyr Leu Ser Leu Leu Ser Gly Leu His Gly Gln Glu Glu
            -10                 -5                   1

CAA GAC CAA TAT TTT GAG TTC TTT CCC CCG TCC CCA CGG TCC GTG GAC         255
Gln Asp Gln Tyr Phe Glu Phe Phe Pro Pro Ser Pro Arg Ser Val Asp
         5                  10                  15

CAG GTC AAG GCT CAG CTC CGC ACC GCG CTG GCC TCT GGA GGC GTC CTG         303
Gln Val Lys Ala Gln Leu Arg Thr Ala Leu Ala Ser Gly Gly Val Leu
 20              25                  30                  35

GAC GCT AGC GGC GAT TAC CGC GTC TAC AGG GGC CAT GGG                     342
Asp Ala Ser Gly Asp Tyr Arg Val Tyr Arg Gly His Gly
                40                  45

(2) INFORMATION FOR SEQ ID NO: 197:

(i) SEQUENCE CHARACTERISTICS:
            (A) LENGTH: 461 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain
```

```
(ix) FEATURE:
     (A) NAME/KEY: other
     (B) LOCATION: complement(149..337)
     (C) IDENTIFICATION METHOD: blastn
     (D) OTHER INFORMATION:   identity 97 region 182..370 id
         AA142966 est (ix) FEATURE:
     (A) NAME/KEY: other
     (B) LOCATION: complement(340..459)
     (C) IDENTIFICATION METHOD: blastn
     (D) OTHER INFORMATION:   identity 97 region 61..180 id
         AA142966 est (ix) FEATURE:
     (A) NAME/KEY: other
     (B) LOCATION: complement(142..337)
     (C) IDENTIFICATION METHOD: blastn
     (D) OTHER INFORMATION:   identity 98 region 183..378 id
         AA019334 est (ix) FEATURE:
     (A) NAME/KEY: other
     (B) LOCATION: complement(340..459)
     (C) IDENTIFICATION METHOD: blastn
     (D) OTHER INFORMATION:   identity 97 region 62..181 id
         AA019334 est (ix) FEATURE:
     (A) NAME/KEY: other
     (B) LOCATION: complement(345..459)
     (C) IDENTIFICATION METHOD: blastn
     (D) OTHER INFORMATION:   identity 95 region 48..162 id N66447
         est (ix) FEATURE:
     (A) NAME/KEY: other
     (B) LOCATION: complement(255..337)
     (C) IDENTIFICATION METHOD: blastn
     (D) OTHER INFORMATION:   identity 97 region 170..252 id N66447
         est (ix) FEATURE:
     (A) NAME/KEY: other
     (B) LOCATION: complement(111..181)
     (C) IDENTIFICATION METHOD: blastn
     (D) OTHER INFORMATION:   identity 95 region 330..400 id N66447
         est (ix) FEATURE:
     (A) NAME/KEY: other
     (B) LOCATION: complement(179..228)
     (C) IDENTIFICATION METHOD: blastn
     (D) OTHER INFORMATION:   identity 98 region 282..331 id N66447
         est (ix) FEATURE:
     (A) NAME/KEY: other
     (B) LOCATION: complement(172..337)
     (C) IDENTIFICATION METHOD: blastn
     (D) OTHER INFORMATION:   identity 97 region 113..278 id R85770
         est (ix) FEATURE:
     (A) NAME/KEY: other
     (B) LOCATION: complement(340..450)
     (C) IDENTIFICATION METHOD: blastn
     (D) OTHER INFORMATION:   identity 98 region 1..111 id R85770
         est (ix) FEATURE:
     (A) NAME/KEY: other
     (B) LOCATION: 188..337
     (C) IDENTIFICATION METHOD: blastn
     (D) OTHER INFORMATION:   identity 99 region 1..150 id R78830
         est (ix) FEATURE:
```

(A) NAME/KEY: other
                (B) LOCATION: 339..459
                (C) IDENTIFICATION METHOD: blastn
                (D) OTHER INFORMATION:  identity 96 region 151..271 id R78830
                     est (ix) FEATURE:
                (A) NAME/KEY: sig_peptide
                (B) LOCATION: 384..455
                (C) IDENTIFICATION METHOD: Von Heijne matrix
                (D) OTHER INFORMATION:  score 9.1 seq LFAFHLLLSFILG/SR (xi) SEQUENCE DESCRIPTION: SEQ ID NO: 197:

```
AACACTGTTG TATAAACTAA TCTTTGCTTG TTTTCTACTC TGTGATCTTT CCATATCATA      60

TTTCATTAAT GATCAGTTAG TGTCAAGGAG TCAAAACAGA TTAAAATTAA TTTCATGTGT     120

ATATGGTGGA AATTTGTGGC TAGTGTGATT TTTGTTTGTY TCCTTTTAAG TACTGTTGAT     180

CAGTTGTGAC ACTTACTGGT TAAACTTACG TTGCTAAAGA TTTCTCTATA ATAAGCCACA     240

CATTATATTT AGACTATATT AAGGGACCTT GGTTTTCTTC TAGATAGCAG CTGTCCCAAA     300

GAAAATATTT CTTCTTTGTC TGTKAAGATT TAGCTATNKA TCTGCCAGTT GTTCAGMGGT     360

TTTGGTTCCA AACTCAACCA GCA ATG TTG AGA GCT GAA CTT AAG ATA GCT GTT     413
                         Met Leu Arg Ala Glu Leu Lys Ile Ala Val
                                  -20                      -15

GTA CTT TTT GCT TTC CAT CTG TTA CTG TCC TTC ATT CTC GGC TCC CGG       461
Val Leu Phe Ala Phe His Leu Leu Leu Ser Phe Ile Leu Gly Ser Arg
              -10                  -5                       1
```

(2) INFORMATION FOR SEQ ID NO: 198:

(i) SEQUENCE CHARACTERISTICS:
                (A) LENGTH: 229 base pairs
                (B) TYPE: NUCLEIC ACID
                (C) STRANDEDNESS: DOUBLE
                (D) TOPOLOGY: LINEAR (ii) MOLECULE TYPE: cDNA (vi) ORIGINAL SOURCE:
                (A) ORGANISM: Homo Sapiens
                (F) TISSUE TYPE: Brain (ix) FEATURE:
                (A) NAME/KEY: other
                (B) LOCATION: complement(1..130)
                (C) IDENTIFICATION METHOD: blastn
                (D) OTHER INFORMATION:  identity 98 region 8..137 id H63707
                     est (ix) FEATURE:
                (A) NAME/KEY: sig_peptide
                (B) LOCATION: 2..166
                (C) IDENTIFICATION METHOD: Von Heijne matrix
                (D) OTHER INFORMATION:  score 9 seq LLILLLRTFLCSA/MI (xi) SEQUENCE DESCRIPTION: SEQ ID NO: 198:

```
A ATG AAT CAT CAA CAG ACA TTA ATT GGG CGC CTG CTC TGT GAT CTC CAT      49
  Met Asn His Gln Gln Thr Leu Ile Gly Arg Leu Leu Cys Asp Leu His
  -55                 -50                 -45                 -40

GGG CTC AGC TTG TCC CCG CCA GTW GCC AAC AAC GTC CAA GCT CTC TTC        97
Gly Leu Ser Leu Ser Pro Pro Val Ala Asn Asn Val Gln Ala Leu Phe
              -35                 -30                  -25

AGA ATG CTT ACT CCT GAA GCT TAT TCC TGT CTT CTA ATT CTT TTG TTG       145
Arg Met Leu Thr Pro Glu Ala Tyr Ser Cys Leu Leu Ile Leu Leu Leu
          -20                 -15                 -10

AGG ACT TTT CTG TGT AGT GCA ATG ATA GCA AAT ACA CTT CAT CTC AAG       193
Arg Thr Phe Leu Cys Ser Ala Met Ile Ala Asn Thr Leu His Leu Lys
      -5                   1                   5
```

```
TAC CAT CTC CAA TTG ATT GAT AAT GCC TGC CCT GAG                229
Tyr His Leu Gln Leu Ile Asp Asn Ala Cys Pro Glu
 10              15                  20
```

(2) INFORMATION FOR SEQ ID NO: 199:

(i) SEQUENCE CHARACTERISTICS:
        (A) LENGTH: 278 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 145..279
        (C) IDENTIFICATION METHOD: blastn
        (D) OTHER INFORMATION: identity 100 region 1..135 id H06014
            est (ix) FEATURE:
        (A) NAME/KEY: other
        (B) LOCATION: 180..279
        (C) IDENTIFICATION METHOD: blastn
        (D) OTHER INFORMATION: identity 100 region 11..110 id R15960
            est (ix) FEATURE:
        (A) NAME/KEY: other
        (B) LOCATION: 204..279
        (C) IDENTIFICATION METHOD: blastn
        (D) OTHER INFORMATION: identity 96 region 1..76 id W67034 est (ix) FEATURE:
        (A) NAME/KEY: sig_peptide
        (B) LOCATION: 27..146
        (C) IDENTIFICATION METHOD: Von Heijne matrix
        (D) OTHER INFORMATION: score 8.6 seq LFCVLGIVLLVTG/IV (xi) SEQUENCE DESCRIPTION: SEQ ID NO: 199:

```
ACCAAACCAA AGCCGTCATC ATTGCA ATG ATC ATC ACT GCG GTG GTA TCC ATT      53
                             Met Ile Ile Thr Ala Val Val Ser Ile
                             -40                 -35

TCA GTC ACC ATC TTC TGC TTT CAG ACC AAG GTG GAC TTC ACC TCG TGC      101
Ser Val Thr Ile Phe Cys Phe Gln Thr Lys Val Asp Phe Thr Ser Cys
    -30             -25                 -20

ACA GGC CTC TTC TGT GTC CTG GGA ATT GTG CTC CTG GTG ACT GGG ATT      149
Thr Gly Leu Phe Cys Val Leu Gly Ile Val Leu Leu Val Thr Gly Ile
-15             -10              -5                          1

GTC ACT AGC ATT GTG CTC TAC TTC CAA TAC GTT TAC TGG CTC CAC ATG      197
Val Thr Ser Ile Val Leu Tyr Phe Gln Tyr Val Tyr Trp Leu His Met
            5                10                  15

CTC TAT GCT GCT CTG GGG GCC ATT TGT TTC ACC CTG TTC CTG GCT TAC      245
Leu Tyr Ala Ala Leu Gly Ala Ile Cys Phe Thr Leu Phe Leu Ala Tyr
        20                  25                  30

GAC ACA CAG CTG GTC CTG GGG AAC CGG AAG CAC                          278
Asp Thr Gln Leu Val Leu Gly Asn Arg Lys His
        35                  40
```

(2) INFORMATION FOR SEQ ID NO: 200:

(i) SEQUENCE CHARACTERISTICS:
        (A) LENGTH: 333 base pairs
        (B) TYPE: NUCLEIC ACID
        (C) STRANDEDNESS: DOUBLE

```
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 55..268
        (C) IDENTIFICATION METHOD: blastn
        (D) OTHER INFORMATION:  identity 95 region 32..245 id T60555
            est (ix) FEATURE:
        (A) NAME/KEY: other
        (B) LOCATION: 22..51
        (C) IDENTIFICATION METHOD: blastn
        (D) OTHER INFORMATION:  identity 90 region 1..30 id T60555 est (ix) FEATURE:
        (A) NAME/KEY: sig_peptide
        (B) LOCATION: 67..261
        (C) IDENTIFICATION METHOD: Von Heijne matrix
        (D) OTHER INFORMATION:  score 8.4 seq LLWFIHLVFVVLX/LF (xi) SEQUENCE DESCRIPTION: SEQ ID NO: 200:

AAGAGGCTTA CGAGSWCCAG GTGGAGAGGC CGGGCTGGCC AAGGCTTCGG CCTCCGGCGT         60

CGGGAA ATG GCG GCG GGG GGC AGG ATG GAG GAC GGT TCC TTG GAT ATC          108
       Met Ala Ala Gly Gly Arg Met Glu Asp Gly Ser Leu Asp Ile
       -65             -60                 -55

ACC CAG AGT ATT GAA GAC GAC CCA CTT CTG GAT GCC CAG CTT CTC CCA         156
Thr Gln Ser Ile Glu Asp Asp Pro Leu Leu Asp Ala Gln Leu Leu Pro
    -50                 -45                 -40

CAC CAC TCA TTA CAA GCT CAC TTT AGA CCC CGA TTC CAT CCT CTT CCT         204
His His Ser Leu Gln Ala His Phe Arg Pro Arg Phe His Pro Leu Pro
-35                 -30                 -25                 -20

ACA GTC ATC ATA GTG AAT CTT CTG TGG TTT ATT CAT CTC GTG TTT GTT         252
Thr Val Ile Ile Val Asn Leu Leu Trp Phe Ile His Leu Val Phe Val
            -15                 -10                 -5

GTW TTA GSA TTG TTT AAC AGG TGT GCT TTG TTC TWA TCC TAT CCC AAA         300
Val Leu Xaa Leu Phe Asn Arg Cys Ala Leu Phe Xaa Ser Tyr Pro Lys
                1                   5                  10

TGG GAC ARG TGC CCA GGA AAT TAC ACA AAC CCA                             333
Trp Asp Xaa Cys Pro Gly Asn Tyr Thr Asn Pro
        15                  20

(2) INFORMATION FOR SEQ ID NO: 201:

(i) SEQUENCE CHARACTERISTICS:
        (A) LENGTH: 337 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 125..306
        (C) IDENTIFICATION METHOD: blastn
        (D) OTHER INFORMATION:  identity 95 region 95..276 id H31193
            est (ix) FEATURE:
        (A) NAME/KEY: other
```

(B) LOCATION: 69..130
        (C) IDENTIFICATION METHOD: blastn
        (D) OTHER INFORMATION:   identity 93 region 40..101 id H31193
            est (ix) FEATURE:
        (A) NAME/KEY: other
        (B) LOCATION: 29..68
        (C) IDENTIFICATION METHOD: blastn
        (D) OTHER INFORMATION:   identity 97 region 1..40 id H31193
            est (ix) FEATURE:
        (A) NAME/KEY: sig_peptide
        (B) LOCATION: 161..208
        (C) IDENTIFICATION METHOD: Von Heijne matrix
        (D) OTHER INFORMATION:   score 7.5 seq GCMLLFVFGFVGG/AV (xi) SEQUENCE DESCRIPTION: SEQ ID NO: 201:

AATCGCTTGG GAGCTGCTGC AGGATGGAGT GGAAAGCTGC TGCTGATGGC ATTGTTTTTG      60

TGGCAGCAAG CTGAATGACA GATCCTCACT ACAAAGATAC CCCTTTGGCC CCCGTGTAGG    120

CCTCCTTGGT TCGGGTGTTT CACCATGCCA GCACAGCGCC ATG AGT CCT GGA TGC    175
                                             Met Ser Pro Gly Cys
                                                     -15

ATG CTG CTG TTT GTG TTT GGC TTT GTT GGC GGG GCG GTG GTC ATT AAT      223
Met Leu Leu Phe Val Phe Gly Phe Val Gly Gly Ala Val Val Ile Asn
    -10                  -5                   1                 5

TCT GCT ATC TTA GTA TCT CTC TCT GTT TTG CTG CTT GTG CAC TTT TCT      271
Ser Ala Ile Leu Val Ser Leu Ser Val Leu Leu Leu Val His Phe Ser
             10                  15                  20

ATT TCT ACC GGT GTG CCA GCT CTG ACG CAG AAC CTA CCA AGG ATA CTC      319
Ile Ser Thr Gly Val Pro Ala Leu Thr Gln Asn Leu Pro Arg Ile Leu
         25                  30                  35

AGA AAA GAA CGC CCC GGG                                              337
Arg Lys Glu Arg Pro Gly
        40

(2) INFORMATION FOR SEQ ID NO: 202:

(i) SEQUENCE CHARACTERISTICS:
        (A) LENGTH: 309 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 105..252
        (C) IDENTIFICATION METHOD: blastn
        (D) OTHER INFORMATION:   identity 94 region 136..283 id
            HSU46355 est (ix) FEATURE:
        (A) NAME/KEY: other
        (B) LOCATION: 53..83
        (C) IDENTIFICATION METHOD: blastn
        (D) OTHER INFORMATION:   identity 90 region 82..112 id HSU46355
            est (ix) FEATURE:
        (A) NAME/KEY: other
        (B) LOCATION: 227..276
        (C) IDENTIFICATION METHOD: blastn
        (D) OTHER INFORMATION:   identity 94 region 206..255 id
            AA011705 est

```
    (ix) FEATURE:
          (A) NAME/KEY: sig_peptide
          (B) LOCATION: 109..153
          (C) IDENTIFICATION METHOD: Von Heijne matrix
          (D) OTHER INFORMATION:  score 7.5 seq LLLGIALLAYVAS/VW (xi) SEQUENCE DESCRIPTION: SEQ ID NO: 202:

AATBGTGCAG CAGGCGGGCC CCCGCGCGGC AGGGSCCTGG ACCCGCGCGG CTCCCTGGGA        60

TGGTGAGCAA GGCGCTGCTG CSCTCGTGTC TGCCGTCAAC CGCAGASG ATG AAG CTG       117
                                                    Met Lys Leu
                                                        -15

CTG CTG GGC ATC GCC TTG CTG GCC TAC GTC GCC TCT GTT TGG GGC AAC       165
Leu Leu Gly Ile Ala Leu Leu Ala Tyr Val Ala Ser Val Trp Gly Asn
        -10                 -5                   1

TTC GTT AAT ATG AGG TCT ATC CAG GAA AAT GGT GAA CTA AAA ATT GAA       213
Phe Val Asn Met Arg Ser Ile Gln Glu Asn Gly Glu Leu Lys Ile Glu
  5                  10                  15                  20

AGC AAG ATT GAA GAG ATG GTT GAA CCA CTA AGA GAG AAA ATC AGA GAT       261
Ser Lys Ile Glu Glu Met Val Glu Pro Leu Arg Glu Lys Ile Arg Asp
              25                  30                  35

TTA GRA AAA AGC TTT ACC CAG AAA TAC CCA CCA GTA AAG TTT TTA TCA       309
Leu Xaa Lys Ser Phe Thr Gln Lys Tyr Pro Pro Val Lys Phe Leu Ser
                40                  45                  50

(2) INFORMATION FOR SEQ ID NO: 203:

(i) SEQUENCE CHARACTERISTICS:
          (A) LENGTH: 491 base pairs
          (B) TYPE: NUCLEIC ACID
          (C) STRANDEDNESS: DOUBLE
          (D) TOPOLOGY: LINEAR (ii) MOLECULE TYPE: CDNA (vi) ORIGINAL SOURCE:
          (A) ORGANISM: Homo Sapiens
          (F) TISSUE TYPE: Brain (ix) FEATURE:
          (A) NAME/KEY: other
          (B) LOCATION: 132..251
          (C) IDENTIFICATION METHOD: blastn
          (D) OTHER INFORMATION:  identity 99 region 170..289 id T60981
              est (ix) FEATURE:
          (A) NAME/KEY: other
          (B) LOCATION: 19..126
          (C) IDENTIFICATION METHOD: blastn
          (D) OTHER INFORMATION:  identity 99 region 57..164 id T60981
              est (ix) FEATURE:
          (A) NAME/KEY: sig_peptide
          (B) LOCATION: 39..107
          (C) IDENTIFICATION METHOD: Von Heijne matrix
          (D) OTHER INFORMATION:  score 7.5 seq LVLLLTLPLHLMA/LL (xi) SEQUENCE DESCRIPTION: SEQ ID NO: 203:

AAGTGCCCCA GCGGAAGACA GCTCAGAGCT GGTCTGCC ATG GAC ATC CTG GTC CCA       56
                                         Met Asp Ile Leu Val Pro
                                                         -20

CTC CTG CAG CTG CTG GTG CTG CTT CTT ACC CTG CCC CTG CAC CTC ATG       104
Leu Leu Gln Leu Leu Val Leu Leu Leu Thr Leu Pro Leu His Leu Met
    -15                 -10                  -5

GCT CTG CTG GGC TGC TGG CAG CCC CTG TGC AAA AGC TAC TTC CCC TAC       152
Ala Leu Leu Gly Cys Trp Gln Pro Leu Cys Lys Ser Tyr Phe Pro Tyr
  1                  5                  10                  15
```

```
CTG ATG GCC GTG CTG ACT CCC AAG AGC AAC CGC AAG ATG GAG AGC AAG        200
Leu Met Ala Val Leu Thr Pro Lys Ser Asn Arg Lys Met Glu Ser Lys
            20                  25                  30

AAA CGG GAG CTC TTC AGC CAG ATA AAG GGG CTT ACA GGA GCC TCC GGG        248
Lys Arg Glu Leu Phe Ser Gln Ile Lys Gly Leu Thr Gly Ala Ser Gly
                35                  40                  45

AAA GTG GCC CTA CTG GAG CTG GGC TGC GGA ACC GGA GCC AAC TTT CAG        296
Lys Val Ala Leu Leu Glu Leu Gly Cys Gly Thr Gly Ala Asn Phe Gln
            50                  55                  60

TTC TAC CCA CCG GGC TGC AGG GTC ACC TGC CTA GAC CCA AAT CCC CAC        344
Phe Tyr Pro Pro Gly Cys Arg Val Thr Cys Leu Asp Pro Asn Pro His
            65                  70                  75

TTT GAG AAG TTC CTG ACA AAG AGC ATG GCT GAG AAC AGG CAC CTC CAA        392
Phe Glu Lys Phe Leu Thr Lys Ser Met Ala Glu Asn Arg His Leu Gln
 80                  85                  90                  95

TAT GAG CGG TTT GTG GTG GCT CCT GGA GAG GAC ATG AGA MAG CTG GCT        440
Tyr Glu Arg Phe Val Val Ala Pro Gly Glu Asp Met Arg Xaa Leu Ala
                100                 105                 110

GAT GGC TCC ATG GAT GTK GTG GTC TGC ACT CTG GTG CTG TGC TCT GTG        488
Asp Gly Ser Met Asp Val Val Val Cys Thr Leu Val Leu Cys Ser Val
            115                 120                 125

CAG                                                                    491
Gln
```

(2) INFORMATION FOR SEQ ID NO: 204:

(i) SEQUENCE CHARACTERISTICS:
        (A) LENGTH: 331 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 25..303
        (C) IDENTIFICATION METHOD: blastn
        (D) OTHER INFORMATION: identity 98 region 1..279 id HSC0ZA041
            est (ix) FEATURE:
        (A) NAME/KEY: other
        (B) LOCATION: 131..286
        (C) IDENTIFICATION METHOD: blastn
        (D) OTHER INFORMATION: identity 97 region 106..261 id R12615
            est (ix) FEATURE:
        (A) NAME/KEY: other
        (B) LOCATION: 71..133
        (C) IDENTIFICATION METHOD: blastn
        (D) OTHER INFORMATION: identity 100 region 47..109 id R12615
            est (ix) FEATURE:
        (A) NAME/KEY: other
        (B) LOCATION: 88..303
        (C) IDENTIFICATION METHOD: blastn
        (D) OTHER INFORMATION: identity 99 region 1..216 id
            HUM401H04B est (ix) FEATURE:
        (A) NAME/KEY: other
        (B) LOCATION: 137..303
        (C) IDENTIFICATION METHOD: blastn (D) OTHER INFORMATION: identity 95 region 92..258 id T78771
                  est (ix) FEATURE:
              (A) NAME/KEY: sig_peptide
              (B) LOCATION: 23..127
              (C) IDENTIFICATION METHOD: Von Heijne matrix
              (D) OTHER INFORMATION: score 7.4 seq SLLLSLELASGSG/QG (xi) SEQUENCE DESCRIPTION: SEQ ID NO: 204:

```
AAAGGGCGGA STTCAGGTCT CC ATG GAG GCG GCT TCT CCT AGC AAC TCG ACG      52
                        Met Glu Ala Ala Ser Pro Ser Asn Ser Thr
                         -35                 -30

GGC GTT GAG CGG ASC GCT GAC CTG ATG GAC GCC GAC AGC CTC CTG CTG      100
Gly Val Glu Arg Xaa Ala Asp Leu Met Asp Ala Asp Ser Leu Leu Leu
-25             -20             -15                     -10

TCT CTG GAG CTG GCG TCC GGC AGT GGG CAG GGC CTC AGC CCG GAC CGT      148
Ser Leu Glu Leu Ala Ser Gly Ser Gly Gln Gly Leu Ser Pro Asp Arg
                -5               1               5

CGG GCC TCG CTG CTC ACG TCT CTT ATG CTG GTT AAG CGC GAC TAC CGC      196
Arg Ala Ser Leu Leu Thr Ser Leu Met Leu Val Lys Arg Asp Tyr Arg
            10              15              20

TAT GAT CGG GTT CTC TTC TGG GGC CGC ATC CTT GGC CTC GTC GCC GAT      244
Tyr Asp Arg Val Leu Phe Trp Gly Arg Ile Leu Gly Leu Val Ala Asp
        25              30              35

TAC TAC ATC GCG CAG GGC CTG AGT GAG GAC CAG CTC GCA CCG CGC AAG      292
Tyr Tyr Ile Ala Gln Gly Leu Ser Glu Asp Gln Leu Ala Pro Arg Lys
    40              45              50              55

ACG CTC TAT AGG TCC AGA TCA AGG AAG AGA CCC GCA CTG                  331
Thr Leu Tyr Arg Ser Arg Ser Arg Lys Arg Pro Ala Leu
                60              65
```

(2) INFORMATION FOR SEQ ID NO: 205:

(i) SEQUENCE CHARACTERISTICS:
              (A) LENGTH: 317 base pairs
              (B) TYPE: NUCLEIC ACID
              (C) STRANDEDNESS: DOUBLE
              (D) TOPOLOGY: LINEAR (ii) MOLECULE TYPE: CDNA (vi) ORIGINAL SOURCE:
              (A) ORGANISM: Homo Sapiens
              (F) TISSUE TYPE: Brain (ix) FEATURE:
              (A) NAME/KEY: other
              (B) LOCATION: 46..119
              (C) IDENTIFICATION METHOD: blastn
              (D) OTHER INFORMATION: identity 93 region 12..85 id N80882
                  est (ix) FEATURE:
              (A) NAME/KEY: other
              (B) LOCATION: 88..119
              (C) IDENTIFICATION METHOD: blastn
              (D) OTHER INFORMATION: identity 100 region 1..32 id H92328
                  est (ix) FEATURE:
              (A) NAME/KEY: sig_peptide
              (B) LOCATION: 108..236
              (C) IDENTIFICATION METHOD: Von Heijne matrix
              (D) OTHER INFORMATION: score 7.4 seq VLVKLLSSSASTS/RP (xi) SEQUENCE DESCRIPTION: SEQ ID NO: 205:

```
AGTTTCGNST CGCGGATCCG GTAGGTCCAG GTGCAGCGGC CGCAGTKCTG CGTCCGTGCG     60

CCGCGGGCTG GGGCGGTCTC AGGTGTGCCG AAGCTCTGGT CAGTGCC ATG ATC CGG     116
```

```
                                                      Met Ile Arg
CAG GAG CGC TCC ACA TCC TAC CAG GAG GCT GTG CGT CCA GCG CTT CCT        164
Gln Glu Arg Ser Thr Ser Tyr Gln Glu Ala Val Arg Pro Ala Leu Pro
-40         -35                 -30                 -25

TCA AGC AAG CCC TGC CTC CTC ACT TCT CCA GCT GTA TTA GTG AAA CTG        212
Ser Ser Lys Pro Cys Leu Leu Thr Ser Pro Ala Val Leu Val Lys Leu
            -20                 -15                 -10

CTC TCC TCC TCC GCC TCC ACT TCT CGG CCC CCA GAC CTT GGT CAT CTT        260
Leu Ser Ser Ser Ala Ser Thr Ser Arg Pro Pro Asp Leu Gly His Leu
            -5              1               5

TGG CAA CCG TCC TCT TCT GTG CCC CTC CAT CGG CCG CCA CAC ACT GCA        308
Trp Gln Pro Ser Ser Ser Val Pro Leu His Arg Pro Pro His Thr Ala
    10              15              20

CCA CCA GCG                                                            317
Pro Pro Ala
25
```

(2) INFORMATION FOR SEQ ID NO: 206:

(i) SEQUENCE CHARACTERISTICS:
        (A) LENGTH: 363 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 26..365
        (C) IDENTIFICATION METHOD: blastn
        (D) OTHER INFORMATION:  identity 96 region 1..340 id N40260
            est (ix) FEATURE:
        (A) NAME/KEY: other
        (B) LOCATION: 17..308
        (C) IDENTIFICATION METHOD: blastn
        (D) OTHER INFORMATION:  identity 93 region 6..297 id W07706
            est (ix) FEATURE:
        (A) NAME/KEY: other
        (B) LOCATION: 311..349
        (C) IDENTIFICATION METHOD: blastn
        (D) OTHER INFORMATION:  identity 100 region 301..339 id W07706
            est (ix) FEATURE:
        (A) NAME/KEY: other
        (B) LOCATION: 79..365
        (C) IDENTIFICATION METHOD: blastn
        (D) OTHER INFORMATION:  identity 95 region 22..308 id W37568
            est (ix) FEATURE:
        (A) NAME/KEY: other
        (B) LOCATION: 140..326
        (C) IDENTIFICATION METHOD: blastn
        (D) OTHER INFORMATION:  identity 93 region 74..260 id W00732
            est (ix) FEATURE:
        (A) NAME/KEY: other
        (B) LOCATION: 328..365
        (C) IDENTIFICATION METHOD: blastn
        (D) OTHER INFORMATION:  identity 100 region 263..300 id W00732
            est (ix) FEATURE:
   (A) NAME/KEY: other
   (B) LOCATION: 79..362
   (C) IDENTIFICATION METHOD: blastn
   (D) OTHER INFORMATION: identity 95 region 14..297 id AA135041 est (ix) FEATURE:
   (A) NAME/KEY: sig_peptide
   (B) LOCATION: 25..147
   (C) IDENTIFICATION METHOD: Von Heijne matrix
   (D) OTHER INFORMATION: score 7.4 seq ILPLLFGCLGVFG/LF (xi) SEQUENCE DESCRIPTION: SEQ ID NO: 206:

```
ACACGTCACT TCCGAGGCGG GAGG ATG AAG TTG ATT GAC TAT GGT CTC TCC          51
                          Met Lys Leu Ile Asp Tyr Gly Leu Ser
                          -40                 -35

GGC TAC CAG GAA GAG TCT GCC GAA GTG AAG GCC ATG GAC TTC ATC ACC         99
Gly Tyr Gln Glu Glu Ser Ala Glu Val Lys Ala Met Asp Phe Ile Thr
        -30             -25                 -20

TCC ACA GCC ATC CTG CCC CTG CTG TTC GGC TGC CTG GGC GTC TTC GGC        147
Ser Thr Ala Ile Leu Pro Leu Leu Phe Gly Cys Leu Gly Val Phe Gly
    -15             -10                  -5

CTC TTC CGG CTG CTG CAG TGG GTG CGC GGG AAG GCC TAC CTG CGG AAT        195
Leu Phe Arg Leu Leu Gln Trp Val Arg Gly Lys Ala Tyr Leu Arg Asn
  1           5                  10                 15

GCT GTG GTG GTG ATC ACA GGC GCC ACC TCA GGG CTG GGC AAA GAA TGT        243
Ala Val Val Val Ile Thr Gly Ala Thr Ser Gly Leu Gly Lys Glu Cys
             20                  25                 30

GCA AAA GTC TTC TAT GCT RMG GGT GCT AAA CTG GTG CTC TGT GAR MCG        291
Ala Lys Val Phe Tyr Ala Xaa Gly Ala Lys Leu Val Leu Cys Glu Xaa
             35                  40                 45

GAA TGG TGG GGC CTA GAA GAG CTC ATC AGA GAA CTC ACC GCT TCT CAT        339
Glu Trp Trp Gly Leu Glu Glu Leu Ile Arg Glu Leu Thr Ala Ser His
         50                  55                 60

GCC ACC AAG GTG CAG ACA CAC AAG                                        363
Ala Thr Lys Val Gln Thr His Lys
 65              70
```

(2) INFORMATION FOR SEQ ID NO: 207:

(i) SEQUENCE CHARACTERISTICS:
      (A) LENGTH: 235 base pairs
      (B) TYPE: NUCLEIC ACID
      (C) STRANDEDNESS: DOUBLE
      (D) TOPOLOGY: LINEAR (ii) MOLECULE TYPE: CDNA (vi) ORIGINAL SOURCE:
      (A) ORGANISM: Homo Sapiens
      (F) TISSUE TYPE: Brain (ix) FEATURE:
      (A) NAME/KEY: other
      (B) LOCATION: 60..181
      (C) IDENTIFICATION METHOD: blastn
      (D) OTHER INFORMATION: identity 97 region 1..122 id AA057454 est (ix) FEATURE:
      (A) NAME/KEY: other
      (B) LOCATION: 182..233
      (C) IDENTIFICATION METHOD: blastn
      (D) OTHER INFORMATION: identity 96 region 122..173 id AA057454 est (ix) FEATURE:
      (A) NAME/KEY: other
      (B) LOCATION: 71..233

```
        (C) IDENTIFICATION METHOD: blastn
        (D) OTHER INFORMATION:  identity 99 region 1..163 id C18312
              est (ix) FEATURE:
        (A) NAME/KEY: other
        (B) LOCATION: 182..233
        (C) IDENTIFICATION METHOD: blastn
        (D) OTHER INFORMATION:  identity 100 region 144..195 id W69247
              est (ix) FEATURE:
        (A) NAME/KEY: other
        (B) LOCATION: 98..144
        (C) IDENTIFICATION METHOD: blastn
        (D) OTHER INFORMATION:  identity 100 region 62..108 id W69247
              est (ix) FEATURE:
        (A) NAME/KEY: other
        (B) LOCATION: 34..78
        (C) IDENTIFICATION METHOD: blastn
        (D) OTHER INFORMATION:  identity 97 region 1..45 id W69247
              est (ix) FEATURE:
        (A) NAME/KEY: other
        (B) LOCATION: 146..233
        (C) IDENTIFICATION METHOD: blastn
        (D) OTHER INFORMATION:  identity 100 region 69..156 id H75891
              est (ix) FEATURE:
        (A) NAME/KEY: other
        (B) LOCATION: 76..144
        (C) IDENTIFICATION METHOD: blastn
        (D) OTHER INFORMATION:  identity 95 region 1..69 id H75891
              est (ix) FEATURE:
        (A) NAME/KEY: other
        (B) LOCATION: 80..233
        (C) IDENTIFICATION METHOD: blastn
        (D) OTHER INFORMATION:  identity 98 region 1..154 id HUML11265
              est (ix) FEATURE:
        (A) NAME/KEY: sig_peptide
        (B) LOCATION: 104..160
        (C) IDENTIFICATION METHOD: Von Heijne matrix
        (D) OTHER INFORMATION:  score 7.4 seq PMLLRALAQAARA/GP (xi) SEQUENCE DESCRIPTION: SEQ ID NO: 207:

ATAAGGGGGA ACCCGCTGGC CCAATGGCAG CGTCCTACAG TGTAGCCTCC GCCTCCCGAT        60

TGACTGGCCT GCTTGGCAAK GCAAGTAGCG GCGGCGCTTC AAG ATG CGC TGC CTG        115
                                                Met Arg Cys Leu

ACC ACG CCT ATG CTG CTG CGG GCC CTG GCC CAG GCT GCA CGT GCA GGA        163
Thr Thr Pro Met Leu Leu Arg Ala Leu Ala Gln Ala Ala Arg Ala Gly
-15             -10                 -5                           1

CCT CCT GGT GGC CGG AGC CTC CAC AGC AGT GCA GTG GCA GCC ACC TAC        211
Pro Pro Gly Gly Arg Ser Leu His Ser Ser Ala Val Ala Ala Thr Tyr
            5                  10                  15

AAG TAT GTG AAC ATG CAG GAT CAA                                        235
Lys Tyr Val Asn Met Gln Asp Gln
            20                25

(2) INFORMATION FOR SEQ ID NO: 208:

(i) SEQUENCE CHARACTERISTICS:
        (A) LENGTH: 385 base pairs
        (B) TYPE: NUCLEIC ACID
        (C) STRANDEDNESS: DOUBLE
        (D) TOPOLOGY: LINEAR
```

(ii) MOLECULE TYPE: cDNA (vi) ORIGINAL SOURCE:
             (A) ORGANISM: Homo Sapiens
             (F) TISSUE TYPE: Brain (ix) FEATURE:
             (A) NAME/KEY: other
             (B) LOCATION: 70..351
             (C) IDENTIFICATION METHOD: blastn
             (D) OTHER INFORMATION: identity 97 region 34..315 id T19063
                 est (ix) FEATURE:
             (A) NAME/KEY: other
             (B) LOCATION: 36..68
             (C) IDENTIFICATION METHOD: blastn
             (D) OTHER INFORMATION: identity 96 region 1..33 id T19063
                 est (ix) FEATURE:
             (A) NAME/KEY: other
             (B) LOCATION: 61..353
             (C) IDENTIFICATION METHOD: blastn
             (D) OTHER INFORMATION: identity 98 region 1..293 id T32338
                 est (ix) FEATURE:
             (A) NAME/KEY: other
             (B) LOCATION: 93..360
             (C) IDENTIFICATION METHOD: blastn
             (D) OTHER INFORMATION: identity 99 region 1..268 id T30463
                 est (ix) FEATURE:
             (A) NAME/KEY: other
             (B) LOCATION: complement(107..265)
             (C) IDENTIFICATION METHOD: blastn
             (D) OTHER INFORMATION: identity 91 region 330..488 id W27204
                 est (ix) FEATURE:
             (A) NAME/KEY: other
             (B) LOCATION: complement(257..385)
             (C) IDENTIFICATION METHOD: blastn
             (D) OTHER INFORMATION: identity 99 region 209..337 id W27204
                 est (ix) FEATURE:
             (A) NAME/KEY: other
             (B) LOCATION: 70..324
             (C) IDENTIFICATION METHOD: blastn
             (D) OTHER INFORMATION: identity 99 region 27..281 id T32187
                 est (ix) FEATURE:
             (A) NAME/KEY: sig_peptide
             (B) LOCATION: 134..334
             (C) IDENTIFICATION METHOD: Von Heijne matrix
             (D) OTHER INFORMATION: score 7 seq IWTLLSSVIRCLC/AI (xi) SEQUENCE DESCRIPTION: SEQ ID NO: 208:

AGACAAATGG CTCAGGTGGA CTCCGGGCTG GAGCTGTCCT GGGGGAGCTT GTTTGCGGCA          60

SGGCTGCTGC TGCCACTGCT GTGCTGGSGG CCCGGTCGCC AGGCAAAAAG CCCTCCCACG         120

TTTGAGGGGA GTC ATG AGC CGT TTC CTG AAT GTG TTA AGA AGT TGG CTG            169
             Met Ser Arg Phe Leu Asn Val Leu Arg Ser Trp Leu
                 -65                 -60

GTT ATG GTG TCC ATC ATA GCC ATG GGG AAC ACG CTG CAG AGC TTC CGA           217
Val Met Val Ser Ile Ile Ala Met Gly Asn Thr Leu Gln Ser Phe Arg
-55             -50                 -45                 -40

GAC CAC ACT TTT CTC TAT GAA AAG CTC TAC ACT GGC AAG CCA AAC CTT           265
Asp His Thr Phe Leu Tyr Glu Lys Leu Tyr Thr Gly Lys Pro Asn Leu
            -35                 -30                 -25

```
GTG AAT GGC CTC CAA GCT CGG ACC TTT GGG ATC TGG ACG CTG CTC TCA        313
Val Asn Gly Leu Gln Ala Arg Thr Phe Gly Ile Trp Thr Leu Leu Ser
        -20                 -15                 -10

TCA GTG ATT CGC TGC CTC TGT GCC ATT GAC ATT CAC AAC AAG ACG CTC        361
Ser Val Ile Arg Cys Leu Cys Ala Ile Asp Ile His Asn Lys Thr Leu
         -5                  1                   5

TAT CAC ATC ACA CTC TGG ACC TTC                                        385
Tyr His Ile Thr Leu Trp Thr Phe
 10                  15
```

(2) INFORMATION FOR SEQ ID NO: 209:

(i) SEQUENCE CHARACTERISTICS:
        (A) LENGTH: 285 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(2..55)
        (C) IDENTIFICATION METHOD: blastn
        (D) OTHER INFORMATION: identity 92 region 34..87 id T86932
           est (ix) FEATURE:
        (A) NAME/KEY: other
        (B) LOCATION: complement(45..86)
        (C) IDENTIFICATION METHOD: blastn
        (D) OTHER INFORMATION: identity 100 region 2..43 id T86932
           est (ix) FEATURE:
        (A) NAME/KEY: sig_peptide
        (B) LOCATION: 199..240
        (C) IDENTIFICATION METHOD: Von Heijne matrix
        (D) OTHER INFORMATION: score 6.8 seq IFLTLSLDSRVSA/IR (xi) SEQUENCE DESCRIPTION: SEQ ID NO: 209:

```
AAATAAAAAT ATCTTAAAAC TGCATTGTAC AGCTCCCTCC CTGCGTTTTA TTAAATGATG         60

TATATTAAAC AAAGATCAAT ATTTTCTTAA TGACTCAGGG TCTTTATTGT TAATGCCAAT        120

TGTTTTTGTA TCTGTGCTAT AATCCCTTAG AGTCAGTAAA GTATGTAGGG GACTGTTTCT        180

TCCTTTGTGT CTGGGTTT ATG ATT TTT CTC ACT CTT TCT TTG GAC TCC AGG         231
                    Met Ile Phe Leu Thr Leu Ser Leu Asp Ser Arg
                                 -10                      -5

GTG TCA GCC ATC AGG TCT CCT AAT TTT GTG TAC CGG TCT CCA ACA DMC        279
Val Ser Ala Ile Arg Ser Pro Asn Phe Val Tyr Arg Ser Pro Thr Xaa
             1               5                  10

CAT GGG                                                                285
His Gly
    15
```

(2) INFORMATION FOR SEQ ID NO: 210:

(i) SEQUENCE CHARACTERISTICS:
        (A) LENGTH: 378 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: other
         (B) LOCATION: 65..270
         (C) IDENTIFICATION METHOD: blastn
         (D) OTHER INFORMATION: identity 97 region 109..314 id
             AA100852 est (ix) FEATURE:
         (A) NAME/KEY: other
         (B) LOCATION: 269..378
         (C) IDENTIFICATION METHOD: blastn
         (D) OTHER INFORMATION: identity 94 region 314..423 id
             AA100852 est (ix) FEATURE:
         (A) NAME/KEY: other
         (B) LOCATION: 65..270
         (C) IDENTIFICATION METHOD: blastn
         (D) OTHER INFORMATION: identity 97 region 109..314 id
             AA161042 est (ix) FEATURE:
         (A) NAME/KEY: other
         (B) LOCATION: 277..361
         (C) IDENTIFICATION METHOD: blastn
         (D) OTHER INFORMATION: identity 94 region 323..407 id
             AA161042 est (ix) FEATURE:
         (A) NAME/KEY: other
         (B) LOCATION: 65..274
         (C) IDENTIFICATION METHOD: blastn
         (D) OTHER INFORMATION: identity 97 region 104..313 id H64488
             est (ix) FEATURE:
         (A) NAME/KEY: other
         (B) LOCATION: 68..256
         (C) IDENTIFICATION METHOD: blastn
         (D) OTHER INFORMATION: identity 97 region 147..335 id
             AA146605 est (ix) FEATURE:
         (A) NAME/KEY: other
         (B) LOCATION: 256..317
         (C) IDENTIFICATION METHOD: blastn
         (D) OTHER INFORMATION: identity 96 region 336..397 id
             AA146605 est (ix) FEATURE:
         (A) NAME/KEY: other
         (B) LOCATION: 80..305
         (C) IDENTIFICATION METHOD: blastn
         (D) OTHER INFORMATION: identity 98 region 129..354 id
             AA088770 est (ix) FEATURE:
         (A) NAME/KEY: sig_peptide
         (B) LOCATION: 76..162
         (C) IDENTIFICATION METHOD: Von Heijne matrix
         (D) OTHER INFORMATION: score 6.8 seq LIFLCGAALLXVG/IW (xi) SEQUENCE DESCRIPTION: SEQ ID NO: 210:

AATACTACAC ACTCATATAG GGGAGGGAGG CTTCTGGGTC CCAGGGCCGC AGGGGCAKKG     60

AAGTCTGGAG CCWYC ATG CAG TGC TTC AGC TTC ATT AAG ACC ATG ATG ATC    111
               Met Gln Cys Phe Ser Phe Ile Lys Thr Met Met Ile
                              -25                     -20

CTC TTC AAT TTG CTC ATC TTT CTG TGT GGT GCA GCC CTG TTR CA GTG      159
Leu Phe Asn Leu Leu Ile Phe Leu Cys Gly Ala Ala Leu Leu Xaa Val
         -15                 -10                  -5

GGC ATC TGG GTG TCA ATC GAT GGG GCA TCC TTT CTG AAG ATC TTC GGG    207

```
Gly Ile Trp Val Ser Ile Asp Gly Ala Ser Phe Leu Lys Ile Phe Gly
 1               5                  10                  15

CCA CTG TCG TCC AGT GCC ATG CAG TTT GTC AAC GTG GGC TAC TTC CTC       255
Pro Leu Ser Ser Ser Ala Met Gln Phe Val Asn Val Gly Tyr Phe Leu
             20                  25                  30

ATC GCA GCC GGC GTT GTG GTC TTT GCT CTY GGT TTC CTG GGC TGC TAT       303
Ile Ala Ala Gly Val Val Val Phe Ala Leu Gly Phe Leu Gly Cys Tyr
             35                  40                  45

SGT GCT AAG ACT GAG AGC WAG TGT GCC CTC GTG ACG TTC TTC TKC ATC       351
Xaa Ala Lys Thr Glu Ser Xaa Cys Ala Leu Val Thr Phe Phe Xaa Ile
             50                  55                  60

CTC CTS CTC ATC TTC ATT GCT GAC GTT                                   378
Leu Leu Leu Ile Phe Ile Ala Asp Val
         65                  70

(2) INFORMATION FOR SEQ ID NO: 211:

(i) SEQUENCE CHARACTERISTICS:
        (A) LENGTH: 327 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 234..288
        (C) IDENTIFICATION METHOD: blastn
        (D) OTHER INFORMATION:   identity 96 region 203..257 id R25833
            est (ix) FEATURE:
        (A) NAME/KEY: other
        (B) LOCATION: 285..317
        (C) IDENTIFICATION METHOD: blastn
        (D) OTHER INFORMATION:   identity 100 region 255..287 id R25833
            est (ix) FEATURE:
        (A) NAME/KEY: sig_peptide
        (B) LOCATION: 37..141
        (C) IDENTIFICATION METHOD: Von Heijne matrix
        (D) OTHER INFORMATION:   score 6.4 seq SACLLLCPTWTNP/QL (xi) SEQUENCE DESCRIPTION: SEQ ID NO: 211:

AAAAAAGGCG GGGTCTCGGC CGGCGCTGAC GCAGCC ATG GCG GAG GCG GCT TTG        54
                                        Met Ala Glu Ala Ala Leu
                                        -35                 -30

GAA GCC GTG CGG ASG AGT TAC GAG AAT TCC CGG CCG CTG CAA GGG AGC       102
Glu Ala Val Arg Xaa Ser Tyr Glu Asn Ser Arg Pro Leu Gln Gly Ser
            -25                 -20                 -15

TCT GCG TGC CTC TTG CTG TGC CCT ACC TGG ACA AAC CCC CAA CTC CGC       150
Ser Ala Cys Leu Leu Leu Cys Pro Thr Trp Thr Asn Pro Gln Leu Arg
        -10                  -5                   1

TCC ACT TCT ACC GGG ACT GGG TCT GCC CCA ACA GGC CGT GCA TTA TCC       198
Ser Thr Ser Thr Gly Thr Gly Ser Ala Pro Thr Gly Arg Ala Leu Ser
          5                  10                  15

GCA ACG CTC TGC AGC ACT GGC CGG CCC TCC ANC DKK TGG TCC CTC CCC       246
Ala Thr Leu Cys Ser Thr Gly Arg Pro Ser Xaa Xaa Trp Ser Leu Pro
 20                  25                  30                  35

TAT TTC AGA GCC ACA GTG GGC TCC ACA GAG GTG AGT GTG GCC GTG ACC       294
Tyr Phe Arg Ala Thr Val Gly Ser Thr Glu Val Ser Val Ala Val Thr
             40                  45                  50
```

```
CCA GAT GGT TAC GCG GAT GCC GTD AGA NGG GAT                                327
Pro Asp Gly Tyr Ala Asp Ala Val Arg Xaa Asp
            55                  60
```

(2) INFORMATION FOR SEQ ID NO: 212:

(i) SEQUENCE CHARACTERISTICS:
        (A) LENGTH: 244 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 82..241
        (C) IDENTIFICATION METHOD: blastn
        (D) OTHER INFORMATION:  identity 99 region 51..210 id C18780
            est (ix) FEATURE:
        (A) NAME/KEY: other
        (B) LOCATION: 48..83
        (C) IDENTIFICATION METHOD: blastn
        (D) OTHER INFORMATION:  identity 94 region 18..53 id C18780
            est (ix) FEATURE:
        (A) NAME/KEY: other
        (B) LOCATION: 163..235
        (C) IDENTIFICATION METHOD: blastn
        (D) OTHER INFORMATION:  identity 97 region 121..193 id T11911
            est (ix) FEATURE:
        (A) NAME/KEY: other
        (B) LOCATION: 116..162
        (C) IDENTIFICATION METHOD: blastn
        (D) OTHER INFORMATION:  identity 95 region 73..119 id T11911
            est (ix) FEATURE:
        (A) NAME/KEY: other
        (B) LOCATION: 204..239
        (C) IDENTIFICATION METHOD: blastn
        (D) OTHER INFORMATION:  identity 94 region 226..261 id T69629
            est (ix) FEATURE:
        (A) NAME/KEY: sig_peptide
        (B) LOCATION: 143..199
        (C) IDENTIFICATION METHOD: Von Heijne matrix
        (D) OTHER INFORMATION:  score 6.4 seq SVFLLMVNGQVES/AQ (xi) SEQUENCE DESCRIPTION: SEQ ID NO: 212:

```
AGCACTCGCG TGGCCTTCGC GAAGGTGTCG CTGCCAAGAA ACGTGTCCTG CGCGCTACGC          60

CGTCTGTTTT TAGGGCAACG CCGGCGTCTC TTAGCAACCG CGCGCGGCCT AGGTGGGTCC         120

CCCCGGCACC CCCAGACCTG CC ATG GCG ACC GCG AGT CCT AGC GTC TTT CTA         172
                        Met Ala Thr Ala Ser Pro Ser Val Phe Leu
                                      -15                 -10

CTC ATG GTC AAC GGG CAG GTG GAG AGC GCC CAG TTT CCA GAG TAT GAT           220
Leu Met Val Asn Gly Gln Val Glu Ser Ala Gln Phe Pro Glu Tyr Asp
                -5                   1               5

GAC CTC TAC TGC AAG TAC TGC CAG                                           244
Asp Leu Tyr Cys Lys Tyr Cys Gln
        10                  15
```

(2) INFORMATION FOR SEQ ID NO: 213:

(i) SEQUENCE CHARACTERISTICS:
       (A) LENGTH: 211 base pairs
       (B) TYPE: NUCLEIC ACID
       (C) STRANDEDNESS: DOUBLE
       (D) TOPOLOGY: LINEAR (ii) MOLECULE TYPE: CDNA (vi) ORIGINAL SOURCE:
       (A) ORGANISM: Homo Sapiens
       (F) TISSUE TYPE: Brain (ix) FEATURE:
       (A) NAME/KEY: other
       (B) LOCATION: 95..208
       (C) IDENTIFICATION METHOD: blastn
       (D) OTHER INFORMATION:  identity 100 region 85..198 id N43024
           est (ix) FEATURE:
       (A) NAME/KEY: other
       (B) LOCATION: 28..95
       (C) IDENTIFICATION METHOD: blastn
       (D) OTHER INFORMATION:  identity 91 region 17..84 id N43024
           est (ix) FEATURE:
       (A) NAME/KEY: other
       (B) LOCATION: 107..199
       (C) IDENTIFICATION METHOD: blastn
       (D) OTHER INFORMATION:  identity 98 region 80..172 id T62095
           est (ix) FEATURE:
       (A) NAME/KEY: other
       (B) LOCATION: 61..106
       (C) IDENTIFICATION METHOD: blastn
       (D) OTHER INFORMATION:  identity 93 region 35..80 id T62095
           est (ix) FEATURE:
       (A) NAME/KEY: other
       (B) LOCATION: 26..60
       (C) IDENTIFICATION METHOD: blastn
       (D) OTHER INFORMATION:  identity 97 region 1..35 id T62095
           est (ix) FEATURE:
       (A) NAME/KEY: other
       (B) LOCATION: 61..208
       (C) IDENTIFICATION METHOD: blastn
       (D) OTHER INFORMATION:  identity 98 region 26..173 id W42796
           est (ix) FEATURE:
       (A) NAME/KEY: other
       (B) LOCATION: 110..208
       (C) IDENTIFICATION METHOD: blastn
       (D) OTHER INFORMATION:  identity 92 region 114..212 id
           AA030227 est (ix) FEATURE:
       (A) NAME/KEY: other
       (B) LOCATION: 110..208
       (C) IDENTIFICATION METHOD: blastn
       (D) OTHER INFORMATION:  identity 92 region 51..149 id AA118270
           est (ix) FEATURE:
       (A) NAME/KEY: sig_peptide
       (B) LOCATION: 104..187
       (C) IDENTIFICATION METHOD: Von Heijne matrix
       (D) OTHER INFORMATION:  score 6 seq IGLMFLMLGCALP/IY (xi) SEQUENCE DESCRIPTION: SEQ ID NO: 213:

```
TCTTCCGGGT GTTGTCTGGC CGCCGTAGCG CRTCTTGGGT CTCCCGGCTG CCGCTGCTGC         60

CGCCGCCGCC TCGGGTCGTG GAGCCAGGAG CGACGTCACC GCC ATG GCA GGC ATC         115
                                             Met Ala Gly Ile
                                                         -25

AAA GCT TTG ATT AGT TTG TCC TTT GGA GGA GCA ATC GGA CTG ATG TTT         163
Lys Ala Leu Ile Ser Leu Ser Phe Gly Gly Ala Ile Gly Leu Met Phe
            -20                 -15                 -10

TTG ATG CTT GGA TGT GCC CTT CCA ATA TAC AAC AAA TAC TGG CCC TGG         211
Leu Met Leu Gly Cys Ala Leu Pro Ile Tyr Asn Lys Tyr Trp Pro Trp
        -5                   1              5
```

(2) INFORMATION FOR SEQ ID NO: 214:

(i) SEQUENCE CHARACTERISTICS:
       (A) LENGTH: 128 base pairs
       (B) TYPE: NUCLEIC ACID
       (C) STRANDEDNESS: DOUBLE
       (D) TOPOLOGY: LINEAR (ii) MOLECULE TYPE: CDNA (vi) ORIGINAL SOURCE:
       (A) ORGANISM: Homo Sapiens
       (F) TISSUE TYPE: Brain (ix) FEATURE:
       (A) NAME/KEY: other
       (B) LOCATION: 3..124
       (C) IDENTIFICATION METHOD: blastn
       (D) OTHER INFORMATION:   identity 99 region 8..129 id AA146587
          est (ix) FEATURE:
       (A) NAME/KEY: other
       (B) LOCATION: 2..124
       (C) IDENTIFICATION METHOD: blastn
       (D) OTHER INFORMATION:   identity 98 region 14..136 id T85006
          est (ix) FEATURE:
       (A) NAME/KEY: other
       (B) LOCATION: 11..124
       (C) IDENTIFICATION METHOD: blastn
       (D) OTHER INFORMATION:   identity 100 region 1..114 id H08511
          est (ix) FEATURE:
       (A) NAME/KEY: other
       (B) LOCATION: 14..124
       (C) IDENTIFICATION METHOD: blastn
       (D) OTHER INFORMATION:   identity 98 region 1..111 id C00740
          est (ix) FEATURE:
       (A) NAME/KEY: other
       (B) LOCATION: 13..124
       (C) IDENTIFICATION METHOD: blastn
       (D) OTHER INFORMATION:   identity 98 region 1..112 id N40664
          est (ix) FEATURE:
       (A) NAME/KEY: sig_peptide
       (B) LOCATION: 12..62
       (C) IDENTIFICATION METHOD: Von Heijne matrix
       (D) OTHER INFORMATION:   score 5.9 seq ILLFGTLLMNAGA/VL (xi) SEQUENCE DESCRIPTION: SEQ ID NO: 214:

```
AGGCCGTAAC G ATG ATC GGA GAC ATC CTG CTG TTC GGG ACG TTG CTG ATG         50
           Met Ile Gly Asp Ile Leu Leu Phe Gly Thr Leu Leu Met
                   -15             -10                  -5

AAT GCC GGG GCG GTG CTG AAC TTT AAG CTG AAA AAG AAG GAC ACG CAG         98
Asn Ala Gly Ala Val Leu Asn Phe Lys Leu Lys Lys Lys Asp Thr Gln
             1               5                  10
```

```
GGC TTT GGG GAG GAG TCC AGG GAG CCT TGG                              128
Gly Phe Gly Glu Glu Ser Arg Glu Pro Trp
         15                  20
```

(2) INFORMATION FOR SEQ ID NO: 215:

(i) SEQUENCE CHARACTERISTICS:
        (A) LENGTH: 150 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 12..143
        (C) IDENTIFICATION METHOD: blastn
        (D) OTHER INFORMATION: identity 99 region 36..167 id
            HUM137D01B est (ix) FEATURE:
        (A) NAME/KEY: other
        (B) LOCATION: 12..142
        (C) IDENTIFICATION METHOD: blastn
        (D) OTHER INFORMATION: identity 99 region 143..273 id
            AA155928 est (ix) FEATURE:
        (A) NAME/KEY: other
        (B) LOCATION: 12..141
        (C) IDENTIFICATION METHOD: blastn
        (D) OTHER INFORMATION: identity 99 region 115..244 id W39572
            est (ix) FEATURE:
        (A) NAME/KEY: other
        (B) LOCATION: complement(12..135)
        (C) IDENTIFICATION METHOD: blastn
        (D) OTHER INFORMATION: identity 95 region 1..124 id M78698
            est (ix) FEATURE:
        (A) NAME/KEY: other
        (B) LOCATION: complement(32..151)
        (C) IDENTIFICATION METHOD: blastn
        (D) OTHER INFORMATION: identity 98 region 346..465 id H99266
            est (ix) FEATURE:
        (A) NAME/KEY: sig_peptide
        (B) LOCATION: 67..114
        (C) IDENTIFICATION METHOD: Von Heijne matrix
        (D) OTHER INFORMATION: score 5.9 seq MILTLSLFGSCIS/NF (xi) SEQUENCE DESCRIPTION: SEQ ID NO: 215:

```
ACACATCCCT CTAAACTACT GTTAGGAACA GCAGTGTTCT CACAGTGTRG GGCAGCCGTC     60

CTTCTA ATG AAG ACA ATG ATA TTG ACA CTG TCC CTC TTT GGC AGT TGC      108
       Met Lys Thr Met Ile Leu Thr Leu Ser Leu Phe Gly Ser Cys
          -15                 -10                  -5

ATT AGT AAC TTT GAA AGG TAT ATG ACT GAG CGT AGC ATC CAG             150
Ile Ser Asn Phe Glu Arg Tyr Met Thr Glu Arg Ser Ile Gln
        1               5                  10
```

(2) INFORMATION FOR SEQ ID NO: 216:

(i) SEQUENCE CHARACTERISTICS:
        (A) LENGTH: 397 base pairs
        (B) TYPE: NUCLEIC ACID

```
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(223..398)
        (C) IDENTIFICATION METHOD: blastn
        (D) OTHER INFORMATION:  identity 96 region 111..286 id HSGT545
            est (ix) FEATURE:
        (A) NAME/KEY: other
        (B) LOCATION: complement(69..219)
        (C) IDENTIFICATION METHOD: blastn
        (D) OTHER INFORMATION:  identity 92 region 291..441 id HSGT545
            est (ix) FEATURE:
        (A) NAME/KEY: other
        (B) LOCATION: complement(2..43)
        (C) IDENTIFICATION METHOD: blastn
        (D) OTHER INFORMATION:  identity 97 region 467..508 id HSGT545
            est (ix) FEATURE:
        (A) NAME/KEY: other
        (B) LOCATION: complement(223..311)
        (C) IDENTIFICATION METHOD: blastn
        (D) OTHER INFORMATION:  identity 92 region 4..92 id AA036134
            est (ix) FEATURE:
        (A) NAME/KEY: other
        (B) LOCATION: complement(46..163)
        (C) IDENTIFICATION METHOD: blastn
        (D) OTHER INFORMATION:  identity 91 region 133..250 id
            AA038839 est (ix) FEATURE:
        (A) NAME/KEY: other
        (B) LOCATION: complement(223..295)
        (C) IDENTIFICATION METHOD: blastn
        (D) OTHER INFORMATION:  identity 97 region 1..73 id AA038839
            est (ix) FEATURE:
        (A) NAME/KEY: other
        (B) LOCATION: 326..387
        (C) IDENTIFICATION METHOD: blastn
        (D) OTHER INFORMATION:  identity 91 region 2..63 id W51392 est (ix) FEATURE:
        (A) NAME/KEY: sig_peptide
        (B) LOCATION: 152..268
        (C) IDENTIFICATION METHOD: Von Heijne matrix
        (D) OTHER INFORMATION:  score 5.9 seq SVSVLSSLGIVLA/VV (xi) SEQUENCE DESCRIPTION: SEQ ID NO: 216:

ACTTTGAGGG TGTCTCTGGC CATGTGGTGT TTGATGCCAG CBGCTCTCGG ATGGCATGGA      60

CGCTTATCGA GCAGCTTCAG GGTGGCAGCT ACAAGAAGAT TGGCTACTAT GACAGCACCA     120

AGGATGATCT TTCCTGGTCC AAAACAGATA A ATG GAT TGG AGG GTC CCC CCC        172
                                  Met Asp Trp Arg Val Pro Pro
                                                           -35

AGC TGR SCA GAC CCT GGT CAT CAA GAC ATT CCG CTT CCT GTC ACA GAN       220
Ser Xaa Xaa Asp Pro Gly His Gln Asp Ile Pro Leu Pro Val Thr Xaa
        -30                 -25                 -20

NNC TTT ATC TCC GTC TCA GTT CTC TCC AGC CTG GGC ATT GTC CTA GCT       268
Xaa Phe Ile Ser Val Ser Val Leu Ser Ser Leu Gly Ile Val Leu Ala
```

```
     -15                 -10                 -5
GTT GTC TGT CTG TCC TTT AAC ATC TAC AAC TCA CAT GTC CGT TAT ATC      316
Val Val Cys Leu Ser Phe Asn Ile Tyr Asn Ser His Val Arg Tyr Ile
 1                   5                  10                  15

CAG AAC TCA CAG CCC AAC CTG AAC AAC CTG ACT GCT GTG GGC TGC TCA      364
Gln Asn Ser Gln Pro Asn Leu Asn Asn Leu Thr Ala Val Gly Cys Ser
                 20                  25                  30

MTG GCT TTA GCT GCT GTC TTC CCC TGG GGC TCG                          397
Xaa Ala Leu Ala Ala Val Phe Pro Trp Gly Ser
             35                  40
```

(2) INFORMATION FOR SEQ ID NO: 217:

(i) SEQUENCE CHARACTERISTICS:
        (A) LENGTH: 373 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 41..337
        (C) IDENTIFICATION METHOD: blastn
        (D) OTHER INFORMATION: identity 97 region 1..297 id H56523
            est (ix) FEATURE:
        (A) NAME/KEY: other
        (B) LOCATION: 38..337
        (C) IDENTIFICATION METHOD: blastn
        (D) OTHER INFORMATION: identity 96 region 1..300 id AA020823
            est (ix) FEATURE:
        (A) NAME/KEY: other
        (B) LOCATION: 43..337
        (C) IDENTIFICATION METHOD: blastn
        (D) OTHER INFORMATION: identity 96 region 7..301 id H99096
            est (ix) FEATURE:
        (A) NAME/KEY: other
        (B) LOCATION: 49..315
        (C) IDENTIFICATION METHOD: blastn
        (D) OTHER INFORMATION: identity 98 region 11..277 id AA083141
            est (ix) FEATURE:
        (A) NAME/KEY: other
        (B) LOCATION: 52..337
        (C) IDENTIFICATION METHOD: blastn
        (D) OTHER INFORMATION: identity 96 region 17..302 id N21197
            est (ix) FEATURE:
        (A) NAME/KEY: sig_peptide
        (B) LOCATION: 35..82
        (C) IDENTIFICATION METHOD: Von Heijne matrix
        (D) OTHER INFORMATION: score 5.8 seq AALPAWLSLQSRA/RT (xi) SEQUENCE DESCRIPTION: SEQ ID NO: 217:

```
AGCTTGTCCC CTCCGGCTTG CCGTCCTCGC AGCC ATG GCG GCC GCC GCG CTC CCA    55
                                    Met Ala Ala Ala Ala Leu Pro
                                        -15                 -10

GCA TGG CTG TCT CTG CAG TCG AGG GCA AGG ACT CTG CGT GCA TTC TCC     103
Ala Trp Leu Ser Leu Gln Ser Arg Ala Arg Thr Leu Arg Ala Phe Ser
         -5                  1                   5
```

```
ACT GCC GTC TAC TCG GCC ACT CCG GTC CCG ASA CCT AGC CTG CCG GAA    151
Thr Ala Val Tyr Ser Ala Thr Pro Val Pro Xaa Pro Ser Leu Pro Glu
         10                  15                  20

AGA ACA CCC GGA AAT GAA AGG CCA CCA AGA AGA AAG GCA CTA CCT CCT    199
Arg Thr Pro Gly Asn Glu Arg Pro Pro Arg Arg Lys Ala Leu Pro Pro
 25                  30                  35

AGG ACA GAG AAA ATG GCT GTT GAC CAG GAC TGG CCT AKT GTT TAC CCA    247
Arg Thr Glu Lys Met Ala Val Asp Gln Asp Trp Pro Xaa Val Tyr Pro
 40                  45                  50                  55

GTT GCA GCA CCA TTT AAA CCC TCT GCA GTA CCT CTT CCT GTT CGA ATG    295
Val Ala Ala Pro Phe Lys Pro Ser Ala Val Pro Leu Pro Val Arg Met
             60                  65                  70

GGT TAT CCA GTA AAA AAG GGC GTS CCA TGG SAA AGG AGG GAA TCT AKG    343
Gly Tyr Pro Val Lys Lys Gly Val Pro Trp Xaa Arg Arg Glu Ser Xaa
             75                  80                  85

ACT TTT AAA GAT TCC AAT TTT CTG CAT TTG                            373
Thr Phe Lys Asp Ser Asn Phe Leu His Leu
         90                  95

(2) INFORMATION FOR SEQ ID NO: 218:

(i) SEQUENCE CHARACTERISTICS:
        (A) LENGTH: 333 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 32..331
        (C) IDENTIFICATION METHOD: blastn
        (D) OTHER INFORMATION:   identity 99 region 1..300 id R13004
            est (ix) FEATURE:
        (A) NAME/KEY: other
        (B) LOCATION: 114..274
        (C) IDENTIFICATION METHOD: blastn
        (D) OTHER INFORMATION:   identity 99 region 54..214 id T80337
            est (ix) FEATURE:
        (A) NAME/KEY: other
        (B) LOCATION: 272..331
        (C) IDENTIFICATION METHOD: blastn
        (D) OTHER INFORMATION:   identity 100 region 213..272 id T80337
            est (ix) FEATURE:
        (A) NAME/KEY: other
        (B) LOCATION: 66..106
        (C) IDENTIFICATION METHOD: blastn
        (D) OTHER INFORMATION:   identity 100 region 6..46 id T80337
            est (ix) FEATURE:
        (A) NAME/KEY: other
        (B) LOCATION: 101..278
        (C) IDENTIFICATION METHOD: blastn
        (D) OTHER INFORMATION:   identity 94 region 70..247 id T08840
            est (ix) FEATURE:
        (A) NAME/KEY: other
        (B) LOCATION: 33..113
        (C) IDENTIFICATION METHOD: blastn
```

(D) OTHER INFORMATION: identity 98 region 1..81 id T08840
                  est (ix) FEATURE:
              (A) NAME/KEY: other
              (B) LOCATION: 101..249
              (C) IDENTIFICATION METHOD: blastn
              (D) OTHER INFORMATION: identity 95 region 72..220 id
                  HSC0CF041 est (ix) FEATURE:
              (A) NAME/KEY: other
              (B) LOCATION: 31..112
              (C) IDENTIFICATION METHOD: blastn
              (D) OTHER INFORMATION: identity 100 region 1..82 id HSC0CF041
                  est (ix) FEATURE:
              (A) NAME/KEY: sig_peptide
              (B) LOCATION: 247..321
              (C) IDENTIFICATION METHOD: Von Heijne matrix
              (D) OTHER INFORMATION: score 5.8 seq LWISACAMLLCHG/SL (xi) SEQUENCE DESCRIPTION: SEQ ID NO: 218:

AAGCTAGGAC ATTCTTCTCC TCCTGGCCCT GGACATCAGA ACCCCAGGCT CTCCAGCCTT        60

TGGACTTCAG GACTGACACA AGCAACCTGC TGGGTTCTTA GGCCTTTGGC TTGTACTGAG       120

ACTTACACCA TCAGCTTCCC TGGTCCTGAG ACTTTTGGAC TTGGATTGAG CCACGCTACT       180

GGCATCCCAG GATCTCCAGC TTGCAGACAG CCTGTCGTGG GACTTCACAG CCTCCATAAT       240

TATAGA ATG GCA ATG GTC TCT GCG ATG TCC TGG GTC CTG TAT TTG TGG          288
       Met Ala Met Val Ser Ala Met Ser Trp Val Leu Tyr Leu Trp
           -25                 -20                 -15

ATA AGT GCT TGT GCA ATG CTA CTC TGC CAT GGA TCC CTT CAG CGG             333
Ile Ser Ala Cys Ala Met Leu Leu Cys His Gly Ser Leu Gln Arg
    -10                  -5                   1

(2) INFORMATION FOR SEQ ID NO: 219:

(i) SEQUENCE CHARACTERISTICS:
              (A) LENGTH: 284 base pairs
              (B) TYPE: NUCLEIC ACID
              (C) STRANDEDNESS: DOUBLE
              (D) TOPOLOGY: LINEAR (ii) MOLECULE TYPE: cDNA (vi) ORIGINAL SOURCE:
              (A) ORGANISM: Homo Sapiens
              (F) TISSUE TYPE: Brain (ix) FEATURE:
              (A) NAME/KEY: other
              (B) LOCATION: complement(2..282)
              (C) IDENTIFICATION METHOD: blastn
              (D) OTHER INFORMATION: identity 100 region 59..339 id H10776
                  est (ix) FEATURE:
              (A) NAME/KEY: other
              (B) LOCATION: complement(64..282)
              (C) IDENTIFICATION METHOD: blastn
              (D) OTHER INFORMATION: identity 96 region 73..291 id N94455
                  est (ix) FEATURE:
              (A) NAME/KEY: other
              (B) LOCATION: complement(2..85)
              (C) IDENTIFICATION METHOD: blastn
              (D) OTHER INFORMATION: identity 95 region 271..354 id N94455
                  est (ix) FEATURE:
              (A) NAME/KEY: other (B) LOCATION: complement(107..282)
                (C) IDENTIFICATION METHOD: blastn
                (D) OTHER INFORMATION:  identity 99 region 58..233 id H64097
                    est (ix) FEATURE:
                (A) NAME/KEY: other
                (B) LOCATION: complement(2..120)
                (C) IDENTIFICATION METHOD: blastn
                (D) OTHER INFORMATION:  identity 94 region 219..337 id H64097
                    est (ix) FEATURE:
                (A) NAME/KEY: other
                (B) LOCATION: complement(38..282)
                (C) IDENTIFICATION METHOD: blastn
                (D) OTHER INFORMATION:  identity 99 region 60..304 id R98226
                    est (ix) FEATURE:
                (A) NAME/KEY: other
                (B) LOCATION: complement(161..282)
                (C) IDENTIFICATION METHOD: blastn
                (D) OTHER INFORMATION:  identity 96 region 33..154 id W60134
                    est (ix) FEATURE:
                (A) NAME/KEY: other
                (B) LOCATION: complement(9..120)
                (C) IDENTIFICATION METHOD: blastn
                (D) OTHER INFORMATION:  identity 96 region 195..306 id W60134
                    est (ix) FEATURE:
                (A) NAME/KEY: sig_peptide
                (B) LOCATION: 51..257
                (C) IDENTIFICATION METHOD: Von Heijne matrix
                (D) OTHER INFORMATION:  score 5.7 seq LCRLLCLVRLFCC/SS (xi) SEQUENCE DESCRIPTION: SEQ ID NO: 219:

ATCAACCATC CAGCTCCCAG CTGGCTAAAC TTTGCCTCCA GTGGTCAAAG ATG GGA          56
                                                       Met Gly

AAA GAG TGG GGT TGG CAG GAG ATG GAA AAC GGA GGT GCC GCC CCA GCA       104
Lys Glu Trp Gly Trp Gln Glu Met Glu Asn Gly Gly Ala Ala Pro Ala
        -65                 -60                 -55

TGG GGG GCA GGT CCC CCA GTC CAC CCT GCC CCT CCC CCT GTG GAG AAG       152
Trp Gly Ala Gly Pro Pro Val His Pro Ala Pro Pro Pro Val Glu Lys
    -50                 -45                 -40

ACG CTT AGT TGG GGG TGT GGG TTT GGG CTC CAT TCT GGA TTC GGC GGT       200
Thr Leu Ser Trp Gly Cys Gly Phe Gly Leu His Ser Gly Phe Gly Gly
-35                 -30                 -25                 -20

TCC GGG GGA GGG GTG GGT CTG TGC CGA TTA CTC TGT CTT GTA CGT TTG       248
Ser Gly Gly Gly Val Gly Leu Cys Arg Leu Leu Cys Leu Val Arg Leu
                -15                 -10                  -5

TTC TGC TGC TCT TCA ATA TTG TAT CAA CGC CAG GGG                       284
Phe Cys Cys Ser Ser Ile Leu Tyr Gln Arg Gln Gly
                1                   5

(2) INFORMATION FOR SEQ ID NO: 220:

(i) SEQUENCE CHARACTERISTICS:
                (A) LENGTH: 361 base pairs
                (B) TYPE: NUCLEIC ACID
                (C) STRANDEDNESS: DOUBLE
                (D) TOPOLOGY: LINEAR (ii) MOLECULE TYPE: cDNA (vi) ORIGINAL SOURCE:
                (A) ORGANISM: Homo Sapiens
                (F) TISSUE TYPE: Brain

```
    (ix) FEATURE:
         (A) NAME/KEY: other
         (B) LOCATION: 137..358
         (C) IDENTIFICATION METHOD: blastn
         (D) OTHER INFORMATION:   identity 97 region 151..372 id N33828
             est (ix) FEATURE:
         (A) NAME/KEY: other
         (B) LOCATION: 2..124
         (C) IDENTIFICATION METHOD: blastn
         (D) OTHER INFORMATION:   identity 99 region 14..136 id N33828
             est (ix) FEATURE:
         (A) NAME/KEY: other
         (B) LOCATION: 138..358
         (C) IDENTIFICATION METHOD: blastn
         (D) OTHER INFORMATION:   identity 98 region 147..367 id N34173
             est (ix) FEATURE:
         (A) NAME/KEY: other
         (B) LOCATION: 1..148
         (C) IDENTIFICATION METHOD: blastn
         (D) OTHER INFORMATION:   identity 98 region 11..158 id N34173
             est (ix) FEATURE:
         (A) NAME/KEY: other
         (B) LOCATION: 35..358
         (C) IDENTIFICATION METHOD: blastn
         (D) OTHER INFORMATION:   identity 99 region 1..324 id T89546
             est (ix) FEATURE:
         (A) NAME/KEY: other
         (B) LOCATION: 138..337
         (C) IDENTIFICATION METHOD: blastn
         (D) OTHER INFORMATION:   identity 98 region 107..306 id H67305
             est (ix) FEATURE:
         (A) NAME/KEY: other
         (B) LOCATION: 42..148
         (C) IDENTIFICATION METHOD: blastn
         (D) OTHER INFORMATION:   identity 99 region 12..118 id H67305
             est (ix) FEATURE:
         (A) NAME/KEY: other
         (B) LOCATION: 138..302
         (C) IDENTIFICATION METHOD: blastn
         (D) OTHER INFORMATION:   identity 98 region 112..276 id T79378
             est (ix) FEATURE:
         (A) NAME/KEY: other
         (B) LOCATION: 33..145
         (C) IDENTIFICATION METHOD: blastn
         (D) OTHER INFORMATION:   identity 100 region 8..120 id T79378
             est (ix) FEATURE:
         (A) NAME/KEY: other
         (B) LOCATION: 317..348
         (C) IDENTIFICATION METHOD: blastn
         (D) OTHER INFORMATION:   identity 100 region 293..324 id T79378
             est (ix) FEATURE:
         (A) NAME/KEY: sig_peptide
         (B) LOCATION: 167..229
         (C) IDENTIFICATION METHOD: Von Heijne matrix
         (D) OTHER INFORMATION:   score 5.6 seq LVLSLQFLLLSYD/LF (xi) SEQUENCE DESCRIPTION: SEQ ID NO: 220:

AATGACAACC GACGTTGGAG TTTGGAGGTG CTTGCCTTAG AGCAAGGGAA ACAGCTCTCA    60
```

```
TTCAAAGGAA CTAGAAGCCT CTCCCTCAGT GGTAGGGAGA CAGCCAGGAG CGGTTTTCTG        120

GGAACTGTGG GATGTGCCCT TGGGGCCCG AGAAAACAGA AGGAAG ATG CTC CAG           175
                                                   Met Leu Gln
                                                   -20

ACC AGT AAC TAC AGC CTG GTG CTC TCT CTG CAG TTC CTG CTG CTG TCC         223
Thr Ser Asn Tyr Ser Leu Val Leu Ser Leu Gln Phe Leu Leu Leu Ser
        -15                 -10                 -5

TAT GAC CTC TTT GTC AAT TCC TTC TCA GAA CTG CTC CAA AAG ACT CCT         271
Tyr Asp Leu Phe Val Asn Ser Phe Ser Glu Leu Leu Gln Lys Thr Pro
    1               5                   10

GTC ATC CAG CTT GTG CTC TTC ATC ATC CAG GAT ATT GCA GTC CTC TTC         319
Val Ile Gln Leu Val Leu Phe Ile Ile Gln Asp Ile Ala Val Leu Phe
 15              20              25                  30

AAC ATC ATC ATC ATT TTC CTC ATG TTC TTC AAC ACC TCC CGG                 361
Asn Ile Ile Ile Ile Phe Leu Met Phe Phe Asn Thr Ser Arg
                35              40
```

(2) INFORMATION FOR SEQ ID NO: 221:

(i) SEQUENCE CHARACTERISTICS:
        (A) LENGTH: 252 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(100..250)
        (C) IDENTIFICATION METHOD: blastn
        (D) OTHER INFORMATION: identity 95 region 256..406 id W72958
           est (ix) FEATURE:
        (A) NAME/KEY: other
        (B) LOCATION: 115..250
        (C) IDENTIFICATION METHOD: blastn
        (D) OTHER INFORMATION: identity 99 region 2..137 id W78821
           est (ix) FEATURE:
        (A) NAME/KEY: other
        (B) LOCATION: 120..250
        (C) IDENTIFICATION METHOD: blastn
        (D) OTHER INFORMATION: identity 99 region 1..131 id AA083784
           est (ix) FEATURE:
        (A) NAME/KEY: other
        (B) LOCATION: 115..250
        (C) IDENTIFICATION METHOD: blastn
        (D) OTHER INFORMATION: identity 98 region 4..139 id W24219
           est (ix) FEATURE:
        (A) NAME/KEY: other
        (B) LOCATION: 145..250
        (C) IDENTIFICATION METHOD: blastn
        (D) OTHER INFORMATION: identity 97 region 39..144 id C15963
           est (ix) FEATURE:
        (A) NAME/KEY: other
        (B) LOCATION: 114..153
        (C) IDENTIFICATION METHOD: blastn
        (D) OTHER INFORMATION: identity 95 region 9..48 id C15963
           est (ix) FEATURE:
            (A) NAME/KEY: sig_peptide
            (B) LOCATION: 172..243
            (C) IDENTIFICATION METHOD: Von Heijne matrix
            (D) OTHER INFORMATION:  score 5.5 seq MGVCLLIPGLATA/CI (xi) SEQUENCE DESCRIPTION: SEQ ID NO: 221:

AGCGCGASGY CCGKCTCTCT TGTGCCCTAG CAGATTCCGT CGCTTCTTCC GGAGCCGTAC        60

GTGGTACCGC CCCGCTCGCG GGCGGCCGCG RGGCTTGCTG GGAAGAGAGG CGAACCAGGT       120

CACCTTTCAA GGACCCAGAA GTAGGGTTTT GGCCTAGGTA ACGGGGCAGA G ATG TGG       177
                                                         Met Trp

TTC GAG ATT CTC CCC GGA CTC TCC GTC ATG GGC GTG TGC TTG TTG ATT        225
Phe Glu Ile Leu Pro Gly Leu Ser Val Met Gly Val Cys Leu Leu Ile
        -20              -15              -10

CCA GGA CTG GCT ACT GCG TGC ATC CGG                                    252
Pro Gly Leu Ala Thr Ala Cys Ile Arg
     -5                   1

(2) INFORMATION FOR SEQ ID NO: 222:

(i) SEQUENCE CHARACTERISTICS:
            (A) LENGTH: 167 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: complement(2..103)
            (C) IDENTIFICATION METHOD: blastn
            (D) OTHER INFORMATION:  identity 98 region 48..149 id AA126155
                est (ix) FEATURE:
            (A) NAME/KEY: other
            (B) LOCATION: complement(98..143)
            (C) IDENTIFICATION METHOD: blastn
            (D) OTHER INFORMATION:  identity 95 region 7..52 id AA126155
                est (ix) FEATURE:
            (A) NAME/KEY: sig_peptide
            (B) LOCATION: 30..95
            (C) IDENTIFICATION METHOD: Von Heijne matrix
            (D) OTHER INFORMATION:  score 5.5 seq LADPLXLFPFSEG/LP (xi) SEQUENCE DESCRIPTION: SEQ ID NO: 222:

ACTGCTCSTG GAGCTCTGCG CTGGTCTTC ATG CGC CCT AGC CCT CTT TCG GGG         53
                                Met Arg Pro Ser Pro Leu Ser Gly
                                    -20              -15

ATA CTG GCC GAC CCC CTC TKC CTT TTC CCC TTT AGT GAA GGC CTC CCC        101
Ile Leu Ala Asp Pro Leu Xaa Leu Phe Pro Phe Ser Glu Gly Leu Pro
             -10              -5                       1

CGT CGC CGC GCG GCT TCC CGG AGC CGA CTG CAG ACT CCC TCA GCC CGG        149
Arg Arg Arg Ala Ala Ser Arg Ser Arg Leu Gln Thr Pro Ser Ala Arg
             5              10              15

TGT TCC CCG CGT CCG GGG                                                167
Cys Ser Pro Arg Pro Gly
     20

(2) INFORMATION FOR SEQ ID NO: 223:

(i) SEQUENCE CHARACTERISTICS:
        (A) LENGTH: 350 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 40..352
        (C) IDENTIFICATION METHOD: blastn
        (D) OTHER INFORMATION:  identity 96 region 30..342 id H15315
            est (ix) FEATURE:
        (A) NAME/KEY: other
        (B) LOCATION: 12..46
        (C) IDENTIFICATION METHOD: blastn
        (D) OTHER INFORMATION:  identity 91 region 1..35 id H15315
            est (ix) FEATURE:
        (A) NAME/KEY: other
        (B) LOCATION: 77..300
        (C) IDENTIFICATION METHOD: blastn
        (D) OTHER INFORMATION:  identity 96 region 1..224 id
            HUM427H08B est (ix) FEATURE:
        (A) NAME/KEY: other
        (B) LOCATION: 22..134
        (C) IDENTIFICATION METHOD: blastn
        (D) OTHER INFORMATION:  identity 91 region 3..115 id AA071651
            est (ix) FEATURE:
        (A) NAME/KEY: other
        (B) LOCATION: 138..326
        (C) IDENTIFICATION METHOD: blastn
        (D) OTHER INFORMATION:  identity 95 region 32..220 id R35596
            est (ix) FEATURE:
        (A) NAME/KEY: other
        (B) LOCATION: 65..111
        (C) IDENTIFICATION METHOD: blastn
        (D) OTHER INFORMATION:  identity 91 region 1..47 id W55530
            est (ix) FEATURE:
        (A) NAME/KEY: sig_peptide
        (B) LOCATION: 261..341
        (C) IDENTIFICATION METHOD: Von Heijne matrix
        (D) OTHER INFORMATION:  score 5.4 seq SLMMAQXFIPAVA/KV (xi) SEQUENCE DESCRIPTION: SEQ ID NO: 223:

AGGAGGGCTG GACAGCAGCT CAGCTCGCTA GCTGCGCGCT TCCCGGCACA GGCAGTGCCA      60

CTGCGCAGGT TGATCAGCGA AACAGCATCC ATTTTAATCT GCGGGGAGNN CCTGCCTTAC     120

CAGGGCGTTC TCTCCGCCCG CCGGTGGATG CTCCGCGCCT GCSCTCCGCA GCCTCGCTCA     180

GCAGTCCTGC GTTGGGGTCT GCGCCCTAGG ATGCACTGAG ATGGTACATC AGGATAACTG     240

CTCGTATCAG GCACAGAAAA ATG AGA GAG AGT CTA TCA DKS AGA AGT TGG CAC     293
                     Met Arg Glu Ser Leu Ser Xaa Arg Ser Trp His
                                       -25                 -20

TTG CCA GCT TCT TTG ATG ATG GCC CAG GKA TTT ATA CCA GCT GTA GCA       341
Leu Pro Ala Ser Leu Met Met Ala Gln Xaa Phe Ile Pro Ala Val Ala
    -15                 -10                 -5

```
AAA GTA GGA                                                                      350
Lys Val Gly
 1
```

(2) INFORMATION FOR SEQ ID NO: 224:

(i) SEQUENCE CHARACTERISTICS:
        (A) LENGTH: 430 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 226..295
        (C) IDENTIFICATION METHOD: blastn
        (D) OTHER INFORMATION: identity 95 region 121..190 id W07343
            est (ix) FEATURE:
        (A) NAME/KEY: sig_peptide
        (B) LOCATION: 251..424
        (C) IDENTIFICATION METHOD: Von Heijne matrix
        (D) OTHER INFORMATION: score 5.4 seq LSLHLLATRACYG/IL (xi) SEQUENCE DESCRIPTION: SEQ ID NO: 224:

```
AACAGGTGGT TGCAGAAGTT TCGTGGTGTC GGGCGCGCGT CTGCACTGCA GACGCAGAGG    60

GTTTGGGAGC GAGCAGTTTC CTGCCCAGGG ATGGGGGTCC TGGCTGCACT TCACGGGGGC   120

GGCCCTTTCG TTTCGCTCTG CGTGACAGGT CTCGCTTGAT TGGGTTTCTC ATGGGTSKCT   180

GGCGTTTCTA CGGCGCGGCT CTCACGGACT CAGGCCAGGC CACTCGCAGG ATTAATTGGA   240

ATTCTTCAAA ATG TCA GGT GTG GTA CCC ACA GCC CCT GAA CAG CCT GCA     289
           Met Ser Gly Val Val Pro Thr Ala Pro Glu Gln Pro Ala
                   -55                     -50

NGT GAA ATG GAA AAT CAA ACA AAA CCA CCA GAT CCA AGG CCT GAT GCT    337
Xaa Glu Met Glu Asn Gln Thr Lys Pro Pro Asp Pro Arg Pro Asp Ala
-45             -40                 -35                 -30

CCT CCT GAA TAC AGT TCT CAT DBG TTT ACC AGG ACC CCC TGG AAA CAG    385
Pro Pro Glu Tyr Ser Ser His Xaa Phe Thr Arg Thr Pro Trp Lys Gln
            -25                 -20                 -15

CTG TCC CTC CAC CTA CTG GCT ACC AGA GCT TGC TAT GGG ATA CTA        430
Leu Ser Leu His Leu Leu Ala Thr Arg Ala Cys Tyr Gly Ile Leu
        -10                 -5                   1
```

(2) INFORMATION FOR SEQ ID NO: 225:

(i) SEQUENCE CHARACTERISTICS:
        (A) LENGTH: 387 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(75..325)
        (C) IDENTIFICATION METHOD: blastn
        (D) OTHER INFORMATION: identity 100 region 82..332 id
            AA004751 est

```
    (ix) FEATURE:
          (A) NAME/KEY: other
          (B) LOCATION: complement(88..255)
          (C) IDENTIFICATION METHOD: blastn
          (D) OTHER INFORMATION:   identity 97 region 153..320 id N27443
              est (ix) FEATURE:
          (A) NAME/KEY: other
          (B) LOCATION: complement(18..105)
          (C) IDENTIFICATION METHOD: blastn
          (D) OTHER INFORMATION:   identity 94 region 304..391 id N27443
              est (ix) FEATURE:
          (A) NAME/KEY: other
          (B) LOCATION: complement(258..325)
          (C) IDENTIFICATION METHOD: blastn
          (D) OTHER INFORMATION:   identity 100 region 81..148 id N27443
              est (ix) FEATURE:
          (A) NAME/KEY: other
          (B) LOCATION: complement(22..325)
          (C) IDENTIFICATION METHOD: blastn
          (D) OTHER INFORMATION:   identity 99 region 80..383 id AA015608
              est (ix) FEATURE:
          (A) NAME/KEY: other
          (B) LOCATION: complement(78..253)
          (C) IDENTIFICATION METHOD: blastn
          (D) OTHER INFORMATION:   identity 99 region 165..340 id H09727
              est (ix) FEATURE:
          (A) NAME/KEY: other
          (B) LOCATION: complement(253..285)
          (C) IDENTIFICATION METHOD: blastn
          (D) OTHER INFORMATION:   identity 96 region 132..164 id H09727
              est (ix) FEATURE:
          (A) NAME/KEY: other
          (B) LOCATION: complement(49..276)
          (C) IDENTIFICATION METHOD: blastn
          (D) OTHER INFORMATION:   identity 97 region 133..360 id
              AA027099 est (ix) FEATURE:
          (A) NAME/KEY: other
          (B) LOCATION: complement(269..325)
          (C) IDENTIFICATION METHOD: blastn
          (D) OTHER INFORMATION:   identity 100 region 83..139 id
              AA027099 est (ix) FEATURE:
          (A) NAME/KEY: sig_peptide
          (B) LOCATION: 139..369
          (C) IDENTIFICATION METHOD: Von Heijne matrix
          (D) OTHER INFORMATION:   score 5.3 seq TWVFTCLVFFCFG/LS (xi) SEQUENCE DESCRIPTION: SEQ ID NO: 225:

AGAAACAGGG AGAAGAGGAA GGCTAGAAGC CTGAGCAAGT GAGGGTAGAA CCTTTTGGGA      60

CTGGCCTTTG AAGCTCTGGC CAGGGATGGG GTGGGGGCCA AAAGGACAGA GCCTGGTATG     120

TCTTCATAGT CATTGAGA ATG TGG AGA TAC CAG TTT GGG TGG GGG GTG ATC      171
                    Met Trp Arg Tyr Gln Phe Gly Trp Gly Val Ile
                        -75                 -70

ACC AGG GGA CCT AGG GAG ATC CCC TTC CCA CCC TCT CTG TTG GCC TCA      219
Thr Arg Gly Pro Arg Glu Ile Pro Phe Pro Pro Ser Leu Leu Ala Ser
    -65                 -60                 -55

GAG TCA CTC CTG CCC CCT CTC CCT GAC TTG GTG CTC ACA TGC ACC TCA      267
Glu Ser Leu Leu Pro Pro Leu Pro Asp Leu Val Leu Thr Cys Thr Ser
```

```
      -50                 -45                 -40                 -35
CTA GGG TTT GTG ACC AGG GTC TGG ATG AGC TTG AAT TTG AAT GAA TTG          315
Leu Gly Phe Val Thr Arg Val Trp Met Ser Leu Asn Leu Asn Glu Leu
                    -30                 -25                 -20

AGT TTG TAT TCT AGA ACC TGG GTT TTT ACA TGT TTG GTC TTT TTT TGT          363
Ser Leu Tyr Ser Arg Thr Trp Val Phe Thr Cys Leu Val Phe Phe Cys
                -15                 -10                  -5

TTT GGK TTG TCA MCC TCG CTA GGG                                          387
Phe Gly Leu Ser Xaa Ser Leu Gly
              1           5
```

(2) INFORMATION FOR SEQ ID NO: 226:

(i) SEQUENCE CHARACTERISTICS:
       (A) LENGTH: 300 base pairs
       (B) TYPE: NUCLEIC ACID
       (C) STRANDEDNESS: DOUBLE
       (D) TOPOLOGY: LINEAR (ii) MOLECULE TYPE: CDNA (vi) ORIGINAL SOURCE:
       (A) ORGANISM: Homo Sapiens
       (F) TISSUE TYPE: Brain (ix) FEATURE:
       (A) NAME/KEY: other
       (B) LOCATION: 123..295
       (C) IDENTIFICATION METHOD: blastn
       (D) OTHER INFORMATION: identity 97 region 121..293 id N78275
           est (ix) FEATURE:
       (A) NAME/KEY: other
       (B) LOCATION: 43..128
       (C) IDENTIFICATION METHOD: blastn
       (D) OTHER INFORMATION: identity 100 region 40..125 id N78275
           est (ix) FEATURE:
       (A) NAME/KEY: other
       (B) LOCATION: 19..295
       (C) IDENTIFICATION METHOD: blastn
       (D) OTHER INFORMATION: identity 99 region 4..280 id R35388
           est (ix) FEATURE:
       (A) NAME/KEY: other
       (B) LOCATION: 40..295
       (C) IDENTIFICATION METHOD: blastn
       (D) OTHER INFORMATION: identity 98 region 14..269 id W03418
           est (ix) FEATURE:
       (A) NAME/KEY: other
       (B) LOCATION: 29..283
       (C) IDENTIFICATION METHOD: blastn
       (D) OTHER INFORMATION: identity 98 region 27..281 id
           HSC29H041 est (ix) FEATURE:
       (A) NAME/KEY: other
       (B) LOCATION: 49..266
       (C) IDENTIFICATION METHOD: blastn
       (D) OTHER INFORMATION: identity 96 region 78..295 id R60376
           est (ix) FEATURE:
       (A) NAME/KEY: sig_peptide
       (B) LOCATION: 184..270
       (C) IDENTIFICATION METHOD: Von Heijne matrix
       (D) OTHER INFORMATION: score 5.2 seq FFMLLGSLLPVKI/IE (xi) SEQUENCE DESCRIPTION: SEQ ID NO: 226:

```
AAGACTGCGC GGCCGTWGGG CGTGCAGCGG CGCCAGTCGG CGGACGAGGG GCCCCCGGGA      60

GTTGCTGGAC TGAGACATGA GCCTCCAACT GTGTGGTTGG GCTCGGTAGC ACATCGTGGG     120

ACTTGGGTGT GCGCCCACAG ATGGTTTGGC CCTGCAGTGA CCAGAGCAGC CCAAGCCGCC     180

ACC ATG GTG AAA TTG CTA GTG GCC AAA ATC CTG TGC ATG GTG GGC GTG      228
    Met Val Lys Leu Leu Val Ala Lys Ile Leu Cys Met Val Gly Val
            -25             Ala Lys Ile -20              Gly -15

TTC TTC TTC ATG CTG CTC GGC TCC CTG CTC CCC GTG AAG ATC ATC GAG      276
Phe Phe Phe Met Leu Leu Gly Ser Leu Leu Pro Val Lys Ile Ile Glu
            -10             -5                           1

ACA GAT TTT GAG AAG GCC CCA GGG                                      300
Thr Asp Phe Glu Lys Ala Pro Gly
        5                   10
```

(2) INFORMATION FOR SEQ ID NO: 227:

(i) SEQUENCE CHARACTERISTICS:
        (A) LENGTH: 76 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(2..73)
        (C) IDENTIFICATION METHOD: blastn
        (D) OTHER INFORMATION: identity 98 region 40..111 id
            HSC39G092 est (ix) FEATURE:
        (A) NAME/KEY: other
        (B) LOCATION: complement(2..73)
        (C) IDENTIFICATION METHOD: blastn
        (D) OTHER INFORMATION: identity 98 region 37..108 id T89094
            est (ix) FEATURE:
        (A) NAME/KEY: sig_peptide
        (B) LOCATION: 11..61
        (C) IDENTIFICATION METHOD: Von Heijne matrix
        (D) OTHER INFORMATION: score 5.2 seq IMCLIGLKANASS/ET (xi) SEQUENCE DESCRIPTION: SEQ ID NO: 227:

```
ATCCTTTTGC ATG CCT GTT TCT ATC ATG TGC TTG ATA GGC CTC AAA GCT       49
           Met Pro Val Ser Ile Met Cys Leu Ile Gly Leu Lys Ala
               -15                 -10                     -5

AAT GCT TCC AGT GAA ACA CAC TCA GGG                                  76
Asn Ala Ser Ser Glu Thr His Ser Gly
 1               5
```

(2) INFORMATION FOR SEQ ID NO: 228:

(i) SEQUENCE CHARACTERISTICS:
        (A) LENGTH: 125 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:

(A) NAME/KEY: other
            (B) LOCATION: 11..120
            (C) IDENTIFICATION METHOD: blastn
            (D) OTHER INFORMATION: identity 100 region 1..110 id
                HSC3IG111 est (ix) FEATURE:
            (A) NAME/KEY: sig_peptide
            (B) LOCATION: 48..98
            (C) IDENTIFICATION METHOD: Von Heijne matrix
            (D) OTHER INFORMATION: score 5.2 seq LLYLVLEKLVSRA/FQ (xi) SEQUENCE DESCRIPTION: SEQ ID NO: 228:

```
AGATACTAAT CCTTTAAAAA AGTGTAAATG GAGAAAAGTT ATATTTT ATG AAG GTT        56
                                                    Met Lys Val
                                                            -15

ATT TTG TTG TAT TTA GTA TTG GAA AAG TTG GTT TCC AGA GCA TTT CAG       104
Ile Leu Leu Tyr Leu Val Leu Glu Lys Leu Val Ser Arg Ala Phe Gln
            -10                  -5                   1

AAT GTC GAA GCA CCA CAC GGG                                           125
Asn Val Glu Ala Pro His Gly
        5
```

(2) INFORMATION FOR SEQ ID NO: 229:

(i) SEQUENCE CHARACTERISTICS:
            (A) LENGTH: 170 base pairs
            (B) TYPE: NUCLEIC ACID
            (C) STRANDEDNESS: DOUBLE
            (D) TOPOLOGY: LINEAR (ii) MOLECULE TYPE: cDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: 81..170
            (C) IDENTIFICATION METHOD: blastn
            (D) OTHER INFORMATION: identity 97 region 54..143 id T09307
                est (ix) FEATURE:
            (A) NAME/KEY: other
            (B) LOCATION: 29..81
            (C) IDENTIFICATION METHOD: blastn
            (D) OTHER INFORMATION: identity 92 region 1..53 id T09307
                est (ix) FEATURE:
            (A) NAME/KEY: other
            (B) LOCATION: 12..77
            (C) IDENTIFICATION METHOD: blastn
            (D) OTHER INFORMATION: identity 98 region 1..66 id AA159859
                est (ix) FEATURE:
            (A) NAME/KEY: other
            (B) LOCATION: 28..75
            (C) IDENTIFICATION METHOD: blastn
            (D) OTHER INFORMATION: identity 95 region 1..48 id H13321
                est (ix) FEATURE:
            (A) NAME/KEY: other
            (B) LOCATION: 15..75
            (C) IDENTIFICATION METHOD: blastn
            (D) OTHER INFORMATION: identity 93 region 10..70 id W02365
                est (ix) FEATURE:
            (A) NAME/KEY: other
            (B) LOCATION: 33..77

```
            (C) IDENTIFICATION METHOD: blastn
            (D) OTHER INFORMATION:  identity 95 region 1..45 id AA113927
                est (ix) FEATURE:
            (A) NAME/KEY: sig_peptide
            (B) LOCATION: 33..89
            (C) IDENTIFICATION METHOD: Von Heijne matrix
            (D) OTHER INFORMATION:  score 5.1 seq LLLGGRVCXPSLA/VG (xi) SEQUENCE DESCRIPTION: SEQ ID NO: 229:

AAGCCGAYYG CTGAAGGCTG GTTTGCGTCG AC ATG GCG GTT ACC CTG AGT CTC          53
                                   Met Ala Val Thr Leu Ser Leu
                                                           -15

TTG CTG GGC GGG CGC GTT TGC SCG CCG TCA CTC GCT GTG GGT TCG CGA         101
Leu Leu Gly Gly Arg Val Cys Xaa Pro Ser Leu Ala Val Gly Ser Arg
        -10                 -5                   1

CCC GGG GGG TGG CGG GCC CAG GCC CTA TTG GCC GGG AGC CGG ACC CCG         149
Pro Gly Gly Trp Arg Ala Gln Ala Leu Leu Ala Gly Ser Arg Thr Pro
 5                  10                  15                  20

ATT CCG ACT GGG AAC CGG AGG                                             170
Ile Pro Thr Gly Asn Arg Arg
                25

(2) INFORMATION FOR SEQ ID NO: 230:

(i) SEQUENCE CHARACTERISTICS:
            (A) LENGTH: 263 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: 57..261
            (C) IDENTIFICATION METHOD: blastn
            (D) OTHER INFORMATION:  identity 97 region 40..244 id R59037
                est (ix) FEATURE:
            (A) NAME/KEY: other
            (B) LOCATION: complement(184..237)
            (C) IDENTIFICATION METHOD: blastn
            (D) OTHER INFORMATION:  identity 100 region 38..91 id R67654
                est (ix) FEATURE:
            (A) NAME/KEY: sig_peptide
            (B) LOCATION: 117..185
            (C) IDENTIFICATION METHOD: Von Heijne matrix
            (D) OTHER INFORMATION:  score 5.1 seq LLPELGVVTPAQG/PR (xi) SEQUENCE DESCRIPTION: SEQ ID NO: 230:

AAGACCATCA ACTATGGAAA GGAGATCTAG GGAACACCGT CTTGAACCCG CCAGGGTTTT         60

GAGTCTCGGA CCCAGGAGAT CCAACCCTGA CCACCCTCCC AGGATGCAGC AGGGGG ATG       119
                                                                Met

TTA AAT CAG ACT TCA GGA AGA ACT TCC TTG CTG CCT GAG TTA GGT GTC         167
Leu Asn Gln Thr Ser Gly Arg Thr Ser Leu Leu Pro Glu Leu Gly Val
        -20                 -15                 -10

GTC ACG CCT GCC CAG GGG CCA AGG AGG CGG GTT TGG TGC GGC CAC TCC         215
Val Thr Pro Ala Gln Gly Pro Arg Arg Arg Val Trp Cys Gly His Ser
        -5                   1                   5                  10

AAG GCC AAA GCG AGA AAA TCT TAC TGC GCA CGC GCA ATA GAC TGC CAG         263
```

```
Lys Ala Lys Ala Arg Lys Ser Tyr Cys Ala Arg Ala Ile Asp Cys Gln
            15                  20                  25
```

(2) INFORMATION FOR SEQ ID NO: 231:

(i) SEQUENCE CHARACTERISTICS:
      (A) LENGTH: 430 base pairs
      (B) TYPE: NUCLEIC ACID
      (C) STRANDEDNESS: DOUBLE
      (D) TOPOLOGY: LINEAR (ii) MOLECULE TYPE: cDNA (vi) ORIGINAL SOURCE:
      (A) ORGANISM: Homo Sapiens
      (F) TISSUE TYPE: Brain (ix) FEATURE:
      (A) NAME/KEY: other
      (B) LOCATION: 99..416
      (C) IDENTIFICATION METHOD: blastn
      (D) OTHER INFORMATION: identity 99 region 1..318 id T31969
         est (ix) FEATURE:
      (A) NAME/KEY: other
      (B) LOCATION: 49..334
      (C) IDENTIFICATION METHOD: blastn
      (D) OTHER INFORMATION: identity 99 region 2..287 id HSB03B072
         est (ix) FEATURE:
      (A) NAME/KEY: other
      (B) LOCATION: complement(2..57)
      (C) IDENTIFICATION METHOD: blastn
      (D) OTHER INFORMATION: identity 100 region 1..56 id W51830
         est (ix) FEATURE:
      (A) NAME/KEY: sig_peptide
      (B) LOCATION: 26..262
      (C) IDENTIFICATION METHOD: Von Heijne matrix
      (D) OTHER INFORMATION: score 5 seq SFLGFSAPTPIQA/LT (xi) SEQUENCE DESCRIPTION: SEQ ID NO: 231:

```
ATGTGATGAT CCGGAGGCTG GGGAG ATG ACA TCA GAA AAC CTG GTC CAA ACT          52
                            Met Thr Ser Glu Asn Leu Val Gln Thr
                                                -75

GCT CCA AAA AAG AAG AAA AAT AAA GGG AAA AAA GGG TTG GAG CCT TCT         100
Ala Pro Lys Lys Lys Lys Asn Lys Gly Lys Lys Gly Leu Glu Pro Ser
-70             -65                 -60                 -55

CAG AGC ACT GCT GCC AAG GTG CCC AAA AAA GCG AAG ACA TGG ATT CCT         148
Gln Ser Thr Ala Ala Lys Val Pro Lys Lys Ala Lys Thr Trp Ile Pro
            -50                 -45                 -40

GAA GTT CAT GAT CAG AAA GCA GAT GTG TCA GCT TGG AAG GAC CTG TTT         196
Glu Val His Asp Gln Lys Ala Asp Val Ser Ala Trp Lys Asp Leu Phe
        -35                 -30                 -25

GTT CCC AGG CCG GTT CTC CGA GCA CTC AGC TTT CTA GGC TTC TCT GCA         244
Val Pro Arg Pro Val Leu Arg Ala Leu Ser Phe Leu Gly Phe Ser Ala
    -20                 -15                 -10

CCC ACA CCA ATC CAA GCC CTG ACC TTG GCA CCT GCC ATC CGT GAC AAA         292
Pro Thr Pro Ile Gln Ala Leu Thr Leu Ala Pro Ala Ile Arg Asp Lys
     -5                  1                   5                  10

CTG GAC ATC CTT GGG GCT GCT GAG ACA GGA AGT GGG AAA ACT CTT GCC         340
Leu Asp Ile Leu Gly Ala Ala Glu Thr Gly Ser Gly Lys Thr Leu Ala
             15                  20                  25

TTT GCC ATC CCA ATG ATT CAT GCG GTG TTG CAG TGG CAG AAG AGG AAT         388
Phe Ala Ile Pro Met Ile His Ala Val Leu Gln Trp Gln Lys Arg Asn
             30                  35                  40
```

```
GCT GCC CCT CCT CCA AGT AAC ACC GAA GCA CCA CCT GGA GAG           430
Ala Ala Pro Pro Pro Ser Asn Thr Glu Ala Pro Pro Gly Glu
        45                  50                  55
```

(2) INFORMATION FOR SEQ ID NO: 232:

(i) SEQUENCE CHARACTERISTICS:
        (A) LENGTH: 252 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 1..37
        (C) IDENTIFICATION METHOD: blastn
        (D) OTHER INFORMATION: identity 97 region 9..45 id W84513
            est (ix) FEATURE:
        (A) NAME/KEY: sig_peptide
        (B) LOCATION: 16..84
        (C) IDENTIFICATION METHOD: Von Heijne matrix
        (D) OTHER INFORMATION: score 4.9 seq WHXLIPLTWACMA/RQ (xi) SEQUENCE DESCRIPTION: SEQ ID NO: 232:

```
AATCTTCTCC GCGCT ATG GCT GCG TTC GGC CGT CAG SCW TTS ART TGG CAC    51
               Met Ala Ala Phe Gly Arg Gln Xaa Xaa Xaa Trp His
                -20                             -15

CKY CTG ATC CCC CTC ACC TGG GCC TGT ATG GCT AGG CAG ACT CCT CAT     99
Xaa Leu Ile Pro Leu Thr Trp Ala Cys Met Ala Arg Gln Thr Pro His
    -10                 -5                   1                  5

CTT GGA GAA CAG AGA AGG ACG ACA GCT TCT TTG TKG CGC AAA CTG ACT    147
Leu Gly Glu Gln Arg Arg Thr Thr Ala Ser Leu Xaa Arg Lys Leu Thr
            10                  15                  20

ACA GCC TCC AAT GGA GGG GTC ATT GAG GAG TTA TCT TGT GTK AGA TCC    195
Thr Ala Ser Asn Gly Gly Val Ile Glu Glu Leu Ser Cys Val Arg Ser
        25                  30                  35

AAT AAC TAT GTG CAG GAA CCA GAG TGC AGG AGG AAT CTT GTT CAG TGC    243
Asn Asn Tyr Val Gln Glu Pro Glu Cys Arg Arg Asn Leu Val Gln Cys
        40                  45                  50

CTC CTC TGG                                                        252
Leu Leu Trp
        55
```

(2) INFORMATION FOR SEQ ID NO: 233:

(i) SEQUENCE CHARACTERISTICS:
        (A) LENGTH: 347 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 44..187
        (C) IDENTIFICATION METHOD: blastn
        (D) OTHER INFORMATION: identity 96 region 1..144 id AA151232
            est (ix) FEATURE:
        (A) NAME/KEY: other
        (B) LOCATION: 187..285
        (C) IDENTIFICATION METHOD: blastn
        (D) OTHER INFORMATION: identity 97 region 143..241 id
            AA151232 est (ix) FEATURE:
        (A) NAME/KEY: other
        (B) LOCATION: 314..349
        (C) IDENTIFICATION METHOD: blastn
        (D) OTHER INFORMATION: identity 100 region 272..307 id
            AA151232 est (ix) FEATURE:
        (A) NAME/KEY: other
        (B) LOCATION: 39..225
        (C) IDENTIFICATION METHOD: blastn
        (D) OTHER INFORMATION: identity 95 region 2..188 id AA040887
            est (ix) FEATURE:
        (A) NAME/KEY: sig_peptide
        (B) LOCATION: 144..314
        (C) IDENTIFICATION METHOD: Von Heijne matrix
        (D) OTHER INFORMATION: score 4.9 seq GWFLSGCPHGSSA/TW (xi) SEQUENCE DESCRIPTION: SEQ ID NO: 233:

AATGGGGATG TTGAATTTGG AAATTGGAGG GGACGCTGGT GGWYKKATTG GGTGCAAGGA      60

GTTGGTGTTG ATGGAGGAGC AGGASRCCAG AGTCCCAGCC CTGGAACCGT TCAGAGTGGA     120

GCAGGCACCA CCTGTAATCT ACT ATG TCC CTG ACT TCA TCT CCA AAG AAG AGG    173
                         Met Ser Leu Thr Ser Ser Pro Lys Lys Arg
                             -55                         -50

AGG AGT ATT TGC TTC GAC AGG TTT TTA ATG CCC CAA AGC CAA AGT GGA      221
Arg Ser Ile Cys Phe Asp Arg Phe Leu Met Pro Gln Ser Gln Ser Gly
    -45                 -40                 -35

CCC AGC TCT CTG GGA GAA AGT TAC AGA ACT GGG GTG GGC TTC CTC ATC      269
Pro Ser Ser Leu Gly Glu Ser Tyr Arg Thr Gly Val Gly Phe Leu Ile
    -30                 -25                 -20

CCC GAG GGA TGG TTC CTG AGC GGC TGC CCC CAT GGC TCC AGC GCT ACG      317
Pro Glu Gly Trp Phe Leu Ser Gly Cys Pro His Gly Ser Ser Ala Thr
-15                 -10                  -5                   1

TGG ACA AAG TGT CAA ACC TCA GCC TCT TTG                              347
Trp Thr Lys Cys Gln Thr Ser Ala Ser Leu
        5                   10

(2) INFORMATION FOR SEQ ID NO: 234:

(i) SEQUENCE CHARACTERISTICS:
        (A) LENGTH: 227 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 115..226
        (C) IDENTIFICATION METHOD: blastn
        (D) OTHER INFORMATION: identity 95 region 135..246 id
            HSC0GF021 est (ix) FEATURE:
        (A) NAME/KEY: sig_peptide
        (B) LOCATION: 90..206

(C) IDENTIFICATION METHOD: Von Heijne matrix
            (D) OTHER INFORMATION: score 4.8 seq SLXFCLSPPPSPS/LR (xi) SEQUENCE DESCRIPTION: SEQ ID NO: 234:

```
AAACCCCATA CCCCCTCCCC ATCTTGTGAT CACCCTCATT ACCTCTTCTG GGCCCCCTGT        60

GGACCTGCGT TGACCCAGCA TGGGCTACA ATG GGG GAG TTG GGT AAT CGC TCC        113
                                Met Gly Glu Leu Gly Asn Arg Ser
                                               -35

CGT TGC ATC CTG TTT CTG TCT GAA AAC CCT TGT CTT TCT GAA TCC ATC        161
Arg Cys Ile Leu Phe Leu Ser Glu Asn Pro Cys Leu Ser Glu Ser Ile
    -30                 -25                 -20

TTT CAG TCT CTS RCA TTC TGT CTT TCC CCT CCT CCT TCA CCT TCC CTC        209
Phe Gln Ser Leu Xaa Phe Cys Leu Ser Pro Pro Pro Ser Pro Ser Leu
-15                 -10                  -5                   1

CGT CCC TCT CCC TCA CGG                                                227
Arg Pro Ser Pro Ser Arg
             5
```

(2) INFORMATION FOR SEQ ID NO: 235:

(i) SEQUENCE CHARACTERISTICS:
        (A) LENGTH: 430 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 101..355
        (C) IDENTIFICATION METHOD: blastn
        (D) OTHER INFORMATION: identity 99 region 83..337 id AA057242
            est (ix) FEATURE:
        (A) NAME/KEY: other
        (B) LOCATION: 57..101
        (C) IDENTIFICATION METHOD: blastn
        (D) OTHER INFORMATION: identity 100 region 40..84 id AA057242
            est (ix) FEATURE:
        (A) NAME/KEY: other
        (B) LOCATION: 357..400
        (C) IDENTIFICATION METHOD: blastn
        (D) OTHER INFORMATION: identity 100 region 338..381 id
            AA057242 est (ix) FEATURE:
        (A) NAME/KEY: other
        (B) LOCATION: 18..51
        (C) IDENTIFICATION METHOD: blastn
        (D) OTHER INFORMATION: identity 100 region 1..34 id AA057242
            est (ix) FEATURE:
        (A) NAME/KEY: other
        (B) LOCATION: 400..431
        (C) IDENTIFICATION METHOD: blastn
        (D) OTHER INFORMATION: identity 100 region 382..413 id
            AA057242 est (ix) FEATURE:
        (A) NAME/KEY: other
        (B) LOCATION: 84..218
        (C) IDENTIFICATION METHOD: blastn
        (D) OTHER INFORMATION: identity 97 region 73..207 id R09808
            est (ix) FEATURE:
    (A) NAME/KEY: other
    (B) LOCATION: 10..51
    (C) IDENTIFICATION METHOD: blastn
    (D) OTHER INFORMATION: identity 100 region 1..42 id R09808
        est (ix) FEATURE:
    (A) NAME/KEY: sig_peptide
    (B) LOCATION: 98..376
    (C) IDENTIFICATION METHOD: Von Heijne matrix
    (D) OTHER INFORMATION: score 4.7 seq VLLLRQXFAQAEK/WY (xi) SEQUENCE DESCRIPTION: SEQ ID NO: 235:

```
AATTTTCYGT GGTCCAACTA CCCTCGGCGA TCCCAGGCTT GGCGGGGCAC CGCCTGGCCT        60

CTCCCGTTCC TTTAGGCTGC CGCCGCTGCC TGCCGCC ATG GCA GAG TTG GGC CTA       115
                                         Met Ala Glu Leu Gly Leu
                                                         -90

AAT GAG CAC CAT CAA AAT GAA GTT ATT AAT TAT ATG CGT TTT GCT CGT        163
Asn Glu His His Gln Asn Glu Val Ile Asn Tyr Met Arg Phe Ala Arg
        -85              -80              -75

TCA AAG AGA GGC TTG AGA CTC AAA ACT GTA GAT TCC TGC TTC CAA GAC        211
Ser Lys Arg Gly Leu Arg Leu Lys Thr Val Asp Ser Cys Phe Gln Asp
-70              -65              -60

CTC AAG GAG AGC AGG CTG GTG GAG GAC ACC TTC ACC ATA GAT GAA GTC        259
Leu Lys Glu Ser Arg Leu Val Glu Asp Thr Phe Thr Ile Asp Glu Val
-55              -50              -45                       -40

TCT GAA GTC CTC AAT GGA TTA CAA GCT GTG GTT CAT AGT GAG GTG GAA        307
Ser Glu Val Leu Asn Gly Leu Gln Ala Val Val His Ser Glu Val Glu
            -35              -30              -25

TCT GAG CTC ATC AAC ACT GCC TAT ACC AAT GTG TTA CTT CTG CGA CAG        355
Ser Glu Leu Ile Asn Thr Ala Tyr Thr Asn Val Leu Leu Leu Arg Gln
            -20              -15              -10

NTG TTT GCA CAA GCT GAG AAG TGG TAT CTT AAG CTA CAG ACA GAC ATC        403
Xaa Phe Ala Gln Ala Glu Lys Trp Tyr Leu Lys Leu Gln Thr Asp Ile
        -5               1                5

TCT GAA CTT GAA AAC CGA GAA TTA TTA                                    430
Ser Glu Leu Glu Asn Arg Glu Leu Leu
10                  15
```

(2) INFORMATION FOR SEQ ID NO: 236:

(i) SEQUENCE CHARACTERISTICS:
        (A) LENGTH: 344 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 20..231
        (C) IDENTIFICATION METHOD: blastn
        (D) OTHER INFORMATION: identity 99 region 1..212 id N33729
            est (ix) FEATURE:
        (A) NAME/KEY: sig_peptide
        (B) LOCATION: 135..281
        (C) IDENTIFICATION METHOD: Von Heijne matrix
        (D) OTHER INFORMATION: score 4.6 seq SWAVGLLYAVAQG/SK (xi) SEQUENCE DESCRIPTION: SEQ ID NO: 236:

```
AATTAGCGAG GCCATGGGGG AAAAAGTCTA ACTGGCGGAA CTCCTGGGAA CTGGGGCGAT        60

GGGCTCTTAG TATCGGAGGA TTGGAGCCAT CTGATTTTTA CCTGAAATTC CTTAGTCTCT       120

CCTGTGTTGG GGAA ATG GTC ACC TTG CCT TCA GGG ACC TGG GCT TTC AGC        170
              Met Val Thr Leu Pro Ser Gly Thr Trp Ala Phe Ser
                      -45                 -40

TGT CCA TAC CTG GCC CTG GTT GAT GGC GGC ATG CTG GGC AGT GCA CGT        218
Cys Pro Tyr Leu Ala Leu Val Asp Gly Gly Met Leu Gly Ser Ala Arg
        -35             -30                 -25

GAA GAC GCA CAT GCA TCT GTT GTT TCC TGG GCA GTT GGT CTT CTT TAT        266
Glu Asp Ala His Ala Ser Val Val Ser Trp Ala Val Gly Leu Leu Tyr
    -20             -15                 -10

GCA GTG GCT CAG GGC TCC AAG AGA AGG AAA GTG CAA GAT GTC AAG CCT        314
Ala Val Ala Gln Gly Ser Lys Arg Arg Lys Val Gln Asp Val Lys Pro
 -5              1               5                  10

CTT NGT TGG TCA AGA ACT GGC ACC CTC GGG                                344
Leu Xaa Trp Ser Arg Thr Gly Thr Leu Gly
         15              20

(2) INFORMATION FOR SEQ ID NO: 237:

(i) SEQUENCE CHARACTERISTICS:
        (A) LENGTH: 419 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 116..419
        (C) IDENTIFICATION METHOD: blastn
        (D) OTHER INFORMATION:  identity 98 region 122..425 id W68799
            est (ix) FEATURE:
        (A) NAME/KEY: other
        (B) LOCATION: 18..117
        (C) IDENTIFICATION METHOD: blastn
        (D) OTHER INFORMATION:  identity 97 region 1..100 id W68799
            est (ix) FEATURE:
        (A) NAME/KEY: other
        (B) LOCATION: 18..209
        (C) IDENTIFICATION METHOD: blastn
        (D) OTHER INFORMATION:  identity 93 region 1..192 id W49697
            est (ix) FEATURE:
        (A) NAME/KEY: other
        (B) LOCATION: 199..290
        (C) IDENTIFICATION METHOD: blastn
        (D) OTHER INFORMATION:  identity 95 region 183..274 id W49697
            est (ix) FEATURE:
        (A) NAME/KEY: other
        (B) LOCATION: 291..367
        (C) IDENTIFICATION METHOD: blastn
        (D) OTHER INFORMATION:  identity 97 region 276..352 id W49697
            est (ix) FEATURE:
        (A) NAME/KEY: other
        (B) LOCATION: 387..417
        (C) IDENTIFICATION METHOD: blastn
```

(D) OTHER INFORMATION: identity 100 region 374..404 id W49697
                  est (ix) FEATURE:
              (A) NAME/KEY: other
              (B) LOCATION: 48..419
              (C) IDENTIFICATION METHOD: blastn
              (D) OTHER INFORMATION: identity 98 region 1..372 id AA149518
                  est (ix) FEATURE:
              (A) NAME/KEY: other
              (B) LOCATION: 171..414
              (C) IDENTIFICATION METHOD: blastn
              (D) OTHER INFORMATION: identity 97 region 116..359 id W17032
                  est (ix) FEATURE:
              (A) NAME/KEY: other
              (B) LOCATION: 57..174
              (C) IDENTIFICATION METHOD: blastn
              (D) OTHER INFORMATION: identity 97 region 1..118 id W17032
                  est (ix) FEATURE:
              (A) NAME/KEY: other
              (B) LOCATION: 78..386
              (C) IDENTIFICATION METHOD: blastn
              (D) OTHER INFORMATION: identity 98 region 1..309 id W78749
                  est (ix) FEATURE:
              (A) NAME/KEY: other
              (B) LOCATION: 386..419
              (C) IDENTIFICATION METHOD: blastn
              (D) OTHER INFORMATION: identity 100 region 310..343 id W78749
                  est (ix) FEATURE:
              (A) NAME/KEY: sig_peptide
              (B) LOCATION: 180..383
              (C) IDENTIFICATION METHOD: Von Heijne matrix
              (D) OTHER INFORMATION: score 4.6 seq LPFSLVSMLVTQG/LV (xi) SEQUENCE DESCRIPTION: SEQ ID NO: 237:

AAGACAGGTG GGGTACTCGG GAAGCTGGAG CGGGCCGGCG GTGCAGTCAC GGGGGAGCGA         60

GGCCTGCTGG GCTTGGCAAC GAGGGACTCG GCCTCGGAGG CGACCCAGAC CACACAGACA        120

CTGGGTCAAG GAGTAAGCAG AGGATAAACA ACTGGAAGGA GAGCAAGCAC AAAGTCATC         179

ATG GCT TCA GCG TCT GCT CGT GGA AAC CAA GAT AAA GAT GCC CAT TTT          227
Met Ala Ser Ala Ser Ala Arg Gly Asn Gln Asp Lys Asp Ala His Phe
        -65                 -60                 -55

CCA CCA CCA AGC AAG CAG AGC CTG TTG TTT TGT CCA AAA TMH NNA CTG          275
Pro Pro Pro Ser Lys Gln Ser Leu Leu Phe Cys Pro Lys Xaa Xaa Leu
    -50                 -45                 -40

CAC ATC CAC AGA GCA GAG ATC TCA AAG ATT ATG CGA GAA TGT CAG GAA          323
His Ile His Arg Ala Glu Ile Ser Lys Ile Met Arg Glu Cys Gln Glu
-35                 -30                 -25

GAA AGT TTC TGG AAG AGA GCT CTG CCT TTT TCT CTT GTA AGC ATG CTT          371
Glu Ser Phe Trp Lys Arg Ala Leu Pro Phe Ser Leu Val Ser Met Leu
-20                 -15                 -10                 -5

GTC ACC CAG GGA CTA GTC TAC CAA GGT TAT TTG GCA GCT AAT TCT AGA          419
Val Thr Gln Gly Leu Val Tyr Gln Gly Tyr Leu Ala Ala Asn Ser Arg
                1                   5                   10

(2) INFORMATION FOR SEQ ID NO: 238:

(i) SEQUENCE CHARACTERISTICS:
              (A) LENGTH: 274 base pairs
              (B) TYPE: NUCLEIC ACID
              (C) STRANDEDNESS: DOUBLE (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(37..269)
        (C) IDENTIFICATION METHOD: blastn
        (D) OTHER INFORMATION: identity 99 region 2..234 id AA147071
            est (ix) FEATURE:
        (A) NAME/KEY: other
        (B) LOCATION: complement(2..31)
        (C) IDENTIFICATION METHOD: blastn
        (D) OTHER INFORMATION: identity 93 region 239..268 id
            AA147071 est (ix) FEATURE:
        (A) NAME/KEY: other
        (B) LOCATION: complement(37..269)
        (C) IDENTIFICATION METHOD: blastn
        (D) OTHER INFORMATION: identity 99 region 58..290 id H98153
            est (ix) FEATURE:
        (A) NAME/KEY: other
        (B) LOCATION: complement(2..31)
        (C) IDENTIFICATION METHOD: blastn
        (D) OTHER INFORMATION: identity 93 region 295..324 id H98153
            est (ix) FEATURE:
        (A) NAME/KEY: other
        (B) LOCATION: complement(37..269)
        (C) IDENTIFICATION METHOD: blastn
        (D) OTHER INFORMATION: identity 98 region 59..291 id N49401
            est (ix) FEATURE:
        (A) NAME/KEY: other
        (B) LOCATION: complement(2..31)
        (C) IDENTIFICATION METHOD: blastn
        (D) OTHER INFORMATION: identity 93 region 296..325 id N49401
            est (ix) FEATURE:
        (A) NAME/KEY: other
        (B) LOCATION: complement(87..269)
        (C) IDENTIFICATION METHOD: blastn
        (D) OTHER INFORMATION: identity 99 region 37..219 id N80022
            est (ix) FEATURE:
        (A) NAME/KEY: sig_peptide
        (B) LOCATION: 62..268
        (C) IDENTIFICATION METHOD: Von Heijne matrix
        (D) OTHER INFORMATION: score 4.5 seq FILSLCVLCIVLT/TG (xi) SEQUENCE DESCRIPTION: SEQ ID NO: 238:

```
AATTAAGTCA KDATACAAAT CAGCACAGAT AACGDMAATG TTTCCAATAT WWTAAAATGT       60

A ATG TTA CTT ATG AAA AGT ATT TTG CTT AAG GTT GTG TGT GTA TTG TGT      109
  Met Leu Leu Met Lys Ser Ile Leu Leu Lys Val Val Cys Val Leu Cys
              -65                 -60                 -55

ATA TAC CTC AAG TTC AAG TTA ATG GCA TTG ATT TAT GTT CCA GAC AAA        157
Ile Tyr Leu Lys Phe Lys Leu Met Ala Leu Ile Tyr Val Pro Asp Lys
            -50                 -45                 -40

AAT AAC ACA AAT AAT AAT ATC CTT CGT TAT AAC CAC AAT GAG ATA AGT        205
Asn Asn Thr Asn Asn Asn Ile Leu Arg Tyr Asn His Asn Glu Ile Ser
            -35                 -30                 -25
```

```
ATT GGC ATT AGT GTT CAG TGC CAT TTT ATA CTT TCT CTC TGT GTT CTC         253
Ile Gly Ile Ser Val Gln Cys His Phe Ile Leu Ser Leu Cys Val Leu
    -20             -15                 -10

TGT ATT GTA CTA ACC ACT GGG                                              274
Cys Ile Val Leu Thr Thr Gly
 -5               1
```

(2) INFORMATION FOR SEQ ID NO: 239:

(i) SEQUENCE CHARACTERISTICS:
        (A) LENGTH: 249 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 100..249
        (C) IDENTIFICATION METHOD: blastn
        (D) OTHER INFORMATION: identity 94 region 20..169 id N41898
           est (ix) FEATURE:
        (A) NAME/KEY: other
        (B) LOCATION: 113..249
        (C) IDENTIFICATION METHOD: blastn
        (D) OTHER INFORMATION: identity 94 region 38..174 id H69272
           est (ix) FEATURE:
        (A) NAME/KEY: sig_peptide
        (B) LOCATION: 100..147
        (C) IDENTIFICATION METHOD: Von Heijne matrix
        (D) OTHER INFORMATION: score 4.5 seq RLLLRRFLASVIS/RK (xi) SEQUENCE DESCRIPTION: SEQ ID NO: 239:

```
AGTTATGTAC GTTCCCCCCC CCGAGGAAGT GAYGACAGGC GTGCCCTTGA CAGGCAGGGA          60

GGGCTAGGCT GTGCATCCCT CCGCTCGCAT GCAGGGAG ATG GCT CAG CGA CTT            114
                                          Met Ala Gln Arg Leu
                                                          -15

CTT CTG AGG AGG TTC CTG GCC TCT GTC ATC TCC AGG AAG CCC TCT CAG          162
Leu Leu Arg Arg Phe Leu Ala Ser Val Ile Ser Arg Lys Pro Ser Gln
    -10             -5                   1                   5

GGT CAG TGG CCA CCC CTC ACT TCC AGA GCC CTG CAG ACC CCA YAA TGC          210
Gly Gln Trp Pro Pro Leu Thr Ser Arg Ala Leu Gln Thr Pro Xaa Cys
                10              15                  20

AGT YCT GGT GGC CTG ACT GTA ACA CCC AAC CCA AGC CGG                      249
Ser Xaa Gly Gly Leu Thr Val Thr Pro Asn Pro Ser Arg
        25                  30
```

(2) INFORMATION FOR SEQ ID NO: 240:

(i) SEQUENCE CHARACTERISTICS:
        (A) LENGTH: 310 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:

```
        (A) NAME/KEY: other
        (B) LOCATION: 51..209
        (C) IDENTIFICATION METHOD: blastn
        (D) OTHER INFORMATION:  identity 99 region 49..207 id N56053
            est (ix) FEATURE:
        (A) NAME/KEY: other
        (B) LOCATION: 2..54
        (C) IDENTIFICATION METHOD: blastn
        (D) OTHER INFORMATION:  identity 96 region 1..53 id N56053
            est (ix) FEATURE:
        (A) NAME/KEY: other
        (B) LOCATION: 211..246
        (C) IDENTIFICATION METHOD: blastn
        (D) OTHER INFORMATION:  identity 100 region 208..243 id N56053
            est (ix) FEATURE:
        (A) NAME/KEY: other
        (B) LOCATION: 275..307
        (C) IDENTIFICATION METHOD: blastn
        (D) OTHER INFORMATION:  identity 96 region 270..302 id N56053
            est (ix) FEATURE:
        (A) NAME/KEY: other
        (B) LOCATION: 51..178
        (C) IDENTIFICATION METHOD: blastn
        (D) OTHER INFORMATION:  identity 98 region 44..171 id R59444
            est (ix) FEATURE:
        (A) NAME/KEY: other
        (B) LOCATION: 212..275
        (C) IDENTIFICATION METHOD: blastn
        (D) OTHER INFORMATION:  identity 100 region 203..266 id R59444
            est (ix) FEATURE:
        (A) NAME/KEY: other
        (B) LOCATION: 7..54
        (C) IDENTIFICATION METHOD: blastn
        (D) OTHER INFORMATION:  identity 95 region 1..48 id R59444
            est (ix) FEATURE:
        (A) NAME/KEY: other
        (B) LOCATION: 274..308
        (C) IDENTIFICATION METHOD: blastn
        (D) OTHER INFORMATION:  identity 100 region 266..300 id R59444
            est (ix) FEATURE:
        (A) NAME/KEY: other
        (B) LOCATION: 178..209
        (C) IDENTIFICATION METHOD: blastn
        (D) OTHER INFORMATION:  identity 100 region 170..201 id R59444
            est (ix) FEATURE:
        (A) NAME/KEY: other
        (B) LOCATION: 51..178
        (C) IDENTIFICATION METHOD: blastn
        (D) OTHER INFORMATION:  identity 98 region 45..172 id AA156837
            est (ix) FEATURE:
        (A) NAME/KEY: other
        (B) LOCATION: 178..246
        (C) IDENTIFICATION METHOD: blastn
        (D) OTHER INFORMATION:  identity 100 region 171..239 id
            AA156837 est (ix) FEATURE:
        (A) NAME/KEY: other
        (B) LOCATION: 247..308
```

```
            (C) IDENTIFICATION METHOD: blastn
            (D) OTHER INFORMATION: identity 100 region 239..300 id
                AA156837 est (ix) FEATURE:
            (A) NAME/KEY: other
            (B) LOCATION: 6..54
            (C) IDENTIFICATION METHOD: blastn
            (D) OTHER INFORMATION: identity 95 region 1..49 id AA156837
                est (ix) FEATURE:
            (A) NAME/KEY: other
            (B) LOCATION: 51..178
            (C) IDENTIFICATION METHOD: blastn
            (D) OTHER INFORMATION: identity 99 region 56..183 id N88392
                est (ix) FEATURE:
            (A) NAME/KEY: other
            (B) LOCATION: 13..54
            (C) IDENTIFICATION METHOD: blastn
            (D) OTHER INFORMATION: identity 95 region 19..60 id N88392
                est (ix) FEATURE:
            (A) NAME/KEY: other
            (B) LOCATION: 247..285
            (C) IDENTIFICATION METHOD: blastn
            (D) OTHER INFORMATION: identity 100 region 249..287 id N88392
                est (ix) FEATURE:
            (A) NAME/KEY: other
            (B) LOCATION: 211..246
            (C) IDENTIFICATION METHOD: blastn
            (D) OTHER INFORMATION: identity 100 region 214..249 id N88392
                est (ix) FEATURE:
            (A) NAME/KEY: other
            (B) LOCATION: 179..209
            (C) IDENTIFICATION METHOD: blastn
            (D) OTHER INFORMATION: identity 100 region 183..213 id N88392
                est (ix) FEATURE:
            (A) NAME/KEY: other
            (B) LOCATION: 7..209
            (C) IDENTIFICATION METHOD: blastn
            (D) OTHER INFORMATION: identity 98 region 1..203 id R18752
                est (ix) FEATURE:
            (A) NAME/KEY: other
            (B) LOCATION: 211..246
            (C) IDENTIFICATION METHOD: blastn
            (D) OTHER INFORMATION: identity 100 region 204..239 id R18752
                est (ix) FEATURE:
            (A) NAME/KEY: sig_peptide
            (B) LOCATION: 2..232
            (C) IDENTIFICATION METHOD: Von Heijne matrix
            (D) OTHER INFORMATION: score 4.4 seq FEARIALLPLLQA/ET (xi) SEQUENCE DESCRIPTION: SEQ ID NO: 240:

A ATG GCG GCG TCA AAG GTG AAG CAG GAC ATG CCT CCR MCG GGG GGC TAT      49
  Met Ala Ala Ser Lys Val Lys Gln Asp Met Pro Pro Xaa Gly Gly Tyr
            -75                 -70                 -65

GGG CCC ATC GAC TAC AAA CGG AAC TTG CCG CGT CGA GGA CTG TCG GGC        97
Gly Pro Ile Asp Tyr Lys Arg Asn Leu Pro Arg Arg Gly Leu Ser Gly
        -60                 -55                 -50

TAC AGC ATG CTG GCC ATA GGG ATT GGA ACC CTG ATC TAC GGG CAC TGG       145
Tyr Ser Met Leu Ala Ile Gly Ile Gly Thr Leu Ile Tyr Gly His Trp
    -45                 -40                 -35                 -30
```

```
AGC ATA ATG AAG TGG AAC CGT GAG CGC AGG CGC CTA CAA ATC GAG GAC      193
Ser Ile Met Lys Trp Asn Arg Glu Arg Arg Arg Leu Gln Ile Glu Asp
            -25                 -20                 -15

TTC GAG GCT CGC ATC GCG CTG TTG CCA CTG TTA CAG GCA GAA ACC GAC      241
Phe Glu Ala Arg Ile Ala Leu Leu Pro Leu Leu Gln Ala Glu Thr Asp
            -10                  -5                   1

CGG AGG ACC TTG CAG ATG CTT CGG GAG AAC CTG GAG GAG GAG GCC ATC      289
Arg Arg Thr Leu Gln Met Leu Arg Glu Asn Leu Glu Glu Glu Ala Ile
          5                  10                  15

ATC ATG AAG GAC GTG CCC GGA                                          310
Ile Met Lys Asp Val Pro Gly
 20                  25

(2) INFORMATION FOR SEQ ID NO: 241:

(i) SEQUENCE CHARACTERISTICS:
        (A) LENGTH: 388 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 93..257
        (C) IDENTIFICATION METHOD: blastn
        (D) OTHER INFORMATION:   identity 99 region 103..267 id H87397
            est (ix) FEATURE:
        (A) NAME/KEY: sig_peptide
        (B) LOCATION: 158..319
        (C) IDENTIFICATION METHOD: Von Heijne matrix
        (D) OTHER INFORMATION:   score 4.3 seq LLSLAILSHISTP/GC (xi) SEQUENCE DESCRIPTION: SEQ ID NO: 241:

AGACAAAGAG AAGGCAAAAT SAGTTTGTGT CCCTGAGTTG CTAAGTGGAG AAGAAACGTC     60

CACCAACCAG GAAACACCTG CCTCCAACTG TTAATAGGTC TGTGAAATGT GCTTTGTTTC    120

TGGTCAGCAT GGACACCCGC TTTAATAGTG GCTTCAG ATG AGG CAC CTT GTG ACA    175
                                        Met Arg His Leu Val Thr
                                                         -50

GAG GAG CTC TTC CCC TGC AGC AAC CTT GAA GAT GTT GTG GAA GAC AAT      223
Glu Glu Leu Phe Pro Cys Ser Asn Leu Glu Asp Val Val Glu Asp Asn
            -45                 -40                 -35

AGC CAT TCT TAC TTC ACT CTG AGG ATC ACG ATG GCG TGC AAG GGT GTG      271
Ser His Ser Tyr Phe Thr Leu Arg Ile Thr Met Ala Cys Lys Gly Val
            -30                 -25                 -20

CCA AGC ACA TTG CTA TCT TTG GCC ATT CTC TCT CAC ATT AGT ACA CCT      319
Pro Ser Thr Leu Leu Ser Leu Ala Ile Leu Ser His Ile Ser Thr Pro
            -15                 -10                  -5

GGA TGT GAA TGG CAC GTT ATC TAT GTA AGC AGT BAT GGT CTC TAT CTT      367
Gly Cys Glu Trp His Val Ile Tyr Val Ser Ser Xaa Gly Leu Tyr Leu
  1               5                  10                  15

GTG GTA GAA ATG ACA GAC CGG                                          388
Val Val Glu Met Thr Asp Arg
                 20

(2) INFORMATION FOR SEQ ID NO: 242:

(i) SEQUENCE CHARACTERISTICS:
```

(A) LENGTH: 391 base pairs
    (B) TYPE: NUCLEIC ACID
    (C) STRANDEDNESS: DOUBLE
    (D) TOPOLOGY: LINEAR (ii) MOLECULE TYPE: cDNA (vi) ORIGINAL SOURCE:
    (A) ORGANISM: Homo Sapiens
    (F) TISSUE TYPE: Brain (ix) FEATURE:
    (A) NAME/KEY: other
    (B) LOCATION: 108..392
    (C) IDENTIFICATION METHOD: blastn
    (D) OTHER INFORMATION: identity 98 region 104..388 id T08101
        est (ix) FEATURE:
    (A) NAME/KEY: other
    (B) LOCATION: 32..110
    (C) IDENTIFICATION METHOD: blastn
    (D) OTHER INFORMATION: identity 98 region 1..79 id T08101
        est (ix) FEATURE:
    (A) NAME/KEY: other
    (B) LOCATION: 108..392
    (C) IDENTIFICATION METHOD: blastn
    (D) OTHER INFORMATION: identity 98 region 39..323 id T27149
        est (ix) FEATURE:
    (A) NAME/KEY: other
    (B) LOCATION: 113..392
    (C) IDENTIFICATION METHOD: blastn
    (D) OTHER INFORMATION: identity 98 region 30..309 id H06555
        est (ix) FEATURE:
    (A) NAME/KEY: other
    (B) LOCATION: 108..316
    (C) IDENTIFICATION METHOD: blastn
    (D) OTHER INFORMATION: identity 99 region 90..298 id
        HSC3CC081 est (ix) FEATURE:
    (A) NAME/KEY: other
    (B) LOCATION: 60..110
    (C) IDENTIFICATION METHOD: blastn
    (D) OTHER INFORMATION: identity 94 region 15..65 id HSC3CC081
        est (ix) FEATURE:
    (A) NAME/KEY: other
    (B) LOCATION: 105..316
    (C) IDENTIFICATION METHOD: blastn
    (D) OTHER INFORMATION: identity 99 region 58..269 id T74159
        est (ix) FEATURE:
    (A) NAME/KEY: other
    (B) LOCATION: 76..105
    (C) IDENTIFICATION METHOD: blastn
    (D) OTHER INFORMATION: identity 93 region 5..34 id T74159
        est (ix) FEATURE:
    (A) NAME/KEY: sig_peptide
    (B) LOCATION: 152..379
    (C) IDENTIFICATION METHOD: Von Heijne matrix
    (D) OTHER INFORMATION: score 4.3 seq FRLLXVFAYGTYA/DY (xi) SEQUENCE DESCRIPTION: SEQ ID NO: 242:

AAGTGGCCAG AGCGACTCTT CAGGGAGGTG GCAGGAAAGG CTTGGAACAG CTGCCGGAGG      60

TGACGGAGCG GCGGCCCCGC CCGGTGCGCT GGAGGTCGAA GCTTCCAGCT CTGGACATCC     120

```
TGAGCCCAAG TCCCCCACAC TCAGTGCAGT G ATG AGT GCG GAA GTG AAG GTG       172
                                   Met Ser Ala Glu Val Lys Val
                                       -75             -70

ACA GGG CAG AAC CAG GAG CAA TTT CTG CTC CTA GCC AAG TCG GCC AAG     220
Thr Gly Gln Asn Gln Glu Gln Phe Leu Leu Leu Ala Lys Ser Ala Lys
            -65             -60                 -55

GGG GCA GCG CTG GCC ACA CTC ATC CAT CAG GTG CTG GAG GCC CCT GGT     268
Gly Ala Ala Leu Ala Thr Leu Ile His Gln Val Leu Glu Ala Pro Gly
        -50             -45             -40

GTC TAC GTG TTT GGA GAA CTG CTG GAC ATG CCC AAT GTT AGA GAG CTG     316
Val Tyr Val Phe Gly Glu Leu Leu Asp Met Pro Asn Val Arg Glu Leu
        -35             -30             -25

GCT GAG AGT NAC TTT GCC TCT ACC TTC CGG CTG CTC AMA GTG TTT GCT     364
Ala Glu Ser Xaa Phe Ala Ser Thr Phe Arg Leu Leu Xaa Val Phe Ala
        -20             -15             -10

TAT GGG ACA TAC GCT GAC TAC TWA GCT                                 391
Tyr Gly Thr Tyr Ala Asp Tyr Xaa Ala
 -5              1
```

(2) INFORMATION FOR SEQ ID NO: 243:

(i) SEQUENCE CHARACTERISTICS:
        (A) LENGTH: 299 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 47..248
        (C) IDENTIFICATION METHOD: blastn
        (D) OTHER INFORMATION:   identity 97 region 15..216 id
            HUM429E03B est (ix) FEATURE:
        (A) NAME/KEY: other
        (B) LOCATION: 244..299
        (C) IDENTIFICATION METHOD: blastn
        (D) OTHER INFORMATION:   identity 94 region 211..266 id
            HUM429E03B est (ix) FEATURE:
        (A) NAME/KEY: other
        (B) LOCATION: 133..299
        (C) IDENTIFICATION METHOD: blastn
        (D) OTHER INFORMATION:   identity 97 region 107..273 id T80259
            est (ix) FEATURE:
        (A) NAME/KEY: other
        (B) LOCATION: 47..139
        (C) IDENTIFICATION METHOD: blastn
        (D) OTHER INFORMATION:   identity 92 region 22..114 id T80259
            est (ix) FEATURE:
        (A) NAME/KEY: other
        (B) LOCATION: 48..292
        (C) IDENTIFICATION METHOD: blastn
        (D) OTHER INFORMATION:   identity 94 region 1..245 id T31768
            est (ix) FEATURE:
        (A) NAME/KEY: other
        (B) LOCATION: 111..299
        (C) IDENTIFICATION METHOD: blastn
        (D) OTHER INFORMATION:   identity 94 region 47..235 id N32697 est (ix) FEATURE:
       (A) NAME/KEY: other
       (B) LOCATION: 64..106
       (C) IDENTIFICATION METHOD: blastn
       (D) OTHER INFORMATION: identity 97 region 1..43 id N32697
           est (ix) FEATURE:
       (A) NAME/KEY: other
       (B) LOCATION: 74..299
       (C) IDENTIFICATION METHOD: blastn
       (D) OTHER INFORMATION: identity 94 region 1..226 id N44613
           est (ix) FEATURE:
       (A) NAME/KEY: sig_peptide
       (B) LOCATION: 165..266
       (C) IDENTIFICATION METHOD: Von Heijne matrix
       (D) OTHER INFORMATION: score 4.3 seq QLFAFLNLLPVEA/DI (xi) SEQUENCE DESCRIPTION: SEQ ID NO: 243:

ACTTCCGCTT CGCCTAGGTG TTGTCGTCCC TGCTAGTACT CCGGGCTGGG GGTCGGTGCG      60

GATATTCAGT CATGAAATCA SGGTAGGGAC TTCTCCCGCA GCGACGCGGC TGGCAAGACT     120

GTTTGTGTWG CGGGGGCCGG ACTTCAAGGT GATTTTACAA CGAG ATG CTG CTC TCC      176
                                                Met Leu Leu Ser

ATA GGG ATG CTC ATG CTG TCA GCC ACA CAA GTS TAS ACC ATC TTG AST      224
Ile Gly Met Leu Met Leu Ser Ala Thr Gln Val Xaa Thr Ile Leu Xaa
-30             -25                 -20                 -15

GTC CAG CTC TTT GCA TTC TTA AAC CTA CTG CCT GTA GAA GCA GAC ATT      272
Val Gln Leu Phe Ala Phe Leu Asn Leu Leu Pro Val Glu Ala Asp Ile
            -10                 -5                  1

KTA GCA TAT AAC TTT GAA AAT GCA TCT                                  299
Xaa Ala Tyr Asn Phe Glu Asn Ala Ser
        5                   10

(2) INFORMATION FOR SEQ ID NO: 244:

(i) SEQUENCE CHARACTERISTICS:
        (A) LENGTH: 312 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(115..313)
        (C) IDENTIFICATION METHOD: blastn
        (D) OTHER INFORMATION: identity 98 region 1..199 id H19659
            est (ix) FEATURE:
        (A) NAME/KEY: other
        (B) LOCATION: complement(2..102)
        (C) IDENTIFICATION METHOD: blastn
        (D) OTHER INFORMATION: identity 97 region 212..312 id H19659
            est (ix) FEATURE:
        (A) NAME/KEY: other
        (B) LOCATION: complement(115..313)
        (C) IDENTIFICATION METHOD: blastn
        (D) OTHER INFORMATION: identity 97 region 1..199 id R72881
            est

```
    (ix) FEATURE:
         (A) NAME/KEY: other
         (B) LOCATION: complement(115..290)
         (C) IDENTIFICATION METHOD: blastn
         (D) OTHER INFORMATION:  identity 98 region 1..176 id H50517
             est (ix) FEATURE:
         (A) NAME/KEY: other
         (B) LOCATION: complement(44..102)
         (C) IDENTIFICATION METHOD: blastn
         (D) OTHER INFORMATION:  identity 100 region 189..247 id H50517
             est (ix) FEATURE:
         (A) NAME/KEY: other
         (B) LOCATION: complement(115..302)
         (C) IDENTIFICATION METHOD: blastn
         (D) OTHER INFORMATION:  identity 96 region 36..223 id H41556
             est (ix) FEATURE:
         (A) NAME/KEY: other
         (B) LOCATION: complement(115..313)
         (C) IDENTIFICATION METHOD: blastn
         (D) OTHER INFORMATION:  identity 95 region 2..200 id R71794
             est (ix) FEATURE:
         (A) NAME/KEY: other
         (B) LOCATION: complement(44..102)
         (C) IDENTIFICATION METHOD: blastn
         (D) OTHER INFORMATION:  identity 96 region 213..271 id R71794
             est (ix) FEATURE:
         (A) NAME/KEY: sig_peptide
         (B) LOCATION: 229..276
         (C) IDENTIFICATION METHOD: Von Heijne matrix
         (D) OTHER INFORMATION:  score 4.2 seq EVVSLSYCGVSWG/RI (xi) SEQUENCE DESCRIPTION: SEQ ID NO: 244:

ACATTTCTGC TCAGATTCCC GCCATCTCCA TTGCATTCAT GTACTACCCT CAGTCTACAC      60

TCACAATCAT CTTCTCCCAA GACTGCTCCC TTTTGTTTTG TGTTTTTTTG AGGGGAATTA     120

AGGAAAAATA AGTGGGGGCA GGTTTGGAGA GCTGCTTCCA GTGGATAGTT GATGAGAATC     180

CTGACCAAAG GAAGGCACCC TTGACTGTYG GGATAGACAG ATGGACCT ATG GGG TGG      237
                                                    Met Gly Trp
                                                        -15

GAG GTG GTG TCC CTT TCA TAC TGT GGT GTC TCT TGG GGA AGG ATC TCC      285
Glu Val Val Ser Leu Ser Tyr Cys Gly Val Ser Trp Gly Arg Ile Ser
        -10                 -5                  1

CCG AAT CTC AAT AAA CCA GTG AAC AGG                                   312
Pro Asn Leu Asn Lys Pro Val Asn Arg
      5              10

(2) INFORMATION FOR SEQ ID NO: 245:

(i) SEQUENCE CHARACTERISTICS:
        (A) LENGTH: 252 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 41..210
```

```
            (C) IDENTIFICATION METHOD: blastn
            (D) OTHER INFORMATION:   identity 98 region 77..246 id R59124
                est (ix) FEATURE:
            (A) NAME/KEY: sig_peptide
            (B) LOCATION: 37..132
            (C) IDENTIFICATION METHOD: Von Heijne matrix
            (D) OTHER INFORMATION:   score 4.2 seq CWELFCLEHGIQA/DG (xi) SEQUENCE DESCRIPTION: SEQ ID NO: 245:

AAAGCTGAGA GGKGCGCGGG CGAGGACAGC GGCASR ATG CGG GAA TGC ATA TCA         54
                                            Met Arg Glu Cys Ile Ser
                                                -30

GTC CAC GTG GGC CAA GCG GGA GTD CAG ATT GGC AAT GCC TGC TGG GAG        102
Val His Val Gly Gln Ala Gly Val Gln Ile Gly Asn Ala Cys Trp Glu
    -25             -20             -15

CTC TTC TGC CTG GAA CAC GGC ATC CAG GCA GAC GGC ACT TTT GAT GCT        150
Leu Phe Cys Leu Glu His Gly Ile Gln Ala Asp Gly Thr Phe Asp Ala
-10              -5                   1               5

CAA GCT AGC AAG ATC AAC GAT GAT GAC TCC TTC ACC ACC TTT TTC AGC        198
Gln Ala Ser Lys Ile Asn Asp Asp Asp Ser Phe Thr Thr Phe Phe Ser
            10              15                  20

GAG ACT GGC ACT TCT CTG CTG ATG GAA CGC CTC TSC CTG GAT TAT GGC        246
Glu Thr Gly Thr Ser Leu Leu Met Glu Arg Leu Xaa Leu Asp Tyr Gly
        25              30                  35

AAG AAA                                                                252
Lys Lys
    40

(2) INFORMATION FOR SEQ ID NO: 246:

(i) SEQUENCE CHARACTERISTICS:
            (A) LENGTH: 172 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: 82..168
            (C) IDENTIFICATION METHOD: blastn
            (D) OTHER INFORMATION:   identity 96 region 107..193 id
                AA088577 est (ix) FEATURE:
            (A) NAME/KEY: other
            (B) LOCATION: 31..71
            (C) IDENTIFICATION METHOD: blastn
            (D) OTHER INFORMATION:   identity 92 region 53..93 id AA088577
                est (ix) FEATURE:
            (A) NAME/KEY: other
            (B) LOCATION: 31..168
            (C) IDENTIFICATION METHOD: blastn
            (D) OTHER INFORMATION:   identity 97 region 24..161 id R16448
                est (ix) FEATURE:
            (A) NAME/KEY: other
            (B) LOCATION: 53..168
            (C) IDENTIFICATION METHOD: blastn
            (D) OTHER INFORMATION:   identity 99 region 23..138 id AA094092
                est
```

```
    (ix) FEATURE:
         (A) NAME/KEY: other
         (B) LOCATION: 31..163
         (C) IDENTIFICATION METHOD: blastn
         (D) OTHER INFORMATION:  identity 96 region 24..156 id R18030
             est (ix) FEATURE:
         (A) NAME/KEY: other
         (B) LOCATION: 60..168
         (C) IDENTIFICATION METHOD: blastn
         (D) OTHER INFORMATION:  identity 97 region 43..151 id W00599
             est (ix) FEATURE:
         (A) NAME/KEY: other
         (B) LOCATION: 29..70
         (C) IDENTIFICATION METHOD: blastn
         (D) OTHER INFORMATION:  identity 95 region 13..54 id W00599
             est (ix) FEATURE:
         (A) NAME/KEY: sig_peptide
         (B) LOCATION: 35..109
         (C) IDENTIFICATION METHOD: Von Heijne matrix
         (D) OTHER INFORMATION:  score 4.2 seq LDLLRGLPRVSLA/NL (xi) SEQUENCE DESCRIPTION: SEQ ID NO: 246:

AAGGGCGCCC TTGAAAGTTC TTGGATCTGC GGGT ATG GCC GGT CCC TTG CAG GGC        55
                                    Met Ala Gly Pro Leu Gln Gly
                                    -25                 -20

GGT GGG GCC CGG GCC CTG GAC CTA CTC CGG GGC CTG CCG CGT GTG AGC        103
Gly Gly Ala Arg Ala Leu Asp Leu Leu Arg Gly Leu Pro Arg Val Ser
        -15                 -10                 -5

CTG GCC AAC TTA AAG CCG AAT CCC GGC TCC AAG AAA CCG GAG AGA AGA        151
Leu Ala Asn Leu Lys Pro Asn Pro Gly Ser Lys Lys Pro Glu Arg Arg
     1               5                  10

CCA AGA GGT CGG AGA AGG TGG                                            172
Pro Arg Gly Arg Arg Trp
 15              20

(2) INFORMATION FOR SEQ ID NO: 247:

(i) SEQUENCE CHARACTERISTICS:
         (A) LENGTH: 359 base pairs
         (B) TYPE: NUCLEIC ACID
         (C) STRANDEDNESS: DOUBLE
         (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: other
         (B) LOCATION: 52..360
         (C) IDENTIFICATION METHOD: blastn
         (D) OTHER INFORMATION:  identity 98 region 1..309 id HSC1ED081
             est (ix) FEATURE:
         (A) NAME/KEY: other
         (B) LOCATION: 171..316
         (C) IDENTIFICATION METHOD: blastn
         (D) OTHER INFORMATION:  identity 98 region 146..291 id
             AA143136 est (ix) FEATURE:
         (A) NAME/KEY: other
         (B) LOCATION: 31..165
         (C) IDENTIFICATION METHOD: blastn
         (D) OTHER INFORMATION:  identity 97 region 6..140 id AA143136
``` est (ix) FEATURE:
      (A) NAME/KEY: other
      (B) LOCATION: 310..341
      (C) IDENTIFICATION METHOD: blastn
      (D) OTHER INFORMATION: identity 96 region 286..317 id
          AA143136 est (ix) FEATURE:
      (A) NAME/KEY: other
      (B) LOCATION: 176..282
      (C) IDENTIFICATION METHOD: blastn
      (D) OTHER INFORMATION: identity 99 region 77..183 id N75929
          est (ix) FEATURE:
      (A) NAME/KEY: other
      (B) LOCATION: 102..165
      (C) IDENTIFICATION METHOD: blastn
      (D) OTHER INFORMATION: identity 98 region 3..66 id N75929
          est (ix) FEATURE:
      (A) NAME/KEY: sig_peptide
      (B) LOCATION: 156..230
      (C) IDENTIFICATION METHOD: Von Heijne matrix
      (D) OTHER INFORMATION: score 4.2 seq MFAASXLAMCAGA/EV (xi) SEQUENCE DESCRIPTION: SEQ ID NO: 247:

```
ATTTTGGGTC CGGCCTGCTC GCMGTCCGCT CCGTCCGCCC TTAGACCTGT TGCCCAGCAT      60

CCCTGCAGTT CGCGGWACAG TCTCTATTAG AGCGCGTGTA TAGAGGCAGA KAGGAGTGAA     120

GTCCACAGTT CCTCTCCTCC TAGAGCCTGC CGACC ATG CCC GCG GGC GTG CCC       173
                                        Met Pro Ala Gly Val Pro
                                        -25                 -20

ATG TCC ACC TAC CTG AAA ATG TTC GCA GCC AGT MTC CTG GCC ATG TGC      221
Met Ser Thr Tyr Leu Lys Met Phe Ala Ala Ser Xaa Leu Ala Met Cys
            -15                 -10                 -5

GCA GGG GCA GAA GTG GTG CAC AGG TAC TAC CGA CCG GAC CTG ACA ATA      269
Ala Gly Ala Glu Val Val His Arg Tyr Tyr Arg Pro Asp Leu Thr Ile
            1               5                   10

CCT GAA ATT CCA CCA AAG CGT GGA GAA CTC AAA ACG GAG CTT TTG GGA      317
Pro Glu Ile Pro Pro Lys Arg Gly Glu Leu Lys Thr Glu Leu Leu Gly
    15              20                  25

CTG AAA GAA AGA AAA CAC AAA CCT CAA GTT TCT CAA CAG GAG              359
Leu Lys Glu Arg Lys His Lys Pro Gln Val Ser Gln Gln Glu
30              35                  40
```

(2) INFORMATION FOR SEQ ID NO: 248:

(i) SEQUENCE CHARACTERISTICS:
       (A) LENGTH: 284 base pairs
       (B) TYPE: NUCLEIC ACID
       (C) STRANDEDNESS: DOUBLE
       (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 10..280
        (C) IDENTIFICATION METHOD: blastn
        (D) OTHER INFORMATION: identity 98 region 17..287 id AA082102
            est (ix) FEATURE:
        (A) NAME/KEY: other (B) LOCATION: 72..224
        (C) IDENTIFICATION METHOD: blastn
        (D) OTHER INFORMATION: identity 98 region 30..182 id R10417
            est (ix) FEATURE:
        (A) NAME/KEY: other
        (B) LOCATION: 221..280
        (C) IDENTIFICATION METHOD: blastn
        (D) OTHER INFORMATION: identity 100 region 180..239 id R10417
            est (ix) FEATURE:
        (A) NAME/KEY: other
        (B) LOCATION: 47..280
        (C) IDENTIFICATION METHOD: blastn
        (D) OTHER INFORMATION: identity 99 region 2..235 id W73318
            est (ix) FEATURE:
        (A) NAME/KEY: other
        (B) LOCATION: 42..224
        (C) IDENTIFICATION METHOD: blastn
        (D) OTHER INFORMATION: identity 97 region 1..183 id R08733
            est (ix) FEATURE:
        (A) NAME/KEY: other
        (B) LOCATION: 237..269
        (C) IDENTIFICATION METHOD: blastn
        (D) OTHER INFORMATION: identity 93 region 198..230 id R08733
            est (ix) FEATURE:
        (A) NAME/KEY: sig_peptide
        (B) LOCATION: 39..110
        (C) IDENTIFICATION METHOD: Von Heijne matrix
        (D) OTHER INFORMATION: score 4.2 seq SLPALALSLRASP/RX (xi) SEQUENCE DESCRIPTION: SEQ ID NO: 248:

AAGTGCGTGC GCGGCGACTG CGACGGGCAG TGGCAGTC ATG GCG GTT CAG TGC GTG        56
                                         Met Ala Val Gln Cys Val
                                                         -20

AGG TTG GCG CGG CGC AGT CTT CCT GCT TTG GCG TTG TCT CTC AGG GCA         104
Arg Leu Ala Arg Arg Ser Leu Pro Ala Leu Ala Leu Ser Leu Arg Ala
        -15                 -10                 -5

TCT CCC CGG KTG TTG TGC ACA GCC ACG AAA CAA AAG AAC AGT GGC CAG         152
Ser Pro Arg Xaa Leu Cys Thr Ala Thr Lys Gln Lys Asn Ser Gly Gln
        1               5                   10

AAC CTG GAA GAG GAC ATG GGT CAG AGT GAA CAG AAG GCA GAT CCT CCT         200
Asn Leu Glu Glu Asp Met Gly Gln Ser Glu Gln Lys Ala Asp Pro Pro
 15              20                  25                  30

GCT ACA GAG AAG ACC CTC CTG GAA GAG AAG GTC AAG TTG GAG GAA CAG         248
Ala Thr Glu Lys Thr Leu Leu Glu Glu Lys Val Lys Leu Glu Glu Gln
                35                  40                  45

CTG AAG GAG ACT GTG GAA AAA TAT AAA CGA GCG AGG                         284
Leu Lys Glu Thr Val Glu Lys Tyr Lys Arg Ala Arg
            50                  55

(2) INFORMATION FOR SEQ ID NO: 249:

(i) SEQUENCE CHARACTERISTICS:
        (A) LENGTH: 307 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain

```
    (ix) FEATURE:
         (A) NAME/KEY: other
         (B) LOCATION: complement(34..74)
         (C) IDENTIFICATION METHOD: blastn
         (D) OTHER INFORMATION: identity 92 region 271..311 id T05270
             est (ix) FEATURE:
         (A) NAME/KEY: sig_peptide
         (B) LOCATION: 182..292
         (C) IDENTIFICATION METHOD: Von Heijne matrix
         (D) OTHER INFORMATION: score 4.2 seq RLMHHYLSTPTSA/RP (xi) SEQUENCE DESCRIPTION: SEQ ID NO: 249:

AAAGGCTGCC CTGTGGCACC ACAATCTAAG CTCAGGGCAT AAAACCCCTT GTGGCTTTGA      60

TGGAATCCAG GGCTCAGACC ATAAAACCCC TCGTGGCCTT TTGAATGTGC ACCGACTTGC     120

TGGCTCCTTG CTTCTTGCTC TCCCAGAATC GTAAATTGAT TGTATCTTGA GTTGGAAGAA    180

C ATG TTC TCC ATT ATC TCA CGT AGC AGA GCA TGT TCC ATG TAC TTC AAA    229
  Met Phe Ser Ile Ile Ser Arg Ser Arg Ala Cys Ser Met Tyr Phe Lys
      -35              -30                 -25

GAA AAT GCT AAA CCG TCA CAG CTA CGC TTG ATG CAC CAC TAC CTT TCT      277
Glu Asn Ala Lys Pro Ser Gln Leu Arg Leu Met His His Tyr Leu Ser
-20              -15                 -10

ACC CCC ACA TCC GCA CGT CCT CAC CAC CTG                              307
Thr Pro Thr Ser Ala Arg Pro His His Leu
-5                1                  5

(2) INFORMATION FOR SEQ ID NO: 250:

(i) SEQUENCE CHARACTERISTICS:
        (A) LENGTH: 212 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
         (A) ORGANISM: Homo Sapiens
         (F) TISSUE TYPE: Brain (ix) FEATURE:
         (A) NAME/KEY: other
         (B) LOCATION: complement(1..209)
         (C) IDENTIFICATION METHOD: blastn
         (D) OTHER INFORMATION: identity 99 region 125..333 id H40205
             est (ix) FEATURE:
         (A) NAME/KEY: other
         (B) LOCATION: complement(80..209)
         (C) IDENTIFICATION METHOD: blastn
         (D) OTHER INFORMATION: identity 96 region 131..260 id H03462
             est (ix) FEATURE:
         (A) NAME/KEY: other
         (B) LOCATION: complement(52..90)
         (C) IDENTIFICATION METHOD: blastn
         (D) OTHER INFORMATION: identity 97 region 251..289 id H03462
             est (ix) FEATURE:
         (A) NAME/KEY: other
         (B) LOCATION: complement(17..54)
         (C) IDENTIFICATION METHOD: blastn
         (D) OTHER INFORMATION: identity 97 region 288..325 id H03462
             est (ix) FEATURE:
         (A) NAME/KEY: other
```

(B) LOCATION: complement(17..209)
        (C) IDENTIFICATION METHOD: blastn
        (D) OTHER INFORMATION: identity 95 region 130..322 id R05443
            est (ix) FEATURE:
        (A) NAME/KEY: other
        (B) LOCATION: complement(128..209)
        (C) IDENTIFICATION METHOD: blastn
        (D) OTHER INFORMATION: identity 98 region 143..224 id T52770
            est (ix) FEATURE:
        (A) NAME/KEY: other
        (B) LOCATION: complement(80..128)
        (C) IDENTIFICATION METHOD: blastn
        (D) OTHER INFORMATION: identity 100 region 225..273 id T52770
            est (ix) FEATURE:
        (A) NAME/KEY: other
        (B) LOCATION: complement(43..74)
        (C) IDENTIFICATION METHOD: blastn
        (D) OTHER INFORMATION: identity 96 region 281..312 id T52770
            est (ix) FEATURE:
        (A) NAME/KEY: other
        (B) LOCATION: complement(57..209)
        (C) IDENTIFICATION METHOD: blastn
        (D) OTHER INFORMATION: identity 98 region 143..295 id
            AA037595 est (ix) FEATURE:
        (A) NAME/KEY: sig_peptide
        (B) LOCATION: 108..155
        (C) IDENTIFICATION METHOD: Von Heijne matrix
        (D) OTHER INFORMATION: score 4.1 seq LLPATSLAGPVLS/TL (xi) SEQUENCE DESCRIPTION: SEQ ID NO: 250:

```
ACTTCTTGTG GACTCACCAA GAGAAACAAA AGGAAGCCTG CACCATTGTA GCCCTGAACT          60

CTTTTCTGGG CACCTGAATC CCAGGAACCC TCAATGAGGT CTTCAAG ATG AAG AGA           116
                                                    Met Lys Arg
                                                        -15

CTG CTG CCA GCT ACC AGC CTG GCT GGC CCT GTC CTG TCC ACC CTC ATT           164
Leu Leu Pro Ala Thr Ser Leu Ala Gly Pro Val Leu Ser Thr Leu Ile
        -10                 -5                   1

GCC CCA ACT CCC ATG TTG TTT TGT GAA GAT AAA AGC TGG GAT CCT GGG           212
Ala Pro Thr Pro Met Leu Phe Cys Glu Asp Lys Ser Trp Asp Pro Gly
    5                   10                  15
```

(2) INFORMATION FOR SEQ ID NO: 251:

(i) SEQUENCE CHARACTERISTICS:
        (A) LENGTH: 357 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 108..308
        (C) IDENTIFICATION METHOD: blastn
        (D) OTHER INFORMATION: identity 95 region 116..316 id
            HSC2TH021 est (ix) FEATURE:
        (A) NAME/KEY: other (B) LOCATION: 16..99
                (C) IDENTIFICATION METHOD: blastn
                (D) OTHER INFORMATION: identity 97 region 24..107 id
                    HSC2TH021 est (ix) FEATURE:
                (A) NAME/KEY: other
                (B) LOCATION: 30..92
                (C) IDENTIFICATION METHOD: blastn
                (D) OTHER INFORMATION: identity 92 region 72..134 id W54529
                    est (ix) FEATURE:
                (A) NAME/KEY: other
                (B) LOCATION: 119..352
                (C) IDENTIFICATION METHOD: blastn
                (D) OTHER INFORMATION: identity 98 region 23..256 id R59681
                    est (ix) FEATURE:
                (A) NAME/KEY: sig_peptide
                (B) LOCATION: 64..273
                (C) IDENTIFICATION METHOD: Von Heijne matrix
                (D) OTHER INFORMATION: score 4 seq IAVLYLHLYDVFG/DP (xi) SEQUENCE DESCRIPTION: SEQ ID NO: 251:

```
AACTGTCCGG GGCTGCGGGG CTTGCTTCCG GCGTCATGGC TCAAAGGGCC TTCCCGAATC      60

CTT ATG CTG ATT ATA ACA AAT CCC TGG CCG AAG TAC TTT GAT GCT GCC      108
    Met Leu Ile Ile Thr Asn Pro Trp Pro Lys Tyr Phe Asp Ala Ala
    -70                 -65                 -60

GGG AGG CTG ACT CCT GAG TTC TCA CAA CGC TTG ACC AAT AAG ATT CGG      156
Gly Arg Leu Thr Pro Glu Phe Ser Gln Arg Leu Thr Asn Lys Ile Arg
-55                 -50                 -45                 -40

GAG CTT CTT CAG CAA ATG GAG AGA GGC CTG AAA TCA GCA GAC CBB MSG      204
Glu Leu Leu Gln Gln Met Glu Arg Gly Leu Lys Ser Ala Asp Xaa Xaa
                -35                 -30                 -25

GAT GGC ACC GGT TAC ACT GGC TGG GCA GGT ATT GCT GTG CTT TAC TTA      252
Asp Gly Thr Gly Tyr Thr Gly Trp Ala Gly Ile Ala Val Leu Tyr Leu
            -20                 -15                 -10

CAT CTT TAT GAT GTA TTT GGG GAC CCT GCC TAC CTA CAG TTA GCA CAT      300
His Leu Tyr Asp Val Phe Gly Asp Pro Ala Tyr Leu Gln Leu Ala His
        -5                  1                   5

GGC TAT GTA AAG CAA AGT CTG AAC TGC TTA ACC AAG CGC TCC ATC ACC      348
Gly Tyr Val Lys Gln Ser Leu Asn Cys Leu Thr Lys Arg Ser Ile Thr
 10                  15                 20                  25

TTC CAA GGG                                                          357
Phe Gln Gly
```

(2) INFORMATION FOR SEQ ID NO: 252:

(i) SEQUENCE CHARACTERISTICS:
                (A) LENGTH: 414 base pairs
                (B) TYPE: NUCLEIC ACID
                (C) STRANDEDNESS: DOUBLE
                (D) TOPOLOGY: LINEAR (ii) MOLECULE TYPE: CDNA (vi) ORIGINAL SOURCE:
                (A) ORGANISM: Homo Sapiens
                (F) TISSUE TYPE: Brain (ix) FEATURE:
                (A) NAME/KEY: other
                (B) LOCATION: 11..238
                (C) IDENTIFICATION METHOD: blastn
                (D) OTHER INFORMATION: identity 100 region 1..228 id R26618
                    est (ix) FEATURE:

(A) NAME/KEY: other
            (B) LOCATION: 283..397
            (C) IDENTIFICATION METHOD: blastn
            (D) OTHER INFORMATION: identity 98 region 96..210 id
                HUM528H09B est (ix) FEATURE:
            (A) NAME/KEY: other
            (B) LOCATION: 202..282
            (C) IDENTIFICATION METHOD: blastn
            (D) OTHER INFORMATION: identity 98 region 16..96 id
                HUM528H09B est (ix) FEATURE:
            (A) NAME/KEY: other
            (B) LOCATION: 283..411
            (C) IDENTIFICATION METHOD: blastn
            (D) OTHER INFORMATION: identity 96 region 110..238 id C18739
                est (ix) FEATURE:
            (A) NAME/KEY: other
            (B) LOCATION: 202..282
            (C) IDENTIFICATION METHOD: blastn
            (D) OTHER INFORMATION: identity 98 region 30..110 id C18739
                est (ix) FEATURE:
            (A) NAME/KEY: other
            (B) LOCATION: 235..411
            (C) IDENTIFICATION METHOD: blastn
            (D) OTHER INFORMATION: identity 97 region 1..177 id R17985
                est (ix) FEATURE:
            (A) NAME/KEY: other
            (B) LOCATION: complement(2..70)
            (C) IDENTIFICATION METHOD: blastn
            (D) OTHER INFORMATION: identity 97 region 9..77 id R40947
                est (ix) FEATURE:
            (A) NAME/KEY: sig_peptide
            (B) LOCATION: 274..336
            (C) IDENTIFICATION METHOD: Von Heijne matrix
            (D) OTHER INFORMATION: score 3.9 seq AWLAQGSSSAGWG/LE (xi) SEQUENCE DESCRIPTION: SEQ ID NO: 252:

ATCAATTTTK TGAATAGTTT CCATTTCAAA TATCTTGTTC TACTTGGTTC ATAAAATAGT      60

GGTTTTCAAA CTGTAGAGCT CTGGACTTCT CACTTCTAGG GCAGAGGGAG CCTGAACAAG     120

TGAGGCTCTG GGTTCCCCAT TCCTAATTAA ACCAATGGAA AGAAGGGGTC TAATAACAAA     180

CTACAGCAAC ACATTTTTCA TTTCAGCTTC ACTGCTGTAT CTCCCAGTCT AACCCTAGCA     240

TCCAGAAGTG GCACAAAACC CCTCTGCTGG CTC ATG TGT GCA ACT GAG ACT GTC     294
                                    Met Cys Ala Thr Glu Thr Val
                                         -20                -15

AGA GCA TGG CTA GCT CAG GGG TCC AGC TCT GCA GGG TGG GGG CTA GAG      342
Arg Ala Trp Leu Ala Gln Gly Ser Ser Ser Ala Gly Trp Gly Leu Glu
            -10                 -5                      1

AGG AAG CAG GGA GTA TCT GCA CAC AGG ATG CCC GCG CTC AGG TGG TTG      390
Arg Lys Gln Gly Val Ser Ala His Arg Met Pro Ala Leu Arg Trp Leu
         5                  10                  15

CAG AAG TCA GTG CCA GGA BCC ATG                                      414
Gln Lys Ser Val Pro Gly Xaa Met
     20                  25

(2) INFORMATION FOR SEQ ID NO: 253:

(i) SEQUENCE CHARACTERISTICS:
            (A) LENGTH: 189 base pairs
            (B) TYPE: NUCLEIC ACID

```
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens
            (F) TISSUE TYPE: Brain (ix) FEATURE:
            (A) NAME/KEY: other
            (B) LOCATION: 124..153
            (C) IDENTIFICATION METHOD: blastn
            (D) OTHER INFORMATION:   identity 90 region 25..54 id N91869
                est (ix) FEATURE:
            (A) NAME/KEY: other
            (B) LOCATION: 124..153
            (C) IDENTIFICATION METHOD: blastn
            (D) OTHER INFORMATION:   identity 90 region 5..34 id H53427
                est (ix) FEATURE:
            (A) NAME/KEY: other
            (B) LOCATION: 124..153
            (C) IDENTIFICATION METHOD: blastn
            (D) OTHER INFORMATION:   identity 90 region 19..48 id H88369
                est (ix) FEATURE:
            (A) NAME/KEY: other
            (B) LOCATION: 124..153
            (C) IDENTIFICATION METHOD: blastn
            (D) OTHER INFORMATION:   identity 90 region 26..55 id T79771
                est (ix) FEATURE:
            (A) NAME/KEY: other
            (B) LOCATION: 124..153
            (C) IDENTIFICATION METHOD: blastn
            (D) OTHER INFORMATION:   identity 90 region 29..58 id H41152
                est (ix) FEATURE:
            (A) NAME/KEY: sig_peptide
            (B) LOCATION: 46..183
            (C) IDENTIFICATION METHOD: Von Heijne matrix
            (D) OTHER INFORMATION:   score 3.9 seq AAAFCLKXXGANT/HP (xi) SEQUENCE DESCRIPTION: SEQ ID NO: 253:

AGAATTTCTC CCACTCTTCG AGCCTACAGC AGACATGTTA GGAGA ATG CTG CTG CTT        57
                                                 Met Leu Leu Leu
                                                     -45

GCA ACA CAC CCA GAG ACG GTG GGG CAG GTG ACA CTG CGT GTG TRC CCG        105
Ala Thr His Pro Glu Thr Val Gly Gln Val Thr Leu Arg Val Xaa Pro
        -40                 -35                 -30

GTG TCT CTG GAA GTG TCT ATA CAG ATG TGT GCT GCT GCT GCT GCT GCT        153
Val Ser Leu Glu Val Ser Ile Gln Met Cys Ala Ala Ala Ala Ala Ala
    -25                 -20                 -15

TTC TGC CTT AAA ATK WCT GGA GCC AAC ACC CAC CCA                        189
Phe Cys Leu Lys Xaa Xaa Gly Ala Asn Thr His Pro
-10                 -5                   1

(2) INFORMATION FOR SEQ ID NO: 254:

(i) SEQUENCE CHARACTERISTICS:
            (A) LENGTH: 300 base pairs
            (B) TYPE: NUCLEIC ACID
            (C) STRANDEDNESS: DOUBLE
            (D) TOPOLOGY: LINEAR (ii) MOLECULE TYPE: CDNA
```

(vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 149..232
        (C) IDENTIFICATION METHOD: blastn
        (D) OTHER INFORMATION: identity 96 region 91..174 id AA081517
            est (ix) FEATURE:
        (A) NAME/KEY: other
        (B) LOCATION: 224..297
        (C) IDENTIFICATION METHOD: blastn
        (D) OTHER INFORMATION: identity 97 region 165..238 id
            AA081517 est (ix) FEATURE:
        (A) NAME/KEY: other
        (B) LOCATION: 90..141
        (C) IDENTIFICATION METHOD: blastn
        (D) OTHER INFORMATION: identity 98 region 34..85 id AA081517
            est (ix) FEATURE:
        (A) NAME/KEY: other
        (B) LOCATION: 76..141
        (C) IDENTIFICATION METHOD: blastn
        (D) OTHER INFORMATION: identity 93 region 20..85 id N53273
            est (ix) FEATURE:
        (A) NAME/KEY: other
        (B) LOCATION: 149..193
        (C) IDENTIFICATION METHOD: blastn
        (D) OTHER INFORMATION: identity 97 region 91..135 id N53273
            est (ix) FEATURE:
        (A) NAME/KEY: other
        (B) LOCATION: complement(237..297)
        (C) IDENTIFICATION METHOD: blastn
        (D) OTHER INFORMATION: identity 100 region 172..232 id H14293
            est (ix) FEATURE:
        (A) NAME/KEY: sig_peptide
        (B) LOCATION: 43..234
        (C) IDENTIFICATION METHOD: Von Heijne matrix
        (D) OTHER INFORMATION: score 3.9 seq GLGGAQLQGGAXG/RG (xi) SEQUENCE DESCRIPTION: SEQ ID NO: 254:

```
AGTCTCTGGG CGCGGCCATG TTGGAGGSTC CGGGCCCGAG TG ATG GCT GCG AGC           54
                                              Met Ala Ala Ser

TCA GCA ACC CCA GCG CCS ASC RGA AGT CAG CGG TGC GGG GCA GAT GCT         102
Ser Ala Thr Pro Ala Pro Xaa Xaa Ser Gln Arg Cys Gly Ala Asp Ala
-60             -55             -50             -45

GGA AGT GCA GCC AGG ATT GTA TTT CGG TGG GGC CGC GGC CGT CGC GGA         150
Gly Ser Ala Ala Arg Ile Val Phe Arg Trp Gly Arg Gly Arg Arg Gly
            -40             -35             -30

GCC AGA TCA CCT GAG GGA AGC GGG CAT CAC GGC CGT GCT AAC AGT GGA         198
Ala Arg Ser Pro Glu Gly Ser Gly His His Gly Arg Ala Asn Ser Gly
        -25             -20             -15

CTC GGA GGA GCC CAG CTT CAA GGC GGG GCC TRG GGT CGA GGA TCT ATG         246
Leu Gly Gly Ala Gln Leu Gln Gly Gly Ala Xaa Gly Arg Gly Ser Met
    -10              -5                    1

GCG CCT CTT CGT GCC AGC GCT GGA CAA ACC CGA GAC GGA CCT ACT CAG         294
Ala Pro Leu Arg Ala Ser Ala Gly Gln Thr Arg Asp Gly Pro Thr Gln
5                  10              15              20

CCA GGG                                                                 300
Pro Gly
```

(2) INFORMATION FOR SEQ ID NO: 255:

(i) SEQUENCE CHARACTERISTICS:
       (A) LENGTH: 151 base pairs
       (B) TYPE: NUCLEIC ACID
       (C) STRANDEDNESS: DOUBLE
       (D) TOPOLOGY: LINEAR (ii) MOLECULE TYPE: cDNA (vi) ORIGINAL SOURCE:
       (A) ORGANISM: Homo Sapiens
       (F) TISSUE TYPE: Brain (ix) FEATURE:
       (A) NAME/KEY: other
       (B) LOCATION: 13..150
       (C) IDENTIFICATION METHOD: blastn
       (D) OTHER INFORMATION: identity 100 region 1..138 id T36282
           est (ix) FEATURE:
       (A) NAME/KEY: other
       (B) LOCATION: 46..150
       (C) IDENTIFICATION METHOD: blastn
       (D) OTHER INFORMATION: identity 99 region 1..105 id T08090
           est (ix) FEATURE:
       (A) NAME/KEY: other
       (B) LOCATION: 46..150
       (C) IDENTIFICATION METHOD: blastn
       (D) OTHER INFORMATION: identity 99 region 1..105 id T08091
           est (ix) FEATURE:
       (A) NAME/KEY: other
       (B) LOCATION: 72..150
       (C) IDENTIFICATION METHOD: blastn
       (D) OTHER INFORMATION: identity 98 region 1..79 id H56620
           est (ix) FEATURE:
       (A) NAME/KEY: other
       (B) LOCATION: 80..150
       (C) IDENTIFICATION METHOD: blastn
       (D) OTHER INFORMATION: identity 100 region 1..71 id AA027983
           est (ix) FEATURE:
       (A) NAME/KEY: sig_peptide
       (B) LOCATION: 2..52
       (C) IDENTIFICATION METHOD: Von Heijne matrix
       (D) OTHER INFORMATION: score 3.9 seq PLAGLAAAALGRA/PP (xi) SEQUENCE DESCRIPTION: SEQ ID NO: 255:

```
A ATG CTG CGG CGC CCG CTG GCC GGG CTG GCT GCG GCC GCC CTG GGC CGG        49
  Met Leu Arg Arg Pro Leu Ala Gly Leu Ala Ala Ala Ala Leu Gly Arg
      -15                 -10                 -5

GCC CCA CCG GAC GGC TTG CTC TGC TCT TTA CCT GGG GTT GCT GTC GAG          97
Ala Pro Pro Asp Gly Leu Leu Cys Ser Leu Pro Gly Val Ala Val Glu
  1               5                  10                  15

GAC CCT GTG CAA GAC TCG GCC GGT TTT TCT TTC TCC CTG ATG GAC AGA         145
Asp Pro Val Gln Asp Ser Ala Gly Phe Ser Phe Ser Leu Met Asp Arg
                 20                  25                  30

CCC AAG                                                                  151
Pro Lys
```

(2) INFORMATION FOR SEQ ID NO: 256:

(i) SEQUENCE CHARACTERISTICS:
       (A) LENGTH: 217 base pairs

```
          (B) TYPE: NUCLEIC ACID
          (C) STRANDEDNESS: DOUBLE
          (D) TOPOLOGY: LINEAR (ii) MOLECULE TYPE: CDNA (vi) ORIGINAL SOURCE:
          (A) ORGANISM: Homo Sapiens
          (F) TISSUE TYPE: Brain (ix) FEATURE:
          (A) NAME/KEY: other
          (B) LOCATION: 3..214
          (C) IDENTIFICATION METHOD: blastn
          (D) OTHER INFORMATION:  identity 99 region 14..225 id H08058
              est (ix) FEATURE:
          (A) NAME/KEY: other
          (B) LOCATION: 2..91
          (C) IDENTIFICATION METHOD: blastn
          (D) OTHER INFORMATION:  identity 100 region 10..99 id R11727
              est (ix) FEATURE:
          (A) NAME/KEY: sig_peptide
          (B) LOCATION: 59..109
          (C) IDENTIFICATION METHOD: Von Heijne matrix
          (D) OTHER INFORMATION:  score 3.8 seq GFVAALVAGGVAG/VS (xi) SEQUENCE DESCRIPTION: SEQ ID NO: 256:

AGACGTGATC CGCTTCTGCT CCGGCTTGGA TTGTAGCCTT GACGAGGTCT GAGCGACC        58

ATG GAC CGG CCG GGG TTC GTG GCA GCG CTG GTG GCT GGT GGG GTA GCA       106
Met Asp Arg Pro Gly Phe Val Ala Ala Leu Val Ala Gly Gly Val Ala
        -15                 -10                  -5

GGT GTT TCT GTT GAC TTG ATA TTA TTT CCT CTG GAT ACC ATT AAA ACC       154
Gly Val Ser Val Asp Leu Ile Leu Phe Pro Leu Asp Thr Ile Lys Thr
  1               5                  10                  15

AGG CTG CAG AGT CCC CAA GGA TTT AGT AAG GCT GGT GGT TTT CAT GGA       202
Arg Leu Gln Ser Pro Gln Gly Phe Ser Lys Ala Gly Gly Phe His Gly
                20                  25                  30

ATA TAT GCT AGC TGG                                                   217
Ile Tyr Ala Ser Trp
            35

(2) INFORMATION FOR SEQ ID NO: 257:

(i) SEQUENCE CHARACTERISTICS:
          (A) LENGTH: 158 base pairs
          (B) TYPE: NUCLEIC ACID
          (C) STRANDEDNESS: DOUBLE
          (D) TOPOLOGY: LINEAR (ii) MOLECULE TYPE: CDNA (vi) ORIGINAL SOURCE:
          (A) ORGANISM: Homo Sapiens
          (F) TISSUE TYPE: Brain (ix) FEATURE:
          (A) NAME/KEY: other
          (B) LOCATION: 39..155
          (C) IDENTIFICATION METHOD: blastn
          (D) OTHER INFORMATION:  identity 98 region 1..117 id C01598
              est (ix) FEATURE:
          (A) NAME/KEY: sig_peptide
          (B) LOCATION: 9..71
          (C) IDENTIFICATION METHOD: Von Heijne matrix
          (D) OTHER INFORMATION:  score 3.8 seq SMDLLTLLFQRRS/HQ (xi) SEQUENCE DESCRIPTION: SEQ ID NO: 257:
```

```
AATCAAGT ATG ATT GTT TGG TTT GAG GGT ATT TCC ATG GAT CTC CTT ACA            50
         Met Ile Val Trp Phe Glu Gly Ile Ser Met Asp Leu Leu Thr
             -20                 -15                 -10

CTG CTA TTC CAG AGG AGA AGC CAC CAG GTC ACT CAA CTC TTA GTA TCA             98
Leu Leu Phe Gln Arg Arg Ser His Gln Val Thr Gln Leu Leu Val Ser
         -5                  1                   5

TCT ACT GGA AAC TGG CTA AGA CAG TAT TTA TGT GCT TCT CTC ACA ATA            146
Ser Thr Gly Asn Trp Leu Arg Gln Tyr Leu Cys Ala Ser Leu Thr Ile
 10                  15                  20                  25

GCA GGA AGA AGG                                                             158
Ala Gly Arg Arg
```

(2) INFORMATION FOR SEQ ID NO: 258:

(i) SEQUENCE CHARACTERISTICS:
        (A) LENGTH: 292 base pairs
        (B) TYPE: NUCLEIC ACID
        (C) STRANDEDNESS: DOUBLE
        (D) TOPOLOGY: LINEAR (ii) MOLECULE TYPE: cDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(192..269)
        (C) IDENTIFICATION METHOD: blastn
        (D) OTHER INFORMATION: identity 92 region 354..431 id N70088
           est (ix) FEATURE:
        (A) NAME/KEY: other
        (B) LOCATION: complement(222..262)
        (C) IDENTIFICATION METHOD: blastn
        (D) OTHER INFORMATION: identity 95 region 399..439 id H30254
           est (ix) FEATURE:
        (A) NAME/KEY: sig_peptide
        (B) LOCATION: 143..202
        (C) IDENTIFICATION METHOD: Von Heijne matrix
        (D) OTHER INFORMATION: score 3.8 seq ALDALMFPARRRA/AV (xi) SEQUENCE DESCRIPTION: SEQ ID NO: 258:

```
AAGCGGCTGT CCTCCCTCGC TTTTGGAGCT CCGACCTCAG CTTCGCCTGC GAGCTGGGTT            60

GTGTAAAGGC TGGTCATTTT GGGGCGCTTA GGGGTGGGTG CCGGGGGGCG CGCTTTCCCT           120

CGTGAAGGTC GCTCCAGGAG TC ATG CGT ACA TTC GTT CAT TTT GCT CTG GAC           172
                        Met Arg Thr Phe Val His Phe Ala Leu Asp
                            -20                 -15

GCA CTG ATG TTC CCG GCT CGC CGC CGT GCC GCA GTC ACG AGG CTC TCC            220
Ala Leu Met Phe Pro Ala Arg Arg Arg Ala Ala Val Thr Arg Leu Ser
-10                  -5                   1                   5

GAA CGC CTT TCA CTG TGT TTC TGT TTA CAT TCG CGT CTG CAA GAC CCG            268
Glu Arg Leu Ser Leu Cys Phe Cys Leu His Ser Arg Leu Gln Asp Pro
                 10                  15                  20

GCG GCG CGA CCG AGG CCC TCT TGG                                            292
Ala Ala Arg Pro Arg Pro Ser Trp
             25                  30
```

(2) INFORMATION FOR SEQ ID NO: 259:

(i) SEQUENCE CHARACTERISTICS:
        (A) LENGTH: 338 base pairs
        (B) TYPE: NUCLEIC ACID

```
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 131..273
        (C) IDENTIFICATION METHOD: blastn
        (D) OTHER INFORMATION:   identity 92 region 120..262 id R10063
            est (ix) FEATURE:
        (A) NAME/KEY: other
        (B) LOCATION: 35..101
        (C) IDENTIFICATION METHOD: blastn
        (D) OTHER INFORMATION:   identity 100 region 26..92 id R10063
            est (ix) FEATURE:
        (A) NAME/KEY: other
        (B) LOCATION: 103..149
        (C) IDENTIFICATION METHOD: blastn
        (D) OTHER INFORMATION:   identity 100 region 93..139 id R10063
            est (ix) FEATURE:
        (A) NAME/KEY: other
        (B) LOCATION: 275..312
        (C) IDENTIFICATION METHOD: blastn
        (D) OTHER INFORMATION:   identity 97 region 266..303 id R10063
            est (ix) FEATURE:
        (A) NAME/KEY: other
        (B) LOCATION: 131..273
        (C) IDENTIFICATION METHOD: blastn
        (D) OTHER INFORMATION:   identity 92 region 130..272 id R12045
            est (ix) FEATURE:
        (A) NAME/KEY: other
        (B) LOCATION: 35..100
        (C) IDENTIFICATION METHOD: blastn
        (D) OTHER INFORMATION:   identity 100 region 36..101 id R12045
            est (ix) FEATURE:
        (A) NAME/KEY: other
        (B) LOCATION: 103..149
        (C) IDENTIFICATION METHOD: blastn
        (D) OTHER INFORMATION:   identity 100 region 103..149 id R12045
            est (ix) FEATURE:
        (A) NAME/KEY: other
        (B) LOCATION: 3..35
        (C) IDENTIFICATION METHOD: blastn
        (D) OTHER INFORMATION:   identity 96 region 5..37 id R12045
            est (ix) FEATURE:
        (A) NAME/KEY: other
        (B) LOCATION: 131..273
        (C) IDENTIFICATION METHOD: blastn
        (D) OTHER INFORMATION:   identity 92 region 125..267 id R12117
            est (ix) FEATURE:
        (A) NAME/KEY: other
        (B) LOCATION: 5..100
        (C) IDENTIFICATION METHOD: blastn
        (D) OTHER INFORMATION:   identity 98 region 1..96 id R12117
            est
```

```
(ix) FEATURE:
    (A) NAME/KEY: other
    (B) LOCATION: 103..149
    (C) IDENTIFICATION METHOD: blastn
    (D) OTHER INFORMATION:  identity 100 region 98..144 id R12117
        est (ix) FEATURE:
    (A) NAME/KEY: other
    (B) LOCATION: 131..273
    (C) IDENTIFICATION METHOD: blastn
    (D) OTHER INFORMATION:  identity 92 region 102..244 id T79499
        est (ix) FEATURE:
    (A) NAME/KEY: other
    (B) LOCATION: 28..102
    (C) IDENTIFICATION METHOD: blastn
    (D) OTHER INFORMATION:  identity 93 region 1..75 id T79499
        est (ix) FEATURE:
    (A) NAME/KEY: other
    (B) LOCATION: 104..149
    (C) IDENTIFICATION METHOD: blastn
    (D) OTHER INFORMATION:  identity 97 region 76..121 id T79499
        est (ix) FEATURE:
    (A) NAME/KEY: other
    (B) LOCATION: 275..312
    (C) IDENTIFICATION METHOD: blastn
    (D) OTHER INFORMATION:  identity 97 region 248..285 id T79499
        est (ix) FEATURE:
    (A) NAME/KEY: other
    (B) LOCATION: 109..178
    (C) IDENTIFICATION METHOD: blastn
    (D) OTHER INFORMATION:  identity 95 region 109..178 id H17371
        est (ix) FEATURE:
    (A) NAME/KEY: other
    (B) LOCATION: 275..332
    (C) IDENTIFICATION METHOD: blastn
    (D) OTHER INFORMATION:  identity 100 region 283..340 id H17371
        est (ix) FEATURE:
    (A) NAME/KEY: other
    (B) LOCATION: 44..106
    (C) IDENTIFICATION METHOD: blastn
    (D) OTHER INFORMATION:  identity 95 region 42..104 id H17371
        est (ix) FEATURE:
    (A) NAME/KEY: sig_peptide
    (B) LOCATION: 42..224
    (C) IDENTIFICATION METHOD: Von Heijne matrix
    (D) OTHER INFORMATION:  score 3.8 seq LVMTFLFRNGSLQ/EK (xi) SEQUENCE DESCRIPTION: SEQ ID NO: 259:

AGCTTACAGT TCCTAACCCC GACCCTGCGC GCASCCGCAC T ATG GCA GCC CCG CCG         56
                                              Met Ala Ala Pro Pro
                                                       -60

CAG CTA AGG GCT CTG CTC GTA GTC GTC AAC GCA CTG CTG CGC AAG CGC         104
Gln Leu Arg Ala Leu Leu Val Val Val Asn Ala Leu Leu Arg Lys Arg
        -55                 -50                 -45

CGC TAC CAC GCT GCG TTG GCC GTG CTT AAG GGC TTC CGG AAC GGG GCT         152
Arg Tyr His Ala Ala Leu Ala Val Leu Lys Gly Phe Arg Asn Gly Ala
-40                 -35                 -30                 -25

GTC TAT GGA GCC AAA ATC CGG GCC CCT CAC GCG CTG GTC ATG ACC TTT         200
Val Tyr Gly Ala Lys Ile Arg Ala Pro His Ala Leu Val Met Thr Phe
                -20                 -15                 -10
```

```
CTC TTC CGG AAT GGC AGC CTC CAG GAG AAG CTG TGG GCC ATA CTG CAG      248
Leu Phe Arg Asn Gly Ser Leu Gln Glu Lys Leu Trp Ala Ile Leu Gln
            -5                   1               5

GCC ACA TAT ATC CAC TCC TGG AAC CTG GCA CGG TTT GTG TTC ACC TAC      296
Ala Thr Tyr Ile His Ser Trp Asn Leu Ala Arg Phe Val Phe Thr Tyr
         10                  15                  20

AAG GGT CTC CGT GCC CTG CAG TCC TAC ATA CAA GGC CCT GGG              338
Lys Gly Leu Arg Ala Leu Gln Ser Tyr Ile Gln Gly Pro Gly
 25              30                  35
```

(2) INFORMATION FOR SEQ ID NO: 260:

(i) SEQUENCE CHARACTERISTICS:
        (A) LENGTH: 364 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 44..158
        (C) IDENTIFICATION METHOD: blastn
        (D) OTHER INFORMATION: identity 99 region 208..322 id
            AA017601 est (ix) FEATURE:
        (A) NAME/KEY: other
        (B) LOCATION: 287..334
        (C) IDENTIFICATION METHOD: blastn
        (D) OTHER INFORMATION: identity 97 region 451..498 id
            AA017601 est (ix) FEATURE:
        (A) NAME/KEY: sig_peptide
        (B) LOCATION: 128..181
        (C) IDENTIFICATION METHOD: Von Heijne matrix
        (D) OTHER INFORMATION: score 3.8 seq GXALGLLPSLAKA/ED (xi) SEQUENCE DESCRIPTION: SEQ ID NO: 260:

```
ACCCAGCTCC CGGAAGTGCG CCCGGAGCCG GCGCCGCGGG CCGAGTGTCC TGGTGAAGAC      60

CTAGTTCTTG CCGGAGACAA TTCCACTGCA GAAGCACTTT ACTTAAAAGG ACTTGCCAGG     120

CTGGACA ATG CCC GTT GAC TTG GGG CAD GCC CTA GGC CTG CTG CCA TCG      169
        Met Pro Val Asp Leu Gly Xaa Ala Leu Gly Leu Leu Pro Ser
                -15                 -10                      -5

CTG GCG AAG GCC GAG GAC TCC CAG TTC TCA GAA TCA GAT GCT GCC CTT      217
Leu Ala Lys Ala Glu Asp Ser Gln Phe Ser Glu Ser Asp Ala Ala Leu
                 1               5                  10

CAA GAG GAA CTC TCC AGC CCT GAG ACC GCA CGC CAG CTT TTC AGG CAG      265
Gln Glu Glu Leu Ser Ser Pro Glu Thr Ala Arg Gln Leu Phe Arg Gln
             15                  20                  25

TTC CGT TAC CAG GTG ATG TCT GGG CCT CAT GAG ACC TTG AAG CDA CTT      313
Phe Arg Tyr Gln Val Met Ser Gly Pro His Glu Thr Leu Lys Xaa Leu
         30                  35                  40

CGG AAG CTC TGT TTC CAG TGG CTA CAG CCA GAG GTT CAC ACC AAA GAG      361
Arg Lys Leu Cys Phe Gln Trp Leu Gln Pro Glu Val His Thr Lys Glu
 45                  50                  55                  60

GGG                                                                    364
Gly
```

(2) INFORMATION FOR SEQ ID NO: 261:

```
    (i) SEQUENCE CHARACTERISTICS:
        (A) LENGTH: 433 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(324..433)
        (C) IDENTIFICATION METHOD: blastn
        (D) OTHER INFORMATION:   identity 100 region 253..362 id H93008
            est (ix) FEATURE:
        (A) NAME/KEY: other
        (B) LOCATION: complement(200..267)
        (C) IDENTIFICATION METHOD: blastn
        (D) OTHER INFORMATION:   identity 92 region 423..490 id H93008
            est (ix) FEATURE:
        (A) NAME/KEY: other
        (B) LOCATION: complement(159..205)
        (C) IDENTIFICATION METHOD: blastn
        (D) OTHER INFORMATION:   identity 93 region 484..530 id H93008
            est (ix) FEATURE:
        (A) NAME/KEY: other
        (B) LOCATION: complement(116..162)
        (C) IDENTIFICATION METHOD: blastn
        (D) OTHER INFORMATION:   identity 91 region 526..572 id H93008
            est (ix) FEATURE:
        (A) NAME/KEY: other
        (B) LOCATION: complement(259..299)
        (C) IDENTIFICATION METHOD: blastn
        (D) OTHER INFORMATION:   identity 97 region 390..430 id H93008
            est (ix) FEATURE:
        (A) NAME/KEY: other
        (B) LOCATION: complement(52..83)
        (C) IDENTIFICATION METHOD: blastn
        (D) OTHER INFORMATION:   identity 90 region 602..633 id H93008
            est (ix) FEATURE:
        (A) NAME/KEY: other
        (B) LOCATION: 67..243
        (C) IDENTIFICATION METHOD: blastn
        (D) OTHER INFORMATION:   identity 100 region 1..177 id AA146840
            est (ix) FEATURE:
        (A) NAME/KEY: other
        (B) LOCATION: 332..417
        (C) IDENTIFICATION METHOD: blastn
        (D) OTHER INFORMATION:   identity 100 region 269..354 id
            AA146840 est (ix) FEATURE:
        (A) NAME/KEY: other
        (B) LOCATION: 242..299
        (C) IDENTIFICATION METHOD: blastn
        (D) OTHER INFORMATION:   identity 100 region 177..234 id
            AA146840 est (ix) FEATURE:
        (A) NAME/KEY: other
        (B) LOCATION: 299..334
```

```
        (C) IDENTIFICATION METHOD: blastn
        (D) OTHER INFORMATION: identity 100 region 235..270 id
            AA146840 est (ix) FEATURE:
        (A) NAME/KEY: other
        (B) LOCATION: 85..299
        (C) IDENTIFICATION METHOD: blastn
        (D) OTHER INFORMATION: identity 99 region 1..215 id AA036893
            est (ix) FEATURE:
        (A) NAME/KEY: other
        (B) LOCATION: 299..412
        (C) IDENTIFICATION METHOD: blastn
        (D) OTHER INFORMATION: identity 97 region 216..329 id
            AA036893 est (ix) FEATURE:
        (A) NAME/KEY: other
        (B) LOCATION: 98..243
        (C) IDENTIFICATION METHOD: blastn
        (D) OTHER INFORMATION: identity 98 region 1..146 id T49176
            est (ix) FEATURE:
        (A) NAME/KEY: other
        (B) LOCATION: 242..299
        (C) IDENTIFICATION METHOD: blastn
        (D) OTHER INFORMATION: identity 100 region 146..203 id T49176
            est (ix) FEATURE:
        (A) NAME/KEY: other
        (B) LOCATION: 344..396
        (C) IDENTIFICATION METHOD: blastn
        (D) OTHER INFORMATION: identity 98 region 250..302 id T49176
            est (ix) FEATURE:
        (A) NAME/KEY: other
        (B) LOCATION: 299..349
        (C) IDENTIFICATION METHOD: blastn
        (D) OTHER INFORMATION: identity 96 region 204..254 id T49176
            est (ix) FEATURE:
        (A) NAME/KEY: other
        (B) LOCATION: 19..243
        (C) IDENTIFICATION METHOD: blastn
        (D) OTHER INFORMATION: identity 100 region 1..225 id H01262
            est (ix) FEATURE:
        (A) NAME/KEY: other
        (B) LOCATION: 242..296
        (C) IDENTIFICATION METHOD: blastn
        (D) OTHER INFORMATION: identity 100 region 225..279 id H01262
            est (ix) FEATURE:
        (A) NAME/KEY: sig_peptide
        (B) LOCATION: 17..232
        (C) IDENTIFICATION METHOD: Von Heijne matrix
        (D) OTHER INFORMATION: score 3.8 seq LMGLALAVYKCQS/MG (xi) SEQUENCE DESCRIPTION: SEQ ID NO: 261:

ACTCAAACAG ATTCCC ATG AAT CTC TTC ATC ATG TAC ATG GCA GGC AAT ACT       52
                  Met Asn Leu Phe Ile Met Tyr Met Ala Gly Asn Thr
                      -70                 -65

ATC TCC ATC TTC CCT ACT ATG ATG GTG TGT ATG ATG GCC TGG CGA CCC        100
Ile Ser Ile Phe Pro Thr Met Met Val Cys Met Met Ala Trp Arg Pro
-60             -55                 -50                 -45

ATT CAG GCA CTT ATG GCC ATT TCA GCC ACT TTC AAG ATG TTA GAA AGT        148
Ile Gln Ala Leu Met Ala Ile Ser Ala Thr Phe Lys Met Leu Glu Ser
            -40                 -35                 -30
```

```
TCA AGC CAG AAG TTT CTT CAG GGT TTG GTC TAT CTC ATT GGG AAC CTG        196
Ser Ser Gln Lys Phe Leu Gln Gly Leu Val Tyr Leu Ile Gly Asn Leu
            -25                 -20                 -15

ATG GGT TTG GCA TTG GCT GTT TAC AAG TGC CAG TCC ATG GGA CTG TTA        244
Met Gly Leu Ala Leu Ala Val Tyr Lys Cys Gln Ser Met Gly Leu Leu
        -10                  -5                   1

CCT ACA CAT GCA TCG GAT TGG TTA GCC TTC ATT GAG CCC CCT GAG AGA        292
Pro Thr His Ala Ser Asp Trp Leu Ala Phe Ile Glu Pro Pro Glu Arg
 5              10                  15                  20

ATG GAG TCA GTG GTG GAG GAC TGC TTT TGT GAA CAT GAG AAA GCA GCG        340
Met Glu Ser Val Val Glu Asp Cys Phe Cys Glu His Glu Lys Ala Ala
            25                  30                  35

CCT GGT CCC TAT GTA TTT GGG TCT TAT TTA CAT CCT TCT TTA AGC CCA        388
Pro Gly Pro Tyr Val Phe Gly Ser Tyr Leu His Pro Ser Leu Ser Pro
            40                  45                  50

GTG GCT CCT CAG CAT ACT CTT AAA CTA ATC ACT TAT GTT AAA AAG            433
Val Ala Pro Gln His Thr Leu Lys Leu Ile Thr Tyr Val Lys Lys
            55                  60                  65
```

(2) INFORMATION FOR SEQ ID NO: 262:

(i) SEQUENCE CHARACTERISTICS:
        (A) LENGTH: 370 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 2..250
        (C) IDENTIFICATION METHOD: blastn
        (D) OTHER INFORMATION: identity 99 region 14..262 id N33874
            est (ix) FEATURE:
        (A) NAME/KEY: other
        (B) LOCATION: 78..270
        (C) IDENTIFICATION METHOD: blastn
        (D) OTHER INFORMATION: identity 98 region 1..193 id H01141
            est (ix) FEATURE:
        (A) NAME/KEY: other
        (B) LOCATION: 283..349
        (C) IDENTIFICATION METHOD: blastn
        (D) OTHER INFORMATION: identity 97 region 207..273 id H01141
            est (ix) FEATURE:
        (A) NAME/KEY: other
        (B) LOCATION: 284..366
        (C) IDENTIFICATION METHOD: blastn
        (D) OTHER INFORMATION: identity 92 region 320..402 id
            AA023741 est (ix) FEATURE:
        (A) NAME/KEY: other
        (B) LOCATION: 74..270
        (C) IDENTIFICATION METHOD: blastn
        (D) OTHER INFORMATION: identity 100 region 2..198 id R27699
            est (ix) FEATURE:
        (A) NAME/KEY: other
        (B) LOCATION: 320..349
        (C) IDENTIFICATION METHOD: blastn (D) OTHER INFORMATION: identity 93 region 253..282 id R27699
                        est (ix) FEATURE:
                    (A) NAME/KEY: other
                    (B) LOCATION: complement(320..366)
                    (C) IDENTIFICATION METHOD: blastn
                    (D) OTHER INFORMATION: identity 97 region 282..328 id N33481
                        est (ix) FEATURE:
                    (A) NAME/KEY: other
                    (B) LOCATION: complement(283..322)
                    (C) IDENTIFICATION METHOD: blastn
                    (D) OTHER INFORMATION: identity 100 region 327..366 id N33481
                        est (ix) FEATURE:
                    (A) NAME/KEY: other
                    (B) LOCATION: complement(235..270)
                    (C) IDENTIFICATION METHOD: blastn
                    (D) OTHER INFORMATION: identity 97 region 379..414 id N33481
                        est (ix) FEATURE:
                    (A) NAME/KEY: sig_peptide
                    (B) LOCATION: 65..217
                    (C) IDENTIFICATION METHOD: Von Heijne matrix
                    (D) OTHER INFORMATION: score 3.8 seq NVLFVAGLAFVIG/LE (xi) SEQUENCE DESCRIPTION: SEQ ID NO: 262:

ACGACTCAGC TTCCCACCCT GGGCTTTCCG AGGTGCTTTC GCCGCTGTCC CCACCACTGC       60

AGCC ATG ATC TCC TTA ACG GAC ACG CAG AAA ATT GGA ATG GGA TTA ACA      109
     Met Ile Ser Leu Thr Asp Thr Gln Lys Ile Gly Met Gly Leu Thr
         -50             -45                 -40

GGA TTT GGA GTG TTT TTC CTG TTC TTT GGA ATG ATT CTC TTT TTT GAC       157
Gly Phe Gly Val Phe Phe Leu Phe Phe Gly Met Ile Leu Phe Phe Asp
-35                 -30                 -25

AAA GCA CTA CTG GCT ATT GGA AAT GTT TTA TTT GTA GCC GGC TTG GCT       205
Lys Ala Leu Leu Ala Ile Gly Asn Val Leu Phe Val Ala Gly Leu Ala
-20                 -15                 -10                 -5

TTT GTA ATT GGT TTA GAA AGA ACA TTC AGA TTC TTC TTC CAA AAA CAT       253
Phe Val Ile Gly Leu Glu Arg Thr Phe Arg Phe Phe Phe Gln Lys His
                1                   5                   10

AAA ATG AAA GCT ACA GGT TTT TTT CTG GGT GGT GTA TTT GTA GTC CTT       301
Lys Met Lys Ala Thr Gly Phe Phe Leu Gly Gly Val Phe Val Val Leu
            15                  20                  25

ATT GGT TGG CCT TTG ATA GGC ATG ATC TTC GAA ATT TAT GGA TTT TTT       349
Ile Gly Trp Pro Leu Ile Gly Met Ile Phe Glu Ile Tyr Gly Phe Phe
        30                  35                  40

CTC TTG TTC AGG GGC TTA GGG                                            370
Leu Leu Phe Arg Gly Leu Gly
45                  50

(2) INFORMATION FOR SEQ ID NO: 263:

(i) SEQUENCE CHARACTERISTICS:
                    (A) LENGTH: 249 base pairs
                    (B) TYPE: NUCLEIC ACID
                    (C) STRANDEDNESS: DOUBLE
                    (D) TOPOLOGY: LINEAR (ii) MOLECULE TYPE: CDNA (vi) ORIGINAL SOURCE:
                    (A) ORGANISM: Homo Sapiens
                    (F) TISSUE TYPE: Brain (ix) FEATURE:
                    (A) NAME/KEY: other (B) LOCATION: 112..249
            (C) IDENTIFICATION METHOD: blastn
            (D) OTHER INFORMATION: identity 97 region 153..290 id
                AA010288 est (ix) FEATURE:
            (A) NAME/KEY: other
            (B) LOCATION: 112..218
            (C) IDENTIFICATION METHOD: blastn
            (D) OTHER INFORMATION: identity 96 region 101..207 id R26319
                est (ix) FEATURE:
            (A) NAME/KEY: other
            (B) LOCATION: 208..247
            (C) IDENTIFICATION METHOD: blastn
            (D) OTHER INFORMATION: identity 92 region 198..237 id R26319
                est (ix) FEATURE:
            (A) NAME/KEY: other
            (B) LOCATION: 110..249
            (C) IDENTIFICATION METHOD: blastn
            (D) OTHER INFORMATION: identity 95 region 24..163 id W69087
                est (ix) FEATURE:
            (A) NAME/KEY: other
            (B) LOCATION: 112..247
            (C) IDENTIFICATION METHOD: blastn
            (D) OTHER INFORMATION: identity 98 region 103..238 id H01791
                est (ix) FEATURE:
            (A) NAME/KEY: other
            (B) LOCATION: complement(112..217)
            (C) IDENTIFICATION METHOD: blastn
            (D) OTHER INFORMATION: identity 98 region 287..392 id
                AA146617 est (ix) FEATURE:
            (A) NAME/KEY: sig_peptide
            (B) LOCATION: 91..189
            (C) IDENTIFICATION METHOD: Von Heijne matrix
            (D) OTHER INFORMATION: score 3.6 seq LAVFQMLKSMCAG/QR (xi) SEQUENCE DESCRIPTION: SEQ ID NO: 263:

AAAAAAGCGA AGGCCGGCCG GGCGGGGAAG GGAAATGGCG AGGCAGGAGT GCGGGGGAGG        60

GAGTGGTCCT TAGCTGAATG CGCCTGCGTT ATG GCG GCC TCC GGC GCC CCA AGG       114
                                 Met Ala Ala Ser Gly Ala Pro Arg
                                                 -30

ATC CTG GTG GAC CTG CTG AAG CTG ASC GTG GCC CCC CTC GCC GTC TTC       162
Ile Leu Val Asp Leu Leu Lys Leu Xaa Val Ala Pro Leu Ala Val Phe
-25                 -20                 -15                 -10

CAG ATG CTC AAG TCC ATG TGT GCC GGG CAG AGG CTA GCG AGC GAG CCC       210
Gln Met Leu Lys Ser Met Cys Ala Gly Gln Arg Leu Ala Ser Glu Pro
                -5                   1                   5

CAG GAC CCT GCG GCC GTG TCT CTG CCC ACG TCG AGC GGG                   249
Gln Asp Pro Ala Ala Val Ser Leu Pro Thr Ser Ser Gly
        10                  15                  20

(2) INFORMATION FOR SEQ ID NO: 264:

(i) SEQUENCE CHARACTERISTICS:
            (A) LENGTH: 324 base pairs
            (B) TYPE: NUCLEIC ACID
            (C) STRANDEDNESS: DOUBLE
            (D) TOPOLOGY: LINEAR (ii) MOLECULE TYPE: CDNA (vi) ORIGINAL SOURCE:
            (A) ORGANISM: Homo Sapiens (F) TISSUE TYPE: Brain (ix) FEATURE:
        (A) NAME/KEY: other
        (B) LOCATION: 52..178
        (C) IDENTIFICATION METHOD: blastn
        (D) OTHER INFORMATION:   identity 98 region 68..194 id W51974
            est (ix) FEATURE:
        (A) NAME/KEY: other
        (B) LOCATION: 173..253
        (C) IDENTIFICATION METHOD: blastn
        (D) OTHER INFORMATION:   identity 98 region 190..270 id W51974
            est (ix) FEATURE:
        (A) NAME/KEY: sig_peptide
        (B) LOCATION: 49..126
        (C) IDENTIFICATION METHOD: Von Heijne matrix
        (D) OTHER INFORMATION:   score 3.6 seq ARSLLQFLRLVGQ/LK (xi) SEQUENCE DESCRIPTION: SEQ ID NO: 264:

```
AAGGAGCTTC GCCGCGGCCT GCTCCGCCCA GCCGGGGTCG GTGGCCGC ATG GCT TCG       57
                                                   Met Ala Ser
                                                          -25

GTC TCC TCT GCG ACC TTC TCG GGC CAC GGG GCT CGG TCC CTA CTG CAG        105
Val Ser Ser Ala Thr Phe Ser Gly His Gly Ala Arg Ser Leu Leu Gln
        -20                 -15                 -10

TTC CTG CGG CTG GTA GGG CAG CTC AAG AGA GTC CCA CGA ACT GGC TGG        153
Phe Leu Arg Leu Val Gly Gln Leu Lys Arg Val Pro Arg Thr Gly Trp
         -5                  1                   5

GTA TAC AGA AAT GTC CAG AGG CCG GAG AGC GTT TCA GAT CAC ATG TAC        201
Val Tyr Arg Asn Val Gln Arg Pro Glu Ser Val Ser Asp His Met Tyr
 10                  15                  20                  25

CGG ATG GCA GTT ATG GCT ATG GTG ATC AAA GAT GAC CGT CTT AAC AAA        249
Arg Met Ala Val Met Ala Met Val Ile Lys Asp Asp Arg Leu Asn Lys
                 30                  35                  40

GAC CGA TGT GTA CGC CTA GCC CTG GTT CAT GAT ATG GCA GAA TGC ATC        297
Asp Arg Cys Val Arg Leu Ala Leu Val His Asp Met Ala Glu Cys Ile
                 45                  50                  55

GTT GGG GAC ATA GCA CCA GCA GAT GGG                                    324
Val Gly Asp Ile Ala Pro Ala Asp Gly
                 60                  65
```

(2) INFORMATION FOR SEQ ID NO: 265:

(i) SEQUENCE CHARACTERISTICS:
        (A) LENGTH: 157 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: complement(2..156)
        (C) IDENTIFICATION METHOD: blastn
        (D) OTHER INFORMATION:   identity 96 region 72..226 id AA134487
            est (ix) FEATURE:
        (A) NAME/KEY: other
        (B) LOCATION: complement(43..156)
        (C) IDENTIFICATION METHOD: blastn
        (D) OTHER INFORMATION:   identity 98 region 73..186 id T23528

```
            est (ix) FEATURE:
         (A) NAME/KEY: other
         (B) LOCATION: complement(6..156)
         (C) IDENTIFICATION METHOD: blastn
         (D) OTHER INFORMATION:   identity 96 region 69..219 id R50519
            est (ix) FEATURE:
         (A) NAME/KEY: sig_peptide
         (B) LOCATION: 86..133
         (C) IDENTIFICATION METHOD: Von Heijne matrix
         (D) OTHER INFORMATION:   score 3.6 seq LAVLLVLFTLNIL/KS (xi) SEQUENCE DESCRIPTION: SEQ ID NO: 265:

ACTGTATAAT RTGTGTATAT KAAAATGTAA TTGATTTCAG YYGAAAGTAT TTTAAAGCTG       60

ATAAATAGCA TTAGGGTTCT TTGCA ATG TGG TAT CTA GCT GTA TTA TTG GTT       112
                           Met Trp Tyr Leu Ala Val Leu Leu Val
                               -15                 -10

TTA TTT ACT TTA AAC ATT TTG AAA AGC TTA TAC TGG CAG CCT GGG           157
Leu Phe Thr Leu Asn Ile Leu Lys Ser Leu Tyr Trp Gln Pro Gly
         -5                  1                   5

(2) INFORMATION FOR SEQ ID NO: 266:

(i) SEQUENCE CHARACTERISTICS:
         (A) LENGTH: 370 base pairs
         (B) TYPE: NUCLEIC ACID
         (C) STRANDEDNESS: DOUBLE
         (D) TOPOLOGY: LINEAR (ii) MOLECULE TYPE: CDNA (vi) ORIGINAL SOURCE:
         (A) ORGANISM: Homo Sapiens
         (F) TISSUE TYPE: Brain (ix) FEATURE:
         (A) NAME/KEY: other
         (B) LOCATION: 41..79
         (C) IDENTIFICATION METHOD: blastn
         (D) OTHER INFORMATION:   identity 92 region 80..118 id T06923
            est (ix) FEATURE:
         (A) NAME/KEY: sig_peptide
         (B) LOCATION: 197..322
         (C) IDENTIFICATION METHOD: Von Heijne matrix
         (D) OTHER INFORMATION:   score 3.5 seq INSLLEXSSLSRC/LE (xi) SEQUENCE DESCRIPTION: SEQ ID NO: 266:

ACATAAAGGA CASACGAGTC CTAATTGACA ACATCTAGTC TTTCTGGATG TTAAAGAGGT       60

TGCCAGTGTA TGACAAAAGT AGAGTTAGTA AACTAATATA TTTTGTACAT TTTGTTTTAC     120

AAGTCCTAGG AAAGATTGTC TTCTGAAAAT TTGATGTCTT CTGGGTTGAW GGAGATGGGA     180

AGGGTTCTAG GCCAGA ATG TTC ACA TTT GGA AGA CTC TTT CAA ATT ATA ACT    232
               Met Phe Thr Phe Gly Arg Leu Phe Gln Ile Ile Thr
                   -40                 -35

GTT GTT ACA TGT TTG CAG TTT ATT CAA GAC TGC TGT ATA CAT AGT AGA      280
Val Val Thr Cys Leu Gln Phe Ile Gln Asp Cys Cys Ile His Ser Arg
-30                 -25                 -20                 -15

CAA ATT AAC TCC TTA CTT GAR RCA TCT AGT CTA TCT AGA TGT TTA GAA      328
Gln Ile Asn Ser Leu Leu Glu Xaa Ser Ser Leu Ser Arg Cys Leu Glu
                -10                  -5                   1

GTG CCG ATG TAT GTY AAA TGT ATA GGT AGT AAA ATA CCA CTT              370
Val Pro Met Tyr Val Lys Cys Ile Gly Ser Lys Ile Pro Leu
         5                  10                 15
```

(2) INFORMATION FOR SEQ ID NO: 267:

(i) SEQUENCE CHARACTERISTICS:
        (A) LENGTH: 301 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 53..297
        (C) IDENTIFICATION METHOD: blastn
        (D) OTHER INFORMATION: identity 96 region 31..275 id
            HUM414A03B est (ix) FEATURE:
        (A) NAME/KEY: other
        (B) LOCATION: 22..51
        (C) IDENTIFICATION METHOD: blastn
        (D) OTHER INFORMATION: identity 100 region 1..30 id
            HUM414A03B est (ix) FEATURE:
        (A) NAME/KEY: other
        (B) LOCATION: 106..256
        (C) IDENTIFICATION METHOD: blastn
        (D) OTHER INFORMATION: identity 99 region 84..234 id H83476
            est (ix) FEATURE:
        (A) NAME/KEY: other
        (B) LOCATION: 48..105
        (C) IDENTIFICATION METHOD: blastn
        (D) OTHER INFORMATION: identity 96 region 27..84 id H83476
            est (ix) FEATURE:
        (A) NAME/KEY: sig_peptide
        (B) LOCATION: 116..268
        (C) IDENTIFICATION METHOD: Von Heijne matrix
        (D) OTHER INFORMATION: score 3.5 seq VGTLCQLDWWIWG/GI (xi) SEQUENCE DESCRIPTION: SEQ ID NO: 267:

```
AAAATCAAGG CAGGGGATGG AGGCAAGTGG GGGTCGCGCC TGGAGCGGAG CRTCGGCCTC      60

CGGAGCCGCA GCTGCAGCCC TGTATTGAGC TGAGATGGCT CGAGCCTAAC ATTCC ATG     118
                                                             Met

ATC CAG GAT CGT GAC AGA TGT GCA CAG GCT GCT GCT GTT GCT GCT GTG     166
Ile Gln Asp Arg Asp Arg Cys Ala Gln Ala Ala Ala Val Ala Ala Val
-50             -45             -40             -35

GGT AAT TTG GAA CCA CGA GGC ACC CCA GGG CCA GAA GAC GAG GCA TTC     214
Gly Asn Leu Glu Pro Arg Gly Thr Pro Gly Pro Glu Asp Glu Ala Phe
            -30             -25             -20

TGT CTG CCT GGA TGT GTG GGA ACT CTC TGC CAA CTT GAT TGG TGG ATC     262
Cys Leu Pro Gly Cys Val Gly Thr Leu Cys Gln Leu Asp Trp Trp Ile
        -15             -10              -5

TGG GGG GGG ATC CAC CCC CAC CCC ACG AGG AAA GCC TGG                 301
Trp Gly Gly Ile His Pro His Pro Thr Arg Lys Ala Trp
  1               5                  10
```

(2) INFORMATION FOR SEQ ID NO: 268:

(i) SEQUENCE CHARACTERISTICS:
        (A) LENGTH: 404 base pairs
        (B) TYPE: NUCLEIC ACID
        (C) STRANDEDNESS: DOUBLE

```
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 261..404
        (C) IDENTIFICATION METHOD: fasta
        (D) OTHER INFORMATION:  identity 100 region 1..144 id HSU16126
            vrt (ix) FEATURE:
        (A) NAME/KEY: sig_peptide
        (B) LOCATION: 261..353
        (C) IDENTIFICATION METHOD: Von Heijne matrix
        (D) OTHER INFORMATION:  score 11.3 seq LLLCLLWIGYSQG/TT (xi) SEQUENCE DESCRIPTION: SEQ ID NO: 268:

AGGATTTCTC CCGGATGCTC TCCGACTAAC ATGGATGTCC CACCATTCCT TGCAGTGGAA      60

GGTTGTTCCT TGGCGCAGTG AGTGAAGAAC ATGCAGCGAT TGCTAATGGG TTTGGGAAGC     120

GGAGACTCCT TCCTCTCTCT ATGACCATGC CGTGATCGTG TCTGCGGTCA CCACTCGACG     180

CATCCTCATT TCTACCCGAA CCCAGGAGCC AACGCTAGA TCGGGGAAGT GGGTGCCGTG      240

CGTGTGGGCA CAGAAACACC ATG AAG ATT ATT TTC CCG ATT CTA AGT AAT CCA    293
                     Met Lys Ile Ile Phe Pro Ile Leu Ser Asn Pro
                     -30                 -25

GTC TTC AGG CGC ACC GTT AAA CTC CTG CTC TGT TTA CTG TGG ATT GGA      341
Val Phe Arg Arg Thr Val Lys Leu Leu Leu Cys Leu Leu Trp Ile Gly
-20             -15                 -10                 -5

TAT TCT CAA GGA ACC ACA CAT GTA TTA AGA TTT GGT GGT ATT TTT GAA      389
Tyr Ser Gln Gly Thr Thr His Val Leu Arg Phe Gly Gly Ile Phe Glu
          1                 5                  10

TAT GTG GAA TCT GGC                                                  404
Tyr Val Glu Ser Gly
        15

(2) INFORMATION FOR SEQ ID NO: 269:

(i) SEQUENCE CHARACTERISTICS:
        (A) LENGTH: 249 base pairs
        (B) TYPE: NUCLEIC ACID
        (C) STRANDEDNESS: DOUBLE
        (D) TOPOLOGY: LINEAR (ii) MOLECULE TYPE: CDNA (vi) ORIGINAL SOURCE:
        (A) ORGANISM: Homo Sapiens
        (F) TISSUE TYPE: Brain (ix) FEATURE:
        (A) NAME/KEY: other
        (B) LOCATION: 52..250
        (C) IDENTIFICATION METHOD: fasta
        (D) OTHER INFORMATION:  identity 99 region 2..200 id HS7B2 vrt (ix) FEATURE:
        (A) NAME/KEY: other
        (B) LOCATION: 14..250
        (C) IDENTIFICATION METHOD: blastn
        (D) OTHER INFORMATION:  identity 98 region 24..260 id R14271
            est (ix) FEATURE:
        (A) NAME/KEY: other
        (B) LOCATION: 14..250
        (C) IDENTIFICATION METHOD: blastn
```

(D) OTHER INFORMATION: identity 98 region 25..261 id R18347
                    est (ix) FEATURE:
                (A) NAME/KEY: other
                (B) LOCATION: 14..233
                (C) IDENTIFICATION METHOD: blastn
                (D) OTHER INFORMATION: identity 97 region 43..262 id H10233
                    est (ix) FEATURE:
                (A) NAME/KEY: other
                (B) LOCATION: 14..240
                (C) IDENTIFICATION METHOD: blastn
                (D) OTHER INFORMATION: identity 99 region 44..270 id
                    HSC0IE021 est (ix) FEATURE:
                (A) NAME/KEY: other
                (B) LOCATION: 42..250
                (C) IDENTIFICATION METHOD: blastn
                (D) OTHER INFORMATION: identity 98 region 1..209 id HSCZSC021
                    est (ix) FEATURE:
                (A) NAME/KEY: sig_peptide
                (B) LOCATION: 79..156
                (C) IDENTIFICATION METHOD: Von Heijne matrix
                (D) OTHER INFORMATION: score 6.6 seq LFWLASGWTPAFA/YS (xi) SEQUENCE DESCRIPTION: SEQ ID NO: 269:

```
AAGTTCGCCC GTNTCCTGGC CTGACCCCCA CCAAGGCCCA TACCGCAGTA GGCTCCTCGG          60

GCTGCCCCTC GGTTGACA ATG GTC TCC AGG ATG GTC TCT ACC ATG CTA TCT          111
                   Met Val Ser Arg Met Val Ser Thr Met Leu Ser
                       -25                 -20

GGC CTA CTG TTT TGG CTG GCA TCT GGA TGG ACT CCA GCA TTT GCT TAC          159
Gly Leu Leu Phe Trp Leu Ala Ser Gly Trp Thr Pro Ala Phe Ala Tyr
-15              -10                 -5                         1

AGC CCC CGG ACC CCT GAC CGG GTC TCA GAA GCA GAT ATC CAG AGG CTG          207
Ser Pro Arg Thr Pro Asp Arg Val Ser Glu Ala Asp Ile Gln Arg Leu
             5                  10                  15

CTT CAT GGT GTT ATG GAG CAA TTG GGC ATT GCC AGG CCC CGG                  249
Leu His Gly Val Met Glu Gln Leu Gly Ile Ala Arg Pro Arg
         20                  25                  30
```

(2) INFORMATION FOR SEQ ID NO: 270:

(i) SEQUENCE CHARACTERISTICS:
                (A) LENGTH: 316 base pairs
                (B) TYPE: NUCLEIC ACID
                (C) STRANDEDNESS: DOUBLE
                (D) TOPOLOGY: LINEAR (ii) MOLECULE TYPE: CDNA (vi) ORIGINAL SOURCE:
                (A) ORGANISM: Homo Sapiens
                (F) TISSUE TYPE: Brain (ix) FEATURE:
                (A) NAME/KEY: other
                (B) LOCATION: 212..311
                (C) IDENTIFICATION METHOD: fasta
                (D) OTHER INFORMATION: identity 93 region 1..101 id HSSCOASN
                    vrt (ix) FEATURE:
                (A) NAME/KEY: other
                (B) LOCATION: 243..311
                (C) IDENTIFICATION METHOD: blastn
                (D) OTHER INFORMATION: identity 94 region 60..128 id AA135265
                    est (ix) FEATURE:
        (A) NAME/KEY: other
        (B) LOCATION: 187..245
        (C) IDENTIFICATION METHOD: blastn
        (D) OTHER INFORMATION:   identity 91 region 5..63 id AA135265
            est (ix) FEATURE:
        (A) NAME/KEY: other
        (B) LOCATION: 269..311
        (C) IDENTIFICATION METHOD: blastn
        (D) OTHER INFORMATION:   identity 100 region 49..91 id R58602
            est (ix) FEATURE:
        (A) NAME/KEY: sig_peptide
        (B) LOCATION: 179..250
        (C) IDENTIFICATION METHOD: Von Heijne matrix
        (D) OTHER INFORMATION:   score 4.8 seq ATMVSGSSGLAXA/RL (xi) SEQUENCE DESCRIPTION: SEQ ID NO: 270:

AGAGTTATTA TCTGCSTSTC CGATAGGATG CCTCTTTGTC TTCACCTGCC ATTCCCGCTG      60

TTTCGTGAAG AATCCTCTGT AAAGGGAAAT TTGTTCAGGC GACTGCTGTG GCCACCCTCT     120

GCCTCCTCCG GCCTCTGCCC CTGGGAGGTC CCCGGGGGCC TGGGAGTGTC ATTGGCGT      178

ATG ACC GCA ACC CTT GCC GCT GCC GCT GAC ATC GCT ACC ATG GTC TCC      226
Met Thr Ala Thr Leu Ala Ala Ala Ala Asp Ile Ala Thr Met Val Ser
              -20             -15                  -10

GGC AGC AGC GGC CTC GCC GNC GCC CGT CTC CTG TCG CGC AST TCC TCC      274
Gly Ser Ser Gly Leu Ala Xaa Ala Arg Leu Leu Ser Arg Xaa Ser Ser
          -5                  1                    5

TGC CGC AGA ATG GAA TTC GGC ATT GTT CCT ACA CAG CCA CGG              316
Cys Arg Arg Met Glu Phe Gly Ile Val Pro Thr Gln Pro Arg
 10                  15                  20

(2) INFORMATION FOR SEQ ID NO: 271:

(i) SEQUENCE CHARACTERISTICS:
        (A) LENGTH: 37 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -14..-1
        (C) IDENTIFICATION METHOD: Von Heijne matrix
        (D) OTHER INFORMATION:   score 10.8 seq LLLLGLCLGLSLC/VG (xi) SEQUENCE DESCRIPTION: SEQ ID NO: 271:

Met Leu Leu Leu Leu Gly Leu Cys Leu Gly Leu Ser Leu Cys Val Gly
              -10                 -5                       1

Ser Gln Glu Glu Ala Gln Ser Trp Gly His Ser Ser Glu Gln Asp Gly
         5                  10                  15

Leu Arg Val Pro Arg
    20

(2) INFORMATION FOR SEQ ID NO: 272:

(i) SEQUENCE CHARACTERISTICS:
        (A) LENGTH: 79 amino acids
        (B) TYPE: AMINO ACID
        (D) TOPOLOGY: LINEAR

```
    (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -26..-1
         (C) IDENTIFICATION METHOD: Von Heijne matrix
         (D) OTHER INFORMATION:   score 10.8 seq VLLFFVLLGMSQA/GS (xi) SEQUENCE DESCRIPTION: SEQ ID NO: 272:

Met Glu Asn Gly Gly Ala Gly Thr Leu Gln Ile Arg Gln Val Leu Leu
    -25                 -20                 -15

Phe Phe Val Leu Leu Gly Met Ser Gln Ala Gly Ser Glu Thr Gly Asn
-10                  -5                   1                   5

Phe Leu Val Met Glu Glu Leu Gln Ser Gly Ser Phe Val Gly Asn Leu
                 10                  15                  20

Ala Lys Thr Leu Gly Leu Glu Val Ser Glu Leu Ser Ser Arg Gly Ala
             25                  30                  35

Arg Val Val Ser Asn Asp Asn Lys Glu Cys Leu Gln Leu Asp Thr
         40                  45                  50

(2) INFORMATION FOR SEQ ID NO: 273:

(i) SEQUENCE CHARACTERISTICS:
         (A) LENGTH: 129 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -126..-1
         (C) IDENTIFICATION METHOD: Von Heijne matrix
         (D) OTHER INFORMATION:   score 10 seq LKLLLFLSTELQA/SQ (xi) SEQUENCE DESCRIPTION: SEQ ID NO: 273:

Met Arg Gly Pro Glu Pro Gly Pro Gln Pro Thr Met Glu Gly Asp Val
    -125                -120                -115

Leu Asp Thr Leu Glu Ala Leu Gly Tyr Lys Gly Pro Leu Leu Glu Glu
-110                -105                -100                 -95

Gln Ala Leu Thr Lys Ala Ala Glu Gly Gly Leu Ser Ser Pro Glu Phe
                 -90                 -85                 -80

Ser Glu Leu Cys Ile Trp Leu Gly Ser Gln Ile Lys Ser Leu Cys Asn
                -75                 -70                 -65

Leu Glu Glu Ser Ile Thr Ser Ala Gly Arg Asp Asp Leu Glu Ser Phe
            -60                 -55                 -50

Gln Leu Glu Ile Ser Gly Phe Leu Lys Glu Met Ala Cys Pro Tyr Ser
            -45                 -40                 -35

Val Leu Ile Ser Gly Asp Ile Lys Asp Arg Leu Lys Lys Glu Asp
-30                 -25                 -20                 -15

Cys Leu Lys Leu Leu Leu Phe Leu Ser Thr Glu Leu Gln Ala Ser Gln
                -10                  -5                   1

Ile (2) INFORMATION FOR SEQ ID NO: 274:
```

(i) SEQUENCE CHARACTERISTICS:
        (A) LENGTH: 44 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -26..-1
        (C) IDENTIFICATION METHOD: Von Heijne matrix
        (D) OTHER INFORMATION:  score 9.6 seq WLIALASWSWALC/RI (xi) SEQUENCE DESCRIPTION: SEQ ID NO: 274:

Met Glu Lys Ser Trp Met Leu Trp Asn Phe Val Glu Arg Trp Leu Ile
    -25              -20              -15

Ala Leu Ala Ser Trp Ser Trp Ala Leu Cys Arg Ile Ser Leu Leu Pro
-10              -5                1                5

Leu Ile Val Thr Phe His Leu Tyr Gly Gly Ser Gly
            10                  15

(2) INFORMATION FOR SEQ ID NO: 275:

(i) SEQUENCE CHARACTERISTICS:
        (A) LENGTH: 89 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -36..-1
        (C) IDENTIFICATION METHOD: Von Heijne matrix
        (D) OTHER INFORMATION:  score 9.5 seq LGLLLLARHWCIA/GV (xi) SEQUENCE DESCRIPTION: SEQ ID NO: 275:

Met Gln Gln Thr Arg Thr Glu Ala Val Ala Gly Ala Phe Ser His Cys
    -35              -30              -25

Leu Gly Phe Cys Gly Met Arg Leu Gly Leu Leu Leu Ala Arg His
-20              -15              -10                  -5

Trp Cys Ile Ala Gly Val Phe Pro Gln Lys Phe Asp Gly Asp Ser Ala
                1                5                  10

Tyr Val Gly Met Ser Asp Gly Asn Pro Glu Leu Leu Ser Thr Ser Gln
            15              20              25

Thr Tyr Asn Gly Gln Ser Glu Asn Asn Glu Asp Tyr Glu Ile Pro Pro
        30              35              40

Ile Thr Pro Pro Asn Leu Pro Glu Ala
45                  50

(2) INFORMATION FOR SEQ ID NO: 276:

(i) SEQUENCE CHARACTERISTICS:
        (A) LENGTH: 53 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION:   score 9.1 seq LVVFLLLPLASGP/QV (xi) SEQUENCE DESCRIPTION: SEQ ID NO: 276:

Met Glu Lys Gly Asn Ala Phe Leu Lys Asn Arg Leu Val Val Phe Leu
             -20                 -15                 -10

Leu Leu Pro Leu Ala Ser Gly Pro Gln Val Lys Arg Lys Ser Glu Ile
             -5                  1                   5

Thr Lys Leu Ile Lys Ala Thr Arg Ile Ile Cys Leu Phe Asn Lys Phe
    10                  15                  20

Ser Arg Gly Asn Gly
 25

(2) INFORMATION FOR SEQ ID NO: 277:

(i) SEQUENCE CHARACTERISTICS:
        (A) LENGTH: 79 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION:   score 9 seq LLMLIVFHAASMA/LQ (xi) SEQUENCE DESCRIPTION: SEQ ID NO: 277:

Met Phe Pro Phe Asn Gln Ala Gly Leu Pro Thr Leu Met Leu Ile
             -20                 -15                 -10

Val Phe His Ala Ala Ser Met Ala Leu Gln Arg Leu Phe Leu Phe Ala
             -5                  1                   5

Leu Val Trp His Ser Lys Pro Ser Gly Leu Met Thr Gly Lys Leu Glu
    10                  15                  20

Ser Gln Ile Pro His Glu Lys Leu Thr His Ile Ser Val Met His Gly
 25              30                  35                      40

Pro Leu Ser Ser His His Ser Tyr Thr His Ile His Leu Phe Leu
             45                  50                  55

(2) INFORMATION FOR SEQ ID NO: 278:

(i) SEQUENCE CHARACTERISTICS:
        (A) LENGTH: 99 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -76..-1
        (C) IDENTIFICATION METHOD: Von Heijne matrix (D) OTHER INFORMATION: score 8.8 seq SLLLWMSSLPSLG/EK (xi) SEQUENCE DESCRIPTION: SEQ ID NO: 278:

Met Thr Ser Arg Ser Leu Arg Arg Cys Ser Cys Leu Arg Val Thr His
    -75              -70                  -65

Asn Lys Glu Ile Leu Ala Ser Thr Val Ser Leu Gly Val Glu Gly Tyr
-60              -55              -50                      -45

Met Leu Gly Gly Gly Ser Arg Ile Asn Ser Ser Asn Leu Asn Asp Gly
                -40              -35              -30

Glu Glu Glu Cys Ser Pro Asp Ser Leu Leu Val Trp Lys Lys Lys Ser
            -25              -20              -15

Leu Leu Leu Trp Met Ser Ser Leu Pro Ser Leu Gly Lys Tyr Phe
        -10              -5               1

Lys Arg Ile Leu Arg Trp Arg Glu His Trp Lys Ser Ser Gly Pro Ile
 5               10                  15                      20

Pro Leu Trp (2) INFORMATION FOR SEQ ID NO: 279:

(i) SEQUENCE CHARACTERISTICS:
        (A) LENGTH: 68 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -53..-1
        (C) IDENTIFICATION METHOD: Von Heijne matrix
        (D) OTHER INFORMATION: score 8.8 seq ILLLLTVLPCIXM/GQ (xi) SEQUENCE DESCRIPTION: SEQ ID NO: 279:

Met Trp Thr Ala Ser Ala Met Asp Phe Arg Thr Cys Ile Ala Ser Xaa
            -50              -45                  -40

Leu Pro Ala Leu Cys Tyr Val Gln Ala Cys Arg Ala Leu Met Ile Ala
        -35              -30              -25

Ala Ser Val Leu Gly Leu Pro Ala Ile Leu Leu Leu Thr Val Leu
    -20              -15              -10

Pro Cys Ile Xaa Met Gly Gln Glu Pro Gly Val Ala Lys Tyr Arg Xaa
 -5              1                5                    10

Ala Gln Leu Ala
        15

(2) INFORMATION FOR SEQ ID NO: 280:

(i) SEQUENCE CHARACTERISTICS:
        (A) LENGTH: 86 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -45..-1
        (C) IDENTIFICATION METHOD: Von Heijne matrix (D) OTHER INFORMATION: score 8.5 seq FALLSLSHPTCQA/GA (xi) SEQUENCE DESCRIPTION: SEQ ID NO: 280:

Met Gly Pro Pro Pro Thr His Ile Lys Tyr Leu His Leu Asn Ile Tyr
-45                 -40                 -35                 -30

Cys Asn Gly Lys Ser Thr Ala Pro Gly Ile Arg Ser His Ser Leu Gly
                -25                 -20                 -15

Phe Ala Leu Leu Ser Leu Ser His Pro Thr Cys Gln Ala Gly Ala Pro
            -10                 -5                   1

Ala Ala Ala Leu Pro Ser Leu Trp Ser Trp Cys Ser Arg Gly Ala Arg
     5                   10                  15

Val Arg Val Gly Arg Met Leu Ser His Leu Tyr Thr Cys Gly Trp Tyr
 20              25                  30                  35

Asp His Asn Pro His Gly
                 40

(2) INFORMATION FOR SEQ ID NO: 281:

(i) SEQUENCE CHARACTERISTICS:
            (A) LENGTH: 19 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -16..-1
            (C) IDENTIFICATION METHOD: Von Heijne matrix
            (D) OTHER INFORMATION: score 8.5 seq LLTFLAFTTLLFA/PP (xi) SEQUENCE DESCRIPTION: SEQ ID NO: 281:

Met Phe Cys Leu Leu Thr Phe Leu Ala Phe Thr Thr Leu Leu Phe Ala
-15                 -10                 -5

Pro Pro Trp
 1

(2) INFORMATION FOR SEQ ID NO: 282:

(i) SEQUENCE CHARACTERISTICS:
            (A) LENGTH: 80 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -29..-1
            (C) IDENTIFICATION METHOD: Von Heijne matrix
            (D) OTHER INFORMATION: score 8.4 seq LKCLLAVLSSLFA/AI (xi) SEQUENCE DESCRIPTION: SEQ ID NO: 282:

Met His Cys Gly Ser Thr Pro Gly Leu Cys Pro Cys Trp Val Pro Phe
                -25                 -20                 -15

Leu Lys Cys Leu Leu Ala Val Leu Ser Ser Leu Phe Ala Ala Ile Ser
            -10                 -5                   1

Val Asp Arg Leu Tyr Leu Ser Phe Cys Ser Asn Cys Ser Glu Ile Tyr

```
                5                   10                  15
Leu Trp Pro Pro Ser Phe Pro Ala Pro Pro Ser Pro Val Val Leu Leu
 20                  25                  30                  35

Val Phe Leu Cys Pro His Gly Thr Ser Leu Ser Phe Leu Lys Leu Pro
                 40                  45                  50
```

(2) INFORMATION FOR SEQ ID NO: 283:

(i) SEQUENCE CHARACTERISTICS:
        (A) LENGTH: 23 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:   score 8.3 seq VCSALLLLGIVSS/KP (xi) SEQUENCE DESCRIPTION: SEQ ID NO: 283:

```
Met Asn Leu Val Cys Ser Ala Leu Leu Leu Leu Gly Ile Val Ser Ser
    -15                 -10                 -5

Lys Pro Tyr Met Arg Lys Arg
 1               5
```

(2) INFORMATION FOR SEQ ID NO: 284:

(i) SEQUENCE CHARACTERISTICS:
        (A) LENGTH: 47 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -35..-1
        (C) IDENTIFICATION METHOD: Von Heijne matrix
        (D) OTHER INFORMATION:   score 8.3 seq AAMLIGLLAWLQT/VP (xi) SEQUENCE DESCRIPTION: SEQ ID NO: 284:

```
Met Ser Val Leu Asp Asp Arg Gln Arg Asp Ile Leu Val Val Gln Lys
-35                 -30                 -25                 -20

Arg His Ser Ser Leu Glu Ala Ala Met Leu Ile Gly Leu Leu Ala Trp
                -15                 -10                 -5

Leu Gln Thr Val Pro Ala His Gly Cys Gln Phe Leu Pro Ile Arg
                 1               5                  10
```

(2) INFORMATION FOR SEQ ID NO: 285:

(i) SEQUENCE CHARACTERISTICS:
        (A) LENGTH: 38 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens

```
          (F) TISSUE TYPE: Brain (ix) FEATURE:
          (A) NAME/KEY: sig_peptide
          (B) LOCATION: -20..-1
          (C) IDENTIFICATION METHOD: Von Heijne matrix
          (D) OTHER INFORMATION:   score 8.3 seq LLIICHYLPLSLC/IP (xi) SEQUENCE DESCRIPTION: SEQ ID NO: 285:

Met Gly Val Asn Gly Arg Arg Leu Leu Ile Ile Cys His Tyr Leu Pro
-20                 -15                 -10                  -5

Leu Ser Leu Cys Ile Pro Ile Pro Ser His Ile Asn Ser Leu Pro Arg
                 1               5                  10

Asn Thr Pro Pro Val Arg
            15

(2) INFORMATION FOR SEQ ID NO: 286:

(i) SEQUENCE CHARACTERISTICS:
          (A) LENGTH: 43 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -31..-1
          (C) IDENTIFICATION METHOD: Von Heijne matrix
          (D) OTHER INFORMATION:   score 8.2 seq LECLLLYLAESSG/LR (xi) SEQUENCE DESCRIPTION: SEQ ID NO: 286:

Met Lys Leu Arg Glu Cys Pro Ala Leu Arg Trp Ser Gln Leu Ser Gln
     -30                 -25                 -20

His Lys Leu Glu Cys Leu Leu Leu Tyr Leu Ala Glu Ser Ser Gly Leu
-15                 -10                  -5                   1

Arg Thr Gly Asn Val Gly Val Leu His Pro Arg
             5                  10

(2) INFORMATION FOR SEQ ID NO: 287:

(i) SEQUENCE CHARACTERISTICS:
          (A) LENGTH: 136 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -109..-1
          (C) IDENTIFICATION METHOD: Von Heijne matrix
          (D) OTHER INFORMATION:   score 8.2 seq LLRLPQLPPXCSA/GE (xi) SEQUENCE DESCRIPTION: SEQ ID NO: 287:

Met Asp Pro Arg Gly Ile Leu Lys Ala Phe Pro Lys Arg Gln Lys Ile
             -105                -100                 -95

His Ala Asp Ala Ser Ser Lys Val Leu Ala Lys Ile Pro Arg Arg Glu
             -90                 -85                  -80

Glu Gly Glu Glu Ala Glu Glu Trp Leu Ser Ser Leu Arg Ala His Val
```

```
            -75                 -70                 -65
Val Arg Thr Gly Ile Gly Arg Ala Arg Ala Glu Leu Phe Glu Lys Gln
        -60                 -55                 -50

Ile Val Gln His Gly Gly Gln Leu Cys Pro Ala Gln Gly Pro Gly Val
-45                 -40                 -35                 -30

Thr His Ile Val Val Asp Glu Gly Met Asp Tyr Glu Arg Ala Leu Arg
                -25                 -20                 -15

Leu Leu Arg Leu Pro Gln Leu Pro Pro Xaa Cys Ser Ala Gly Glu Val
            -10                 -5                   1

Ser Leu Ala Glu Leu Val Pro Ser Gly Glu Ala Gly Gly Cys Ser
     5                  10                  15

Trp Ile Gln His Leu His Pro Ser
 20                  25
```

(2) INFORMATION FOR SEQ ID NO: 288:

(i) SEQUENCE CHARACTERISTICS:
        (A) LENGTH: 26 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:   score 8 seq LFLVAVLVKVAEA/RK (xi) SEQUENCE DESCRIPTION: SEQ ID NO: 288:

```
Met Phe Trp Lys Leu Ser Leu Ser Leu Phe Leu Val Ala Val Leu Val
    -20                 -15                 -10

Lys Val Ala Glu Ala Arg Lys Asn Arg Ser
-5                   1                   5
```

(2) INFORMATION FOR SEQ ID NO: 289:

(i) SEQUENCE CHARACTERISTICS:
        (A) LENGTH: 26 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -18..-1
        (C) IDENTIFICATION METHOD: Von Heijne matrix
        (D) OTHER INFORMATION:   score 7.9 seq LFSLLVLQSMATG/AT (xi) SEQUENCE DESCRIPTION: SEQ ID NO: 289:

```
Met Ala Phe Leu Gly Leu Phe Ser Leu Leu Val Leu Gln Ser Met Ala
            -15                 -10                 -5

Thr Gly Ala Thr Phe Pro Glu Glu Ala Pro
             1                   5
```

(2) INFORMATION FOR SEQ ID NO: 290:

```
      (i) SEQUENCE CHARACTERISTICS:
          (A) LENGTH: 70 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -18..-1
          (C) IDENTIFICATION METHOD: Von Heijne matrix
          (D) OTHER INFORMATION:   score 7.9 seq LFSLLVLQSMATG/AT (xi) SEQUENCE DESCRIPTION: SEQ ID NO: 290:

Met Ala Phe Leu Gly Leu Phe Ser Leu Leu Val Leu Gln Ser Met Ala
            -15                 -10                  -5

Thr Gly Ala Thr Phe Pro Glu Glu Ala Ile Ala Asp Leu Ser Val Asn
  1                   5                  10

Met Tyr Asn Arg Leu Arg Ala Val Gly Ser Trp Arg Arg Glu Gly Ala
 15                  20                  25                  30

Ser Arg Gln Ile Ala Ser Cys Leu Pro Ala Phe Leu Leu His Leu Pro
             35                  40                  45

Leu Thr His Thr His Gly
             50

(2) INFORMATION FOR SEQ ID NO: 291:

(i) SEQUENCE CHARACTERISTICS:
          (A) LENGTH: 103 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -55..-1
          (C) IDENTIFICATION METHOD: Von Heijne matrix
          (D) OTHER INFORMATION:   score 7.8 seq ALLVALLFTLIHR/RR (xi) SEQUENCE DESCRIPTION: SEQ ID NO: 291:

Met Ser Phe Ser Leu Asn Phe Thr Leu Pro Ala Asn Thr Thr Ser Ser
-55                 -50                 -45                 -40

Pro Val Thr Gly Gly Lys Glu Thr Asp Cys Gly Pro Ser Leu Gly Leu
            -35                 -30                 -25

Ala Ala Gly Ile Pro Leu Leu Val Ala Thr Ala Leu Leu Val Ala Leu
            -20                 -15                 -10

Leu Phe Thr Leu Ile His Arg Arg Ser Ser Ile Glu Ala Met Glu
             -5                   1                   5

Glu Ser Asp Arg Pro Cys Glu Ile Ser Glu Ile Asp Asp Asn Pro Lys
 10                  15                  20                  25

Ile Ser Glu Asn Pro Arg Arg Ser Pro Thr His Glu Lys Asn Thr Met
             30                  35                  40

Gly Ala Gln Glu Ala Arg Trp
             45

(2) INFORMATION FOR SEQ ID NO: 292:
```

```
    (i) SEQUENCE CHARACTERISTICS:
        (A) LENGTH: 82 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -80..-1
        (C) IDENTIFICATION METHOD: Von Heijne matrix
        (D) OTHER INFORMATION:   score 7.7 seq LVLFLSLALLVTP/TS (xi) SEQUENCE DESCRIPTION: SEQ ID NO: 292:

Met Ser Thr Trp Tyr Leu Ala Leu Asn Lys Ser Tyr Lys Asn Lys Asp
-80              -75                 -70                 -65

Ser Val Arg Ile Tyr Leu Ser Leu Cys Thr Val Ser Ile Lys Phe Thr
                -60                 -55                 -50

Tyr Phe His Asp Ile Gln Thr Asn Cys Leu Thr Thr Trp Lys His Ser
            -45                 -40                 -35

Arg Cys Arg Phe Tyr Trp Ala Phe Gly Gly Ser Ile Leu Gln His Ser
        -30                 -25                 -20

Val Asp Pro Leu Val Leu Phe Leu Ser Leu Ala Leu Leu Val Thr Pro
    -15                 -10                  -5

Thr Ser
   1

(2) INFORMATION FOR SEQ ID NO: 293:

(i) SEQUENCE CHARACTERISTICS:
        (A) LENGTH: 43 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -19..-1
        (C) IDENTIFICATION METHOD: Von Heijne matrix
        (D) OTHER INFORMATION:   score 7.7 seq LQLLCCIFTLVLQ/HY (xi) SEQUENCE DESCRIPTION: SEQ ID NO: 293:

Met Ala Ile Gly Ile Ser Leu Gln Leu Leu Cys Cys Ile Phe Thr Leu
                -15                 -10                  -5

Val Leu Gln His Tyr Leu Leu Gly Ser His Pro Tyr Ile Thr Cys Ile
                 1               5                  10

His Ser Gln Leu Leu Leu Asp Ile Gln Gln Gln
        15                  20

(2) INFORMATION FOR SEQ ID NO: 294:

(i) SEQUENCE CHARACTERISTICS:
        (A) LENGTH: 74 amino acids
        (B) TYPE: AMINO ACID
        (D) TOPOLOGY: LINEAR (ii) MOLECULE TYPE: PROTEIN
```

```
    (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -19..-1
         (C) IDENTIFICATION METHOD: Von Heijne matrix
         (D) OTHER INFORMATION:   score 7.6 seq LLNLLLLSLFAGL/DP (xi) SEQUENCE DESCRIPTION: SEQ ID NO: 294:

Met Gln Ala Thr Ser Asn Leu Leu Asn Leu Leu Leu Ser Leu Phe
                -15                 -10                 -5

Ala Gly Leu Asp Pro Ser Lys Asn Lys Lys Arg Gly Ser Ser Phe Ser
  1               5                       10

Phe Lys Phe Pro Leu Leu Asp Asp Thr Pro Phe Leu Xaa Ser Arg Ile
    15                  20                  25

Glu Asn Ser Ala Thr His His Leu His Tyr Gly Leu Asn Met Ile Leu
 30              35              40                      45

Trp Val Asn Trp Lys Pro Lys Leu Thr Leu
                50              55

(2) INFORMATION FOR SEQ ID NO: 295:

(i) SEQUENCE CHARACTERISTICS:
         (A) LENGTH: 34 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -31..-1
         (C) IDENTIFICATION METHOD: Von Heijne matrix
         (D) OTHER INFORMATION:   score 7.6 seq VTLLCGWPGSHWC/AP (xi) SEQUENCE DESCRIPTION: SEQ ID NO: 295:

Met Met Lys Trp Lys Pro Glu Asp Leu Gly Ser Val Pro Cys Glu Ala
    -30                 -25                 -20

Phe Ser Val Thr Leu Leu Cys Gly Trp Pro Gly Ser His Trp Cys Ala
-15                 -10                 -5                   1

Pro Pro (2) INFORMATION FOR SEQ ID NO: 296:

(i) SEQUENCE CHARACTERISTICS:
         (A) LENGTH: 78 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -19..-1
         (C) IDENTIFICATION METHOD: Von Heijne matrix
         (D) OTHER INFORMATION:   score 7.6 seq LLNLLLLSLFAGL/DP (xi) SEQUENCE DESCRIPTION: SEQ ID NO: 296:
```

```
Met Gln Ala Thr Ser Asn Leu Leu Asn Leu Leu Leu Ser Leu Phe
            -15                 -10                 -5

Ala Gly Leu Asp Pro Ser Lys Thr Gln Ile Ser Pro Lys Glu Gly Trp
             1               5                  10

Gln Val Tyr Ser Ser Ala Gln Asp Pro Asp Gly Arg Cys Ile Cys Thr
         15                  20                  25

Val Val Ala Pro Glu Gln Asn Leu Cys Ser Arg Asp Ala Lys Ser Arg
 30                  35                  40                  45

Gln Leu Arg Gln Leu Leu Glu Lys Val Gln Asn Met Ser Arg
             50                  55
```

(2) INFORMATION FOR SEQ ID NO: 297:

(i) SEQUENCE CHARACTERISTICS:
        (A) LENGTH: 80 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -48..-1
        (C) IDENTIFICATION METHOD: Von Heijne matrix
        (D) OTHER INFORMATION:   score 7.5 seq FVILLLFIFTVVS/LV (xi) SEQUENCE DESCRIPTION: SEQ ID NO: 297:

```
Met Ala Ser Ser His Trp Asn Glu Thr Thr Thr Ser Val Tyr Gln Tyr
             -45                 -40                 -35

Leu Gly Phe Gln Val Gln Lys Ile Tyr Pro Phe His Asp Asn Trp Asn
         -30                 -25                 -20

Thr Ala Cys Phe Val Ile Leu Leu Phe Ile Phe Thr Val Val Ser
         -15                 -10                 -5

Leu Val Val Leu Ala Phe Leu Tyr Glu Val Leu Asp Cys Cys Cys Cys
 1                   5                  10                  15

Val Lys Asn Lys Thr Val Lys Asp Leu Lys Ser Glu Pro Asn Pro Arg
             20                  25                  30
```

(2) INFORMATION FOR SEQ ID NO: 298:

(i) SEQUENCE CHARACTERISTICS:
        (A) LENGTH: 35 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -33..-1
        (C) IDENTIFICATION METHOD: Von Heijne matrix
        (D) OTHER INFORMATION:   score 7.4 seq ITCCVLLLLNCSG/VW (xi) SEQUENCE DESCRIPTION: SEQ ID NO: 298:

```
Met Leu Trp Phe Ser Gly Val Gly Ala Leu Ala Glu Arg Tyr Cys Arg
             -30                 -25                 -20

Arg Ser Pro Gly Ile Thr Cys Cys Val Leu Leu Leu Asn Cys Ser
         -15                 -10                 -5
```

```
Gly Val Trp
    1

(2) INFORMATION FOR SEQ ID NO: 299:

(i) SEQUENCE CHARACTERISTICS:
        (A) LENGTH: 31 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -25..-1
        (C) IDENTIFICATION METHOD: Von Heijne matrix
        (D) OTHER INFORMATION:  score 7.3 seq LIFFLNVTQLVRG/RG (xi) SEQUENCE DESCRIPTION: SEQ ID NO: 299:

Met Leu Phe Leu Gln Met Gly Lys Gln Ser Trp Thr Leu Ile Phe Phe
-25              -20              -15                      -10

Leu Asn Val Thr Gln Leu Val Arg Gly Arg Gly Pro Gly Gly Arg
                -5                   1               5

(2) INFORMATION FOR SEQ ID NO: 300:

(i) SEQUENCE CHARACTERISTICS:
        (A) LENGTH: 36 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -27..-1
        (C) IDENTIFICATION METHOD: Von Heijne matrix
        (D) OTHER INFORMATION:  score 7.2 seq LLLGLCSPPXXSL/AS (xi) SEQUENCE DESCRIPTION: SEQ ID NO: 300:

Met Glu Leu Arg Xaa Xaa Pro Pro Gly Gly Arg Glu Val Gln Leu Leu
         -25              -20                  -15

Leu Gly Leu Cys Ser Pro Pro Xaa Xaa Ser Leu Ala Ser Phe Pro Lys
    -10              -5                   1               5

Ala Ala Gln Met (2) INFORMATION FOR SEQ ID NO: 301:

(i) SEQUENCE CHARACTERISTICS:
        (A) LENGTH: 24 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -14..-1
```

(C) IDENTIFICATION METHOD: Von Heijne matrix
            (D) OTHER INFORMATION:  score 7 seq LWSLLSSSGSHFG/IP (xi) SEQUENCE DESCRIPTION: SEQ ID NO: 301:

Met Leu Trp Ser Leu Leu Ser Ser Ser Gly Ser His Phe Gly Ile Pro
                -10                  -5                   1

His His Thr Phe Pro Gln Glu Gly
             5                  10

(2) INFORMATION FOR SEQ ID NO: 302:

(i) SEQUENCE CHARACTERISTICS:
        (A) LENGTH: 112 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -52..-1
        (C) IDENTIFICATION METHOD: Von Heijne matrix
        (D) OTHER INFORMATION:  score 7 seq SVWLCLLCYFAFP/FQ (xi) SEQUENCE DESCRIPTION: SEQ ID NO: 302:

Met Asp Ile Ser Gly Leu Ile Pro Gly Leu Val Ser Thr Phe Ile Leu
        -50                 -45                 -40

Leu Ser Xaa Ser Asp His Tyr Gly Arg Lys Phe Pro Met Ile Leu Ser
    -35                 -30                 -25

Ser Val Gly Ala Leu Ala Thr Ser Val Trp Leu Cys Leu Leu Cys Tyr
-20                 -15                 -10                  -5

Phe Ala Phe Pro Phe Gln Leu Leu Ile Ala Ser Thr Phe Ile Gly Ala
                 1                   5                  10

Phe Xaa Gly Asn Tyr Thr Thr Phe Trp Gly Ala Cys Phe Ala Tyr Ile
            15                  20                  25

Val Asp Gln Cys Lys Glu Xaa Xaa Gln Lys Thr Ile Arg Ile Ala Ile
        30                  35                  40

Ile Asp Phe Leu Leu Gly Leu Val Thr Gly Leu Thr Val Leu Ser Ser
45                  50                  55                  60

(2) INFORMATION FOR SEQ ID NO: 303:

(i) SEQUENCE CHARACTERISTICS:
        (A) LENGTH: 36 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -30..-1
        (C) IDENTIFICATION METHOD: Von Heijne matrix
        (D) OTHER INFORMATION:  score 7 seq LFVILLITSLIFC/SL (xi) SEQUENCE DESCRIPTION: SEQ ID NO: 303:

Met Xaa Val Phe Phe Ser Lys Asn Arg Phe Glu Met Tyr Phe Ser Leu
-30                 -25                 -20                 -15

-continued

```
Leu Leu Phe Val Ile Leu Leu Ile Thr Ser Leu Ile Phe Cys Ser Leu
            -10                  -5                          1

Tyr Val Ala Arg
         5
```

(2) INFORMATION FOR SEQ ID NO: 304:

(i) SEQUENCE CHARACTERISTICS:
        (A) LENGTH: 34 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -23..-1
        (C) IDENTIFICATION METHOD: Von Heijne matrix
        (D) OTHER INFORMATION:  score 6.9 seq SLSLLASHHSVSC/SN (xi) SEQUENCE DESCRIPTION: SEQ ID NO: 304:

```
Met Pro Val Pro Ala Cys Trp Ile Ser Ser Ser Leu Ser Leu Leu Ala
            -20                 -15                     -10

Ser His His Ser Val Ser Cys Ser Asn Ile Phe Leu Asn Phe Asn Pro
         -5                  1                   5

Asp Arg
 10
```

(2) INFORMATION FOR SEQ ID NO: 305:

(i) SEQUENCE CHARACTERISTICS:
        (A) LENGTH: 59 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:  score 6.9 seq LLACGSLLPGLWQ/HL (xi) SEQUENCE DESCRIPTION: SEQ ID NO: 305:

```
Met Cys Pro Val Phe Ser Lys Gln Leu Leu Ala Cys Gly Ser Leu Leu
            -20                 -15                     -10

Pro Gly Leu Trp Gln His Leu Thr Ala Asn His Trp Pro Pro Phe Ser
 -5                  1                   5                   10

Xaa Phe Leu Cys Thr Val Cys Ser Gly Ser Ser Glu Gln Ile Ser Glu
             15                  20                  25

Tyr Thr Ala Ser Ala Thr Pro Pro Leu Cys Leu
             30                  35
```

(2) INFORMATION FOR SEQ ID NO: 306:

(i) SEQUENCE CHARACTERISTICS:
        (A) LENGTH: 128 amino acids
        (B) TYPE: AMINO ACID
        (D) TOPOLOGY: LINEAR

```
    (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -76..-1
         (C) IDENTIFICATION METHOD: Von Heijne matrix
         (D) OTHER INFORMATION:   score 6.9 seq LLPLSAWPPWAWH/HH (xi) SEQUENCE DESCRIPTION: SEQ ID NO: 306:

Met Ala Leu Thr Ile His Gly Glu Arg Met Arg Pro Asp Trp Glu Ser
    -75                 -70                 -65

Pro Trp Ile Thr Ser Ser Gln Ala Gln Ser Leu Ser Leu Gly Gly Ser
-60                 -55                 -50                 -45

Pro Ser Ser Arg Gly Pro Leu Val Pro Arg Gly Glu Tyr Leu Ala Ser
                -40                 -35                 -30

Cys Pro Glu Gly Val Arg Ser His Ser His Leu Leu Pro Arg Ser Leu
            -25                 -20                 -15

Leu Pro Leu Ser Ala Trp Pro Pro Trp Ala Trp His His His Gly Pro
        -10                  -5                   1

Gly Thr Gln Ser Leu Val Gly Cys Leu Cys Ala Met Ser Pro Leu Leu
  5                  10                  15                  20

Pro Thr His Leu Ser Leu Pro Val Leu Glu Pro Ser Gly Thr Pro Ala
                 25                  30                  35

Leu Lys Asp Arg Arg Pro Cys Glu Val Gly Ile Pro Ile Pro Pro Arg
                 40                  45                  50

(2) INFORMATION FOR SEQ ID NO: 307:

(i) SEQUENCE CHARACTERISTICS:
        (A) LENGTH: 95 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -92..-1
         (C) IDENTIFICATION METHOD: Von Heijne matrix
         (D) OTHER INFORMATION:   score 6.8 seq ILIASSLPTLSHP/AP (xi) SEQUENCE DESCRIPTION: SEQ ID NO: 307:

Met Ala Ala Arg Phe Arg Cys Gly His Leu Cys Val Pro Glu Val Pro
    -90                 -85                 -80

Arg Gly Pro Ala Ser His Ala Glu Gly Gly Gly Arg Leu Ser Arg
-75                 -70                 -65

Lys Ala Ala His Gln Ala Gln Leu Cys Trp Arg Ala Gly Gly Asp Gly
-60                 -55                 -50                 -45

Arg Gly Asn Phe Asn Pro Met Asn Phe Leu Val Ala Gly Thr Phe Ala
                -40                 -35                 -30

Ser Ser Cys His Ser Pro Pro Leu Leu Trp Ser Leu Pro Pro Arg Ile
            -25                 -20                 -15

Leu Ile Ala Ser Ser Leu Pro Thr Leu Ser His Pro Ala Pro Gly
        -10                  -5                   1
```

(2) INFORMATION FOR SEQ ID NO: 308:

(i) SEQUENCE CHARACTERISTICS:
       (A) LENGTH: 87 amino acids
       (B) TYPE: AMINO ACID
       (D) TOPOLOGY: LINEAR (ii) MOLECULE TYPE: PROTEIN (vi) ORIGINAL SOURCE:
       (A) ORGANISM: Homo Sapiens
       (F) TISSUE TYPE: Brain (ix) FEATURE:
       (A) NAME/KEY: sig_peptide
       (B) LOCATION: -29..-1
       (C) IDENTIFICATION METHOD: Von Heijne matrix
       (D) OTHER INFORMATION:  score 6.8 seq VLSLICSCFYTQP/HP (xi) SEQUENCE DESCRIPTION: SEQ ID NO: 308:

Met Ala Ser Thr Ile Ser Ala Tyr Lys Glu Lys Met Lys Glu Leu Ser
            -25                 -20                 -15

Val Leu Ser Leu Ile Cys Ser Cys Phe Tyr Thr Gln Pro His Pro Asn
            -10                  -5                   1

Thr Val Tyr Gln Tyr Gly Asp Met Glu Val Lys Gln Leu Asp Lys Arg
     5                  10                  15

Ala Ser Gly Gln Ser Phe Glu Val Ile Leu Lys Ser Pro Ser Asp Leu
 20                  25                  30                  35

Ser Pro Glu Ser Pro Met Leu Ser Ser Pro Lys Lys Lys Asp Thr
             40                  45                  50

Ser Leu Glu Glu Leu Gln Lys
             55

(2) INFORMATION FOR SEQ ID NO: 309:

(i) SEQUENCE CHARACTERISTICS:
       (A) LENGTH: 120 amino acids
       (B) TYPE: AMINO ACID
       (D) TOPOLOGY: LINEAR (ii) MOLECULE TYPE: PROTEIN (vi) ORIGINAL SOURCE:
       (A) ORGANISM: Homo Sapiens
       (F) TISSUE TYPE: Brain (ix) FEATURE:
       (A) NAME/KEY: sig_peptide
       (B) LOCATION: -114..-1
       (C) IDENTIFICATION METHOD: Von Heijne matrix
       (D) OTHER INFORMATION:  score 6.7 seq LIPMAILLGQTQS/NS (xi) SEQUENCE DESCRIPTION: SEQ ID NO: 309:

Met Leu Gln Val Tyr Gly Lys Pro Val Tyr Gln Gly His Arg Ser Thr
            -110                -105                -100

Leu Lys Lys Gly Pro Tyr Leu Arg Phe Asn Ser Pro Ser Pro Lys Ser
             -95                 -90                 -85

Arg Pro Gln Arg Pro Lys Val Ile Glu Arg Val Lys Gly Thr Lys Val
             -80                 -75                 -70

Lys Ser Ile Arg Thr Gln Thr Asp Phe Tyr Ala Thr Lys Pro Lys Lys
     -65                 -60                 -55

Met Asp Ser Lys Met Lys His Ser Val Pro Val Leu Pro His Gly Asp
-50                 -45                 -40                 -35

Gln Gln Tyr Leu Phe Ser Pro Ser Arg Glu Met Pro Thr Phe Ser Gly
             -30                 -25                 -20

```
Thr Leu Glu Gly His Leu Ile Pro Met Ala Ile Leu Leu Gly Gln Thr
            -15                 -10                  -5

Gln Ser Asn Ser Asp Thr Met Pro
     1               5
```

(2) INFORMATION FOR SEQ ID NO: 310:

(i) SEQUENCE CHARACTERISTICS:
       (A) LENGTH: 127 amino acids
       (B) TYPE: AMINO ACID
       (D) TOPOLOGY: LINEAR (ii) MOLECULE TYPE: PROTEIN (vi) ORIGINAL SOURCE:
       (A) ORGANISM: Homo Sapiens
       (F) TISSUE TYPE: Brain (ix) FEATURE:
       (A) NAME/KEY: sig_peptide
       (B) LOCATION: -118..-1
       (C) IDENTIFICATION METHOD: Von Heijne matrix
       (D) OTHER INFORMATION:   score 6.7 seq LLFAKLFGHLTSA/RR (xi) SEQUENCE DESCRIPTION: SEQ ID NO: 310:

```
Met Ser Val Leu Glu Ile Ser Gly Met Ile Met Asn Arg Val Asn Ser
         -115                 -110                 -105

His Ile Pro Gly Ile Gly Tyr Gln Ile Phe Gly Asn Ala Val Ser Leu
         -100                  -95                  -90

Ile Leu Gly Leu Thr Pro Phe Val Phe Arg Leu Ser Gln Ala Thr Asp
     -85                  -80                  -75

Leu Glu Gln Leu Thr Ala His Ser Ala Ser Glu Leu Tyr Val Ile Ala
-70                   -65                  -60                  -55

Phe Gly Ser Asn Glu Asp Val Ile Val Leu Ser Met Val Ile Ile Ser
             -50                  -45                  -40

Phe Val Val Arg Val Ser Leu Val Trp Ile Phe Phe Leu Leu Cys
             -35                  -30                  -25

Val Ala Glu Arg Thr Tyr Lys Gln Arg Leu Leu Phe Ala Lys Leu Phe
         -20                  -15                  -10

Gly His Leu Thr Ser Ala Arg Arg Ala Arg Lys Ser Glu Val Pro
     -5                    1                    5
```

(2) INFORMATION FOR SEQ ID NO: 311:

(i) SEQUENCE CHARACTERISTICS:
       (A) LENGTH: 71 amino acids
       (B) TYPE: AMINO ACID
       (D) TOPOLOGY: LINEAR (ii) MOLECULE TYPE: PROTEIN (vi) ORIGINAL SOURCE:
       (A) ORGANISM: Homo Sapiens
       (F) TISSUE TYPE: Brain (ix) FEATURE:
       (A) NAME/KEY: sig_peptide
       (B) LOCATION: -69..-1
       (C) IDENTIFICATION METHOD: Von Heijne matrix
       (D) OTHER INFORMATION:   score 6.7 seq FFKLLLLGAMCSG/AR (xi) SEQUENCE DESCRIPTION: SEQ ID NO: 311:

```
Met Cys Lys Gly Ile Lys Ala Gly Asp Thr Cys Glu Lys Leu Val Gly
             -65                  -60                  -55

Tyr Ser Ala Val Tyr Arg Val Cys Phe Gly Met Ala Cys Phe Phe Phe
             -50                  -45                  -40
```

```
Ile Phe Cys Leu Leu Thr Leu Lys Ile Asn Asn Ser Lys Ser Cys Arg
        -35             -30                 -25

Ala His Ile His Asn Gly Phe Trp Phe Phe Lys Leu Leu Leu Leu Gly
    -20                 -15                 -10

Ala Met Cys Ser Gly Ala Arg
 -5                   1
```

(2) INFORMATION FOR SEQ ID NO: 312:

(i) SEQUENCE CHARACTERISTICS:
        (A) LENGTH: 114 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -104..-1
        (C) IDENTIFICATION METHOD: Von Heijne matrix
        (D) OTHER INFORMATION: score 6.6 seq HFSHVVWFHPTWA/QQ (xi) SEQUENCE DESCRIPTION: SEQ ID NO: 312:

```
Met Ser Asp Ser Ala Gly Gly Arg Ala Gly Leu Arg Arg Tyr Pro Lys
            -100                -95                 -90

Leu Pro Val Trp Val Val Glu Asp His Gln Glu Val Leu Pro Phe Ile
        -85                 -80                 -75

Tyr Arg Ala Ile Gly Ser Lys His Leu Pro Ala Ser Asn Val Ser Phe
        -70                 -65                 -60

Leu His Phe Asp Ser His Pro Asp Leu Leu Ile Pro Val Asn Met Pro
    -55                 -50                 -45

Ala Asp Thr Val Phe Asp Lys Glu Thr Leu Phe Gly Glu Leu Ser Ile
-40                 -35                 -30                 -25

Glu Asn Trp Ile Met Pro Ala Val Tyr Ala Gly His Phe Ser His Val
                -20                 -15                 -10

Val Trp Phe His Pro Thr Trp Ala Gln Gln Ile Arg Glu Gly Arg His
             -5                   1                    5

His Phe
     10
```

(2) INFORMATION FOR SEQ ID NO: 313:

(i) SEQUENCE CHARACTERISTICS:
        (A) LENGTH: 109 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -47..-1
        (C) IDENTIFICATION METHOD: Von Heijne matrix
        (D) OTHER INFORMATION: score 6.3 seq SSCVLLTALVALA/AY (xi) SEQUENCE DESCRIPTION: SEQ ID NO: 313:

```
Met Ser Ser Cys Arg Gly Gln Lys Val Ala Gly Gly Leu Arg Val Val
```

-continued

```
                    -45                     -40                      -35
Ser Pro Phe Pro Leu Cys Gln Pro Ala Gly Glu Pro Ser Arg Gly Lys
    -30                      -25                   -20

Met Arg Ser Ser Cys Val Leu Leu Thr Ala Leu Val Ala Leu Ala Ala
-15                  -10                  -5                      1

Tyr Tyr Val Tyr Ile Pro Leu Pro Gly Ser Val Ser Asp Pro Trp Lys
                5                     10                  15

Leu Met Leu Leu Asp Ala Thr Phe Arg Gly Ala Xaa Xaa Xaa Ser Xaa
        20                      25                  30

Leu Val Xaa Tyr Leu Gly Leu Ser Xaa His Leu Leu Ala Leu Xaa Xaa
        35                      40                  45

Xaa Leu Phe Leu Leu Ala Lys Lys Ala Arg Gly Leu Leu
50                       55                  60
```

(2) INFORMATION FOR SEQ ID NO: 314:

(i) SEQUENCE CHARACTERISTICS:
        (A) LENGTH: 72 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -42..-1
        (C) IDENTIFICATION METHOD: Von Heijne matrix
        (D) OTHER INFORMATION:   score 6.1 seq DLAVALSLLPAWT/ES (xi) SEQUENCE DESCRIPTION: SEQ ID NO: 314:

```
Met Ile Ile Pro Phe Lys Ile Lys Asn Leu Gly Gly Arg Val Leu Leu
        -40                     -35                  -30

Ser Gly Arg Glu Met Phe Pro Ala Ser Val Arg Ala Pro Asp Leu Ala
    -25                     -20                  -15

Val Ala Leu Ser Leu Leu Pro Ala Trp Thr Glu Ser Pro Thr Arg Gly
-10                  -5                       1                   5

Ser His Gln Ser Gln Ala Arg Ala His Ser Arg Ala Leu Arg Lys Gln
                10                      15                  20

Ser Arg Asn Thr Arg Ser Pro Arg
        25                  30
```

(2) INFORMATION FOR SEQ ID NO: 315:

(i) SEQUENCE CHARACTERISTICS:
        (A) LENGTH: 60 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -53..-1
        (C) IDENTIFICATION METHOD: Von Heijne matrix
        (D) OTHER INFORMATION:   score 6 seq ALILLLLAQKGPS/XF (xi) SEQUENCE DESCRIPTION: SEQ ID NO: 315:

```
Met Val Cys Ser Ala Pro Arg Lys Ile Val Val Arg Ala Phe Ile Thr
        -50             -45             -40

Ile Ile Phe Ile Tyr Tyr Ala Ile Lys Lys Arg Ala Asn Glu Pro Ala
        -35             -30             -25

Ala Tyr Leu Met Leu Lys Pro Glu Ala Leu Ile Leu Leu Leu Leu Ala
    -20              -15             -10

Gln Lys Gly Pro Ser Xaa Phe Leu Leu Val Trp Arg
-5                    1               5
```

(2) INFORMATION FOR SEQ ID NO: 316:

(i) SEQUENCE CHARACTERISTICS:
        (A) LENGTH: 60 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -40..-1
        (C) IDENTIFICATION METHOD: Von Heijne matrix
        (D) OTHER INFORMATION:  score 5.9 seq VCSALCSLGEVRP/XE (xi) SEQUENCE DESCRIPTION: SEQ ID NO: 316:

```
Met Thr Glu Ser Ser Met Lys Lys Leu Ala Ser Thr Leu Leu Asp Ala
-40                 -35             -30              -25

Ile Thr Asp Lys Asp Pro Leu Val Gln Glu Gln Val Cys Ser Ala Leu
            -20             -15             -10

Cys Ser Leu Gly Glu Val Arg Pro Xaa Glu Thr Leu Arg Ala Cys Glu
            -5               1               5

Glu Tyr Leu Arg Xaa Met Thr Ser Trp His Thr Arg
    10              15              20
```

(2) INFORMATION FOR SEQ ID NO: 317:

(i) SEQUENCE CHARACTERISTICS:
        (A) LENGTH: 59 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -43..-1
        (C) IDENTIFICATION METHOD: Von Heijne matrix
        (D) OTHER INFORMATION:  score 5.9 seq VFLFHCTSGLSSC/KC (xi) SEQUENCE DESCRIPTION: SEQ ID NO: 317:

```
Met Gln Glu Thr Asp Cys Asn Lys Arg Trp Gly Arg Gly Leu Gly Gly
            -40             -35             -30

Leu Trp Ser Glu Thr Gly Arg Arg Phe His Cys Lys Ser Phe Val Phe
    -25             -20             -15

Leu Phe His Cys Thr Ser Gly Leu Ser Ser Cys Lys Cys Ser Lys Lys
    -10              -5               1              5

His Xaa Lys Tyr Cys Phe Cys Phe Val Ala Ser
        10              15
```

(2) INFORMATION FOR SEQ ID NO: 318:

(i) SEQUENCE CHARACTERISTICS:
        (A) LENGTH: 45 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -17..-1
        (C) IDENTIFICATION METHOD: Von Heijne matrix
        (D) OTHER INFORMATION: score 5.8 seq VPWLSSTVSCAQG/LR (xi) SEQUENCE DESCRIPTION: SEQ ID NO: 318:

```
Met Leu Leu Glu Val Pro Trp Leu Ser Ser Thr Val Ser Cys Ala Gln
        -15                 -10                 -5

Gly Leu Arg Leu Ala Gln His Arg Val Pro Phe Phe Tyr Ser Asn Val
  1               5                  10                      15

Ser Leu Cys Lys Leu Leu Leu Pro Ala Xaa Leu His Gly
                 20                  25
```

(2) INFORMATION FOR SEQ ID NO: 319:

(i) SEQUENCE CHARACTERISTICS:
        (A) LENGTH: 105 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -29..-1
        (C) IDENTIFICATION METHOD: Von Heijne matrix
        (D) OTHER INFORMATION: score 5.7 seq SPAFLAVAGPGWA/RP (xi) SEQUENCE DESCRIPTION: SEQ ID NO: 319:

```
Met Ser Gly Gly Arg Met Gln Ala Arg Cys Ser Gln Ser Thr Trp
              -25                 -20                 -15

Ser Pro Ala Phe Leu Ala Val Ala Gly Pro Gly Trp Ala Arg Pro Gly
               -10                  -5                   1

Cys Xaa Leu Arg Thr Lys Tyr Asp Ser Gln Leu Ala Arg His Leu Leu
         5                  10                  15

Gln Pro Gln Phe Pro Gly Leu Thr Leu Gly Thr Leu Val Gln Pro Ala
 20              25                  30                      35

His Trp Gly Met Gly Gly Gly Thr Gly Gly Val Leu Gly Glu Gly Gly
                 40                  45                  50

Gly His Ser Tyr Ala Glu His Gly Thr Cys Leu Gln Ser Cys Ser Thr
             55                  60                  65

Asp Val Leu Xaa His Val Leu Leu Ala
             70                  75
```

(2) INFORMATION FOR SEQ ID NO: 320:

(i) SEQUENCE CHARACTERISTICS:

(A) LENGTH: 125 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -18..-1
        (C) IDENTIFICATION METHOD: Von Heijne matrix
        (D) OTHER INFORMATION:  score 5.6 seq WHFLASFFPRAGC/HG (xi) SEQUENCE DESCRIPTION: SEQ ID NO: 320:

Met Leu Gln Met Leu Trp His Phe Leu Ala Ser Phe Phe Pro Arg Ala
            -15                 -10                  -5

Gly Cys His Gly Ser Arg Glu Gly Asp Asp Arg Glu Val Arg Gly Thr
         1               5                  10

Pro Ala Pro Ala Trp Arg Asp Gln Met Ala Ser Phe Leu Gly Lys Gln
 15              20                  25                  30

Asp Gly Arg Ala Glu Ala Thr Glu Lys Arg Pro Thr Ile Leu Leu Val
                 35                  40                  45

Val Gly Pro Ala Glu Gln Phe Pro Lys Lys Ile Val Gln Ala Gly Asp
             50                  55                  60

Lys Asp Leu Asp Gly Gln Leu Asp Phe Glu Glu Phe Val His Tyr Leu
         65                  70                  75

Gln Asp His Glu Lys Lys Leu Arg Leu Val Phe Lys Ser Leu Asp Lys
     80                  85                  90

Lys Asn Asp Gly Arg Ile Asp Ala Gln Glu Ile Met Gln
 95                 100                 105

(2) INFORMATION FOR SEQ ID NO: 321:

(i) SEQUENCE CHARACTERISTICS:
        (A) LENGTH: 37 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -20..-1
        (C) IDENTIFICATION METHOD: Von Heijne matrix
        (D) OTHER INFORMATION:  score 5.6 seq SLVCLLAMGKGLG/SS (xi) SEQUENCE DESCRIPTION: SEQ ID NO: 321:

Met Tyr Ser His Pro Val Ser Ser Leu Val Cys Leu Leu Ala Met Gly
-20                 -15                 -10                  -5

Lys Gly Leu Gly Ser Ser Gln Ala Leu Val Gln Pro Asp Thr Trp Pro
                 1               5                  10

His Thr Ser Pro Arg
         15

(2) INFORMATION FOR SEQ ID NO: 322:

(i) SEQUENCE CHARACTERISTICS:
        (A) LENGTH: 92 amino acids
        (B) TYPE: AMINO ACID (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -35..-1
            (C) IDENTIFICATION METHOD: Von Heijne matrix
            (D) OTHER INFORMATION:   score 5.6 seq FIFMEVLGSGAFS/EV (xi) SEQUENCE DESCRIPTION: SEQ ID NO: 322:

Met Gly Arg Lys Glu Glu Asp Asp Cys Ser Xaa Trp Lys Lys Gln Thr
-35              -30              -25              -20

Thr Asn Ile Arg Lys Thr Phe Ile Phe Met Glu Val Leu Gly Ser Gly
              -15              -10                       -5

Ala Phe Ser Glu Val Phe Leu Val Lys Gln Arg Leu Thr Gly Lys Leu
              1               5                        10

Phe Ala Leu Lys Cys Ile Lys Lys Ser Pro Ala Phe Arg Asp Ser Ser
              15              20              25

Leu Glu Asn Glu Ile Ala Val Leu Lys Lys Ile Lys His Glu Asn Ile
30              35              40              45

Val Thr Leu Glu Asp Ile Tyr Glu Ser Thr Gln Gly
              50              55

(2) INFORMATION FOR SEQ ID NO: 323:

(i) SEQUENCE CHARACTERISTICS:
            (A) LENGTH: 48 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -29..-1
            (C) IDENTIFICATION METHOD: Von Heijne matrix
            (D) OTHER INFORMATION:   score 5.6 seq LLPNQSLFSLARA/VR (xi) SEQUENCE DESCRIPTION: SEQ ID NO: 323:

Met Met Ile Ala Val Phe Gly Asn Ala Asn Asp Arg Asn Val Leu Thr
              -25              -20              -15

Leu Leu Pro Asn Gln Ser Leu Phe Ser Leu Ala Arg Ala Val Arg Asn
        -10              -5                        1

His Leu Leu Leu Glu Glu Arg Arg Leu Thr Thr Tyr Gly Val Leu Cys
      5               10              15

(2) INFORMATION FOR SEQ ID NO: 324:

(i) SEQUENCE CHARACTERISTICS:
            (A) LENGTH: 58 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain

```
     (ix) FEATURE:
          (A) NAME/KEY: sig_peptide
          (B) LOCATION: -19..-1
          (C) IDENTIFICATION METHOD: Von Heijne matrix
          (D) OTHER INFORMATION:   score 5.6 seq LVVTAWFFGMCRS/KA (xi) SEQUENCE DESCRIPTION: SEQ ID NO: 324:

Met Phe Phe Glu Leu Pro Leu Val Val Thr Ala Trp Phe Phe Gly Met
              -15                 -10                  -5

Cys Arg Ser Lys Ala Leu Leu Gly Asn Ala Arg Ser Ala Leu Cys Leu
             1               5                   10

Gln Thr Lys Ala Cys Ala Ser Ser Thr Gln Pro Asp Thr His Asn Glu
         15                  20                  25

His His Pro Arg Asn Pro Cys Pro Tyr Leu
 30              35

(2) INFORMATION FOR SEQ ID NO: 325:

(i) SEQUENCE CHARACTERISTICS:
          (A) LENGTH: 54 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -44..-1
          (C) IDENTIFICATION METHOD: Von Heijne matrix
          (D) OTHER INFORMATION:   score 5.5 seq FLLIVANVHFSQT/WV (xi) SEQUENCE DESCRIPTION: SEQ ID NO: 325:

Met Asn His Asn Ile Ile Ile Cys Val Met Tyr Ile Val Pro Phe Leu
              -40                 -35                 -30

Met Thr Lys Cys Leu Tyr Phe Cys His Ser Cys Lys Arg Gly Ser Phe
             -25                 -20                 -15

Leu Leu Ile Val Ala Asn Val His Phe Ser Gln Thr Trp Val Phe Ser
         -10                  -5                   1

Gly Lys Pro Tyr Lys Gly
 5               10

(2) INFORMATION FOR SEQ ID NO: 326:

(i) SEQUENCE CHARACTERISTICS:
          (A) LENGTH: 53 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -21..-1
          (C) IDENTIFICATION METHOD: Von Heijne matrix
          (D) OTHER INFORMATION:   score 5.5 seq LTGLCXCCLQALG/LA (xi) SEQUENCE DESCRIPTION: SEQ ID NO: 326:

Met Ser Cys Gly Ser Ala Ala Ser Leu Thr Gly Leu Cys Xaa Cys Cys
 -20                 -15                 -10
```

```
Leu Gln Ala Leu Gly Leu Ala Trp Arg Arg Gly Leu Thr Gly Pro
 -5              1               5                      10

Gly Leu Pro Pro Val Leu Gln Ile Cys Cys Pro Arg Ser Leu Arg Gly
             15                  20                  25

Val Thr Ala Pro Thr
             30
```

(2) INFORMATION FOR SEQ ID NO: 327:

(i) SEQUENCE CHARACTERISTICS:
        (A) LENGTH: 68 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -46..-1
        (C) IDENTIFICATION METHOD: Von Heijne matrix
        (D) OTHER INFORMATION:   score 5.4 seq VLFFVGLITNGLA/MR (xi) SEQUENCE DESCRIPTION: SEQ ID NO: 327:

```
Met Gln Ala Val Asp Asn Leu Thr Ser Ala Pro Gly Asn Thr Ser Leu
-45                 -40                 -35

Cys Thr Arg Asp Tyr Lys Ile Thr Gln Val Leu Phe Pro Leu Leu Tyr
-30                 -25                 -20                 -15

Thr Val Leu Phe Phe Val Gly Leu Ile Thr Asn Gly Leu Ala Met Arg
             -10                  -5                       1

Ile Phe Phe Gln Ile Arg Ser Lys Ser Asn Phe Ile Ile Phe Leu Lys
             5                   10                  15

Asn Thr Val Lys
         20
```

(2) INFORMATION FOR SEQ ID NO: 328:

(i) SEQUENCE CHARACTERISTICS:
        (A) LENGTH: 28 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -20..-1
        (C) IDENTIFICATION METHOD: Von Heijne matrix
        (D) OTHER INFORMATION:   score 5.3 seq LCSSCCSWGPAAG/AL (xi) SEQUENCE DESCRIPTION: SEQ ID NO: 328:

```
Met Ala Ala Ala Met Xaa Leu Leu Cys Ser Ser Cys Cys Ser Trp Gly
-20                 -15                 -10                  -5

Pro Ala Ala Gly Ala Leu Gln Asn Pro Gln Arg Gly
                 1                   5
```

(2) INFORMATION FOR SEQ ID NO: 329:

(i) SEQUENCE CHARACTERISTICS:
        (A) LENGTH: 30 amino acids (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -25..-1
        (C) IDENTIFICATION METHOD: Von Heijne matrix
        (D) OTHER INFORMATION:   score 5.3 seq SVVKVLSLRKAQA/QS (xi) SEQUENCE DESCRIPTION: SEQ ID NO: 329:

Met Asp Phe Ile Lys Asp Gln Ser Leu Ser His Arg Ser Val Val Lys
-25                 -20                 -15                 -10

Val Leu Ser Leu Arg Lys Ala Gln Ala Gln Ser Ile Leu Glu
                -5                   1                  5

(2) INFORMATION FOR SEQ ID NO: 330:

(i) SEQUENCE CHARACTERISTICS:
        (A) LENGTH: 75 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -28..-1
        (C) IDENTIFICATION METHOD: Von Heijne matrix
        (D) OTHER INFORMATION:   score 5.3 seq RISCAFSLASSTA/RQ (xi) SEQUENCE DESCRIPTION: SEQ ID NO: 330:

Met Thr Arg Pro Phe Trp Ala Ser Cys Ser Thr Trp Ala Thr Ser Arg
            -25                 -20                 -15

Ile Ser Cys Ala Phe Ser Leu Ala Ser Ser Thr Ala Arg Gln Thr Ser
        -10                  -5                   1

Ile Ala Cys Cys Ala Thr His Arg Thr Ala Trp Ala Ser Arg Pro Gly
  5                  10                  15                  20

Pro Arg Arg Pro Trp Cys Cys Arg Tyr Ser Lys Pro Leu Thr Thr Trp
                25                  30                  35

Pro Val Arg Met Met Arg Arg Glu Gly Ser Xaa
                40                  45

(2) INFORMATION FOR SEQ ID NO: 331:

(i) SEQUENCE CHARACTERISTICS:
        (A) LENGTH: 35 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:   score 5.3 seq CAVSLTTAAVAFG/DE (xi) SEQUENCE DESCRIPTION: SEQ ID NO: 331:

Met Lys Ser Cys Ala Val Ser Leu Thr Thr Ala Ala Val Ala Phe Gly
    -15             -10              -5

Asp Glu Ala Lys Lys Met Ala Glu Gly Lys Ala Ser Arg Glu Ser Glu
 1           5                  10                  15

Glu Glu Thr (2) INFORMATION FOR SEQ ID NO: 332:

(i) SEQUENCE CHARACTERISTICS:
        (A) LENGTH: 39 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:   score 5.2 seq LSLSLICLRMSLS/LY (xi) SEQUENCE DESCRIPTION: SEQ ID NO: 332:

Met Ser Ile His Glu Cys Ala Cys Leu Ser Leu Ser Leu Ile Cys Leu
    -20                 -15                 -10

Arg Met Ser Leu Ser Leu Tyr Pro Pro Ala Ser Met Ile Leu Leu
 -5              1               5                   10

Pro Gln Thr Trp Lys Pro Arg
                15

(2) INFORMATION FOR SEQ ID NO: 333:

(i) SEQUENCE CHARACTERISTICS:
        (A) LENGTH: 42 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -15..-1
        (C) IDENTIFICATION METHOD: Von Heijne matrix
        (D) OTHER INFORMATION:   score 5.2 seq SGLSFLSVFSLWC/EP (xi) SEQUENCE DESCRIPTION: SEQ ID NO: 333:

Met Leu Ser Gly Leu Ser Phe Leu Ser Val Phe Ser Leu Trp Cys Glu
-15              -10              -5                        1

Pro Thr Leu Pro Ala Leu Gly Asn Gly Ser Val Leu Gly Val Arg Xaa
             5                  10                  15

Ser Ser Ser Ser Ser Ala Gln Cys Ser Leu
            20              25

(2) INFORMATION FOR SEQ ID NO: 334:

(i) SEQUENCE CHARACTERISTICS:
        (A) LENGTH: 87 amino acids
        (B) TYPE: AMINO ACID

```
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -85..-1
        (C) IDENTIFICATION METHOD: Von Heijne matrix
        (D) OTHER INFORMATION:   score 5.2 seq LYSILHFPFWVHG/RX (xi) SEQUENCE DESCRIPTION: SEQ ID NO: 334:

Met Gly Leu Lys Asp Lys Ser Gln Ala Pro Ala Ser Gly Leu Gly Val
-85                 -80                 -75                 -70

Leu Arg Gly Gln Arg Ser Gly Ser Phe Ile Ser Met Pro Ala Pro Ala
                -65                 -60                 -55

Ser Gly Gln Xaa Pro Glu Glu Ser Arg Ser Pro Ala Pro Pro Val Ala
            -50                 -45                 -40

Ser Arg Ser Gln Asn Arg Gly Tyr Arg Pro Trp His Gly Pro Leu Trp
        -35                 -30                 -25

Val His Gln Ser Val Arg Phe Gly Leu Tyr Ser Ile Leu His Phe Pro
    -20                 -15                 -10

Phe Trp Val His Gly Arg Xaa
 -5                       1

(2) INFORMATION FOR SEQ ID NO: 335:

(i) SEQUENCE CHARACTERISTICS:
        (A) LENGTH: 67 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -43..-1
        (C) IDENTIFICATION METHOD: Von Heijne matrix
        (D) OTHER INFORMATION:   score 5.2 seq PMQLLQVLSDVLA/EI (xi) SEQUENCE DESCRIPTION: SEQ ID NO: 335:

Met Ser Asp Gln Ile Lys Phe Ile Met Asp Ser Leu Asn Lys Glu Pro
                -40                 -35                 -30

Phe Arg Lys Asn Tyr Asn Leu Ile Thr Phe Asp Ser Leu Glu Pro Met
            -25                 -20                 -15

Gln Leu Leu Gln Val Leu Ser Asp Val Leu Ala Glu Ile Asp Pro Lys
    -10                  -5                  1                   5

Val Arg Val Phe Ser Phe Phe Leu Met Gly Ser Arg Lys Pro Ile Ser
                 10                  15                  20

Pro Ser Trp (2) INFORMATION FOR SEQ ID NO: 336:

(i) SEQUENCE CHARACTERISTICS:
        (A) LENGTH: 110 amino acids
        (B) TYPE: AMINO ACID
        (D) TOPOLOGY: LINEAR (ii) MOLECULE TYPE: PROTEIN
```

(vi) ORIGINAL SOURCE:
    (A) ORGANISM: Homo Sapiens
    (F) TISSUE TYPE: Brain (ix) FEATURE:
    (A) NAME/KEY: sig_peptide
    (B) LOCATION: -104..-1
    (C) IDENTIFICATION METHOD: Von Heijne matrix
    (D) OTHER INFORMATION: score 5.1 seq SSVASLTATPSLA/SP (xi) SEQUENCE DESCRIPTION: SEQ ID NO: 336:

Met Ser Pro Ser Cys Leu His Pro Asp Leu Trp Ser Met Cys Leu Glu
            -100                -95                 -90

Val Pro Ser Phe Thr Ala Thr Asp Ser Val Asn Cys Gly Cys Cys Leu
        -85                 -80                 -75

Glu Leu Ala Thr Glu Pro Ala Arg Asn Ile Arg Ser Thr Thr Arg Ala
    -70                 -65                 -60

Ser Leu Leu Arg Cys Ser Ser Phe Thr Ser Thr Arg Asn Ser Thr Gly
    -55                 -50                 -45

Ile Ser Ala Leu Pro Pro Ala Ala Pro Met Ala Trp Pro Phe Ser Ala
-40                 -35                 -30                 -25

Ser Leu Ser Thr Leu Pro Val Pro Leu Thr His Ser Ser Val Ala Ser
                -20                 -15                 -10

Leu Thr Ala Thr Pro Ser Leu Ala Ser Pro Thr Arg Met Met
            -5                  1                   5

(2) INFORMATION FOR SEQ ID NO: 337:

(i) SEQUENCE CHARACTERISTICS:
        (A) LENGTH: 24 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION: score 5.1 seq SFHLLLDPSSTQS/SI (xi) SEQUENCE DESCRIPTION: SEQ ID NO: 337:

Met Asp Leu Ser Phe His Leu Leu Leu Asp Pro Ser Ser Thr Gln Ser
-15                 -10                 -5

Ser Ile Leu Lys His Leu Pro Cys
 1               5

(2) INFORMATION FOR SEQ ID NO: 338:

(i) SEQUENCE CHARACTERISTICS:
        (A) LENGTH: 53 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -26..-1

(C) IDENTIFICATION METHOD: Von Heijne matrix
                (D) OTHER INFORMATION:   score 5 seq VISVLILVGFGAC/IY (xi) SEQUENCE DESCRIPTION: SEQ ID NO: 338:

Met Pro His Phe Leu Asp Trp Phe Val Xaa Val Tyr Leu Val Ile Ser
    -25                 -20                 -15

Val Leu Ile Leu Val Gly Phe Gly Ala Cys Ile Tyr Tyr Phe Glu Pro
-10                  -5                   1               5

Gly Leu Gln Glu Ala His Lys Trp Arg Met Xaa Arg Pro Trp Trp Thr
             10                  15                  20

Ala Thr Ser Thr Gly
            25

(2) INFORMATION FOR SEQ ID NO: 339:

(i) SEQUENCE CHARACTERISTICS:
        (A) LENGTH: 39 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -30..-1
        (C) IDENTIFICATION METHOD: Von Heijne matrix
        (D) OTHER INFORMATION:   score 5 seq IVGLLAQLEKINA/EP (xi) SEQUENCE DESCRIPTION: SEQ ID NO: 339:

Met Ser Lys Leu Lys Val Ile Pro Glu Lys Ser Leu Thr Asn Asn Ser
-30                 -25                 -20                 -15

Arg Ile Val Gly Leu Leu Ala Gln Leu Glu Lys Ile Asn Ala Glu Pro
                -10                  -5                   1

Ser Glu Ser Asp Thr Ser Arg
             5

(2) INFORMATION FOR SEQ ID NO: 340:

(i) SEQUENCE CHARACTERISTICS:
        (A) LENGTH: 43 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -23..-1
        (C) IDENTIFICATION METHOD: Von Heijne matrix
        (D) OTHER INFORMATION:   score 5 seq LIPAMAFLSCVRP/ES (xi) SEQUENCE DESCRIPTION: SEQ ID NO: 340:

Met Met Ser Ala Ser Arg Leu Ala Gly Thr Leu Ile Pro Ala Met Ala
            -20                 -15                 -10

Phe Leu Ser Cys Val Arg Pro Glu Ser Xaa Glu Pro Cys Val Glu Val
         -5                   1               5

Val Pro Asn Ile Thr Tyr Gln Cys Met Glu Leu
 10              15                  20

(2) INFORMATION FOR SEQ ID NO: 341:

(i) SEQUENCE CHARACTERISTICS:
        (A) LENGTH: 65 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -49..-1
        (C) IDENTIFICATION METHOD: Von Heijne matrix
        (D) OTHER INFORMATION:  score 4.9 seq VTVCCXLVAFLFC/IL (xi) SEQUENCE DESCRIPTION: SEQ ID NO: 341:

```
Met Val Asp Gly Thr Gln Leu Arg Gly Leu Thr Arg Met Tyr Gln Val
            -45                 -40                 -35

Pro Leu Xaa Leu Asp Arg Asp Glu Thr Leu Val Arg Leu Arg Phe Thr
        -30                 -25                 -20

Met Val Ala Leu Val Thr Val Cys Cys Xaa Leu Val Ala Phe Leu Phe
    -15                 -10                  -5

Cys Ile Leu Trp Ser Leu Leu Phe His Phe Lys Glu Thr Thr Ala Thr
 1           5                   10                  15

Gly
```

(2) INFORMATION FOR SEQ ID NO: 342:

(i) SEQUENCE CHARACTERISTICS:
        (A) LENGTH: 34 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -26..-1
        (C) IDENTIFICATION METHOD: Von Heijne matrix
        (D) OTHER INFORMATION:  score 4.9 seq LISMLQMLAVIIT/NT (xi) SEQUENCE DESCRIPTION: SEQ ID NO: 342:

```
Met Lys Gln Asn Phe Leu Val Leu Asn Ser Val Trp Tyr Leu Ile Ser
    -25                 -20                 -15

Met Leu Gln Met Leu Ala Val Ile Ile Thr Asn Thr Thr Ile Thr Thr
-10              -5                   1                   5

Ile Gly
```

(2) INFORMATION FOR SEQ ID NO: 343:

(i) SEQUENCE CHARACTERISTICS:
        (A) LENGTH: 124 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain

```
    (ix) FEATURE:
         (A) NAME/KEY: sig_peptide
         (B) LOCATION: -59..-1
         (C) IDENTIFICATION METHOD: Von Heijne matrix
         (D) OTHER INFORMATION:   score 4.9 seq LVEMCLEVLGSSA/GD (xi) SEQUENCE DESCRIPTION: SEQ ID NO: 343:

Met Glu Cys Gln Asn Ser Ser Leu Lys Lys Cys Leu Val Glu Lys
             -55                 -50                 -45

Ser Leu Val Lys Ala Ser Tyr Leu Ile Ala Phe Gln Thr Ala Ala Ser
             -40                 -35                 -30

Lys Lys Pro Phe Ser Ile Ala Glu Glu Leu Ile Lys Pro Tyr Leu Val
         -25                 -20                 -15

Glu Met Cys Leu Glu Val Leu Gly Ser Ser Ala Gly Asp Lys Met Lys
    -10                  -5                    1                 5

Thr Ile Pro Leu Ser Asn Val Thr Ile Gln His Arg Ile Asp Glu Leu
                 10                  15                  20

Ser Ala Asp Ile Glu Asp Gln Leu Ile Gln Lys Val Arg Glu Ser Lys
             25                  30                  35

Trp Phe Ala Leu Gln Ile Asp Glu Ser Ser Glu Ile Ser Asn Ile Thr
             40                  45                  50

Leu Leu Leu Cys Tyr Ile Arg Phe Ile Asp Tyr Asp
             55                  60                  65

(2) INFORMATION FOR SEQ ID NO: 344:

(i) SEQUENCE CHARACTERISTICS:
        (A) LENGTH: 27 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -23..-1
         (C) IDENTIFICATION METHOD: Von Heijne matrix
         (D) OTHER INFORMATION:   score 4.8 seq VMWLVALLEMCVC/KK (xi) SEQUENCE DESCRIPTION: SEQ ID NO: 344:

Met His Ser Ser Ile Lys Thr Lys Gly Ser Val Met Trp Leu Val Ala
             -20                 -15                 -10

Leu Leu Glu Met Cys Val Cys Lys Lys Ser Arg
         -5                   1

(2) INFORMATION FOR SEQ ID NO: 345:

(i) SEQUENCE CHARACTERISTICS:
        (A) LENGTH: 44 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -18..-1
         (C) IDENTIFICATION METHOD: Von Heijne matrix
```

(D) OTHER INFORMATION:   score 4.8 seq LEAISSLSSFVLG/RM (xi) SEQUENCE DESCRIPTION: SEQ ID NO: 345:

Met Thr Val Leu Pro Leu Glu Ala Ile Ser Ser Leu Ser Ser Phe Val
            -15                 -10                  -5

Leu Gly Arg Met Asn Ser Arg Gly Ala Gly Lys Thr Gln Asn Leu Asp
         1               5                  10

Ala Ser Ser Leu Leu Leu Leu Cys Cys Leu Ile Leu
 15              20                  25

(2) INFORMATION FOR SEQ ID NO: 346:

(i) SEQUENCE CHARACTERISTICS:
        (A) LENGTH: 125 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -30..-1
        (C) IDENTIFICATION METHOD: Von Heijne matrix
        (D) OTHER INFORMATION:   score 4.8 seq ILFCVGAVGACTL/SV (xi) SEQUENCE DESCRIPTION: SEQ ID NO: 346:

Met Gly Thr Ala Ser Arg Ser Asn Ile Ala Arg His Leu Gln Thr Asn
-30              -25                 -20                 -15

Leu Ile Leu Phe Cys Val Gly Ala Val Gly Ala Cys Thr Leu Ser Val
             -10                  -5                    1

Thr Gln Pro Trp Tyr Leu Glu Val Asp Tyr Thr His Glu Ala Val Thr
         5                  10                  15

Ile Lys Cys Thr Phe Ser Ala Thr Gly Cys Pro Ser Glu Gln Pro Thr
         20                  25                  30

Cys Leu Trp Phe Arg Tyr Gly Ala His Gln Pro Glu Asn Leu Cys Leu
 35                  40                  45                  50

Asp Gly Cys Lys Ser Glu Ala Xaa Lys Phe Thr Val Arg Glu Ala Leu
                 55                  60                  65

Lys Glu Asn Gln Val Ser Leu Thr Val Asn Arg Val Thr Ser Asn Asp
             70                  75                  80

Ser Ala Ile Tyr Ile Cys Gly Ile Ala Phe Pro Ser Val
             85                  90                  95

(2) INFORMATION FOR SEQ ID NO: 347:

(i) SEQUENCE CHARACTERISTICS:
        (A) LENGTH: 46 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -25..-1
        (C) IDENTIFICATION METHOD: Von Heijne matrix
        (D) OTHER INFORMATION:   score 4.8 seq ALFYSVVVSTVSG/NE (xi) SEQUENCE DESCRIPTION: SEQ ID NO: 347:

Met Asn Ser Ser Lys Glu Glu Met Arg Glu Leu Ala Ala Leu Phe Tyr
-25          -20           -15              -10

Ser Val Val Val Ser Thr Val Ser Gly Asn Glu Leu Lys Ser Met Ile
             -5                1                5

Glu Gln Leu Ile Lys Thr Thr Lys Asp Asn His Ser Leu Arg
         10              15              20

(2) INFORMATION FOR SEQ ID NO: 348:

(i) SEQUENCE CHARACTERISTICS:
        (A) LENGTH: 81 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -52..-1
        (C) IDENTIFICATION METHOD: Von Heijne matrix
        (D) OTHER INFORMATION:   score 4.7 seq LLAKALHLLKSSC/AP (xi) SEQUENCE DESCRIPTION: SEQ ID NO: 348:

Met Ser Gln Asp Gly Gly Xaa Gly Glu Leu Lys His Met Val Met Ser
        -50             -45              -40

Phe Arg Val Ser Glu Leu Gln Val Leu Leu Gly Phe Ala Gly Arg Asn
        -35             -30              -25

Lys Ser Gly Arg Lys His Glu Leu Leu Ala Lys Ala Leu His Leu Leu
-20             -15              -10                   -5

Lys Ser Ser Cys Ala Pro Ser Val Gln Met Lys Ile Lys Glu Leu Tyr
                 1               5                10

Arg Arg Arg Phe Pro Arg Lys Thr Leu Gly Pro Ser Asp Leu Ser Ser
            15              20              25

Gly (2) INFORMATION FOR SEQ ID NO: 349:

(i) SEQUENCE CHARACTERISTICS:
        (A) LENGTH: 47 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -29..-1
        (C) IDENTIFICATION METHOD: Von Heijne matrix
        (D) OTHER INFORMATION:   score 4.7 seq LCYLSIFCLGVLF/II (xi) SEQUENCE DESCRIPTION: SEQ ID NO: 349:

Met Pro Cys Ile Ser Leu Leu Gly Leu Leu Tyr Asn Phe Val Gln Val
            -25             -20              -15

Leu Cys Tyr Leu Ser Ile Phe Cys Leu Gly Val Leu Phe Ile Ile Glu
            -10              -5                1

Arg Gly Ser Leu Lys Val Ser Lys Leu Ile Cys Arg Pro Pro Gly

```
                 5                  10                 15
```

(2) INFORMATION FOR SEQ ID NO: 350:

(i) SEQUENCE CHARACTERISTICS:
        (A) LENGTH: 47 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -15..-1
        (C) IDENTIFICATION METHOD: Von Heijne matrix
        (D) OTHER INFORMATION:   score 4.7 seq IAVLFCFFLLIIF/QT (xi) SEQUENCE DESCRIPTION: SEQ ID NO: 350:

```
Met Lys Ile Ala Val Leu Phe Cys Phe Phe Leu Leu Ile Ile Phe Gln
-15              -10                 -5                       1

Thr Asp Phe Gly Lys Asn Glu Glu Ile Pro Arg Lys Gln Arg Arg Lys
             5                  10                 15

Ile Tyr His Arg Arg Leu Arg Lys Ser Ser Thr Ser His Lys Gln
         20                  25                 30
```

(2) INFORMATION FOR SEQ ID NO: 351:

(i) SEQUENCE CHARACTERISTICS:
        (A) LENGTH: 48 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -43..-1
        (C) IDENTIFICATION METHOD: Von Heijne matrix
        (D) OTHER INFORMATION:   score 4.7 seq STWSSASLRGSWQ/QG (xi) SEQUENCE DESCRIPTION: SEQ ID NO: 351:

```
Met Ala Lys Gln Lys Pro His Val Leu Gly Ser Arg Val Met Pro Ala
        -40                 -35                 -30

Ser Cys Val Ser Glu Arg Arg Arg Lys Pro Ser Phe Gln Val Ser Thr
        -25                 -20                 -15

Trp Ser Ser Ala Ser Leu Arg Gly Ser Trp Gln Gln Gly Met Pro Gly
        -10                  -5                  1               5
```

(2) INFORMATION FOR SEQ ID NO: 352:

(i) SEQUENCE CHARACTERISTICS:
        (A) LENGTH: 17 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:

(A) NAME/KEY: sig_peptide
            (B) LOCATION: -15..-1
            (C) IDENTIFICATION METHOD: Von Heijne matrix
            (D) OTHER INFORMATION:  score 4.6 seq FLYLKSVFDVSLG/AR (xi) SEQUENCE DESCRIPTION: SEQ ID NO: 352:

Met Gly Phe Leu Tyr Leu Lys Ser Val Phe Asp Val Ser Leu Gly Ala
-15              -10              -5                        1

Arg (2) INFORMATION FOR SEQ ID NO: 353:

(i) SEQUENCE CHARACTERISTICS:
            (A) LENGTH: 69 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -61..-1
            (C) IDENTIFICATION METHOD: Von Heijne matrix
            (D) OTHER INFORMATION:  score 4.6 seq LLLLHGGGHSALS/WA (xi) SEQUENCE DESCRIPTION: SEQ ID NO: 353:

Met Arg Met Gly Pro Gly Arg Lys Arg Asp Phe Ser Pro Val Pro Trp
    -60              -55              -50

Ser Gln Tyr Phe Glu Ser Met Glu Asp Val Glu Val Glu Asn Glu Thr
-45              -40              -35                      -30

Gly Lys Asp Thr Phe Arg Val Tyr Lys Ser Gly Ser Glu Gly Pro Val
                -25              -20              -15

Leu Leu Leu Leu His Gly Gly Gly His Ser Ala Leu Ser Trp Ala Val
                -10              -5                        1

Phe Thr Ala Ala Xaa
            5

(2) INFORMATION FOR SEQ ID NO: 354:

(i) SEQUENCE CHARACTERISTICS:
            (A) LENGTH: 23 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -13..-1
            (C) IDENTIFICATION METHOD: Von Heijne matrix
            (D) OTHER INFORMATION:  score 4.6 seq MIFLLYLLPSSEE/RR (xi) SEQUENCE DESCRIPTION: SEQ ID NO: 354:

Met Ile Phe Leu Leu Tyr Leu Leu Pro Ser Ser Glu Glu Arg Arg Lys
            -10              -5                        1

Leu Leu Phe Ser Pro His Arg
        5                10

(2) INFORMATION FOR SEQ ID NO: 355:

(i) SEQUENCE CHARACTERISTICS:
    (A) LENGTH: 70 amino acids
    (B) TYPE: AMINO ACID
    (D) TOPOLOGY: LINEAR (ii) MOLECULE TYPE: PROTEIN (vi) ORIGINAL SOURCE:
    (A) ORGANISM: Homo Sapiens
    (F) TISSUE TYPE: Brain (ix) FEATURE:
    (A) NAME/KEY: sig_peptide
    (B) LOCATION: -61..-1
    (C) IDENTIFICATION METHOD: Von Heijne matrix
    (D) OTHER INFORMATION:  score 4.6 seq LLLLHGGGHSALS/WA (xi) SEQUENCE DESCRIPTION: SEQ ID NO: 355:

Met Arg Met Gly Pro Gly Arg Lys Arg Asp Phe Ser Pro Val Pro Trp
    -60                 -55                 -50

Ser Gln Tyr Phe Glu Ser Met Glu Asp Val Glu Val Glu Asn Glu Thr
    -45             -40              -35             -30

Gly Lys Asp Thr Phe Arg Val Tyr Lys Ser Gly Ser Glu Gly Pro Val
                -25                 -20                 -15

Leu Leu Leu Leu His Gly Gly Gly His Ser Ala Leu Ser Trp Ala Val
                -10             -5                   1

Phe Thr Ala Ala Thr Trp
                5

(2) INFORMATION FOR SEQ ID NO: 356:

(i) SEQUENCE CHARACTERISTICS:
        (A) LENGTH: 30 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:  score 4.5 seq LLNLISILASIPS/QF (xi) SEQUENCE DESCRIPTION: SEQ ID NO: 356:

Met Leu Ser Leu Leu Asn Leu Ile Ser Ile Leu Ala Ser Ile Pro Ser
    -15                 -10                 -5

Gln Phe Lys Pro Gln Phe Ser Lys Leu Pro Leu Ser Gly Arg
 1               5                   10

(2) INFORMATION FOR SEQ ID NO: 357:

(i) SEQUENCE CHARACTERISTICS:
        (A) LENGTH: 28 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide

```
            (B) LOCATION: -25..-1
            (C) IDENTIFICATION METHOD: Von Heijne matrix
            (D) OTHER INFORMATION:   score 4.5 seq LMLLWPVHPLLVG/HR (xi) SEQUENCE DESCRIPTION: SEQ ID NO: 357:

Met Gly Thr Thr Ser Asn Met Val Thr Thr Ile His Leu Met Leu Leu
-25             -20             -15                     -10

Trp Pro Val His Pro Leu Leu Val Gly His Arg Gly
            -5                   1

(2) INFORMATION FOR SEQ ID NO: 358:

(i) SEQUENCE CHARACTERISTICS:
        (A) LENGTH: 147 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -101..-1
        (C) IDENTIFICATION METHOD: Von Heijne matrix
        (D) OTHER INFORMATION:   score 4.4 seq ISHILAFFAASDG/IV (xi) SEQUENCE DESCRIPTION: SEQ ID NO: 358:

Met Gly Asp Pro Glu Arg Pro Glu Ala Ala Gly Leu Asp Gln Asp Glu
    -100            -95             -90

Arg Ser Ser Ser Asp Thr Asn Glu Ser Glu Ile Lys Ser Asn Glu Glu
-85             -80             -75                     -70

Pro Leu Leu Arg Lys Ser Ser Arg Arg Phe Val Ile Phe Pro Ile Gln
                -65             -60                 -55

Tyr Pro Asp Ile Trp Lys Met Tyr Lys Gln Ala Gln Ala Ser Phe Trp
                -50             -45                 -40

Thr Ala Glu Glu Val Asp Leu Ser Lys Asp Leu Pro His Trp Asn Lys
        -35             -30                 -25

Leu Lys Ala Asp Glu Lys Tyr Phe Ile Ser His Ile Leu Ala Phe Phe
    -20             -15                 -10

Ala Ala Ser Asp Gly Ile Val Asn Glu Asn Leu Val Glu Arg Phe Ser
 -5              1              5                      10

Gln Glu Val Gln Val Pro Glu Ala Arg Cys Phe Tyr Gly Phe Gln Ile
             15              20              25

Leu Ile Glu Asn Val His Ser Glu Met Tyr Ser Leu Leu Ile Asp Thr
         30              35              40

Tyr Ile Arg
    45

(2) INFORMATION FOR SEQ ID NO: 359:

(i) SEQUENCE CHARACTERISTICS:
        (A) LENGTH: 65 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
```

```
        (A) NAME/KEY: sig_peptide
        (B) LOCATION: -16..-1
        (C) IDENTIFICATION METHOD: Von Heijne matrix
        (D) OTHER INFORMATION:  score 4.4 seq GLFSLLPHPPCVG/RV (xi) SEQUENCE DESCRIPTION: SEQ ID NO: 359:

Met Asp Ala Gly Leu Phe Ser Leu Leu Pro His Pro Pro Cys Val Gly
    -15             -10             -5

Arg Val Leu Pro Gln Ser Arg Tyr His Leu His Pro Arg Ser Pro Leu
 1           5               10                  15

Val Glu Asp Thr Cys Phe Phe Gln Arg Leu Lys Lys Ile Leu Asn Lys
            20              25              30

Ile Gly Asn Leu Phe His Ser Thr Lys Ser Leu Cys Val Ser Leu Ala
        35              40              45

Pro (2) INFORMATION FOR SEQ ID NO: 360:

(i) SEQUENCE CHARACTERISTICS:
        (A) LENGTH: 19 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -14..-1
        (C) IDENTIFICATION METHOD: Von Heijne matrix
        (D) OTHER INFORMATION:  score 4.4 seq LITLTYLIQGESA/RT (xi) SEQUENCE DESCRIPTION: SEQ ID NO: 360:

Met Leu Ile Thr Leu Thr Tyr Leu Ile Gln Gly Glu Ser Ala Arg Thr
              -10             -5                  1

Thr Phe Glu
        5

(2) INFORMATION FOR SEQ ID NO: 361:

(i) SEQUENCE CHARACTERISTICS:
        (A) LENGTH: 31 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -26..-1
        (C) IDENTIFICATION METHOD: Von Heijne matrix
        (D) OTHER INFORMATION:  score 4.4 seq RVQCLCAIPFAFS/LT (xi) SEQUENCE DESCRIPTION: SEQ ID NO: 361:

Met Tyr Thr Gly Phe Arg Ile Glu Ala Thr Leu Leu Thr Arg Val Gln
    -25             -20             -15

Cys Leu Cys Ala Ile Pro Phe Ala Phe Ser Leu Thr Gly Ile Arg
-10             -5              1               5

(2) INFORMATION FOR SEQ ID NO: 362:
```

```
        (i) SEQUENCE CHARACTERISTICS:
            (A) LENGTH: 56 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -47..-1
            (C) IDENTIFICATION METHOD: Von Heijne matrix
            (D) OTHER INFORMATION:   score 4.4 seq ISHILAFFAASDG/IV (xi) SEQUENCE DESCRIPTION: SEQ ID NO: 362:

Met Tyr Lys Gln Ala Gln Ala Ser Phe Trp Thr Ala Glu Glu Val Asp
        -45                 -40                 -35

Leu Ser Lys Asp Leu Pro His Trp Asn Lys Leu Lys Ala Asp Glu Lys
        -30                 -25                 -20

Tyr Phe Ile Ser His Ile Leu Ala Phe Phe Ala Ala Ser Asp Gly Ile
-15                 -10                  -5                   1

Val Asn Glu Asn Leu Val Glu Arg
             5

(2) INFORMATION FOR SEQ ID NO: 363:

(i) SEQUENCE CHARACTERISTICS:
            (A) LENGTH: 48 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -28..-1
            (C) IDENTIFICATION METHOD: Von Heijne matrix
            (D) OTHER INFORMATION:   score 4.3 seq FLGLAAMASPSRN/SQ (xi) SEQUENCE DESCRIPTION: SEQ ID NO: 363:

Met Leu Leu His Leu Cys Ser Val Lys Asn Leu Tyr Gln Asn Arg Phe
            -25                 -20                 -15

Leu Gly Leu Ala Ala Met Ala Ser Pro Ser Arg Asn Ser Gln Ser Arg
        -10                  -5                   1

Arg Arg Cys Lys Glu Pro Leu Arg Tyr Ser Tyr Asn Pro Asp Gln Gly
 5                   10                  15                  20

(2) INFORMATION FOR SEQ ID NO: 364:

(i) SEQUENCE CHARACTERISTICS:
            (A) LENGTH: 55 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
```

```
            (B) LOCATION: -18..-1
            (C) IDENTIFICATION METHOD: Von Heijne matrix
            (D) OTHER INFORMATION:   score 4.3 seq WTCLKSFPSPTSS/HA (xi) SEQUENCE DESCRIPTION: SEQ ID NO: 364:

Met Pro Cys Pro Thr Trp Thr Cys Leu Lys Ser Phe Pro Ser Pro Thr
            -15                 -10                  -5

Ser Ser His Ala Ser Ser Leu His Leu Pro Pro Ser Cys Thr Arg Leu
             1               5                  10

Thr Leu Thr Gln Thr Leu Arg Thr Gly Met His Leu Ser Arg Ala Leu
 15              20                  25                  30

Gln Gly Thr Leu Thr Arg Gln
                 35

(2) INFORMATION FOR SEQ ID NO: 365:

(i) SEQUENCE CHARACTERISTICS:
         (A) LENGTH: 73 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -33..-1
         (C) IDENTIFICATION METHOD: Von Heijne matrix
         (D) OTHER INFORMATION:   score 4.3 seq LLGWGLNLTLGQG/AP (xi) SEQUENCE DESCRIPTION: SEQ ID NO: 365:

Met Glu Asp Leu Phe Ser Pro Ser Ile Xaa Pro Pro Ala Pro Asn Ile
            -30                 -25                 -20

Ser Val Pro Ile Leu Leu Gly Trp Gly Leu Asn Leu Thr Leu Gly Gln
            -15                 -10                  -5

Gly Ala Pro Ala Ser Gly Pro Pro Ser Arg Arg Val Arg Leu Val Phe
 1               5                  10                  15

Leu Gly Val Ile Leu Val Val Ala Val Ala Xaa Asn Thr Thr Val Leu
                 20                  25                  30

Cys Arg Leu Cys Gly Gly Gly Pro
                 35              40

(2) INFORMATION FOR SEQ ID NO: 366:

(i) SEQUENCE CHARACTERISTICS:
         (A) LENGTH: 55 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -52..-1
         (C) IDENTIFICATION METHOD: Von Heijne matrix
         (D) OTHER INFORMATION:   score 4.1 seq VMLETCGLLVSLG/HP (xi) SEQUENCE DESCRIPTION: SEQ ID NO: 366:

Met Ala Glu Thr Lys Asp Ala Ala Gln Met Leu Val Thr Phe Lys Asp
 -50                 -45                 -40
```

```
Val Ala Val Thr Phe Thr Arg Glu Glu Trp Arg Gln Leu Asp Leu Ala
    -35                 -30                 -25

Gln Arg Thr Leu Tyr Arg Glu Val Met Leu Glu Thr Cys Gly Leu Leu
-20                 -15                 -10                  -5

Val Ser Leu Gly His Pro Arg
                         1

(2) INFORMATION FOR SEQ ID NO: 367:

(i) SEQUENCE CHARACTERISTICS:
        (A) LENGTH: 45 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -13..-1
        (C) IDENTIFICATION METHOD: Von Heijne matrix
        (D) OTHER INFORMATION:  score 4.1 seq MLILSQNIAQLEA/QV (xi) SEQUENCE DESCRIPTION: SEQ ID NO: 367:

Met Leu Ile Leu Ser Gln Asn Ile Ala Gln Leu Glu Ala Gln Val Glu
            -10                 -5                       1

Lys Val Thr Lys Glu Lys Ile Ser Ala Ile Asn Gln Leu Glu Glu Asn
      5                  10                  15

Ser Lys Pro Ala Gly Phe Ser Gly Lys Trp Met Ser Gln
 20                  25                  30

(2) INFORMATION FOR SEQ ID NO: 368:

(i) SEQUENCE CHARACTERISTICS:
        (A) LENGTH: 97 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:  score 4.1 seq GLWAHSWTCSCSA/AX (xi) SEQUENCE DESCRIPTION: SEQ ID NO: 368:

Met Leu Leu Gly Ala Ser Ala Gln Gly Leu Trp Ala His Ser Trp Thr
    -20                 -15                 -10

Cys Ser Cys Ser Ala Ala Xaa Arg Ser Val His Pro Gly Gly Asp Trp
 -5                   1                   5                  10

Met Gln Gln Phe Gln Ala Gly Phe Leu Pro Pro Gln Val Pro Ala His
                15                  20                  25

Leu Ser Leu Thr Trp Asp Val Ser Leu Leu Pro Pro Cys Leu Val Pro
            30                  35                  40

Lys Ala Leu Glu Phe Val Val His Phe Leu Lys Asn Asp Ile Phe Tyr
      45                  50                  55

Leu Thr Gln Tyr Ile Lys Asn Val Ile Ser Glu Cys Thr Phe Ser Phe
```

-continued

```
              60                  65                  70                  75
Phe (2) INFORMATION FOR SEQ ID NO: 369:

(i) SEQUENCE CHARACTERISTICS:
        (A) LENGTH: 68 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -15..-1
        (C) IDENTIFICATION METHOD: Von Heijne matrix
        (D) OTHER INFORMATION:  score 4.1 seq APLELSCWGGGWG/LP (xi) SEQUENCE DESCRIPTION: SEQ ID NO: 369:

Met Ala Ala Pro Leu Glu Leu Ser Cys Trp Gly Gly Gly Trp Gly Leu
-15                 -10                 -5                   1

Pro Ser Val His Ser Glu Ser Leu Val Val Met Ala Tyr Ala Lys Phe
                5                  10                  15

Ser Gly Ala Pro Leu Lys Val Asn Val Ile Asp Asn Thr Trp Arg Gly
             20                  25                  30

Ser Arg Gly Asp Val Pro Ile Leu Thr Thr Glu Asp Asp Met Val Ser
         35                  40                  45

Gln Pro Ala Arg
 50

(2) INFORMATION FOR SEQ ID NO: 370:

(i) SEQUENCE CHARACTERISTICS:
        (A) LENGTH: 69 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -20..-1
        (C) IDENTIFICATION METHOD: Von Heijne matrix
        (D) OTHER INFORMATION:  score 4.1 seq LGFLNCYIAVARS/GG (xi) SEQUENCE DESCRIPTION: SEQ ID NO: 370:

Met Ser Xaa Val Gly Ile Asp Leu Gly Phe Leu Asn Cys Tyr Ile Ala
-20                 -15                 -10                  -5

Val Ala Arg Ser Gly Gly Ile Glu Thr Ile Ala Asn Glu Tyr Ser Asp
                 1                   5                  10

Arg Cys Thr Pro Ala Cys Ile Ser Leu Gly Ser Arg Thr Arg Ala Ile
             15                  20                  25

Gly Asn Ala Ala Lys Ser Gln Ile Val Thr Asn Val Arg Asn Thr Ile
         30                  35                  40

His Gly Phe Lys Lys
 45
```

(2) INFORMATION FOR SEQ ID NO: 371:

(i) SEQUENCE CHARACTERISTICS:
        (A) LENGTH: 43 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -19..-1
        (C) IDENTIFICATION METHOD: Von Heijne matrix
        (D) OTHER INFORMATION:   score 4.1 seq FVVFSTMFTASSP/GE (xi) SEQUENCE DESCRIPTION: SEQ ID NO: 371:

Met Glu Tyr Ser Lys Xaa Phe Val Val Phe Ser Thr Met Phe Thr Ala
                -15                 -10                 -5

Ser Ser Pro Gly Glu Asp Phe Pro Pro Phe Phe Ser Gln Met Xaa Arg
            1               5                   10

Leu Ser Arg Asn Tyr Phe Pro Cys Pro Pro Xaa
    15                  20

(2) INFORMATION FOR SEQ ID NO: 372:

(i) SEQUENCE CHARACTERISTICS:
        (A) LENGTH: 72 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -40..-1
        (C) IDENTIFICATION METHOD: Von Heijne matrix
        (D) OTHER INFORMATION:   score 4.1 seq LPFRLPWASTATA/RC (xi) SEQUENCE DESCRIPTION: SEQ ID NO: 372:

Met Pro Met Ala Ser Ser Pro Pro Ser Pro His Pro Gln Glu Pro
-40                 -35                 -30                 -25

Ala Pro Leu Leu Pro Ser Leu Pro Arg Leu Ser Leu Pro Phe Arg Leu
                -20                 -15                 -10

Pro Trp Ala Ser Thr Ala Thr Ala Arg Cys Pro Pro Ser Pro Leu Gly
            -5                  1                   5

Ser Leu Xaa Leu Met Leu Cys Ile Pro Thr Gly Phe Thr Pro Thr Gln
    10                  15                  20

Pro Arg Ala Pro Arg Pro Pro Gly
25                  30

(2) INFORMATION FOR SEQ ID NO: 373:

(i) SEQUENCE CHARACTERISTICS:
        (A) LENGTH: 55 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (F) TISSUE TYPE: Brain (ix) FEATURE:
    (A) NAME/KEY: sig_peptide
    (B) LOCATION: -38..-1
    (C) IDENTIFICATION METHOD: Von Heijne matrix
    (D) OTHER INFORMATION:  score 4 seq WALGLKFLSSSSQ/NF (xi) SEQUENCE DESCRIPTION: SEQ ID NO: 373:

```
Met Gln His Val Xaa Gly His Xaa Pro Asp Pro Ile Ala Ile Met Tyr
            -35             -30             -25

Val Cys Pro Pro Cys Gly His Thr Thr Trp Ala Leu Gly Leu Lys Phe
        -20             -15             -10

Leu Ser Ser Ser Ser Gln Asn Phe Cys Ala Pro Val Leu Phe Leu Ile
     -5              1               5                       10

Leu His Thr Gly Gly Gln Arg
                 15
```

(2) INFORMATION FOR SEQ ID NO: 374:

(i) SEQUENCE CHARACTERISTICS:
        (A) LENGTH: 53 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -30..-1
        (C) IDENTIFICATION METHOD: Von Heijne matrix
        (D) OTHER INFORMATION:  score 4 seq AGFLKCLLLSSLQ/SY (xi) SEQUENCE DESCRIPTION: SEQ ID NO: 374:

```
Met Gly Trp Glu Met Thr Cys Ile Lys Ser Phe Phe Trp Ala Arg Ser
-30             -25             -20             -15

His Ala Gly Phe Leu Lys Cys Leu Leu Leu Ser Ser Leu Gln Ser Tyr
            -10              -5                       1

Lys Glu Ala Ala Val Ile Phe Pro Leu Thr Asp Leu Leu Lys Leu Lys
         5               10              15

Asp Tyr Gly Glu Trp
     20
```

(2) INFORMATION FOR SEQ ID NO: 375:

(i) SEQUENCE CHARACTERISTICS:
        (A) LENGTH: 38 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -36..-1
        (C) IDENTIFICATION METHOD: Von Heijne matrix
        (D) OTHER INFORMATION:  score 4 seq VQLSFAATTPVLA/DK (xi) SEQUENCE DESCRIPTION: SEQ ID NO: 375:

Met Val Phe Gly Gly Val Cys Pro Ser Val Thr Ser Ile Ile Ala Glu

```
                  -35              -30              -25
Ser Leu Gln Gly Trp Asn Leu Val Gln Leu Ser Phe Ala Ala Thr Thr
 -20              -15              -10               -5

Pro Val Leu Ala Asp Lys
              1
```

(2) INFORMATION FOR SEQ ID NO: 376:

(i) SEQUENCE CHARACTERISTICS:
        (A) LENGTH: 24 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION: score 4 seq ITWSLLFLYQCSL/HF (xi) SEQUENCE DESCRIPTION: SEQ ID NO: 376:

```
Met His Phe Ile Thr Trp Ser Leu Leu Phe Leu Tyr Gln Cys Ser Leu
     -15              -10               -5

His Phe Ile Ile Ile Lys Ala Gly
  1               5
```

(2) INFORMATION FOR SEQ ID NO: 377:

(i) SEQUENCE CHARACTERISTICS:
        (A) LENGTH: 41 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -36..-1
        (C) IDENTIFICATION METHOD: Von Heijne matrix
        (D) OTHER INFORMATION: score 3.9 seq CWPSVASPSSSWS/SP (xi) SEQUENCE DESCRIPTION: SEQ ID NO: 377:

```
Met Ser Gly Ala Ser Pro Ile Glu Arg Thr Pro Met Glu Glu Ala Pro
 -35              -30              -25

Ser Ser Cys Pro Thr Ser Ser Cys Trp Pro Ser Val Ala Ser Pro Ser
 -20              -15              -10               -5

Ser Ser Trp Ser Ser Pro Trp Ala Ser
              1               5
```

(2) INFORMATION FOR SEQ ID NO: 378:

(i) SEQUENCE CHARACTERISTICS:
        (A) LENGTH: 50 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (F) TISSUE TYPE: Brain (ix) FEATURE:
            (A) NAME/KEY: sig_peptide
            (B) LOCATION: -37..-1
            (C) IDENTIFICATION METHOD: Von Heijne matrix
            (D) OTHER INFORMATION: score 3.9 seq PGPSLRLFSGSQA/SV (xi) SEQUENCE DESCRIPTION: SEQ ID NO: 378:

Met Glu Trp Ala Gly Lys Gln Arg Asp Phe Gln Val Arg Ala Ala Pro
        -35                 -30                 -25

Gly Trp Asp His Leu Ala Ser Phe Pro Gly Pro Ser Leu Arg Leu Phe
    -20                 -15                 -10

Ser Gly Ser Gln Ala Ser Val Cys Ser Leu Cys Ser Gly Phe Gly Ala
 -5                   1                   5                  10

Gln Glu (2) INFORMATION FOR SEQ ID NO: 379:

(i) SEQUENCE CHARACTERISTICS:
            (A) LENGTH: 67 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -60..-1
            (C) IDENTIFICATION METHOD: Von Heijne matrix
            (D) OTHER INFORMATION: score 3.9 seq AKVVSLSLQTSSA/HH (xi) SEQUENCE DESCRIPTION: SEQ ID NO: 379:

Met Ile Ala Phe Phe Asp Glu Asp Asn Pro Arg Lys Arg Arg Ser Tyr
-60                 -55                 -50                 -45

Ser Phe Thr Gln Ser Ala Gly Ile Leu Cys Gln Glu Thr Thr Tyr Ser
                -40                 -35                 -30

Thr Pro His Thr Lys Leu Glu Lys Ala Lys Ser Pro Thr Ala Asp Ala
            -25                 -20                 -15

Lys Val Val Ser Leu Ser Leu Gln Thr Ser Ser Ala His His Arg Gly
        -10                  -5                   1

Gly Xaa Gly
  5

(2) INFORMATION FOR SEQ ID NO: 380:

(i) SEQUENCE CHARACTERISTICS:
            (A) LENGTH: 87 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -48..-1
            (C) IDENTIFICATION METHOD: Von Heijne matrix
            (D) OTHER INFORMATION: score 3.9 seq ALFCTLPCPVERG/QQ (xi) SEQUENCE DESCRIPTION: SEQ ID NO: 380:

```
Met Gly Lys Ser Ile Xaa Ser Leu Cys Ser Val Xaa Leu Lys Ala Arg
        -45                 -40                 -35

Leu Lys Gly Xaa Leu Glu Ala Val His Leu Cys Leu Arg Ala Gln Lys
        -30                 -25                 -20

Arg Arg Thr Ala Leu Phe Cys Thr Leu Pro Cys Pro Val Glu Arg Gly
        -15                 -10                  -5

Gln Gln Val Pro Gly Xaa Xaa Xaa Arg Leu Arg Leu Ala Ser Pro Ser
  1              5                  10                  15

Val Ala Lys Val Phe Gln Cys Phe Leu Ser Lys Leu Cys Val Trp Asn
                 20                  25                  30

Ile Lys Asp Gly Leu Ser Arg
        35
```

(2) INFORMATION FOR SEQ ID NO: 381:

(i) SEQUENCE CHARACTERISTICS:
        (A) LENGTH: 53 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -15..-1
        (C) IDENTIFICATION METHOD: Von Heijne matrix
        (D) OTHER INFORMATION: score 3.9 seq LHMTLFRVPFTFS/XF (xi) SEQUENCE DESCRIPTION: SEQ ID NO: 381:

```
Met Cys Leu His Met Thr Leu Phe Arg Val Pro Phe Thr Phe Ser Xaa
-15                 -10                  -5                   1

Phe Trp Lys Gly Ala Gly Arg Gln Glu Glu Cys Ser Phe Lys Pro Ser
                 5                  10                  15

Leu Tyr Tyr Tyr Lys Leu Ile Met Val Leu Lys Ile Ala Leu Leu Leu
        20                  25                  30

Ser Pro Pro Lys
        35
```

(2) INFORMATION FOR SEQ ID NO: 382:

(i) SEQUENCE CHARACTERISTICS:
        (A) LENGTH: 23 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -14..-1
        (C) IDENTIFICATION METHOD: Von Heijne matrix
        (D) OTHER INFORMATION: score 3.9 seq LNILKTLTSAALP/SP (xi) SEQUENCE DESCRIPTION: SEQ ID NO: 382:

```
Met Leu Asn Ile Leu Lys Thr Leu Thr Ser Ala Ala Leu Pro Ser Pro
                -10                 -5                       1

Ser Pro Arg Pro Asn Lys Arg
```

5

(2) INFORMATION FOR SEQ ID NO: 383:

(i) SEQUENCE CHARACTERISTICS:
        (A) LENGTH: 51 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -40..-1
        (C) IDENTIFICATION METHOD: Von Heijne matrix
        (D) OTHER INFORMATION: score 3.9 seq SPLLCLYHPPVYT/ST (xi) SEQUENCE DESCRIPTION: SEQ ID NO: 383:

Met Arg Ala Arg Val Trp Pro Arg Ser His Gly Ile Pro Val Pro Ser
-40              -35              -30              -25

Phe Leu Ser Lys Ser Ser Leu Ser His Thr Pro Ser Pro Leu Leu Cys
         -20              -15              -10

Leu Tyr His Pro Pro Val Tyr Thr Ser Thr Thr Thr Pro Ser Ile Pro
         -5                1                5

Pro Arg Leu
    10

(2) INFORMATION FOR SEQ ID NO: 384:

(i) SEQUENCE CHARACTERISTICS:
        (A) LENGTH: 51 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -36..-1
        (C) IDENTIFICATION METHOD: Von Heijne matrix
        (D) OTHER INFORMATION: score 3.9 seq SLCLSLLIPGPKP/LV (xi) SEQUENCE DESCRIPTION: SEQ ID NO: 384:

Met Trp Asn Ala Val Ala Ile Ile Cys Asn Gly Ser Trp Cys Gln Thr
    -35              -30              -25

Xaa Ser Thr Ser Gly Leu Glu Ser Leu Cys Leu Ser Leu Leu Ile Pro
-20              -15              -10                       -5

Gly Pro Lys Pro Leu Val Ser Val Gly Ile Asn Gln Leu Leu Leu Thr
             1                5                10

Ser Ser Arg
    15

(2) INFORMATION FOR SEQ ID NO: 385:

(i) SEQUENCE CHARACTERISTICS:
        (A) LENGTH: 23 amino acids
        (B) TYPE: AMINO ACID
        (D) TOPOLOGY: LINEAR (ii) MOLECULE TYPE: PROTEIN

```
    (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -14..-1
         (C) IDENTIFICATION METHOD: Von Heijne matrix
         (D) OTHER INFORMATION:   score 3.9 seq LRLGLFKISWARC/LS (xi) SEQUENCE DESCRIPTION: SEQ ID NO: 385:

Met Leu Arg Leu Gly Leu Phe Lys Ile Ser Trp Ala Arg Cys Leu Ser
             -10                 -5                   1

Tyr Ser Lys Thr Gln Xaa Glu
             5

(2) INFORMATION FOR SEQ ID NO: 386:

(i) SEQUENCE CHARACTERISTICS:
        (A) LENGTH: 61 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -36..-1
         (C) IDENTIFICATION METHOD: Von Heijne matrix
         (D) OTHER INFORMATION:   score 3.9 seq VVEILPYLPCLTA/RD (xi) SEQUENCE DESCRIPTION: SEQ ID NO: 386:

Met Pro Phe Ala Glu Asp Lys Thr Tyr Lys Tyr Ile Cys Arg Asn Phe
    -35                 -30                 -25

Ser Asn Phe Cys Asn Val Asp Val Val Glu Ile Leu Pro Tyr Leu Pro
    -20                 -15                 -10                 -5

Cys Leu Thr Ala Arg Asp Gln Asp Arg Leu Arg Ala Thr Cys Thr Leu
                 1                   5                  10

Ser Gly Asn Arg Asp Thr Leu Trp His Leu Phe Asn Thr
             15                  20                  25

(2) INFORMATION FOR SEQ ID NO: 387:

(i) SEQUENCE CHARACTERISTICS:
        (A) LENGTH: 40 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -36..-1
         (C) IDENTIFICATION METHOD: Von Heijne matrix
         (D) OTHER INFORMATION:   score 3.8 seq GTDSLSFLPPCPC/CP (xi) SEQUENCE DESCRIPTION: SEQ ID NO: 387:

Met Pro Gly Ser Ser Gly Leu Arg Phe Ile Cys Lys Ser Arg Asn His
    -35                 -30                 -25

Pro Gln Phe Gly Ser Phe Ser Gly Thr Asp Ser Leu Ser Phe Leu Pro
```

```
        -20                -15                -10                 -5
Pro Cys Pro Cys Cys Pro Ala Ala
                         1
```

(2) INFORMATION FOR SEQ ID NO: 388:

(i) SEQUENCE CHARACTERISTICS:
      (A) LENGTH: 66 amino acids
      (B) TYPE: AMINO ACID
      (D) TOPOLOGY: LINEAR (ii) MOLECULE TYPE: PROTEIN (vi) ORIGINAL SOURCE:
      (A) ORGANISM: Homo Sapiens
      (F) TISSUE TYPE: Brain (ix) FEATURE:
      (A) NAME/KEY: sig_peptide
      (B) LOCATION: -57..-1
      (C) IDENTIFICATION METHOD: Von Heijne matrix
      (D) OTHER INFORMATION:   score 3.8 seq QLXLVMEFCGAGS/VT (xi) SEQUENCE DESCRIPTION: SEQ ID NO: 388:

```
Met Asp Val Thr Gly Asp Glu Glu Glu Ile Lys Gln Glu Ile Asn
    -55                 -50                 -45

Met Leu Lys Lys Tyr Ser His His Arg Asn Ile Ala Thr Tyr Tyr Gly
    -40                 -35                 -30

Ala Phe Ile Lys Lys Asn Pro Pro Gly Met Asp Asp Gln Leu Xaa Leu
-25                 -20                 -15                 -10

Val Met Glu Phe Cys Gly Ala Gly Ser Val Thr Asp Leu Ile Lys Asn
                -5                   1                   5

Thr Gly
```

(2) INFORMATION FOR SEQ ID NO: 389:

(i) SEQUENCE CHARACTERISTICS:
      (A) LENGTH: 26 amino acids
      (B) TYPE: AMINO ACID
      (D) TOPOLOGY: LINEAR (ii) MOLECULE TYPE: PROTEIN (vi) ORIGINAL SOURCE:
      (A) ORGANISM: Homo Sapiens
      (F) TISSUE TYPE: Brain (ix) FEATURE:
      (A) NAME/KEY: sig_peptide
      (B) LOCATION: -24..-1
      (C) IDENTIFICATION METHOD: Von Heijne matrix
      (D) OTHER INFORMATION:   score 3.8 seq KLFLVFLLNICKG/IV (xi) SEQUENCE DESCRIPTION: SEQ ID NO: 389:

```
Met Ile Phe Gly Leu Tyr Phe Val Leu Ala Val Lys Leu Phe Leu Val
                -20                 -15                 -10

Phe Leu Leu Asn Ile Cys Lys Gly Ile Val
            -5                   1
```

(2) INFORMATION FOR SEQ ID NO: 390:

(i) SEQUENCE CHARACTERISTICS:
      (A) LENGTH: 46 amino acids
      (B) TYPE: AMINO ACID
      (D) TOPOLOGY: LINEAR (ii) MOLECULE TYPE: PROTEIN

```
    (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -34..-1
         (C) IDENTIFICATION METHOD: Von Heijne matrix
         (D) OTHER INFORMATION:  score 3.6 seq IKCSSWISSLASG/IP (xi) SEQUENCE DESCRIPTION: SEQ ID NO: 390:

Met Arg Lys Lys Arg Val Glu Glu Leu Ile Val Phe Pro Gly Glu Val
             -30                 -25                 -20

Thr Ser Phe Ser Ser Ile Lys Cys Ser Ser Trp Ile Ser Ser Leu Ala
             -15                 -10                  -5

Ser Gly Ile Pro His Ser Leu Gly Phe Ser Leu Pro Pro Gly
             1               5                  10

(2) INFORMATION FOR SEQ ID NO: 391:

(i) SEQUENCE CHARACTERISTICS:
        (A) LENGTH: 57 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -28..-1
         (C) IDENTIFICATION METHOD: Von Heijne matrix
         (D) OTHER INFORMATION:  score 3.6 seq ACLFSXFLAVSRH/PN (xi) SEQUENCE DESCRIPTION: SEQ ID NO: 391:

Met Pro Ser Ser Ser Leu Ala Glu Leu Cys Leu Met Gln Gln Asp Ala
             -25                 -20                 -15

Cys Leu Phe Ser Xaa Phe Leu Ala Val Ser Arg His Pro Asn Tyr Xaa
             -10                  -5                   1

Cys Ser Ile Ser Thr Lys Gly Glu Val Arg Glu Lys Leu Val Pro Trp
 5               10                  15                  20

Ile Thr His Gln Met Ala Arg Met Leu
                 25

(2) INFORMATION FOR SEQ ID NO: 392:

(i) SEQUENCE CHARACTERISTICS:
        (A) LENGTH: 46 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -40..-1
         (C) IDENTIFICATION METHOD: Von Heijne matrix
         (D) OTHER INFORMATION:  score 3.6 seq LQMRMQLPCLVLG/EE (xi) SEQUENCE DESCRIPTION: SEQ ID NO: 392:

Met Asp Leu Trp Ser Cys Leu Phe Pro Val Met Leu Met Glu Pro Ser
-40              -35                 -30                 -25
```

```
Lys Gly Leu Glu Asp Ser Glu Trp Lys Met Ala Leu Gln Met Arg Met
            -20                 -15                 -10

Gln Leu Pro Cys Leu Val Leu Gly Glu Gln Thr Leu Gly
         -5                   1                   5

(2) INFORMATION FOR SEQ ID NO: 393:

(i) SEQUENCE CHARACTERISTICS:
        (A) LENGTH: 37 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -27..-1
        (C) IDENTIFICATION METHOD: Von Heijne matrix
        (D) OTHER INFORMATION:   score 3.6 seq AVPLPTTSTLTSA/ST (xi) SEQUENCE DESCRIPTION: SEQ ID NO: 393:

Met Ser Gly Lys Gly Lys Cys Arg Pro Ile Ala Leu Arg Arg Ala Val
            -25                 -20                 -15

Pro Leu Pro Thr Thr Ser Thr Leu Thr Ser Ala Ser Thr Gly Phe Leu
    -10                  -5                   1                   5

Trp Ile Leu Lys Glu
             10

(2) INFORMATION FOR SEQ ID NO: 394:

(i) SEQUENCE CHARACTERISTICS:
        (A) LENGTH: 26 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -18..-1
        (C) IDENTIFICATION METHOD: Von Heijne matrix
        (D) OTHER INFORMATION:   score 3.6 seq IQKSSGLFCPSQA/QS (xi) SEQUENCE DESCRIPTION: SEQ ID NO: 394:

Met Thr Pro Lys Ala Ile Gln Lys Ser Ser Gly Leu Phe Cys Pro Ser
            -15                 -10                  -5

Gln Ala Gln Ser Ala Arg Pro Ala Glu Lys
             1                   5

(2) INFORMATION FOR SEQ ID NO: 395:

(i) SEQUENCE CHARACTERISTICS:
        (A) LENGTH: 103 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain
```

(ix) FEATURE:
            (A) NAME/KEY: sig_peptide
            (B) LOCATION: -72..-1
            (C) IDENTIFICATION METHOD: Von Heijne matrix
            (D) OTHER INFORMATION: score 3.6 seq CTSLLQLYDASNS/EW (xi) SEQUENCE DESCRIPTION: SEQ ID NO: 395:

Met Pro Asp Gln Phe Asp Gln Ala Val Val Leu Asn Gln Leu Arg Tyr
        -70                 -65                 -60

Ser Gly Met Leu Glu Thr Val Arg Ile Arg Lys Ala Gly Tyr Ala Val
        -55                 -50                 -45

Arg Arg Pro Phe Gln Asp Phe Tyr Lys Arg Tyr Lys Val Leu Met Arg
-40                 -35                 -30                 -25

Asn Leu Ala Leu Pro Glu Asp Val Arg Gly Lys Cys Thr Ser Leu Leu
                -20                 -15                 -10

Gln Leu Tyr Asp Ala Ser Asn Ser Glu Trp Gln Leu Gly Lys Thr Lys
            -5                  1                   5

Val Phe Leu Arg Glu Ser Leu Glu Gln Lys Leu Glu Lys Arg Arg Glu
        10                  15                  20

Glu Glu Val Ser His Ala Gly
 25                  30

(2) INFORMATION FOR SEQ ID NO: 396:

(i) SEQUENCE CHARACTERISTICS:
        (A) LENGTH: 19 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -15..-1
        (C) IDENTIFICATION METHOD: Von Heijne matrix
        (D) OTHER INFORMATION: score 3.6 seq LVSFFLELNVLQQ/WP (xi) SEQUENCE DESCRIPTION: SEQ ID NO: 396:

Met Cys Leu Val Ser Phe Phe Leu Glu Leu Asn Val Leu Gln Gln Trp
-15                 -10                 -5                   1

Pro Ala Gly (2) INFORMATION FOR SEQ ID NO: 397:

(i) SEQUENCE CHARACTERISTICS:
        (A) LENGTH: 44 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -13..-1
        (C) IDENTIFICATION METHOD: Von Heijne matrix
        (D) OTHER INFORMATION: score 3.6 seq MRSLACLTPCGHA/GS (xi) SEQUENCE DESCRIPTION: SEQ ID NO: 397:

```
Met Arg Ser Leu Ala Cys Leu Thr Pro Cys Gly His Ala Gly Ser Arg
            -10                 -5                      1

Leu Gln Ser Ser Leu Ser Lys Tyr Leu Val Leu Pro Asn Leu Glu Cys
         5               10              15

Leu Phe Phe Leu Phe Leu Ile Ser Asn Arg Arg Trp
 20              25              30

(2) INFORMATION FOR SEQ ID NO: 398:

(i) SEQUENCE CHARACTERISTICS:
        (A) LENGTH: 82 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -13..-1
        (C) IDENTIFICATION METHOD: Von Heijne matrix
        (D) OTHER INFORMATION:   score 3.5 seq MHLLSNWANPASS/RR (xi) SEQUENCE DESCRIPTION: SEQ ID NO: 398:

Met His Leu Leu Ser Asn Trp Ala Asn Pro Ala Ser Ser Arg Arg Pro
            -10                 -5                      1

Ser Met Ala Ala Ser Gly Thr Ser Trp Ile Ser Ser Thr Leu Ala His
         5               10              15

Ser Leu Ser Leu Arg Asp Val Ser Glu Arg Leu Cys Ser Cys Trp Arg
 20              25              30              35

Thr Ile Ser Met Gly Pro Cys Ala Arg Gly Ser Pro Met Asn Ser Ser
             40              45              50

Gly Val His Arg Lys Ser Ser Arg Leu Phe Tyr Ile Arg Thr Pro Met
             55              60              65

Arg Arg (2) INFORMATION FOR SEQ ID NO: 399:

(i) SEQUENCE CHARACTERISTICS:
        (A) LENGTH: 118 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION:   score 3.5 seq FAMLHSVWRLIPA/FR (xi) SEQUENCE DESCRIPTION: SEQ ID NO: 399:

Met Trp Ser Gly Lys Trp Ala Leu Val Ser Pro Phe Ala Met Leu His
            -20                 -15                    -10

Ser Val Trp Arg Leu Ile Pro Ala Phe Arg Gly Tyr Ala Gln Gln Asp
         -5                       1                5

Ala Gln Glu Phe Leu Cys Glu Leu Leu Asp Lys Ile Gln Arg Glu Leu
 10              15              20
```

```
Glu Thr Thr Gly Thr Ser Leu Pro Ala Leu Ile Pro Thr Ser Gln Arg
 25              30                  35                  40

Lys Leu Ile Lys Gln Val Leu Asn Val Val Asn Asn Ile Phe His Gly
                 45              50                  55

Gln Leu Leu Ser Gln Val Thr Cys Leu Ala Cys Asp Asn Lys Ser Asn
             60                  65              70

Thr Ile Glu Pro Phe Trp Asp Leu Ser Leu Glu Xaa Pro Glu Arg Tyr
         75                  80              85

Gln Cys Ser Xaa Lys Gly
         90
```

(2) INFORMATION FOR SEQ ID NO: 400:

(i) SEQUENCE CHARACTERISTICS:
        (A) LENGTH: 41 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -20..-1
        (C) IDENTIFICATION METHOD: Von Heijne matrix
        (D) OTHER INFORMATION: score 3.5 seq KFCLICLLTFIFH/HC (xi) SEQUENCE DESCRIPTION: SEQ ID NO: 400:

```
Met Lys Val His Met His Thr Lys Phe Cys Leu Ile Cys Leu Leu Thr
-20              -15                 -10                  -5

Phe Ile Phe His His Cys Asn His Cys His Glu Glu His Asp His Gly
                  1               5                  10

Pro Glu Ala Leu His Arg Gln Gln Gly
             15              20
```

(2) INFORMATION FOR SEQ ID NO: 401:

(i) SEQUENCE CHARACTERISTICS:
        (A) LENGTH: 49 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION: score 3.5 seq ALSLFYTADTSHG/SE (xi) SEQUENCE DESCRIPTION: SEQ ID NO: 401:

```
Met Gly Arg Arg His Trp Val Leu Thr His Ser Ala Leu Ser Leu Phe
                 -20              -15                 -10

Tyr Thr Ala Asp Thr Ser His Gly Ser Glu Lys Pro Tyr Leu Ser Leu
             -5                   1               5

Phe Gly Arg Glu Gly Gly Arg Glu Gly Ser Asn Pro Lys Tyr Tyr Ser
         10              15                  20

Phe
```

-continued

25

(2) INFORMATION FOR SEQ ID NO: 402:

(i) SEQUENCE CHARACTERISTICS:
        (A) LENGTH: 93 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:   score 12.5 seq FVVLLALVAGVLG/NE (xi) SEQUENCE DESCRIPTION: SEQ ID NO: 402:

```
Met Ala Val Phe Val Val Leu Leu Ala Leu Val Ala Gly Val Leu Gly
    -15                 -10                 -5

Asn Glu Phe Ser Ile Leu Lys Ser Pro Gly Ser Val Val Phe Arg Asn
 1               5                  10                  15

Gly Asn Trp Pro Ile Pro Gly Glu Arg Ile Pro Asp Val Ala Ala Leu
             20                  25                  30

Ser Met Gly Phe Ser Val Lys Glu Asp Leu Ser Trp Pro Gly Leu Ala
             35                  40                  45

Val Gly Asn Leu Phe His Arg Pro Arg Ala Ser Val Met Val Met Val
         50                  55                  60

Lys Gly Val Asn Asn Xaa Pro Leu Pro Pro Xaa Trp Xaa
 65                  70                  75
```

(2) INFORMATION FOR SEQ ID NO: 403:

(i) SEQUENCE CHARACTERISTICS:
        (A) LENGTH: 65 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:   score 10.1 seq LLLQLAVLGAALA/AA (xi) SEQUENCE DESCRIPTION: SEQ ID NO: 403:

```
Met Ala Pro Leu Leu Leu Gln Leu Ala Val Leu Gly Ala Ala Leu Ala
    -15                 -10                 -5

Ala Ala Ala Leu Val Leu Ile Ser Ile Val Ala Phe Thr Thr Ala Thr
 1               5                  10                  15

Lys Met Pro Ala Leu His Arg His Glu Glu Glu Lys Phe Phe Leu Asn
             20                  25                  30

Ala Lys Gly Gln Lys Glu Thr Leu Pro Ser Ile Trp Asp Ser Pro Thr
             35                  40                  45

Arg
```

(2) INFORMATION FOR SEQ ID NO: 404:

(i) SEQUENCE CHARACTERISTICS:
        (A) LENGTH: 84 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -50..-1
        (C) IDENTIFICATION METHOD: Von Heijne matrix
        (D) OTHER INFORMATION:   score 9.8 seq LLRLLQLVSTCVA/FS (xi) SEQUENCE DESCRIPTION: SEQ ID NO: 404:

```
Met Pro Val Thr Val Thr Arg Thr Thr Ile Thr Thr Thr Thr Thr Ser
-50                 -45                 -40                 -35

Ser Ser Gly Leu Gly Ser Pro Met Ile Val Gly Ser Pro Arg Ala Leu
            -30                 -25                 -20

Thr Gln Pro Leu Gly Leu Leu Arg Leu Leu Gln Leu Val Ser Thr Cys
            -15                 -10                  -5

Val Ala Phe Ser Leu Val Ala Ser Val Gly Ala Trp Thr Gly Ser Met
  1               5                  10

Gly Asn Trp Ser Met Phe Thr Trp Cys Phe Cys Phe Ser Val Thr Leu
 15              20                  25                  30

Ile Ile Leu Ile
```

(2) INFORMATION FOR SEQ ID NO: 405:

(i) SEQUENCE CHARACTERISTICS:
        (A) LENGTH: 72 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -18..-1
        (C) IDENTIFICATION METHOD: Von Heijne matrix
        (D) OTHER INFORMATION:   score 9.2 seq VFLCSLLAPMVLA/SA (xi) SEQUENCE DESCRIPTION: SEQ ID NO: 405:

```
Met Glu Leu Val Leu Val Phe Leu Cys Ser Leu Leu Ala Pro Met Val
            -15                 -10                  -5

Leu Ala Ser Ala Ala Glu Lys Glu Lys Glu Met Asp Pro Phe His Tyr
  1               5                  10

Asp Tyr Gln Thr Leu Arg Ile Gly Gly Leu Val Phe Ala Val Val Leu
 15              20                  25                  30

Phe Ser Val Gly Ile Leu Leu Ile Leu Ser Arg Arg Cys Lys Cys Ser
                 35                  40                  45

Phe Asn Gln Lys Pro Arg Asn Arg
             50
```

(2) INFORMATION FOR SEQ ID NO: 406:

(i) SEQUENCE CHARACTERISTICS:

```
            (A) LENGTH: 70 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -46..-1
            (C) IDENTIFICATION METHOD: Von Heijne matrix
            (D) OTHER INFORMATION:   score 7.9 seq LLGLLSAEQLAEA/SV (xi) SEQUENCE DESCRIPTION: SEQ ID NO: 406:

Met Gly Pro Ile Trp Ser Ser Tyr Tyr Gly Asn Cys Arg Ser Leu Leu
    -45                 -40                 -35

Phe Val Met Asp Ala Ser Asp Pro Thr Gln Leu Ser Ala Ser Cys Val
-30             -25                 -20                 -15

Gln Leu Leu Gly Leu Leu Ser Ala Glu Gln Leu Ala Glu Ala Ser Val
            -10                 -5                  1

Leu Ile Leu Phe Asn Lys Ile Asp Leu Pro Cys Tyr Met Ser Thr Glu
            5                   10                  15

Glu Met Lys Ser Leu Ile
    20

(2) INFORMATION FOR SEQ ID NO: 407:

(i) SEQUENCE CHARACTERISTICS:
            (A) LENGTH: 57 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -47..-1
            (C) IDENTIFICATION METHOD: Von Heijne matrix
            (D) OTHER INFORMATION:   score 7.9 seq LLLPRVLLTMASG/SP (xi) SEQUENCE DESCRIPTION: SEQ ID NO: 407:

Met Ser Gly Gly Arg Ala Pro Ala Val Leu Leu Gly Val Ala Ser
        -45                 -40                 -35

Leu Leu Leu Ser Phe Val Trp Met Pro Ala Leu Leu Pro Val Ala Ser
    -30             -25                 -20

Arg Leu Leu Leu Leu Pro Arg Val Leu Leu Thr Met Ala Ser Gly Ser
-15             -10                 -5                  1

Pro Pro Thr Gln Pro Ser Pro Ala Trp
            5                   10

(2) INFORMATION FOR SEQ ID NO: 408:

(i) SEQUENCE CHARACTERISTICS:
            (A) LENGTH: 92 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
```

(F) TISSUE TYPE: Brain (ix) FEATURE:
        (A) NAME/KEY: sig_peptide
        (B) LOCATION: -40..-1
        (C) IDENTIFICATION METHOD: Von Heijne matrix
        (D) OTHER INFORMATION:   score 7.9 seq SLLLLFGGQFASS/QE (xi) SEQUENCE DESCRIPTION: SEQ ID NO: 408:

Met Ala Leu Ser Cys Thr Leu Asn Arg Tyr Leu Leu Met Ala Gln
-40              -35              -30              -25

Glu His Leu Glu Phe Arg Leu Pro Glu Ile Xaa Ser Leu Leu Leu Leu
             -20              -15              -10

Phe Gly Gly Gln Phe Ala Ser Ser Gln Glu Thr Tyr Gly Lys Ser Pro
             -5                1                5

Phe Trp Ile Leu Ser Ile Pro Ser Glu Asp Ile Ala Arg Asn Leu Met
         10              15              20

Lys Arg Thr Val Cys Ala Lys Ser Ile Phe Glu Leu Trp Gly His Gly
 25              30              35              40

Gln Ser Pro Glu Glu Leu Tyr Ser Ser Leu Lys Asn
             45              50

(2) INFORMATION FOR SEQ ID NO: 409:

(i) SEQUENCE CHARACTERISTICS:
        (A) LENGTH: 91 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -53..-1
        (C) IDENTIFICATION METHOD: Von Heijne matrix
        (D) OTHER INFORMATION:   score 7.1 seq IAVGLGVAALAFA/GR (xi) SEQUENCE DESCRIPTION: SEQ ID NO: 409:

Met Ala Ala Arg Gly Val Ile Ala Pro Val Gly Glu Ser Leu Arg Tyr
         -50              -45              -40

Ala Glu Tyr Leu Gln Pro Ser Ala Lys Arg Pro Asp Ala Asp Val Asp
 -35              -30              -25

Gln Gln Arg Leu Val Arg Ser Leu Ile Ala Val Gly Leu Gly Val Ala
 -20              -15              -10

Ala Leu Ala Phe Ala Gly Arg Tyr Ala Phe Arg Ile Trp Lys Pro Leu
 -5                1                5                10

Glu Gln Val Ile Thr Glu Thr Ala Lys Lys Ile Ser Thr Pro Ser Phe
             15              20              25

Ser Ser Tyr Tyr Lys Gly Gly Phe Glu Arg Arg
             30              35

(2) INFORMATION FOR SEQ ID NO: 410:

(i) SEQUENCE CHARACTERISTICS:
        (A) LENGTH: 31 amino acids
        (B) TYPE: AMINO ACID
        (D) TOPOLOGY: LINEAR (ii) MOLECULE TYPE: PROTEIN (vi) ORIGINAL SOURCE:

```
            (A) ORGANISM: Homo Sapiens
            (F) TISSUE TYPE: Brain (ix) FEATURE:
            (A) NAME/KEY: sig_peptide
            (B) LOCATION: -28..-1
            (C) IDENTIFICATION METHOD: Von Heijne matrix
            (D) OTHER INFORMATION:  score 6.6 seq VLGXLFLGGLCRG/WD (xi) SEQUENCE DESCRIPTION: SEQ ID NO: 410:

Met Arg Met Cys Ala Gly Ser Ile Tyr Lys Ser Ala Thr Gln Ala Val
            -25                 -20                 -15

Leu Gly Xaa Leu Phe Leu Gly Gly Leu Cys Arg Gly Trp Asp Ala
        -10                  -5                   1

(2) INFORMATION FOR SEQ ID NO: 411:

(i) SEQUENCE CHARACTERISTICS:
            (A) LENGTH: 80 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -78..-1
            (C) IDENTIFICATION METHOD: Von Heijne matrix
            (D) OTHER INFORMATION:  score 6.3 seq TLIMLLSWQLSVS/SV (xi) SEQUENCE DESCRIPTION: SEQ ID NO: 411:

Met Ala Glu Arg Arg Pro Leu Ser Pro Ile Pro Ser Xaa Arg Arg
            -75                 -70                 -65

Pro Ser Glu Pro Ser Arg Pro Arg Pro Ala Ala Gly Xaa Arg Ser
        -60                 -55                 -50

Leu Pro Arg Pro Gly Asp Glu Glu Leu Gln Leu Pro Cys Ala Val His
    -45                 -40                 -35

Asp Leu Ile Phe Trp Arg Asp Val Lys Lys Thr Gly Phe Val Phe Gly
-30                 -25                 -20                 -15

Thr Thr Leu Ile Met Leu Leu Ser Trp Gln Leu Ser Val Ser Ser Val
                -10                 -5                   1

(2) INFORMATION FOR SEQ ID NO: 412:

(i) SEQUENCE CHARACTERISTICS:
            (A) LENGTH: 133 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -109..-1
            (C) IDENTIFICATION METHOD: Von Heijne matrix
            (D) OTHER INFORMATION:  score 6 seq LQLLLGMTASAVA/AL (xi) SEQUENCE DESCRIPTION: SEQ ID NO: 412:

Met Ala Ala Pro Val Leu Leu Arg Val Ser Val Pro Arg Trp Glu Arg
            -105                -100                -95
```

```
Val Ala Arg Tyr Ala Val Cys Ala Ala Gly Ile Leu Leu Ser Ile Tyr
            -90             -85                 -80

Ala Tyr His Val Glu Arg Glu Lys Glu Arg Asp Pro Glu His Arg Ala
        -75             -70                 -65

Leu Cys Asp Leu Gly Pro Trp Val Lys Cys Ser Ala Ala Leu Ala Ser
    -60             -55             -50

Arg Trp Gly Arg Gly Phe Gly Leu Leu Gly Ser Ile Phe Gly Lys Asp
-45             -40                 -35                 -30

Gly Val Leu Asn Gln Pro Asn Ser Val Phe Gly Leu Ile Phe Tyr Ile
                -25             -20                 -15

Leu Gln Leu Leu Leu Gly Met Thr Ala Ser Val Ala Ala Leu Ile
            -10              -5                  1

Leu Met Thr Ser Ser Ile Met Ser Val Val Gly Ser Cys Thr Trp Pro
      5               10                  15

Thr Phe Cys Thr Thr
 20
```

(2) INFORMATION FOR SEQ ID NO: 413:

(i) SEQUENCE CHARACTERISTICS:
        (A) LENGTH: 106 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -34..-1
        (C) IDENTIFICATION METHOD: Von Heijne matrix
        (D) OTHER INFORMATION:   score 5.9 seq LGAAALALLLANT/DV (xi) SEQUENCE DESCRIPTION: SEQ ID NO: 413:

```
Met Ser Phe Leu Gln Asp Pro Ser Phe Phe Thr Met Gly Met Trp Ser
            -30                 -25                 -20

Ile Gly Ala Gly Ala Leu Gly Ala Ala Ala Leu Ala Leu Leu Leu Ala
            -15             -10              -5

Asn Thr Asp Val Phe Leu Ser Lys Pro Xaa Lys Ala Ala Leu Glu Tyr
 1               5                   10

Leu Glu Asp Ile Asp Leu Lys Thr Leu Glu Lys Glu Pro Arg Thr Phe
 15              20                  25                  30

Lys Ala Lys Glu Leu Trp Glu Lys Asn Gly Ala Val Ile Met Ala Val
                 35              40                  45

Arg Arg Pro Gly Cys Phe Leu Cys Arg Glu Glu Ala Ala Asp Leu Ser
             50              55                  60

Ser Leu Lys Ser Met Leu Asp Gln Leu Gly
             65                  70
```

(2) INFORMATION FOR SEQ ID NO: 414:

(i) SEQUENCE CHARACTERISTICS:
        (A) LENGTH: 56 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (F) TISSUE TYPE: Brain (ix) FEATURE:
            (A) NAME/KEY: sig_peptide
            (B) LOCATION: -37..-1
            (C) IDENTIFICATION METHOD: Von Heijne matrix
            (D) OTHER INFORMATION: score 4.9 seq MLIMLGIFFNVHS/AV (xi) SEQUENCE DESCRIPTION: SEQ ID NO: 414:

Met Ala Ser Leu Leu Cys Cys Gly Pro Lys Leu Ala Ala Cys Gly Ile
        -35                 -30                 -25

Val Leu Ser Ala Trp Gly Val Ile Met Leu Ile Met Leu Gly Ile Phe
    -20                 -15                 -10

Phe Asn Val His Ser Ala Val Leu Ile Glu Asp Val Pro Phe Thr Glu
 -5                   1               5                  10

Lys Asp Phe Glu Asn Gly Pro Arg
            15

(2) INFORMATION FOR SEQ ID NO: 415:

(i) SEQUENCE CHARACTERISTICS:
        (A) LENGTH: 32 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -20..-1
        (C) IDENTIFICATION METHOD: Von Heijne matrix
        (D) OTHER INFORMATION: score 4.9 seq XSLFLHAVSSSFT/QL (xi) SEQUENCE DESCRIPTION: SEQ ID NO: 415:

Met Ile Leu Pro Tyr Arg Met Xaa Ser Leu Phe Leu His Ala Val Ser
-20                 -15                 -10                  -5

Ser Ser Phe Thr Gln Leu Arg Ser Cys Gln Gly Asp Arg Val Trp Arg
              1               5                  10

(2) INFORMATION FOR SEQ ID NO: 416:

(i) SEQUENCE CHARACTERISTICS:
        (A) LENGTH: 78 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -63..-1
        (C) IDENTIFICATION METHOD: Von Heijne matrix
        (D) OTHER INFORMATION: score 4.8 seq LYTVRALAGRAWA/AV (xi) SEQUENCE DESCRIPTION: SEQ ID NO: 416:

Met Ala Thr Leu Val Glu Leu Pro Asp Ser Val Leu Leu Glu Ile Phe
            -60                 -55                 -50

Ser Tyr Leu Pro Val Arg Asp Arg Ile Arg Ile Ser Arg Val Cys His
        -45                 -40                 -35

Arg Trp Lys Arg Leu Val Asp Asp Arg Trp Leu Trp Arg His Val Asp

-continued

```
          -30              -25              -20
Leu Thr Leu Tyr Thr Val Arg Ala Leu Ala Gly Arg Ala Trp Ala Ala
-15              -10               -5                        1

Val Ala Val Pro Gly Xaa Arg Arg Pro Pro Leu Pro Pro Trp
             5               10              15
```

(2) INFORMATION FOR SEQ ID NO: 417:

(i) SEQUENCE CHARACTERISTICS:
        (A) LENGTH: 92 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -41..-1
        (C) IDENTIFICATION METHOD: Von Heijne matrix
        (D) OTHER INFORMATION:   score 4.7 seq LFSCFCFLSHKFG/KK (xi) SEQUENCE DESCRIPTION: SEQ ID NO: 417:

```
Met Lys Asn Ala Cys Ile Val Leu Pro Pro Thr Pro Pro Ser Leu
    -40              -35              -30

Gln Pro Ser Ala Ser Leu Leu Ala Pro Asn Arg Phe Leu Phe Ser Cys
-25              -20              -15                       -10

Phe Cys Phe Leu Ser His Lys Phe Gly Lys Lys Val Ile Tyr Phe Asn
                 -5               1                5

Tyr Leu Ser Glu Leu His Glu His Leu Lys Tyr Asp Gln Leu Val Ile
            10              15                  20

Pro Pro Glu Val Leu Arg Tyr Asp Glu Lys Leu Gln Ser Leu His Glu
        25              30              35

Gly Arg Thr Pro Xaa Pro Thr Lys Thr Pro Pro Gly
40              45              50
```

(2) INFORMATION FOR SEQ ID NO: 418:

(i) SEQUENCE CHARACTERISTICS:
        (A) LENGTH: 55 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -28..-1
        (C) IDENTIFICATION METHOD: Von Heijne matrix
        (D) OTHER INFORMATION:   score 4.6 seq PLQWSLLVAVVAG/SV (xi) SEQUENCE DESCRIPTION: SEQ ID NO: 418:

```
Met Ala Phe Gly Leu Gln Met Phe Ile Gln Arg Lys Phe Pro Tyr Pro
            -25              -20              -15

Leu Gln Trp Ser Leu Leu Val Ala Val Val Ala Gly Ser Val Val Ser
        -10              -5                   1

Tyr Gly Val Thr Arg Val Xaa Ser Glu Lys Cys Asn Asn Leu Trp Leu
 5              10              15                      20
```

```
Phe Leu Glu Thr Gly Leu Gly
              25

(2) INFORMATION FOR SEQ ID NO: 419:

(i) SEQUENCE CHARACTERISTICS:
        (A) LENGTH: 69 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -53..-1
        (C) IDENTIFICATION METHOD: Von Heijne matrix
        (D) OTHER INFORMATION:   score 4.5 seq LLWTPLLSPGSLR/VI (xi) SEQUENCE DESCRIPTION: SEQ ID NO: 419:

Met Tyr Cys Lys Ile Leu Val Leu Met Leu His Thr Glu Leu Ile Arg
            -50                 -45                 -40

Thr Asp Tyr Ser Ser Val Asp Gln Leu Leu Leu Asn Tyr Pro Ala Glu
        -35                 -30                 -25

Glu Gly Leu Gly Arg Glu Arg Ser Leu Leu Trp Thr Pro Leu Leu Ser
    -20                 -15                 -10

Pro Gly Ser Leu Arg Val Ile Leu Glu Ser Arg Glu Val Pro Val Ser
-5                   1                   5                  10

Leu Trp Pro Gln Thr
            15

(2) INFORMATION FOR SEQ ID NO: 420:

(i) SEQUENCE CHARACTERISTICS:
        (A) LENGTH: 86 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -26..-1
        (C) IDENTIFICATION METHOD: Von Heijne matrix
        (D) OTHER INFORMATION:   score 4.5 seq ENSLIILLQGLQG/RV (xi) SEQUENCE DESCRIPTION: SEQ ID NO: 420:

Met Ala Val Ser His Ser Val Lys Glu Arg Thr Ile Ser Glu Asn Ser
       -25                 -20                 -15

Leu Ile Ile Leu Leu Gln Gly Leu Gln Gly Arg Val Thr Thr Val Asp
-10                  -5                   1                   5

Leu Arg Asp Glu Ser Val Ala His Gly Arg Ile Asp Xaa Val Asp Ala
            10                  15                  20

Phe Met Asn Ile Arg Leu Ala Lys Val Thr Tyr Thr Asp Arg Trp Gly
            25                  30                  35

His Gln Val Lys Leu Asp Asp Leu Phe Val Thr Gly Arg Asn Val Arg
        40                  45                  50

Tyr Val His Ile Pro Asp
55                  60
```

(2) INFORMATION FOR SEQ ID NO: 421:

(i) SEQUENCE CHARACTERISTICS:
        (A) LENGTH: 91 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -23..-1
        (C) IDENTIFICATION METHOD: Von Heijne matrix
        (D) OTHER INFORMATION: score 4.4 seq QFILLGTTSVVTA/AL (xi) SEQUENCE DESCRIPTION: SEQ ID NO: 421:

```
Met Glu Ser Gly Gly Arg Pro Ser Leu Cys Gln Phe Ile Leu Leu Gly
              -20                 -15                 -10

Thr Thr Ser Val Val Thr Ala Ala Leu Tyr Ser Val Tyr Arg Gln Lys
         -5                   1                   5

Ala Arg Val Ser Gln Glu Leu Lys Gly Ala Lys Lys Val His Leu Gly
 10                  15                  20                  25

Glu Asp Leu Lys Ser Ile Leu Ser Glu Ala Pro Gly Lys Cys Val Pro
                 30                  35                  40

Tyr Ala Val Ile Glu Gly Ala Val Arg Ser Val Lys Glu Thr Leu Asn
                 45                  50                  55

Ser Gln Phe Val Glu Asn Cys Xaa Gly Val Arg
             60                  65
```

(2) INFORMATION FOR SEQ ID NO: 422:

(i) SEQUENCE CHARACTERISTICS:
        (A) LENGTH: 142 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -139..-1
        (C) IDENTIFICATION METHOD: Von Heijne matrix
        (D) OTHER INFORMATION: score 4.3 seq GILVPHSLRQAQA/SF (xi) SEQUENCE DESCRIPTION: SEQ ID NO: 422:

```
Met Ala Ala Leu Asp Leu Arg Ala Xaa Trp Ile Arg Trp Ser Cys Ser
              -135                -130                -125

Cys Leu Gly Xaa Leu Xaa Gly Ala Gly Gly Glu Thr Asn Gly Val Glu
              -120                -115                -110

Arg Pro Gly Gly Gly Gly Leu Ala Leu Ala Arg Gln Gly Ser Leu Arg
         -105                -100                 -95

Asp Gly Arg Gln Val Gly Arg Ala Pro Ala Val Cys Phe Pro His Gly
     -90                 -85                  -80

Ala Pro Gly Leu Pro Pro Arg Gln Arg Xaa Xaa Gly Xaa Pro Glu
-75                  -70                 -65                 -60

Val Gln Gly Gly Glu Ser Trp Cys Pro Arg Pro Arg Gly Gly Gly Ala
```

```
                -55                 -50                 -45
Ser Arg Thr Gly Leu Arg Arg Lys Gly Pro Thr Lys Thr Pro Glu
            -40                 -35                 -30

Pro Glu Ser Ser Glu Ala Pro Gln Asp Pro Leu Asn Trp Phe Gly Ile
        -25                 -20                 -15

Leu Val Pro His Ser Leu Arg Gln Ala Gln Ala Ser Phe Arg
    -10                  -5                   1

(2) INFORMATION FOR SEQ ID NO: 423:

(i) SEQUENCE CHARACTERISTICS:
        (A) LENGTH: 29 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:   score 4.1 seq WWISLLPSLLSIC/KV (xi) SEQUENCE DESCRIPTION: SEQ ID NO: 423:

Met Ala Phe Leu Pro Ser Pro Ala Trp Trp Ile Ser Leu Leu Pro Ser
    -20                 -15                 -10

Leu Leu Ser Ile Cys Lys Val Leu Met Pro Lys Leu Lys
 -5              1                5

(2) INFORMATION FOR SEQ ID NO: 424:

(i) SEQUENCE CHARACTERISTICS:
        (A) LENGTH: 127 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -49..-1
        (C) IDENTIFICATION METHOD: Von Heijne matrix
        (D) OTHER INFORMATION:   score 3.8 seq PAFHLPLPGPTLA/FL (xi) SEQUENCE DESCRIPTION: SEQ ID NO: 424:

Met Glu Pro Lys Val Ala Glu Leu Lys Gln Lys Ile Glu Asp Thr Leu
            -45                 -40                 -35

Cys Pro Phe Gly Phe Glu Val Tyr Pro Phe Gln Val Ala Trp Tyr Asn
            -30                 -25                 -20

Glu Leu Leu Pro Pro Ala Phe His Leu Pro Leu Pro Gly Pro Thr Leu
            -15                 -10                  -5

Ala Phe Leu Val Leu Ser Thr Pro Ala Met Phe Asp Arg Ala Leu Lys
     1               5                  10                  15

Pro Phe Leu Gln Ser Cys His Leu Arg Met Leu Thr Asp Pro Val Asp
                 20                  25                  30

Gln Cys Val Ala Tyr His Leu Gly Arg Val Arg Glu Ser Leu Pro Glu
             35                  40                  45
```

-continued

```
Leu Gln Ile Glu Ile Ile Ala Xaa Xaa Arg Gly Ala Pro Gln Pro Thr
        50                  55                  60

Pro Gln Asp Pro Gly Pro Asp Ser Ser His Val Ala Gly Ala Ala
        65                  70                  75
```

(2) INFORMATION FOR SEQ ID NO: 425:

(i) SEQUENCE CHARACTERISTICS:
        (A) LENGTH: 98 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -13..-1
        (C) IDENTIFICATION METHOD: Von Heijne matrix
        (D) OTHER INFORMATION: score 3.7 seq MLVLRSGLTKALA/SR (xi) SEQUENCE DESCRIPTION: SEQ ID NO: 425:

```
Met Leu Val Leu Arg Ser Gly Leu Thr Lys Ala Leu Ala Ser Arg Thr
        -10                 -5                   1

Leu Ala Pro Gln Val Cys Ser Ser Phe Ala Thr Gly Pro Arg Gln Tyr
        5                   10                  15

Asp Gly Thr Phe Tyr Glu Phe Arg Thr Tyr Leu Lys Pro Ser Asn
 20                  25                  30                  35

Met Asn Ala Phe Met Glu Asn Leu Lys Lys Asn Ile His Leu Arg Thr
                40                  45                  50

Ser Tyr Ser Glu Leu Val Gly Phe Trp Ser Val Glu Phe Gly Gly Arg
                55                  60                  65

Thr Asn Lys Val Phe His Ile Trp Lys Tyr Asp Asn Phe Ala His Arg
                70                  75                  80

Ala Glu
    85
```

(2) INFORMATION FOR SEQ ID NO: 426:

(i) SEQUENCE CHARACTERISTICS:
        (A) LENGTH: 27 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -23..-1
        (C) IDENTIFICATION METHOD: Von Heijne matrix
        (D) OTHER INFORMATION: score 10.5 seq LLFVLLLFSLLPA/CL (xi) SEQUENCE DESCRIPTION: SEQ ID NO: 426:

```
Met Ser Gly Gly His Leu Ala Asp Leu Thr Leu Leu Phe Val Leu Leu
            -20                 -15                 -10

Leu Phe Ser Leu Leu Pro Ala Cys Leu Pro Arg
            -5                   1
```

(2) INFORMATION FOR SEQ ID NO: 427:

```
    (i) SEQUENCE CHARACTERISTICS:
        (A) LENGTH: 54 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -51..-1
        (C) IDENTIFICATION METHOD: Von Heijne matrix
        (D) OTHER INFORMATION:  score 10.1 seq LLGALTLLGLVTS/FY (xi) SEQUENCE DESCRIPTION: SEQ ID NO: 427:

Met Lys Pro Ser Arg Thr Pro Ala Arg Leu Trp Met Leu Pro Gln Gln
    -50                 -45                 -40

Gln Ala Gly Ala Val Val Ala Ala Pro Thr Glu Arg His Pro Thr
-35             -30              -25                 -20

His His Met Ala Gly Trp Leu Leu Gly Ala Leu Thr Leu Leu Gly Leu
                -15              -10                  -5

Val Thr Ser Phe Tyr Lys
                 1

(2) INFORMATION FOR SEQ ID NO: 428:

(i) SEQUENCE CHARACTERISTICS:
        (A) LENGTH: 131 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -64..-1
        (C) IDENTIFICATION METHOD: Von Heijne matrix
        (D) OTHER INFORMATION:  score 9.5 seq LSLLAALAHLAAA/EK (xi) SEQUENCE DESCRIPTION: SEQ ID NO: 428:

Met Gly Glu Ser Ile Pro Leu Ala Ala Pro Val Pro Val Glu Gln Ala
                -60                 -55                 -50

Val Leu Glu Thr Phe Phe Ser His Leu Gly Ile Phe Ser Tyr Asp Lys
                -45                 -40                 -35

Ala Lys Asp Asn Val Glu Lys Glu Arg Glu Ala Asn Lys Ser Ala Gly
            -30                 -25                 -20

Gly Ser Trp Leu Ser Leu Leu Ala Ala Leu Ala His Leu Ala Ala Ala
    -15                 -10                  -5

Glu Lys Val Tyr His Ser Leu Thr Tyr Leu Gly Gln Lys Leu Gly Gly
  1                 5                  10                  15

Gln Ser Phe Phe Ser Arg Lys Asp Ser Ile Arg Thr Ile Tyr Thr Ser
                 20                  25                  30

Leu His Asn Glu Leu Lys Lys Val Val Thr Gly Arg Gly Ala Xaa Xaa
                 35                  40                  45

Trp Asp Cys Ser Ser Arg Gly Arg Thr Pro Phe Pro Pro Val Arg Ala
     50                  55                  60

Ala Tyr Gly
```

(2) INFORMATION FOR SEQ ID NO: 429:

(i) SEQUENCE CHARACTERISTICS:
        (A) LENGTH: 86 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -38..-1
        (C) IDENTIFICATION METHOD: Von Heijne matrix
        (D) OTHER INFORMATION: score 9.3 seq QLLYLSLLSGLHG/QE (xi) SEQUENCE DESCRIPTION: SEQ ID NO: 429:

```
Met Gln Met Ser Tyr Ala Ile Arg Cys Ala Phe Tyr Gln Leu Leu Leu
            -35                 -30                 -25

Ala Ala Leu Met Leu Val Ala Met Leu Gln Leu Leu Tyr Leu Ser Leu
        -20                 -15                 -10

Leu Ser Gly Leu His Gly Gln Glu Glu Gln Asp Gln Tyr Phe Glu Phe
    -5                   1                   5                  10

Phe Pro Pro Ser Pro Arg Ser Val Asp Gln Val Lys Ala Gln Leu Arg
                15                  20                  25

Thr Ala Leu Ala Ser Gly Gly Val Leu Asp Ala Ser Gly Asp Tyr Arg
            30                  35                  40

Val Tyr Arg Gly His Gly
            45
```

(2) INFORMATION FOR SEQ ID NO: 430:

(i) SEQUENCE CHARACTERISTICS:
        (A) LENGTH: 26 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION: score 9.1 seq LFAFHLLLSFILG/SR (xi) SEQUENCE DESCRIPTION: SEQ ID NO: 430:

```
Met Leu Arg Ala Glu Leu Lys Ile Ala Val Val Leu Phe Ala Phe His
                -20                 -15                 -10

Leu Leu Leu Ser Phe Ile Leu Gly Ser Arg
            -5                   1
```

(2) INFORMATION FOR SEQ ID NO: 431:

(i) SEQUENCE CHARACTERISTICS:
        (A) LENGTH: 76 amino acids
        (B) TYPE: AMINO ACID
        (D) TOPOLOGY: LINEAR (ii) MOLECULE TYPE: PROTEIN (vi) ORIGINAL SOURCE:
    (A) ORGANISM: Homo Sapiens
    (F) TISSUE TYPE: Brain (ix) FEATURE:
    (A) NAME/KEY: sig_peptide
    (B) LOCATION: -55..-1
    (C) IDENTIFICATION METHOD: Von Heijne matrix
    (D) OTHER INFORMATION:  score 9 seq LLILLLRTFLCSA/MI (xi) SEQUENCE DESCRIPTION: SEQ ID NO: 431:

```
Met Asn His Gln Gln Thr Leu Ile Gly Arg Leu Leu Cys Asp Leu His
-55             -50                 -45                 -40

Gly Leu Ser Leu Ser Pro Pro Val Ala Asn Asn Val Gln Ala Leu Phe
            -35                 -30                 -25

Arg Met Leu Thr Pro Glu Ala Tyr Ser Cys Leu Leu Ile Leu Leu Leu
            -20                 -15             -10

Arg Thr Phe Leu Cys Ser Ala Met Ile Ala Asn Thr Leu His Leu Lys
        -5               1               5

Tyr His Leu Gln Leu Ile Asp Asn Ala Cys Pro Glu
 10              15              20
```

(2) INFORMATION FOR SEQ ID NO: 432:

(i) SEQUENCE CHARACTERISTICS:
        (A) LENGTH: 84 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -40..-1
        (C) IDENTIFICATION METHOD: Von Heijne matrix
        (D) OTHER INFORMATION:  score 8.6 seq LFCVLGIVLLVTG/IV (xi) SEQUENCE DESCRIPTION: SEQ ID NO: 432:

```
Met Ile Ile Thr Ala Val Val Ser Ile Ser Val Thr Ile Phe Cys Phe
-40             -35                 -30                 -25

Gln Thr Lys Val Asp Phe Thr Ser Cys Thr Gly Leu Phe Cys Val Leu
            -20                 -15             -10

Gly Ile Val Leu Leu Val Thr Gly Ile Val Thr Ser Ile Val Leu Tyr
             -5              1               5

Phe Gln Tyr Val Tyr Trp Leu His Met Leu Tyr Ala Ala Leu Gly Ala
     10              15              20

Ile Cys Phe Thr Leu Phe Leu Ala Tyr Asp Thr Gln Leu Val Leu Gly
 25              30              35              40

Asn Arg Lys His
```

(2) INFORMATION FOR SEQ ID NO: 433:

(i) SEQUENCE CHARACTERISTICS:
        (A) LENGTH: 89 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (F) TISSUE TYPE: Brain (ix) FEATURE:
        (A) NAME/KEY: sig_peptide
        (B) LOCATION: -65..-1
        (C) IDENTIFICATION METHOD: Von Heijne matrix
        (D) OTHER INFORMATION: score 8.4 seq LLWFIHLVFVVLX/LF (xi) SEQUENCE DESCRIPTION: SEQ ID NO: 433:

```
Met Ala Ala Gly Gly Arg Met Glu Asp Gly Ser Leu Asp Ile Thr Gln
-65                 -60                 -55                 -50

Ser Ile Glu Asp Asp Pro Leu Leu Asp Ala Gln Leu Leu Pro His His
            -45                 -40                 -35

Ser Leu Gln Ala His Phe Arg Pro Arg Phe His Pro Leu Pro Thr Val
        -30                 -25                 -20

Ile Ile Val Asn Leu Leu Trp Phe Ile His Leu Val Phe Val Val Leu
    -15                 -10                  -5

Xaa Leu Phe Asn Arg Cys Ala Leu Phe Xaa Ser Tyr Pro Lys Trp Asp
  1           5                  10                  15

Xaa Cys Pro Gly Asn Tyr Thr Asn Pro
              20
```

(2) INFORMATION FOR SEQ ID NO: 434:

(i) SEQUENCE CHARACTERISTICS:
        (A) LENGTH: 59 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION: score 7.5 seq GCMLLFVFGFVGG/AV (xi) SEQUENCE DESCRIPTION: SEQ ID NO: 434:

```
Met Ser Pro Gly Cys Met Leu Leu Phe Val Phe Gly Phe Val Gly Gly
-15                 -10                  -5

Ala Val Val Ile Asn Ser Ala Ile Leu Val Ser Leu Ser Val Leu Leu
  1           5                  10                  15

Leu Val His Phe Ser Ile Ser Thr Gly Val Pro Ala Leu Thr Gln Asn
            20                  25                  30

Leu Pro Arg Ile Leu Arg Lys Glu Arg Pro Gly
            35                  40
```

(2) INFORMATION FOR SEQ ID NO: 435:

(i) SEQUENCE CHARACTERISTICS:
        (A) LENGTH: 67 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -15..-1

(C) IDENTIFICATION METHOD: Von Heijne matrix
            (D) OTHER INFORMATION:   score 7.5 seq LLLGIALLAYVAS/VW (xi) SEQUENCE DESCRIPTION: SEQ ID NO: 435:

Met Lys Leu Leu Leu Gly Ile Ala Leu Leu Ala Tyr Val Ala Ser Val
-15                 -10                 -5                    1

Trp Gly Asn Phe Val Asn Met Arg Ser Ile Gln Glu Asn Gly Glu Leu
            5                   10                  15

Lys Ile Glu Ser Lys Ile Glu Glu Met Val Glu Pro Leu Arg Glu Lys
        20                  25                  30

Ile Arg Asp Leu Xaa Lys Ser Phe Thr Gln Lys Tyr Pro Pro Val Lys
        35                  40                  45

Phe Leu Ser
50

(2) INFORMATION FOR SEQ ID NO: 436:

(i) SEQUENCE CHARACTERISTICS:
        (A) LENGTH: 151 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -23..-1
        (C) IDENTIFICATION METHOD: Von Heijne matrix
        (D) OTHER INFORMATION:   score 7.5 seq LVLLLTLPLHLMA/LL (xi) SEQUENCE DESCRIPTION: SEQ ID NO: 436:

Met Asp Ile Leu Val Pro Leu Leu Gln Leu Leu Val Leu Leu Leu Thr
            -20                 -15                 -10

Leu Pro Leu His Leu Met Ala Leu Leu Gly Cys Trp Gln Pro Leu Cys
        -5                  1                   5

Lys Ser Tyr Phe Pro Tyr Leu Met Ala Val Leu Thr Pro Lys Ser Asn
10              15                  20                  25

Arg Lys Met Glu Ser Lys Lys Arg Glu Leu Phe Ser Gln Ile Lys Gly
            30                  35                  40

Leu Thr Gly Ala Ser Gly Lys Val Ala Leu Leu Glu Leu Gly Cys Gly
            45                  50                  55

Thr Gly Ala Asn Phe Gln Phe Tyr Pro Pro Gly Cys Arg Val Thr Cys
            60                  65                  70

Leu Asp Pro Asn Pro His Phe Glu Lys Phe Leu Thr Lys Ser Met Ala
    75                  80                  85

Glu Asn Arg His Leu Gln Tyr Glu Arg Phe Val Val Ala Pro Gly Glu
90                  95                  100                 105

Asp Met Arg Xaa Leu Ala Asp Gly Ser Met Asp Val Val Cys Thr
            110                 115                 120

Leu Val Leu Cys Ser Val Gln
            125

(2) INFORMATION FOR SEQ ID NO: 437:

(i) SEQUENCE CHARACTERISTICS:
        (A) LENGTH: 103 amino acids
        (B) TYPE: AMINO ACID
        (D) TOPOLOGY: LINEAR (ii) MOLECULE TYPE: PROTEIN (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: -35..-1
             (C) IDENTIFICATION METHOD: Von Heijne matrix
             (D) OTHER INFORMATION:  score 7.4 seq SLLLSLELASGSG/QG (xi) SEQUENCE DESCRIPTION: SEQ ID NO: 437:

Met Glu Ala Ala Ser Pro Ser Asn Ser Thr Gly Val Glu Arg Xaa Ala
-35              -30              -25              -20

Asp Leu Met Asp Ala Asp Ser Leu Leu Leu Ser Leu Glu Leu Ala Ser
             -15              -10                           -5

Gly Ser Gly Gln Gly Leu Ser Pro Asp Arg Arg Ala Ser Leu Leu Thr
             1               5                   10

Ser Leu Met Leu Val Lys Arg Asp Tyr Arg Tyr Asp Arg Val Leu Phe
        15              20              25

Trp Gly Arg Ile Leu Gly Leu Val Ala Asp Tyr Tyr Ile Ala Gln Gly
30              35              40              45

Leu Ser Glu Asp Gln Leu Ala Pro Arg Lys Thr Leu Tyr Arg Ser Arg
             50              55              60

Ser Arg Lys Arg Pro Ala Leu
             65

(2) INFORMATION FOR SEQ ID NO: 438:

(i) SEQUENCE CHARACTERISTICS:
            (A) LENGTH: 70 amino acids
            (B) TYPE: AMINO ACID
            (D) TOPOLOGY: LINEAR (ii) MOLECULE TYPE: PROTEIN (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: -43..-1
             (C) IDENTIFICATION METHOD: Von Heijne matrix
             (D) OTHER INFORMATION:  score 7.4 seq VLVKLLSSSASTS/RP (xi) SEQUENCE DESCRIPTION: SEQ ID NO: 438:

Met Ile Arg Gln Glu Arg Ser Thr Ser Tyr Gln Glu Ala Val Arg Pro
             -40              -35              -30

Ala Leu Pro Ser Ser Lys Pro Cys Leu Leu Thr Ser Pro Ala Val Leu
        -25              -20              -15

Val Lys Leu Leu Ser Ser Ser Ala Ser Thr Ser Arg Pro Pro Asp Leu
-10                   -5                    1               5

Gly His Leu Trp Gln Pro Ser Ser Ser Val Pro Leu His Arg Pro Pro
             10              15              20

His Thr Ala Pro Pro Ala
             25

(2) INFORMATION FOR SEQ ID NO: 439:

(i) SEQUENCE CHARACTERISTICS:
            (A) LENGTH: 113 amino acids
            (B) TYPE: AMINO ACID (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -41..-1
        (C) IDENTIFICATION METHOD: Von Heijne matrix
        (D) OTHER INFORMATION:  score 7.4 seq ILPLLFGCLGVFG/LF (xi) SEQUENCE DESCRIPTION: SEQ ID NO: 439:

Met Lys Leu Ile Asp Tyr Gly Leu Ser Gly Tyr Gln Glu Glu Ser Ala
    -40                 -35                 -30

Glu Val Lys Ala Met Asp Phe Ile Thr Ser Thr Ala Ile Leu Pro Leu
-25                 -20                 -15                 -10

Leu Phe Gly Cys Leu Gly Val Phe Gly Leu Phe Arg Leu Leu Gln Trp
              -5                   1                   5

Val Arg Gly Lys Ala Tyr Leu Arg Asn Ala Val Val Ile Thr Gly
             10                  15                  20

Ala Thr Ser Gly Leu Gly Lys Glu Cys Ala Lys Val Phe Tyr Ala Xaa
             25                  30                  35

Gly Ala Lys Leu Val Leu Cys Glu Xaa Glu Trp Trp Gly Leu Glu Glu
 40                  45                  50                  55

Leu Ile Arg Glu Leu Thr Ala Ser His Ala Thr Lys Val Gln Thr His
                 60                  65                  70

Lys (2) INFORMATION FOR SEQ ID NO: 440:

(i) SEQUENCE CHARACTERISTICS:
        (A) LENGTH: 44 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -19..-1
        (C) IDENTIFICATION METHOD: Von Heijne matrix
        (D) OTHER INFORMATION:  score 7.4 seq PMLLRALAQAARA/GP (xi) SEQUENCE DESCRIPTION: SEQ ID NO: 440:

Met Arg Cys Leu Thr Thr Pro Met Leu Leu Arg Ala Leu Ala Gln Ala
              -15                 -10                  -5

Ala Arg Ala Gly Pro Pro Gly Gly Arg Ser Leu His Ser Ser Ala Val
              1                   5                  10

Ala Ala Thr Tyr Lys Tyr Val Asn Met Gln Asp Gln
         15                  20                  25

(2) INFORMATION FOR SEQ ID NO: 441:

(i) SEQUENCE CHARACTERISTICS:
        (A) LENGTH: 84 amino acids
        (B) TYPE: AMINO ACID
        (D) TOPOLOGY: LINEAR (ii) MOLECULE TYPE: PROTEIN (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: -67..-1
              (C) IDENTIFICATION METHOD: Von Heijne matrix
              (D) OTHER INFORMATION:   score 7 seq IWTLLSSVIRCLC/AI (xi) SEQUENCE DESCRIPTION: SEQ ID NO: 441:

Met Ser Arg Phe Leu Asn Val Leu Arg Ser Trp Leu Val Met Val Ser
        -65                 -60                 -55

Ile Ile Ala Met Gly Asn Thr Leu Gln Ser Phe Arg Asp His Thr Phe
    -50                 -45                 -40

Leu Tyr Glu Lys Leu Tyr Thr Gly Lys Pro Asn Leu Val Asn Gly Leu
-35             -30                 -25                 -20

Gln Ala Arg Thr Phe Gly Ile Trp Thr Leu Leu Ser Ser Val Ile Arg
                -15                 -10                 -5

Cys Leu Cys Ala Ile Asp Ile His Asn Lys Thr Leu Tyr His Ile Thr
                1                   5                   10

Leu Trp Thr Phe
        15

(2) INFORMATION FOR SEQ ID NO: 442:

(i) SEQUENCE CHARACTERISTICS:
              (A) LENGTH: 29 amino acids
              (B) TYPE: AMINO ACID
              (D) TOPOLOGY: LINEAR (ii) MOLECULE TYPE: PROTEIN (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: -14..-1
              (C) IDENTIFICATION METHOD: Von Heijne matrix
              (D) OTHER INFORMATION:   score 6.8 seq IFLTLSLDSRVSA/IR (xi) SEQUENCE DESCRIPTION: SEQ ID NO: 442:

Met Ile Phe Leu Thr Leu Ser Leu Asp Ser Arg Val Ser Ala Ile Arg
                -10                 -5                  1

Ser Pro Asn Phe Val Tyr Arg Ser Pro Thr Xaa His Gly
                5                   10                  15

(2) INFORMATION FOR SEQ ID NO: 443:

(i) SEQUENCE CHARACTERISTICS:
              (A) LENGTH: 101 amino acids
              (B) TYPE: AMINO ACID
              (D) TOPOLOGY: LINEAR (ii) MOLECULE TYPE: PROTEIN (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: -29..-1
              (C) IDENTIFICATION METHOD: Von Heijne matrix
              (D) OTHER INFORMATION:   score 6.8 seq LIFLCGAALLXVG/IW -continued (xi) SEQUENCE DESCRIPTION: SEQ ID NO: 443:

Met Gln Cys Phe Ser Phe Ile Lys Thr Met Met Ile Leu Phe Asn Leu
            -25              -20              -15

Leu Ile Phe Leu Cys Gly Ala Ala Leu Leu Xaa Val Gly Ile Trp Val
            -10              -5                        1

Ser Ile Asp Gly Ala Ser Phe Leu Lys Ile Phe Gly Pro Leu Ser Ser
        5                  10                  15

Ser Ala Met Gln Phe Val Asn Val Gly Tyr Phe Leu Ile Ala Ala Gly
 20                  25                  30                  35

Val Val Val Phe Ala Leu Gly Phe Leu Gly Cys Tyr Xaa Ala Lys Thr
            40                  45                  50

Glu Ser Xaa Cys Ala Leu Val Thr Phe Phe Xaa Ile Leu Leu Leu Ile
        55                  60                  65

Phe Ile Ala Asp Val
        70

(2) INFORMATION FOR SEQ ID NO: 444:

(i) SEQUENCE CHARACTERISTICS:
        (A) LENGTH: 97 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -35..-1
        (C) IDENTIFICATION METHOD: Von Heijne matrix
        (D) OTHER INFORMATION: score 6.4 seq SACLLLCPTWTNP/QL (xi) SEQUENCE DESCRIPTION: SEQ ID NO: 444:

Met Ala Glu Ala Ala Leu Glu Ala Val Arg Xaa Ser Tyr Glu Asn Ser
-35              -30              -25              -20

Arg Pro Leu Gln Gly Ser Ser Ala Cys Leu Leu Cys Pro Thr Trp
            -15              -10              -5

Thr Asn Pro Gln Leu Arg Ser Thr Ser Thr Gly Thr Gly Ser Ala Pro
            1                  5                  10

Thr Gly Arg Ala Leu Ser Ala Thr Leu Cys Ser Thr Gly Arg Pro Ser
    15                  20                  25

Xaa Xaa Trp Ser Leu Pro Tyr Phe Arg Ala Thr Val Gly Ser Thr Glu
 30                  35                  40                  45

Val Ser Val Ala Val Thr Pro Asp Gly Tyr Ala Asp Ala Val Arg Xaa
            50                  55                  60

Asp (2) INFORMATION FOR SEQ ID NO: 445:

(i) SEQUENCE CHARACTERISTICS:
        (A) LENGTH: 34 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain

```
        (ix) FEATURE:
              (A) NAME/KEY: sig_peptide
              (B) LOCATION: -19..-1
              (C) IDENTIFICATION METHOD: Von Heijne matrix
              (D) OTHER INFORMATION:  score 6.4 seq SVFLLMVNGQVES/AQ (xi) SEQUENCE DESCRIPTION: SEQ ID NO: 445:

Met Ala Thr Ala Ser Pro Ser Val Phe Leu Leu Met Val Asn Gly Gln
            -15                 -10                 -5

Val Glu Ser Ala Gln Phe Pro Glu Tyr Asp Asp Leu Tyr Cys Lys Tyr
  1               5                  10

Cys Gln
   15

(2) INFORMATION FOR SEQ ID NO: 446:

(i) SEQUENCE CHARACTERISTICS:
              (A) LENGTH: 36 amino acids
              (B) TYPE: AMINO ACID
              (D) TOPOLOGY: LINEAR (ii) MOLECULE TYPE: PROTEIN (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: -28..-1
              (C) IDENTIFICATION METHOD: Von Heijne matrix
              (D) OTHER INFORMATION:  score 6 seq IGLMFLMLGCALP/IY (xi) SEQUENCE DESCRIPTION: SEQ ID NO: 446:

Met Ala Gly Ile Lys Ala Leu Ile Ser Leu Ser Phe Gly Gly Ala Ile
            -25                 -20                 -15

Gly Leu Met Phe Leu Met Leu Gly Cys Ala Leu Pro Ile Tyr Asn Lys
            -10                  -5                  1

Tyr Trp Pro Trp
   5

(2) INFORMATION FOR SEQ ID NO: 447:

(i) SEQUENCE CHARACTERISTICS:
              (A) LENGTH: 39 amino acids
              (B) TYPE: AMINO ACID
              (D) TOPOLOGY: LINEAR (ii) MOLECULE TYPE: PROTEIN (vi) ORIGINAL SOURCE:
              (A) ORGANISM: Homo Sapiens
              (F) TISSUE TYPE: Brain (ix) FEATURE:
              (A) NAME/KEY: sig_peptide
              (B) LOCATION: -17..-1
              (C) IDENTIFICATION METHOD: Von Heijne matrix
              (D) OTHER INFORMATION:  score 5.9 seq ILLFGTLLMNAGA/VL (xi) SEQUENCE DESCRIPTION: SEQ ID NO: 447:

Met Ile Gly Asp Ile Leu Leu Phe Gly Thr Leu Leu Met Asn Ala Gly
            -15                 -10                 -5

Ala Val Leu Asn Phe Lys Leu Lys Lys Lys Asp Thr Gln Gly Phe Gly
  1               5                  10                  15

Glu Glu Ser Arg Glu Pro Trp
                  20
```

(2) INFORMATION FOR SEQ ID NO: 448:

(i) SEQUENCE CHARACTERISTICS:
        (A) LENGTH: 28 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION: score 5.9 seq MILTLSLFGSCIS/NF (xi) SEQUENCE DESCRIPTION: SEQ ID NO: 448:

```
Met Lys Thr Met Ile Leu Thr Leu Ser Leu Phe Gly Ser Cys Ile Ser
    -15                 -10                 -5
Asn Phe Glu Arg Tyr Met Thr Glu Arg Ser Ile Gln
  1           5                  10
```

(2) INFORMATION FOR SEQ ID NO: 449:

(i) SEQUENCE CHARACTERISTICS:
        (A) LENGTH: 82 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -39..-1
        (C) IDENTIFICATION METHOD: Von Heijne matrix
        (D) OTHER INFORMATION: score 5.9 seq SVSVLSSLGIVLA/VV (xi) SEQUENCE DESCRIPTION: SEQ ID NO: 449:

```
Met Asp Trp Arg Val Pro Pro Ser Xaa Xaa Asp Pro Gly His Gln Asp
            -35                 -30                 -25
Ile Pro Leu Pro Val Thr Xaa Xaa Phe Ile Ser Val Ser Val Leu Ser
        -20                 -15                 -10
Ser Leu Gly Ile Val Leu Ala Val Val Cys Leu Ser Phe Asn Ile Tyr
         -5                   1              5
Asn Ser His Val Arg Tyr Ile Gln Asn Ser Gln Pro Asn Leu Asn Asn
 10              15                  20                  25
Leu Thr Ala Val Gly Cys Ser Xaa Ala Leu Ala Ala Val Phe Pro Trp
                30                  35                  40
Gly Ser
```

(2) INFORMATION FOR SEQ ID NO: 450:

(i) SEQUENCE CHARACTERISTICS:
        (A) LENGTH: 113 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens (F) TISSUE TYPE: Brain (ix) FEATURE:
          (A) NAME/KEY: sig_peptide
          (B) LOCATION: -16..-1
          (C) IDENTIFICATION METHOD: Von Heijne matrix
          (D) OTHER INFORMATION: score 5.8 seq AALPAWLSLQSRA/RT (xi) SEQUENCE DESCRIPTION: SEQ ID NO: 450:

Met Ala Ala Ala Ala Leu Pro Ala Trp Leu Ser Leu Gln Ser Arg Ala
    -15                 -10                  -5

Arg Thr Leu Arg Ala Phe Ser Thr Ala Val Tyr Ser Ala Thr Pro Val
 1               5                  10                  15

Pro Xaa Pro Ser Leu Pro Glu Arg Thr Pro Gly Asn Glu Arg Pro Pro
             20                  25                  30

Arg Arg Lys Ala Leu Pro Pro Arg Thr Glu Lys Met Ala Val Asp Gln
             35                  40                  45

Asp Trp Pro Xaa Val Tyr Pro Val Ala Ala Pro Phe Lys Pro Ser Ala
         50                  55                  60

Val Pro Leu Pro Val Arg Met Gly Tyr Pro Val Lys Lys Gly Val Pro
 65                  70                  75                  80

Trp Xaa Arg Arg Glu Ser Xaa Thr Phe Lys Asp Ser Asn Phe Leu His
                 85                  90                  95

Leu (2) INFORMATION FOR SEQ ID NO: 451:

(i) SEQUENCE CHARACTERISTICS:
         (A) LENGTH: 29 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -25..-1
         (C) IDENTIFICATION METHOD: Von Heijne matrix
         (D) OTHER INFORMATION: score 5.8 seq LWISACAMLLCHG/SL (xi) SEQUENCE DESCRIPTION: SEQ ID NO: 451:

Met Ala Met Val Ser Ala Met Ser Trp Val Leu Tyr Leu Trp Ile Ser
-25                 -20                 -15                 -10

Ala Cys Ala Met Leu Leu Cys His Gly Ser Leu Gln Arg
                 -5                   1

(2) INFORMATION FOR SEQ ID NO: 452:

(i) SEQUENCE CHARACTERISTICS:
         (A) LENGTH: 78 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -69..-1
         (C) IDENTIFICATION METHOD: Von Heijne matrix (D) OTHER INFORMATION: score 5.7 seq LCRLLCLVRLFCC/SS (xi) SEQUENCE DESCRIPTION: SEQ ID NO: 452:

Met Gly Lys Glu Trp Gly Trp Gln Glu Met Glu Asn Gly Gly Ala Ala
            -65                 -60                 -55

Pro Ala Trp Gly Ala Gly Pro Pro Val His Pro Ala Pro Pro Pro Val
            -50                 -45                 -40

Glu Lys Thr Leu Ser Trp Gly Cys Gly Phe Gly Leu His Ser Gly Phe
            -35                 -30                 -25

Gly Gly Ser Gly Gly Gly Val Gly Leu Cys Arg Leu Leu Cys Leu Val
            -20                 -15                 -10

Arg Leu Phe Cys Cys Ser Ser Ile Leu Tyr Gln Arg Gln Gly
 -5                   1               5

(2) INFORMATION FOR SEQ ID NO: 453:

(i) SEQUENCE CHARACTERISTICS:
        (A) LENGTH: 65 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION: score 5.6 seq LVLSLQFLLLSYD/LF (xi) SEQUENCE DESCRIPTION: SEQ ID NO: 453:

Met Leu Gln Thr Ser Asn Tyr Ser Leu Val Leu Ser Leu Gln Phe Leu
    -20                 -15                 -10

Leu Leu Ser Tyr Asp Leu Phe Val Asn Ser Phe Ser Glu Leu Leu Gln
 -5                   1               5                   10

Lys Thr Pro Val Ile Gln Leu Val Leu Phe Ile Ile Gln Asp Ile Ala
            15                  20                  25

Val Leu Phe Asn Ile Ile Ile Ile Phe Leu Met Phe Phe Asn Thr Ser
            30                  35                  40

Arg (2) INFORMATION FOR SEQ ID NO: 454:

(i) SEQUENCE CHARACTERISTICS:
        (A) LENGTH: 27 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION: score 5.5 seq MGVCLLIPGLATA/CI (xi) SEQUENCE DESCRIPTION: SEQ ID NO: 454:

Met Trp Phe Glu Ile Leu Pro Gly Leu Ser Val Met Gly Val Cys Leu
    -20                 -15                 -10

```
Leu Ile Pro Gly Leu Ala Thr Ala Cys Ile Arg
         -5                            1
```

(2) INFORMATION FOR SEQ ID NO: 455:

(i) SEQUENCE CHARACTERISTICS:
        (A) LENGTH: 46 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -22..-1
        (C) IDENTIFICATION METHOD: Von Heijne matrix
        (D) OTHER INFORMATION:  score 5.5 seq LADPLXLFPFSEG/LP (xi) SEQUENCE DESCRIPTION: SEQ ID NO: 455:

```
Met Arg Pro Ser Pro Leu Ser Gly Ile Leu Ala Asp Pro Leu Xaa Leu
        -20                 -15                 -10

Phe Pro Phe Ser Glu Gly Leu Pro Arg Arg Arg Ala Ala Ser Arg Ser
        -5                   1               5                 10

Arg Leu Gln Thr Pro Ser Ala Arg Cys Ser Pro Arg Pro Gly
                15                  20
```

(2) INFORMATION FOR SEQ ID NO: 456:

(i) SEQUENCE CHARACTERISTICS:
        (A) LENGTH: 30 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -27..-1
        (C) IDENTIFICATION METHOD: Von Heijne matrix
        (D) OTHER INFORMATION:  score 5.4 seq SLMMAQXFIPAVA/KV (xi) SEQUENCE DESCRIPTION: SEQ ID NO: 456:

```
Met Arg Glu Ser Leu Ser Xaa Arg Ser Trp His Leu Pro Ala Ser Leu
        -25                 -20                 -15

Met Met Ala Gln Xaa Phe Ile Pro Ala Val Ala Lys Val Gly
    -10                  -5                       1
```

(2) INFORMATION FOR SEQ ID NO: 457:

(i) SEQUENCE CHARACTERISTICS:
        (A) LENGTH: 60 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide (B) LOCATION: -58..-1
          (C) IDENTIFICATION METHOD: Von Heijne matrix
          (D) OTHER INFORMATION:   score 5.4 seq LSLHLLATRACYG/IL (xi) SEQUENCE DESCRIPTION: SEQ ID NO: 457:

Met Ser Gly Val Val Pro Thr Ala Pro Glu Gln Pro Ala Xaa Glu Met
            -55                 -50                 -45

Glu Asn Gln Thr Lys Pro Pro Asp Pro Arg Pro Asp Ala Pro Pro Glu
        -40                 -35                 -30

Tyr Ser Ser His Xaa Phe Thr Arg Thr Pro Trp Lys Gln Leu Ser Leu
    -25                 -20                 -15

His Leu Leu Ala Thr Arg Ala Cys Tyr Gly Ile Leu
-10                  -5                   1

(2) INFORMATION FOR SEQ ID NO: 458:

(i) SEQUENCE CHARACTERISTICS:
          (A) LENGTH: 83 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -77..-1
          (C) IDENTIFICATION METHOD: Von Heijne matrix
          (D) OTHER INFORMATION:   score 5.3 seq TWVFTCLVFFCFG/LS (xi) SEQUENCE DESCRIPTION: SEQ ID NO: 458:

Met Trp Arg Tyr Gln Phe Gly Trp Gly Val Ile Thr Arg Gly Pro Arg
    -75                 -70                 -65

Glu Ile Pro Phe Pro Pro Ser Leu Leu Ala Ser Glu Ser Leu Leu Pro
    -60                 -55                 -50

Pro Leu Pro Asp Leu Val Leu Thr Cys Thr Ser Leu Gly Phe Val Thr
-45                 -40                 -35                 -30

Arg Val Trp Met Ser Leu Asn Leu Asn Glu Leu Ser Leu Tyr Ser Arg
            -25                 -20                 -15

Thr Trp Val Phe Thr Cys Leu Val Phe Phe Cys Phe Gly Leu Ser Xaa
                -10                 -5                   1

Ser Leu Gly
     5

(2) INFORMATION FOR SEQ ID NO: 459:

(i) SEQUENCE CHARACTERISTICS:
          (A) LENGTH: 39 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -29..-1
          (C) IDENTIFICATION METHOD: Von Heijne matrix
          (D) OTHER INFORMATION:   score 5.2 seq FFMLLGSLLPVKI/IE (xi) SEQUENCE DESCRIPTION: SEQ ID NO: 459:

```
Met Val Lys Leu Leu Val Ala Lys Ile Leu Cys Met Val Gly Val Phe
            -25                 -20                 -15

Phe Phe Met Leu Leu Gly Ser Leu Leu Pro Val Lys Ile Ile Glu Thr
            -10                  -5                          1

Asp Phe Glu Lys Ala Pro Gly
          5               10
```

(2) INFORMATION FOR SEQ ID NO: 460:

(i) SEQUENCE CHARACTERISTICS:
        (A) LENGTH: 22 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -17..-1
        (C) IDENTIFICATION METHOD: Von Heijne matrix
        (D) OTHER INFORMATION: score 5.2 seq IMCLIGLKANASS/ET (xi) SEQUENCE DESCRIPTION: SEQ ID NO: 460:

```
Met Pro Val Ser Ile Met Cys Leu Ile Gly Leu Lys Ala Asn Ala Ser
        -15                 -10                  -5

Ser Glu Thr His Ser Gly
  1               5
```

(2) INFORMATION FOR SEQ ID NO: 461:

(i) SEQUENCE CHARACTERISTICS:
        (A) LENGTH: 26 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -17..-1
        (C) IDENTIFICATION METHOD: Von Heijne matrix
        (D) OTHER INFORMATION: score 5.2 seq LLYLVLEKLVSRA/FQ (xi) SEQUENCE DESCRIPTION: SEQ ID NO: 461:

```
Met Lys Val Ile Leu Leu Tyr Leu Val Leu Glu Lys Leu Val Ser Arg
        -15                 -10                  -5

Ala Phe Gln Asn Val Glu Ala Pro His Gly
  1                   5
```

(2) INFORMATION FOR SEQ ID NO: 462:

(i) SEQUENCE CHARACTERISTICS:
        (A) LENGTH: 46 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain

```
    (ix) FEATURE:
         (A) NAME/KEY: sig_peptide
         (B) LOCATION: -19..-1
         (C) IDENTIFICATION METHOD: Von Heijne matrix
         (D) OTHER INFORMATION:  score 5.1 seq LLLGGRVCXPSLA/VG (xi) SEQUENCE DESCRIPTION: SEQ ID NO: 462:

Met Ala Val Thr Leu Ser Leu Leu Leu Gly Gly Arg Val Cys Xaa Pro
            -15                 -10                 -5

Ser Leu Ala Val Gly Ser Arg Pro Gly Gly Trp Arg Ala Gln Ala Leu
              1              5                  10

Leu Ala Gly Ser Arg Thr Pro Ile Pro Thr Gly Asn Arg Arg
     15                  20                  25

(2) INFORMATION FOR SEQ ID NO: 463:

(i) SEQUENCE CHARACTERISTICS:
        (A) LENGTH: 49 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -23..-1
         (C) IDENTIFICATION METHOD: Von Heijne matrix
         (D) OTHER INFORMATION:  score 5.1 seq LLPELGVVTPAQG/PR (xi) SEQUENCE DESCRIPTION: SEQ ID NO: 463:

Met Leu Asn Gln Thr Ser Gly Arg Thr Ser Leu Leu Pro Glu Leu Gly
            -20                 -15                 -10

Val Val Thr Pro Ala Gln Gly Pro Arg Arg Arg Val Trp Cys Gly His
            -5                   1              5

Ser Lys Ala Lys Ala Arg Lys Ser Tyr Cys Ala Arg Ala Ile Asp Cys
 10                  15                  20                  25

Gln (2) INFORMATION FOR SEQ ID NO: 464:

(i) SEQUENCE CHARACTERISTICS:
        (A) LENGTH: 135 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -79..-1
         (C) IDENTIFICATION METHOD: Von Heijne matrix
         (D) OTHER INFORMATION:  score 5 seq SFLGFSAPTPIQA/LT (xi) SEQUENCE DESCRIPTION: SEQ ID NO: 464:

Met Thr Ser Glu Asn Leu Val Gln Thr Ala Pro Lys Lys Lys Asn
            -75                 -70                 -65

Lys Gly Lys Lys Gly Leu Glu Pro Ser Gln Ser Thr Ala Ala Lys Val
       -60                  -55                 -50
```

```
Pro Lys Lys Ala Lys Thr Trp Ile Pro Glu Val His Asp Gln Lys Ala
    -45             -40                 -35

Asp Val Ser Ala Trp Lys Asp Leu Phe Val Pro Arg Pro Val Leu Arg
    -30             -25                 -20

Ala Leu Ser Phe Leu Gly Phe Ser Ala Pro Thr Pro Ile Gln Ala Leu
-15             -10                  -5                       1

Thr Leu Ala Pro Ala Ile Arg Asp Lys Leu Asp Ile Leu Gly Ala Ala
             5                  10                  15

Glu Thr Gly Ser Gly Lys Thr Leu Ala Phe Ala Ile Pro Met Ile His
            20                  25                  30

Ala Val Leu Gln Trp Gln Lys Arg Asn Ala Ala Pro Pro Pro Ser Asn
            35                  40                  45

Thr Glu Ala Pro Pro Gly Glu
50                  55
```

(2) INFORMATION FOR SEQ ID NO: 465:

(i) SEQUENCE CHARACTERISTICS:
        (A) LENGTH: 79 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -23..-1
        (C) IDENTIFICATION METHOD: Von Heijne matrix
        (D) OTHER INFORMATION: score 4.9 seq WHXLIPLTWACMA/RQ (xi) SEQUENCE DESCRIPTION: SEQ ID NO: 465:

```
Met Ala Ala Phe Gly Arg Gln Xaa Xaa Xaa Trp His Xaa Leu Ile Pro
            -20                 -15                 -10

Leu Thr Trp Ala Cys Met Ala Arg Gln Thr Pro His Leu Gly Glu Gln
         -5                   1                   5

Arg Arg Thr Thr Ala Ser Leu Xaa Arg Lys Leu Thr Thr Ala Ser Asn
10                  15                  20                  25

Gly Gly Val Ile Glu Glu Leu Ser Cys Val Arg Ser Asn Asn Tyr Val
             30                  35                  40

Gln Glu Pro Glu Cys Arg Arg Asn Leu Val Gln Cys Leu Leu Trp
             45                  50                  55
```

(2) INFORMATION FOR SEQ ID NO: 466:

(i) SEQUENCE CHARACTERISTICS:
        (A) LENGTH: 68 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -57..-1
        (C) IDENTIFICATION METHOD: Von Heijne matrix
        (D) OTHER INFORMATION: score 4.9 seq GWFLSGCPHGSSA/TW (xi) SEQUENCE DESCRIPTION: SEQ ID NO: 466:

```
Met Ser Leu Thr Ser Ser Pro Lys Lys Arg Arg Ser Ile Cys Phe Asp
        -55                 -50                 -45

Arg Phe Leu Met Pro Gln Ser Gln Ser Gly Pro Ser Ser Leu Gly Glu
        -40                 -35                 -30

Ser Tyr Arg Thr Gly Val Gly Phe Leu Ile Pro Glu Gly Trp Phe Leu
-25                 -20                 -15                  -10

Ser Gly Cys Pro His Gly Ser Ser Ala Thr Trp Thr Lys Cys Gln Thr
                 -5                   1                   5

Ser Ala Ser Leu
         10
```

(2) INFORMATION FOR SEQ ID NO: 467:

(i) SEQUENCE CHARACTERISTICS:
        (A) LENGTH: 46 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -39..-1
        (C) IDENTIFICATION METHOD: Von Heijne matrix
        (D) OTHER INFORMATION:   score 4.8 seq SLXFCLSPPPSPS/LR (xi) SEQUENCE DESCRIPTION: SEQ ID NO: 467:

```
Met Gly Glu Leu Gly Asn Arg Ser Arg Cys Ile Leu Phe Leu Ser Glu
             -35                 -30                 -25

Asn Pro Cys Leu Ser Glu Ser Ile Phe Gln Ser Leu Xaa Phe Cys Leu
             -20                 -15                 -10

Ser Pro Pro Pro Ser Pro Ser Leu Arg Pro Ser Pro Ser Arg
         -5                   1                   5
```

(2) INFORMATION FOR SEQ ID NO: 468:

(i) SEQUENCE CHARACTERISTICS:
        (A) LENGTH: 111 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -93..-1
        (C) IDENTIFICATION METHOD: Von Heijne matrix
        (D) OTHER INFORMATION:   score 4.7 seq VLLLRQXFAQAEK/WY (xi) SEQUENCE DESCRIPTION: SEQ ID NO: 468:

```
Met Ala Glu Leu Gly Leu Asn Glu His His Gln Asn Glu Val Ile Asn
             -90                 -85                 -80

Tyr Met Arg Phe Ala Arg Ser Lys Arg Gly Leu Arg Leu Lys Thr Val
             -75                 -70                 -65

Asp Ser Cys Phe Gln Asp Leu Lys Glu Ser Arg Leu Val Glu Asp Thr
             -60                 -55                 -50

Phe Thr Ile Asp Glu Val Ser Glu Val Leu Asn Gly Leu Gln Ala Val
```

```
                    -45                 -40                 -35                 -30
Val His Ser Glu Val Glu Ser Glu Leu Ile Asn Thr Ala Tyr Thr Asn
                        -25                 -20                 -15

Val Leu Leu Leu Arg Gln Xaa Phe Ala Gln Ala Glu Lys Trp Tyr Leu
            -10                  -5                           1

Lys Leu Gln Thr Asp Ile Ser Glu Leu Glu Asn Arg Glu Leu Leu
     5                  10                  15
```

(2) INFORMATION FOR SEQ ID NO: 469:

(i) SEQUENCE CHARACTERISTICS:
        (A) LENGTH: 70 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -49..-1
        (C) IDENTIFICATION METHOD: Von Heijne matrix
        (D) OTHER INFORMATION: score 4.6 seq SWAVGLLYAVAQG/SK (xi) SEQUENCE DESCRIPTION: SEQ ID NO: 469:

```
Met Val Thr Leu Pro Ser Gly Thr Trp Ala Phe Ser Cys Pro Tyr Leu
                -45                 -40                 -35

Ala Leu Val Asp Gly Gly Met Leu Gly Ser Ala Arg Glu Asp Ala His
            -30                 -25                 -20

Ala Ser Val Val Ser Trp Ala Val Gly Leu Leu Tyr Ala Val Ala Gln
        -15                 -10                  -5

Gly Ser Lys Arg Arg Lys Val Gln Asp Val Lys Pro Leu Xaa Trp Ser
     1                   5                  10                  15

Arg Thr Gly Thr Leu Gly
              20
```

(2) INFORMATION FOR SEQ ID NO: 470:

(i) SEQUENCE CHARACTERISTICS:
        (A) LENGTH: 80 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -68..-1
        (C) IDENTIFICATION METHOD: Von Heijne matrix
        (D) OTHER INFORMATION: score 4.6 seq LPFSLVSMLVTQG/LV (xi) SEQUENCE DESCRIPTION: SEQ ID NO: 470:

```
Met Ala Ser Ala Ser Ala Arg Gly Asn Gln Asp Lys Asp Ala His Phe
                -65                 -60                 -55

Pro Pro Pro Ser Lys Gln Ser Leu Leu Phe Cys Pro Lys Xaa Xaa Leu
        -50                 -45                 -40

His Ile His Arg Ala Glu Ile Ser Lys Ile Met Arg Glu Cys Gln Glu
    -35                 -30                 -25
```

-continued

```
Glu Ser Phe Trp Lys Arg Ala Leu Pro Phe Ser Leu Val Ser Met Leu
-20             -15             -10              -5

Val Thr Gln Gly Leu Val Tyr Gln Gly Tyr Leu Ala Ala Asn Ser Arg
             1               5                  10
```

(2) INFORMATION FOR SEQ ID NO: 471:

(i) SEQUENCE CHARACTERISTICS:
        (A) LENGTH: 71 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -69..-1
        (C) IDENTIFICATION METHOD: Von Heijne matrix
        (D) OTHER INFORMATION:  score 4.5 seq FILSLCVLCIVLT/TG (xi) SEQUENCE DESCRIPTION: SEQ ID NO: 471:

```
Met Leu Leu Met Lys Ser Ile Leu Leu Lys Val Val Cys Val Leu Cys
             -65             -60              -55

Ile Tyr Leu Lys Phe Lys Leu Met Ala Leu Ile Tyr Val Pro Asp Lys
             -50             -45              -40

Asn Asn Thr Asn Asn Asn Ile Leu Arg Tyr Asn His Asn Glu Ile Ser
             -35             -30              -25

Ile Gly Ile Ser Val Gln Cys His Phe Ile Leu Ser Leu Cys Val Leu
 -20             -15             -10

Cys Ile Val Leu Thr Thr Gly
 -5              1
```

(2) INFORMATION FOR SEQ ID NO: 472:

(i) SEQUENCE CHARACTERISTICS:
        (A) LENGTH: 50 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:  score 4.5 seq RLLLRRFLASVIS/RK (xi) SEQUENCE DESCRIPTION: SEQ ID NO: 472:

```
Met Ala Gln Arg Leu Leu Arg Arg Phe Leu Ala Ser Val Ile Ser
 -15              -10              -5

Arg Lys Pro Ser Gln Gly Gln Trp Pro Pro Leu Thr Ser Arg Ala Leu
  1              5                10              15

Gln Thr Pro Xaa Cys Ser Xaa Gly Gly Leu Thr Val Thr Pro Asn Pro
             20              25              30

Ser Arg
```

(2) INFORMATION FOR SEQ ID NO: 473:

(i) SEQUENCE CHARACTERISTICS:
            (A) LENGTH: 103 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -77..-1
            (C) IDENTIFICATION METHOD: Von Heijne matrix
            (D) OTHER INFORMATION:  score 4.4 seq FEARIALLPLLQA/ET (xi) SEQUENCE DESCRIPTION: SEQ ID NO: 473:

Met Ala Ala Ser Lys Val Lys Gln Asp Met Pro Pro Xaa Gly Gly Tyr
        -75              -70              -65
Gly Pro Ile Asp Tyr Lys Arg Asn Leu Pro Arg Arg Gly Leu Ser Gly
    -60              -55              -50
Tyr Ser Met Leu Ala Ile Gly Ile Gly Thr Leu Ile Tyr Gly His Trp
-45              -40              -35              -30
Ser Ile Met Lys Trp Asn Arg Glu Arg Arg Arg Leu Gln Ile Glu Asp
             -25              -20              -15
Phe Glu Ala Arg Ile Ala Leu Leu Pro Leu Leu Gln Ala Glu Thr Asp
             -10               -5               1
Arg Arg Thr Leu Gln Met Leu Arg Glu Asn Leu Glu Glu Glu Ala Ile
     5               10               15
Ile Met Lys Asp Val Pro Gly
20               25

(2) INFORMATION FOR SEQ ID NO: 474:

(i) SEQUENCE CHARACTERISTICS:
            (A) LENGTH: 77 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
            (A) NAME/KEY: sig_peptide
            (B) LOCATION: -54..-1
            (C) IDENTIFICATION METHOD: Von Heijne matrix
            (D) OTHER INFORMATION:  score 4.3 seq LLSLAILSHISTP/GC (xi) SEQUENCE DESCRIPTION: SEQ ID NO: 474:

Met Arg His Leu Val Thr Glu Glu Leu Phe Pro Cys Ser Asn Leu Glu
             -50              -45              -40
Asp Val Val Glu Asp Asn Ser His Ser Tyr Phe Thr Leu Arg Ile Thr
             -35              -30              -25
Met Ala Cys Lys Gly Val Pro Ser Thr Leu Leu Ser Leu Ala Ile Leu
        -20              -15              -10
Ser His Ile Ser Thr Pro Gly Cys Glu Trp His Val Ile Tyr Val Ser
    -5               1                5                     10
Ser Xaa Gly Leu Tyr Leu Val Val Glu Met Thr Asp Arg
             15               20

(2) INFORMATION FOR SEQ ID NO: 475:

```
    (i) SEQUENCE CHARACTERISTICS:
        (A) LENGTH: 80 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -76..-1
        (C) IDENTIFICATION METHOD: Von Heijne matrix
        (D) OTHER INFORMATION:  score 4.3 seq FRLLXVFAYGTYA/DY (xi) SEQUENCE DESCRIPTION: SEQ ID NO: 475:

Met Ser Ala Glu Val Lys Val Thr Gly Gln Asn Gln Glu Gln Phe Leu
    -75                 -70                 -65

Leu Leu Ala Lys Ser Ala Lys Gly Ala Ala Leu Ala Thr Leu Ile His
-60                 -55                 -50                 -45

Gln Val Leu Glu Ala Pro Gly Val Tyr Val Phe Gly Glu Leu Leu Asp
                -40                 -35                 -30

Met Pro Asn Val Arg Glu Leu Ala Glu Ser Xaa Phe Ala Ser Thr Phe
                -25                 -20                 -15

Arg Leu Leu Xaa Val Phe Ala Tyr Gly Thr Tyr Ala Asp Tyr Xaa Ala
        -10                  -5                   1

(2) INFORMATION FOR SEQ ID NO: 476:

(i) SEQUENCE CHARACTERISTICS:
        (A) LENGTH: 45 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -34..-1
        (C) IDENTIFICATION METHOD: Von Heijne matrix
        (D) OTHER INFORMATION:  score 4.3 seq QLFAFLNLLPVEA/DI (xi) SEQUENCE DESCRIPTION: SEQ ID NO: 476:

Met Leu Leu Ser Ile Gly Met Leu Met Leu Ser Ala Thr Gln Val Xaa
                -30                 -25                 -20

Thr Ile Leu Xaa Val Gln Leu Phe Ala Phe Leu Asn Leu Leu Pro Val
            -15                 -10                  -5

Glu Ala Asp Ile Xaa Ala Tyr Asn Phe Glu Asn Ala Ser
             1                   5                  10

(2) INFORMATION FOR SEQ ID NO: 477:

(i) SEQUENCE CHARACTERISTICS:
        (A) LENGTH: 28 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain
```

(ix) FEATURE:
            (A) NAME/KEY: sig_peptide
            (B) LOCATION: -16..-1
            (C) IDENTIFICATION METHOD: Von Heijne matrix
            (D) OTHER INFORMATION:  score 4.2 seq EVVSLSYCGVSWG/RI (xi) SEQUENCE DESCRIPTION: SEQ ID NO: 477:

Met Gly Trp Glu Val Val Ser Leu Ser Tyr Cys Gly Val Ser Trp Gly
    -15                 -10                 -5

Arg Ile Ser Pro Asn Leu Asn Lys Pro Val Asn Arg
  1               5                  10

(2) INFORMATION FOR SEQ ID NO: 478:

(i) SEQUENCE CHARACTERISTICS:
          (A) LENGTH: 72 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -32..-1
          (C) IDENTIFICATION METHOD: Von Heijne matrix
          (D) OTHER INFORMATION:  score 4.2 seq CWELFCLEHGIQA/DG (xi) SEQUENCE DESCRIPTION: SEQ ID NO: 478:

Met Arg Glu Cys Ile Ser Val His Val Gly Gln Ala Gly Val Gln Ile
        -30                 -25                 -20

Gly Asn Ala Cys Trp Glu Leu Phe Cys Leu Glu His Gly Ile Gln Ala
    -15                 -10                 -5

Asp Gly Thr Phe Asp Ala Gln Ala Ser Lys Ile Asn Asp Asp Asp Ser
  1               5                  10                  15

Phe Thr Thr Phe Phe Ser Glu Thr Gly Thr Ser Leu Leu Met Glu Arg
               20                  25                  30

Leu Xaa Leu Asp Tyr Gly Lys Lys
         35                  40

(2) INFORMATION FOR SEQ ID NO: 479:

(i) SEQUENCE CHARACTERISTICS:
          (A) LENGTH: 46 amino acids
          (B) TYPE: AMINO ACID
          (D) TOPOLOGY: LINEAR (ii) MOLECULE TYPE: PROTEIN (vi) ORIGINAL SOURCE:
          (A) ORGANISM: Homo Sapiens
          (F) TISSUE TYPE: Brain (ix) FEATURE:
          (A) NAME/KEY: sig_peptide
          (B) LOCATION: -25..-1
          (C) IDENTIFICATION METHOD: Von Heijne matrix
          (D) OTHER INFORMATION:  score 4.2 seq LDLLRGLPRVSLA/NL (xi) SEQUENCE DESCRIPTION: SEQ ID NO: 479:

Met Ala Gly Pro Leu Gln Gly Gly Ala Arg Ala Leu Asp Leu Leu
-25                 -20                 -15                 -10

Arg Gly Leu Pro Arg Val Ser Leu Ala Asn Leu Lys Pro Asn Pro Gly
         -5                   1                   5

```
Ser Lys Lys Pro Glu Arg Arg Pro Arg Gly Arg Arg Trp
         10              15                  20
```

(2) INFORMATION FOR SEQ ID NO: 480:

(i) SEQUENCE CHARACTERISTICS:
        (A) LENGTH: 68 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -25..-1
        (C) IDENTIFICATION METHOD: Von Heijne matrix
        (D) OTHER INFORMATION: score 4.2 seq MFAASXLAMCAGA/EV (xi) SEQUENCE DESCRIPTION: SEQ ID NO: 480:

```
Met Pro Ala Gly Val Pro Met Ser Thr Tyr Leu Lys Met Phe Ala Ala
-25                 -20                 -15                 -10

Ser Xaa Leu Ala Met Cys Ala Gly Ala Glu Val Val His Arg Tyr Tyr
             -5                   1                   5

Arg Pro Asp Leu Thr Ile Pro Glu Ile Pro Pro Lys Arg Gly Glu Leu
             10                  15                  20

Lys Thr Glu Leu Leu Gly Leu Lys Glu Arg Lys His Lys Pro Gln Val
         25                  30                  35

Ser Gln Gln Glu
 40
```

(2) INFORMATION FOR SEQ ID NO: 481:

(i) SEQUENCE CHARACTERISTICS:
        (A) LENGTH: 82 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION: score 4.2 seq SLPALALSLRASP/RX (xi) SEQUENCE DESCRIPTION: SEQ ID NO: 481:

```
Met Ala Val Gln Cys Val Arg Leu Ala Arg Arg Ser Leu Pro Ala Leu
             -20                 -15                 -10

Ala Leu Ser Leu Arg Ala Ser Pro Arg Xaa Leu Cys Thr Ala Thr Lys
             -5                   1                   5

Gln Lys Asn Ser Gly Gln Asn Leu Glu Glu Asp Met Gly Gln Ser Glu
         10                  15                  20

Gln Lys Ala Asp Pro Pro Ala Thr Glu Lys Thr Leu Leu Glu Glu Lys
 25                  30                  35                  40

Val Lys Leu Glu Glu Gln Leu Lys Glu Thr Val Glu Lys Tyr Lys Arg
             45                  50                  55

Ala Arg
```

(2) INFORMATION FOR SEQ ID NO: 482:

(i) SEQUENCE CHARACTERISTICS:
        (A) LENGTH: 42 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -37..-1
        (C) IDENTIFICATION METHOD: Von Heijne matrix
        (D) OTHER INFORMATION:  score 4.2 seq RLMHHYLSTPTSA/RP (xi) SEQUENCE DESCRIPTION: SEQ ID NO: 482:

Met Phe Ser Ile Ile Ser Arg Ser Arg Ala Cys Ser Met Tyr Phe Lys
         -35                 -30                 -25

Glu Asn Ala Lys Pro Ser Gln Leu Arg Leu Met His His Tyr Leu Ser
    -20                 -15                 -10

Thr Pro Thr Ser Ala Arg Pro His His Leu
 -5                  1               5

(2) INFORMATION FOR SEQ ID NO: 483:

(i) SEQUENCE CHARACTERISTICS:
        (A) LENGTH: 35 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -16..-1
        (C) IDENTIFICATION METHOD: Von Heijne matrix
        (D) OTHER INFORMATION:  score 4.1 seq LLPATSLAGPVLS/TL (xi) SEQUENCE DESCRIPTION: SEQ ID NO: 483:

Met Lys Arg Leu Leu Pro Ala Thr Ser Leu Ala Gly Pro Val Leu Ser
    -15                 -10                 -5

Thr Leu Ile Ala Pro Thr Pro Met Leu Phe Cys Glu Asp Lys Ser Trp
 1               5                   10                  15

Asp Pro Gly (2) INFORMATION FOR SEQ ID NO: 484:

(i) SEQUENCE CHARACTERISTICS:
        (A) LENGTH: 98 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -70..-1

(C) IDENTIFICATION METHOD: Von Heijne matrix
            (D) OTHER INFORMATION:  score 4 seq IAVLYLHLYDVFG/DP (xi) SEQUENCE DESCRIPTION: SEQ ID NO: 484:

Met Leu Ile Ile Thr Asn Pro Trp Pro Lys Tyr Phe Asp Ala Ala Gly
-70                 -65                 -60                 -55

Arg Leu Thr Pro Glu Phe Ser Gln Arg Leu Thr Asn Lys Ile Arg Glu
            -50                 -45                 -40

Leu Leu Gln Gln Met Glu Arg Gly Leu Lys Ser Ala Asp Xaa Xaa Asp
            -35                 -30                 -25

Gly Thr Gly Tyr Thr Gly Trp Ala Gly Ile Ala Val Leu Tyr Leu His
            -20                 -15                 -10

Leu Tyr Asp Val Phe Gly Asp Pro Ala Tyr Leu Gln Leu Ala His Gly
    -5                   1                   5                  10

Tyr Val Lys Gln Ser Leu Asn Cys Leu Thr Lys Arg Ser Ile Thr Phe
                15                  20                  25

Gln Gly (2) INFORMATION FOR SEQ ID NO: 485:

(i) SEQUENCE CHARACTERISTICS:
        (A) LENGTH: 47 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:  score 3.9 seq AWLAQGSSSAGWG/LE (xi) SEQUENCE DESCRIPTION: SEQ ID NO: 485:

Met Cys Ala Thr Glu Thr Val Arg Ala Trp Leu Ala Gln Gly Ser Ser
    -20                 -15                 -10

Ser Ala Gly Trp Gly Leu Glu Arg Lys Gln Gly Val Ser Ala His Arg
-5                   1                   5                  10

Met Pro Ala Leu Arg Trp Leu Gln Lys Ser Val Pro Gly Xaa Met
                15                  20                  25

(2) INFORMATION FOR SEQ ID NO: 486:

(i) SEQUENCE CHARACTERISTICS:
        (A) LENGTH: 48 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -46..-1
        (C) IDENTIFICATION METHOD: Von Heijne matrix
        (D) OTHER INFORMATION:  score 3.9 seq AAAFCLKXXGANT/HP (xi) SEQUENCE DESCRIPTION: SEQ ID NO: 486:

Met Leu Leu Leu Ala Thr His Pro Glu Thr Val Gly Gln Val Thr Leu

```
                   -45             -40             -35
Arg Val Xaa Pro Val Ser Leu Glu Val Ser Ile Gln Met Cys Ala Ala
-30             -25             -20             -15

Ala Ala Ala Ala Phe Cys Leu Lys Xaa Xaa Gly Ala Asn Thr His Pro
            -10              -5                   1
```

(2) INFORMATION FOR SEQ ID NO: 487:

(i) SEQUENCE CHARACTERISTICS:
        (A) LENGTH: 86 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -64..-1
        (C) IDENTIFICATION METHOD: Von Heijne matrix
        (D) OTHER INFORMATION:  score 3.9 seq GLGGAQLQGGAXG/RG (xi) SEQUENCE DESCRIPTION: SEQ ID NO: 487:

```
Met Ala Ala Ser Ser Ala Thr Pro Ala Pro Xaa Xaa Ser Gln Arg Cys
            -60             -55             -50

Gly Ala Asp Ala Gly Ser Ala Ala Arg Ile Val Phe Arg Trp Gly Arg
            -45             -40             -35

Gly Arg Arg Gly Ala Arg Ser Pro Glu Gly Ser Gly His His Gly Arg
        -30             -25             -20

Ala Asn Ser Gly Leu Gly Gly Ala Gln Leu Gln Gly Gly Ala Xaa Gly
    -15             -10              -5

Arg Gly Ser Met Ala Pro Leu Arg Ala Ser Ala Gly Gln Thr Arg Asp
  1           5              10              15

Gly Pro Thr Gln Pro Gly
            20
```

(2) INFORMATION FOR SEQ ID NO: 488:

(i) SEQUENCE CHARACTERISTICS:
        (A) LENGTH: 50 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -17..-1
        (C) IDENTIFICATION METHOD: Von Heijne matrix
        (D) OTHER INFORMATION:  score 3.9 seq PLAGLAAAALGRA/PP (xi) SEQUENCE DESCRIPTION: SEQ ID NO: 488:

```
Met Leu Arg Arg Pro Leu Ala Gly Leu Ala Ala Ala Ala Leu Gly Arg
    -15             -10              -5

Ala Pro Pro Asp Gly Leu Leu Cys Ser Leu Pro Gly Val Ala Val Glu
  1           5              10                      15

Asp Pro Val Gln Asp Ser Ala Gly Phe Ser Phe Ser Leu Met Asp Arg
            20              25              30
```

```
Pro Lys (2) INFORMATION FOR SEQ ID NO: 489:

(i) SEQUENCE CHARACTERISTICS:
        (A) LENGTH: 53 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -17..-1
        (C) IDENTIFICATION METHOD: Von Heijne matrix
        (D) OTHER INFORMATION:  score 3.8 seq GFVAALVAGGVAG/VS (xi) SEQUENCE DESCRIPTION: SEQ ID NO: 489:

Met Asp Arg Pro Gly Phe Val Ala Ala Leu Val Ala Gly Gly Val Ala
        -15                 -10                  -5

Gly Val Ser Val Asp Leu Ile Leu Phe Pro Leu Asp Thr Ile Lys Thr
  1               5                  10                  15

Arg Leu Gln Ser Pro Gln Gly Phe Ser Lys Ala Gly Gly Phe His Gly
                20                  25                  30

Ile Tyr Ala Ser Trp
            35

(2) INFORMATION FOR SEQ ID NO: 490:

(i) SEQUENCE CHARACTERISTICS:
        (A) LENGTH: 50 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -21..-1
        (C) IDENTIFICATION METHOD: Von Heijne matrix
        (D) OTHER INFORMATION:  score 3.8 seq SMDLLTLLFQRRS/HQ (xi) SEQUENCE DESCRIPTION: SEQ ID NO: 490:

Met Ile Val Trp Phe Glu Gly Ile Ser Met Asp Leu Leu Thr Leu Leu
    -20                 -15                 -10

Phe Gln Arg Arg Ser His Gln Val Thr Gln Leu Leu Val Ser Ser Thr
 -5               1                   5                  10

Gly Asn Trp Leu Arg Gln Tyr Leu Cys Ala Ser Leu Thr Ile Ala Gly
                15                  20                  25

Arg Arg (2) INFORMATION FOR SEQ ID NO: 491:

(i) SEQUENCE CHARACTERISTICS:
        (A) LENGTH: 50 amino acids
        (B) TYPE: AMINO ACID
        (D) TOPOLOGY: LINEAR (ii) MOLECULE TYPE: PROTEIN
```

(vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -20..-1
         (C) IDENTIFICATION METHOD: Von Heijne matrix
         (D) OTHER INFORMATION:  score 3.8 seq ALDALMFPARRRA/AV (xi) SEQUENCE DESCRIPTION: SEQ ID NO: 491:

Met Arg Thr Phe Val His Phe Ala Leu Asp Ala Leu Met Phe Pro Ala
-20             -15                 -10                 -5

Arg Arg Arg Ala Ala Val Thr Arg Leu Ser Glu Arg Leu Ser Leu Cys
                 1               5                   10

Phe Cys Leu His Ser Arg Leu Gln Asp Pro Ala Ala Arg Pro Arg Pro
        15                  20                  25

Ser Trp
    30

(2) INFORMATION FOR SEQ ID NO: 492:

(i) SEQUENCE CHARACTERISTICS:
        (A) LENGTH: 99 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -61..-1
         (C) IDENTIFICATION METHOD: Von Heijne matrix
         (D) OTHER INFORMATION:  score 3.8 seq LVMTFLFRNGSLQ/EK (xi) SEQUENCE DESCRIPTION: SEQ ID NO: 492:

Met Ala Ala Pro Pro Gln Leu Arg Ala Leu Leu Val Val Val Asn Ala
    -60             -55                 -50

Leu Leu Arg Lys Arg Arg Tyr His Ala Ala Leu Ala Val Leu Lys Gly
-45             -40                 -35                 -30

Phe Arg Asn Gly Ala Val Tyr Gly Ala Lys Ile Arg Ala Pro His Ala
                -25             -20                 -15

Leu Val Met Thr Phe Leu Phe Arg Asn Gly Ser Leu Gln Glu Lys Leu
                -10             -5                  1

Trp Ala Ile Leu Gln Ala Thr Tyr Ile His Ser Trp Asn Leu Ala Arg
    5               10                  15

Phe Val Phe Thr Tyr Lys Gly Leu Arg Ala Leu Gln Ser Tyr Ile Gln
20              25                  30                  35

Gly Pro Gly (2) INFORMATION FOR SEQ ID NO: 493:

(i) SEQUENCE CHARACTERISTICS:
        (A) LENGTH: 79 amino acids
        (B) TYPE: AMINO ACID
        (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
              (A) NAME/KEY: sig_peptide
              (B) LOCATION: -18..-1
              (C) IDENTIFICATION METHOD: Von Heijne matrix
              (D) OTHER INFORMATION:   score 3.8 seq GXALGLLPSLAKA/ED (xi) SEQUENCE DESCRIPTION: SEQ ID NO: 493:

Met Pro Val Asp Leu Gly Xaa Ala Leu Gly Leu Leu Pro Ser Leu Ala
            -15                 -10                  -5

Lys Ala Glu Asp Ser Gln Phe Ser Glu Ser Asp Ala Ala Leu Gln Glu
              1               5                 10

Glu Leu Ser Ser Pro Glu Thr Ala Arg Gln Leu Phe Arg Gln Phe Arg
 15              20                  25                      30

Tyr Gln Val Met Ser Gly Pro His Glu Thr Leu Lys Xaa Leu Arg Lys
                35                  40                      45

Leu Cys Phe Gln Trp Leu Gln Pro Glu Val His Thr Lys Glu Gly
            50                  55                  60

(2) INFORMATION FOR SEQ ID NO: 494:

(i) SEQUENCE CHARACTERISTICS:
            (A) LENGTH: 139 amino acids
            (B) TYPE: AMINO ACID
            (D) TOPOLOGY: LINEAR (ii) MOLECULE TYPE: PROTEIN (vi) ORIGINAL SOURCE:
            (A) ORGANISM: Homo Sapiens
            (F) TISSUE TYPE: Brain (ix) FEATURE:
              (A) NAME/KEY: sig_peptide
              (B) LOCATION: -72..-1
              (C) IDENTIFICATION METHOD: Von Heijne matrix
              (D) OTHER INFORMATION:   score 3.8 seq LMGLALAVYKCQS/MG (xi) SEQUENCE DESCRIPTION: SEQ ID NO: 494:

Met Asn Leu Phe Ile Met Tyr Met Ala Gly Asn Thr Ile Ser Ile Phe
            -70                 -65                 -60

Pro Thr Met Met Val Cys Met Met Ala Trp Arg Pro Ile Gln Ala Leu
    -55                 -50                 -45

Met Ala Ile Ser Ala Thr Phe Lys Met Leu Glu Ser Ser Gln Lys
-40             -35                 -30                     -25

Phe Leu Gln Gly Leu Val Tyr Leu Ile Gly Asn Leu Met Gly Leu Ala
            -20                 -15                 -10

Leu Ala Val Tyr Lys Cys Gln Ser Met Gly Leu Leu Pro Thr His Ala
             -5              1                  5

Ser Asp Trp Leu Ala Phe Ile Glu Pro Pro Glu Arg Met Glu Ser Val
    10                  15                  20

Val Glu Asp Cys Phe Cys Glu His Glu Lys Ala Ala Pro Gly Pro Tyr
 25                 30                  35                      40

Val Phe Gly Ser Tyr Leu His Pro Ser Leu Ser Pro Val Ala Pro Gln
                45                  50                  55

His Thr Leu Lys Leu Ile Thr Tyr Val Lys Lys
                60                  65

(2) INFORMATION FOR SEQ ID NO: 495:

(i) SEQUENCE CHARACTERISTICS:
            (A) LENGTH: 102 amino acids
            (B) TYPE: AMINO ACID

```
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -51..-1
         (C) IDENTIFICATION METHOD: Von Heijne matrix
         (D) OTHER INFORMATION:  score 3.8 seq NVLFVAGLAFVIG/LE (xi) SEQUENCE DESCRIPTION: SEQ ID NO: 495:

Met Ile Ser Leu Thr Asp Thr Gln Lys Ile Gly Met Gly Leu Thr Gly
    -50                 -45                 -40

Phe Gly Val Phe Phe Leu Phe Phe Gly Met Ile Leu Phe Phe Asp Lys
-35                 -30                 -25                 -20

Ala Leu Leu Ala Ile Gly Asn Val Leu Phe Val Ala Gly Leu Ala Phe
                -15                 -10                  -5

Val Ile Gly Leu Glu Arg Thr Phe Arg Phe Phe Gln Lys His Lys
                 1               5                  10

Met Lys Ala Thr Gly Phe Phe Leu Gly Gly Val Phe Val Val Leu Ile
         15                  20                  25

Gly Trp Pro Leu Ile Gly Met Ile Phe Glu Ile Tyr Gly Phe Phe Leu
 30                  35                  40                  45

Leu Phe Arg Gly Leu Gly
                50

(2) INFORMATION FOR SEQ ID NO: 496:

(i) SEQUENCE CHARACTERISTICS:
         (A) LENGTH: 53 amino acids
         (B) TYPE: AMINO ACID
         (D) TOPOLOGY: LINEAR (ii) MOLECULE TYPE: PROTEIN (vi) ORIGINAL SOURCE:
         (A) ORGANISM: Homo Sapiens
         (F) TISSUE TYPE: Brain (ix) FEATURE:
         (A) NAME/KEY: sig_peptide
         (B) LOCATION: -33..-1
         (C) IDENTIFICATION METHOD: Von Heijne matrix
         (D) OTHER INFORMATION:  score 3.6 seq LAVFQMLKSMCAG/QR (xi) SEQUENCE DESCRIPTION: SEQ ID NO: 496:

Met Ala Ala Ser Gly Ala Pro Arg Ile Leu Val Asp Leu Leu Lys Leu
            -30                 -25                 -20

Xaa Val Ala Pro Leu Ala Val Phe Gln Met Leu Lys Ser Met Cys Ala
        -15                 -10                  -5

Gly Gln Arg Leu Ala Ser Glu Pro Gln Asp Pro Ala Ala Val Ser Leu
 1               5                  10                  15

Pro Thr Ser Ser Gly
            20

(2) INFORMATION FOR SEQ ID NO: 497:

(i) SEQUENCE CHARACTERISTICS:
         (A) LENGTH: 92 amino acids
         (B) TYPE: AMINO ACID
         (D) TOPOLOGY: LINEAR
```

(ii) MOLECULE TYPE: PROTEIN (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: -26..-1
             (C) IDENTIFICATION METHOD: Von Heijne matrix
             (D) OTHER INFORMATION: score 3.6 seq ARSLLQFLRLVGQ/LK (xi) SEQUENCE DESCRIPTION: SEQ ID NO: 497:

Met Ala Ser Val Ser Ser Ala Thr Phe Ser Gly His Gly Ala Arg Ser
    -25                 -20                 -15

Leu Leu Gln Phe Leu Arg Leu Val Gly Gln Leu Lys Arg Val Pro Arg
-10                  -5                   1                   5

Thr Gly Trp Val Tyr Arg Asn Val Gln Arg Pro Glu Ser Val Ser Asp
                10                  15                  20

His Met Tyr Arg Met Ala Val Met Ala Met Val Ile Lys Asp Asp Arg
                25                  30                  35

Leu Asn Lys Asp Arg Cys Val Arg Leu Ala Leu Val His Asp Met Ala
    40                  45                  50

Glu Cys Ile Val Gly Asp Ile Ala Pro Ala Asp Gly
55                  60                  65

(2) INFORMATION FOR SEQ ID NO: 498:

(i) SEQUENCE CHARACTERISTICS:
             (A) LENGTH: 24 amino acids
             (B) TYPE: AMINO ACID
             (D) TOPOLOGY: LINEAR (ii) MOLECULE TYPE: PROTEIN (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: -16..-1
             (C) IDENTIFICATION METHOD: Von Heijne matrix
             (D) OTHER INFORMATION: score 3.6 seq LAVLLVLFTLNIL/KS (xi) SEQUENCE DESCRIPTION: SEQ ID NO: 498:

Met Trp Tyr Leu Ala Val Leu Leu Val Leu Phe Thr Leu Asn Ile Leu
    -15                 -10                 -5

Lys Ser Leu Tyr Trp Gln Pro Gly
  1                   5

(2) INFORMATION FOR SEQ ID NO: 499:

(i) SEQUENCE CHARACTERISTICS:
             (A) LENGTH: 58 amino acids
             (B) TYPE: AMINO ACID
             (D) TOPOLOGY: LINEAR (ii) MOLECULE TYPE: PROTEIN (vi) ORIGINAL SOURCE:
             (A) ORGANISM: Homo Sapiens
             (F) TISSUE TYPE: Brain (ix) FEATURE:
             (A) NAME/KEY: sig_peptide
             (B) LOCATION: -42..-1
             (C) IDENTIFICATION METHOD: Von Heijne matrix
             (D) OTHER INFORMATION: score 3.5 seq INSLLEXSSLSRC/LE (xi) SEQUENCE DESCRIPTION: SEQ ID NO: 499:

Met Phe Thr Phe Gly Arg Leu Phe Gln Ile Ile Thr Val Val Thr Cys
        -40             -35              -30

Leu Gln Phe Ile Gln Asp Cys Cys Ile His Ser Arg Gln Ile Asn Ser
    -25             -20              -15

Leu Leu Glu Xaa Ser Ser Leu Ser Arg Cys Leu Glu Val Pro Met Tyr
-10              -5                  1                5

Val Lys Cys Ile Gly Ser Lys Ile Pro Leu
            10              15

(2) INFORMATION FOR SEQ ID NO: 500:

(i) SEQUENCE CHARACTERISTICS:
        (A) LENGTH: 62 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -51..-1
        (C) IDENTIFICATION METHOD: Von Heijne matrix
        (D) OTHER INFORMATION:  score 3.5 seq VGTLCQLDWWIWG/GI (xi) SEQUENCE DESCRIPTION: SEQ ID NO: 500:

Met Ile Gln Asp Arg Asp Arg Cys Ala Gln Ala Ala Val Ala Ala
    -50             -45              -40

Val Gly Asn Leu Glu Pro Arg Gly Thr Pro Gly Pro Glu Asp Glu Ala
-35             -30              -25              -20

Phe Cys Leu Pro Gly Cys Val Gly Thr Leu Cys Gln Leu Asp Trp Trp
            -15              -10              -5

Ile Trp Gly Gly Ile His Pro His Pro Thr Arg Lys Ala Trp
        1               5               10

(2) INFORMATION FOR SEQ ID NO: 501:

(i) SEQUENCE CHARACTERISTICS:
        (A) LENGTH: 48 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -31..-1
        (C) IDENTIFICATION METHOD: Von Heijne matrix
        (D) OTHER INFORMATION:  score 11.3 seq LLLCLLWIGYSQG/TT (xi) SEQUENCE DESCRIPTION: SEQ ID NO: 501:

Met Lys Ile Ile Phe Pro Ile Leu Ser Asn Pro Val Phe Arg Arg Thr
    -30             -25              -20

Val Lys Leu Leu Leu Cys Leu Leu Trp Ile Gly Tyr Ser Gln Gly Thr
-15             -10              -5                1

Thr His Val Leu Arg Phe Gly Gly Ile Phe Glu Tyr Val Glu Ser Gly
            5               10              15

-continued (2) INFORMATION FOR SEQ ID NO: 502:

(i) SEQUENCE CHARACTERISTICS:
        (A) LENGTH: 57 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -26..-1
        (C) IDENTIFICATION METHOD: Von Heijne matrix
        (D) OTHER INFORMATION:  score 6.6 seq LFWLASGWTPAFA/YS (xi) SEQUENCE DESCRIPTION: SEQ ID NO: 502:

```
Met Val Ser Arg Met Val Ser Thr Met Leu Ser Gly Leu Leu Phe Trp
    -25             -20             -15

Leu Ala Ser Gly Trp Thr Pro Ala Phe Ala Tyr Ser Pro Arg Thr Pro
-10              -5                   1                   5

Asp Arg Val Ser Glu Ala Asp Ile Gln Arg Leu Leu His Gly Val Met
             10                  15                  20

Glu Gln Leu Gly Ile Ala Arg Pro Arg
             25              30
```

(2) INFORMATION FOR SEQ ID NO: 503:

(i) SEQUENCE CHARACTERISTICS:
        (A) LENGTH: 46 amino acids
        (B) TYPE: AMINO ACID
        (D) TOPOLOGY: LINEAR (ii) MOLECULE TYPE: PROTEIN (vi) ORIGINAL SOURCE:
        (A) ORGANISM: Homo Sapiens
        (F) TISSUE TYPE: Brain (ix) FEATURE:
        (A) NAME/KEY: sig_peptide
        (B) LOCATION: -24..-1
        (C) IDENTIFICATION METHOD: Von Heijne matrix
        (D) OTHER INFORMATION:  score 4.8 seq ATMVSGSSGLAXA/RL (xi) SEQUENCE DESCRIPTION: SEQ ID NO: 503:

```
Met Thr Ala Thr Leu Ala Ala Ala Asp Ile Ala Thr Met Val Ser
        -20              -15                  -10

Gly Ser Ser Gly Leu Ala Xaa Ala Arg Leu Leu Ser Arg Xaa Ser Ser
             -5              1               5

Cys Arg Arg Met Glu Phe Gly Ile Val Pro Thr Gln Pro Arg
    10              15                  20
```